US012698278B2

(12) United States Patent
Baek et al.

(10) Patent No.: US 12,698,278 B2
(45) Date of Patent: Aug. 4, 2026

(54) PREPARATION OF SUBSTITUTED 1,2-DIAMINOHETEROCYCLIC COMPOUND DERIVATIVES AND THEIR USE AS PHARMACEUTICAL AGENTS

(71) Applicant: AVELOS THERAPEUTICS INC., Seoul (KR)

(72) Inventors: Ki Seon Baek, Seoul (KR); Ja Heouk Khoo, Gunpo-si (KR); Soongyu Choi, Seoul (KR); Young Whan Park, Goyang-si (KR); Simon Ward, Cardiff (GB); Darren Le Grand, East Grinstead (GB); Ryan West, Glasgow (GB); Penelope Turner, Winchester (GB); Samuele Maramai, Buonconvento (IT); Tristan Reuillon, Mölndal (SE)

(73) Assignee: AVELOS THERAPEUTICS INC., Seoul (KR)

(*) Notice: Subject to any disclaimer, the term of this patent is extended or adjusted under 35 U.S.C. 154(b) by 353 days.

(21) Appl. No.: 18/568,365

(22) PCT Filed: Jun. 9, 2022

(86) PCT No.: PCT/KR2022/008105
§ 371 (c)(1),
(2) Date: Dec. 8, 2023

(87) PCT Pub. No.: WO2022/260441
PCT Pub. Date: Dec. 15, 2022

(65) Prior Publication Data

US 2024/0300936 A1 Sep. 12, 2024

(30) Foreign Application Priority Data

Jun. 9, 2021 (GB) ...................................... 2108249

(51) Int. Cl.

| | |
|---|---|
| ***C07D 413/14*** | (2006.01) |
| ***A61K 31/506*** | (2006.01) |
| ***A61K 31/53*** | (2006.01) |
| ***A61K 31/5377*** | (2006.01) |
| ***A61P 35/00*** | (2006.01) |
| ***C07D 401/14*** | (2006.01) |
| ***C07D 403/04*** | (2006.01) |
| ***C07D 403/14*** | (2006.01) |
| ***C07D 405/14*** | (2006.01) |
| ***C07D 417/14*** | (2006.01) |
| ***C07D 471/04*** | (2006.01) |
| ***C07D 513/04*** | (2006.01) |

(52) U.S. Cl.
CPC .......... *C07D 413/14* (2013.01); *A61K 31/506* (2013.01); *A61K 31/53* (2013.01); *A61K 31/5377* (2013.01); *A61P 35/00* (2018.01); *C07D 401/14* (2013.01); *C07D 403/04* (2013.01); *C07D 403/14* (2013.01); *C07D 405/14* (2013.01); *C07D 417/14* (2013.01); *C07D 471/04* (2013.01); *C07D 513/04* (2013.01)

(58) Field of Classification Search
CPC .. C07D 413/14; C07D 401/14; C07D 403/04; C07D 403/14; C07D 405/14; C07D 417/14; C07D 471/04; C07D 513/04
See application file for complete search history.

(56) References Cited

U.S. PATENT DOCUMENTS

| | | | | |
|---|---|---|---|---|
| 2011/0275611 | A1 | 11/2011 | Axten | |
| 2021/0347772 | A1* | 11/2021 | Gray | A61P 35/00 |

FOREIGN PATENT DOCUMENTS

| | | | |
|---|---|---|---|
| JP | 2012508223 | A | 4/2012 |
| JP | 2012509335 | A | 4/2012 |
| JP | 2016504289 | A | 2/2016 |
| JP | 2017516826 | A | 6/2017 |
| WO | 2010059658 | A1 | 5/2010 |
| WO | 2012101654 | A2 | 8/2012 |
| WO | 2014084778 | A1 | 6/2014 |
| WO | 2015187089 | A1 | 12/2015 |

OTHER PUBLICATIONS

Medina J.R. et al, Structure-Based Design of Potent and Selective 3-Phosphoinositide-Dependent Kinase-1 (PDK1) Inhibitors, Journal of Medicinal Chemistry, 2011, vol. 54, p. 1871-1895.
Kim A.-Y. et al., MKI-1, a Novel Small-Molecule Inhibitor of MASTL, Exerts Antitumor and Radiosensitizer Activities Through PP2A Activation in Breast Cancer, Frontiers in Oncology, 2020, vol. 10, article 571601.
Klug D.M. et al, Hit-to-Lead Optimization of Benzoxazepinoindazoles as Human African Trypanosomiasis Therapeutics, Journal of Medicinal Chemistry, 2020, vol. 63, p. 2527-2546.
CAS register No. 2411592-23-7, 1252031-03-0, REGISTRYSTN[online], Mar. 11, 2020.
Medina, J.R. et al., "Structure-Based Design of Potent and Selective 3-Phosphoinositide-Dependent Kinase-1 (PDK1) Inhibitors," Journal of Medicinal Chemistry, Feb. 22, 2011, vol. 54, No. 6, pp. 1871-1895.

(Continued)

*Primary Examiner* — Timothy R Rozof
(74) *Attorney, Agent, or Firm* — Dinsmore & Shohl LLP

(57) ABSTRACT

This invention relates to compounds which are microtubule associated serine/threonine-like kinase (MASTL) inhibitors and the use of the compounds in the treatment of diseases and medical conditions mediated by MASTL, for example in the treatment of cancer and other target related diseases.

17 Claims, No Drawings

(56) References Cited

OTHER PUBLICATIONS

Kotasthane, A. et al., "Applying conformational selection theory to improve crossdocking efficiency in 3-phosphoinositide dependent protein kinase-1," Proteins: structure, function, and bioinformatics, Mar. 2014, vol. 82, No. 3, pp. 436-451.
Large, Jonathan M. et al., "Preparation and evaluation of trisubstituted pyrimidines as phosphatidylinositol 3-kinase inhibitors. 3-Hydroxyphenol analogues and bioisosteric replacements", Bioorganic & Medicinal Chemistry, Jan. 1, 2011, vol. 19, No. 2, pp. 836-851.
Cervi, Giovanni et al., "Discovery of 2-(Cyclohexylmethylamino)pyrimidines as a New Class of Reversible Valosine Containing Protein Inhibitors", Journal of Medicinal Chemistry, Dec. 12, 2014, vol. 57, No. 24, pp. 10443-10454.

* cited by examiner

PREPARATION OF SUBSTITUTED 1,2-DIAMINOHETEROCYCLIC COMPOUND DERIVATIVES AND THEIR USE AS PHARMACEUTICAL AGENTS

CROSS-REFERENCE TO RELATED APPLICATIONS

The present application is a national phase of International Application No. PCT/KR2022/008105 filed on Jun. 9, 2022, which claims priority to Great Britain Application No. 2108249.0 filed on Jun. 9, 2021, the entire contents of which are herein incorporated by reference.

TECHNICAL FIELD

This invention relates to compounds which are microtubule associated serine/threonine-like kinase (MASTL) inhibitors and the use of the compounds in the treatment of diseases and medical conditions mediated by MASTL, for example in the treatment of cancer and other target related diseases.

BACKGROUND ART

Microtubule-associated serine/threonine kinase-like (MASTL), also known as Greatwall kinase (GWL), is a member of the AGC kinase family that regulates the mitotic phosphatase complex PP2A/B55. MASTL is located on human chromosome 10p12.1 and encodes a protein of 850 amino acids. It is unique amongst kinases as it contains an approximately 500 amino acid insertion between kinase subdomains VII and VIII that corresponds to the activation loop. The protein modulates mitotic entry and exit through its ability to inactivate the phosphatase PP2A/B55 (Castilho et al., (2009). The M phase kinase Greatwall (Gwl) promotes inactivation of PP2A/B55delta, a phosphatase directed against CDK phosphosites. (Mol. Biol. Cell. 20(22): 4777-89). MASTL inhibits the phosphatase indirectly through phosphorylation of ENSA and ARPP19 at S67 and S62 (pENSA/pARPP19), respectively (Gharbi-Ayachi et al., (2010). The substrate of Greatwall kinase, Arpp19, controls mitosis by inhibiting protein phosphatase 2A. (Science 330 1673-1677). pENSA and pARPP19 are substrates of PP2A/B55 and inhibit the complex by binding tightly to it and un-dergoing de-phosphorylation at a very slow rate, thus inhibiting the catalytic activity of PP2A/B55 by ‘unfair competition’ (Williams et al., (2014). Greatwall-phosphorylated Endosulfine is both an inhibitor and a substrate of PP2A-B55 heterotrimers. (*eLife* 3:e01695.). Entry into cellular mitosis is governed by a rapid increase in the phosphorylation of numerous substrates by CDK1/CCNB1, which is accompanied by a reduction in the activity of PP2A/B55. MASTL is a substrate of CDK1/CCNB1 and a combination of their activities ensure MASTL activity peaks at mitosis. MASTL activity is essential to coordinate exit from mitosis by delaying the increase of PP2A/B55 activity until chromosomal segregation is complete. APC/C dependent ubiquitination of CCNB1, followed by its subsequent degradation by the proteasome, initiates anaphase entry. This attenuates CDK1 activity leading to the eventual deactivation of MASTL and an increase in the PP2A/B55 phosphatase activity that is required for timely exit from mitosis. Temporal control of PP2A/B55 reactivation by the PP2A-B55-ENSA/ARPP19-MASTL pathway is essential for orderly cytokinesis following chromosomal segregation (Cundell et al., (2013). The BEG (PP2A-B55/ENSA/Greatwall) pathway ensures cytokinesis follows chromosome separation. (*Mol. Cell* 52 393-405). Inhibiting the kinase activity of MASTL will result in premature cytokinesis, causing chromosome segregation defects and aneuploidy.

MASTL has been shown to be essential for cell-cycle progression during embryogenesis in a number of organisms, including mouse, frog and fruit-fly. In mouse it remains essential for up to one year after birth after which, its loss (total deletion) is tolerated (Belén Sanz Castillo: Role of MASTL in mammals: Molecular functions and physiological relevance, 2017). Furthermore a siRNA screen identified MASTL as a gene that can specifically inhibit the proliferation of transformed (thyroid cancer) cells but not non-transformed cells (Anania et al., (2015) Identification of thyroid tumor cell vulnerabilities through a siRNA-based functional screening. (Oncotarget 6, 34629-34648). These studies show that MASTL essentiality is not universal and that it is confined to embryonic and early development stages of organisms. Moreover, the studies show that the cell cycle control mechanisms in some cancer cells have reverted back to a state similar to that of embryonic cell cycles (where MASTL activity is essential) to render them sensitive to MASTL loss. Therefore inhibitors of MASTL kinase will have broad applicability across a multitude of cancers while also having a good therapeutic window, and as such is an ideal target for cancer therapy.

A number of studies have demonstrated that MASTL plays a critical role in cancer development. Overexpression of MASTL has been identified in a range of other human tumours, including breast (Álvarez-Fernández et al. (2017), oral (Wang et al., (2014). Mastl kinase, a promising therapeutic target, promotes cancer recurrence. (*Oncotarget* 5 11479-11489.) and gastric (Sun et al., (2017). Mastl overexpression is associated with epithelial to mesenchymal transition and predicts a poor clinical outcome in gastric cancer. (*Oncol. Lett.* 14 7283-7287.). Therapeutic relevance of the PP2A-B55 inhibitory kinase MASTL/Greatwall in breast cancer. (Cell Death Differ. 25, 828-840; Zhuge et al., (2017)). MASTL is a potential poor prognostic indicator in ER+ breast cancer. (*Eur. Rev. Med. Pharmacol. Sci.* 21 2413-2420.), and colon (Vera et al., (2015). Greatwall promotes cell transformation by hyperactivating AKT in human malignancies. (eLife 4, e10115.). Mouse xenograft studies using doxycycline inducible knock out of MASTL by CRISPR/Cas9 in MDA-MB-231 cells showed a significant reduction in the tumour size when MASTL was depleted relative to control animals. Expression levels of MASTL protein correlated with aggressiveness in ER+ breast cancer and were prognostic for poor patient survival (Álvarez-Fernández et al., (2018). Therapeutic relevance of the PP2A-B55 inhibitory kinase MASTL/Greatwall in breast cancer. (*Cell Death Differ.* 25 828-840). Upregulation of MASTL is correlated with cancer progression in head and neck tumours, and it is frequently associated with more aggressive forms of the disease (Wang et al., (2014). Mastl kinase, a promising therapeutic target, promotes cancer recurrence. (Oncotarget 5, 11479-11489). A high throughput siRNA screen in BCPAP thyroid cancer identified vulnerabilities to the loss of MASTL, which resulted in a significant reduction in cell proliferation (Anania et al. (2015)). In colorectal cancer, upregulation of MASTL is correlated with poor patient survival and can act as a prognostic biomarker for latent disease aggressiveness (Uppada et al., (2018). MASTL induces colon cancer progression and chemoresistance by promoting Wnt/β-catenin signaling. (*Mol. Cancer* 17:111). In support of a therapeutic window, normal colonocytes do not express MASTL, or do so only at very low levels. Depletion of MASTL in HCT-116 cells resulted in G2/M arrest, induction of apoptosis through regulation of the anti-apoptotic proteins (Survivin and Bcl-xL, probably via Gskβ activation) and importantly reduced growth in vivo. In addition to having a direct effect on HCT-116 cell proliferation, the MASTL derived regulation of anti-apoptotic proteins resulted in increased sensitivity to 5-FU treatment. MASTL has been highlighted as a potential new therapeutic target for several cancers, such as acute myeloid leukemia (Tzelepis et al. (2016). A CRISPR dropout screen identifies genetic vulnerabilities and therapeutic targets in acute myeloid leukemia. (Cell Rep. 17, 1193-1205.), head and neck squamous cell carcinoma (Wang et al., 2014) and thyroid carcinoma (Anania et al., 2015).

In addition to its role as a regulator of the G2/M checkpoint, MASTL can inactivate checkpoint signalling and help recovery from DNA damage, supporting a role in potentiating effects of DNA damaging agents (Peng et al., (2010). A novel role for greatwall kinase in recovery from DNA damage. (*Cell Cycle* 9 4364-4369). An unbiased genome-wide siRNA loss of function screen in NSCLC cells identified MASTL as the primary hit for sensitising the cells to irradiation. The effect was not observed in primary human fibroblast, indicating the potential for selective sensitization of tumour cells over untransformed cells (Nagel et al., (2015). Genome-wide siRNA Screen identifies the radiosensitizing effect of downregulation of MASTL and FOXM1 in NSCLC. (*Mol. Cancer Ther.* 14 1434-1444). A similar effect was observed in a xenograft tumour model of UM-SSC-11-B cells derived from head and necks squamous cell carcinomas refractory to cisplatin (Wang et al., 2014). MASTL depletion re-sensitised the cells to cisplatin treatment. Additional flow cytometry studies in UM-SSC-11-B cells showed an increase sub G1 population and induction of apoptosis, while normal oral keratinocyte OKF4 cells depleted of MASTL were resistant to cell death with or without cisplatin treatment.

In addition to the role of MASTL in cancer through regulation of DNA damage repair pathways and mitosis, it also has a role in modulating PP2A activity in interphase (Belén Sanz Castillo, 2017). A point mutation in the MASTL gene was found to lead to an autosomal dominant inherited thrombocytopenia (Drachman et al., Autosomal dominant thrombocytopenia: incomplete megakaryocyte differentiation and linkage to human chromosome 10. (Blood. 2000; 96:118-125.), providing evidence of the role of MASTL in megakaryocytopoeisis. More recently it was discovered that this point mutation in MASTL does not result in reduced activity, as originally thought, but rather is accompanied by increased phosphorylation of the Cdk and PP2A substrates, indicating a gain-of-function alteration that results in decreased PP2A activity (Hurtado et al., (2018) Thrombocytopenia-associated mutations in Ser/Thr kinase MASTL deregulate actin cytoskeletal dynamics in platelets. (J Clin Invest. 128(12): 5351-5367). A MASTL inhibitor may therefore have therapeutic potential in the treatment of metabolic diseases (such as diabetes and obesity) and platelet disorders, including the rare genetic disease MASTL-linked thrombocytopenia, through its effects on the regulation of the PI3K/AKT pathway and the cytoskeleton, respectively.

There is therefore a need for MASTL inhibitors which are expected to provide a beneficial therapeutic effect, for example in the treatment of cancer.

SUMMARY OF INVENTION

In accordance with the present inventions there is provided a compound of the formula (I), or a pharmaceutically acceptable salt thereof:

(I)

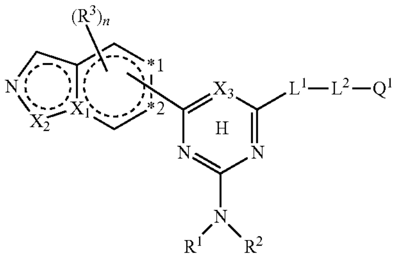

wherein;

wherein the H ring in formula (I) is bonded to the carbon atom $^{*1}$ or $^{*2}$;

$R^1$ is selected from: H, $C_{1-6}$ alkyl and $C_{1-6}$ haloalkyl;

$R^2$ is selected from: H, $C_{1-6}$ alkyl, $C_{2-6}$ alkenyl, $C_{2-6}$ alkynyl, $C_{1-6}$ haloalkyl and $Q^3$-$L^3$-, wherein said $C_{1-6}$ alkyl is optionally substituted by one or more $R^6$ substituents;

$L^3$ is a bond or is selected from: $C_{1-6}$ alkylene, $C_{2-6}$ alkenylene and $C_{2-6}$ alkynylene;

$Q^3$ is selected from: $C_{3-6}$ cycloalkyl, 3- to 6-membered heterocyclyl, $C_{6-12}$ aryl, and 5- or 6-membered heteroaryl, wherein said $C_{3-6}$ cycloalkyl and 3- to 6-membered heterocyclyl is optionally substituted by one or more $R^7$, wherein said $C_{6-12}$ aryl, and 5- or 6-membered heteroaryl is optionally substituted by one or more $R^1$;

$R^3$ is each independently selected from: halo, $C_{1-6}$ alkyl and amino;

$X_1$ is N and $X_2$ is $CR^4$, or $X_1$ is C and $X_2$ is $NR^5$;

X3 is C or N;

$R^4$ is selected from: H, halo, CN, $C_{1-6}$ alkyl and $C_{1-6}$ haloalkyl;

$R^5$ is selected from: H, $C_{1-6}$ alkyl, $Q^4$-$L^4$- wherein said $C_{1-6}$ alkyl is optionally substituted by one or more $R^9$, $L^4$ is a bond or $C_{1-4}$ alkylene;

$Q^4$ is selected from: $C_{3-6}$ cycloalkyl, 3- to 6-membered heterocyclyl, $C_{6-12}$ aryl, and 5 or 6 membered heteroaryl, wherein said $C_{3-6}$ cycloalkyl and 3- to 6-membered heterocyclyl is optionally substituted by one or more $R^{10}$, and said $C_{6-12}$ aryl, and 5- or 6-membered heteroaryl is optionally substituted by one or more $R^{11}$;

$L^1$ is a bond or is selected from: $NR^{12}$, O, S and $Q^5$ $R^{12}$ is selected from H, $C_{1-4}$ alkyl, $C_{1-4}$ haloalkyl, $C_{3-6}$ cycloalkyl, $C_{3-6}$ cycloalkyl-$C_{1-4}$ alkyl and $C_{1-4}$ alkyl-$OR^{A5}$, wherein said $C_{3-6}$ cycloalkyl and $C_{3-6}$ cycloalkyl-$C_{1-4}$ alkyl is optionally substituted by one or more substituents selected from: =O, halo, $C_{1-4}$ alkyl and $C_{1-4}$ haloalkyl, $Q^5$ is 4- to 6-membered heterocyclylene containing 1 ring nitrogen atom and optionally 1 ring atom selected from O, S and N, wherein $Q^5$ is bonded to the H ring in formula (I) by a ring carbon or ring nitrogen atom in $Q^5$, wherein $Q^5$ is optionally substituted by one or more substituents selected from: =O, halo, $C_{1-4}$ alkyl and $C_{1-4}$ haloalkyl;

$L^2$ is a bond or $-[CR^{13}R^{14}]_p-$, p is an integer from 1 to 4;

$R^{13}$ and $R^{14}$ are each independently selected from: H, $C_{1-4}$ alkyl, and $C_{1-4}$ haloalkyl, OH, COOH, $C(O)NR^{X1}R^{X2}$, and $C_{3-6}$ cycloalkyl, or an $R^{13}$ and an $R^{14}$ attached to the same carbon atom in $L^2$ together form a $C_{3-6}$ cycloalkyl or 3-6-membered heterocyclyl, wherein said $C_{1-4}$alkyl is optionally substituted by OH, O—$C_{1-4}$alkyl, 3- to 6-membered heterocyclyl, 5- to 10-membered heteroaryl, or $C_{6-10}$ aryl optionally substituted by halogen or $C_{1-6}$ haloalkyl;

wherein $R^{X1}$ and $R^{X2}$ are independently selected from: H, $C_{1-4}$alkyl optionally substituted by OH or 3- to 6-membered heterocyclyl, and 5- to 10-membered heteroaryl, or an $R^{X1}$ and an $R^{X2}$ attached to the same nitrogen atom together to form a 3- to 6-membered heterocyclyl;

wherein said $C_{3-6}$ cycloalkyl or 3- to 6-membered heterocyclyl is optionally substituted by one or more substituents selected from: =O, halo, $C_{1-4}$ alkyl and $C_{1-4}$ haloalkyl;

$Q^1$ is selected from: $C_{3-12}$ cycloalkyl, $C_{3-12}$ cycloalkenyl, 3- to 12-membered heterocyclyl, $C_{6-10}$ aryl, 5- to 10-membered heteroaryl, COOH, $C(O)NR^{Z1}R^{Z2}$, and C(O)O—$C_{1-6}$alkyl;

wherein each $R^{Z1}$ and $R^{Z2}$ is each independently selected from; H, $C_{1-6}$ alkyl optionally substituted by OH, $C_{3-6}$ cycloalkyl, $C_{6-10}$aryl, or 5- to 10-membered heteroaryl; or an $R^{Z1}$ and an $R^{Z2}$ attached to the same nitrogen atom together to form a 3-6-membered heterocyclyl;

wherein said $C_{3-12}$ cycloalkyl, $C_{3-12}$ cycloalkenyl and 3- to 12-membered heterocyclyl is optionally substituted by one or more $R^{15}$, wherein said $C_{6-10}$ aryl and 5- to 10-membered heteroaryl is optionally substituted by one or more $R^{16}$;

each $R^{15}$ is independently selected from: halo, =O, —CN, —$NO_2$, $C_{1-6}$ alkyl, $C_{2-6}$ alkenyl, $C_{2-6}$ alkynyl, $C_{1-6}$ haloalkyl, —$OR^{17}$, —$S(O)_{x1}R^{17}$, —$NR^{17}R^{B1}$, —$C(O)R^{17}$, —$OC(O)R^{17}$, —$C(O)OR^{17}$, —$NR^{B1}C(O)R^{17}$, —$NR^{B1}C(O)OR^{17}$, —$C(O)NR^{17}R^{B1}$, —$OC(O)NR^{17}R^{B1}$, —$NR^{B1}SO_2R^{17}$, —$SO_2NR^{17}R^{B1}$ and —$NR^{A1}C(O)NR^{17}R^{B1}$, wherein said $C_{1-6}$ alkyl, $C_{2-6}$ alkenyl and $C_{2-6}$ alkynyl is optionally substituted by 1 or more $R^{18}$, and $R^{17}$ is selected from: H, $C_{1-6}$ alkyl and $C_{1-6}$ haloalkyl, wherein said $C_{1-6}$ alkyl is optionally substituted by one or more $R^{19}$;

each $R^{16}$ is independently selected from: halo, —CN, —$NO_2$, $C_{1-6}$ alkyl, $C_{2-6}$ alkenyl, $C_{2-6}$alkynyl, $C_{1-6}$ haloalkyl, —$OR^{20}$, —$S(O)_{x2}R^{20}$, —$NR^{20}R^{B2}$, —$C(O)R^{20}$, —$OC(O)R^{20}$, —$C(O)OR^{20}$, —$NR^{B2}C(O)R^{20}$, —$NR^{B2}C(O)OR^{20}$, —$C(O)NR^{20}R^{B2}$, —$OC(O)NR^{20}R^{B2}$, —$NR^{B2}SO_2R^{20}$, —$SO_2NR^{20}R^{B2}$ and —$NR^{A2}C(O)NR^{20}R^{B2}$, wherein said $C_{1-6}$ alkyl, $C_{2-6}$ alkenyl and $C_{2-6}$ alkynyl is optionally substituted by 1 or more $R^{21}$, and wherein $R^{20}$ is selected from: H, $C_{1-6}$ alkyl and $C_{1-6}$ haloalkyl, wherein said $C_{1-6}$ alkyl is optionally substituted by one or more $R^{22}$;

$R^6$, $R^7$, $R^9$, $R^{10}$, $R^{18}$, $R^{19}$, $R^{21}$ and $R^{22}$ are each independently selected from: halo, =O, —CN, —$NO_2$, $C_{1-4}$ alkyl, $C_{1-4}$ haloalkyl, —$OR^{A3}$, —$S(O)_{x3}R^{A4}$, —$NR^{A3}R^{B3}$, —$C(O)R^{A3}$, —$OC(O)R^{A3}$, —$C(O)OR^{A3}$, —$NR^{B3}C(O)R^{A3}$, —$NR^{B3}C(O)OR^{A3}$, —$C(O)NR^{A3}R^{B3}$, —$NR^{B4}SO_2R^{A3}$ and —$SO_2NR^{A3}R^{B3}$;

$R^1$ and $R^{11}$ are each independently selected from: halo, =O, —CN, —$NO_2$, $C_{1-4}$ alkyl, $C_{1-4}$ haloalkyl, —$OR^{A4}$, —$S(O)_{x4}R^{A4}$, —$NR^{A4}R^{B4}$, —$C(O)R^{A4}$, —$OC(O)R^{A4}$, —$C(O)OR^{A4}$, —$NR^{B4}C(O)R^{A4}$, —$NR^{B4}C(O)OR^{A4}$, —$C(O)NR^{A4}R^{B4}$, —$NR^{B4}SO_2R^{A4}$ and —$SO_2NR^{A4}R^{B4}$;

$R^{1A}$, $R^{1B}$, $R^{A2}$, $R^{B2}$, $R^{A3}$, $R^{B3}$, $R^{A4}$, $R^{B4}$ and $R^{A5}$ are each independently selected from: H, $C_{1-4}$ alkyl and $C_{1-4}$ haloalkyl, or any —$NR^{A3}R^{B3}$, —$NR^{A4}R^{B4}$, —$NR^{17}R^{B1}$ or —$NR^{20}R^{B2}$, within a substituent may form a 4- to 6-membered heterocyclyl, wherein said 4- to 6-membered heterocyclyl is optionally substituted by one or more substituents selected from: halo, =O, $C_{1-4}$ alkyl and $C_{1-4}$ haloalkyl;

n is an integer from 0 to 4; and x1, x2, x3 and x4 are each independently selected from: 0, 1 or 2.

Also provided is a pharmaceutical composition comprising a compound of the invention, or a pharmaceutically acceptable salt thereof, and a pharmaceutically acceptable excipient.

Also provided is a compound of the invention, or a pharmaceutically acceptable salt thereof, for use as a medicament. In some embodiments the compound of the invention, or a pharmaceutically acceptable salt thereof, is for use in the treatment of a disease or medical condition mediated by microtubule associated serine/threonine-like kinase (MASTL).

Also provided is a method of treating a disease or medical condition mediated by MASTL in a subject in need thereof, the method comprising administering to the subject an effective amount of a compound of the invention, or a pharmaceutically acceptable salt thereof.

In certain embodiments the compounds of the invention are for use in the treatment of proliferative diseases, for example cancer. In certain embodiments a compound of the invention is for use in the prevention or inhibition of cancer progression, for example by preventing or inhibiting cancer cell migration, cancer cell invasion and/or preventing or inhibiting cancer metastasis.

In certain embodiments the compounds of the invention are for use in the treatment of a cancer.

In certain embodiments the compounds of the invention are for use in the treatment of a cancer that overexpresses MASTL.

In certain embodiments the compounds of the invention are for use in the treatment of a cancer selected from: breast, ovarian, lung, colorectal, prostate, oral, gastric, adrenocortical, pancreatic, kidney, sarcoma, liver, endometrial, thyroid, head or neck, brain (e.g. glioma), melanoma (e.g. ocular melanoma) and haematological cancer (e.g. leukaemia, such as AML, lymphoma, myeloma and multiple myeloma).

In certain embodiments, the compounds of the invention are for use in the treatment or prevention of a metabolic disorder, or symptoms or conditions associated with a metabolic disease.

In certain embodiments, the metabolic disorder may be insulin resistance, diabetes or obesity. Symptoms and conditions associated with a metabolic disorder may include one or more of: increased blood sugar, increased cholesterol, increased triglyceride levels, heart disease, stroke, high blood pressure, and an increased risk of blood clots (e.g. deep vein thrombosis).

In certain embodiments, the compounds of the invention are for use in the treatment of a platelet disorder, such as thrombocytopenia.

The compounds of the invention may be used alone or in combination with one or more anticancer agents and/or radiotherapy as described herein.

DISCLOSURE OF INVENTION

Solution to Problem

Detailed Description

Definitions

Unless otherwise stated, the following terms used in the specification and claims have the following meanings set out below.

The terms "treating" or "treatment" refers to any indicia of success in the treatment or amelioration of a disease, pathology or condition, including any objective or subjective parameter such as abatement; remission; diminishing of symptoms or making the pathology or condition more tolerable to the patient; slowing in the rate of degeneration or decline; making the final point of degeneration less debilitating; improving a patient's physical or mental well-being. For example, certain methods herein treat cancer by decreasing a symptom of cancer. Symptoms of cancer would be known or may be determined by a person of ordinary skill in the art. The term "treating" and conjugations thereof, include prevention of a pathology, condition, or disease (e.g. preventing the development of one or more symptoms of a cancer associated with MASTL.

The term "associated" or "associated with" in the context of a substance or substance activity or function associated with a disease (e.g. cancer) means that the disease (e.g. cancer) is caused by (in whole or in part), or a symptom of the disease is caused by (in whole or in part) the substance or substance activity or function. For example, a symptom of a disease or condition associated with MASTL pathway activity may be a symptom that results (entirely or partially) from an increase in the level of activity of MASTL protein pathway. As used herein, what is described as being associated with a disease, if a causative agent, could be a target for treatment of the disease. For example, a disease associated with an increase in the level of activity of MASTL, may be treated with an agent (e.g. compound as described herein) effective for decreasing the level of activity of MASTL.

As defined herein, the term "inhibition", "inhibit", "inhibiting" and the like in reference to a protein-inhibitor (e.g. antagonist) interaction means negatively affecting (e.g. decreasing) the level of activity or function of the protein (e.g. a component of the MASTL) protein pathway relative to the level of activity or function of the protein pathway in the absence of the inhibitor). In some embodiments inhibition refers to reduction of a disease or symptoms of disease (e.g. cancer associated with an increased level of activity of MASTL. In some embodiments, inhibition refers to a reduction in the level of activity of a signal transduction pathway or signalling pathway associated with MASTL. Thus, inhibition may include, at least in part, partially or totally blocking stimulation, decreasing, preventing, or delaying activation, or inactivating, desensitizing, or down-regulating signal transduction or enzymatic activity or the amount of a protein (e.g. the MASTL). Inhibition may include, at least in part, partially or totally decreasing stimulation, decreasing activation, or deactivating, desensitizing, or down-regulating signal transduction or enzymatic activity or the amount of a protein (e.g. a component of a MASTL protein pathway) that may modulate the level of another protein or modulate cell survival, cell proliferation or cell motility relative to a non-disease control.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

The term "halo" or "halogen" refers to one of the halogens, group 17 of the periodic table. In particular the term refers to fluorine, chlorine, bromine and iodine. Preferably, the term refers to fluorine or chlorine.

The term $C_{m-n}$ refers to a group with m to n carbon atoms.

The term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, iso-butyl, sec-butyl, tert-butyl, n-pentyl and n-hexyl. "$C_{1-4}$ alkyl" similarly refers to such groups containing up to 4 carbon atoms. Alkylene groups are divalent alkyl groups and may likewise be linear or branched and have two points of attachment to the remainder of the molecule. Furthermore, an alkylene group may, for example, correspond to one of those alkyl groups listed in this paragraph. For example, $C_{1-6}$ alkylene may be $—CH_2—$, $—CH_2CH_2—$, $—CH_2CH(CH_3)—$, $—CH_2CH_2CH_2—$ or $—CH_2CH(CH_3)CH_2—$. The alkyl and alkylene groups may be unsubstituted or substituted by one or more substituents. Possible substituents are described herein. For example, substituents for an alkyl or alkylene group may be halogen, e.g. fluorine, chlorine, bromine and iodine, OH, $C_1$-$C_4$ alkoxy, —NR'R" amino, wherein R' and R" are independently H or alkyl. Other substituents for the alkyl group may alternatively be used.

The term "$C_{1-6}$ haloalkyl", e.g. "$C_{1-4}$ haloalkyl" refers to a hydrocarbon chain substituted with at least one halogen atom independently chosen at each occurrence, for example fluorine, chlorine, bromine and iodine. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A haloalkyl group may be, for example, $—CX_3$, $—CHX_2$, $—CH_2CX_3$, $—CH_2CHX_2$ or $—CX(CH_3)CH_3$ wherein X is a halo (e.g. F, Cl, Br or I). A fluoroalkyl group, i.e. a hydrocarbon chain substituted with at least one fluorine atom (e.g. $—CF_3$, $—CHF_2$, $—CH_2CF_3$ or $—CH_2CHF_2$).

The term "$C_{2-6}$ alkenyl" includes a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl. Alkenylene groups are divalent alkenyl groups and may likewise be linear or branched and have two points of attachment to the remainder of the molecule. Furthermore, an alkenylene group may, for example, correspond to one of those alkenyl groups listed in this paragraph. For example alkenylene may be $—CH{=}CH—$, $—CH_2CH═CH—$, $—CH(CH_3)CH═CH—$ or $—CH_2CH═CH—$. Alkenyl and alkenylene groups may unsubstituted or substituted by one or more substituents. Possible substituents are described herein. For example, substituents may be those described above as substituents for alkyl groups.

The term "$C_{2-6}$ alkynyl" includes a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl. Alkynylene groups are divalent alkynyl groups and may likewise be linear or branched and have two points of attachment to the remainder of the molecule. Furthermore, an alkynylene group may, for example, correspond to one of those alkynyl groups listed in this paragraph. For example alkynylene may be $—C≡C—$, $—CH_2C≡C—$, $—CH_2C≡CCH_2—$, $—CH(CH_3)CH═C—$ or $—CH_2C≡CCH_3$. Alkynyl and alkynylene groups may unsubstituted or substituted by one or more substituents. Possible substituents are described herein. For example, substituents may be those described above as substituents for alkyl groups.

The term "$C_{3-12}$ cycloalkyl" includes a saturated hydrocarbon ring system containing 3 to 12 carbon atoms. The cycloalkyl group may be monocyclic or a fused, bridged or spiro saturated hydrocarbon ring system. The term "$C_{3-6}$ cycloalkyl" includes a saturated hydrocarbon ring system containing 3, 4, 5 or 6 carbon atoms. For example, the $C_3$-$C_{12}$ cycloalkyl may be cyclopropyl, cyclobutyl, cyclopentyl, cyclohexyl, bicyclo[1.1.1]pentane, bicyclo[2.1.1]hexane, bicyclo[2.2.1]heptane (norbornane), bicyclo[2.2.2]octane or tricyclo[3.3.1.1]decane (adamantyl). For example, the "$C_3$-$C_6$ cycloalkyl" may be cyclopropyl, cyclobutyl, cyclopentyl, cyclohexyl, bicyclo[2.1.1]hexane or bicyclo[1.1.1]pentane. Suitably the "$C_3$-$C_6$ cycloalkyl" may be cyclopropyl, cyclobutyl, cyclopentyl or cyclohexyl.

The term "$C_{3-12}$ cycloalkenyl" includes a hydrocarbon ring system containing 3 to 12 carbon atoms and at least one double bond (e.g. 1 or 2 double bonds). The cycloalkenyl group may be monocyclic or a fused, bridged or spiro hydrocarbon ring system. For example, $C_{3-12}$ cycloalkenyl may be cyclobutenyl, cyclopentenyl, cyclohexenyl, The term "heterocyclyl", "heterocyclic" or "heterocycle" includes a non-aromatic saturated or partially saturated monocyclic or fused, bridged, or spiro bicyclic heterocyclic ring system. Monocyclic heterocyclic rings may contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles may contain from 7 to 12-member atoms in the ring. Bicyclic heterocyclic(s) rings may be fused, spiro, or bridged ring systems. The heterocyclyl group may be a 3-12, for example, a 3- to 9- (e.g. a 3- to 7-) membered non-aromatic monocyclic or bicyclic saturated or partially saturated group comprising 1, 2 or 3 heteroatoms independently selected from O, S and N in the ring system (in other words 1, 2 or 3 of the atoms forming the ring system are selected from O, S and N). By partially saturated it is meant that the ring may comprise one or two double bonds. This applies particularly to monocyclic rings with from 5 to 7 members. The double bond will typically be between two carbon atoms but may be between a carbon atom and a nitrogen atom. Bicyclic systems may be spiro-fused, i.e. where the rings are linked to each other through a single carbon atom; vicinally fused, i.e. where the rings are linked to each other through two adjacent carbon or nitrogen atoms; or they may be share a bridgehead, i.e. the rings are linked to each other through two non-adjacent carbon or nitrogen atoms (a bridged ring system). Examples of heterocyclic groups include cyclic ethers such as oxiranyl, oxetanyl, tetrahydrofuranyl, dioxanyl, and substituted cyclic ethers. Heterocycles comprising at least one nitrogen in a ring position include, for example, azetidinyl, pyrrolidinyl, piperidinyl, piperazinyl, morpholinyl, thiomorpholinyl, tetrahydrotriazinyl, tetrahydropyrazolyl, tetrahydropyridinyl, homopiperidinyl, homopiperazinyl, 2,5-diaza-bicyclo[2.2.1]heptanyl and the like. Typical sulfur containing heterocycles include tetrahydrothienyl, dihydro-1,3-dithiol, tetrahydro-2H-thiopyran, and hexahydrothiepine. Other heterocycles include dihydro oxathiolyl, tetrahydro oxazolyl, tetrahydro-oxadiazolyl, tetrahydrodioxazolyl, tetrahydrooxathiazolyl, hexahydrotriazinyl, tetrahydro oxazinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (═O), for example, 2 oxopyrrolidinyl, 2-oxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. For example, the term "piperidino" or "morpholino" refers to a piperidin-1-yl or morpholin-4-yl ring that is linked via the ring nitrogen. Reference to "heterocyclylene", for example as may be represented by L refers to a divalent "heterocyclyl", for example 3,2-morpholinylene.

The term "bridged ring systems" includes ring systems in which two rings share more than two atoms, see for example Advanced Organic Chemistry, by Jerry March, 4th Edition, Wiley Interscience, pages 131-133, 1992. Suitably the bridge is formed between two non-adjacent carbon or nitrogen atoms in the ring system. The bridge connecting the bridgehead atoms may be a bond or comprise one or more atoms. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane, and quinuclidine.

The term "spiro bi-cyclic ring systems" includes ring systems in which two ring systems share one common spiro carbon atom, i.e. the heterocyclic ring is linked to a further carbocyclic or heterocyclic ring through a single common spiro carbon atom. Examples of spiro ring systems include 3,8-diaza-bicyclo[3.2.1]octane, 2,5-diaza-bicyclo[2.2.1]heptane, 6-azaspiro[3.4]octane, 2-oxa-6-azaspiro[3.4]octane, 2-azaspiro[3.3]heptane, 2-oxa-6-azaspiro[3.3]heptane, 6-oxa-2-azaspiro[3.4]octane, 2,7-diaza-spiro[4.4]nonane, 2-azaspiro[3.5]nonane, 2-oxa-7-azaspiro[3.5]nonane and 2-oxa-6-azaspiro[3.5]nonane.

"Heterocyclyl-$C_{m-n}$ alkyl" includes a heterocyclyl group covalently attached to a $C_{m-n}$ alkylene group, both of which are defined herein; and wherein the Heterocyclyl-$C_{m-n}$ alkyl group is linked to the remainder of the molecule via a carbon atom in the alkylene group. The groups "aryl-$C_m$ alkyl", "heteroaryl-$C_m$ alkyl" and "cycloalkyl-$C_{m-n}$ alkyl" are defined in the same way.

"—$C_{m-n}$ alkyl" substituted by —NRR" and "$C_{m-n}$ alkyl" substituted by —OR" similarly refer to an —NRR" or —OR" group covalently attached to a $C_{m-n}$ alkylene group and wherein the group is linked to the remainder of the molecule via a carbon atom in the alkylene group.

The term "aromatic" when applied to a substituent as a whole includes a single ring or polycyclic ring system with 4n+2 electrons in a conjugated π system within the ring or ring system where all atoms contributing to the conjugated π system are in the same plane.

The term "aryl" includes an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" includes an aromatic mono- or bicyclic ring incorporating one or more (for example 1-4, particularly 1, 2 or 3) heteroatoms selected from nitrogen, oxygen or sulfur. The ring or ring system has 4n+2 electrons in a conjugated π system where all atoms contributing to the conjugated π system are in the same plane.

Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 1H-pyrazolo[4,3-d]-oxazolyl, 4H-imidazo[4,5-d]thiazolyl, pyrazino[2,3-d]pyridazinyl, imidazo[2,1-b]thiazolyl and imidazo[1,2-b][1,2,4]triazinyl. Examples of heteroaryl groups comprising at least one nitrogen in a ring position include pyrrolyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, indolyl, isoindolyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl and pteridinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five-membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six-membered heteroaryl groups include but are not limited to pyridyl, pyrazinyl, pyridazinyl, pyrimidinyl and triazinyl.

Particular examples of bicyclic heteroaryl groups containing a six-membered ring fused to a five-membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "oxo," or "═O" as used herein, means an oxygen that is double bonded to a carbon atom.

The term "optionally substituted" includes either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without undue effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in "  "

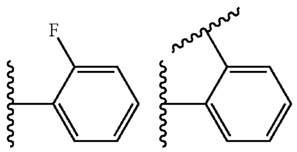

"Meta" substitution is a substitution pattern where two substituents are on carbons one carbon removed from each other, i.e. with a single carbon atom between the substituted carbons. In other words there is a substituent on the second atom away from the atom with another substituent. For example the groups below are meta substituted:

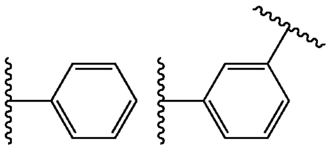

"Para" substitution is a substitution pattern where two substituents are on carbons two carbons removed from each other, i.e. with two carbon atoms between the substituted carbons. In other words there is a substituent on the third atom away from the atom with another substituent. For example the groups below are para substituted:

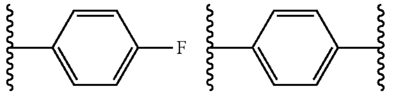

Reference to a —NRR' group forming a 4 to 6 membered heterocyclyl refers to R and R' together with the nitrogen atom to which they are attached forming a 4 to 6 membered heterocyclyl group. For example, an —NRR' such as a —$NR^{A1}R^{B1}$, —$NR^{A4}R^{B4}$, —$NR^{A5}R^{B5}$, —$NR^{17}R^{B2}$ or —$NR^{20}R^{B3}$ group may form:

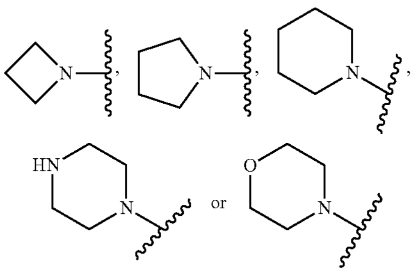

, , , or

Similarly an —NRR' group within a substituent may form a carbonyl-linked 4 to 6 membered heterocyclyl, for example a —C(O)NRR' group may form:

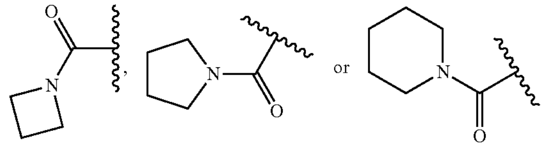

, or

—NRR' groups within substituents such as —OC(O)NRR', —$SO_2$NRR' and —NRC(O)NRR', -, may similarly form a 4 to 6 membered heterocyclyl within such substituents.

The phrase "compound of the invention" means those compounds which are disclosed herein, both generically and specifically. Accordingly compounds of the invention include compounds of the formulae (I) (II), (III), (IV), (V), (VI), (VII) or (VIII) and the compounds in the Examples.

A bond terminating in a "  " or "*" represents that the bond is connected to  another atom that is not shown in the structure. A bond terminating inside a cyclic structure and not terminating at an atom of the ring structure represents that the bond may be connected to any of the atoms in the ring structure where allowed by valency.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed con-currently with or previous to this specification in connection with this application and which are open to public inspection with this specification, and the contents of all such papers and documents are incorporated herein by reference.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or more preferably less than 550.

Suitable or preferred features of any compounds of the present invention may also be suitable features of any other aspect.

The invention contemplates pharmaceutically acceptable salts of the compounds of the invention. These may include the acid addition and base salts of the compounds. These may be acid addition and base salts of the compounds.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of the invention may be prepared by for example, one or more of the following methods:

(i) by reacting the compound of the invention with the desired acid or base;

(ii) by removing an acid- or base-labile protecting group from a suitable precursor of the compound of the invention or by ring-opening a suitable cyclic precursor, for example, a lactone or lactam, using the desired acid or base; or (iii) by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterized by the absolute configuration of its asymmetric centre and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Where a compound of the invention has two or more stereo centres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diastereomeric mixtures. Where the mixture is a mixture of enantiomers the enantiomeric excess may be any of those disclosed above. Where the compound is a single stereoisomer the compounds may still contain other diastereoisomers or enantiomers as impurities. Hence a single stereoisomer does not necessarily have an enantiomeric excess (e.e.) or diastereomeric excess (d.e.) of 100% but could have an e.e. or d.e. of about at least 85%, for example at least 90%, at least 95% or at least 99%.

The compounds of this invention may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess MASTL inhibitory activity.

Z/E (e.g. cis/trans) isomers may be separated by conventional techniques well known to those skilled in the art, for example, chromatography and fractional crystallisation.

Conventional techniques for the preparation/isolation of individual enantiomers when necessary include chiral synthesis from a suitable optically pure precursor or resolution of the racemate (or the racemate of a salt or derivative) using, for example, chiral high-pressure liquid chromatography (HPLC). Thus, chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and for specific examples, 0 to 5% by volume of an alkylamine e.g. 0.1% diethylamine. Concentration of the eluate affords the enriched mixture.

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

Compounds and salts described in this specification may be isotopically-labelled (or "radio-labelled"). Accordingly, one or more atoms are replaced by an atom having an atomic mass or mass number different from the atomic mass or mass number typically found in nature. Examples of radionuclides that may be incorporated include $^{2}H$ (also written as "D" for deuterium), $^{3}H$ (also written as "T" for tritium), $^{11}C$, $^{13}C$, $^{14}C$, $^{15}O$, $^{17}O$, $^{18}O$, $^{13}N$, $^{15}N$, $^{18}F$, $^{36}Cl$, $^{123}I$, $^{25}I$, $^{32}P$, $^{35}S$ and the like. The radionuclide that is used will depend on the specific application of that radio-labelled derivative. For example, for in-vitro competition assays, $^{3}H$ or $^{14}C$ are often useful. For radio-imaging applications, $^{11}C$ or $^{18}F$ are often useful. In some embodiments, the radionuclide is $^{3}H$. In some embodiments, the radionuclide is $^{14}C$. In some embodiments, the radionuclide is $^{11}C$. And in some embodiments, the radionuclide is $^{18}F$.

Isotopically-labelled compounds can generally be prepared by conventional techniques known to those skilled in the art or by processes analogous to those described using an appropriate isotopically-labelled reagent in place of the non-labelled reagent previously employed.

The selective replacement of hydrogen with deuterium in a compound may modulate the metabolism of the compound, the PK/PD properties of the compound and/or the toxicity of the compound. For example, deuteration may increase the half-life or reduce the clearance of the compound in-vivo. Deuteration may also inhibit the formation of toxic metabolites, thereby improving safety and tolerability. It is to be understood that the invention encompasses deuterated derivatives of compounds of formula (I). As used herein, the term deuterated derivative refers to compounds of the invention where in a particular position at least one hydrogen atom is replaced by deuterium. For example, one or more hydrogen atoms in a $C_{1-4}$-alkyl group may be replaced by deuterium to form a deuterated $C_{1-4}$-alkyl group.

Certain compounds of the invention may exist in solvated as well as unsolvated forms such as, for example, hydrated forms. It is to be understood that the invention encompasses all such solvated forms that possess MASTL inhibitory activity.

It is also to be understood that certain compounds of the invention may exhibit poly-morphism, and that the invention encompasses all such forms that possess MASTL inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

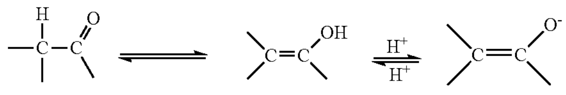

keto enol enolate

Amino substituted triazines can exhibit hindered rotation about the SP2 carbon-N bond giving rise to diastereomers (blocked rotamers) (Amm et al. (1998), Mag. Reson. Chem. 36 587-596). Reference to a compound of the invention encompasses all such blocked-rotamer forms of the compound.

The in-vivo effects of a compound of the invention may be exerted in part by one or more metabolites that are formed within the human or animal body after administration of a compound of the invention.

It is further to be understood that a suitable pharmaceutically-acceptable pro-drug of a compound of the formula (I) also forms an aspect of the present invention. Accordingly, the compounds of the invention encompass pro-drug forms of the compounds and the compounds of the invention may be administered in the form of a pro-drug (i.e. a compound that is broken down in the human or animal body to release a compound of the invention). A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in-vivo-cleavable ester derivatives that may be formed at a carboxy group or a hydroxy group in a compound of the invention and in-vivo-cleavable amide derivatives that may be formed at a carboxy group or an amino group in a compound of the invention.

Accordingly, the present invention includes those compounds of the invention as defined herein when made available by organic synthesis and when made available within the human or animal body by way of cleavage of a pro-drug thereof. Accordingly, the present invention includes those compounds of the formula (I) that are produced by organic synthetic means and also such compounds that are produced in the human or animal body by way of metabolism of a precursor compound, that is a compound of the formula (I) may be a synthetically-produced compound or a metabolically-produced compound.

A suitable pharmaceutically-acceptable pro-drug of a compound of the invention is one that is based on reasonable medical judgement as being suitable for administration to the human or animal body without undesirable pharmacological activities and without undue toxicity.

Various forms of pro-drug have been described, for example in the following documents:

a) Methods in Enzymology, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988);
f) N. Kakeya, et al., Chem. Pharm. Bull., 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the formula I that possesses a carboxy group is, for example, an in-vivo-cleavable ester thereof. An in-vivo-cleavable ester of a compound of the invention containing a carboxy group is, for example, a pharmaceutically-acceptable ester which is cleaved in the human or animal body to produce the parent acid. Suitable pharmaceutically-acceptable esters for carboxy include $C_{1-6}$ alkyl esters such as methyl, ethyl and tert-butyl, $C_{1-6}$ alkoxymethyl esters such as methoxymethyl esters, $C_{1-6}$ alkanoyloxymethyl esters such as pivaloyloxymethyl esters, 3-phthalidyl esters, $C_3$ cycloalkylcarbonyloxy-$C_{1-6}$ alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$ alkoxycarbonyloxy-$C_{1-6}$ alkyl esters such as methoxycarbonyloxymethyl and 1-methoxycarbonyloxyethyl esters. A suitable pharmaceutically-acceptable prodrug of a compound of the invention that possesses a hydroxy group is, for example, an in-vivo-cleavable ester or ether thereof. An in-vivo-cleavable ester or ether of a compound of the invention containing a hydroxy group is, for example, a pharmaceutically-acceptable ester or ether which is cleaved in the human or animal body to produce the parent hydroxy compound. Suitable pharmaceutically-acceptable ester forming groups for a hydroxy group include inorganic esters such as phosphate esters (including phosphoramidic cyclic esters). Further suitable pharmaceutically-acceptable ester forming groups for a hydroxy group include $C_{1-10}$ alkanoyl groups such as acetyl, benzoyl, phenylacetyl and substituted benzoyl and phenylacetyl groups, $C_{1-10}$ alkoxycarbonyl groups such as ethoxycarbonyl, N,N—$(C_{1-6}$ alkyl$)_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-$(C_{1-4}$ alkyl)piperazin-1-ylmethyl. Suitable pharmaceutically-acceptable ether forming groups for a hydroxy group include α-acyloxyalkyl groups such as acetoxymethyl and pivaloyloxymethyl groups.

A suitable pharmaceutically-acceptable pro-drug of a compound of the invention that possesses a carboxy group is, for example, an in-vivo-cleavable amide thereof, for example an amide formed with an amine such as ammonia, a $C_4$ alkylamine such as methylamine, a $(C_{1-4}$ alkyl$)_2$amine such as dimethylamine, N-ethyl-N-methylamine or diethylamine, a $C_{1-4}$ alkoxy-$C_{2-4}$ alkylamine such as 2-methoxyethylamine, a phenyl-$C_{1-4}$ alkylamine such as benzylamine and amino acids such as glycine or an ester thereof.

A suitable pharmaceutically-acceptable pro-drug of a compound of the invention that possesses an amino group is, for example, an in-vivo-cleavable amide or carbamate derivative thereof. Suitable pharmaceutically-acceptable amides from an amino group include, for example an amide formed with $C_{1-10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-$(C_{1-4}$ alkyl)piperazin-1-ylmethyl. Suitable pharmaceutically-acceptable carbamates from an amino group include, for example acyloxyalkoxycarbonyl and benzyloxycarbonyl groups.

Compounds

In some embodiments the compound of formula (I) is a compound of the formula (II), or a pharmaceutically acceptable salt thereof:

(II)

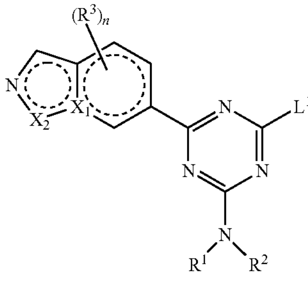

In some embodiments the compound of formula (I) is a compound of the formula (III), or a pharmaceutically acceptable salt thereof:

(III)

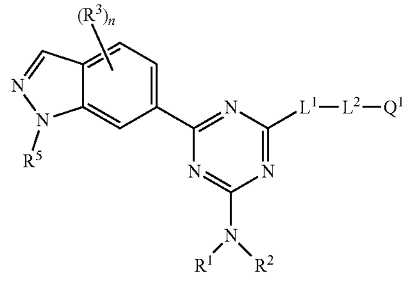

In some embodiments the compound of formula (I) is a compound of the formula (IV), or a pharmaceutically acceptable salt thereof:

(IV)

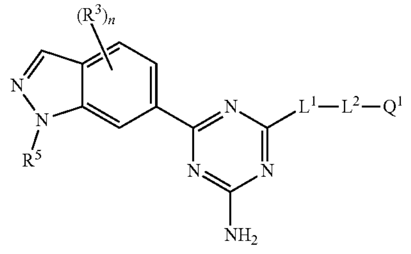

In some embodiments the compound of formula (I) is a compound of the formula (V), or a pharmaceutically acceptable salt thereof:

(V)

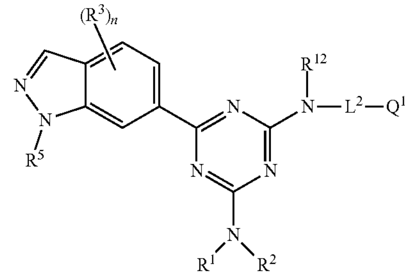

In some embodiments the compound of formula (I) is a compound of the formula (VI), or a pharmaceutically acceptable salt thereof:

(VI)

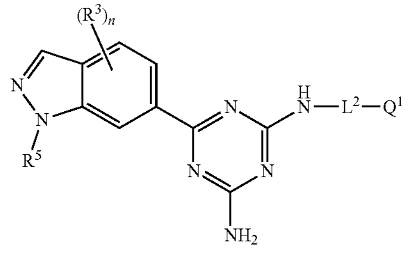

In some embodiments the compound of formula (I) is a compound of the formula (VII), or a pharmaceutically acceptable salt thereof:

(VII)

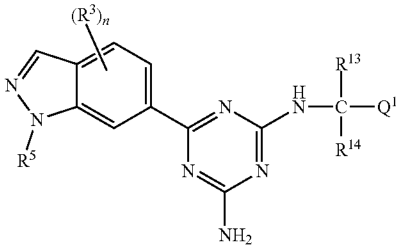

In some embodiments the compound of formula (I) is a compound of the formula (VIII), or a pharmaceutically acceptable salt thereof:

(VIII)

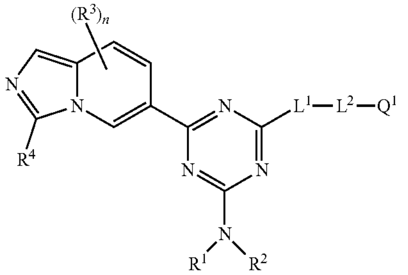

In some embodiments the compound of formula (I) is a compound of the formula (IX), or a pharmaceutically acceptable salt thereof:

(IX)

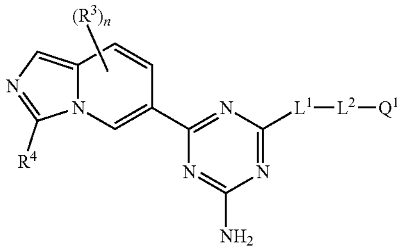

In some embodiments the compound of formula (I) is a compound of the formula (X), or a pharmaceutically acceptable salt thereof:

(X)

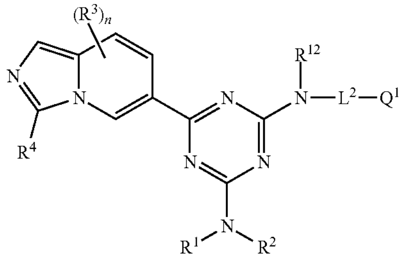

In some embodiments the compound of formula (I) is a compound of the formula (XI), or a pharmaceutically acceptable salt thereof:

(XI)

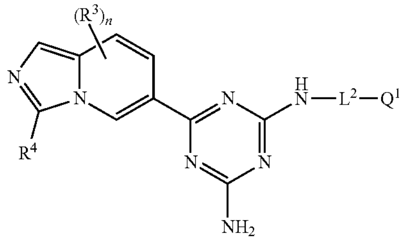

In some embodiments the compound of formula (I) is a compound of the formula (XII), or a pharmaceutically acceptable salt thereof:

(XII)

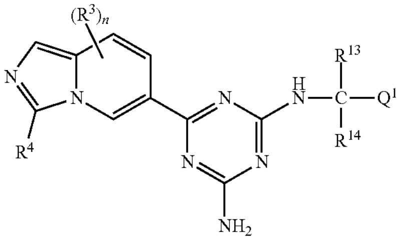

In some embodiments the compound of formula (I) is a compound of the formula (XIII), or a pharmaceutically acceptable salt thereof:

(XIII)

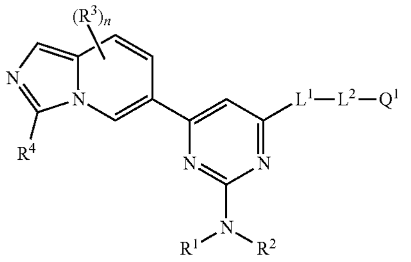

In some embodiments the compound of formula (I) is a compound of the formula (XIV), or a pharmaceutically acceptable salt thereof:

(XIV)

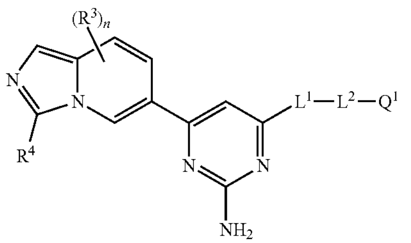

In another embodiment there is provided a compound selected from any one of the Examples herein, or a pharmaceutically acceptable salt, or prodrug thereof.

Particular compounds of the invention are those which have an $IC_{50}$ of less than or equal to 2 mM, 1.5 mM, 1 mM, 750 nM, 500 nM, 250 nM, 200 nM, 150 nM, 100 nM, 90 nM, 80 nM, 70 nM, 60 nM, 50 mM, 40 nM, 30 mM, 20 nM, 15 nM, 10 nM, 8 nM, 5 nM, 4 nM, 3 nM, 2 nM or 1 nM when tested in the MASTL activity assay described in the Examples.

In some embodiments compounds of the invention include, for example, compounds of formulae (I), (II), (III), (IV), (V), (VI), (VII), (VIII), (IX), X), (XI), (XII), (XIII), or (XIV) or a pharmaceutically acceptable salt thereof, wherein, unless otherwise stated, each of $R^1$, $R^2$, $R^3$, $L^1$, $L^2$ and $Q^1$ has any of the meanings defined hereinbefore or in any of paragraphs (1) to (96) hereinafter:

1. $R^1$ is H.

2. Both $R^1$ and $R^2$ are H.

3. $R^1$ is H and $R^2$ is $C_{1-6}$ alkyl, optionally wherein said $C_{1-6}$ alkyl is substituted by one or more $R^6$ substituents, as defined above.

4. $R^1$ is H and $R^2$ is $C_{1-6}$ alkyl, optionally wherein said $C_{1-6}$ alkyl is substituted by one or more $R^6$ substituents, wherein $R^6$ is selected from halo, $=O$, $-OR^{A3}$, $-SR^{A4}$, $C(O)R^{A3}$, $-OC(O)R^{A3}$, $-C(O)OR^{A3}$, $-S(O)_2R^{A4}$ and $-NR^{A3}R^{B3}$.

5. $R^1$ is H and $R^2$ is $C_{1-6}$ alkyl, preferably wherein $R^2$ is methyl.

6. $R^1$ is H and $R^2$ is $Q^3$-$L^3$, wherein:

$L^3$ is a bond or $C_{1-6}$ alkylene, preferably wherein $L^3$ is methylene; and $Q^3$ is as defined above.

7. $R^1$ is H and $R^2$ is $Q^3$-$L^3$, wherein:

$L^3$ is a bond or $C_{1-6}$ alkylene, preferably wherein $L^3$ is methylene; and $Q^3$ is $C_{3-6}$ cycloalkyl or 3- to 6-membered heterocyclyl, optionally substituted by one or more $R^7$.

8. $R^1$ is H and $R^2$ is $Q^3$-$L^3$, wherein:

$L^3$ is a bond or $C_{1-6}$ alkylene, preferably wherein $L^3$ is methylene; and $Q^3$ is a 3- to 6-membered heterocyclyl, optionally substituted by one or more $R^7$.

9. $R^1$ is H and $R^2$ is $Q^3$-$L^3$, wherein:

$L^3$ is a bond or $C_{1-6}$ alkylene, preferably wherein $L^3$ is methylene; and $Q^3$ is $C_{6-12}$ aryl or a 5- or 6-membered heteroaryl, preferably wherein $Q^3$ is $C_6$ aryl, optionally substituted by one or more $R^1$.

10. $R^1$ is H and $R^2$ is $Q^3$-$L^3$, wherein:

$L^3$ is methylene; and $Q^3$ is $C_6$ aryl, optionally substituted by one or more $R^1$.

11. $R^1$ and $R^2$ are as defined in any one of paragraphs 6-8 above, wherein each $R^7$ is independently selected from halo, $=O$, $-CN$, $-NO_2$, $C_{1-4}$ alkyl, $C_{1-4}$ haloalkyl, $-OR^{A3}$, and $-C(O)R^{A3}$, wherein $R^{A3}$ is as defined above.

12. $R^1$ and $R^2$ are as defined in any one of paragraphs 6-8 above, wherein each $R^7$ is halo (e.g. F).

13. $R^1$ and $R^2$ are as defined in any one of paragraphs 6, 9 or 10 above, wherein each $R^1$ is independently selected from halo, $=O$, $-CN$, $-NO_2$, $C_{1-4}$ alkyl, $C_{1-4}$ haloalkyl, $-OR^{A4}$, and $-C(O)R^{A4}$, wherein $R^{A4}$ is as defined above.

14. $R^1$ and $R^2$ are as defined in paragraph 9 or 10 above, wherein each $R^1$ is halo (e.g. F).

15. n is 0.

16. n is 1.

17. Each $R^3$ is halo, optionally wherein each $R^3$ is independently selected from fluoro and chloro.

18. Each $R^3$ is $C_{1-6}$ alkyl, optionally wherein each $R^3$ is methyl.

19. Each $R^3$ is amino.

20. n is 1 and $R^3$ is fluoro.

21. In the compound of formulas III, IV, V, VI, and VII, $R^3$ is attached at the 3-, 4- and/or 7-position of the indazole ring.

22. In the compound of formulas VIII, IX, X, XI, XII, XIII and XIV, the group of the formula:

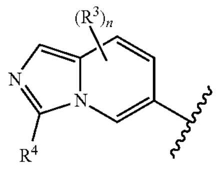

is selected from any of the following structures:

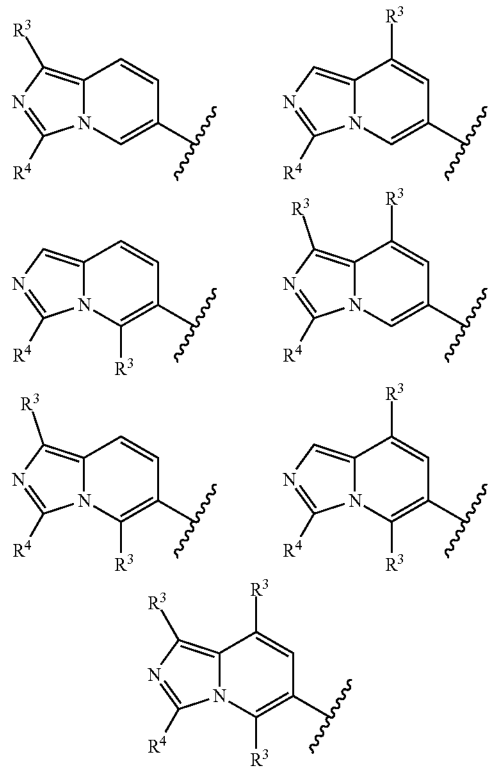

23. $R^4$ or $R^5$ is H.

24. $R^4$ or $R^5$ is $C_{1-6}$ alkyl, optionally methyl.

25. $R^4$ is CN.

26. $R^5$ is $Q^4$-$L^4$- as defined above.

27. $R^5$ is $Q^4$-$L^4$- wherein $L^4$ is a bond and $Q^4$ is selected from: $C_{3-6}$ cycloalkyl; 3- to 6-membered heterocyclyl; $C_{6-12}$ aryl; and 5 or 6 membered heteroaryl.

28. $R^5$ is $Q^4$-$L^4$- wherein $L^4$ is a bond and $Q^4$ is a 5- or 6-membered heterocyclyl containing an oxygen atom.

29. $R^5$ is $Q^4$-$L^4$- wherein $L^4$ is a bond and $Q^4$ is selected from:

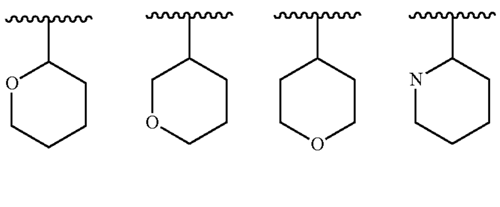

-continued

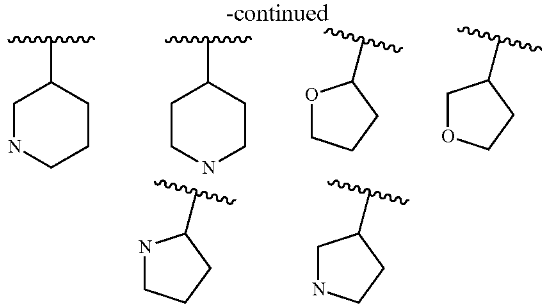

30. $R^5$ is $Q^4$-$L^4$- wherein $L^4$ is $C_{1-4}$ alkylene and $Q^4$ is selected from: $C_{3-6}$ cycloalkyl; 3- to 6-membered heterocyclyl; $C_{6-12}$ aryl; and 5 or 6 membered heteroaryl.

31. In any of the compounds of formulas IV, VI, VII, IX, XI, XII, XIII and XIV, $R^4$ or $R^5$ is H or $C_{1-6}$ alkyl, optionally wherein $R^4$ or $R^5$ is methyl, and n is 0.

32. In any of the compounds of formulas IV, VI, VII, IX, XI, XII, XIII and XIV, $R^4$ or $R^5$ is H or $C_{1-6}$ alkyl, optionally wherein $R^4$ or $R^5$ is methyl, n is 1 and $R^3$ is halo, preferably fluoro.

33. $R^1$ is H and $R^2$ is $C_{1-6}$ alkyl, preferably $R^2$ is methyl, $R^4$ or $R^5$ is H and n is 0.

34. $R^1$ and $R^2$ are as defined by any of paragraphs 3-8 above, $R^4$ or $R^5$ is H and n is 0.

35. $R^1$ and $R^2$ are as defined by any of paragraphs 3-9 above, $R^4$ or $R^5$ is H, n is 1 and $R^3$ is halo, preferably fluoro.

36. $R^1$ and $R^2$ are as defined by any of paragraphs 3-9 above, $R^4$ or $R^5$ is H or methyl, n is 0 or 1 and $R^3$ is halo, preferably fluoro.

37. $L^1$ is 0 or S. Preferably $L^1$ is O.

38. $L^1$ is a bond.

39. $L^1$ is $NR^{12}$, wherein $R^{12}$ is selected from $C_{3-6}$ cycloalkyl, $C_{1-4}$ alkyl and —$C_{1-4}$ alkyl-$OR^{45}$, for example $R^{12}$ is selected from H, $C_{3-4}$ cycloalkyl and $C_{1-3}$ alkyl (e.g. methyl or ethyl).

40. $L^1$ is $NR^{12}$, wherein $R^{12}$ is $C_{3-6}$ cycloalkyl, for example $C_3$ cycloalkyl.

41. $L^1$ is NH.

42. $L^1$ is $NR^{12}$ wherein $R^{12}$ is —$CH_3$.

43. $L^1$ is $Q^5$ wherein $Q^5$ is as defined above.

44. $L^1$ is $Q^5$ wherein $Q^5$ is a 4- to 6-membered heterocyclylene containing an N atom and one or two additional heteroatoms which are independently selected from N, O and S. Optionally, $Q^5$ is bonded to the H ring in formula (I) by the ring nitrogen atom in $Q^5$.

45. $L^1$ is $Q^5$ wherein $Q^5$ is a 4- to 6-membered heterocyclylene containing 1 ring nitrogen atom and one O atom, wherein $Q^5$ is bonded to the H ring in formula (I) by the ring nitrogen atom in $Q^5$.

46. $L^2$ is a bond.

47. $L^2$ is —$[CR^{13}R^{14}]$ as defined above.

48. $L^2$ is —$[CR^{13}R^{14}]_p$, wherein $R^{13}$ and $R^{14}$ are each independently selected from: H, and $C_{1-4}$ alkyl (e.g. methyl, $CH_3$), 49. $L^2$ is —$[CR^{13}R^{14}]_p$, wherein p is an integer from 1 to 2, and $R^{13}$ and $R^{14}$ are each independently selected from: H, $C_{1-4}$ alkyl, $C_{1-4}$ haloalkyl, OH, COOH, $C(O)NR^{X1}R^{X2}$, and $C_{3-6}$ cycloalkyl, or an $R^{13}$ and an $R^{14}$ attached to the same carbon atom in $L^2$ together form a $C_{3-6}$ cycloalkyl. In some embodiments, said $C_{1-4}$ alkyl is optionally substituted by OH, O—$C_{1-4}$ alkyl, 3- to 6-membered heterocyclyl, 5- to 10-membered heteroaryl, or $C_{6-10}$ aryl. In some embodiments, said $C_{6-10}$ aryl is optionally substituted by halogen or $C_{1-6}$ haloalkyl.

50. $L^2$ is —$[CR^{13}R^{14}]_p$, wherein p is 1, and $R^{13}$ and $R^{14}$ are both H or $C_{1-4}$ alkyl. For example, both $R^{13}$ and $R^{14}$ may be methyl ($CH_3$).

51. $L^2$ is —$C(CH_3)_2CH_2$— or —$CH_2C(CH_3)_2$— or —$CH_2CH_2$—.

52. $L^2$ is —$[CR^{13}R^{14}]_p$, wherein $R^{13}$ and an $R^{14}$ are attached to the same carbon atom in $L^2$ together form a $C_{3-6}$ cycloalkyl or 3-6-membered heterocyclyl. In some embodiments, $R^{13}$ and an $R^{14}$ are attached to the same carbon atom in $L^2$ and together form a $C_3$ cycloalkyl (i.e. cyclopropyl) or a $C_4$ cycloalkyl (i.e. cyclobutyl). In some embodiments, $R^{13}$ and an $R^{14}$ may be attached to the same carbon atom in $L^2$ and together form a 3-6-membered heterocyclyl, such as an oxiranyl or oxetanyl, tetrahydrofuranyl or tetrahydropyranyl group. In such embodiments, p may be 1.

53. $R^{X1}$ and $R^{X2}$ are independently selected from: H, $C_{1-4}$alkyl, and 5- to 10-membered heteroaryl, or an $R^{X1}$ and an $R^{X2}$ attached to the same nitrogen atom together to form a 3- to 6-membered heterocyclyl. In some embodiments, said $C_{1-4}$alkyl is optionally substituted by OH or 3- to 6-membered heterocyclyl.

54. Neither $L^1$ nor $L^2$ are a bond.

55. -$L^1$-$L^2$- is selected from any of the following structures:

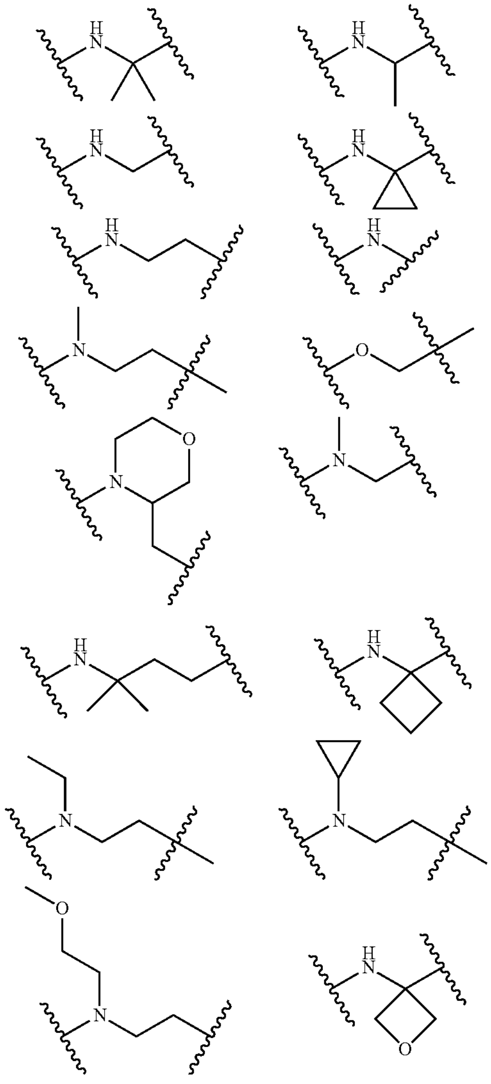

-continued

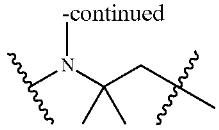

56. $Q^1$ is a 5- to 10-membered heteroaryl group, preferably a 5- or 6-membered heteroaryl group, wherein the heteroaryl group comprises one or two heteroatoms independently selected from O, N and S, optionally wherein the heteroaryl group is substituted by one or more $R^{16}$ as defined above.

57. $Q^1$ is a $C_{6-10}$aryl, preferably a $C_6$ aryl, optionally substituted by one or more $R^{16}$ as defined above.

58. $Q^1$ is a 8-, 9- or 10-membered bicyclic heteroaryl group comprising 1, 2 or 3 heteroatoms. The heteroatoms may be independently selected from O, N and S. In some embodiments, the bicyclic heteroaryl group comprises a $C_5$ or a $C_6$ aryl ring fused to a 5- or 6-membered heterocycle. In certain embodiments, the 5- or 6-membered heterocycle comprises a single heteroatom, such as an oxygen atom. Optionally the bicyclic heteroaryl group is substituted by one or more $R^{16}$ as defined above.

59. $Q^1$ is selected from: $C_{3-12}$cycloalkyl, $C_{3-12}$cycloalkenyl, 3- to 12-membered heterocyclyl, $C_{6-10}$ aryl, 5- to 10-membered heteroaryl, COOH, $C(O)NR^{Z1}R^{Z2}$, and C(O)O—$C_{1-6}$alkyl. Each $R^{Z1}$ and $R^{Z2}$ is each independently selected from; H, $C_{1-6}$ alkyl, $C_{3-6}$ cycloalkyl, $C_{6-10}$aryl, and 5- to 10-membered heteroaryl; or an $R^{Z1}$ and an $R^{Z2}$ attached to the same nitrogen atom together to form a 3-6-membered heterocyclyl. In some embodiments, said $C_{1-6}$ alkyl is optionally substituted by OH.

60. $Q^1$ is as defined by paragraphs 56, 57, 58 or 59, wherein the heteroaryl or aryl group is substituted by one, two or three $R^{16}$ and $R^{16}$ is independently selected from halo (preferably chloro and/or fluoro), $C_{1-6}$alkyl, $C_{1-6}$haloalkyl.

61. $Q^1$ is as defined by any one of paragraphs 56-60 and is substituted by one or more $R^{16}$, wherein least one $R^{16}$ is $C_{1-6}$alkyl, such as methyl, ethyl, propyl (e.g. isopropyl) or butyl (e.g. t-butyl). Optionally the $C_{1-6}$ alkyl is substituted by one or more $R^{21}$ groups as defined above. In some embodiments, the $C_{1-6}$ alkyl is substituted by one or more $R^{21}$, wherein at least one $R^{21}$ is $—NR^{A3}R^{B3}$. Preferably, $—NR^{A3}R^{B3}$ forms a 5- or 6-membered heterocyclyl group. In some embodiments, the $C_{1-6}$ alkyl is substituted by one or more $—OR^{20}$ groups, wherein $R^{20}$ is H or $C_{1-6}$ alkyl, such as methyl, ethyl, or propyl (e.g. isopropyl), preferably methyl.

62. $Q^1$ is as defined by any one of paragraphs 56-61 and is substituted by one or more $R^{16}$, wherein least one $R^{16}$ is halo or $C_{1-6}$haloalkyl. For example, $Q^1$ may substituted by one, two or three $R^{16}$. In certain embodiments, each $R^{16}$ is independently selected from chloro, fluoro, $CHF_2$, $CF_3$, Chloroform, $CCl_3$, $CH_2CF_3$, and $CH_2CCl_3$. In some embodiments, $Q^1$ is substituted by one, two or three $R^{16}$, wherein each $R^{16}$ is independently selected from fluoro or chloro.

63. $Q^1$ is as defined by any one of paragraphs 56-62 and is substituted by two or more $R^{16}$, wherein least one $R^{16}$ is halo (e.g. fluoro or chloro) and at least one $R^{16}$ is $C_{1-6}$ alkyl. In some embodiments, the $C_{1-6}$ alkyl is substituted by one or more $—OR^{20}$ groups, wherein $R^{20}$ is H or $C_{1-6}$ alkyl, such as methyl, ethyl, or propyl (e.g. isopropyl), preferably methyl.

64. $Q^1$ is a 3- to 12-membered heterocyclyl group, preferably a 5- to 6-membered heterocyclyl group. Optionally, the heterocyclyl group is substituted by one or more $R^{15}$, as defined above. In some embodiments, $R^{15}$ is a $C_{1-6}$ alkyl group.

65. $Q^1$ is a $C_{3-12}$cycloalkyl, $C_{3-12}$cycloalkenyl and 3- to 12-membered heterocyclyl which is optionally substituted by one or more $R^{15}$, wherein each $R^{15}$ is independently selected from halo, $C_{1-6}$ alkyl, $C_{1-6}$haloalkyl, and $OR^{17}$, optionally wherein the $C_{1-6}$ alkyl is substituted by one or more $R^{18}$, wherein each $R^{17}$ is independently selected from: H and $C_{1-6}$ alkyl;

wherein each $R^{18}$ is independently selected from: halo, $—NR^{A3}R^{B3}$ and $OR^{A3}$;

wherein each $R^{A3}$ is independently selected from H and $C_{1-4}$ alkyl, or $—NR^{A3}R^{B3}$ may form a 4- to 6-membered heterocyclyl.

66. $Q^1$ is a $C_{6-10}$ aryl or a 5- to 10-membered heteroaryl which is optionally substituted by one or more $R^{16}$, wherein each $R^{16}$ is independently selected from halo, $C_{1-6}$ alkyl, $C_{1-6}$haloalkyl, and $OR^{20}$, optionally wherein the $C_{1-6}$ alkyl is substituted by one or more $R^{21}$, wherein each $R^{20}$ is independently selected from: H and $C_{1-6}$ alkyl;

wherein each $R^{21}$ is independently selected from: halo, $—NR^{A3}R^{B3}$ and $OR^{A3}$;

wherein each $R^{A3}$ is independently selected from H and $C_{1-4}$ alkyl, or $—NR^{A3}R^{B3}$ may form a 4- to 6-membered heterocyclyl.

67. $Q^1$ is selected from:

a 5- to 10-membered heteroaryl, a $C_{6-10}$ aryl, a $C_{3-12}$ cycloalkyl or a 3- to 12-membered heterocyclyl, optionally wherein said 5- to 10-membered heteroaryl or $C_{6-10}$ aryl is substituted by one or more $R^{16}$, optionally wherein said $C_{3-12}$cycloalkyl or a 3- to 12-membered heterocyclyl is substituted by one or more $R^{15}$, wherein each $R^{15}$ or $R^{16}$ is independently selected from: halo (preferably F and/or Cl); $C_{1-6}$haloalkyl (preferably $CHF_2$, $CF_3$, $CH_2CF_3$, $CHCl_2$, $CCl_3$, $CH_2CCl_3$); methyl, ethyl, propyl (e.g. isopropyl), butyl (e.g. t-butyl), methoxy, methoxymethyl, methoxyethyl, and a $C_{1-4}$ alkyl substituted with a 5-membered heterocycle.

68. $Q^1$ is selected from the group consisting of pyrrolyl, imidazolyl, pyrazolyl, triazolyl, pyridinyl, pyrimidinyl, pyridazinyl, pyrazinyl, furyl, thiazolyl, thiophenyl, oxazolyl, isoxazolyl, and isothiazolyl.

69. $Q^1$ is pyrazolyl.

70. $Q^1$ is pyridinyl.

71. $Q^1$ is triazolyl.

72. $Q^1$ is a $C_{6-10}$ aryl group. In some embodiments, $Q^1$ is a phenyl group.

73. $Q^1$ is an aryl or a heteroaryl as defined by any of paragraphs 68 to 72, wherein the aryl or heteroaryl is substituted by one or more $R^{16}$, wherein each $R^{16}$ is independently selected from halo, $C_{1-6}$ alkyl, $C_{1-6}$ haloalkyl, and $OR^{20}$, optionally wherein the $C_{1-6}$ alkyl is substituted by one or more $R^{21}$, wherein each $R^{20}$ is independently selected from: H and $C_{1-6}$ alkyl;

wherein each $R^{21}$ is independently selected from: halo, $—NR^{A3}R^{B3}$ and $OR^{A3}$;

wherein each $R^{A3}$ is independently selected from H and $C_{1-4}$ alkyl, or $—NR^{A3}R^{B3}$ may form a 4- to 6-membered heterocyclyl.

74. $Q^1$ is as defined in any of paragraphs 56 to 73, wherein $Q^1$ is bonded to $-L^1-L^2-$ by a ring carbon in $Q^1$ 75. $Q^1$ is
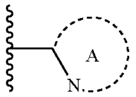
wherein ring A is a 5- or 6-membered heteroaryl comprising a ring nitrogen in the ortho-position relative to the bond to -L1-L2- and optionally 1 or 2 further heteroatoms independently selected from O, S and N, optionally wherein the heteroaryl is substituted by one or more $R^{16}$. Examples of $Q^1$ include
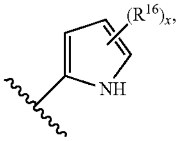, 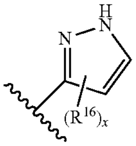, 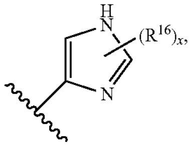, 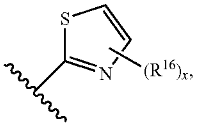, 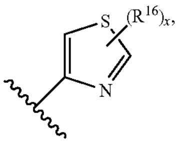, 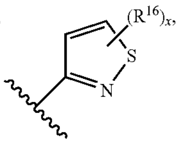, 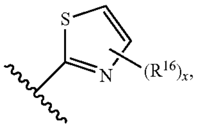, 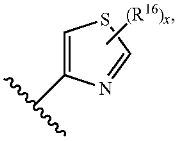, 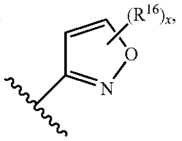, 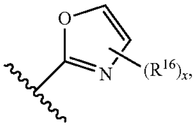, 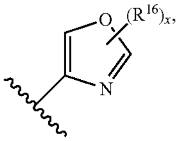, 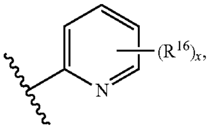, 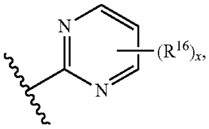, 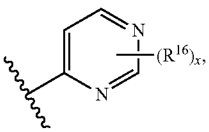, 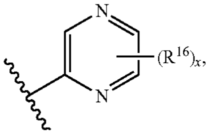, and
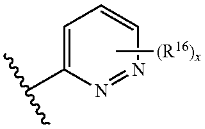
76. $Q^1$ has a structure selected from:
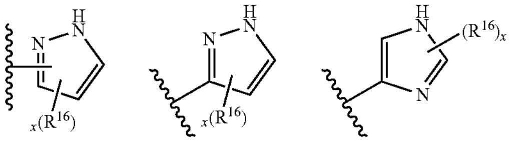
-continued
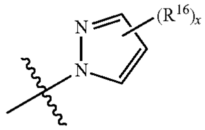
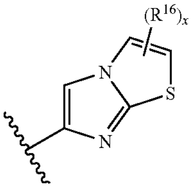
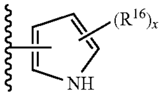
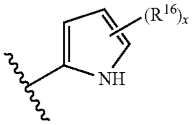
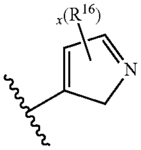
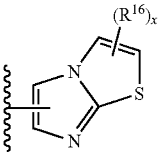
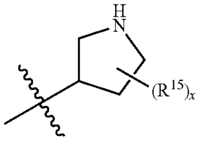
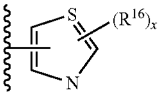
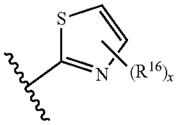
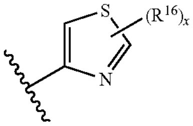
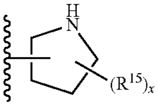
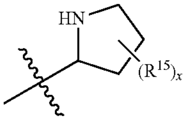
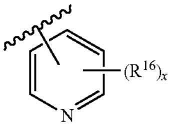
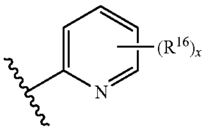
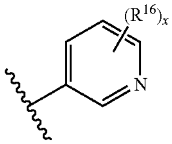
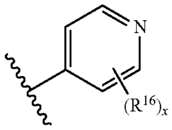
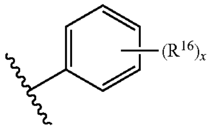
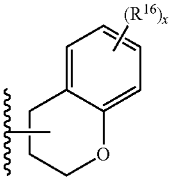
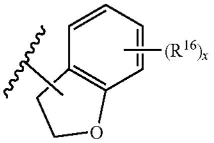
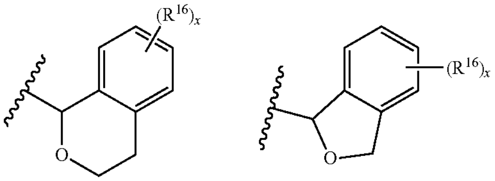
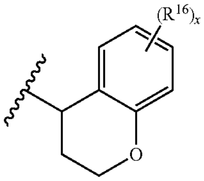
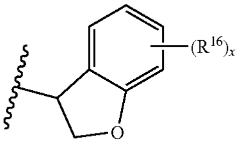

-continued

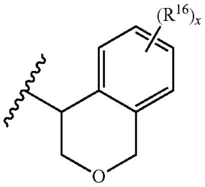
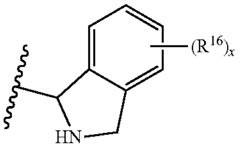
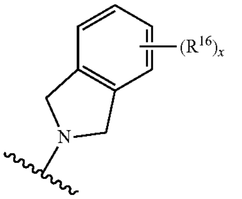
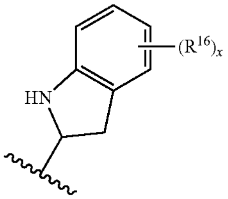

wherein $R^{15}$ and $R^{16}$ is as defined above, and x is 0, 1, 2 or 3. Optionally, $R^{15}$ or $R^{16}$ is independently selected from halo (preferably chloro and/or fluoro), $C_{1-6}$alkyl, $C_{1-6}$ haloalkyl.

77. $Q^1$ is defined by paragraph 75 or 76, wherein each $R^{16}$ is independently selected from halo, $C_{1-6}$ alkyl, $C_{1-6}$ haloalkyl, and $OR^{20}$, optionally wherein the $C_{1-6}$ alkyl is substituted by one or more $R^{21}$, wherein each $R^{20}$ is independently selected from: H and $C_{1-6}$ alkyl;

wherein each $R^{21}$ is independently selected from: halo, —$NR^{A3}R^{B3}$ and $OR^{A3}$;

wherein each $R^{A3}$ is independently selected from H and $C_{1-4}$ alkyl, or —$NR^{A3}R^{B3}$ may form a 4- to 6-membered heterocyclyl.

78. $Q^1$ is defined by paragraph 76, wherein each $R^{15}$ is independently selected from halo, $C_{1-6}$ alkyl, $C_{1-6}$haloalkyl, and $OR^{17}$, optionally wherein the $C_{1-6}$ alkyl is substituted by one or more $R^{11}$, wherein each $R^{17}$ is independently selected from: H and $C_{1-6}$ alkyl;

wherein each $R^{11}$ is independently selected from: halo, —$NR^{A3}R^{B3}$ and $OR^{A3}$;

wherein each $R^{A3}$ is independently selected from H and $C_{1-4}$ alkyl, or —$NR^{A3}R^{B3}$ may form a 4- to 6-membered heterocyclyl.

79. $Q^1$ has a structure selected from:

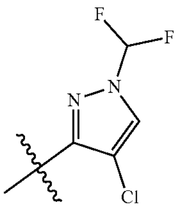
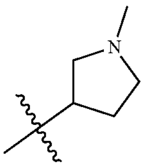
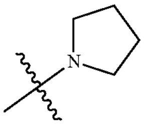
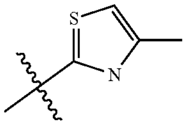
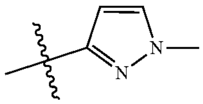

-continued

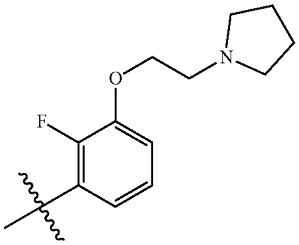
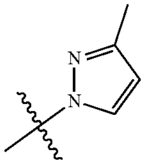
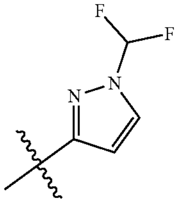
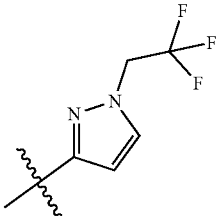
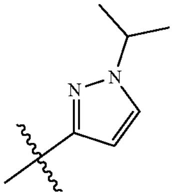
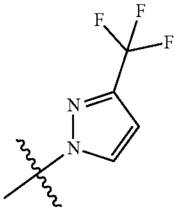
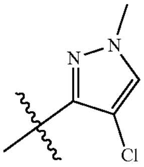
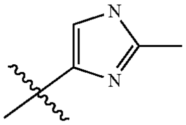
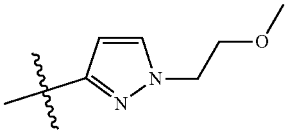
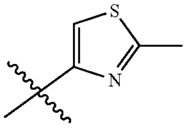
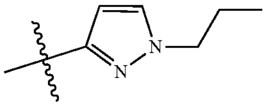
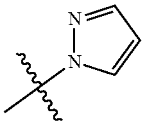
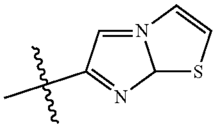
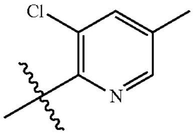
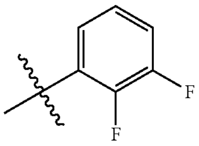
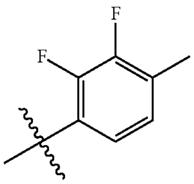
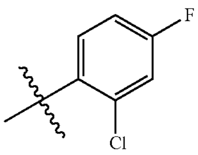
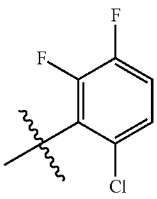
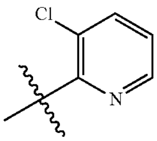
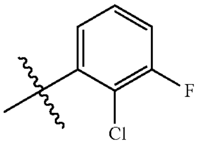

-continued

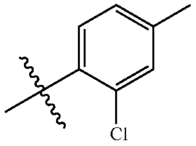
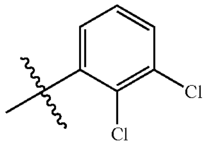
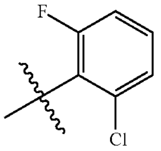
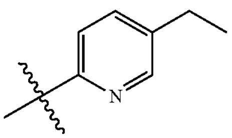
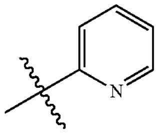
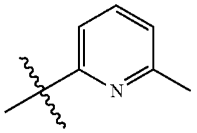
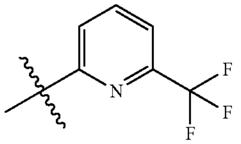
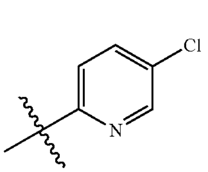
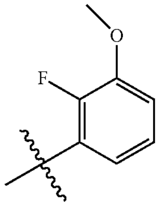
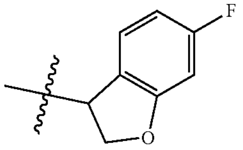
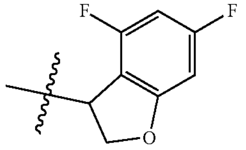
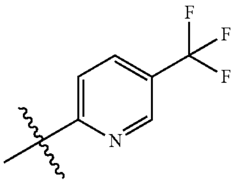
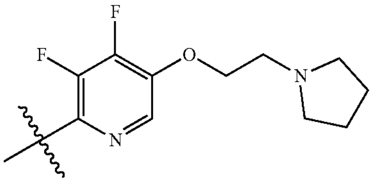
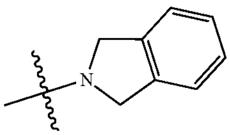
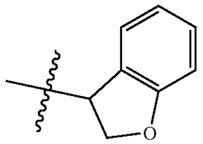
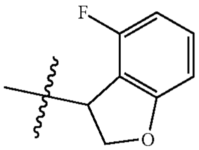
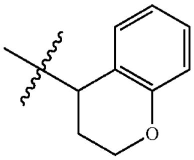
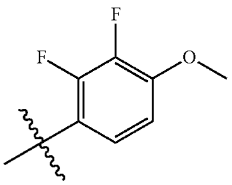
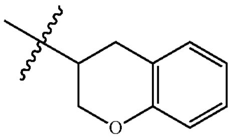

-continued

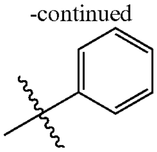

80. $L^1$ is O;

$L^2$ is as defined by any of paragraphs 44 to 53; and $Q^1$ as defined by any one of paragraphs 56 to 79. In some embodiments $Q^1$ is any of the structures shown in paragraph 79.

81. $L^1$ is $Q^5$ wherein $Q^5$ is a 4- to 6-membered heterocyclene containing 1 ring nitrogen atom and one O atom, wherein $Q^5$ is bonded to the H ring in formula (I) by the ring nitrogen atom in $Q^5$;

$L^2$ is as defined by any one of paragraphs 44 to 53; and $Q^1$ is as defined by any one of paragraphs 56 to 79. In some embodiments $Q^1$ is any of the structures shown in paragraph 79.

82. $L^1$ is $Q^5$ wherein $Q^5$ is a 4- to 6-membered heterocyclene containing 1 ring nitrogen atom and one O atom, wherein $Q^5$ is bonded to the H ring in formula (I) by the ring nitrogen atom in $Q^5$;

$L^2$ is $-[CR^{13}R^{14}]_p$, wherein p is 1, and $R^{13}$ and $R^{14}$ are both H; and $Q^1$ is as defined by any one of paragraphs 56 to 79; preferably $Q^1$ is any of the structures shown in paragraph 79.

83. $L^1$ is $NR^{12}$, wherein $R^{12}$ is methyl;

$L^2$ is as defined by any of paragraphs 44 to 53; and $Q^1$ as defined by any one of paragraphs 56 to 79. In some embodiments $Q^1$ is any of the structures shown in paragraph 79.

84. $L^1$ is $NR^{12}$, wherein $R^{12}$ is $C_{1-4}$ alkyl (e.g. methyl or ethyl);

$L^2$ is $-[CR^{13}R^{14}]_p$, wherein p is 1, and each $R^{13}$ and $R^{14}$ is H; and $Q^1$ is as defined by any one of paragraphs 56 to 79; preferably $Q^1$ is any of the structures shown in paragraph 79.

85. $L^1$ is $NR^{12}$, wherein $R^{12}$ is $C_{1-4}$ alkyl (e.g. methyl or ethyl);

$L^2$ is $-[CR^{13}R^{14}]_p$, wherein p is 2, and each $R^{13}$ and $R^{14}$ is H; and $Q^1$ is as defined by any one of paragraphs 56 to 9; preferably $Q^1$ is any of the structures shown in paragraph 79.

86. $L^1$ is $NR^{12}$, wherein $R^{12}$ is $C_{3-6}$ cycloalkyl, e.g. $C_3$ cycloalkyl;

$L^2$ is $-[CR^{13}R^{14}]_p$, wherein p is 2, and each $R^{13}$ and $R^{14}$ is H; and $Q^1$ is as defined by any one of paragraphs 56 to 79; preferably $Q^1$ is any of the structures shown in paragraph 79.

87. In the compound of formula VII, XII or XIV:

$R^{13}$ and $R^{14}$ are each independently selected from: H, and $C_{1-4}$ alkyl; and $Q^1$ is as defined by any one of paragraphs 56 to 79.

88. In the compound of formula VII, XII or XIV:

$R^{13}$ and $R^{14}$ are both H or methyl; and $Q^1$ is any of the structures shown in paragraph 79.

89. In the compound of formula VII, XII or XIV:

$R^{13}$ and $R^{14}$ together form a $C_{3-6}$ cycloalkyl, preferably a cyclopropyl or cyclobutyl group; and $Q^1$ is as defined by any one of paragraphs 56 to 79; preferably $Q^1$ is any of the structures shown in paragraph 79.

90. $L^1$ is H;

$L^2$ is —$[CR^{13}R^{14}]_p$, wherein p is 2 and each $R^{13}$ and $R^{14}$ is H; and $Q^1$ is as defined by any one of paragraphs 56 to 79; preferably $Q^1$ is any of the structures shown in paragraph 79.

91. $L^1$ is H;

$L^2$ is —$[CR^{13}R^{14}]_p$, wherein p is 2, both $R^{13}$ are $CH_3$ and both $R^{14}$ are H;

$Q^1$ is as defined by any one of paragraphs 56 to 79; preferably $Q^1$ is any of the structures shown in paragraph 79.

92. $L^2$ is a bond and $Q^1$ is a 5- to 10-membered heteroaryl group. In some embodiments, $Q^1$ is a 8-, 9- or 10-membered bicyclic heteroaryl group comprising 1, 2 or 3 heteroatoms. In some embodiments, the bicyclic heteroaryl group comprises a $C_5$ or a $C_6$ aryl ring fused to a 5- or 6-membered heterocycle. In certain embodiments, the 5- or 6-membered heterocycle comprises a single heteroatom, such as an oxygen atom. Optionally the bicyclic heteroaryl group is substituted by one or more $R^{16}$.

93. $L^1$ and $L^2$ together have a structure selected from any of those shown in paragraph 54, and $Q^1$ is as defined by any one of paragraphs 56 to 79; preferably $Q^1$ is any of the structures shown in paragraph 77.

94. $Q^1$ is as defined in any one of paragraphs 56 to 79 wherein $L^1$ is O, $NR^{12}$ or S, $L^2$ is a bond, and $Q^1$ is bonded to $-L^1-L^2-$ by a ring carbon in $Q^1$.

95. $Q^1$ is as defined in any one of paragraphs 56 to 79 wherein $L^2$ is —$[CR^{13}R^{14}]_p$— and p is 2, 3 or 4, and wherein $Q^1$ is bonded to $-L^1-L^2-$ by a ring nitrogen. Optionally, $L^1$ is NH or $NR^{12}$, wherein $R^{12}$ is $C_{3-6}$ cycloalkyl (e.g. cyclopropyl) or $C_{1-4}$ alkyl (e.g. methyl or ethyl).

96. $-L^1-L^2-Q$ is selected from any of the following structures:

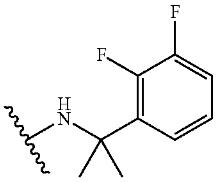
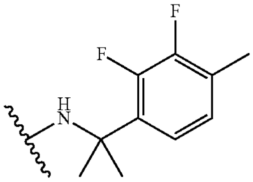
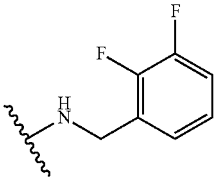
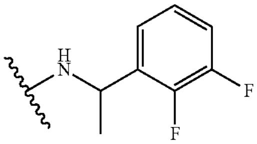
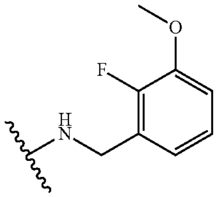
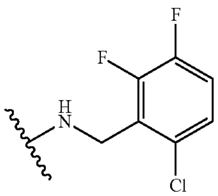

-continued

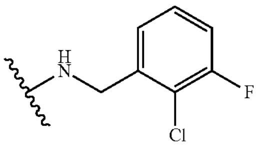
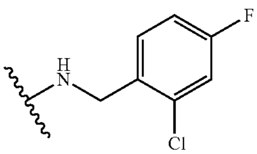
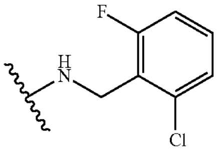
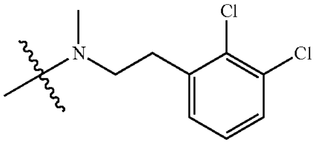
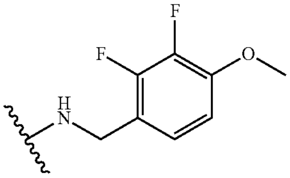
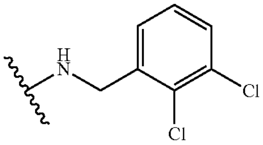
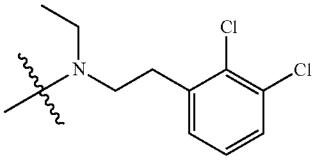
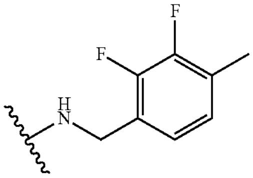
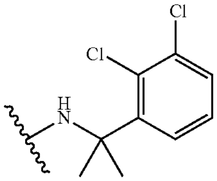
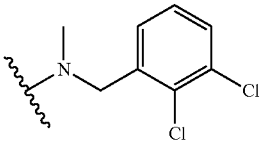
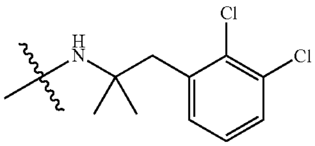
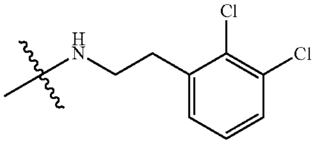
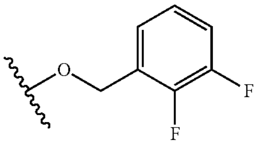
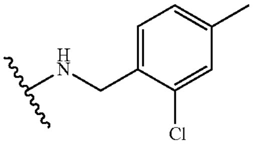
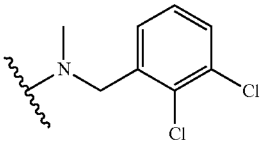

-continued
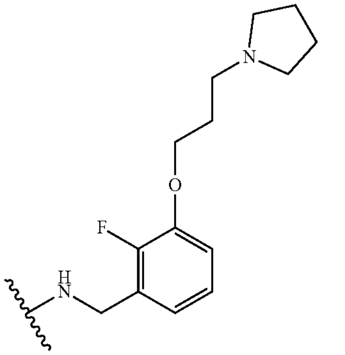
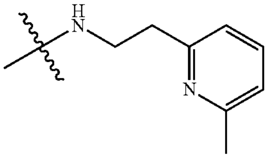
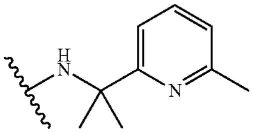
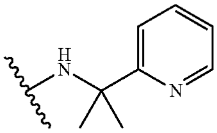
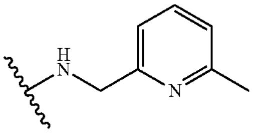
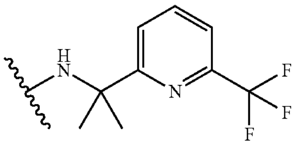
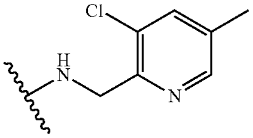
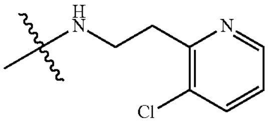
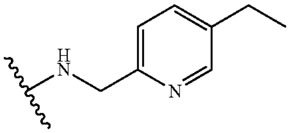
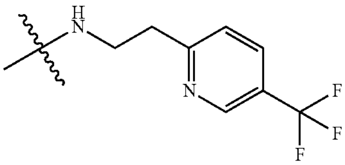
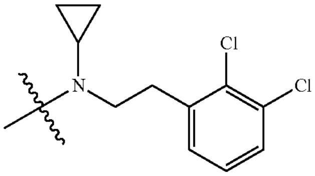
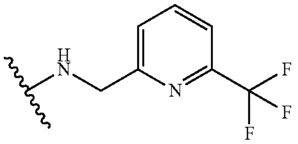
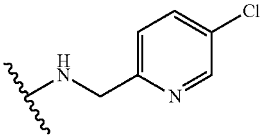
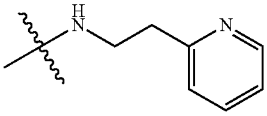
-continued
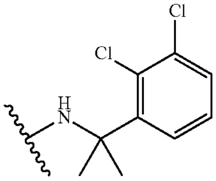
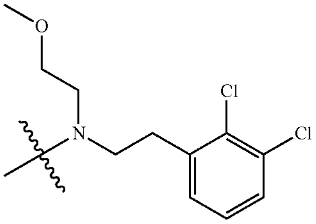
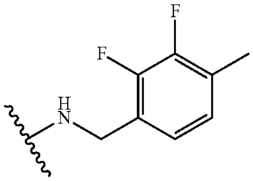
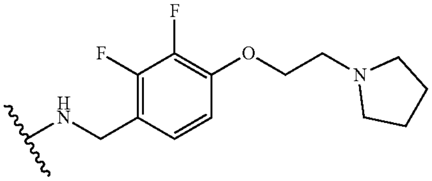
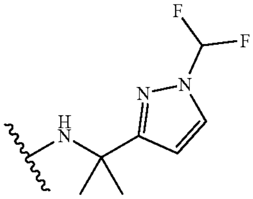
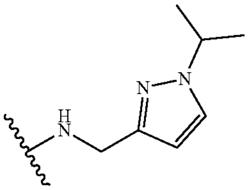
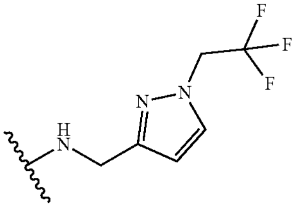
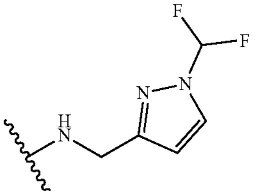
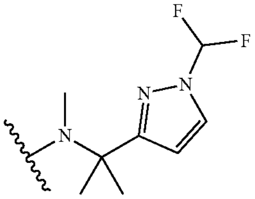
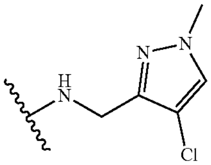
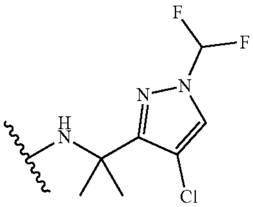
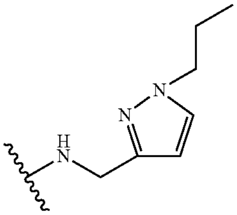
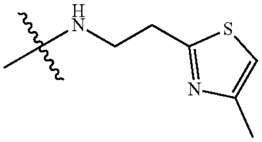
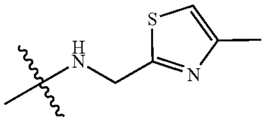
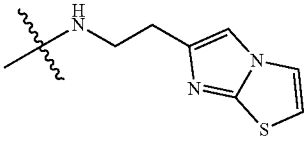

-continued

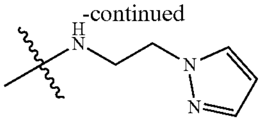
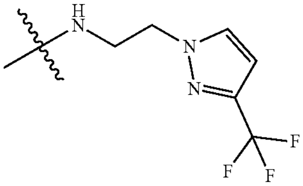
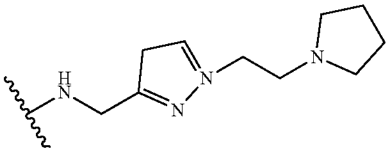
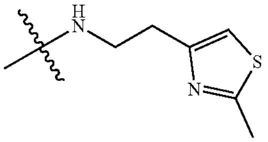
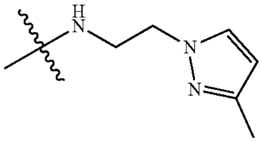
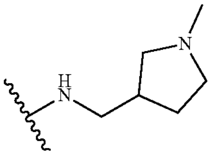
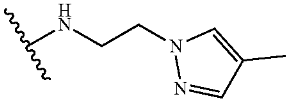
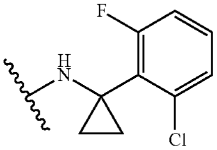
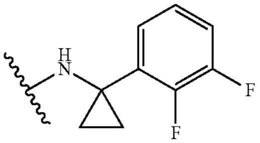
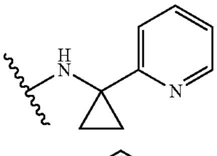
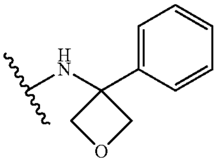
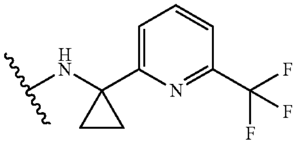
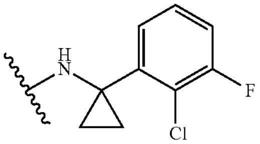
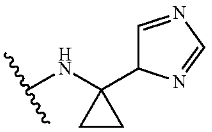
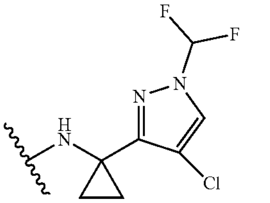
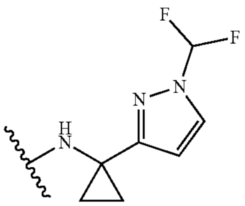
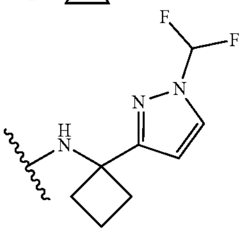
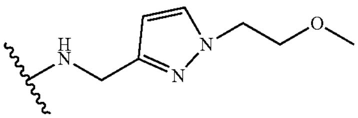

-continued

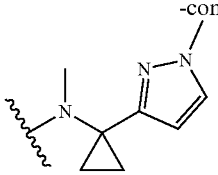
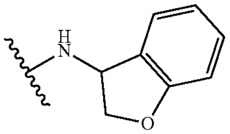
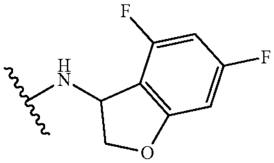
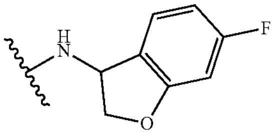
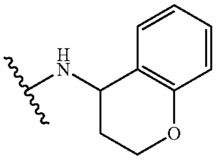
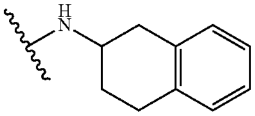
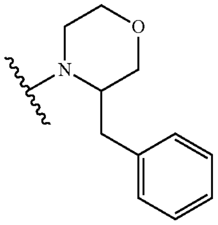
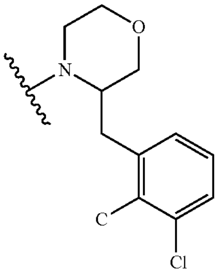
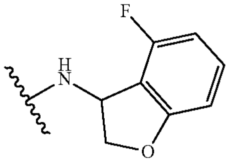
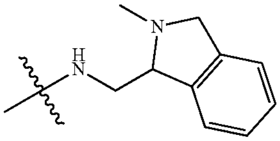
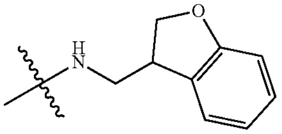

97. In the compound of formula VII, XII or XIV:

$R^4$ or $R^5$ is selected from: H, $C_{1-6}$ alkyl and $Q^4$-$L^4$- wherein $L^4$ is a bond and $Q^4$ is selected from: $C_{3-6}$ cycloalkyl; 3- to 6-membered heterocyclyl; $C_{6-12}$ aryl; and 5 or 6 membered heteroaryl, preferably wherein $Q^4$ is a 3- to 6-membered heterocyclyl, for example a 6-membered heterocyclyl;

n is 0 or 1;

when n is 1, $R^3$ is halo, preferably fluoro;

$R^{13}$ and $R^{14}$ are each independently selected from: H, $C_{1-4}$ alkyl and $C_{1-4}$ haloalkyl, or an $R^{13}$ and an $R^{14}$ attached to the same carbon atom in $L^2$ together form a $C_{3-6}$ cycloalkyl or 3-6-membered heterocyclyl, wherein said $C_{3-6}$ cycloalkyl or 3- to 6-membered heterocyclyl is optionally substituted by one or more substituents selected from: =O, halo, $C_{1-4}$ alkyl and $C_{1-4}$ haloalkyl; and $Q^1$ is as defined by any one of paragraphs 56 to 79, preferably $Q^1$ is any of the structures shown in paragraph 79.

98. In the compound of formula VII. XII, or XIV:

$R^4$ or $R^5$ is selected from: H and $C_{1-6}$ alkyl (e.g. methyl);

n is 0 or 1;

when n is 1, $R^3$ is halo, preferably fluoro;

$R^{13}$ and $R^{14}$ are each independently selected from: H, $C_{1-4}$ alkyl and $C_{1-4}$ haloalkyl, or an $R^{13}$ and an $R^{14}$ attached to the same carbon atom in $L^2$ together form a $C_{3-6}$ cycloalkyl, preferably a $C_{3-4}$ cycloalkyl; and $Q^1$ is selected from:

a 5- to 10-membered heteroaryl, a $C_{6-10}$ aryl, a $C_{3-12}$cycloalkyl or a 3- to 12-membered heterocyclyl, optionally wherein said 5- to 10-membered heteroaryl or $C_{6-10}$ aryl is substituted by one or more $R^{16}$, optionally wherein said $C_{3-12}$cycloalkyl or a 3- to 12-membered heterocyclyl is substituted by one or more $R^{15}$, wherein each $R^{15}$ is independently selected from: halo (preferably chloro and/or fluoro), $C_{1-6}$ alkyl, $C_{1-6}$haloalkyl, and $OR^{17}$, optionally wherein the $C_{1-6}$ alkyl is substituted by one or more $R^{18}$, wherein each $R^{16}$ is independently selected from: halo (preferably chloro and/or fluoro), $C_{1-6}$ alkyl, $C_{1-6}$haloalkyl, and $OR^{20}$, optionally wherein the $C_{1-6}$ alkyl is substituted by one or more $R^{21}$, wherein each $R^{17}$ and $R^{20}$ is independently selected from: H and $C_{1-6}$ alkyl;

wherein each $R^{18}$ and $R^{21}$ is independently selected from: halo, —$NR^{A3}R^{B3}$ and $OR^{A3}$;

wherein each $R^{A3}$ is independently selected from H and $C_{1-4}$ alkyl, or —$NR^{A3}R^{B3}$ may form a 4- to 6-membered heterocyclyl.

99. In the compound of formula VII, XII or XIV:

$R^4$ or $R^5$ is selected from: H and $C_{1-6}$ alkyl (e.g. methyl);

n is 0 or 1;

when n is 1, $R^3$ is halo, preferably fluoro;

$R^{13}$ and $R^{14}$ are each independently selected from: H, $C_{1-4}$ alkyl and $C_{1-4}$ haloalkyl, or an $R^{13}$ and an $R^{14}$ attached to the same carbon atom in $L^2$ together form a $C_{3-6}$ cycloalkyl, preferably a $C_{3-4}$ cycloalkyl; and $Q^1$ is selected from:

a 5- to 10-membered heteroaryl, a $C_{6-10}$ aryl, a $C_{3-12}$cycloalkyl or a 3- to 12-membered heterocyclyl, optionally wherein said 5- to 10-membered heteroaryl or $C_{6-10}$ aryl is substituted by one or more $R^{16}$, optionally wherein said $C_{3-12}$cycloalkyl or a 3- to 12-membered heterocyclyl is substituted by one or more $R^{15}$, wherein each $R^{15}$ or $R^{16}$ is independently selected from: halo (preferably F and/or Cl); $C_{1-6}$haloalkyl (preferably $CHF_2$, $CF_3$, $CH_2CF_3$, CHCl, $CCl_3$, $CH_2CCl_3$); methyl, ethyl, propyl (e.g. isopropyl), butyl (e.g. t-butyl), methoxy, methoxymethyl, methoxyethyl, and a $C_{1-4}$ alkyl substituted with a 5-membered heterocycle.

100. In the compound as defined by any one of paragraphs 35-79:

$R^4$ or $R^5$ is H or methyl;

n is 0 or 1, if n is 1 then $R^3$ is halo, preferably F; and $R^1$ and $R^2$ are defined by any one of paragraphs 1 to 14.

In some embodiments, the compound of the invention is any one of the compounds selected from Table 1, or a pharmaceutically acceptable salt thereof:

TABLE 1

| No. | Structure |
|---|---|
| 1 | 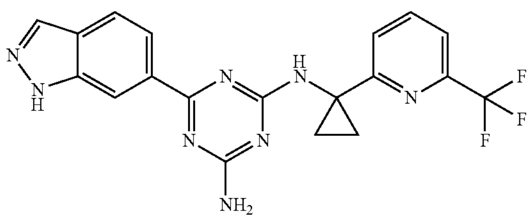 |
| 2 | 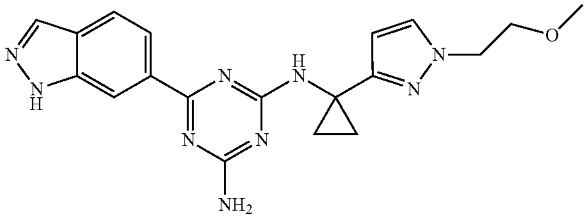 |
| 3 | 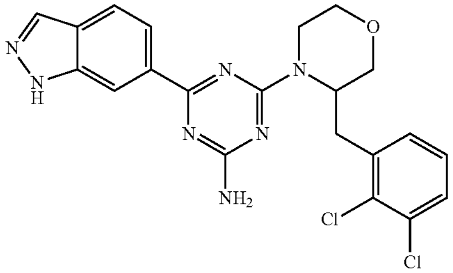 |

TABLE 1-continued
| No. | Structure |
| --- | --- |
| 4 | 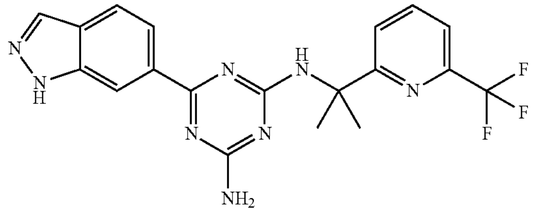 |
| 5 | 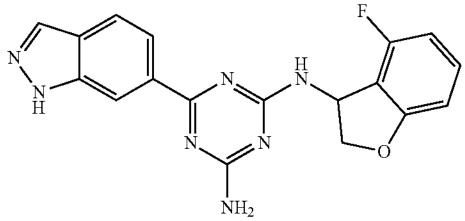 |
| 6 | 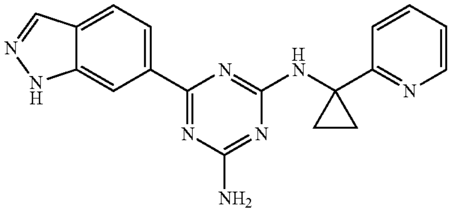 |
| 7 | 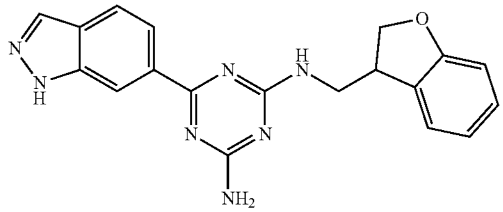 |
| 8 | 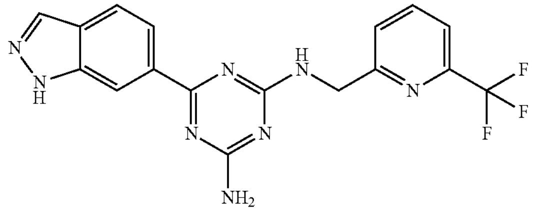 |
| 9 | 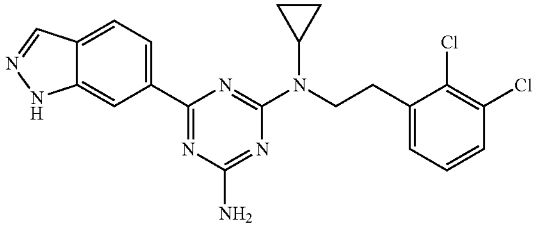 |
| 10 | 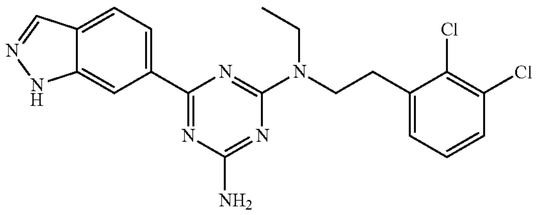 |

TABLE 1-continued
| No. | Structure |
|---|---|
| 11 | 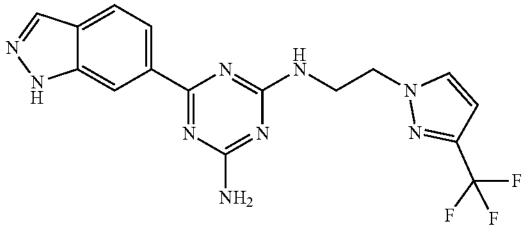 |
| 12 | 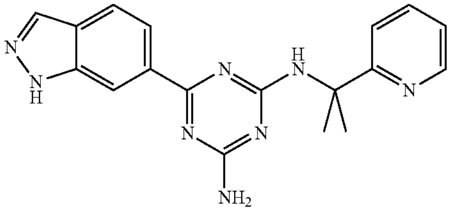 |
| 13 | 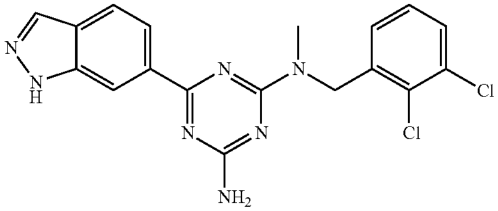 |
| 14 | 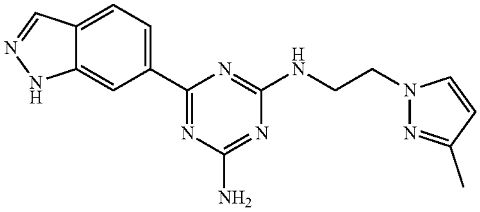 |
| 15 | 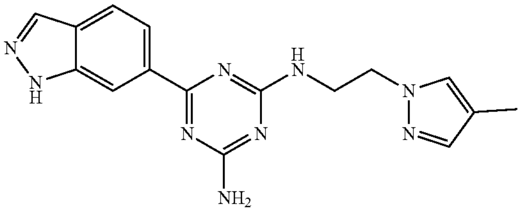 |
| 16 | 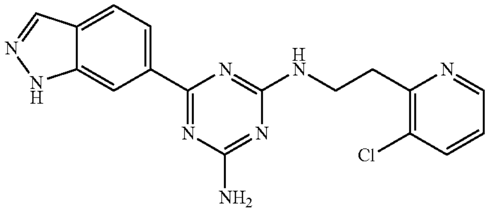 |
| 17 | 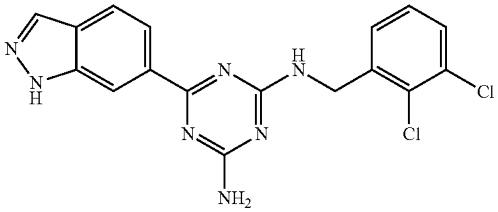 |

TABLE 1-continued
| No. | Structure |
| --- | --- |
| 18 | 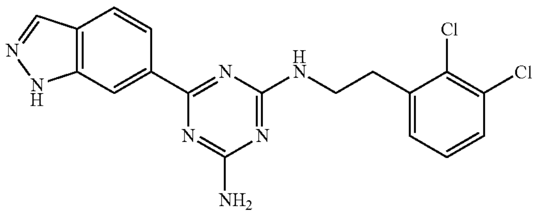 |
| 19 | 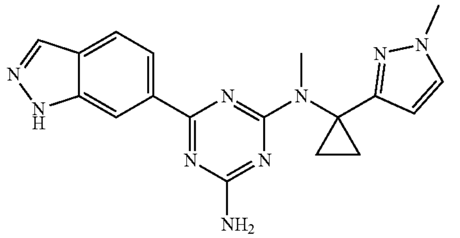 |
| 20 | 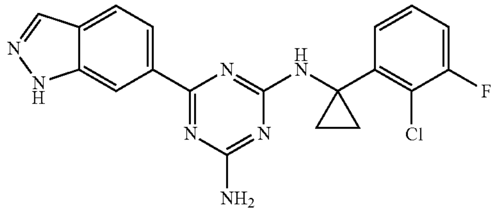 |
| 21 | 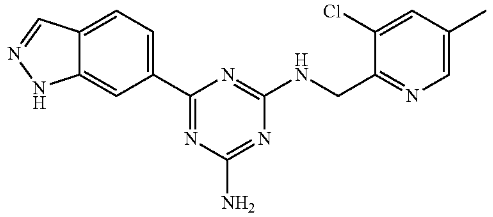 |
| 22 | 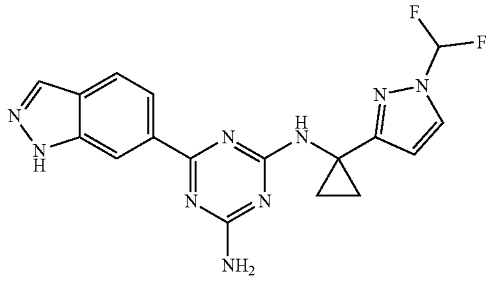 |
| 23 | 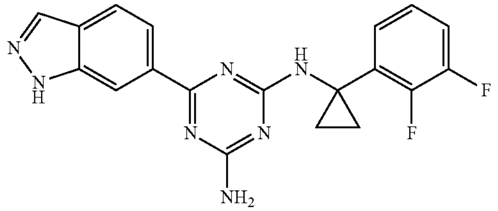 |

TABLE 1-continued
| No. | Structure |
| --- | --- |
| 24 | 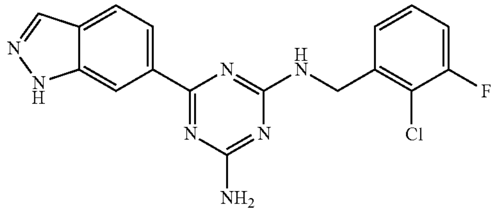 |
| 25 | 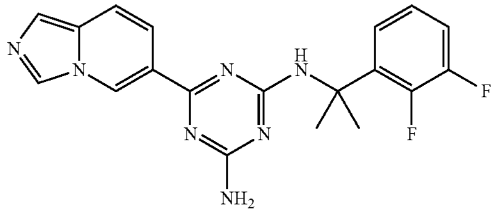 |
| 26 | 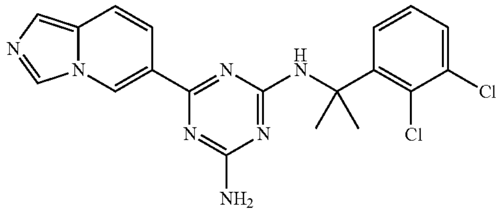 |
| 27 | 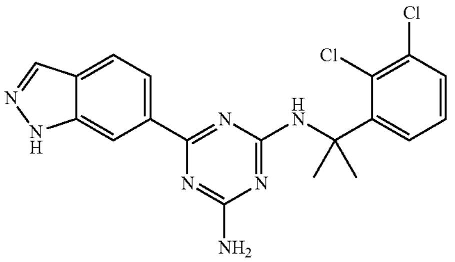 |
| 28 | 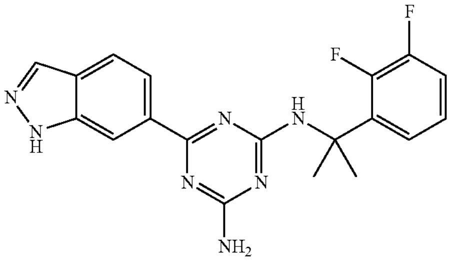 |
| 29 | 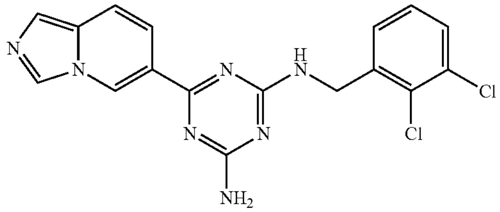 |

TABLE 1-continued
| No. | Structure |
| --- | --- |
| 30 | 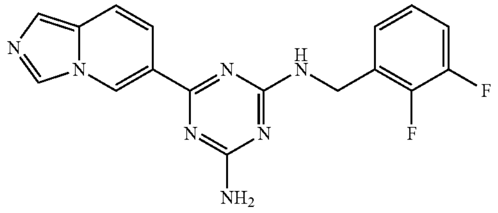 |
| 31 | 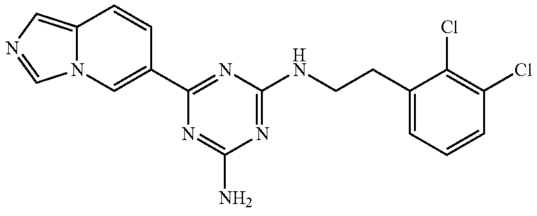 |
| 32 | 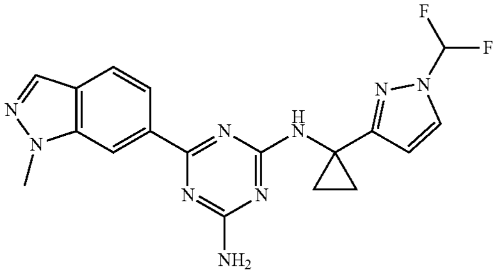 [SMILES: Cn1ncc2ccc(-c3nc(N)nc(NC4(c5ccn(C(F)F)n5)CC4)n3)cc21] |
| 33 | 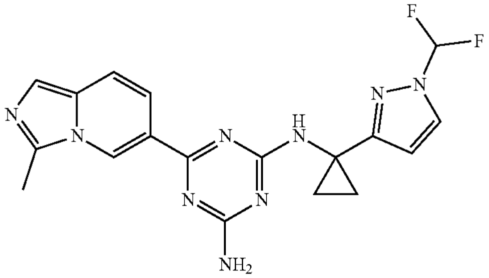 |
| 34 | 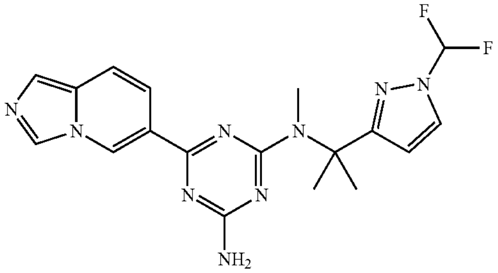 [SMILES: CN(c1nc(N)nc(-c2ccc3cncn3c2)n1)C(C)(C)c1ccn(C(F)F)n1] |
| 35 | 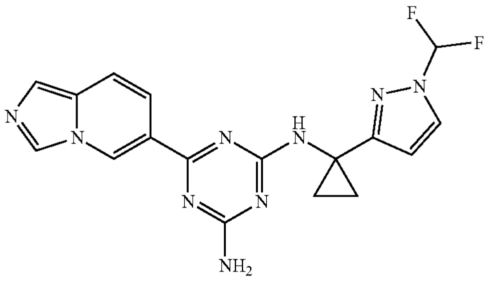 |

TABLE 1-continued
| No. | Structure |
| --- | --- |
| 36 | 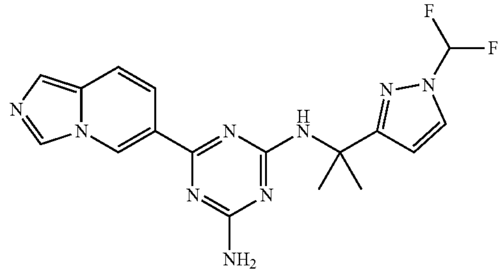 [SMILES: CC(C)(Nc1nc(N)nc(-c2ccc3cncn3c2)n1)c1ccn(C(F)F)n1] |
| 37 | 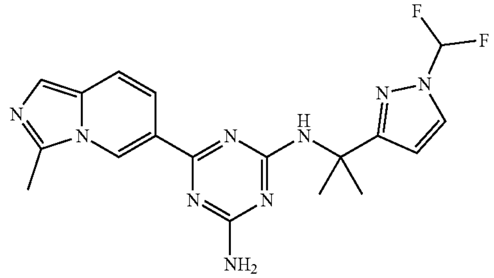 |
| 38 | 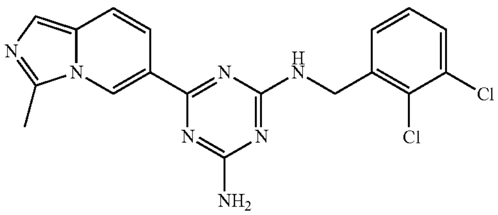 [SMILES: Cc1ncc2ccc(-c3nc(N)nc(NCc4cccc(Cl)c4Cl)n3)cn12] |
| 39 | 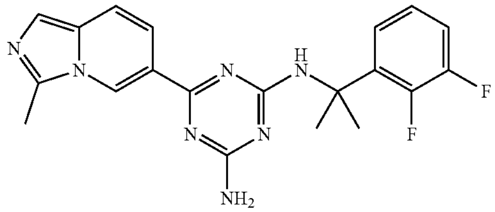 |
| 40 | 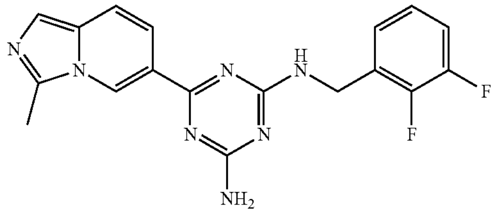 |
| 41 | 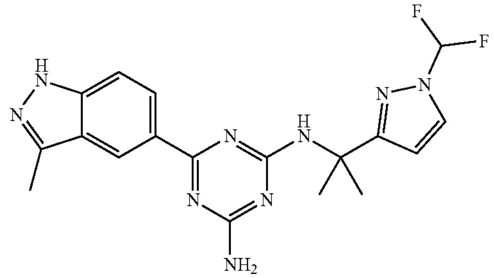 |

TABLE 1-continued
| No. | Structure |
| --- | --- |
| 42 | 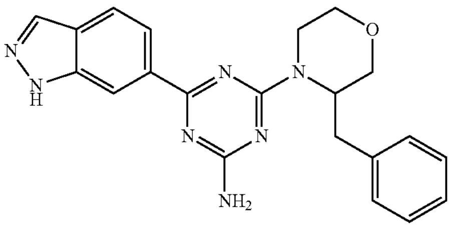 [SMILES: Nc1nc(-c2ccc3cn[nH]c3c2)nc(N2CCOCC2Cc2ccccc2)n1] |
| 43 | 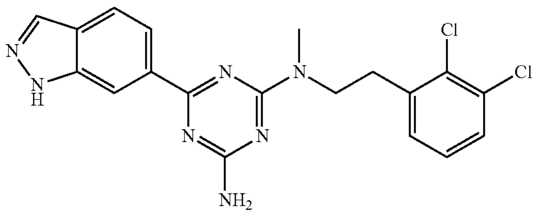 [SMILES: CN(CCc1cccc(Cl)c1Cl)c1nc(N)nc(-c2ccc3cn[nH]c3c2)n1] |
| 44 | 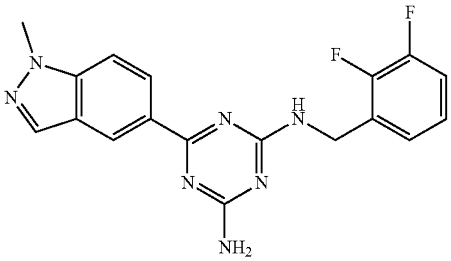 [SMILES: Cn1ncc2cc(-c3nc(N)nc(NCc4cccc(F)c4F)n3)ccc21] |
| 45 | 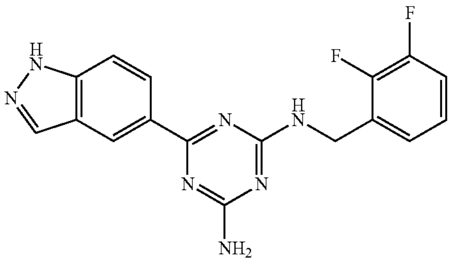 [SMILES: Nc1nc(NCc2cccc(F)c2F)nc(-c2ccc3[nH]ncc3c2)n1] |
| 46 | 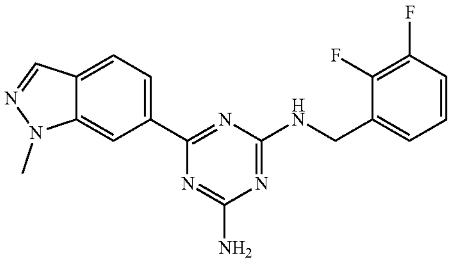 [SMILES: Cn1ncc2ccc(-c3nc(N)nc(NCc4cccc(F)c4F)n3)cc21] |
| 47 | 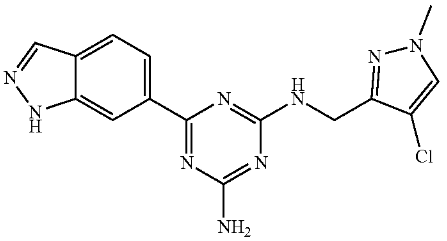 [SMILES: Cn1cc(Cl)c(CNc2nc(N)nc(-c3ccc4cn[nH]c4c3)n2)n1] |

TABLE 1-continued
| No. | Structure |
|---|---|
| 48 | 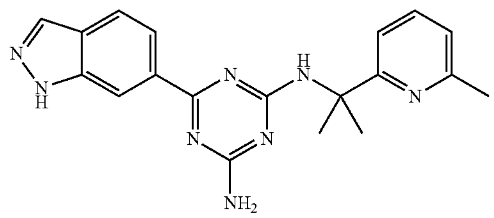 [SMILES: Cc1cccc(C(C)(C)Nc2nc(N)nc(-c3ccc4cn[nH]c4c3)n2)n1] |
| 49 | 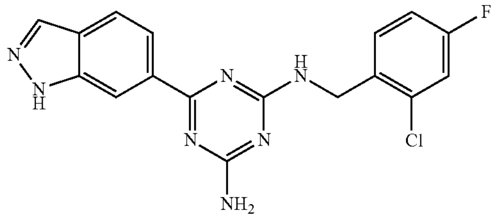 [SMILES: Nc1nc(NCc2ccc(F)cc2Cl)nc(-c2ccc3cn[nH]c3c2)n1] |
| 50 | 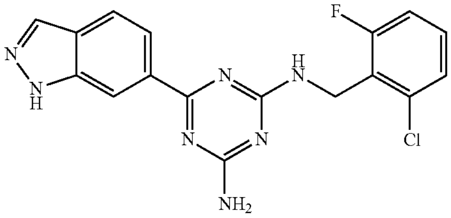 [SMILES: Nc1nc(NCc2c(F)cccc2Cl)nc(-c2ccc3cn[nH]c3c2)n1] |
| 51 | 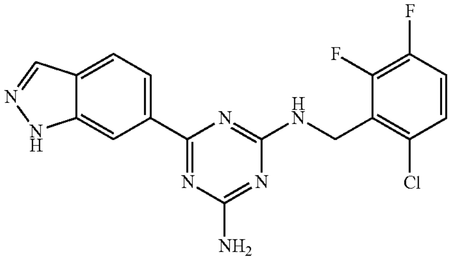 [SMILES: Nc1nc(NCc2c(Cl)ccc(F)c2F)nc(-c2ccc3cn[nH]c3c2)n1] |
| 52 | 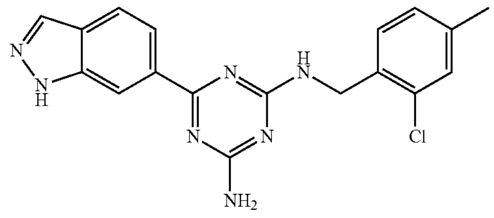 [SMILES: Cc1ccc(CNc2nc(N)nc(-c3ccc4cn[nH]c4c3)n2)c(Cl)c1] |
| 53 | 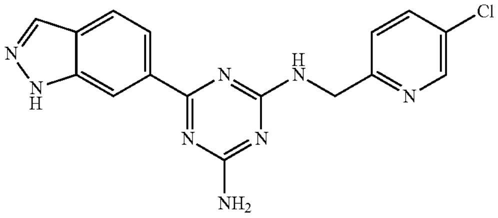 |

TABLE 1-continued
| No. | Structure |
|---|---|
| 54 | 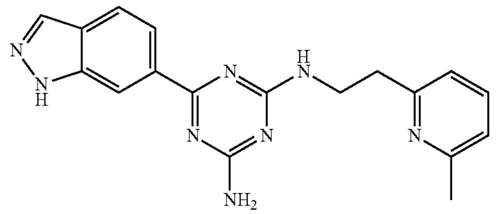 |
| 55 | 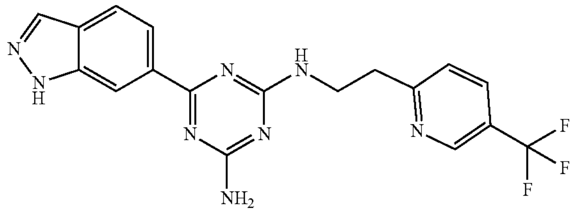 |
| 56 | 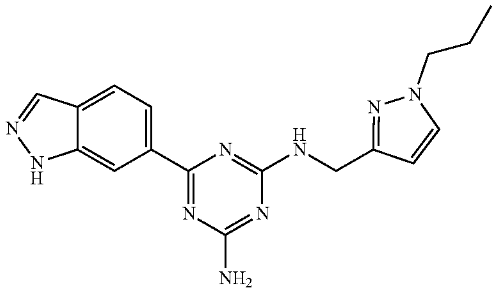 |
| 57 | 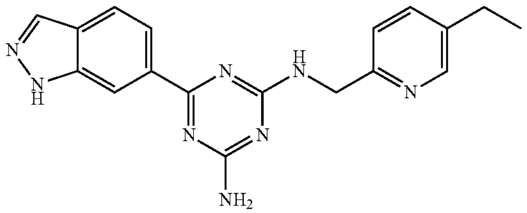 [SMILES: CCc1ccc(CNc2nc(N)nc(-c3ccc4cn[nH]c4c3)n2)nc1] |
| 58 | 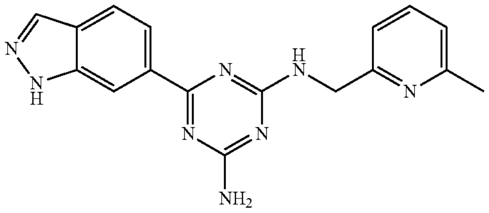 |
| 59 | 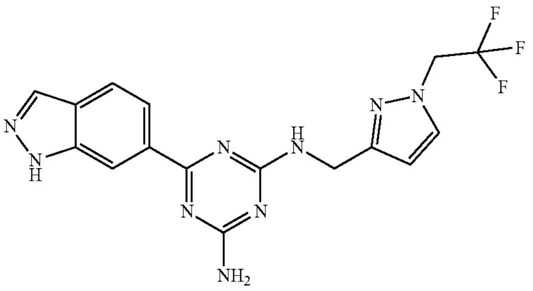 [SMILES: Nc1nc(NCc2ccn(CC(F)(F)F)n2)nc(-c2ccc3cn[nH]c3c2)n1] |

TABLE 1-continued
| No. | Structure |
|---|---|
| 60 | 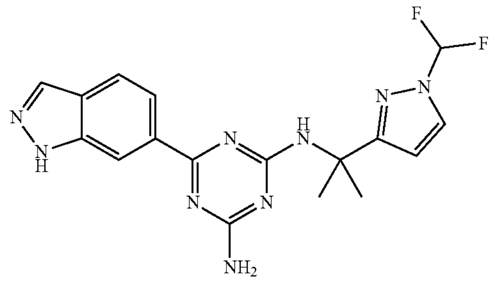 [SMILES: CC(C)(Nc1nc(N)nc(-c2ccc3cn[nH]c3c2)n1)c1ccn(C(F)F)n1] |
| 61 | 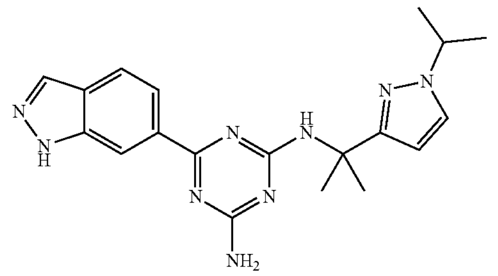 [SMILES: CC(C)n1ccc(C(C)(C)Nc2nc(N)nc(-c3ccc4cn[nH]c4c3)n2)n1] |
| 62 | 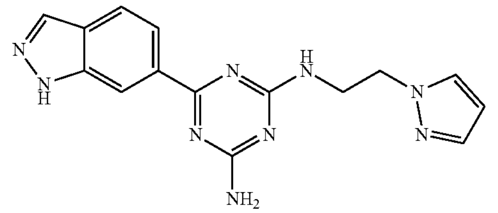 [SMILES: Nc1nc(NCCn2cccn2)nc(-c2ccc3cn[nH]c3c2)n1] |
| 63 | 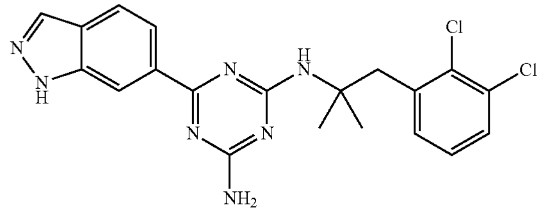 [SMILES: CC(C)(Cc1cccc(Cl)c1Cl)Nc1nc(N)nc(-c2ccc3cn[nH]c3c2)n1] |
| 64 | 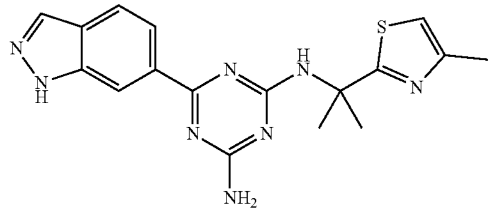 [SMILES: Cc1csc(C(C)(C)Nc2nc(N)nc(-c3ccc4cn[nH]c4c3)n2)n1] |
| 65 | 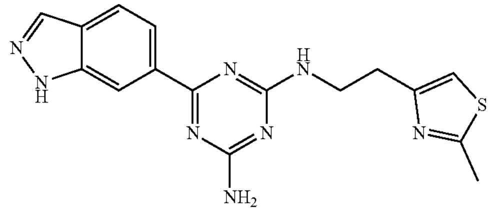 [SMILES: Cc1nc(CCNc2nc(N)nc(-c3ccc4cn[nH]c4c3)n2)cs1] |

TABLE 1-continued
| No. | Structure |
|---|---|
| 66 | 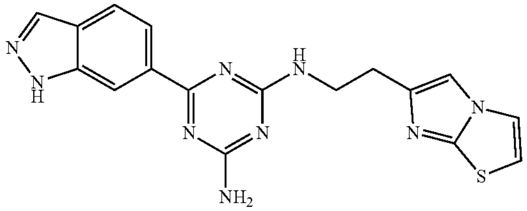 [SMILES: Nc1nc(NCCc2cn3ccsc3n2)nc(-c2ccc3cn[nH]c3c2)n1] |
| 67 | 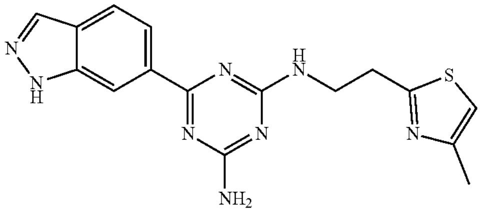 [SMILES: Cc1csc(CCNc2nc(N)nc(-c3ccc4cn[nH]c4c3)n2)n1] |
| 68 | 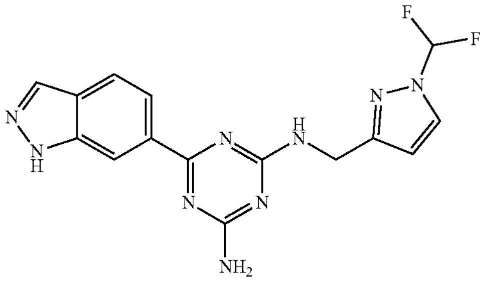 [SMILES: Nc1nc(NCc2ccn(C(F)F)n2)nc(-c2ccc3cn[nH]c3c2)n1] |
| 69 | 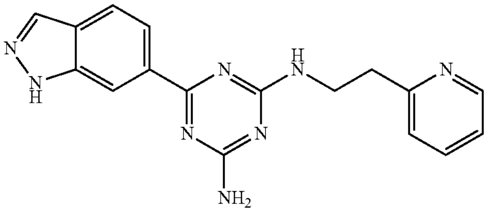 [SMILES: Nc1nc(NCCc2ccccn2)nc(-c2ccc3cn[nH]c3c2)n1] |
| 70 | 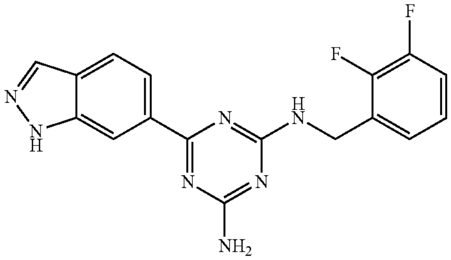 [SMILES: Nc1nc(NCc2cccc(F)c2F)nc(-c2ccc3cn[nH]c3c2)n1] |
| 71 | 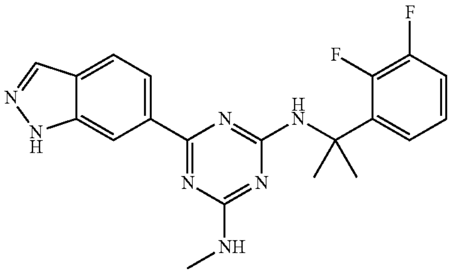 [SMILES: CNc1nc(NC(C)(C)c2cccc(F)c2F)nc(-c2ccc3cn[nH]c3c2)n1] |

TABLE 1-continued
| No. | Structure |
| --- | --- |
| 72 | 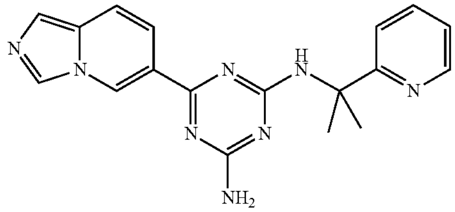 [SMILES: CC(C)(Nc1nc(N)nc(-c2ccc3cncn3c2)n1)c1ccccn1] |
| 73 | 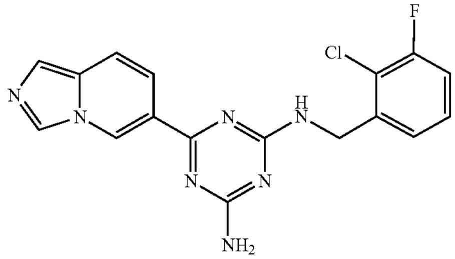 [SMILES: Nc1nc(NCc2cccc(F)c2Cl)nc(-c2ccc3cncn3c2)n1] |
| 74 | 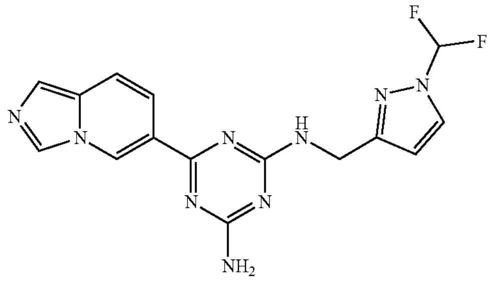 [SMILES: Nc1nc(NCc2ccn(C(F)F)n2)nc(-c2ccc3cncn3c2)n1] |
| 75 | 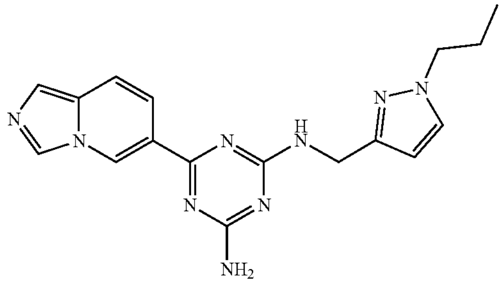 [SMILES: CCCn1ccc(CNc2nc(N)nc(-c3ccc4cncn4c3)n2)n1] |
| 76 | 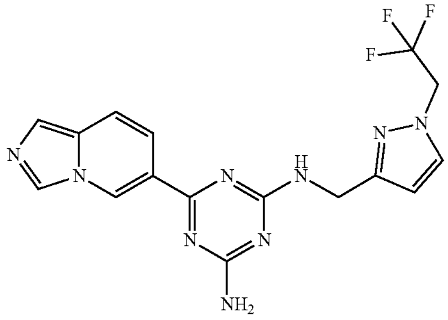 [SMILES: Nc1nc(NCc2ccn(CC(F)(F)F)n2)nc(-c2ccc3cncn3c2)n1] |

TABLE 1-continued
| No. | Structure |
|---|---|
| 77 | 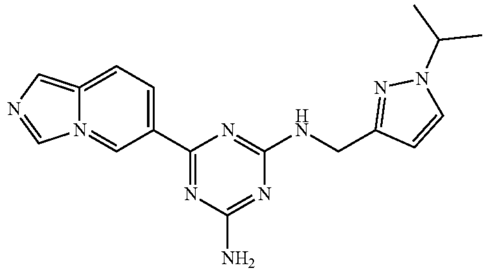 |
| 78 | 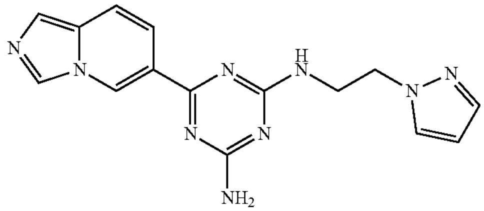 [SMILES: Nc1nc(NCCn2cccn2)nc(-c2ccc3cncn3c2)n1] |
| 79 | 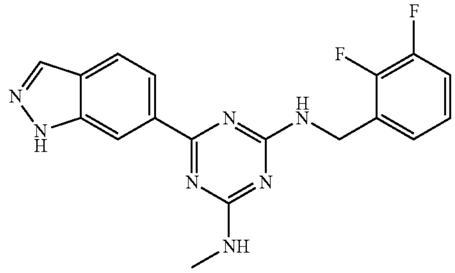 [SMILES: CNc1nc(NCc2cccc(F)c2F)nc(-c2ccc3cn[nH]c3c2)n1] |
| 80 | 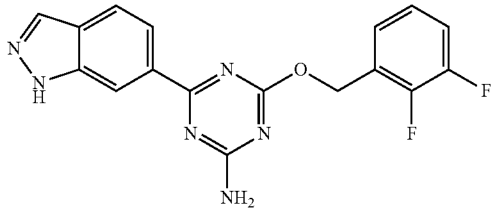 [SMILES: Nc1nc(OCc2cccc(F)c2F)nc(-c2ccc3cn[nH]c3c2)n1] |
| 81 | 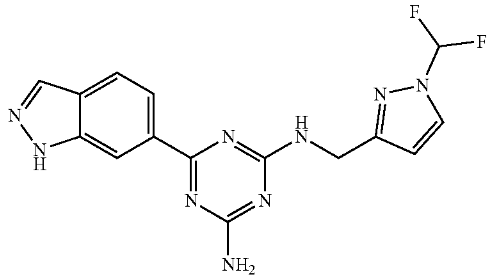 [SMILES: Nc1nc(NCc2ccn(C(F)F)n2)nc(-c2ccc3cn[nH]c3c2)n1] |
| 82 | 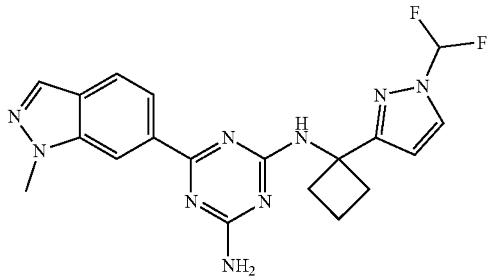 [SMILES: Cn1ncc2ccc(-c3nc(N)nc(NC4(c5ccn(C(F)F)n5)CCC4)n3)cc21] |

TABLE 1-continued
| No. | Structure |
|---|---|
| 83 | 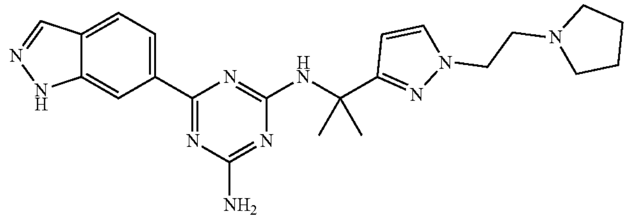 [SMILES: CC(C)(Nc1nc(N)nc(-c2ccc3cn[nH]c3c2)n1)c1ccn(CCN2CCCC2)n1] |
| 84 | 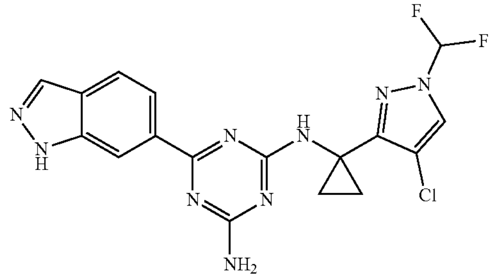 [SMILES: Nc1nc(NC2(c3nn(C(F)F)cc3Cl)CC2)nc(-c2ccc3cn[nH]c3c2)n1] |
| 85 | 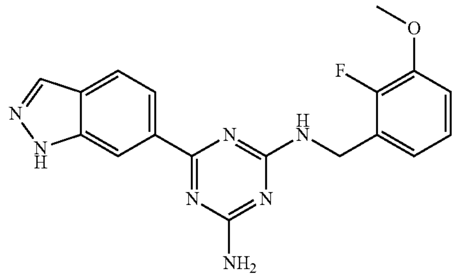 [SMILES: COc1cccc(CNc2nc(N)nc(-c3ccc4cn[nH]c4c3)n2)c1F] |
| 86 | 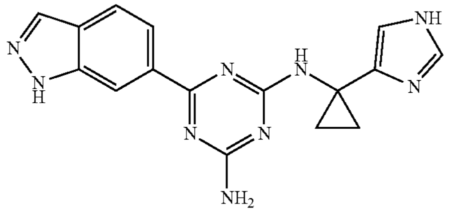 [SMILES: Nc1nc(NC2(c3c[nH]cn3)CC2)nc(-c2ccc3cn[nH]c3c2)n1] |
| 87 | 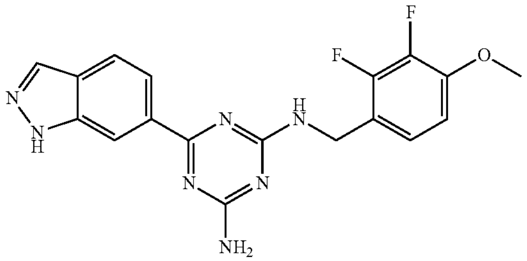 [SMILES: COc1ccc(CNc2nc(N)nc(-c3ccc4cn[nH]c4c3)n2)c(F)c1F] |
| 88 | 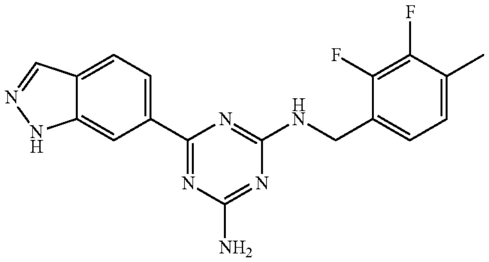 [SMILES: Cc1ccc(CNc2nc(N)nc(-c3ccc4cn[nH]c4c3)n2)c(F)c1F] |

TABLE 1-continued
| No. | Structure |
|---|---|
| 89 | 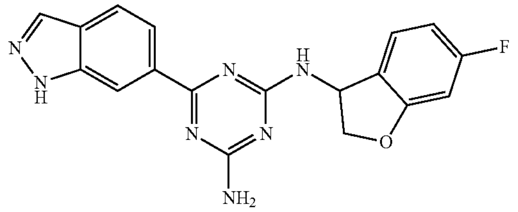 [SMILES: Nc1nc(NC2COc3cc(F)ccc32)nc(-c2ccc3cn[nH]c3c2)n1] |
| 90 | 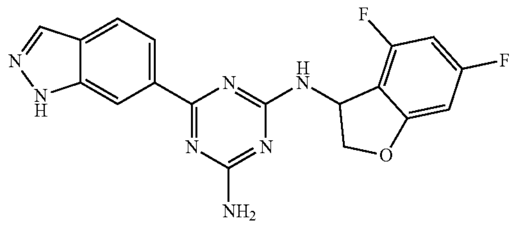 [SMILES: Nc1nc(NC2COc3cc(F)cc(F)c32)nc(-c2ccc3cn[nH]c3c2)n1] |
| 91 | 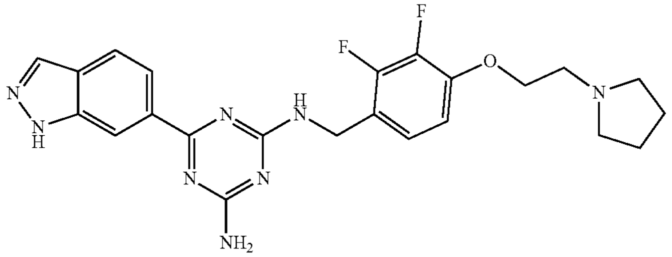 [SMILES: Nc1nc(NCc2ccc(OCCN3CCCC3)c(F)c2F)nc(-c2ccc3cn[nH]c3c2)n1] |
| 92 | 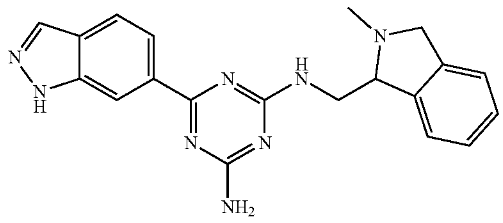 [SMILES: CN1Cc2ccccc2C1CNc1nc(N)nc(-c2ccc3cn[nH]c3c2)n1] |
| 93 | 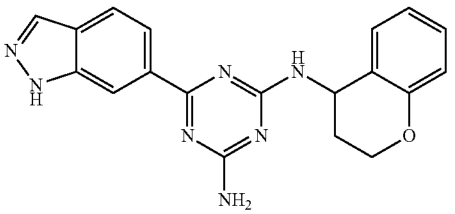 [SMILES: Nc1nc(NC2CCOc3ccccc32)nc(-c2ccc3cn[nH]c3c2)n1] |
| 94 | 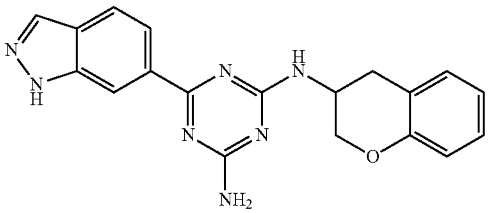 [SMILES: Nc1nc(NC2COc3ccccc3C2)nc(-c2ccc3cn[nH]c3c2)n1] |

TABLE 1-continued
| No. | Structure |
| --- | --- |
| 95 | 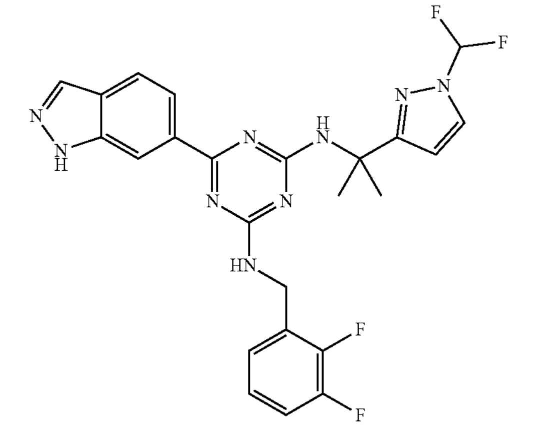 [SMILES: CC(C)(Nc1nc(NCc2cccc(F)c2F)nc(-c2ccc3cn[nH]c3c2)n1)c1ccn(C(F)F)n1] |
| 96 | 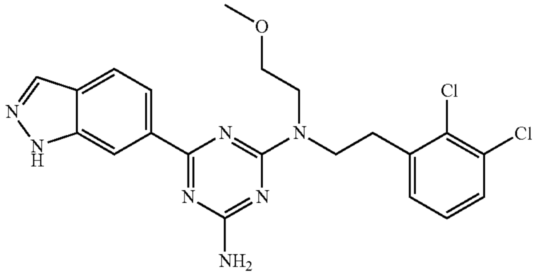 [SMILES: COCCN(CCc1cccc(Cl)c1Cl)c1nc(N)nc(-c2ccc3cn[nH]c3c2)n1] |
| 97 | 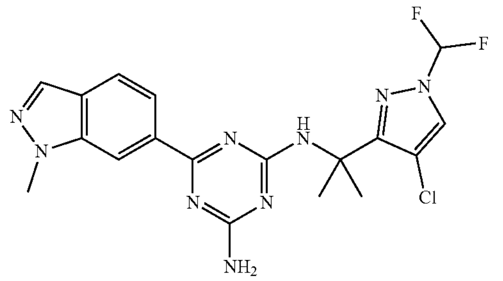 [SMILES: Cn1ncc2ccc(-c3nc(N)nc(NC(C)(C)c4nn(C(F)F)cc4Cl)n3)cc21] |
| 98 | 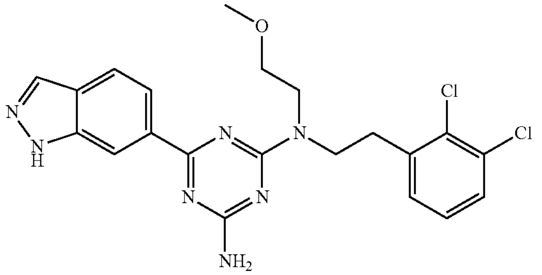 [SMILES: COCCN(CCc1cccc(Cl)c1Cl)c1nc(N)nc(-c2ccc3cn[nH]c3c2)n1] |
| 99 | 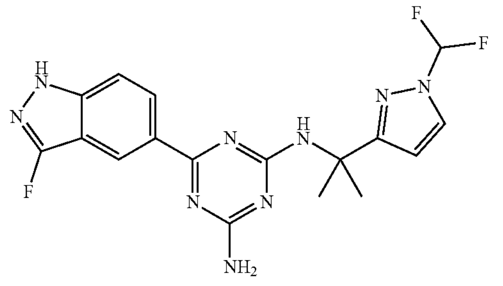 |

TABLE 1-continued
| No. | Structure |
| --- | --- |
| 100 | 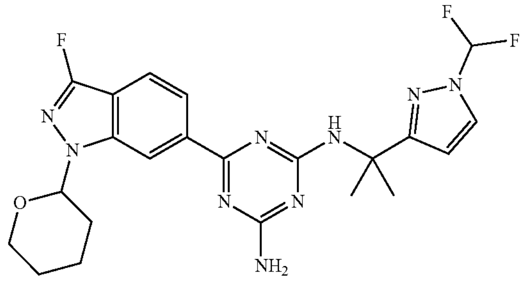 [SMILES: CC(C)(Nc1nc(N)nc(-c2ccc3c(F)nn(C4CCCCO4)c3c2)n1)c1ccn(C(F)F)n1] |
| 101 | 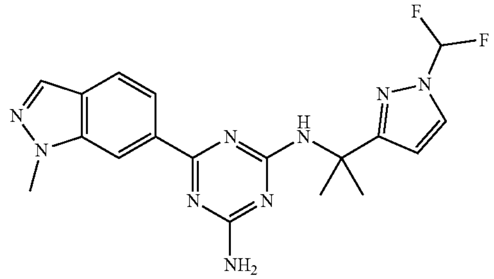 [SMILES: Cn1ncc2ccc(-c3nc(N)nc(NC(C)(C)c4ccn(C(F)F)n4)n3)cc21] |
| 102 | 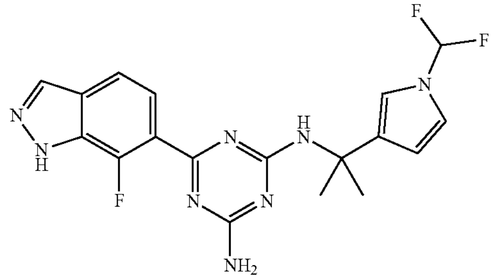 |
| 103 | 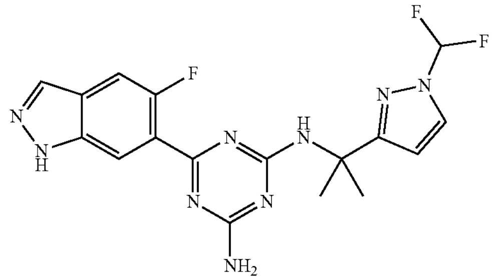 [SMILES: CC(C)(Nc1nc(N)nc(-c2cc3[nH]ncc3cc2F)n1)c1ccn(C(F)F)n1] |
| 104 | 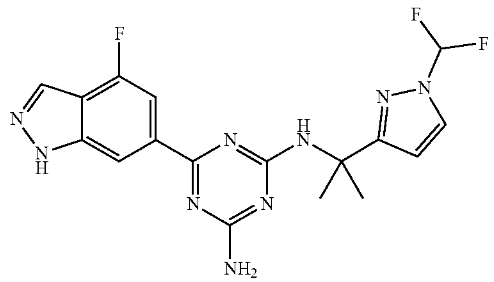 [SMILES: CC(C)(Nc1nc(N)nc(-c2cc(F)c3cn[nH]c3c2)n1)c1ccn(C(F)F)n1] |

TABLE 1-continued
| No. | Structure |
|---|---|
| 105 | 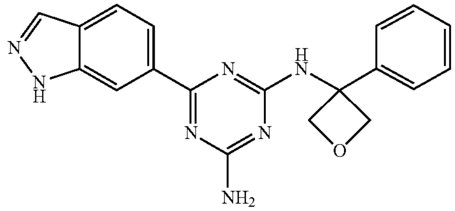 [SMILES: Nc1nc(NC2(c3ccccc3)COC2)nc(-c2ccc3cn[nH]c3c2)n1] |
| 106 | 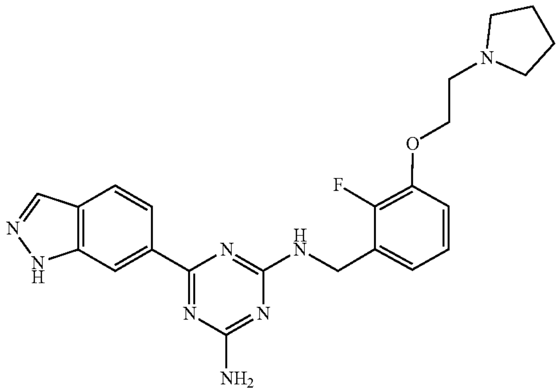 [SMILES: Nc1nc(NCc2cccc(OCCN3CCCC3)c2F)nc(-c2ccc3cn[nH]c3c2)n1] |
| 107 | 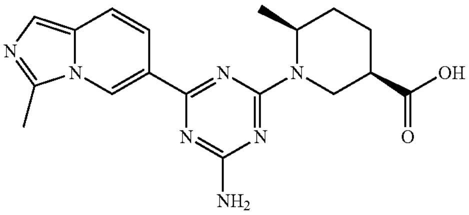 [SMILES: Cc1ncc2ccc(-c3nc(N)nc(N4C[C@H](C(=O)O)CC[C@@H]4C)n3)cn12] |
| 108 | 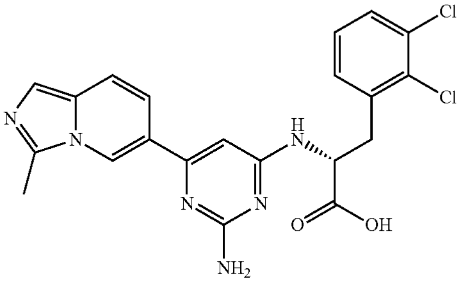 [SMILES: Cc1ncc2ccc(-c3cc(N[C@H](Cc4cccc(Cl)c4Cl)C(=O)O)nc(N)n3)cn12] |
| 109 | 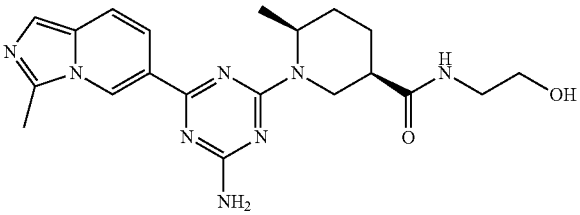 [SMILES: Cc1ncc2ccc(-c3nc(N)nc(N4C[C@H](C(=O)NCCO)CC[C@@H]4C)n3)cn12] |
| 110 | 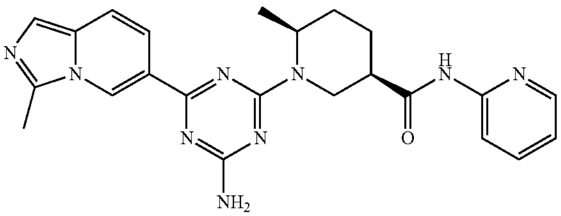 [SMILES: Cc1ncc2ccc(-c3nc(N)nc(N4C[C@H](C(=O)Nc5ccccn5)CC[C@@H]4C)n3)cn12] |

TABLE 1-continued
| No. | Structure |
| --- | --- |
| 111 | 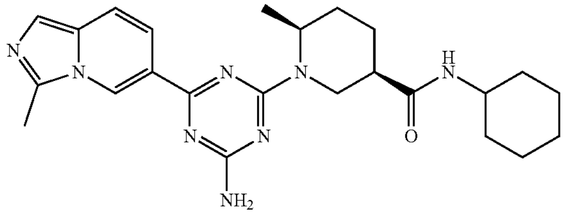 |
| 112 | 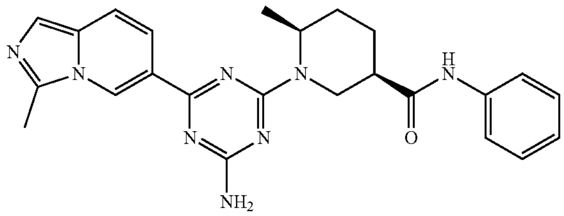 |
| 113 | 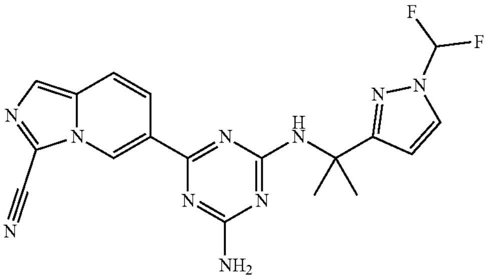 [SMILES: CC(C)(Nc1nc(N)nc(-c2ccc3cnc(C#N)n3c2)n1)c1ccn(C(F)F)n1] |
| 114 | 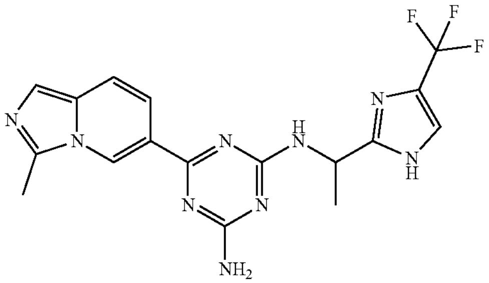 [SMILES: Cc1ncc2ccc(-c3nc(N)nc(NC(C)c4nc(C(F)(F)F)c[nH]4)n3)cn12] |
| 115 | 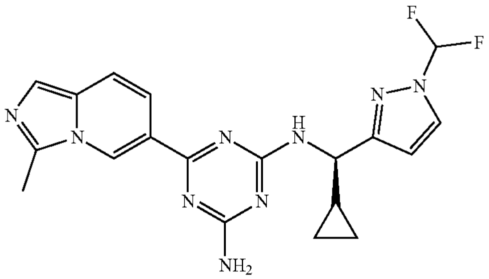 [SMILES: Cc1ncc2ccc(-c3nc(N)nc(N[C@@H](c4ccn(C(F)F)n4)C4CC4)n3)cn12] |
| 116 | 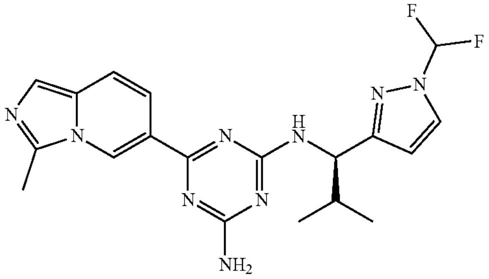 [SMILES: Cc1ncc2ccc(-c3nc(N)nc(N[C@@H](c4ccn(C(F)F)n4)C(C)C)n3)cn12] |

TABLE 1-continued
| No. | Structure |
| --- | --- |
| 117 | 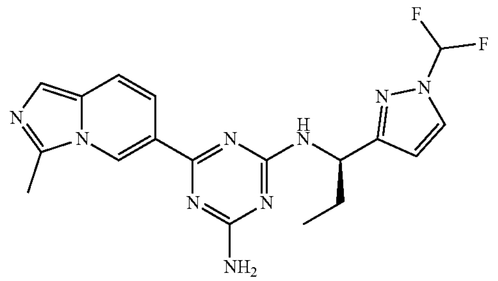 [SMILES: CC[C@@H](Nc1nc(N)nc(-c2ccc3cnc(C)n3c2)n1)c1ccn(C(F)F)n1] |
| 118 | 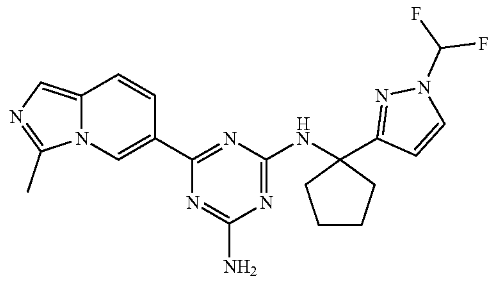 [SMILES: Cc1ncc2ccc(-c3nc(N)nc(NC4(c5ccn(C(F)F)n5)CCCC4)n3)cn12] |
| 119 | 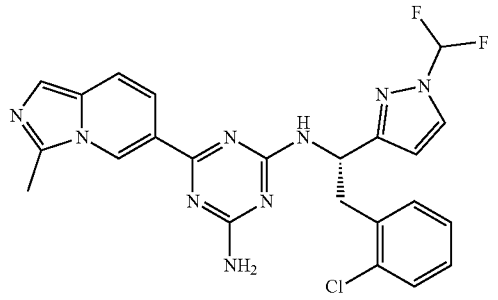 [SMILES: Cc1ncc2ccc(-c3nc(N)nc(N[C@@H](Cc4ccccc4Cl)c4ccn(C(F)F)n4)n3)cn12] |
| 120 | 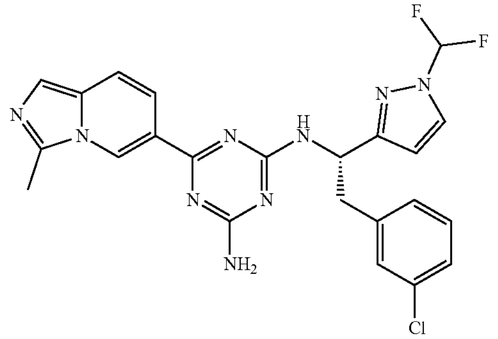 [SMILES: Cc1ncc2ccc(-c3nc(N)nc(N[C@@H](Cc4cccc(Cl)c4)c4ccn(C(F)F)n4)n3)cn12] |
| 121 | 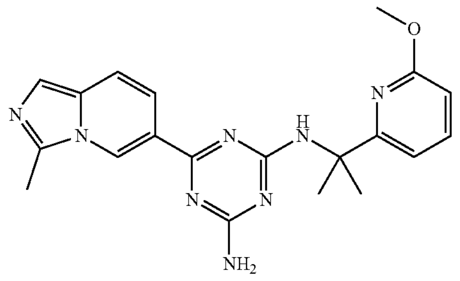 [SMILES: COc1cccc(C(C)(C)Nc2nc(N)nc(-c3ccc4cnc(C)n4c3)n2)n1] |

TABLE 1-continued
| No. | Structure |
|---|---|
| 122 | 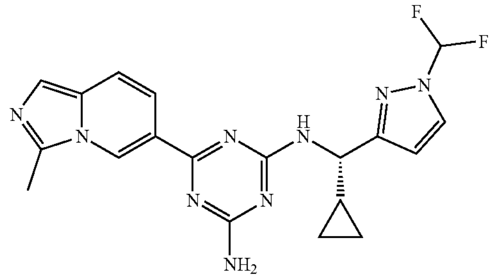 [SMILES: Cc1ncc2ccc(-c3nc(N)nc(N[C@H](c4ccn(C(F)F)n4)C4CC4)n3)cn12] |
| 123 | 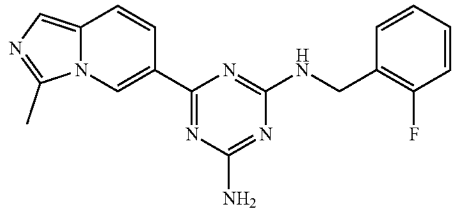 [SMILES: Cc1ncc2ccc(-c3nc(N)nc(NCc4ccccc4F)n3)cn12] |
| 124 | 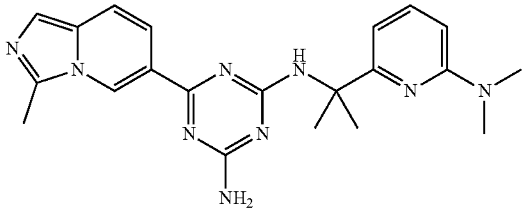 [SMILES: Cc1ncc2ccc(-c3nc(N)nc(NC(C)(C)c4cccc(N(C)C)n4)n3)cn12] |
| 125 | 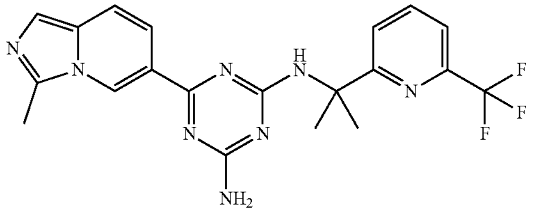 [SMILES: Cc1ncc2ccc(-c3nc(N)nc(NC(C)(C)c4cccc(C(F)(F)F)n4)n3)cn12] |
| 126 | 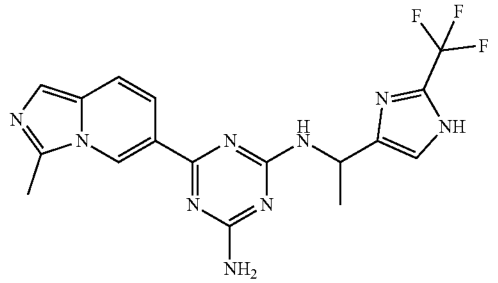 [SMILES: Cc1ncc2ccc(-c3nc(N)nc(NC(C)c4c[nH]c(C(F)(F)F)n4)n3)cn12] |
| 127 | 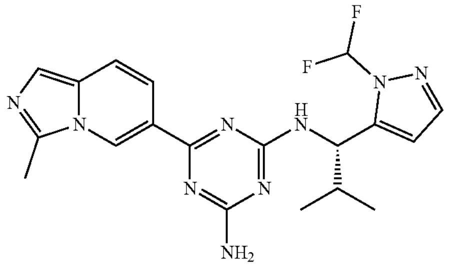 |

TABLE 1-continued
| No. | Structure |
| --- | --- |
| 128 | 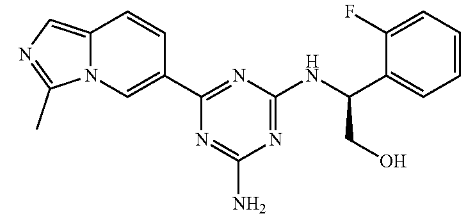 [SMILES: Cc1ncc2ccc(-c3nc(N)nc(N[C@H](CO)c4ccccc4F)n3)cn12] |
| 129 | 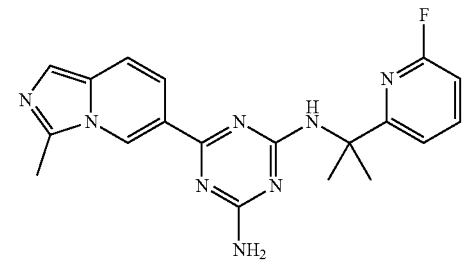 |
| 130 | 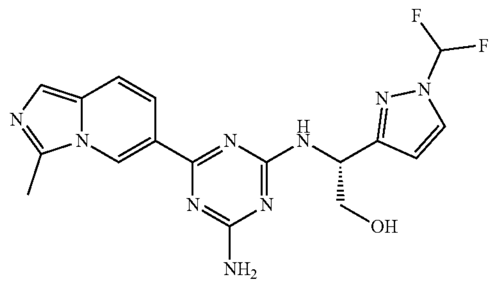 [SMILES: Cc1ncc2ccc(-c3nc(N)nc(N[C@@H](CO)c4ccn(C(F)F)n4)n3)cn12] |
| 131 | 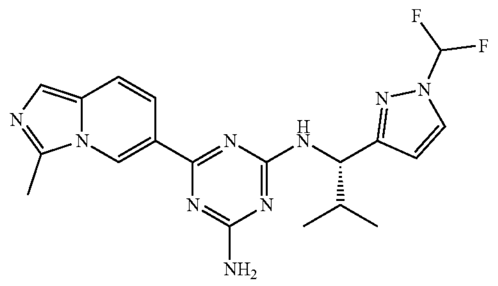 [SMILES: Cc1ncc2ccc(-c3nc(N)nc(N[C@H](c4ccn(C(F)F)n4)C(C)C)n3)cn12] |
| 132 | 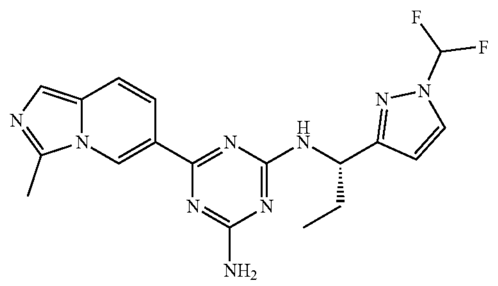 [SMILES: CC[C@H](Nc1nc(N)nc(-c2ccc3cnc(C)n3c2)n1)c1ccn(C(F)F)n1] |

TABLE 1-continued
| No. | Structure |
| --- | --- |
| 133 | 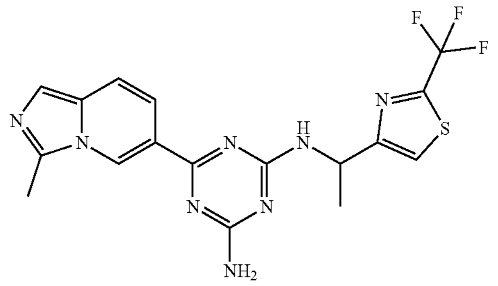 [SMILES: Cc1ncc2ccc(-c3nc(N)nc(NC(C)c4csc(C(F)(F)F)n4)n3)cn12] |
| 134 | 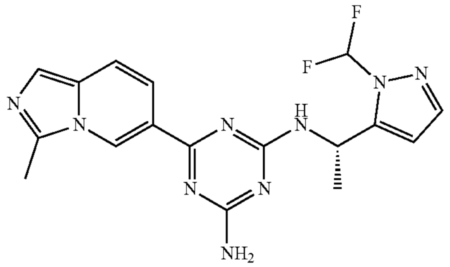 [SMILES: Cc1ncc2ccc(-c3nc(N)nc(N[C@@H](C)c4ccnn4C(F)F)n3)cn12] |
| 135 | 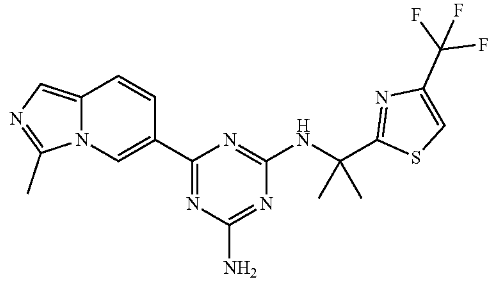 [SMILES: Cc1ncc2ccc(-c3nc(N)nc(NC(C)(C)c4nc(C(F)(F)F)cs4)n3)cn12] |
| 136 | 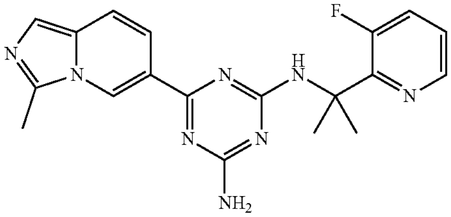 [SMILES: Cc1ncc2ccc(-c3nc(N)nc(NC(C)(C)c4ncccc4F)n3)cn12] |
| 137 | 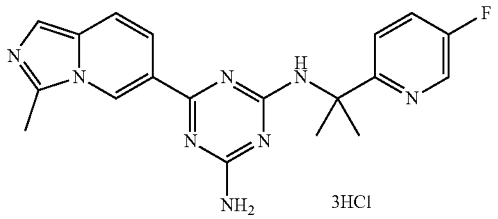 [SMILES: Cc1ncc2ccc(-c3nc(N)nc(NC(C)(C)c4ccc(F)cn4)n3)cn12] 3HCl |
| 138 | 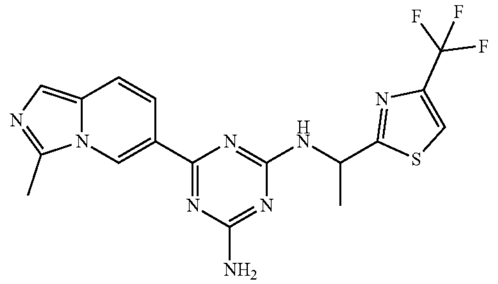 [SMILES: Cc1ncc2ccc(-c3nc(N)nc(NC(C)c4nc(C(F)(F)F)cs4)n3)cn12] |

TABLE 1-continued
| No. | Structure |
| --- | --- |
| 139 | 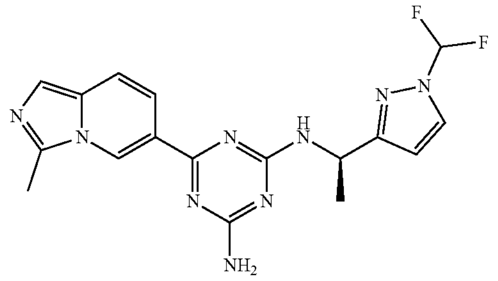 [SMILES: Cc1ncc2ccc(-c3nc(N)nc(N[C@H](C)c4ccn(C(F)F)n4)n3)cn12] |
| 140 | 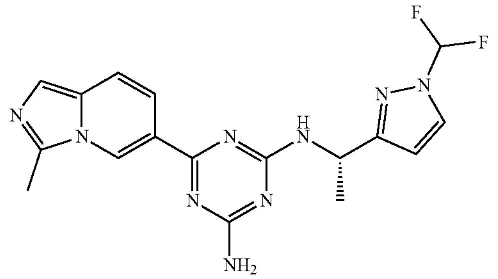 [SMILES: Cc1ncc2ccc(-c3nc(N)nc(N[C@@H](C)c4ccn(C(F)F)n4)n3)cn12] |
| 141 | 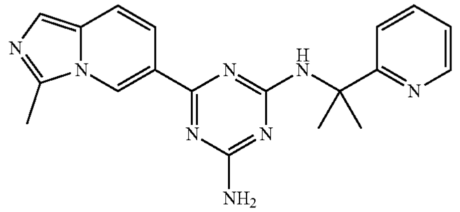 |
| 142 | 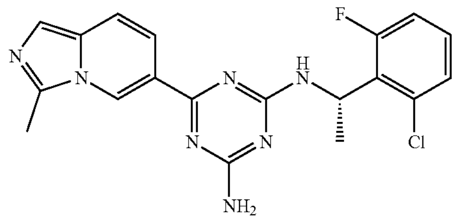 [SMILES: Cc1ncc2ccc(-c3nc(N)nc(N[C@@H](C)c4c(F)cccc4Cl)n3)cn12] |
| 143 | 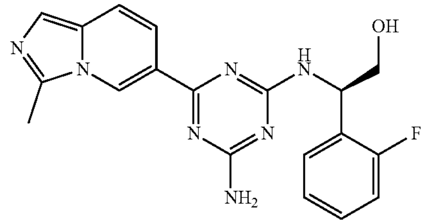 [SMILES: Cc1ncc2ccc(-c3nc(N)nc(N[C@@H](CO)c4ccccc4F)n3)cn12] |
| 144 | 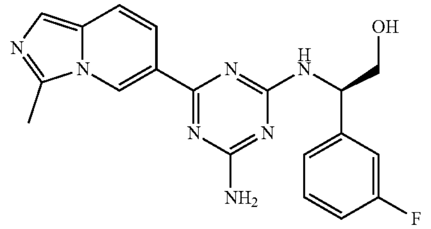 [SMILES: Cc1ncc2ccc(-c3nc(N)nc(N[C@@H](CO)c4cccc(F)c4)n3)cn12] |

TABLE 1-continued
| No. | Structure |
|---|---|
| 145 | 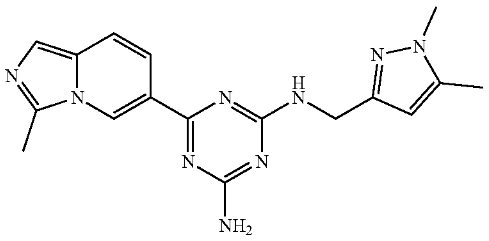 [SMILES: Cc1cc(CNc2nc(N)nc(-c3ccc4cnc(C)n4c3)n2)nn1C] |
| 146 | 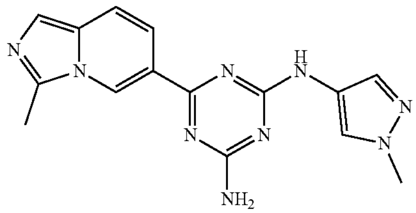 [SMILES: Cc1ncc2ccc(-c3nc(N)nc(Nc4cnn(C)c4)n3)cn12] |
| 147 | 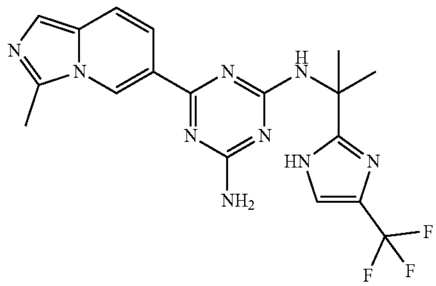 [SMILES: Cc1ncc2ccc(-c3nc(N)nc(NC(C)(C)c4nc(C(F)(F)F)c[nH]4)n3)cn12] |
| 148 | 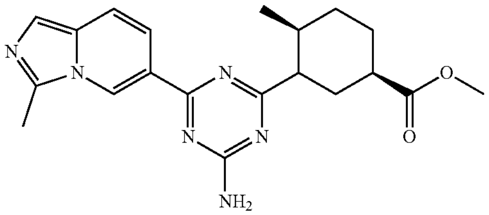 [SMILES: COC(=O)[C@@H]1CC[C@H](C)C(c2nc(N)nc(-c3ccc4cnc(C)n4c3)n2)C1] |
| 149 | 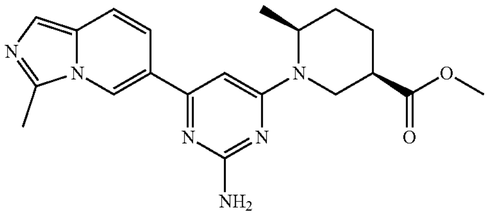 [SMILES: COC(=O)[C@@H]1CC[C@H](C)N(c2cc(-c3ccc4cnc(C)n4c3)nc(N)n2)C1] |
| 150 | 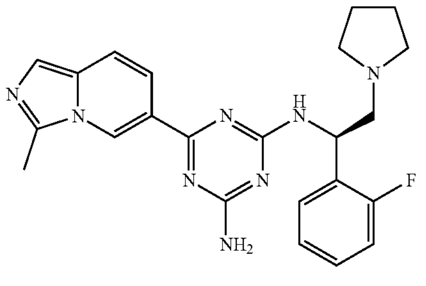 [SMILES: Cc1ncc2ccc(-c3nc(N)nc(N[C@@H](CN4CCCC4)c4ccccc4F)n3)cn12] |

TABLE 1-continued
| No. | Structure |
| --- | --- |
| 151 | 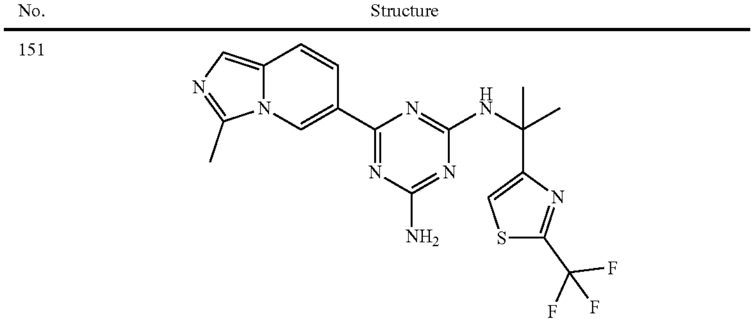 |
| 152 | 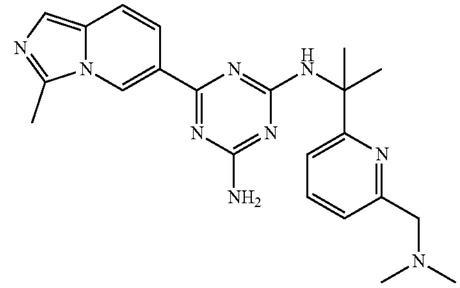 [SMILES: Cc1ncc2ccc(-c3nc(N)nc(NC(C)(C)c4cccc(CN(C)C)n4)n3)cn12] |
| 153 | 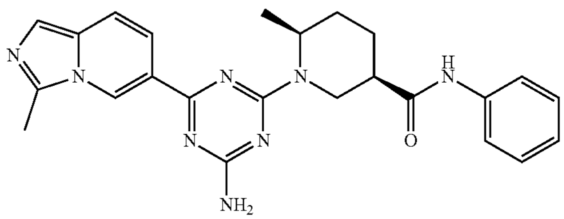 [SMILES: Cc1ncc2ccc(-c3nc(N)nc(N4C[C@H](C(=O)Nc5ccccc5)CC[C@@H]4C)n3)cn12] |
| 154 | 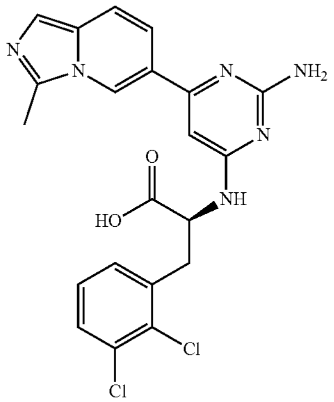 [SMILES: Cc1ncc2ccc(-c3cc(N[C@@H](Cc4cccc(Cl)c4Cl)C(=O)O)nc(N)n3)cn12] |

TABLE 1-continued
| No. | Structure |
| --- | --- |
| 155 | 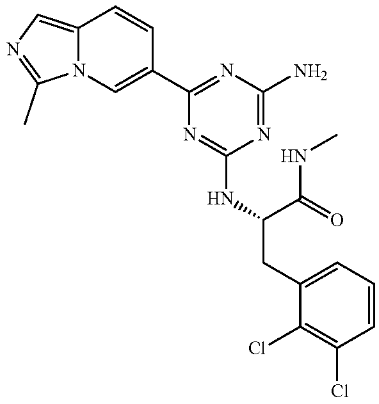 [SMILES: CNC(=O)[C@H](Cc1cccc(Cl)c1Cl)Nc1nc(N)nc(-c2ccc3cnc(C)n3c2)n1] |
| 156 | 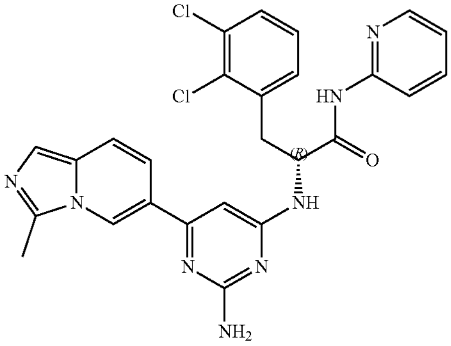 |
| 157 | 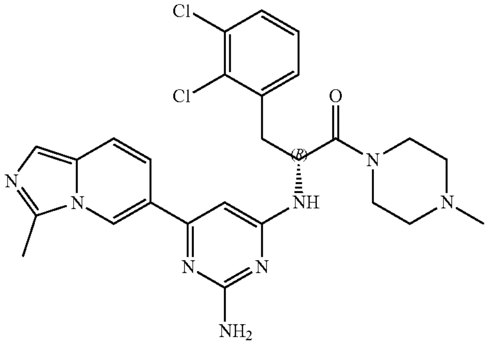 |
| 158 | 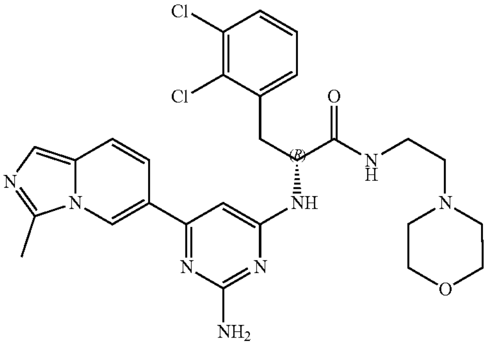 |

TABLE 1-continued
| No. | Structure |
| --- | --- |
| 159 | 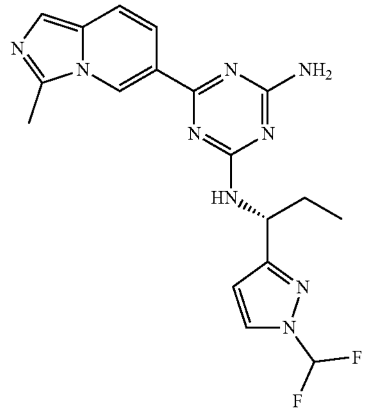 [SMILES: CC[C@@H](Nc1nc(N)nc(-c2ccc3cnc(C)n3c2)n1)c1ccn(C(F)F)n1] |
| 160 | 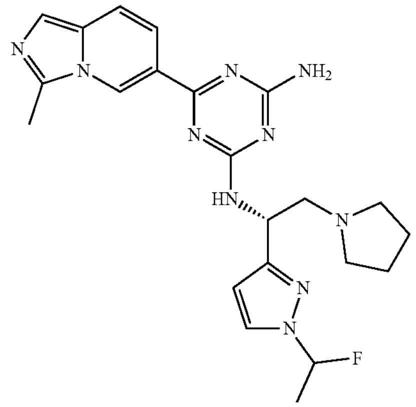 [SMILES: Cc1ncc2ccc(-c3nc(N)nc(N[C@H](CN4CCCC4)c4ccn(C(C)F)n4)n3)cn12] |
| 161 | 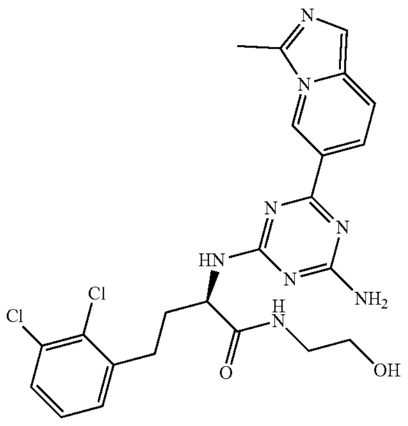 |

TABLE 1-continued
| No. | Structure |
| --- | --- |
| 162 | 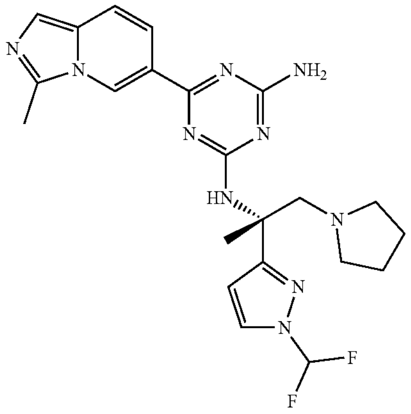 [SMILES: Cc1ncc2ccc(-c3nc(N)nc(N[C@](C)(CN4CCCC4)c4ccn(C(F)F)n4)n3)cn12] |
| 163 | 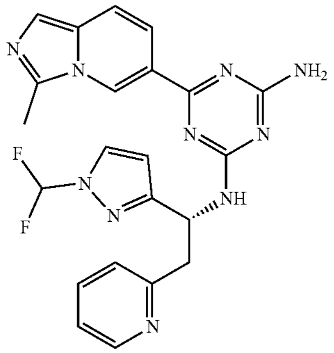 [SMILES: Cc1ncc2ccc(-c3nc(N)nc(N[C@H](Cc4ccccn4)c4ccn(C(F)F)n4)n3)cn12] |
| 164 | 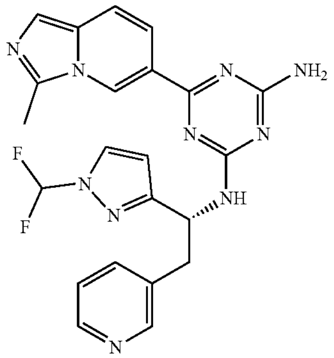 [SMILES: Cc1ncc2ccc(-c3nc(N)nc(N[C@H](Cc4cccnc4)c4ccn(C(F)F)n4)n3)cn12] |
| 165 | 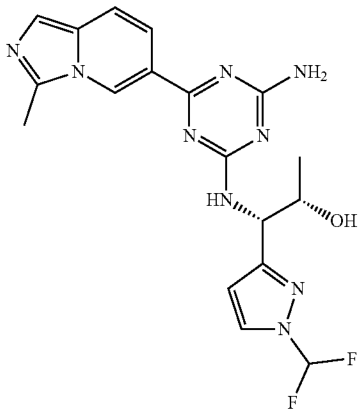 [SMILES: Cc1ncc2ccc(-c3nc(N)nc(N[C@@H](c4ccn(C(F)F)n4)[C@H](C)O)n3)cn12] |

TABLE 1-continued
| No. | Structure |
| --- | --- |
| 166 | 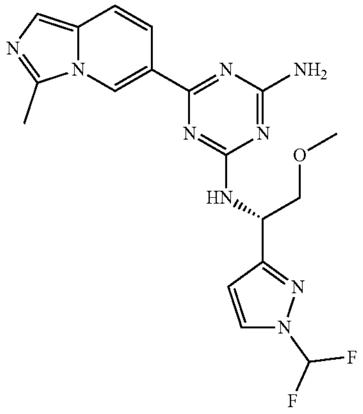 [SMILES: COC[C@@H](Nc1nc(N)nc(-c2ccc3cnc(C)n3c2)n1)c1ccn(C(F)F)n1] |
| 167 | 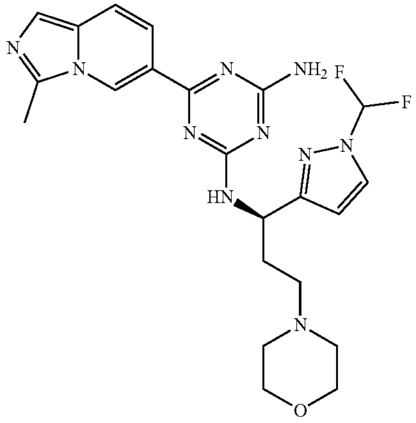 [SMILES: Cc1ncc2ccc(-c3nc(N)nc(N[C@H](CCN4CCOCC4)c4ccn(C(F)F)n4)n3)cn12] |
| 168 | 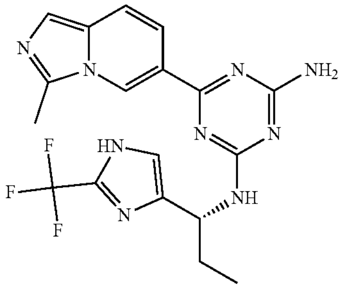 [SMILES: CC[C@@H](Nc1nc(N)nc(-c2ccc3cnc(C)n3c2)n1)c1c[nH]c(C(F)(F)F)n1] |
| 169 | 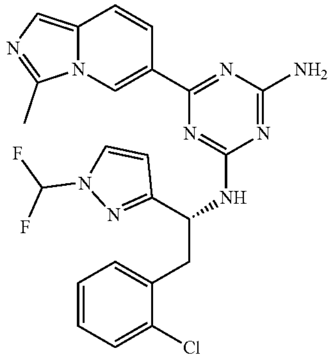 [SMILES: Cc1ncc2ccc(-c3nc(N)nc(N[C@H](Cc4ccccc4Cl)c4ccn(C(F)F)n4)n3)cn12] |

TABLE 1-continued
| No. | Structure |
| --- | --- |
| 170 | 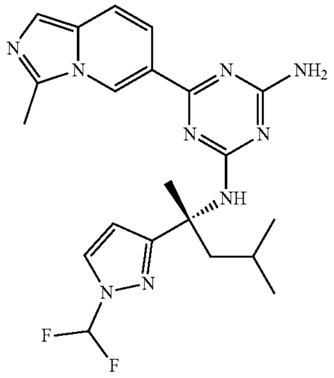 [SMILES: Cc1ncc2ccc(-c3nc(N)nc(N[C@](C)(CC(C)C)c4ccn(C(F)F)n4)n3)cn12] |
| 171 | 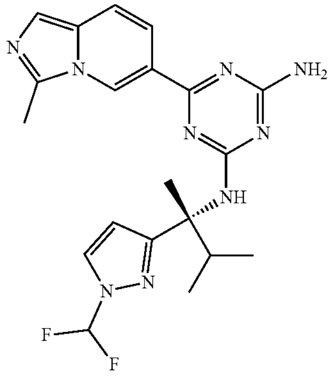 [SMILES: Cc1ncc2ccc(-c3nc(N)nc(N[C@@](C)(c4ccn(C(F)F)n4)C(C)C)n3)cn12] |
| 172 | 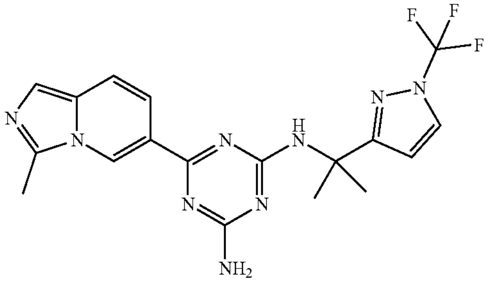 [SMILES: Cc1ncc2ccc(-c3nc(N)nc(NC(C)(C)c4ccn(C(F)(F)F)n4)n3)cn12] |
| 173 | 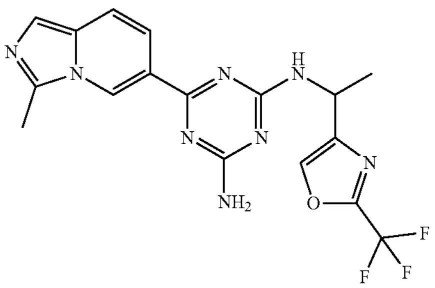 [SMILES: Cc1ncc2ccc(-c3nc(N)nc(NC(C)c4coc(C(F)(F)F)n4)n3)cn12] |

TABLE 1-continued
| No. | Structure |
| --- | --- |
| 174 | 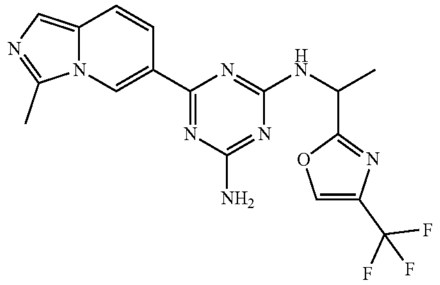 [SMILES: Cc1ncc2ccc(-c3nc(N)nc(NC(C)c4nc(C(F)(F)F)co4)n3)cn12] |
| 175 | 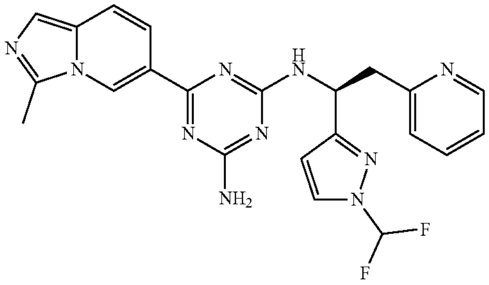 [SMILES: Cc1ncc2ccc(-c3nc(N)nc(N[C@@H](Cc4ccccn4)c4ccn(C(F)F)n4)n3)cn12] |
| 176 | 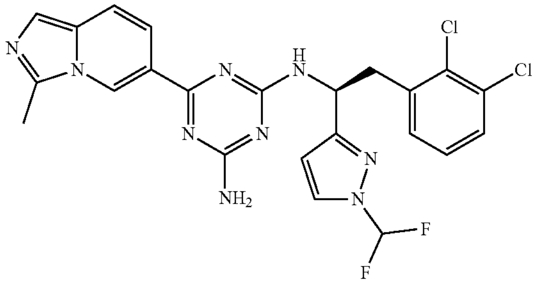 [SMILES: Cc1ncc2ccc(-c3nc(N)nc(N[C@@H](Cc4cccc(Cl)c4Cl)c4ccn(C(F)F)n4)n3)cn12] |
| 177 | 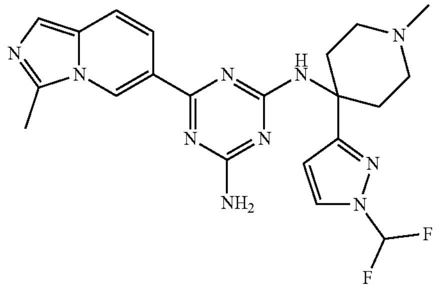 [SMILES: Cc1ncc2ccc(-c3nc(N)nc(NC4(c5ccn(C(F)F)n5)CCN(C)CC4)n3)cn12] |
| 178 | 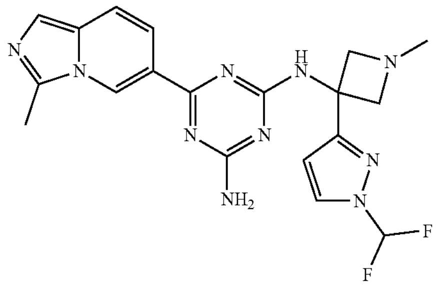 [SMILES: Cc1ncc2ccc(-c3nc(N)nc(NC4(c5ccn(C(F)F)n5)CN(C)C4)n3)cn12] |

TABLE 1-continued
| No. | Structure |
| --- | --- |
| 179 | 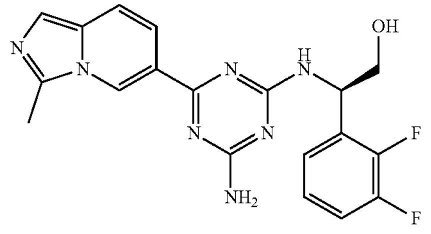 [SMILES: Cc1ncc2ccc(-c3nc(N)nc(N[C@@H](CO)c4cccc(F)c4F)n3)cn12] |
| 180 | 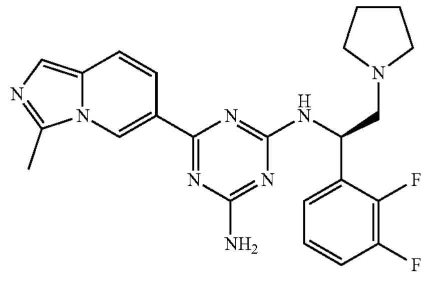 [SMILES: Cc1ncc2ccc(-c3nc(N)nc(N[C@@H](CN4CCCC4)c4cccc(F)c4F)n3)cn12] |
| 181 | 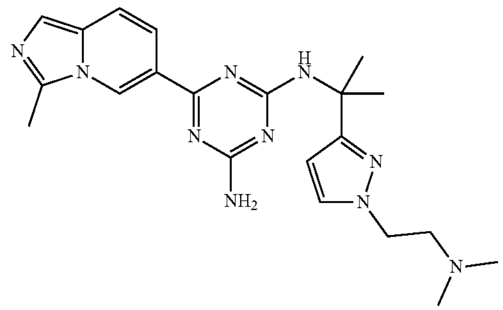 [SMILES: Cc1ncc2ccc(-c3nc(N)nc(NC(C)(C)c4ccn(CCN(C)C)n4)n3)cn12] |
| 182 | 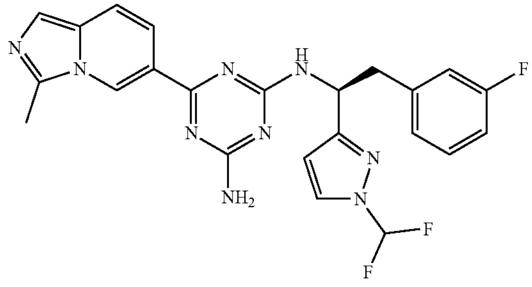 [SMILES: Cc1ncc2ccc(-c3nc(N)nc(N[C@@H](Cc4cccc(F)c4)c4ccn(C(F)F)n4)n3)cn12] |
| 183 | 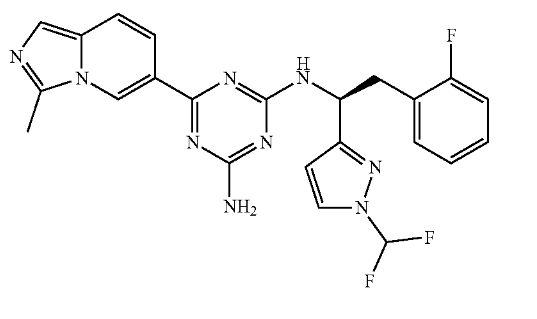 [SMILES: Cc1ncc2ccc(-c3nc(N)nc(N[C@@H](Cc4ccccc4F)c4ccn(C(F)F)n4)n3)cn12] |

TABLE 1-continued
| No. | Structure |
| --- | --- |
| 184 | 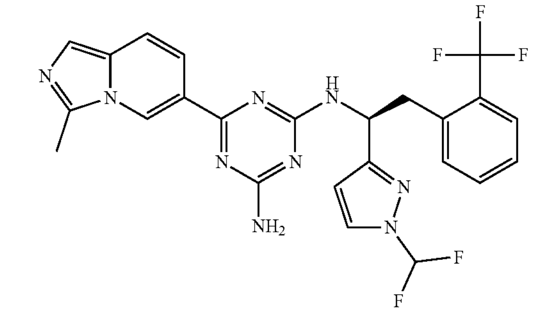 [SMILES: Cc1ncc2ccc(-c3nc(N)nc(N[C@@H](Cc4ccccc4C(F)(F)F)c4ccn(C(F)F)n4)n3)cn12] |
| 185 | 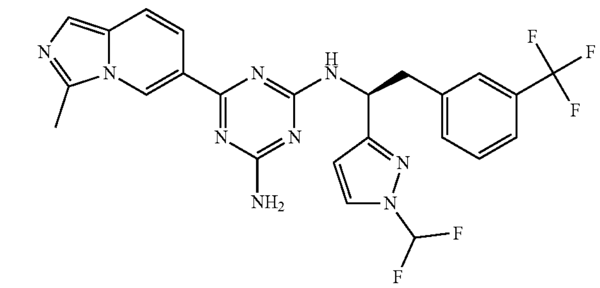 [SMILES: Cc1ncc2ccc(-c3nc(N)nc(N[C@@H](Cc4cccc(C(F)(F)F)c4)c4ccn(C(F)F)n4)n3)cn12] |
| 186 | 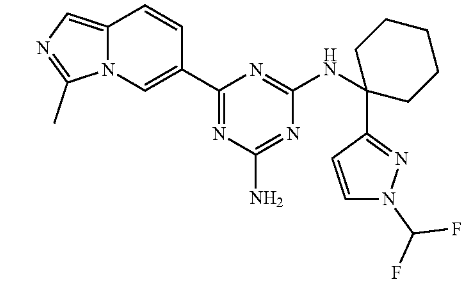 [SMILES: Cc1ncc2ccc(-c3nc(N)nc(NC4(c5ccn(C(F)F)n5)CCCCC4)n3)cn12] |
| 187 | 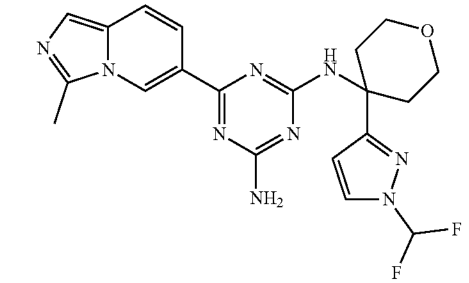 [SMILES: Cc1ncc2ccc(-c3nc(N)nc(NC4(c5ccn(C(F)F)n5)CCOCC4)n3)cn12] |
| 188 | 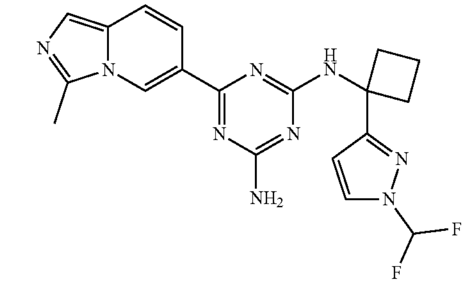 [SMILES: Cc1ncc2ccc(-c3nc(N)nc(NC4(c5ccn(C(F)F)n5)CCC4)n3)cn12] |

TABLE 1-continued
| No. | Structure |
| --- | --- |
| 189 | 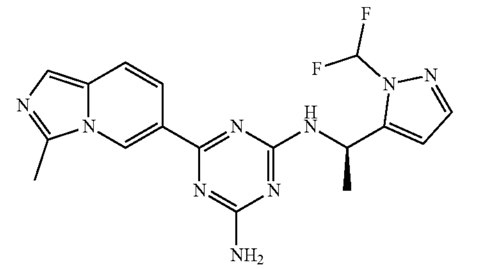 [SMILES: Cc1ncc2ccc(-c3nc(N)nc(N[C@H](C)c4ccnn4C(F)F)n3)cn12] |
| 190 | 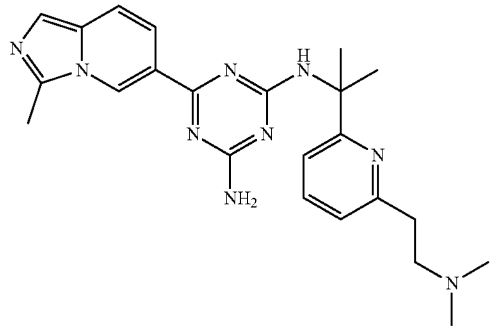 [SMILES: Cc1ncc2ccc(-c3nc(N)nc(NC(C)(C)c4cccc(CCN(C)C)n4)n3)cn12] |
| 191 | 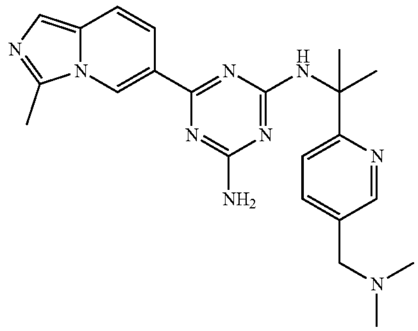 [SMILES: Cc1ncc2ccc(-c3nc(N)nc(NC(C)(C)c4ccc(CN(C)C)cn4)n3)cn12] |
| 192 | 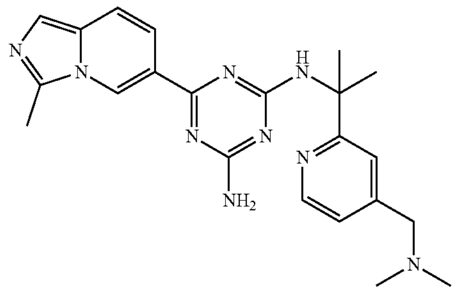 [SMILES: Cc1ncc2ccc(-c3nc(N)nc(NC(C)(C)c4cc(CN(C)C)ccn4)n3)cn12] |
| 193 | 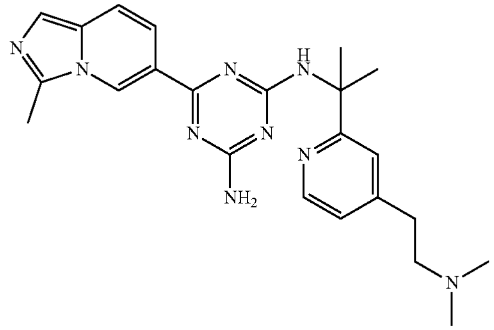 [SMILES: Cc1ncc2ccc(-c3nc(N)nc(NC(C)(C)c4cc(CCN(C)C)ccn4)n3)cn12] |

TABLE 1-continued
| No. | Structure |
| --- | --- |
| 194 | 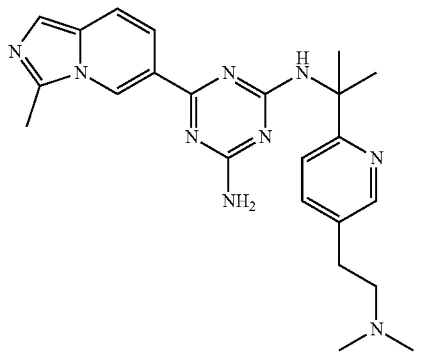 [SMILES: Cc1ncc2ccc(-c3nc(N)nc(NC(C)(C)c4ccc(CCN(C)C)cn4)n3)cn12] |
| 195 | 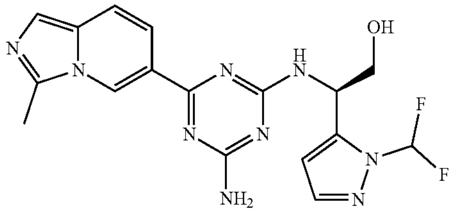 [SMILES: Cc1ncc2ccc(-c3nc(N)nc(N[C@@H](CO)c4ccnn4C(F)F)n3)cn12] |
| 196 | 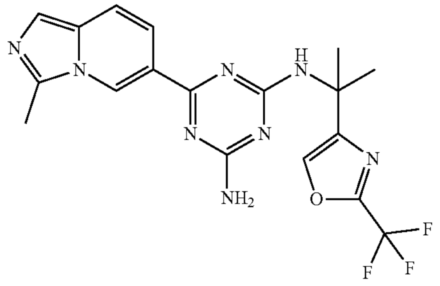 [SMILES: Cc1ncc2ccc(-c3nc(N)nc(NC(C)(C)c4coc(C(F)(F)F)n4)n3)cn12] |
| 197 | 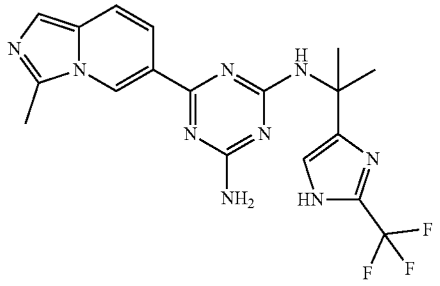 [SMILES: Cc1ncc2ccc(-c3nc(N)nc(NC(C)(C)c4c[nH]c(C(F)(F)F)n4)n3)cn12] |
| 198 | 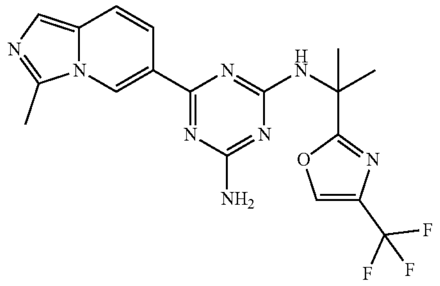 [SMILES: Cc1ncc2ccc(-c3nc(N)nc(NC(C)(C)c4nc(C(F)(F)F)co4)n3)cn12] |

TABLE 1-continued
| No. | Structure |
| --- | --- |
| 199 | 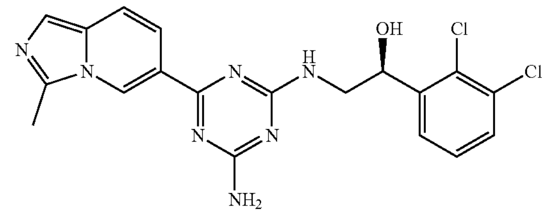 [SMILES: Cc1ncc2ccc(-c3nc(N)nc(NC[C@@H](O)c4cccc(Cl)c4Cl)n3)cn12] |
| 200 | 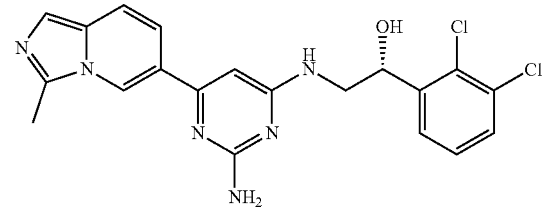 [SMILES: Cc1ncc2ccc(-c3cc(NC[C@H](O)c4cccc(Cl)c4Cl)nc(N)n3)cn12] |
| 201 | 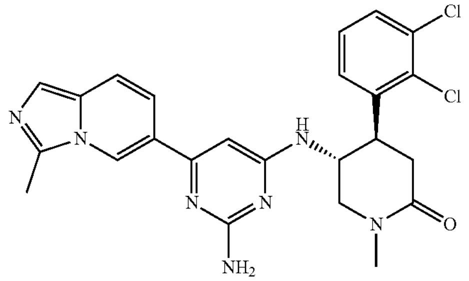 [SMILES: Cc1ncc2ccc(-c3cc(N[C@H]4CN(C)C(=O)C[C@@H]4c4cccc(Cl)c4Cl)nc(N)n3)cn12] |
| 202 | 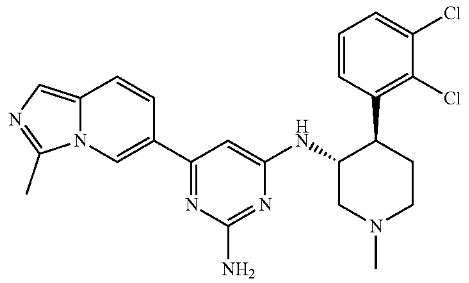 [SMILES: Cc1ncc2ccc(-c3cc(N[C@H]4CN(C)CC[C@@H]4c4cccc(Cl)c4Cl)nc(N)n3)cn12] |
| 203 | 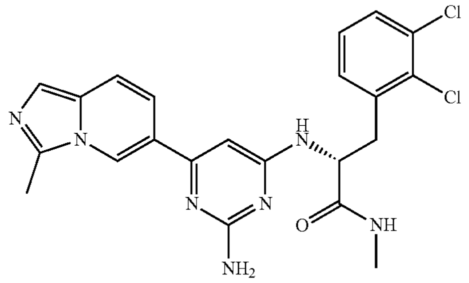 [SMILES: CNC(=O)[C@@H](Cc1cccc(Cl)c1Cl)Nc1cc(-c2ccc3cnc(C)n3c2)nc(N)n1] |
| 204 | 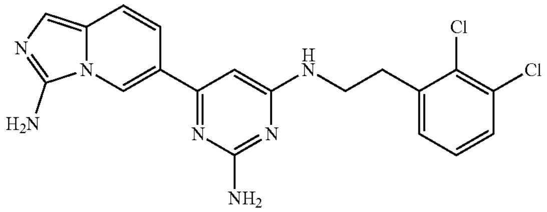 [SMILES: Nc1nc(NCCc2cccc(Cl)c2Cl)cc(-c2ccc3cnc(N)n3c2)n1] |

TABLE 1-continued
| No. | Structure |
|---|---|
| 205 | 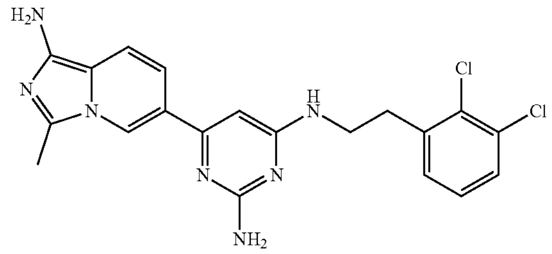 [SMILES: Cc1nc(N)c2ccc(-c3cc(NCCc4cccc(Cl)c4Cl)nc(N)n3)cn12] |
| 206 | 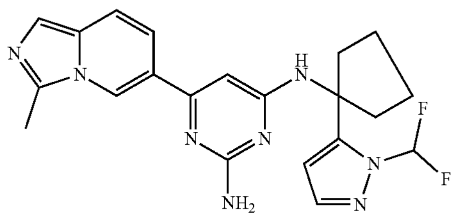 [SMILES: Cc1ncc2ccc(-c3cc(NC4(c5ccnn5C(F)F)CCCC4)nc(N)n3)cn12] |
| 207 | 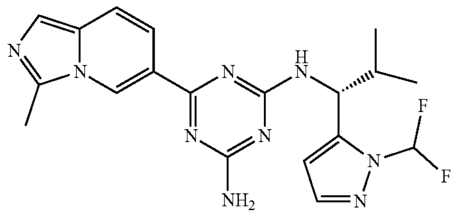 [SMILES: Cc1ncc2ccc(-c3nc(N)nc(N[C@@H](c4ccnn4C(F)F)C(C)C)n3)cn12] |
| 208 | 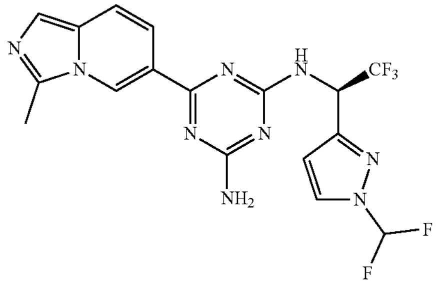 [SMILES: Cc1ncc2ccc(-c3nc(N)nc(N[C@H](c4ccn(C(F)F)n4)C(F)(F)F)n3)cn12] |
| 209 | 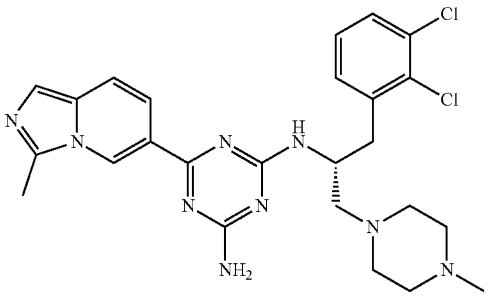 [SMILES: Cc1ncc2ccc(-c3nc(N)nc(N[C@H](Cc4cccc(Cl)c4Cl)CN4CCN(C)CC4)n3)cn12] |
| 210 | 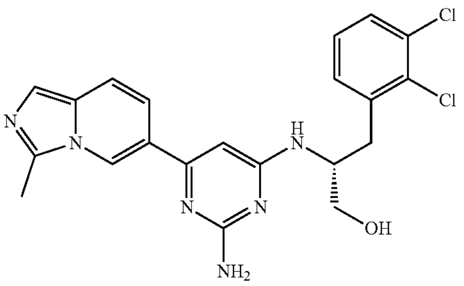 [SMILES: Cc1ncc2ccc(-c3cc(N[C@@H](CO)Cc4cccc(Cl)c4Cl)nc(N)n3)cn12] |

TABLE 1-continued
| No. | Structure |
| --- | --- |
| 211 | 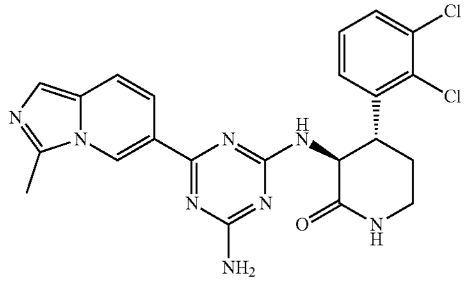 [SMILES: Cc1ncc2ccc(-c3nc(N)nc(N[C@@H]4C(=O)NCC[C@H]4c4cccc(Cl)c4Cl)n3)cn12] |
| 212 | 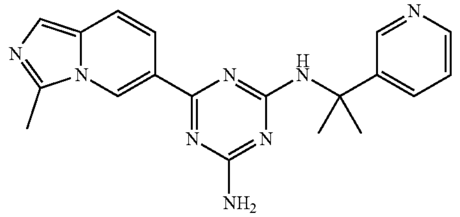 [SMILES: Cc1ncc2ccc(-c3nc(N)nc(NC(C)(C)c4cccnc4)n3)cn12] |
| 213 | 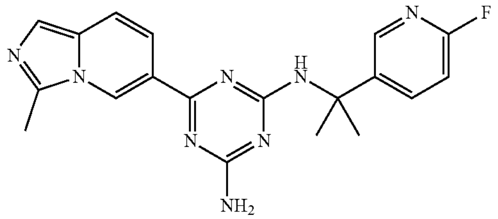 [SMILES: Cc1ncc2ccc(-c3nc(N)nc(NC(C)(C)c4ccc(F)nc4)n3)cn12] |
| 214 | 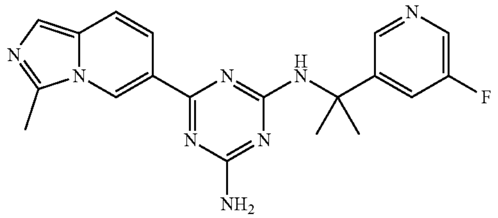 [SMILES: Cc1ncc2ccc(-c3nc(N)nc(NC(C)(C)c4cncc(F)c4)n3)cn12] |
| 215 | 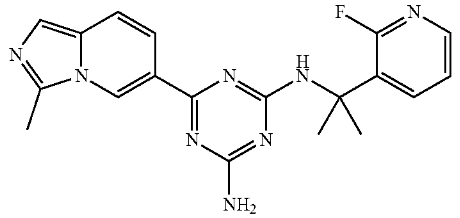 [SMILES: Cc1ncc2ccc(-c3nc(N)nc(NC(C)(C)c4cccnc4F)n3)cn12] |
| 216 | 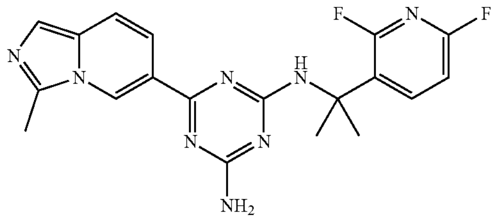 [SMILES: Cc1ncc2ccc(-c3nc(N)nc(NC(C)(C)c4ccc(F)nc4F)n3)cn12] |

TABLE 1-continued
| No. | Structure |
| --- | --- |
| 217 | 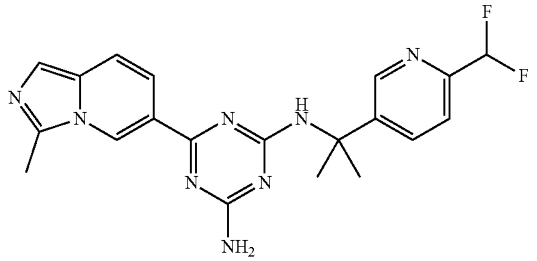 [SMILES: Cc1ncc2ccc(-c3nc(N)nc(NC(C)(C)c4ccc(C(F)F)nc4)n3)cn12] |
| 218 | 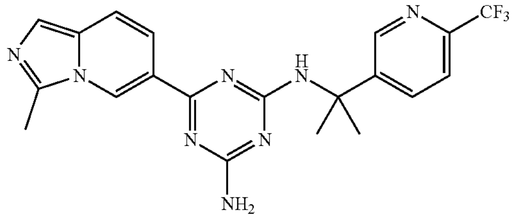 [SMILES: Cc1ncc2ccc(-c3nc(N)nc(NC(C)(C)c4ccc(C(F)(F)F)nc4)n3)cn12] |
| 219 | 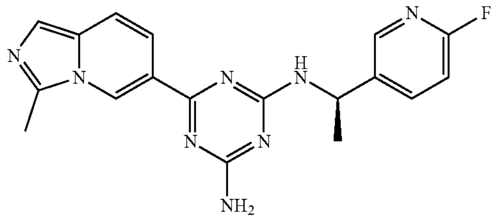 [SMILES: Cc1ncc2ccc(-c3nc(N)nc(N[C@H](C)c4ccc(F)nc4)n3)cn12] |
| 220 | 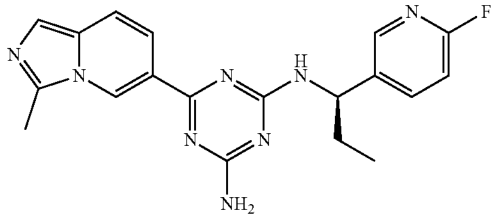 [SMILES: CC[C@@H](Nc1nc(N)nc(-c2ccc3cnc(C)n3c2)n1)c1ccc(F)nc1] |
| 221 | 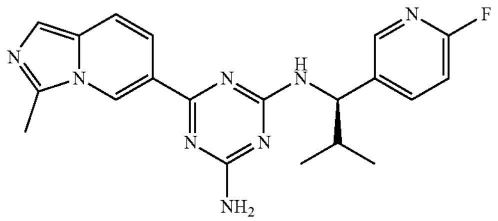 [SMILES: Cc1ncc2ccc(-c3nc(N)nc(N[C@@H](c4ccc(F)nc4)C(C)C)n3)cn12] |
| 222 | 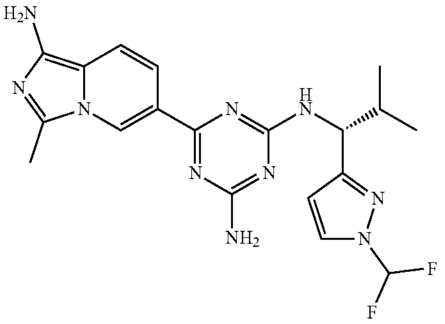 [SMILES: Cc1nc(N)c2ccc(-c3nc(N)nc(N[C@@H](c4ccn(C(F)F)n4)C(C)C)n3)cn12] |

TABLE 1-continued
| No. | Structure |
|---|---|
| 223 | 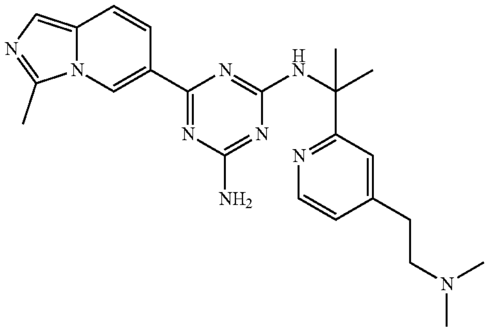 [SMILES: Cc1ncc2ccc(-c3nc(N)nc(NC(C)(C)c4cc(CCN(C)C)ccn4)n3)cn12] |
| 224 | 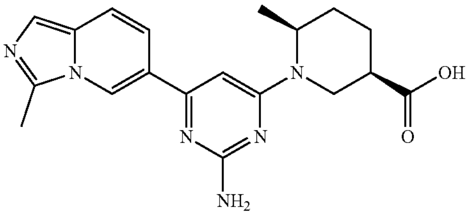 [SMILES: Cc1ncc2ccc(-c3cc(N4C[C@H](C(=O)O)CC[C@@H]4C)nc(N)n3)cn12] |
| 225 | 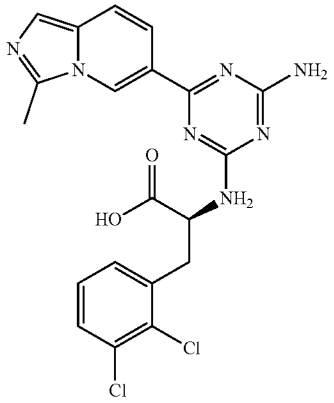 [SMILES: Cc1ncc2ccc(-c3nc(N)nc(N[C@@H](Cc4cccc(Cl)c4Cl)C(=O)O)n3)cn12] |
| 226 | 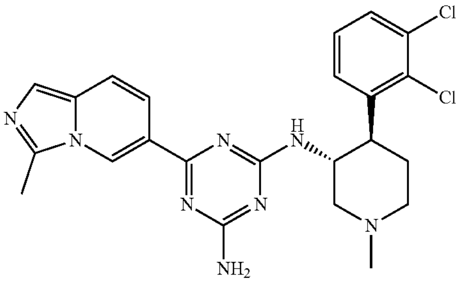 |
| 227 | 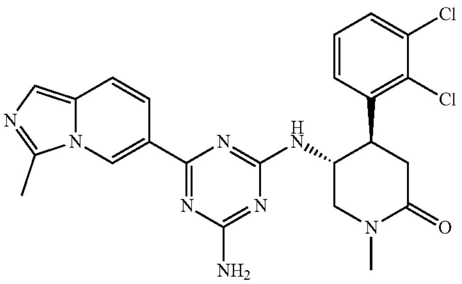 [SMILES: Cc1ncc2ccc(-c3nc(N)nc(N[C@H]4CN(C)C(=O)C[C@@H]4c4cccc(Cl)c4Cl)n3)cn12] |

TABLE 1-continued

| No. | Structure |
| --- | --- |
| 228 | 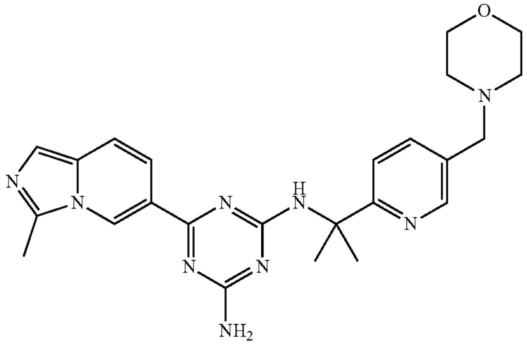 [SMILES: Cc1ncc2ccc(-c3nc(N)nc(NC(C)(C)c4ccc(CN5CCOCC5)cn4)n3)cn12] |
| 229 | 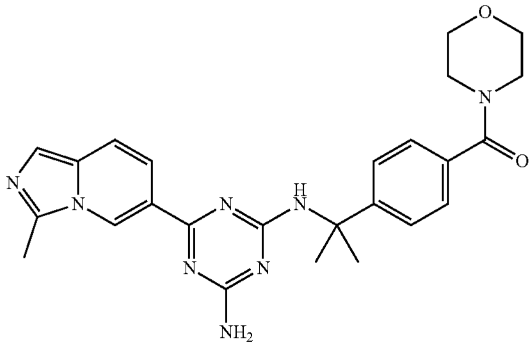 [SMILES: Cc1ncc2ccc(-c3nc(N)nc(NC(C)(C)c4ccc(C(=O)N5CCOCC5)cc4)n3)cn12] |

In certain embodiments there is provided a compound selected from any one of the Examples herein, or a pharmaceutically acceptable salt thereof.

Pharmaceutical Compositions

In accordance with another aspect, the present invention provides a pharmaceutical composition comprising a compound of the invention, or a pharmaceutically acceptable salt thereof, and a pharmaceutically acceptable excipient.

Conventional procedures for the selection and preparation of suitable pharmaceutical compositions are described in, for example, "Pharmaceuticals—The Science of Dosage Form Designs", M. E. Aulton, Churchill Livingstone, 1988.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intraperitoneal dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of a condition is an amount sufficient to symptomatically relieve in a warm-blooded animal, particularly a human the symptoms of the condition or to slow the progression of the condition.

The amount of active ingredient that is combined with one or more excipients to produce a single dosage form will necessarily vary depending upon the host treated and the particular route of administration. For example, a formulation intended for oral administration to humans will generally contain, for example, from 0.1 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the invention will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, a daily dose selected from 0.1 mg/kg to 100 mg/kg, 1 mg/kg to 750 mg/kg, 1 mg/kg to 600 mg/kg, 1 mg/kg to 550 mg/kg, 1 mg/kg to 75 mg/kg, 1 mg/kg to 50 mg/kg, 1 mg/kg to 20 mg/kg or 5 mg/kg to 10 mg/kg body weight is received, given if required in divided doses. In general, lower doses will be administered when a parenteral route is employed. Thus, for example, for intravenous, subcutaneous, intramuscular or intraperitoneal administration, a dose in the range, for example, 0.1 mg/kg to 30 mg/kg body weight will generally be used. In certain embodiments the compound of the invention is administered intravenously, for example in a daily dose of from 1 mg/kg to 750 mg/kg, 1 mg/kg to 600 mg/kg, 1 mg/kg to 550 mg/kg, or 5 mg/kg to 550 mg/kg, for example at about 10, 20, 30, 40, 50, 60, 70, 80, 90, 100, 125, 150, 175, 180, 200, 225, 250, 275, 300, 350, 400, 450, 500, 540, 550 or 575 mg/kg. Similarly, for administration by inhalation, a dose in the range, for example, 0.05 mg/kg to 25 mg/kg body weight will be used. Suitably the compound of the invention is administered orally, for example in the form of a tablet, or capsule dosage form. The daily dose administered orally may be, for example a total daily dose selected from 1 mg to 1000 mg, 5 mg to 1000 mg, 10 mg to 750 mg or 25 mg to 500 mg. Typically, unit dosage forms will contain about 0.5 mg to 0.5 g of a compound of this invention. In a particular embodiment the compound of the invention is administered parenterally, for example by intravenous administration. In another particular embodiment the compound of the invention is administered orally.

Therapeutic Uses and Applications

In accordance with another aspect, the present invention provides a compound of the invention, or a pharmaceutically acceptable salt thereof, for use as a medicament.

A further aspect of the invention provides the compound of the invention, or a pharmaceutically acceptable salt thereof, is for use in the treatment of a disease or medical condition mediated by microtubule associated serine/threonine-like kinase (MASTL).

Also provided is the use of a compound of the invention, or a pharmaceutically acceptable salt thereof, in the manufacture of a medicament for the treatment of a disease or medical condition mediated by MASTL.

Also provided is a method of treating a disease or medical condition mediated by MASTL in a subject in need thereof, the method comprising administering to the subject an effective amount of a compound of the invention, or a pharmaceutically acceptable salt thereof.

In the following sections of the application reference is made to a compound of the invention, or a pharmaceutically acceptable salt thereof for use in the treatment of certain diseases or conditions. It is to be understood that any reference herein to a compound for a particular use is also intended to be a reference to (i) the use of the compound of the invention, or pharmaceutically acceptable salt thereof, in the manufacture of a medicament for the treatment of that disease or condition; and (ii) a method of treating the disease or condition in a subject, the method comprising administering to the subject a therapeutically effective amount of the compound of the invention, or pharmaceutically acceptable salt thereof.

The disease of medical condition mediated by MASTL may be any of the diseases or medical conditions listed in this application, for example a proliferative disease, particularly cancer.

The subject to which the compound of the invention is administered may be a warm-blooded mammal, for example human or animal. In particular embodiments the subject or patient is a human. In other embodiments the subject is an animal, for example a rat, mouse, dog, cat, a primate or a horse.

The association of MASTL with diseases in humans and animals is set out in the Background of the Invention. This disclosure and the associated references provide further support for the therapeutic uses of the compounds of the invention. As such the supporting references linking MASTL with diseases and conditions also form part of the disclosure of the utility of the compounds of the invention in the treatment and prevention of the medical conditions described herein.

Proliferative Diseases

MASTL has been shown to play a role in a number of diseases, including various cancers, and there is growing interest in the use of MASTL inhibitors as a therapeutic strategy (Marzec and Burgess, The Oncogenic Functions of MASTL Kinase, Front Cell Dev. Biol. (2018); 6:162). This is supported by the observation that MASTL inhibition is able to reduce tumour growth in vitro and in vivo (Wang et al., (2014), Vera et al., (2015), Anania et al., (2015), Alvarez-Fernandez et al., (2018)). MASTL depletion has been shown to increase the radiosensitivity of breast cancer cells and reduce the formation of radioresistant breast cancer cells suggesting the therapeutic combination of MASTL inhibitors with radiotherapy (Yoon et al., MASTL inhibition promotes mitotic catastrophe through PP2A activation to inhibit cancer growth and radioresistance in breast cancer cells, BMC Cancer (2018) 18, 716). Knockdown of MASTL was also found to reduce the viability of thyroid cancer cells without significantly affecting normal cell proliferation (Anania et al., 2015), suggesting that MASTL inhibitors may be relatively non-toxic.

In certain embodiments the compounds of the invention are for use in the treatment of proliferative diseases, including cancer and benign proliferative disease.

Cancer

In certain embodiments a compound of the invention is for use in the prevention or inhibition of cancer progression, for example by preventing or inhibiting cancer cell migration, cancer cell invasion and/or preventing or inhibiting cancer metastasis.

In certain embodiments the compounds of the invention are for use in the treatment of a cancer.

In certain embodiments the compounds of the invention are for use in the treatment of a cancer that overexpresses MASTL.

Compounds of the invention may useful in the treatment and/or prevention of, for example:

Carcinoma, including for example tumours derived from stratified squamous epithelia (squamous cell carcinomas) and tumours arising within organs or glands (adenocarcinomas). Examples include breast, colon, lung, prostate, ovary, esophageal carcinoma (including, but not limited to, esophageal adenocarcinoma and squamous cell carcinoma), basal-like breast carcinoma, basal cell carcinoma (a form of skin cancer), squamous cell carcinoma (various tissues), head and neck carcinoma (including, but not limited to, squamous cell carcinomas), stomach carcinoma (including, but not limited to, stomach adenocarcinoma, gastrointestinal stromal tumour), signet ring cell carcinoma, bladder carcinoma (including transitional cell carcinoma (a malignant neoplasm of the bladder)), bronchogenic carcinoma, colorectal carcinoma (including, but not limited to, colon carcinoma and rectal carcinoma), anal carcinoma, gastric carcinoma, lung carcinoma (including but not limited to small cell carcinoma and non-small cell carcinoma of the lung, lung adenocarcinoma, squamous cell carcinoma, large cell carcinoma, bronchioloalveolar carcinoma, and mesothelioma), neuroendocrine tumours (including but not limited to carcinoids of the gastrointestinal tract, breast, and other organs), adrenocortical carcinoma, thyroid carcinoma, pancreatic carcinoma, breast carcinoma (including, but not limited to, ductal carcinoma, lobular carcinoma, inflammatory breast cancer, clear cell carcinoma, mucinous carcinoma), ovarian carcinoma (including, but not limited to, ovarian epithelial carcinoma or surface epithelial-stromal tumour including serous tumour, endometrioid tumour and mucinous cystadenocarcinoma, sex-cord-stromal tumour), liver and bile duct carcinoma (including, but not limited to, hepatocellular carcinoma, cholangiocarcinoma and hemangioma), prostate carcinoma, adenocarcinoma, brain tumours (including, but not limited to glioma, glioblastoma and medulloblastoma), germ cell tumours, sweat gland carcinoma, sebaceous gland carcinoma, papillary carcinoma, papillary adenocarcinoma, cystadenocarcinoma, kidney carcinoma (including, but not limited to, renal cell carcinoma, clear cell carcinoma and Wilm's tumour), medullary carcinoma, ductal carcinoma in situ or bile duct carcinoma, choriocarcinoma, seminoma, embryonal carcinoma, cervical carcinoma, uterine carcinoma (including, but not limited to, endometrial adenocarcinoma, uterine papillary serous carcinoma, uterine clear-cell carcinoma, uterine sarcomas and leiomyosarcomas, mixed mullerian tumours), testicular carcinoma, osteogenic carcinoma, epithelial carcinoma, sarcomatoid carcinoma, nasopharyngeal carcinoma, laryngeal carcinoma; oral and oropharyngeal squamous carcinoma;

Sarcomas, including: osteosarcoma and osteogenic sarcoma (bone); chondrosarcoma (cartilage); leiomyosarcoma (smooth muscle); rhabdomyosarcoma (skeletal muscle); mesothelial sarcoma and mesothelioma (membranous lining of body cavities); fibrosarcoma (fibrous tissue); angiosarcoma and hemangioendothelioma (blood vessels); liposarcoma (adipose tissue); glioma and astrocytoma (neurogenic connective tissue found in the brain); myxosarcoma (primitive embryonic connective tissue); chordoma, endotheliosarcoma, lymphangiosarcoma, lymphangioendotheliosarcoma, synovioma, Ewing's sarcoma, mesenchymous and mixed mesodermal tumour (mixed connective tissue types) and other soft tissue sarcomas;

Solid tumours of the nervous system including medulloblastoma, craniopharyngioma, ependymoma, pinealoma, hemangioblastoma, acoustic neuroma, oligodendroglioma, meningioma, neuroblastoma and schwannoma;

Melanoma, uveal melanoma and retinoblastoma;

Myeloma and multiple myeloma, including light chain myeloma, non secretory myeloma, plasmacytoma, amyloidosis, smoldering multiple myeloma (SMM), immunoglobulin D myeloma, immunoglobulin E myeloma, and conditions related to myeloma including monoclonal gammopathy of undetermined significance (MGUS);

Hematopoietic tumours, including: myelogenous and granulocytic leukaemia (malignancy of the myeloid and granulocytic white blood cell series, e.g. acute myeloid leukemia (AML)); lymphatic, lymphocytic, and lymphoblastic leukaemia (malignancy of the lymphoid and lymphocytic blood cell series); polycythemia vera and erythremia (malignancy of various blood cell products, but with red cells predominating); myelofibrosis; and Lymphomas, including: Hodgkin and Non-Hodgkin lymphomas.

In some embodiments, a compound of the invention, or a pharmaceutically acceptable salt thereof is for use in the treatment of a solid tumour, for example any of the solid tumours listed above.

In certain embodiments the compounds of the invention are for use in the treatment of a cancer selected from: breast, ovarian, lung, colorectal, prostate, oral, gastric, adrenocortical, pancreatic, kidney, sarcoma, liver, endometrial, thyroid, head or neck, brain (e.g. glioma), melanoma (e.g. ocular melanoma) and haematological cancer (e.g. leukaemia, such as AML, lymphoma, myeloma and multiple myeloma).

In another embodiment the compound of the invention, or a pharmaceutically acceptable salt thereof, is for use in the treatment of a breast cancer selected from Luminal A breast cancer (hormone-receptor positive (estrogen-receptor and/or progesterone-receptor positive), HER2 negative and low levels of the protein Ki-67); Luminal B breast cancer (hormone-receptor positive (estrogen-receptor and/or progesterone-receptor positive), and either HER2 positive or HER2 negative with high levels of Ki-67); triple negative breast cancer (i.e. the tumour is estrogen receptor-negative, progesterone receptor-negative and HER2-negative); HER2 positive breast cancer or normal-like breast cancer (classifications as defined in Table 1 of Dai et al. Am. J. Cancer Research. 2015; 5(10):2929-2943).

In an embodiment a compound of the invention, or a pharmaceutically acceptable salt thereof is for use in the treatment of a cancer selected from: pancreatic cancer, triple negative breast cancer (i.e. the tumour is estrogen receptor-negative, progesterone receptor-negative and HER2-negative), hormone refractory prostate cancer and non-small cell lung cancer.

In embodiments the compounds of the invention provide an anti-cancer effect on a cancer (for example any of the cancers disclosed herein) selected from one or more of an anti-proliferative effect, a pro-apoptotic effect, an anti-mitotic effect an antiangiogenic effect, inhibition of cell migration, inhibition or prevention of tumour invasion and/or preventing or inhibiting metastasis.

Compounds of the invention may be used to prevent or inhibit the progression of a cancer. A compound of the invention may be for use in slowing, delaying or stopping cancer progression. The progress of a cancer is typically determined by assigning a stage to the cancer. Staging is typically carried out by assigning a number from I to IV to the cancer, with I being an isolated cancer and IV being an advanced stage of the disease where the cancer that has spread to other organs. The stage generally takes into account the size of a tumour, whether it has invaded adjacent organs, the number of lymph nodes it has spread to, and whether the cancer has metastasised. Preventing or inhibiting progression of the cancer is particularly important for preventing the spread of the cancer, for example the progression from Stage I to Stage II where the cancer spreads locally, or the progression from Stage III to Stage IV where the cancer metastasises to other organs.

It may be that a compound of the invention is for use in the treatment of a cancer wherein the cancer is a primary cancer, which may be a second primary cancer.

It may be that a compound of the invention is for use in the prevention or inhibition of occurrence of a second primary cancer.

It may be that a compound of the invention is for use in the treatment of a cancer wherein the cancer is refractory (resistant) to an anti-cancer agent (e.g. chemotherapy) and/or radio therapy. The cancer may be resistant at the beginning of treatment or it may become resistant during treatment.

It may be that a compound of the invention is for use in the treatment of a cancer wherein the cancer is a recurrent cancer, which may be local, regional or distant. A recurrent cancer is a cancer which returns after initial treatment and after a period of time during which the cancer cannot be detected. The same cancer may return in the same tissue or in a different part of the body.

It may be that a compound of the invention is for use in the prevention or inhibition of recurrence of a cancer.

It may be that a compound of the invention is for use in the treatment of a cancer wherein the cancer is a metastatic or secondary cancer.

It may be that a compound of the invention is for use in the prevention or inhibition of cancer metastasis. The treatment of a metastatic cancer may be the same or different to the therapy previously used to treat the primary tumour. For example, in certain embodiments, a primary tumour may be surgically resected and a compound of the invention is for use in preventing the spread of cancer cells that may remain following surgery, or which may have already escaped the primary tumour. In other embodiments, the primary tumour may be treated using radiotherapy. In yet other embodiments, the primary tumour may be treated by chemotherapy. Combination therapies are commonly used to treat cancer to improve the treatment and, typically, maximise the length and depth of the remission. Any of the combination therapies disclosed herein may be used with a compound of the invention.

When the primary tumour has already metastasised and a secondary tumour has established, a compound of the invention may be used to treat the secondary tumour. This may involve both treatment of the secondary tumour and prevention of that secondary tumour metastasising. Reference to metastasis herein is intended to encompass metastasis of any of the tumours disclosed herein. Generally, the secondary tumour will be in a different tissue to that of the primary tumour. For example the secondary tumour may be a secondary tumour in bone. In a particular embodiment a compound of the invention is for use in the treatment of a secondary tumour in bone, for example for use in the treatment of a secondary bone tumour, wherein the primary tumour is a breast or prostate tumour.

Benign Proliferative Disease

A compound of the invention, or a pharmaceutically acceptable salt thereof the invention may be for use in the treatment of a benign proliferative disease. The benign disease may be a benign tumour, for example hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, moles, uterine fibroids, thyroid adenomas, adrenocortical adenomas or pituitary adenomas.

In some embodiments, the benign proliferative disease is a hyperproliferative skin disorder. Benign hyperproliferative skin disorders include psoriasis, common warts, keratoacanthoma, seborrhea, ichthyosis, actinic keratosis, Bowen's Disease, papilloma, seborrhoeic keratosis, eczema, atopic dermatitis, keloids, and Epidermolysis Bullosa (EB).

Other Diseases and Conditions

In certain embodiments, the compounds of the invention are for use in the treatment or prevention of a metabolic disorder, or symptoms or conditions associated with a metabolic disorder.

The metabolic disorder may be a glucose metabolism disorder, or a body weight disorder.

The term "glucose metabolism disorder" encompasses any disorder characterized by a clinical symptom or a combination of clinical symptoms that is associated with an elevated level of glucose and/or an elevated level of insulin in a subject relative to a healthy individual. Elevated levels of glucose and/or insulin may be manifested in the following diseases, disorders and conditions: hyperglycemia, type II diabetes, gestational diabetes, type I diabetes, insulin resistance, impaired glucose tolerance, hyperinsulinemia, impaired glucose metabolism, prediabetes, other metabolic disorders (such as metabolic syndrome), and obesity, among others.

The term "insulin resistance" as used herein refers to a condition wherein a normal amount of insulin is unable to produce a normal physiological or molecular response.

The term "hyperglycemia", as used herein, refers to a condition in which an elevated amount of glucose circulates in the blood plasma of a subject relative to a healthy individual. Hyperglycemia can be diagnosed using methods known in the art, including measurement of fasting blood glucose levels.

The term "hyperinsulinemia", as used herein, refers to a condition in which there are elevated levels of circulating insulin when, concomitantly, blood glucose levels are either elevated or normal. Hyperinsulinemia can be caused by insulin resistance which is associated with dyslipidemia, such as high triglycerides, high cholesterol, high low-density lipoprotein (LDL) and low high-density lipoprotein (HDL); high uric acids levels; polycystic ovary syndrome; type II diabetes and obesity. Hyperinsulinemia can be diagnosed as having a plasma insulin level higher than about 2 μl/ml.

The phrase "body weight disorder" refers to conditions associated with excessive body weight and/or enhanced appetite. Various parameters are used to determine whether a subject is overweight compared to a reference healthy individual, including the subject's age, height, sex and health status. For example, a subject may be considered overweight or obese by assessment of the subject's Body Mass Index (BMI), which is calculated by dividing a subject's weight in kilograms by the subject's height in meters. An adult having a BMI in the range of −18.5 to −24.9 kg/m is considered to have a normal weight; an adult having a BMI between −25 and −29.9 kg/m may be considered overweight (pre-obese); and an adult having a BMI of −30 kg/m or higher may be considered obese. Thus, in some embodiments the body weight disorder is obesity.

Symptoms and conditions associated with metabolic disorders may thus include, but are not limited to, increased blood sugar (hyperglycaemia), decreased insulin production, metabolic syndrome, increased cholesterol, increased triglyceride levels, heart disease, stroke, high blood pressure, an increased risk of blood clots (e.g. deep vein thrombosis), glucosuria, metabolic acidosis, diabetic neuropathy, diabetic nephropathy, diabetic retinopathy, and diabetic cardiomyopathy.

The term "metabolic syndrome" refers to an associated cluster of traits that includes, but is not limited to, hyperinsulinemia, abnormal glucose tolerance, redistribution of fat to the abdominal or upper body compartment, hypertension, dysfibrinolysis, and dyslipidemia characterized by high triglycerides, low high density lipoprotein (HDL)-cholesterol, and high small dense low density lipoprotein (LDL) particles. Subjects having metabolic syndrome are at risk for development of type 2 diabetes and/or other disorders (e.g., atherosclerosis).

Compounds of the invention may be used to prevent or inhibit the progression or symptoms of the metabolic disorder or condition associated therewith. For example, compounds of the invention may lower blood glucose, insulin, triglyceride, or cholesterol levels to a range found in a healthy subject; reduce body weight; improve glucose tolerance, energy expenditure, or insulin sensitivity; delay the onset or progression of diabetes; reduce blood pressure; and/or reduce the risk of blood clots, heart disease or stroke.

In certain embodiments, the compounds of the invention are for use in the treatment of a platelet disorder, such as thrombocytopenia.

The compounds of the invention may be used alone or in combination with one or more anticancer agents and/or radiotherapy as described herein.

Combination Therapies

The compounds of the invention may be used alone to provide a therapeutic effect. The compounds of the invention may also be used in combination with one or more additional therapies.

In some embodiments, the compounds of the invention are used in combination with one or more anti-cancer agents and/or radiotherapy.

The rationale for this is based on results showing that overexpression of MASTL is associated with resistance to cisplatin (Wang et al., 2014) by accelerating checkpoint recovery (Wong et al., 2016). Conversely, knockdown of MASTL has been observed to sensitize cancer cells to cisplatin, radiotherapy and 5-fluorouracil (5FU) in several cancer types (Wang et al., (2014). Mastl kinase, a promising therapeutic target, promotes cancer recurrence. *Oncotarget* 5 11479-11489; Nagel et al., (2015). Genome-wide siRNA Screen identifies the radiosensitizing effect of downregulation of MASTL and FOXM1 in NSCLC. (*Mol. Cancer Ther.* 14 1434-1444; Uppada et al (2018). MASTL induces colon cancer progression and chemoresistance by promoting Wnt/β-catenin signaling. (*Mol. Cancer* 17:111; Yoon et al., (2018). MASTL inhibition promotes mitotic catastrophe through PP2A activation to inhibit cancer growth and radioresistance in breast cancer cells. *BMC Cancer* 18:716).

Compounds of the invention may therefore be used to prevent or reduce resistance of cells to anti-cancer agents, including chemotherapeutic agents, radiotherapy.

Such chemotherapy may include one or more of the following categories of anti-cancer agents:

(i) antiproliferative/antineoplastic drugs and combinations thereof, such as alkylating agents (for example cis-platin, oxaliplatin, carboplatin, cyclophosphamide, nitrogen mustard, uracil mustard, bendamustin, melphalan, chlorambucil, chlormethine, busulphan, temozolamide, nitrosoureas, ifosamide, melphalan, pipobroman, triethylene-melamine, triethylenethiophoporamine, carmustine, lomustine, stroptozocin and dacarbazine); antimetabolites (for example gemcitabine and antifolates such as fluoropyrimidines like 5-fluorouracil and tegafur, raltitrexed, methotrexate, pemetrexed, cytosine arabinoside, floxuridine, cytarabine, 6-mercaptopurine, 6-thioguanine, fludarabine phosphate, pentostatine, and gemcitabine and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, irinotecan, mitoxantrone and camptothecin); bleomcin, dactinomycin, daunorubicin, doxorubicin, epirubicin, idarubicin, ara-C, paclitaxel (Taxol™), nab paclitaxel (albumin-bound paclitaxel), docetaxel, mithramycin, deoxyco-formycin, mitomycin-C, L-asparaginase, interferons (especially IFN-alpha), etoposide, teniposide, DNA-demethylating agents, (for example, azacitidine or decitabine); and histone de-acetylase (HDAC) inhibitors (for example vorinostat, MS-275, panobinostat, romidepsin, valproic acid, mocetinostat (MGCD0103) and pracinostat SB939);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride; and navelbene, CPT-ll, anastrazole, letrazole, capecitabine, reloxafme, cyclophosphamide, ifosamide, and droloxafine;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib, 6-acrylamido-N-(3-chloro-4-fluorophenyl)-7-(3-morpholinopropoxy)-quinazolin-4-amine (CI 1033), afatinib, vandetanib, osimertinib and rociletinib) erbB2 tyrosine kinase inhibitors such as lapatinib) and antibodies to costimulatory molecules such as CTLA-4, 4-1BB and PD-1, or antibodies to cytokines (IL-10, TGF-beta); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors, for example dalotuzumab; aurora kinase inhibitors and cyclin dependent kinase inhibitors such as CDK2 and/or CDK4 inhibitors; CCR2, CCR4 or CCR6 antagonists; RAF kinase inhibitors such as those described in WO2006043090, WO2009077766, WO2011092469 or WO2015075483; and Hedgehog inhibitors, for example vismodegib.

(v) antiangiogenic agents such as those which inhibit the effects of vascular endothelial growth factor, [for example the anti-vascular endothelial cell growth factor antibody bevacizumab (Avastin™)]; thalidomide; lenalidomide; and for example, a VEGF receptor tyrosine kinase inhibitor such as vandetanib, vatalanib, sunitinib, axitinib, pazopanib and cabozantinib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); gp100; dendritic cell-based vaccines (such as Ad.p53 DC); toll-like receptor modulators for example TLR-7 or TLR-9 agonists; PD-1, PD-L1, PD-L2 and CTL4-A modulators (for example Nivolumab), antibodies and vaccines; other IDO inhibitors (such as indoximod); anti-PD-1 monoclonal antibodies (such as MK-3475 and nivolumab); anti-PDL1 monoclonal antibodies (such as MEDI-4736 and RG-7446); anti-PDL2 monoclonal antibodies; and anti-CTLA-4 antibodies (such as ipilumumab), CAR-T cell therapies; and (viii) cytotoxic agents for example fludaribine (fludara), cladribine, pentostatin (Nipent™);

(ix) targeted therapies, for example PI3K inhibitors, for example idelalisib and perifosine; SMAC (second mitochondria derived activator of caspases) mimetics, also known as Inhibitor of Apoptosis Proteins (IAP) antagonists (IAP antagonists). These agents act to suppress IAPs, for example XIAP, cIAP1 and cIAP2, and thereby reestablish cellular apoptotic pathways. Particular SMAC mimetics include Birinapant (TL32711, TetraLogic Pharmaceuticals), LCL161 (Novartis), AEG40730 (Aegera Therapeutics), SM-164 (University of Michigan), LBW242 (Novartis), ML101 (Sanford-Burnham Medical Research Institute), AT-406 (Ascenta Therapeutics/University of Michigan), GDC-0917 (Genentech), AEG35156 (Aegera Therapeutic), and HGS1029 (Human Genome Sciences); and agents which target ubiquitin proteasome system (UPS), for example, bortezomib, carfilzomib, marizomib (NPI-0052) and MLN9708; a CXCR4 antagonist, for example plerixafor or BL-8040;

(x) PARP inhibitors, for example niraparib (MK-4827), talazoparib (BMN-673), veliparib (ABT-888); olaparib, CEP 9722, and BGB-290

(xi) chimeric antigen receptors, anticancer vaccines and arginase inhibitors;

(xii) agents which degrade hyaluronan, for example the hyaluronidase enzyme PEGPH20

The additional anti-cancer agent may be a single agent or one or more of the additional agents listed herein.

Particular anti-cancer agents which may be used together with a compound of the invention include, for example, paclitaxel (including nab paclitaxel), gemcitabine, oxaliplatin, irinotecan, leucovorin and 5-fluorouracil. In some embodiments the additional anti-cancer agent selected from capecitabine, gemcitabine and 5-fluorouracil (5FU).

In some embodiments, the compounds of the invention are used in combination with one or more therapies for treating or preventing a metabolic disorder, including therapeutic agents, LDL apheresis, dietary restrictions and/or surgery (e.g. bariatric surgery).

Therapeutic agents for treating or preventing a metabolic disorder may include one or more of the following categories of agents:

(i) diabetes treatments, for example metformin, sulfonylureas (e.g. glyburide, glipizide and glimepiride), meglitinides (e.g. repaglinide and nateglinide), thiazolidinediones (e.g. rosiglitazone and pioglitazone), DPP-4 inhibitors (e.g. sitagliptin, saxagliptin and linagliptin), GLP-1 receptor agonists (e.g. exenatide, liraglutide and semaglutide), SGLT2 inhibitors (e.g. canagliflozin, dapagliflozin and empagliflozin), insulin (e.g. long-acting insulin such as glargine or insulin detemir) and aspirin;

(ii) cholesterol-lowering agents, for example statins (e.g. Atorvastatin, Lovastatin, Pitavastatin, Pravastatin, Rosuvastatin, Simvastatin); cholesterol absorption inhibitors (e.g. ezetimibe); PCSK9 inhibitors (e.g. repatha and praluent);

(iii) triglyceride-lowering agents, for example statins, fibrates, nicotinic acid, and omega-3 fatty acids;

(iv) anti-clotting agent, for example anticoagulants (e.g. heparin, warfarin, rivaroxaban, dabigatran, apixaban, edoxaban, enoxaparin, fondaparinux);

(v) blood-pressure lowering agents, for example diuretics (e.g. thiazide diuretics such as chlorthalidone, chlorothiazide, hydrochlorothiazide, indapamide and metolazone; potassium-sparing diuretics such as amiloride, spironolactone and triamterene; loop diuretics such as bumetanide, furosemide, torsemide; combination diuretics such as amiloride hydrochloride/hydrochlorothiazide, spironolactone/hydrochlorothiazide, triamterene/hydrochlorothiazide), beta blockers (e.g. acebutolol, atenolol, betaxolol, bisoprolol, bisoprolol/hydrochlorothiazide, metoprolol tartrate, metoprolol succinate, nadolol, pindolol, propranolol, solotol, timolol), ACE inhibitors (e.g. benazepril, captopril, enalapril, fosinopril, lisinopril, moexipril, perindopril, quinapril, ramipril, trandolapril), angiotensis II receptor blockers (ARBs) (e.g. candesartan, eprosartan, irbesartan, losartan, telmisartan, valsartan), calcium channel blockers (e.g. amlodipine, diltiazem, felodipine, isradipine, nicardipine, nifedipine, nisoldipine, verapamil), alpha blockers (e.g. doxazosin, prazosin, terazosin), alpha-beta blockers (e.g. carvedilol, labetalol), central agonists (e.g. methyldopa, clonidine, guanfacine), vasodilators (e.g. hydralazine, minoxidil), aldosterone receptor antagonists (e.g. eplerenone, spironolactone), direct renin inhibitors (e.g. aliskiren).

Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

In some embodiments in which a combination treatment is used, the amount of the compound of the invention and the amount of the other pharmaceutically active agent(s) are, when combined, therapeutically effective to treat a targeted disorder in the patient. In this context, the combined amounts are "therapeutically effective amount" if they are, when combined, sufficient to reduce or completely alleviate symptoms or other detrimental effects of the disorder; cure the disorder; reverse, completely stop, or slow the progress of the disorder; or reduce the risk of the disorder getting worse. Typically, such amounts may be determined by one skilled in the art by, for example, starting with the dosage range described in this specification for the compound of the invention and an approved or otherwise published dosage range(s) of the other pharmaceutically active compound(s).

According to a further aspect of the invention there is provided a compound of the invention as defined hereinbefore and an additional anti-cancer agent as defined hereinbefore, for use in the conjoint treatment of cancer.

According to a further aspect of the invention there is provided a pharmaceutical product comprising a compound of the invention as defined hereinbefore and an additional anti-cancer agent as defined hereinbefore for the conjoint treatment of cancer.

According to a further aspect of the invention there is provided a method of treatment of a human or animal subject suffering from a cancer comprising administering to the subject a therapeutically effective amount of a compound of the invention, or a pharmaceutically acceptable salt thereof simultaneously, sequentially or separately with an additional anti-cancer agent as defined hereinbefore.

According to a further aspect of the invention there is provided a compound of the invention, or a pharmaceutically acceptable salt thereof for use simultaneously, sequentially or separately with an additional anti-cancer agent as defined hereinbefore, in the treatment of a cancer.

The compound of the invention may also be used be used in combination with radiotherapy. Suitable radiotherapy treatments include, for example X-ray therapy, proton beam therapy or electron beam therapies. Radiotherapy may also encompass the use of radionuclide agents, for example $^{131}I$, $^{32}P$, $^{90}Y$, $^{89}Sr$, $^{153}Sm$ or $^{223}Ra$. Such radionuclide therapies are well known and commercially available.

According to a further aspect of the invention there is provided a compound of the invention, or a pharmaceutically acceptable salt thereof as defined hereinbefore for use in the treatment of cancer conjointly with radiotherapy.

According to a further aspect of the invention there is provided a method of treatment of a human or animal subject suffering from a cancer comprising administering to the subject a therapeutically effective amount of a compound of the invention, or a pharmaceutically acceptable salt thereof simultaneously, sequentially or separately with radiotherapy.

Biological Assays

The biological effects of the compounds may be assessed using one of more of the assays described herein in the Examples.

In certain embodiments the compounds have an $pIC_{50}$ of 7.0 or less in the MASTLwt activity assay described in the Examples.

Synthesis

Compounds of the invention may be prepared using analogous methods to the General Synthetic Methods described in the Examples. In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl or trifluoroacetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively, an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3 \cdot OEt_2$. A suitable alternative protecting group for a primary amino group is, for example, a phthaloyl group which may be removed by treatment with an alkylamine, for example dimethylamino-propylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, or sodium hydroxide, or ammonia. Alternatively, an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

EXAMPLES

Throughout this specification these abbreviations have the following meanings:

Aq.=aqueous DCM=dichloromethane
DMF=N,N-dimethylformamide DMSO=dimethyl sulfoxide
Et=ethyl EtOAc=ethyl acetate
h=hours MeOH=methanol
Me=methyl min=minutes
mol=mole cPr=cyclopropyl
iPr=isopropyl Rt=retention time
RT=Room temperature Sat.=saturated
THF=tetrahydrofuran T3P=propylphosphonic anhydride
DIEA=N,N-Diisopropylethylamine Et3N=Triethylamine
HOBt=1-Hydroxybenzotriazole hydrate NH4Cl=Ammonium chloride
EDCI·HCl=1-Ethyl-3-(3-dimethylaminopropyl)carbodiimide Hydrochloride
EtOH=Ethanol NaOAc=Sodium acetate
NaHCO3=Sodium bicarbonate NaOH=Sodium hydroxide
KF=Potassium fluoride MeMgBr=Methylmagnesium bromide
NaBH3CN=Sodium cyanoborohydride NH3=Ammonia
HATU=1-[Bis(dimethylamino)methylene]-1H-1,2,3-triazolo[4,5-b]pyridinium 3-oxid hexafluorophosphate
NBS=N-Bromosuccinimide NH2NH2·H2O=Hydrazine monohydrate
H3PO4=Phosphoric acid Na2SO4=Sodium sulfate
MeCN=Acetonitrile

Materials and Methods

Solvents, reagents and starting materials were purchased from commercial vendors and used as received unless otherwise described. All reactions were performed at RT unless otherwise stated. Flash column chromatography was carried out using pre-packed columns filled with Merck silica gel 60 (40-63 μm) or C18 silica on an ISCO Combiflash Rf or a Biotage Isolera Prime.

LCMS

LCMS data was recorded on a Waters 2695 HPLC using a Waters 2487 UV detector and a Thermo LCQ ESI-MS. Samples were eluted through a Phenomenex Luna 3μ C18 50 mm×4.6 mm column, using water and Acetonitrile acidified by 0.1% formic acid at 1.5 mL/min and detected at 254 nm.

The following methods were used:

The gradient employed was:

| Time (minutes) | % Water + 0.1% formic acid | % Acetonitrile + 0.1% formic acid |
|---|---|---|
| Method 1: 4 minute method | | |
| 0.0 | 65 | 35 |
| 3.5 | 10 | 90 |
| 3.9 | 10 | 90 |
| 4.0 | 65 | 35 |
| Method 2: 5 minute method | | |
| 0.0 | 90 | 10 |
| 0.5 | 90 | 10 |
| 4.0 | 10 | 90 |
| 4.7 | 10 | 90 |
| 4.8 | 65 | 35 |
| 5.0 | 65 | 35 |
| Method 3: 10 minute method | | |
| 0.0 | 95 | 5 |
| 8.0 | 5 | 95 |
| 8.5 | 5 | 95 |
| 9.0 | 95 | 5 |
| 9.5 | 95 | 5 |

LCMS (MDAP) data was recorded on a Shimadzu Prominence Series coupled to a LCMS-2020 ESI and APCI mass spectrometer. Samples were eluted through a Phenomenex Gemini 5μ C18 110 Å 250 mm×4.6 mm column, using water and Acetonitrile acidified by 0.1% formic acid at 1 mL/min and detected at 254 nm.

The following methods were used:

The gradient employed was:

| Time (minutes) | % Water + 0.1% formic acid | % Acetonitrile + 0.1% formic acid |
|---|---|---|
| Method 4: Analytical 5-95 | | |
| 0.0 | 95 | 5 |
| 1.0 | 95 | 5 |
| 21.0 | 5 | 95 |
| 25.0 | 5 | 95 |
| 30.0 | 70 | 30 |
| Method 5: Analytical 30-90 | | |
| 0.0 | 70 | 30 |
| 1.0 | 70 | 30 |
| 21.0 | 10 | 90 |
| 25.0 | 10 | 90 |
| 30.0 | 70 | 30 |
| Method 6: Analytical 5-95 (8 minutes) | | |
| 0.0 | 95 | 5 |
| 0.5 | 95 | 5 |
| 5.5 | 5 | 95 |
| 7.0 | 5 | 95 |
| 7.5 | 70 | 30 |
| Method 7: Analytical 5-95 (5 minutes) | | |
| 0.0 | 95 | 5 |
| 0.5 | 95 | 5 |
| 5.5 | 5 | 95 |
| 7.0 | 5 | 95 |
| 7.5 | 95 | 5 |

UPLC-MS was performed on a Waters Acquity UPLC system consisting of an Acquity I-Class Sample Manager-FL, Acquity I-Class Binary Solvent Manager and an Acquity UPLC Column Manager. UV detection was afforded using an Acquity UPLC PDA detector (scanning from 210 to 400 nm), whilst mass detection was achieved using aa Acquity QDa detector (mass scanning from 100-1250 Da; positive and negative modes simultaneously). A Waters Acquity UPLC BEH C18 column (2.1×50 mm, 1.7 μm) was used to separate the analytes.

| Time (Minutes) | 0.1% ammonia in water | 0.1% ammonia in Acetonitrile |
|---|---|---|
| The gradient employed was: | | |
| Method 8 (Basic 2 min) | | |
| 0.00 | 95 | 5 |
| 0.25 | 95 | 5 |
| 1.25 | 5 | 95 |
| 1.55 | 5 | 95 |
| 1.65 | 95 | 5 |
| 2.00 | 95 | 5 |
| Method 9 (Basic 4 min) | | |
| 0.00 | 95 | 5 |
| 0.25 | 95 | 5 |
| 2.75 | 5 | 95 |
| 3.25 | 5 | 95 |
| 3.35 | 95 | 5 |
| 4.00 | 95 | 5 |

Mass Directed Purification was performed on a Shimadzu Prominence Series coupled to a LCMS-2020 ESI and APCI mass spectrometer using a Phenomenex Gemini 5μ C18 250 mm×21.2 mm column, using water and Acetonitrile acidified by 0.1% formic acid at 15 mL/min and detected at 254 nm.

The gradient employed was:

| Time (minutes) | % Water + 0.1% formic acid | % Acetonitrile + 0.1% formic acid |
|---|---|---|
| 0.0 | 95 | 5 |
| 1.0 | 95 | 5 |
| 21.0 | 5 | 95 |
| 25.0 | 5 | 95 |
| 30.0 | 70 | 30 |

NMR

NMR was also used to characterise final compounds. NMR spectra were recorded at 500 MHz on a Varian VNMRS 500 MHz spectrometer (at 25° C.), or a Bruker Avanced 400 MHz NMR spectrometer, or a Varian VNMRS 600 MHz spectrometer using residual isotopic solvent (Chloroform, δH=7.27 ppm, DMSO δH=2.50 ppm, methanol δH=3.31 ppm) as an internal reference. Chemical shifts are quoted in parts per million (ppm). Coupling constants (J) are recorded in Hertz.

For many of the triazine containing compounds, rotamers and/or tautomers resulted in complex NMR structures. These were resolved to the expected pattern using variable temperature (Vt) NMR at 90° C.-120° C.

Chemical Synthesis

Microwave reactions were conducted using a Biotage Initiator 8+ microwave reactor.

General Method A

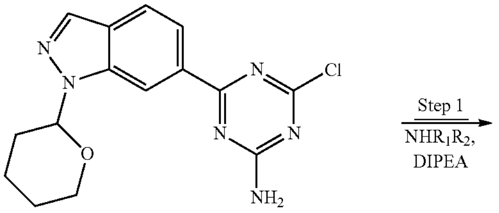

Intermediate X

-continued

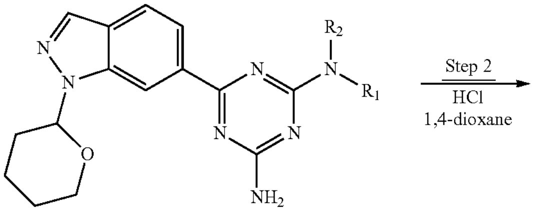

Product I

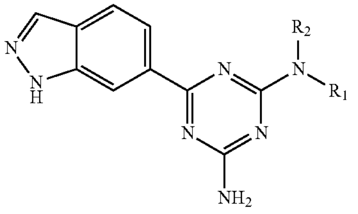

Produc II

Step 1. 4-chloro-6-(1-tetrahydropyran-2-ylindazol-6-yl)-1,3,5-triazin-2-amine (Intermediate X) (1.0 mol equiv.) is added to a mixture of the appropriate amine (1.8 to 2.0 mol equiv.) and N,N-diisopropylethylamine (5-10 mol equiv.) in 1,4-dioxane at RT. The reaction mixture is heated at 80-120° C. from 2 h to 7 days then concentrated to dryness under reduced pressure. The crude material is purified by flash chromatography to afford the THP protected Product I.

Step 2. A solution of the THP protected Product I from step 1 in 1,4-dioxane/methanol (1:1) is treated with 4 M HCl in 1,4-dioxane at RT. The reaction mixture is heated at 25-120° C. for 1-24 h in a sealed vial. The reaction mixture is then concentrated to dryness under reduced pressure and the crude material is purified by flash chromatography to afford the desired Product II.

General Method B

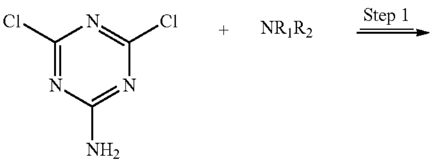

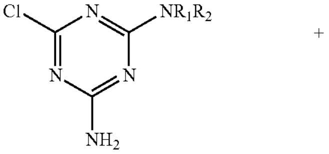

Product III

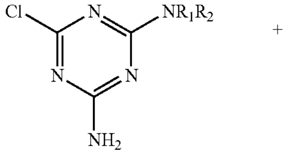

Product III

-continued

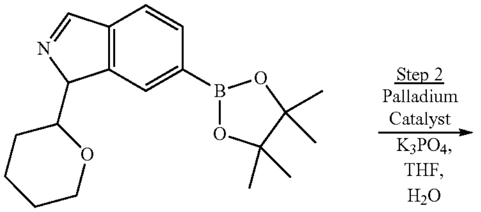

Intermediate V

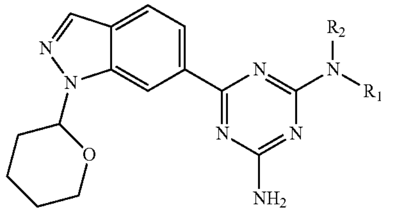

Product I

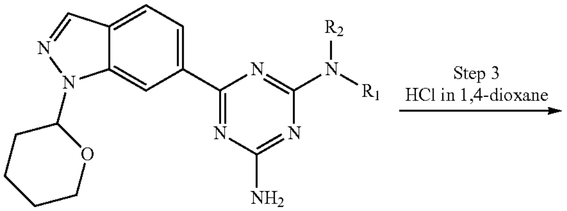

Product I

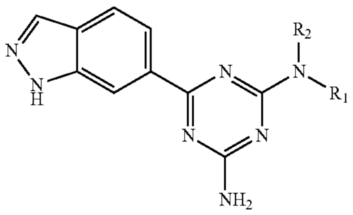

Product II

Step 1: To a stirred solution of 2-Amino-4,6-dichlorotriazine in 1,4-dioxane is added N,N-diisopropylethylamine followed by the addition of the appropriate amine. The resulting mixture is stirred at RT for 12 h. Volatiles are removed under reduced pressure and the crude material is purified by chromatography on silica to afford Product III.

Step 2: A stirred solution of Product III, potassium phosphate tribasic and a palladium catalyst, such as bis[2-(di-tert-butylphosphanyl)cyclopenta-2,4-dien-1-yl]iron; dichloropalladium, in tetrahydrofuran and water is first degassed by bubbling $N_2$ directly into the solution. The mixture is heated to 80° C. then a solution of 1-tetrahydropyran-2-yl-6-(4,4,5,5-tetramethyl-1,3,2-dioxaborolan-2-yl)indazole (Intermediate V) in THF is added and the reaction mixture is stirred at 60-100° C. for 2-24 h. The reaction mixture is concentrated to dryness under reduced pressure and the crude is purified by flash column chromatography to afford Product I.

Step 3: A solution of Product I in methyl alcohol is treated with 4 M HCl in 1,4-dioxane and heated at 60° C. for 2-16 h. The resulting suspension is filtered and the filtered solid washed with solvent such as 1,4-dioxane, ethyl acetate and/or diethyl ether. The solid material is further purified by flash column chromatography to afford the desired Product II.

Method C

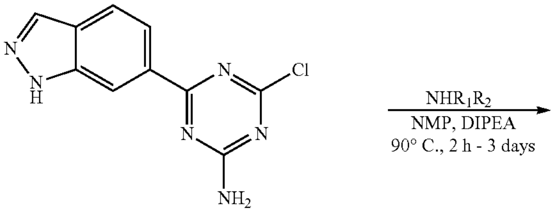

Intermediate Z

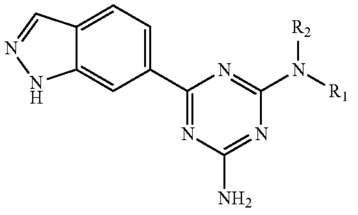

Product II

A solution of Intermediate Z in NMP is treated with the appropriate amine and N,N-diisopropylethylamine and the reaction mixture stirred at 90° C. for a period of time between 2 h to 3 days. The reaction is allowed to cool to room temperature and either purified by flash silica chromatography or diluted with 9:1 DMSO:water and purified by prep-HPLC.

General Method D

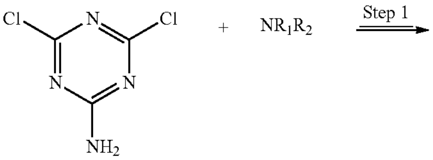

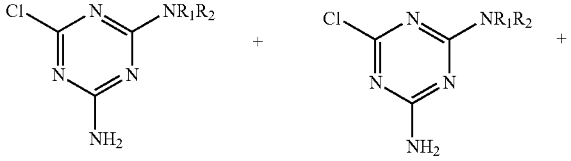

Product III

Product III

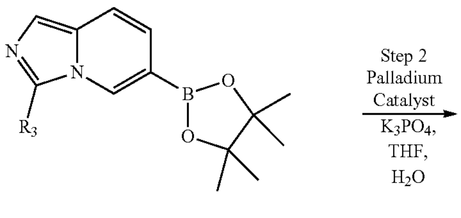

Intermediate W-Y

-continued

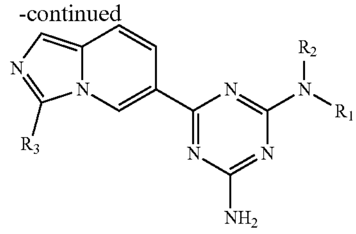

Product IV

Step 1: To a stirred solution of 2-Amino-4,6-dichlorotriazine in 1,4-dioxane is added N,N-diisopropylethylamine followed by the addition of the appropriate amine. The resulting mixture is stirred at RT for 12 h or heated in a microwave for 1-2 hr. Volatiles are removed under reduced pressure and the crude material is purified by chromatography on silica to afford Product III.

Step 2: A stirred solution of Product III, Intermediate W-Y, potassium phosphate tribasic and a palladium catalyst, such as bis[2-(di-tert-butylphosphanyl)cyclopenta-2,4-dien-1-yl]iron; dichloropalladium, in tetrahydrofuran and water was degassed by bubbling $N_2$ directly into the solution. The mixture is heated to 90-120° C. 2-24 h. The reaction mixture is concentrated to dryness under reduced pressure and the crude is purified by flash column chromatography to afford Product IV.

Or alternatively, intermediate W-Y is synthesised in situ

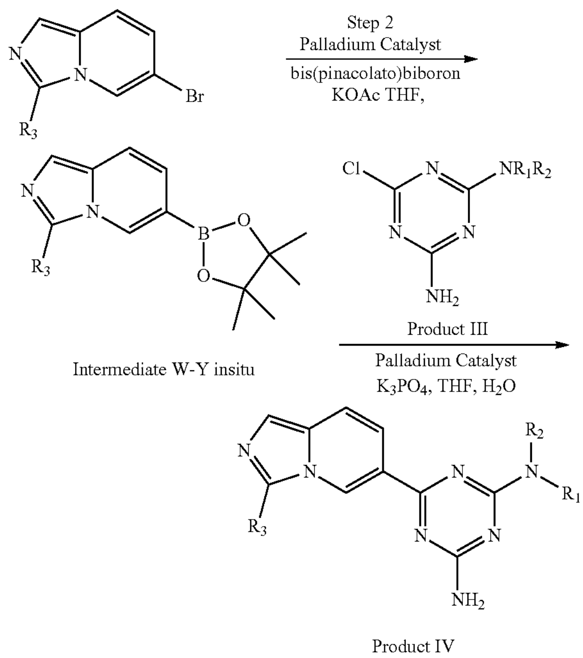

Product IV

Step 2: A palladium catalyst, such as [1,1'-bis(Diphenylphosphino)ferrocene]dichloropalladium (II), is added to a degassed solution of the appropriately substituted 6-bromoimidazo[1,5-a]pyridine, potassium acetate and bis(pinacolato)diboron and the mixture heated to 90-120° C. 6-24 h. The mixture is cooled to RT and Product III, a second palladium catalyst, such as and bis[2-(di-tert-butylphosphanyl)cyclopenta-2,4-dien-1-yl]iron; dichloropalladium and potassium tribasic added. The reaction mixture is heated to 70-120° C. for 8-24 h. The reaction mixture is concentrated to dryness under reduced pressure and the crude is purified by flash column chromatography to afford Product IV.

General Method E

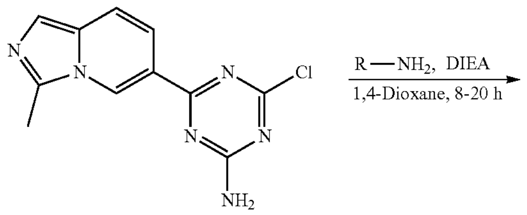

Key intermediate 2 (X=N)
Key intermediate 3 (X=C)

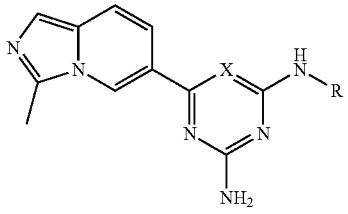

To a solution methyl imidazopyridinyl triazine amine of pyrimidine amine in 1,4-dioxane was added substituted amine and DIEA. Then, the reaction mixture was heated to 90-120° C. and stirred for 10-20 h. The reaction mixture was concentrated under reduced pressure to give a residue. The residue was purified by prep-HPLC to obtain target compounds.

General Method F

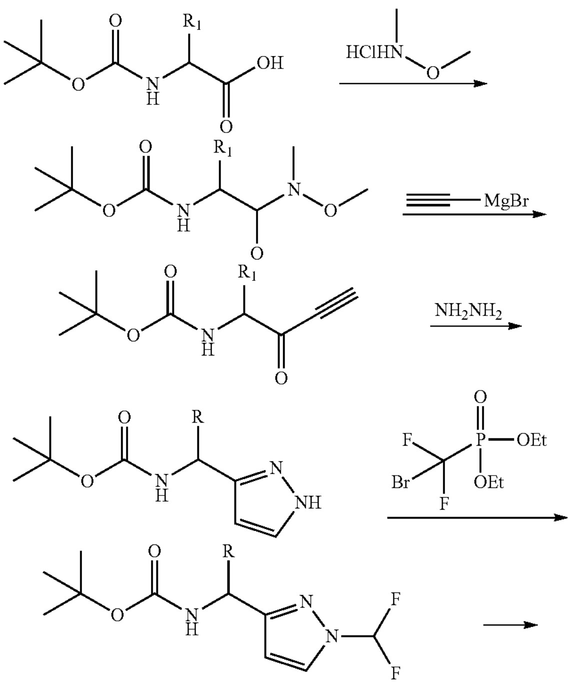

-continued

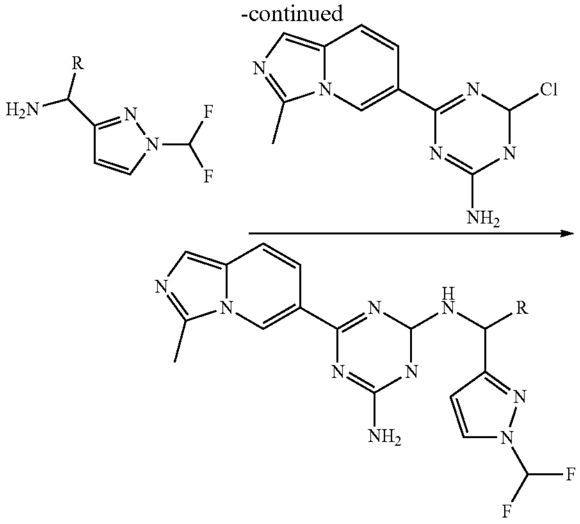

Step 1

A solution of amino acid, Et3N, HOBt in anhydrous DCM was cooled to 0° C., EDCI·HCl was added, followed by stirring at 20° C.-50° C. for 30 minutes. Then, N-methoxymethanamine was added, followed by stirring at 20° C.-50° C. for another 10-20 h. The crude product was purified by recrystallization.

Step 2

(methoxy(methyl)amino)carbamate in THF was cooled to −78° C. under nitrogen, bromo(ethynyl)magnesium was added dropwise, and the mixture was stirred at −78° C. for 1 hr. Then the mixture was allowed to warm to 20-50° C. and stirred for another 10-20 hr. The residue was purified by silica gel column chromatography to give target compounds.

Step 3 t-butyl carbamate (2.6 g, 11.64 mmol) was dissolved in EtOH, $NH_2NH_2 \cdot H_2O$ was added and the reaction mixture was heated to 50-80° C. for 30 min-1 h then allowed to cool to 20° C. for 0.5-2 h. The residue was purified by silica gel column chromatography to give target compounds.

Step 4

KF and tert-butyl pyrazol carbamate were combined in a flask under $N_2$. Acetonitrile was then added followed by 1-[[bromo(difluoro)methyl]-ethoxy-phosphoryl]oxyethane. The reaction mixture was stirred at 20° C.-50° C. for 10-20 h. The residue was purified by silica gel column chromatography to give target compounds.

Step 5

To a solution of difluoromethyl pyrazol carbamate in DCM, HCl/1,4-dioxane was added, and the reaction mixture was stirred at 20-30° C. for 10-20 h. The residue was diluted with 1M NaOH solution and extracted organic phase. The mixture was evaporated under reduced pressure.

Step 6

To a solution methyl imidazopyridinyl triazine amine, Key Intermediate 2 and DIEA were taken up into a microwave tube in 1,4-dioxane. The sealed tube was heated at 100-120° C. for 1-5 h under microwave. The reaction mixture was concentrated under reduced pressure to give a residue. The residue was purified by prep-HPLC to obtain target compounds.

Example 1

6-(1H-indazol-6-yl)-N2-[1-[6-(trifluoromethyl)-2-pyridyl]cyclopropyl]-1,3,5-triazine-2,4-diamine hydrochloride

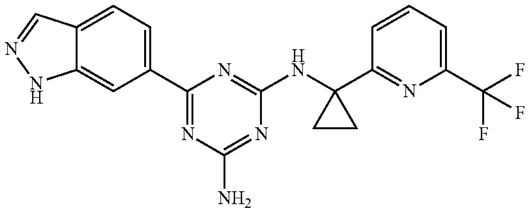 [SMILES: Nc1nc(NC2(c3cccc(C(F)(F)F)n3)CC2)nc(-c2ccc3cn[nH]c3c2)n1]

Example 1 was synthesised in accordance with general method A.

Step 1: 6-(1-tetrahydropyran-2-ylindazol-6-yl)-N4-[1-[6-(trifluoromethyl)-2-pyridyl]cyclopropyl]-1,3,5-triazine-2,4-diamine 4-chloro-6-(1-tetrahydropyran-2-ylindazol-6-yl)-1,3,5-triazin-2-amine (Intermediate X) (69 mg, 0.21 mmol) was added to a mixture of 1-[6-(trifluoromethyl)-2-pyridyl]cyclopropanamine (Intermediate H) (76 mg, 0.38 mmol) and N,N-diisopropylethylamine (0.36 mL, 2.09 mmol) in 1,4-dioxane (7 mL) at 25° C. The reaction mixture was heated at 120° C. for 5 days then concentrated to dryness under reduced pressure. The crude material was purified by flash chromatography (25 g silica eluting with a gradient of 0-70% EtOAc in hexane) to afford the titled compound (64 mg, 0.12 mmol, 59% yield).

Step 2: 6-(1H-indazol-6-yl)-N2-[1-[6-(trifluoromethyl)-2-pyridyl]cyclopropyl]-1,3,5-triazine-2,4-diamine hydrochloride To a solution of 6-(1-tetrahydropyran-2-ylindazol-6-yl)-N2-[1-[6-(trifluoromethyl)-2-pyridyl]cyclopropyl]-1,3,5-triazine-2,4-diamine (59 mg, 0.12 mmol) in 1,4-dioxane (5 mL) and methyl alcohol (5 mL) was added 4M HCl in 1,4-dioxane (1.19 mL, 4.75 mmol) at 25° C. The reaction mixture was heated for 9 hours at 60° C. in sealed vial. The reaction mixture was concentrated to dryness under reduced pressure. The crude material was purified by flash chromatography (25 g silica eluting with a gradient of 0-1% methanol in EtOAc) to afford the title compound (23 mg, 0.05 mmol, 41% yield). $^1H$ NMR (399 MHz, DMSO-d6, VT 90° C.) δ 13.01 (s, 1H), 8.42 (s, 1H), 8.04 (s, 1H), 7.92-7.85 (m, 2H), 7.77-7.67 (m, 1H), 7.64 (d, J=8.1 Hz, 1H), 7.55 (d, J=7.6 Hz, 1H), 6.53 (s, 2H), 1.61 (q, J=4.3 Hz, 2H), 1.39 (q, J=4.3 Hz, 2H). LCMS-MDAP Rt=19.18 min >95% (Method 4) m/z ($ESI^+$) 413.20 $[M+H]^+$;

Example 2

6-(1H-indazol-6-yl)-N2-[1-[1-(2-methoxyethyl)pyrazol-3-yl]cyclopropyl]-1,3,5-triazine-2,4-diamine

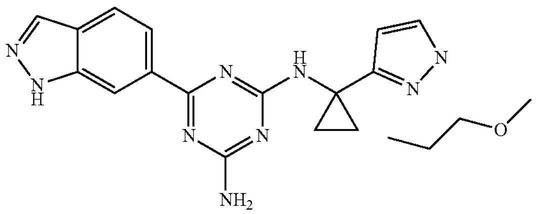

Synthesised by General Method A Using the Following Reagents and Conditions:

Step 1: Intermediate X (60 mg, 0.18 mmol), 1-[1-(2-methoxyethyl)pyrazol-3-yl]cyclopropanamine (Intermediate E) (89 mg, 0.49 mmol) N,N-diisopropylethylamine (0.16 mL, 0.91 mmol) and 1,4-dioxane (6 mL) heated at 90° C. for 72 h.

Step 2: N2-[1-[1-(2-methoxyethyl)pyrazol-3-yl]cyclopropyl]-6-(1-tetrahydropyran-2-ylindazol-6-yl)-1,3,5-triazine-2,4-diamine (52 mg, 0.11 mmol), 1,4-dioxane (4.5 mL) and methyl alcohol (4.5 mL) and 4M HCl in 1,4-dioxane (1.1 mL, 4.37 mmol) heated to 60° C. for 10 h. Purification by flash chromatography afforded the title compound (16 mg, 0.04 mmol, 37% yield).

$^1$H NMR (399 MHz, DMSO-d6, VT 90° C.) δ 13.00 (s, 1H), 8.46 (s, 1H), 8.10-7.99 (m, 2H), 7.73 (d, J=8.5 Hz, 1H), 7.53 (s, 1H), 7.40 (d, J=2.2 Hz, 1H), 6.42 (s, 2H), 6.04 (d, J=2.2 Hz, 1H), 4.10 (t, J=5.5 Hz, 2H), 3.62 (t, J=5.5 Hz, 2H), 3.17 (s, 3H), 1.23 (dt, J=21.9, 2.7 Hz, 4H).

LCMS MDAP Rt=12.95 min, >98% (Method 4); m/z (ESI$^+$) 392.20 [M+H]$^+$.

Example 3

4-[3-[(2,3-dichlorophenyl)methyl]morpholin-4-yl]-6-(1H-indazol-6-yl)-1,3,5-triazin-2-amine hydrochloride

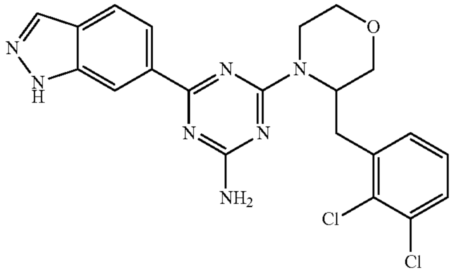 [SMILES: Nc1nc(-c2ccc3cn[nH]c3c2)nc(N2CCOCC2Cc2cccc(Cl)c2Cl)n1]

Synthesised by General Method A Using the Following Reagents and Conditions:

Step 1: Intermediate X (6.5 mg, 0.02 mmol), 3-[(2,3-dichlorophenyl)methyl]morpholine (Intermediate P) (7.3 mg, 0.03 mmol), N,N-diisopropylethylamine (0.01 mL, 0.04 mmol) and 1,4-dioxane (0.5 mL). The reaction mixture was heated in the microwave to 120° C. for 2 hours.

Step 2: 4-[3-[(2,3-dichlorophenyl)methyl]morpholin-4-yl]-6-(1-tetrahydropyran-2-ylindazol-6-yl)-1,3,5-triazin-2-amine (0.02 mmol), 4M HCl in 1,4-dioxane, heated to 60° C. for 16 h. Purification by flash chromatography afforded the title compound.

$^1$H NMR (399 MHz, DMSO-d6) (VT at 90° C.) δ 8.42 (s, 1H), 8.05 (d, J=1.0 Hz, 1H), 7.96 (d, J=8.4 Hz, 1H), 7.73 (dd, J=8.7, 0.9 Hz, 1H), 7.52-7.45 (m, 1H), 7.36-7.23 (m, 3H), 7.12 (t, J=7.9 Hz, 1H), 6.48 (s, 2H), 5.14 (s, 1H), 4.50 (d, J=11.2 Hz, 1H), 3.97 (d, J=9.3 Hz, 1H), 3.78-3.67 (m, 3H), 3.60-3.36 (m, 2H), 2.93 (d, J=6.7 Hz, 1H).

LCMS-LCQ Rt=6.06 min, 95% (Method 3); m/z (ESI$^+$) 456.42 [M+H]$^+$.

Example 4

6-(1H-indazol-6-yl)-N2-[1-methyl-1-[6-(trifluoromethyl)-2-pyridyl]ethyl]-1,3,5-triazine-2,4-diamine hydrochloride

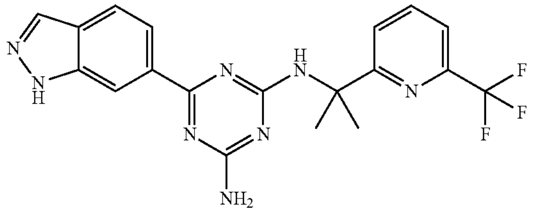 [SMILES: CC(C)(Nc1nc(N)nc(-c2ccc3cn[nH]c3c2)n1)c1cccc(C(F)(F)F)n1]

Synthesised by General Method A Using the Following Reagents and Conditions:

Step 1: Intermediate X (55 mg, 0.17 mmol), 2-[6-(trifluoromethyl)-2-pyridyl]propan-2-amine hydrochloride (Intermediate K) (60 mg, 0.25 mmol), N,N-diisopropylethylamine (0.29 mL, 1.66 mmol), 1,4-dioxane (5.5 mL) heated at 120° C. for 4 days.

Step 2: N2-[1-methyl-1-[6-(trifluoromethyl)-2-pyridyl]ethyl]-6-(1-tetrahydropyran-2-ylindazol-6-yl)-1,3,5-triazine-2,4-diamine (39 mg, 0.08 mmol), 1,4-dioxane (3.2 mL), methyl alcohol (3.2 mL), 4M HCl in 1,4-dioxane (0.78 mL, 3.13 mmol) heated for 10 hours at 60° C. Purification by flash chromatography afforded the title compound (19.5 mg, 0.0400 mmol, 54% yield). $^1$H NMR (399 MHz, DMSO-d6, VT 90° C.) δ 8.29 (s, 1H), 8.02 (d, J=1.1 Hz, 1H), 7.93 (t, J=7.9 Hz, 1H), 7.75 (d, J=8.1 Hz, 1H), 7.60 (d, J=7.5 Hz, 2H), 7.29 (s, 1H), 6.36 (s, 2H), 1.77 (s, 6H). LCMS MDAP Rt=18.16, >98% (Method 4); m/z (ESI$^+$) 415.2 [M+H]$^+$.

Example 5

N2-(4-fluoro-2,3-dihydrobenzofuran-3-yl)-6-(1H-indazol-6-yl)-1,3,5-triazine-2,4-diamine

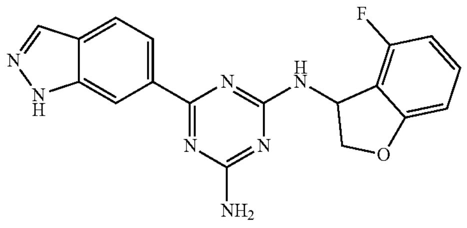

Synthesised by General Method A Using the Following Reagents and Conditions:

Step 1: Intermediate X (50 mg, 0.15 mmol), 4-fluoro-2,3-dihydro-1-benzofuran-3-amine hydrochloride (47 mg, 0.25 mmol), N,N-diisopropylethylamine (0.18 mL, 1.06 mmol) and 1,4-dioxane (12 mL) heated at 80° C. for 4 days.

Step 2: N2-(4-fluoro-2,3-dihydrobenzofuran-3-yl)-6-(1-tetrahydropyran-2-ylindazol-6-yl)-1,3,5-triazine-2,4-diamine (57 mg, 0.13 mmol), 1,4-dioxane (5 mL), methyl alcohol (5 mL) and 4M HCl in 1,4-dioxane (1.27 mL, 5.1 mmol) heated for 12 hours at 60° C. Purification by flash chromatography afforded the title compound (26 mg, 0.07 mmol, 53% yield). $^1$H NMR (399 MHz, DMSO-d6, VT 90° C.) δ 8.48 (d, J=1.2 Hz, 1H), 8.05 (d, J=1.1 Hz, 1H), 8.03 (d, J=1.3 Hz, 1H), 7.75 (dd, J=8.5, 0.9 Hz, 1H), 7.60 (s, 1H), 7.22 (td, J=8.2, 5.9 Hz, 1H), 6.69 (d, J=8.1 Hz, 1H), 6.63 (t, J=8.7 Hz, 1H), 6.58 (s, 2H), 6.13-5.95 (m, 1H), 4.81 (t, J=9.1 Hz, 1H), 4.43 (dd, J=9.6, 5.0 Hz, 1H). LCMS-LCQ Rt=5.18, >95% (Method 3); m/z (ESI$^+$) 364.11 [M+H]$^+$.

Example 6

6-(1H-indazol-6-yl)-N2-[1-(2-pyridyl)cyclopropyl]-1,3,5-triazine-2,4-diamine

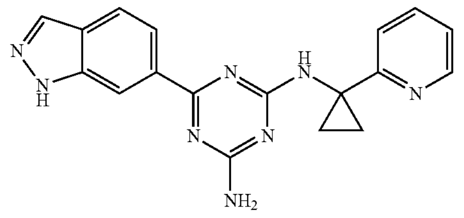 [SMILES: Nc1nc(NC2(c3ccccn3)CC2)nc(-c2ccc3cn[nH]c3c2)n1]

Synthesised by General Method A Using the Following Reagents and Conditions:

Step 1: Intermediate X (40 mg, 0.12 mmol), 1-(pyridin-2-yl)cyclopropan-1-amine (40 mg, 0.30 mmol) N,N-diisopropylethylamine (0.13 mL, 0.76 mmol) and 1,4-dioxane (4 mL) heated at 100° C. for 7 days.

Step 2: N2-[1-(2-pyridyl)cyclopropyl]-6-(1-tetrahydropyran-2-ylindazol-6-yl)-1,3,5-triazine-2,4-diamine (52 mg, 0.12 mmol), 1,4-dioxane (5 mL), methyl alcohol (5 mL) and 4M HCl in 1,4-dioxane (1.21 mL, 4.83 mmol) heated for 12 h at 60° C. Purification by flash chromatography afforded the title compound (17 mg, 0.04 mmol, 36% yield). $^1$H NMR (600 MHz, DMSO-d6) δ 13.29 (s, 0.57H), 13.18 (s, 0.34H), 8.48 (s, 1H), 8.44 (d, J=4.8 Hz, 0.31H), 8.42-8.37 (m, 0.56H), 8.28 (s, 0.31H), 8.14 (s, 1H), 8.10 (s, 0.63H), 8.08-7.98 (m, 0.46H), 7.83 (d, J=8.6 Hz, 0.30H), 7.79 (d, J=8.5 Hz, 0.55H), 7.67 (d, J=8.5 Hz, 0.31H), 7.63 (t, J=7.7 Hz, 0.50H), 7.59 (t, J=7.7 Hz, 0.29H), 7.32 (t, J=7.4 Hz, 1H), 7.14-7.03 (m, 1H), 6.84 (s, 2H), 1.63-1.57 (m, 1H), 1.53 (q, J=4.2 Hz, 1H), 1.34-1.25 (m, 2H), 1.21 (s, 0.18H). LCMS MDAP Rt=11.04 min, >97% (Method 4); m/z (ESI$^+$) 345.1 [M+H]$^+$.

Example 7

N2-(2,3-dihydrobenzofuran-3-ylmethyl)-6-(1H-indazol-6-yl)-1,3,5-triazine-2,4-diamine

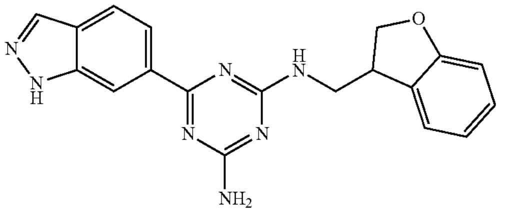

Synthesised by General Method A Using the Following Reagents and Conditions:

Step 1: Intermediate X (54 mg, 0.16 mmol), 2,3-dihydro-1-benzofuran-3-ylmethanamine (40 mg, 0.27 mmol), N,N-diisopropylethylamine (0.14 mL, 0.82 mmol) and 1,4-dioxane (13 mL) heated at 60° C. for 72 hours.

Step 2: N2-(2,3-dihydrobenzofuran-3-ylmethyl)-6-(1-tetrahydropyran-2-ylindazol-6-yl)-1,3,5-triazine-2,4-diamine (52 mg, 0.12 mmol), methyl alcohol (5 mL) and 4M HCl in 1,4-dioxane (1.17 mL, 4.69 mmol) heated for 14 hours at 60° C. Purification by flash chromatography afforded the title compound (27 mg, 0.07 mmol, 63% yield). $^1$H NMR (600 MHz, DMSO-d6) δ 13.26 (s, 1H), 8.49 (s, 0.45H), 8.46 (s, 0.60H), 8.09 (s, 1H), 8.07 (d, J=8.5 Hz, 0.37H), 8.02 (d, J=8.5 Hz, 0.61H), 7.78 (t, J=7.9 Hz, 1H), 7.59 (t, J=5.5 Hz, 0.69H), 7.41 (t, J=6.1 Hz, 0.48H), 7.32 (d, J=7.3 Hz, 0.49H), 7.27 (d, J=7.3 Hz, 0.65H), 7.10 (t, J=7.8 Hz, 1H), 6.90 (s, 2H), 6.83 (q, J=7.7 Hz, 1H), 6.76 (t, J=8.5 Hz, 1H), 4.55 (t, J=9.0 Hz, 1H), 4.49-4.43 (m, 0.48H), 4.43-4.38 (m, 0.70H), 3.84-3.72 (m, 1H), 3.74-3.66 (m, 1H), 3.62-3.53 (m, 0.55H), 3.52-3.44 (m, 0.41H), 3.43-3.34 (m, 0.59H). LCMS MDAP Rt=15.4 min, >98% (Method 4); m/z (ESI$^+$) 360.1 [M+H]$^+$.

Example 8

6-(1H-indazol-6-yl)-N2-[[6-(trifluoromethyl)-2-pyridyl]methyl]-1,3,5-triazine-2,4-diamine

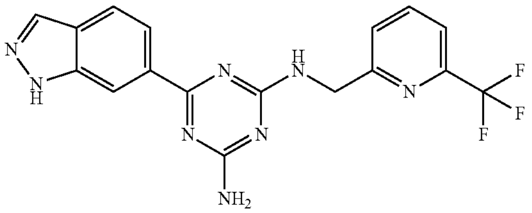 [SMILES: Nc1nc(NCc2cccc(C(F)(F)F)n2)nc(-c2ccc3cn[nH]c3c2)n1]

Synthesised by General Method A Using the Following Reagents and Conditions:

Step 1: Intermediate X (50 mg, 0.15 mmol), [6-(trifluoromethyl)pyridin-2-yl]methanamine (44 mg, 0.25 mmol), N,N-diisopropylethylamine (0.13 mL, 0.76 mmol), 1,4-dioxane (5 mL) heated at 60° C. for 48 hours.

Step 2: 6-(1-tetrahydropyran-2-ylindazol-6-yl)-N2-[[6-(trifluoromethyl)-2-pyridyl]methyl]-1,3,5-triazine-2,4-diamine (64 mg, 0.14 mmol), methyl alcohol (9 mL) and 4M HCl in 1,4-dioxane (1.36 mL, 5.44 mmol) heated for 13 hours at 60° C. Purification by flash chromatography afforded the title compound (5 mg, 0.01 mmol, 9%). $^1$H NMR (600 MHz, DMSO-d6) δ 13.48-13.04 (m, 1H), 8.49 (s, 0.50H), 8.40 (s, 0.36H), 8.10 (s, 1H), 8.09-7.99 (m, 1H), 7.98 (t, J=6.4 Hz, 1H), 7.90 (d, J=8.5 Hz, 0.56H), 7.84-7.60 (m, 2H), 7.10-6.74 (m, 2H), 4.75 (d, J=6.1 Hz, 1H), 4.67 (d, J=6.2 Hz, 1H). LCMS LCQ, Rt=5.08 min >95% (Method 3); m/z (ESI$^+$) 387.34 [M+H]$^+$.

Example 9

N2-cyclopropyl-N2-[2-(2,3-dichlorophenyl)ethyl]-6-(1H-indazol-6-yl)-1,3,5-triazine-2,4-diamine

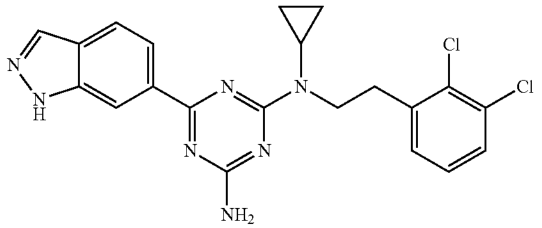 [SMILES: Nc1nc(-c2ccc3cn[nH]c3c2)nc(N(CCc2cccc(Cl)c2Cl)C2CC2)n1]

Synthesised by General Method A Using the Following Reagents and Conditions:

Step 1: Intermediate X (30 mg, 0.09 mmol), N-[2-(2,3-dichlorophenyl)ethyl]cyclopropanamine (31 mg, 0.14 mmol), N,N-diisopropylethylamine (0.04 mL, 0.23 mmol) and 1,4-dioxane (3 mL) heated at 60° C. for 5 days.

Step 2: N2-cyclopropyl-N2-[2-(2,3-dichlorophenyl)ethyl]-6-(1-tetrahydropyran-2-ylindazol-6-yl)-1,3,5-triazine-2,4-diamine (40 mg, 0.08 mmol), 1,4-dioxane (5 mL), methyl alcohol (5 mL) and 4M HCl in 1,4-dioxane (0.76 mL, 3.05 mmol) heated for 14 hours at 60° C. Purification by flash chromatography afforded the title compound (20 mg, 0.04 mmol, 58% yield). $^1$H NMR (399 MHz, DMSO-d6, VT 90° C.) δ 8.51 (s, 1H), 8.10-8.02 (m, 2H), 7.75 (d, J=8.3 Hz, 1H), 7.41 (dd, J=7.9, 1.6 Hz, 1H), 7.32 (dd, J=7.7, 1.7 Hz, 1H), 7.24 (t, J=7.8 Hz, 1H), 6.51 (s, 2H), 3.87 (t, J=7.2 Hz, 2H), 3.13 (t, J=7.3 Hz, 2H), 2.86-2.68 (m, 1H), 0.93-0.76 (m, 2H), 0.76-0.54 (m, 2H). LCMS LCQ Rt=7.03 min, >98% (Method 3); m/z (ESI$^+$) 440/442 (Cl isotopes) [M+H]$^+$.

Example 10

N2-[2-(2,3-dichlorophenyl)ethyl]-N2-ethyl-6-(1H-indazol-6-yl)-1,3,5-triazine-2,4-diamine

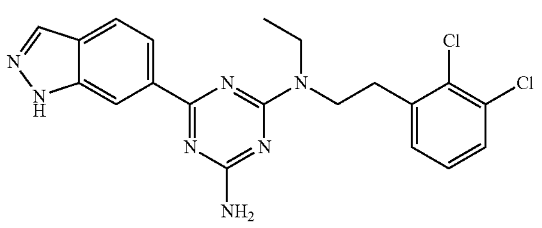 [SMILES: CCN(CCc1cccc(Cl)c1Cl)c1nc(N)nc(-c2ccc3cn[nH]c3c2)n1]

Synthesised by General Method A Using the Following Reagents and Conditions:

Step 1: Intermediate X (52 mg, 0.16 mmol), 2-(2,3-dichlorophenyl)-N-ethyl-ethanamine (56 mg, 0.26 mmol), N,N-diisopropylethylamine (0.14 mL, 0.79 mmol) and 1,4-dioxane (6 mL) heated at 60° C. for 20 hours.

Step 2: N2-[2-(2,3-dichlorophenyl)ethyl]-N2-ethyl-6-(1-tetrahydropyran-2-ylindazol-6-yl)-1,3,5-triazine-2,4-diamine (63 mg, 0.12 mmol), methyl alcohol (4 mL) and 4 M HCl in 1,4-dioxane (1.23 mL, 4.92 mmol) heated at 60° C. for 16 hours. Purification by flash chromatography afforded the title compound. (39 mg, 0.09 mmol, 72% yield). $^1$H NMR (600 MHz, DMSO-d6) δ 13.26 (s, 1H), 8.49 (s, 0.42H), 8.46 (s, 0.59H), 8.10 (s, 1H), 8.08-7.98 (m, 1H), 7.78 (dd, J=8.5, 3.4 Hz, 1H), 7.50 (d, J=8.0 Hz, 0.37H), 7.42 (t, J=7.8 Hz, 1H), 7.33 (d, J=7.6 Hz, 1H), 7.31-7.24 (m, 1H), 6.83 (s, 2H), 3.88 (t, J=7.2 Hz, 1H), 3.71 (t, J=7.6 Hz, 1H), 3.63 (t, J=7.1 Hz, 1H), 3.55 (q, J=7.0 Hz, 1H), 3.13 (t, J=7.3 Hz, 1H), 3.09 (t, J=7.7 Hz, 1H), 1.15 (t, J=7.1 Hz, 1H), 1.10 (t, J=7.0 Hz, 2H). LCMS MDAP, Rt=18.96 min, >97% (Method 4); m/z (ESI$^+$) 428/430 (Cl isotopes) [M+H]$^+$.

Example 11

6-(1H-indazol-6-yl)-N2-[2-[3-(trifluoromethyl)pyrazol-1-yl]ethyl]-1,3,5-triazine-2,4-diamine

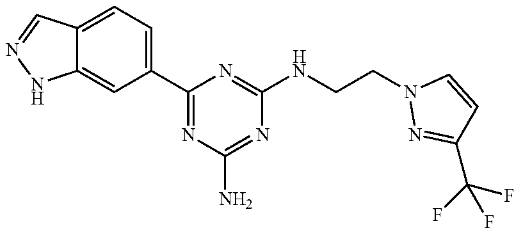 [SMILES: Nc1nc(NCCn2ccc(C(F)(F)F)n2)nc(-c2ccc3cn[nH]c3c2)n1]

Synthesised by General Method A Using the Following Reagents and Conditions:

Step 1: Intermediate X (60 mg, 0.18 mmol), 2-[3-(trifluoromethyl)-1H-pyrazol-1-yl]ethan-1-amine (54 mg, 0.30 mmol), N,N-diisopropylethylamine (0.11 mL, 0.63 mmol) and 1,4-dioxane (3.6 mL) heated at 60° C. for 24 hours.

Step 2: 6-(1-tetrahydropyran-2-ylindazol-6-yl)-N2-[2-[3-(trifluoromethyl)pyrazol-1-yl]ethyl]-1,3,5-triazine-2,4-diamine (67 mg, 0.14 mmol), methyl alcohol (3.5 mL) and 4 M HCl in 1,4-dioxane (1.4 mL, 5.6 mmol) heated at 60° C. for 16 hours. Purification by flash chromatography afforded the title compound (22. mg, 0.0500 mmol, 38% yield). $^1$H NMR (600 MHz, DMSO-d6) δ 13.25 (s, 1H), 8.48 (s, 0.38H), 8.44 (s, 0.49H), 8.12-8.08 (m, 1H), 8.06 (d, J=8.5 Hz, 0.41H), 8.00 (d, J=8.5 Hz, 0.53H), 7.94 (s, 0.54H), 7.91 (s, 0.42H), 7.81-7.71 (m, 1H), 7.43 (t, J=5.7 Hz, 0.59H), 7.20 (t, J=5.2 Hz, 0.20H), 6.93 (s, 1H), 6.78 (s, 1H), 6.68 (s, 0.41H), 6.63 (s, 0.38H), 4.43 (t, J=5.5 Hz, 1H), 4.39 (t, J=6.4 Hz, 1H), 3.79 (q, J=6.1 Hz, 1H), 3.68 (q, J=6.2 Hz, 1H). LCMS MDAP Rt=15.09 min, >95% (Method 4); m/z (ESI$^+$) 390 [M+H]$^+$.

Example 12

6-(1H-indazol-6-yl)-N2-[1-methyl-1-(2-pyridyl) ethyl]-1,3,5-triazine-2,4-diamine hydrochloride

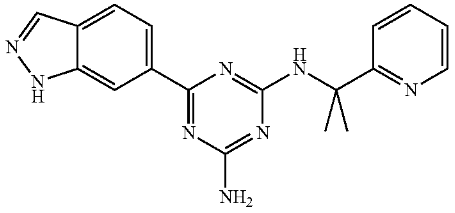

Synthesised by General Method A Using the Following Reagents and Conditions:

Step 1: Intermediate X (200 mg, 0.60 mmol), 2-(2-Pyridyl)-2-propylamine (135 mg, 1 mmol), N,N-diisopropylethylamine (0.32 mL, 1.81 mmol) and 1,4-dioxane (20 mL) heated at 100° C. for 4 days.

Step 2: N2-[1-methyl-1-(2-pyridyl)ethyl]-6-(1-tetrahydropyran-2-ylindazol-6-yl)-1,3,5-triazine-2,4-diamine (105 mg, 0.24 mmol), 1,4-dioxane (10 mL), methyl alcohol (10 mL) and 4M HCl in 1,4-dioxane (2.44 mL, 9.76 mmol) heated for 12 hours at 60° C. Purification by flash chromatography afforded the title compound (93 mg, 0.24 mmol, 97% yield). $^1$H NMR (600 MHz, DMSO-d6) δ 13.37 (s, 0.36H), 13.30 (s, 0.66H), 8.56 (s, 1H), 8.50 (s, 0.43H), 8.07 (s, 1.11H), 8.03 (s, 0.76H), 7.82-7.52 (m, 3H), 7.46 (d, J=8.1 Hz, 1H), 7.19 (s, 0.39H), 7.13 (s, 0.68H), 6.90-6.36 (m, 2H), 1.73 (s, 6H). LCMS MDAP Rt=10.22 min, >97% (Method 4); m/z (ESI$^+$) 371.1 [M+H]$^+$.

Example 13

N2-[(2,3-dichlorophenyl)methyl]-6-(1H-indazol-6-yl)-N2-methyl-1,3,5-triazine-2,4-diamine

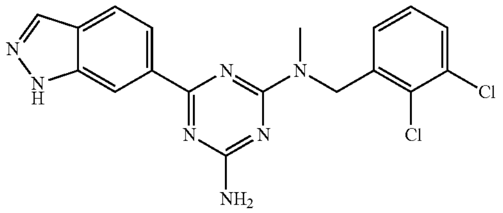

Synthesised by General Method A Using the Following Reagents and Conditions:

Step 1: Intermediate X (50 mg, 0.15 mmol), (2,3-dichlorophenyl)methyl](methyl)amine hydrochloride (41 mg, 0.18 mmol) and N,N-diisopropylethylamine (0.08 mL, 0.45 mmol) and 1,4-dioxane (2 mL) heated to 60° C. for 20 h.

Step 2: N2-[(2,3-dichlorophenyl)methyl]-N2-methyl-6-(1-tetrahydropyran-2-ylindazol-6-yl)-1,3,5-triazine-2,4-diamine (69 mg, 0.14 mmol), methanol (1 ml) and 4M Hydrochloric acid in 1,4-dioxane (3 mL, 12 mmol) stirred at RT for 90 min. Purification by flash chromatography afforded the title compound (17 mg, 0.04 mmol, 29%). $^1$H NMR (600 MHz, DMSO-d6) δ 13.27 (s, 0.5H), 13.20 (s, 0.5H), 8.55 (s, 0.5H), 8.38 (s, 0.5H), 8.12 (d, J=8.9 Hz, 1H), 8.07 (s, 0.4H), 7.92 (d, J=8.6 Hz, 0.6H), 7.81 (d, J=8.4 Hz, 0.5H), 7.73 (d, J=8.6 Hz, 0.5H), 7.55-7.52 (m, 1H), 7.33 (q, J=8.1 Hz, 1H), 7.11 (d, J=7.7 Hz, 0.5H), 7.08-7.03 (m, 1.5H), 6.93 (s, 2H), 5.08 (s, 1H), 4.92 (s, 1H), 3.28 (s, 0.3H), 3.12 (s, 1.6H). LCMS-MDAP Rt=18.89 min, >95% (Method 4); m/z (ESI$^+$) 401.95, 399.95 (Cl isotopes) [M+H]$^+$.

Example 14

6-(1H-indazol-6-yl)-N2-[2-(3-methylpyrazol-1-yl) ethyl]-1,3,5-triazine-2,4-diamine

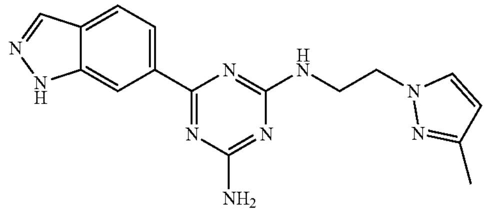 [SMILES: Cc1ccn(CCNc2nc(N)nc(-c3ccc4cn[nH]c4c3)n2)n1]

Synthesised by General Method A Using the Following Reagents and Conditions:

Step 1: Intermediate X (60 mg, 0.18 mmol), 2-(3-methyl-1H-pyrazol-1-yl)ethan-1-amine (37 mg, 0.30 mmol), N,N-diisopropylethylamine (0.08 mL, 0.45 mmol) and 1,4-dioxane (3.5 mL) heated at 60° C. for 40 hours.

Step 2: N2-[2-(3-methylpyrazol-1-yl)ethyl]-6-(1-tetrahydropyran-2-ylindazol-6-yl)-1,3,5-triazine-2,4-diamine (72 mg, 0.17 mmol), methyl alcohol (5 mL) and 4 M HCl in 1,4-dioxane (1.72 mL, 6.87 mmol) was heated at 60° C. for 16 hours. Purification by flash chromatography afforded the title compound (37 mg, 0.11 mmol, 62%). $^1$H NMR (600 MHz, DMSO-d6) δ 13.26 (s, 1H), 8.49 (s, 0.37H), 8.44 (s, 0.47H), 8.16-8.04 (m, 1H), 8.00 (d, J=8.3 Hz, 1H), 7.83-7.71 (m, 1H), 7.55 (s, 0.55H), 7.52 (s, 0.42H), 7.34 (t, J=5.6 Hz, 0.58H), 7.13 (t, J=5.6 Hz, 0.44H), 6.93 (s, 1H), 6.79 (s, 1H), 5.97 (s, 0.52H), 5.94 (s, 0.37H), 4.23 (t, J=6.1 Hz, 1H), 4.19 (t, J=6.6 Hz, 1H), 3.73 (q, J=6.2 Hz, 1H), 3.62 (q, J=6.3 Hz, 1H), 2.13 (s, 2H), 2.11 (s, 1H). LCMS MDAP Rt=12.43 min, >97% (Method 4); m/z (ESI$^+$) 336 [M+H]$^+$.

Example 15

6-(1H-indazol-6-yl)-N2-[2-(4-methylpyrazol-1-yl) ethyl]-1,3,5-triazine-2,4-diamine

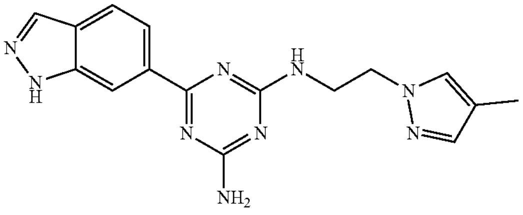 [SMILES: Cc1cnn(CCNc2nc(N)nc(-c3ccc4cn[nH]c4c3)n2)c1]

Synthesised by General Method A Using the Following Reagents and Conditions:

Step 1: Intermediate X (50 mg, 0.15 mmol), 2-(4-methyl-1H-pyrazol-1-yl)ethan-1-amine (21.76 mg, 0.17 mmol), N,N-diisopropylethylamine (0.07 mL, 0.38 mmol) and 1,4-dioxane (3 mL) heated at 60° C. for 40 hours.

Step 2: N2-[2-(4-methylpyrazol-1-yl)ethyl]-6-(1-tetrahydropyran-2-ylindazol-6-yl)-1,3,5-triazine-2,4-diamine (50 mg, 0.12 mmol), methyl alcohol (3 mL) and 4 M HCl in 1,4-dioxane (0.89 mL, 3.58 mmol) heated at 60° C. for 21 hours. Purification by flash chromatography afforded the title compound (50 mg, 0.12 mmol, 51%). $^1$H NMR (600 MHz, DMSO-d6) δ 13.26 (s, 1H), 8.49 (s, 0.36H), 8.44 (s, 0.46H), 8.14-8.04 (m, 1H), 8.00 (d, J=8.5 Hz, 1H), 7.83-7.73 (m, 1H), 7.46 (d, J=9.3 Hz, 1H), 7.33 (t, J=5.8 Hz, 0.59H), 7.22 (s, 1H), 7.13 (t, J=5.8 Hz, 0.43H), 6.94 (s, 1H), 6.78 (s, 1H), 4.25 (t, J=6.5 Hz, 1H), 4.20 (t, J=6.1 Hz, 1H), 3.72 (q, J=6.4 Hz, 1H), 3.62 (q, J=6.3 Hz, 1H), 1.97 (s, 2H), 1.94 (s, 1H). LCMS MDAP Rt=12.55 min, >98% (Method 4); m/z (ESI$^+$) 336 [M+H]$^+$.

Example 16

N2-[2-(3-chloro-2-pyridyl)ethyl]-6-(1H-indazol-6-yl)-1,3,5-triazine-2,4-diamine hydrochloride

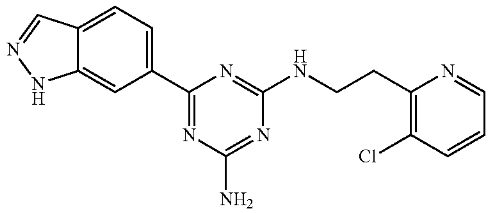

Synthesised by General Method A Using the Following Reagents and Conditions:

Step 1: Intermediate X (75 mg, 0.23 mmol), 2-(3-chloro-2-pyridyl)ethylammonium chloride (53 mg, 0.27 mmol) N,N-diisopropylethylamine (0.1 mL, 0.57 mmol) and 1,4-dioxane (4.5 mL) heated to 60° C. for 12 hours.

Step 2: N2-[2-(3-chloro-2-pyridyl)ethyl]-6-(1-tetrahydropyran-2-ylindazol-6-yl)-1,3,5-triazine-2,4-diamine (50 mg, 0.11 mmol), methyl alcohol (1 mL) and 4 M HCl in 1,4-dioxane (0.83 mL, 3.33 mmol) heated at 60° C. or 18 h. Filtration afforded the title compound (30 mg, 0.08 mmol, 70% yield). $^1$H NMR (399 MHz, DMSO-d6, VT 90° C.) δ 8.52 (s, 1H), 8.49-8.42 (m, 1H), 8.15 (s, 1H), 7.98 (dt, J=9.4, 1.7 Hz, 1H), 7.91-7.85 (m, 1H), 7.85-7.78 (m, 1H), 7.30-7.20 (m, 1H), 3.94-3.79 (m, 2H), 3.24 (t, J=7.1 Hz, 2H). LCMS MDAP Rt=14.07 min, 70% (Method 4); m/z (ESI$^+$) 367.1 [M+H]$^+$.

Example 17

N4-[(2,3-dichlorophenyl)methyl]-6-(1H-indazol-6-yl)-1,3,5-triazine-2,4-diamine

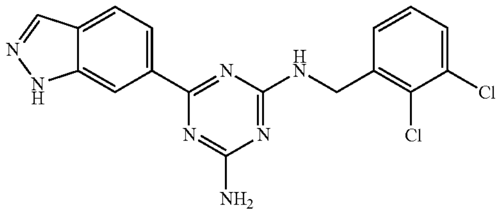

Synthesised by General Method A Using the Following Reagents and Conditions:

Step 1: Intermediate X (60 mg, 0.18 mmol), 1-(2,3-dichlorophenyl)methanamine (0.03 mL, 0.22 mmol) N,N diisopropylethylamine (0.09 mL, 0.54 mmol) and 1,4-dioxane (1 mL) heated to 60° C. for 16 h.

Step 2: N 4-[(2,3-dichlorophenyl)methyl]-6-(1-tetrahydropyran-2-ylindazol-6-yl)-1,3,5-triazine-2,4-diamine (85 mg, 0.18 mmol), 1.25 M HCl in methanol (0.87 mL, 1.08 mmol) and 4 M HCl in 1,4-dioxane (0.9 mL, 3.61 mmol) stirred at RT for 1 h. Purification by flash chromatography (silica, eluting with gradient 0-10% methanol in DCM) followed by trituration with diethyl ether afforded the title (2.2 mg, 0.01 mmol, 3%). $^1$H NMR (600 MHz, DMSO-d6) δ 13.29 (s, 0.6H), 13.22 (s, 0.4H), 8.48 (s, 0.6H), 8.41 (s, 0.4H), 8.13-8.01 (m, 1H), 8.00-7.83 (m, 1H), 7.76 (dd, J=28.6, 9.0 Hz, 1H), 7.52 (d, J=8.5 Hz, 1H), 7.45-7.17 (m, 2H), 7.07-6.74 (m, 2H), 4.72 (d, J=6.2 Hz, 0.8H), 4.58 (d, J=6.2 Hz, 1.2H). LCMS MDAP Rt=17.41 min (Method 4); m/z (ESI$^+$) 385.90 [M+H]$^+$.

Example 18

N2-[2-(2,3-dichlorophenyl)ethyl]-6-(1H-indazol-6-yl)-1,3,5-triazine-2,4-diamine

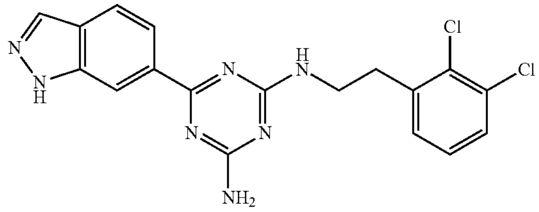 [SMILES: Nc1nc(NCCc2cccc(Cl)c2Cl)nc(-c2ccc3cn[nH]c3c2)n1]

Synthesised by General Method A Using the Following Reagents and Conditions:

Step 1: Intermediate X (125 mg, 0.38 mmol), 2-(2,3-dichlorophenyl)ethanamine (83 mg, 0.43 mmol) N,N diisopropylethylamine (0.16 mL, 0.94 mmol) and 1,4-dioxane (2 mL) heated to 60° C. for 2 h.

Step 2: N 2-[2-(2,3-dichlorophenyl)ethyl]-6-(1-tetrahydropyran-2-ylindazol-6-yl)-1,3,5-triazine-2,4-diamine (65 mg, 0.13 mmol), 1.25 M HCl in methanol (1 mL, 1.34 mmol) and 4 M HCl in 1,4-dioxane (1 mL, 4 mmol) heated to 60° C. for 3 h. Purification by flash chromatography (silica, eluting with gradient 0-10% methanol in DCM) afforded the title compound (23 mg, 0.05 mmol, 41% Yield). $^1$H NMR—(500 MHz, D6-DMSO) δH 13.25 (s, 1H), 8.47 (s, 0.5H*), 8.44 (s, 0.5H*) 8.09 (s, 0.5H*), 8.04 (d, 8.6 Hz, 0.5H*), 8.00 (d, J=8.6 Hz, 0.5H*), 7.77 (t, J=8.6 Hz, 1H), 7.49 (d, J=7.6 Hz, 0.5H*), 7.47-7.40 (m, 1H), 7.36 (d, 7.6 Hz, 0.5H*) 7.33-7.21 (m, 2H), 6.94-6.81 (br, 1.5H*), 6.78-6.69 (br, 1H), 3.65 (q, J=6.5 Hz, 1H), 3.52 (q, J=6.8 Hz), 3.10-3.02 (m, 2H) (*unusual splitting resolved on VT-NMR at 90° C.). LCMS Rt=5.76 min, >95% (Method 3) 5-95% Acetonitrile:Water (0.1% Formic)); m/z (ESI$^+$) 400.14 [M+H]$^+$.

Example 19

6-(1H-indazol-6-yl)-N2-methyl-N2-[1-(1-methylpyrazol-3-yl)cyclopropyl]-1,3,5-triazine-2,4-diamine

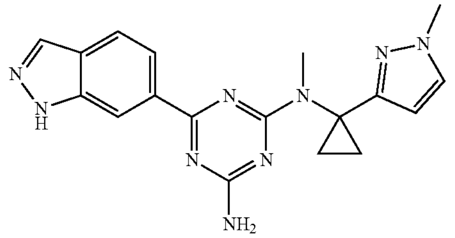

Synthesised by General Method B.

Step 1: 6-Chloro-N4-methyl-N 4-[1-(1-methylpyrazol-3-yl)cyclopropyl]-1,3,5-triazine-2,4-diamine N-Methyl-1-(1-methylpyrazol-3-yl)cyclopropanamine (Intermediate D) (100 mg, 0.67 mmol) was suspended in 1,4-dioxane (4 mL) and 2-Amino-4,6-dichlorotriazine (100 mg, 0.61 mmol) was added followed by N,N-diisopropylethylamine (0.32 mL, 1.82 mmol). The mixture was heated to 90° C. for 12 h. The solvent was evaporated to dryness under reduced pressure and the crude material purified by flash column chromatography (Silica eluting with a gradient 0-10% methanol in DCM) to afford the title compound as a white solid (55 mg, 0.19 mmol, 31% yield). LCMS-LCQ Rt=3.00 min (Method 2); m/z ($ESI^+$) 280.19, 282.20 (Cl isotopes) $[M+H]^+$.

Step 2: N4-Methyl-N 4-[1-(1-methylpyrazol-3-yl)cyclopropyl]-6-(1-tetrahydropyran-2-ylindazol-6-yl)-1,3,5-triazine-2,4-diamine A stirred solution of 6-chloro-N4-methyl-N 4-[1-(1-methylpyrazol-3-yl)cyclopropyl]-1,3,5-triazine-2,4-diamine (38 mg, 0.14 mmol), potassium phosphate tribasic (86 mg, 0.41 mmol), and bis[2-(di-tert-butylphosphanyl)cyclopenta-2,4-dien-1-yl]iron; dichloropalladium (9 mg, 0.01 mmol) in tetrahydrofuran (5 mL) and water (0.5 mL) was degassed by bubbling $N_2$ directly into the solution. The mixture was heated to 80° C. then a solution of 1-tetrahydropyran-2-yl-6-(4,4,5,5-tetramethyl-1,3,2-dioxaborolan-2-yl)indazole (Intermediate V) (111 mg, 0.34 mmol) in THF (4 mL) was added and the reaction was stirred at 80° C. for 12 h. The mixture was concentrated to dryness under reduced pressure and the crude was purified by flash column chromatography (silica gel, eluting with a gradient 30 to 100% EtOAc in petroleum ether) to afford the title compound as a white solid (40 mg, 0.09 mmol, 63% yield). $^1$H NMR (399 MHz, DMSO-$d_6$) δ 8.62 (s, 1H), 8.11 (d, J=8.5 Hz, 1H), 7.76 (d, J=8.5 Hz, 1H), 7.38 (d, J=2.2 Hz, 1H), 6.59-6.42 (m, 3H), 5.93 (d, J=2.1 Hz, 1H), 5.80 (d, J=9.1 Hz, 1H), 3.88 (d, J=11.2 Hz, 1H), 3.76-3.65 (m, 4H), 3.22 (s, 3H), 2.46-2.33 (m, 1H), 2.13-1.96 (m, 2H), 1.86-1.68 (m, 1H), 1.65-1.54 (m, 2H), 1.47-1.30 (m, 4H); LCMS MDAP Rt=16.58 min (Method 4); m/z ($ESI^+$) 446.3 $[M+H]^+$.

Step 3: 6-(1H-Indazol-6-yl)-N2-methyl-N 2-[1-(1-methylpyrazol-3-yl)cyclopropyl]-1,3,5-triazine-2,4-diamine A solution of N2-methyl-N 2-[1-(1-methylpyrazol-3-yl)cyclopropyl]-6-(1-tetrahydropyran-2-ylindazol-6-yl)-1,3,5-triazine-2,4-diamine (40 mg, 0.09 mmol) in methyl alcohol (1 mL) and 4 M HCl in 1,4-dioxane (0.22 mL, 0.90 mmol) was heated at 40° C. for 16 h. The resulting suspension was filtered and the filtered solid washed with diethyl ether and petroleum ether, then dried in oven at 50° C. for 2 h to afford the title compound. $^1$H NMR (399 MHz, DMSO-d6) δ 8.57 (s, 1H), 8.14 (s, 1H), 8.04 (d, J=8.6 Hz, 1H), 7.87 (d, J=8.6 Hz, 1H), 7.46 (d, J=2.2 Hz, 1H), 6.03 (d, J=2.2 Hz, 1H), 3.74 (s, 3H), 3.32 (s, 3H), 1.46 (d, J=4.2 Hz, 4H). LCMS MDAP Rt=13.45 min (Method 4); m/z ($ESI^+$) 362.2 $[M+H]^+$.

Example 20

N2-[1-(2-Chloro-3-fluoro-phenyl)cyclopropyl]-6-(1H-indazol-6-yl)-1,3,5-triazine-2,4-diamine

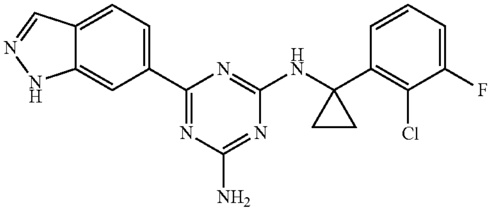

Synthesised by General Method B

Step 1: 6-Chloro-N 4-[1-(2-chloro-3-fluoro-phenyl)cyclopropyl]-1,3,5-triazine-2,4-diamine To a stirred solution of 2-amino-4,6-dichlorotriazine (506 mg, 3.0 mmol) in 1,4-dioxane (15 mL), N,N-diisopropylethylamine (1.34 mL, 7.68 mmol) was added followed by the addition of 1-(2-chloro-3-fluoro-phenyl)cyclopropanamine (570 mg, 3.07 mmol). The resulting mixture was stirred at RT for 12 h. The reaction mixture was evaporated to dryness under reduced pressure and the crude reside was purified by chromatography (silica, eluting with a gradient 50 to 100% EtOAc in petroleum ether) to afford the title compound as a white powder (600 mg, 1.81 mmol, 59% yield). $^1$H NMR (600 MHz, DMSO-$d_6$) δ 8.40 (d, J=102.2 Hz, 1H), 7.79-7.47 (m, 1H), 7.32 (s, 1H), 7.30-7.18 (m, 2H), 7.10 (d, J=98.6 Hz, 1H), 1.21-1.14 (m, 2H), 1.12-1.04 (m, 2H).

Step 2: N 4-[1-(2-Chloro-3-fluoro-phenyl)cyclopropyl]-6-(1-tetrahydropyran-2-ylindazol-6-yl)-1,3,5-triazine-2,4-diamine A stirred solution of 6-chloro-N 4-[1-(2-chloro-3-fluoro-phenyl)cyclopropyl]-1,3,5-triazine-2,4-diamine (70 mg, 0.22 mmol), potassium phosphate tribasic (142 mg, 0.67 mmol), and bis[2-(di-tert-butylphosphanyl)cyclopenta-2,4-dien-1-yl]iron; dichloropalladium (14.5 mg, 0.02 mmol) in tetrahydrofuran (5 mL) and water (0.5 mL) was degassed by bubbling N2 directly into the solution. The mixture was warm up to 80° C. then a solution of 1-tetrahydropyran-2-yl-6-(4,4,5,5-tetramethyl-1,3,2-dioxaborolan-2-yl)indazole (Intermediate V) (183 mg, 0.56 mmol) in THF (5 mL) was added and the reaction was stirred at 80° C. for 12 h. The mixture was concentrated to dryness and the crude was purified by flash column chromatography (Silica, eluting with a gradient of 30 to 100% EtOAc in petroleum ether) to afford the title compound as a white solid (75 mg, 0.15 mmol, 67% yield). LCMS-LCQ Rt=3.50 min (Method 1); m/z ($ESI^+$) 480.27 $[M+H]^+$.

Step 3: N2-[1-(2-Chloro-3-fluoro-phenyl)cyclopropyl]-6-(1H-indazol-6-yl)-1,3,5-triazine-2,4-diamine A solution of N 2-[1-(2-chloro-3-fluoro-phenyl)cyclopropyl]-6-(1-tetrahydropyran-2-ylindazol-6-yl)-1,3,5-triazine-2,4-diamine (75 mg, 0.16 mmol) in methyl alcohol (1 mL) and 4 M HCl in 1,4-dioxane (0.4 mL, 1.56 mmol) was heated at 40° C. for 16 h. The resulting suspension was filtered, washed with diethyl ether and petroleum ether, then dried in oven at 50° C. for 2 h to afford the title compound (55 mg, 0.14 mmol, 88%). $^1H$ NMR (399 MHz, DMSO-$d_6$, VT 90° C.) δ 8.48 (s, 1H), 8.11 (s, 1H), 7.97 (d, J=8.7 Hz, 1H), 7.81 (dd, J=17.6, 8.1 Hz, 2H), 7.31 (q, J=7.5, 7.1 Hz, 1H), 7.25-7.15 (m, 1H), 1.35 (t, J=3.7 Hz, 2H), 1.24 (t, J=3.7 Hz, 2H). LCMS MDAP Rt=18.32 min (Method 4); m/z ($ESI^+$) 396.1 [M+H].

Example 21

N2-[(3-chloro-5-methyl-2-pyridyl)methyl]-6-(1H-indazol-6-yl)-1,3,5-triazine-2,4-diamine

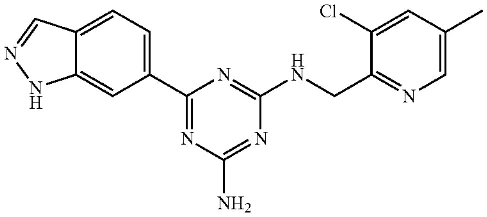

Synthesised by General Method B:

Step 1: 6-Chloro-N 4-[(3-chloro-5-methyl-2-pyridyl)methyl]-1,3,5-triazine-2,4-diamine N,N-Diisopropylethylamine (0.43 mL, 2.49 mmol) was added to a suspension of 2-amino-4,6-dichlorotriazine (90 mg, 0.55 mmol) and (3-chloro-5-methyl-2-pyridyl)methanamine (78 mg, 0.50 mmol) in 1,4-dioxane (2 mL). The reaction mixture was stirred at RT for 16 h then partitioned between ethyl acetate and water. The organic phase was separated, dried ($MgSO_4$), filtered and concentrated to dryness under reduced pressure. The residue was dry loaded onto celite and purified by flash silica chromatography eluting with a gradient of 0-5% methanol in DCM to afford the title compound as a white solid (44 mg, 0.15 mmol, 29%). $^1H$ NMR (600 MHz, Chloroform-d) δ 8.26 (s, 1H), 7.52 (d, J=2.4 Hz, 1H), 7.16-6.90 (m, 1H), 5.53-5.09 (m, 2H), 4.78-4.61 (m, 2H), 2.33 (s, 3H). LCMS MDAP Rt=2.51 min (Method 6); m/z ($ESI^+$) 284.85 $[M+H]^+$.

Step 2: N 2-[(3-Chloro-5-methyl-2-pyridyl)methyl]-6-(1-tetrahydropyran-2-ylindazol-6-yl)-1,3,5-triazine-2,4-diamine Bis[2-(di-tert-butylphosphanyl)cyclopenta-2,4-dien-1-yl] iron; dichloropalladium (5.0 mg, 0.01 mmol) was added to a degassed mixture of 1-tetrahydropyran-2-yl-6-(4,4,5,5-tetramethyl-1,3,2-dioxaborolan-2-yl)indazole (Intermediate V) (60 mg, 0.19 mmol), 6-chloro-N 2-[(3-chloro-5-methyl-2-pyridyl)methyl]-1,3,5-triazine-2,4-diamine (44 mg, 0.15 mmol) and potassium phosphate tribasic (98 mg, 0.46 mmol) in tetrahydrofuran (1 mL) and water (0.25 mL). The reaction mixture was heated to 60° C. for 16 h then cooled to RT and filtered through a pad of celite. The celite pad was washed successively with ethyl acetate and water. The organic phase of the filtrate was separated, washed with brine, dried (MgSO4), filtered and concentrated to dryness under reduced pressure. The residue was purified by flash silica chromatography eluting with 0-10% methanol in DCM. The product containing fractions were combined and concentrated under reduced pressure and re-purified by flash silica chromatography eluting with a gradient of 0-60% ethyl acetate in petroleum ether. To afford the title compound as a white solid which was take on directly to the next step.

Step 3: N2-[(3-Chloro-5-methyl-2-pyridyl)methyl]-6-(1H-indazol-6-yl)-1,3,5-triazine-2,4-diamine N2-[(3-Chloro-5-methyl-2-pyridyl)methyl]-6-(1-tetrahydropyran-2-ylindazol-6-yl)-1,3,5-triazine-2,4-diamine (26 mg, 0.06 mmol) was dissolved methanol (1 mL) and of 4 M HCl in 1,4-dioxane (2 mL) added. The resulting solution was stirred for 2 h at RT, then concentrated to dryness under reduced pressure. The residue was purified by flash silica chromatography eluting with a gradient of 0-15% methanol in ethyl acetate, to afford the title compound as an off white solid (12 mg, 0.03 mmol, 20% Yield). $^1H$ NMR (399 MHz, DMSO-d6) (VT at 90° C.) δ 13.01 (s, 1H), 8.49 (s, 1H), 8.32 (s, 1H), 8.07-7.99 (m, 2H), 7.77-7.69 (m, 2H), 7.06 (s, 1H), 6.53 (s, 2H), 4.75 (d, J=5.4 Hz, 2H), 2.28 (s, 3H). LCMS MDAP Rt=14.78 min (Method 4); m/z ($ESI^+$) 367.1 $[M+H]^+$.

Example 22

N2-[1-[1-(Difluoromethyl)pyrazol-3-yl]cyclopropyl]-6-(1H-indazol-6-yl)-1,3,5-triazine-2,4-diamine

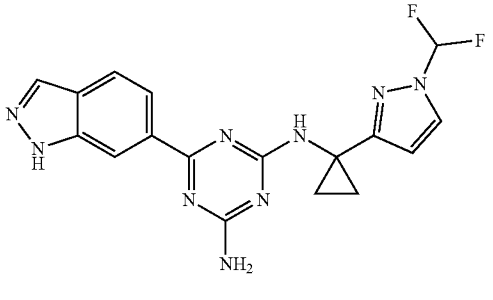 [SMILES: Nc1nc(NC2(c3ccn(C(F)F)n3)CC2)nc(-c2ccc3cn[nH]c3c2)n1]

Synthesised by General Method B:

Step 1: 6-Chloro-N 4-[1-[1-(difluoromethyl)pyrazol-3-yl]cyclopropyl]-1,3,5-triazine-2,4-diamine 2-Amino-4,6-dichlorotriazine (322 mg, 1.95 mmol), [1-[1-(difluoromethyl)pyrazol-3-yl]cyclopropyl]ammonium chloride (Intermediate G) (273 mg, 1.3 mmol) and N,N-diisopropylethylamine (0.45 mL, 2.6 mmol) were dissolved in 1,4-dioxane (20 mL), and the reaction mixture was stirred 48 h. The reaction mixture was dry loaded directly onto celite and purified by flash silica chromatography, eluting with a gradient of 0-100% ethyl acetate in petroleum ether to afford the title compound as a white solid (187 mg, 0.59 mmol, 45% yield). $^1$H NMR (600 MHz, Chloroform-d) δ 7.66 (d, J=2.7 Hz, 1H), 7.06 (t, J=60.9 Hz, 1H), 6.35-6.25 (m, 1H), 6.06 (s, 1H), 5.26 (m, 2H), 1.48-1.44 (m, 2H), 1.31-1.28 (m, 2H). LCMS LCQ Rt=4.58 min (Method 3); m/z (ESI$^+$) 302.22 [M+H]$^+$.

Step 2: N 4-[1-[1-(Difluoromethyl)pyrazol-3-yl]cyclopropyl]-6-(1-tetrahydropyran-2-ylindazol-6-yl)-1,3,5-triazine-2,4-diamine Bis[2-(di-tert-butylphosphanyl)cyclopenta-2,4-dien-1-yl]iron; dichloropalladium (8 mg, 0.01 mmol) was added to a suspension of 6-chloro-N 4-[1-[1-(difluoromethyl)pyrazol-3-yl]cyclopropyl]-1,3,5-triazine-2,4-diamine (189 mg, 0.63 mmol), 1-tetrahydropyran-2-yl-6-(4,4,5,5-tetramethyl-1,3,2-dioxaborolan-2-yl)indazole (Intermediate V) (247 mg, 0.75 mmol) and potassium phosphate tribasic (266 mg, 1.25 mmol) in tetrahydrofuran (8 mL) and water (2 mL). The biphasic mixture was degassed with nitrogen for 5 min then sealed and heated to 80° C. for 16 h. The reaction mixture was cooled to RT and partitioned between ethyl acetate and brine. The organic phase was separated, dried ($MgSO_4$), filtered and concentrated to dryness under reduced pressure. The residue was purified by flash silica chromatography eluting with a gradient of 0-100% ethyl acetate in petroleum ether to afford the title compound as a colourless oil (204 mg, 0.41 mmol, 66% yield). $^1$H NMR (600 MHz, Chloroform-d) δ 8.71-8.51 (m, 1H), 8.12-8.03 (m, 1H), 7.76-7.60 (m, 2H), 7.08 (t, J=60.9 Hz, 1H), 6.53-6.17 (m, 2H), 5.88-5.70 (m, 1H), 5.58-5.33 (m, 2H), 4.08-3.97 (m, 1H), 3.81-3.67 (m, 1H), 2.60 (s, 1H), 2.20-2.10 (m, 1H), 2.08-2.03 (m, 1H), 1.81-1.68 (m, 3H), 1.67-1.59 (m, 1H), 1.58-1.46 (m, 2H), 1.43-1.31 (m, 2H). LCMS LCQ Rt=6.11 min (Method 3); m/z (ESI$^+$) 468.29 [M+H]$^+$.

Step 3: N2-[1-[1-(difluoromethyl)pyrazol-3-yl]cyclopropyl]-6-(1H-indazol-6-yl)-1,3,5-triazine-2,4-diamine To N 2-[1-[1-(difluoromethyl)pyrazol-3-yl]cyclopropyl]-6-(1-tetrahydropyran-2-ylindazol-6-yl)-1,3,5-triazine-2,4-diamine (204 mg, 0.44 mmol) dissolved in 1,4-dioxane (10 mL) was added 4 M HCl in 1,4-dioxane (5.5 mL, 21.8 mmol). The reaction mixture was stirred at RT for 16 h then diluted with diethyl ether (10 mL) and the resulting precipitate collected by filtration. The solid was dried under vacuum to afford the title compound (125 mg, 0.28 mmol, 65% yield). $^1$H NMR (399 MHz, DMSO-d6) (VT at 90° C.) δ 9.34 (s, 2H), 8.59 (s, 1H), 8.18 (s, 1H), 8.09-7.86 (m, 3H), 7.62 (t, J=59.8 Hz, 1H), 6.44 (d, J=2.7 Hz, 1H), 3.58 (s, 1H), 1.42 (dd, J=6.3, 4.3 Hz, 4H). LCMS MDAP Rt=10.253 min, 96% (Method 5); m/z (ESI$^+$) 384.2 [M+H]$^+$.

Examples 23

N2-[1-(2,3-Difluorophenyl)cyclopropyl]-6-(1H-indazol-6-yl)-1,3,5-triazine-2,4-diamine

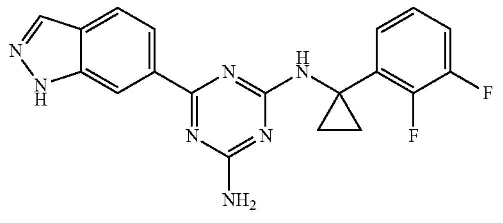

Synthesised by General Method B:

Step 1: 6-Chloro-N4-[1-(2,3-difluorophenyl)cyclopropyl]-1,3,5-triazine-2,4-diamine To a stirred solution of 2-amino-4,6-dichlorotriazine (240 mg, 1.45 mmol) in 1,4-dioxane (3.5 mL), was added N,N-diisopropylethylamine (0.63 mL, 3.64 mmol) followed by the addition of 1-(2,3-difluorophenyl)cyclopropanamine (Intermediate J) (120 mg, 0.71 mmol). The resulting mixture was stirred at RT for 12 h. The solvent was removed under reduced pressure and the crude was purified by flash chromatography (silica gel, eluting with a gradient of 50 to 100% EtOAc in petroleum ether) to afford the title compound as a white powder (150 mg, 0.48 mmol, 67% yield). $^1$H NMR (600 MHz, Chloroform-d) δ 7.30 (dt, J=75.5, 7.1 Hz, 1H), 7.04-6.88 (m, 2H), 2.89 (s, 3H), 1.27-1.16 (m, 4H).

Step 2: N 4-[1-(2,3-Difluorophenyl)cyclopropyl]-6-(1-tetrahydropyran-2-ylindazol-6-yl)-1,3,5-triazine-2,4-diamine A stirred solution of 6-chloro-N 4-[1-(2,3-difluorophenyl)cyclopropyl]-1,3,5-triazine-2,4-diamine (75 mg, 0.25 mmol), potassium phosphate tribasic (158 mg, 0.75 mmol), and bis[2-(di-tert-butylphosphanyl)cyclopenta-2,4-dien-1-yl]iron; dichloropalladium (16 mg, 0.02 mmol) in tetrahydrofuran (5 mL) and water (0.5 mL) was degassed by bubbling N2 directly into the solution. The mixture was warm up to 80° C. then a solution of 1-tetrahydropyran-2-yl-6-(4,4,5,5-tetramethyl-1,3,2-dioxaborolan-2-yl)indazole (Intermediate V) (204 mg, 0.62 mmol) in THF (4 mL) was added and the reaction was stirred at 80° C. for 12 h. The reaction mixture was concentrated to dryness under reduced pressure and the crude was purified by flash column chromatography (silica gel, eluting with a gradient of 30-100% EtOAc in petroleum ether) to afford the title compound as a white solid (80 mg, 0.17 mmol, 69% yield). LCMS MDAP Rt=3.21 min (Method 6); m/z (ESI$^+$) 464.15 [M+H]$^+$.

Step 3: N2-[1-(2,3-difluorophenyl)cyclopropyl]-6-(1H-indazol-6-yl)-1,3,5-triazine-2,4-diamine A solution of N 2-[1-(2,3-difluorophenyl)cyclopropyl]-6-(1-tetrahydropyran-2-ylindazol-6-yl)-1,3,5-triazine-2,4-diamine (80 mg, 0.17 mmol) in methyl alcohol (1 mL) and 4 M HCl in 1,4-dioxane (0.4 mL, 1.73 mmol) was heated at 40° C. for 16 h. A precipitate formed, which was filtered, washed with diethyl ether and petroleum ether, then dried in oven at 50 C for 2 h to afford the title compound (53 mg, 0.13 mmol, 65% yield). $^1$H NMR (399 MHz, DMSO-$d_6$) δ 9.14 (s, 1H), 8.54 (s, 1H), 8.14 (d, J=1.0 Hz, 1H), 7.98 (d, J=8.6 Hz, 1H), 7.88 (dd, J=8.6, 0.9 Hz, 1H), 7.62-7.43 (m, 1H), 7.28-7.16 (m, 1H), 7.16-7.09 (m, 1H), 1.35 (s, 4H). LCMS-MDAP Rt=2.97 min (Method 6); m/z (ESI$^+$) 380.05 [M+H]$^+$.

Example 24

N2-[(2-chloro-3-fluoro-phenyl)methyl]-6-(1H-indazol-6-yl)-1,3,5-triazine-2,4-diamine

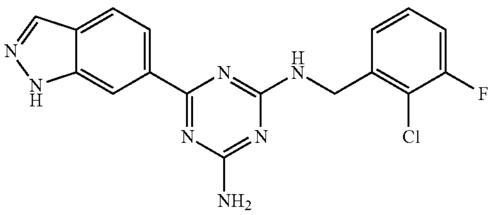

Synthesised by General Method B:

Step 1: 6-chloro-N4-[(2-chloro-3-fluoro-phenyl)methyl]-1,3,5-triazine-2,4-diamine 2-Amino-4,6-dichlorotriazine (1.0 g, 6.0 mmol) was added to a solution of N,N-diisopropylethylamine (2.64 mL, 15.15 mmol) and 2-Chloro-3-fluorobenzylamine (0.97 g, 6.0 mmol) in 1,4-dioxane (60 mL) and stirred at 25° C. for 20 hours. The reaction mixture was dry loaded directly onto celite and purified by flash chromatography on silica (40 g) eluting with a gradient of 0-5% methanol in DCM to afford the title compound (0.75 g, 2.56 mmol, 42% yield). $^1$H NMR (600 MHz, DMSO-d6) δ 8.26 (t, J=6.3 Hz, 0.66H), 8.12 (t, J=6.2 Hz, 0.27H), 7.41-7.18 (m, 4H), 7.16-7.07 (m, 1H), 4.58-4.42 (m, 2H). LCMS MDAP Rt=3.36 min, >98% (Method 7); m/z (ESI$^+$) 288/290 [M+H]$^+$.

Step 2: N4-[(2-chloro-3-fluoro-phenyl)methyl]-6-(1-tetrahydropyran-2-ylindazol-6-yl)-1,3,5-triazine-2,4-diamine A mixture of 6-chloro-N4-[(2-chloro-3-fluoro-phenyl)methyl]-1,3,5-triazine-2,4-diamine (250 mg, 0.87 mmol), 1-tetrahydropyran-2-yl-6-(4,4,5,5-tetramethyl-1,3,2-dioxaborolan-2-yl)indazole (Intermediate V) (570 mg, 1.74 mmol) and potassium phosphate tribasic (553 mg, 2.6 mmol) in tetrahydrofuran (12 mL) and water (1.2 mL) was de-gassed for 5 minutes. Bis[2-(di-tert-butylphosphanyl)cyclopenta-2,4-dien-1-yl]iron; dichloropalladium (56.55 mg, 0.09 mmol) was added and the reaction mixture was de-gassed for 5 minutes and then immediately heated in a sealed vessel to 65° C. The reaction mixture was stirred at 65° C. for 2.5 hours then directly loaded onto celite and subjected to flash chromatography on SiO2 (24 g) eluting with a gradient of 0-100% EtOAc in petroleum ether to afford the title compound (266 mg, 0.56 mmol, 64% yield). $^1$H NMR (600 MHz, DMSO-d6) δ 8.57 (s, 0.66H), 8.48 (s, 0.46H), 8.20-8.10 (m, 1.60H), 8.06 (d, J=8.5 Hz, 0.43H), 7.94 (t, J=6.3 Hz, 1H), 7.84 (d, J=8.2 Hz, 1H), 7.79 (d, J=8.5 Hz, 0.47H), 7.48-7.18 (m, 3H), 7.07-6.75 (m, 2H), 5.90 (d, J=8.7 Hz, 0.70H), 5.80 (d, J=9.4 Hz, 0.49H), 4.83-4.67 (m, 1H), 4.62 (d, J=5.9 Hz, 1H), 3.94-3.82 (m, 1H), 3.81-3.64 (m, 1H), 2.48-2.35 (m, 1H), 2.16-2.00 (m, 2H), 1.78 (s, 1H), 1.61 (s, 2H). LCMS MDAP Rt=6.26 min, >95% (Method 7); m/z (ESI$^+$) 454/456 [M+H]$^+$.

Step 3: N2-[(2-chloro-3-fluoro-phenyl)methyl]-6-(1H-indazol-6-yl)-1,3,5-triazine-2,4-diamine A solution of N2-[(2-chloro-3-fluoro-phenyl)methyl]-6-(1-tetrahydropyran-2-ylindazol-6-yl)-1,3,5-triazine-2,4-diamine (264 mg, 0.58 mmol) in methyl alcohol (15 mL) and 4 M HCl in 1,4-dioxane (6 mL, 23 mmol) was heated at 60° C. for 20 hours. The reaction mixture concentrated under reduced pressure and the crude reside dissolved in methanol and eluted onto an SCX-2 cartridge (2×10 g) and eluted with 2M NH3 in methanol (with DCM to aid solubility). The fractions were concentrated under reduced pressure and the crude material purified by flash chromatography on SiO2 eluting with a gradient of 0-30% methanol in DCM to afford the title compound (250 mg, 0.64 mmol, 80% yield). $^1$H NMR (600 MHz, DMSO-d6) δ 13.28 (s, 0.53H), 13.23 (s, 0.34H), 8.48 (s, 0.46H), 8.42 (s, 0.30H), 8.13-8.01 (m, 1H), 7.97 (d, J=8.5 Hz, 0.31H), 7.89 (t, J=6.2 Hz, 1H), 7.79 (d, J=8.5 Hz, 0.50H), 7.74 (d, J=8.3 Hz, 1H), 7.38-7.16 (m, 3H), 6.92 (s, 2H), 4.72 (d, J=6.1 Hz, 1H), 4.59 (d, J=6.1 Hz, 1H). LCMS MDAP Rt=23.4 min; >95% (Method 4); m/z (ESI$^+$) 370/372 [M+H]$^+$.

Example 25

N4-[1-(2,3-Difluorophenyl)-1-methyl-ethyl]-6-imidazo[1,5-a]pyridin-6-yl-1,3,5-triazine-2,4-diamine

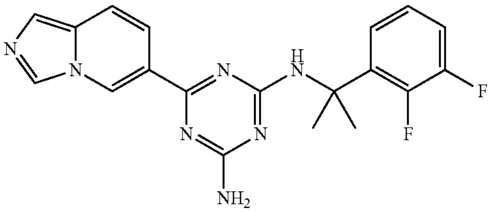

Synthesised by General Method D:

Step 1: 6-Chloro-N 4-[1-(2,3-difluorophenyl)-1-methyl-ethyl]-1,3,5-triazine-2,4-diamine 2-Amino-4,6-dichlorotriazine (300 mg, 1.82 mmol) was dissolved in 1,4-dioxane (10.5 mL) and 2-(2,3-difluorophenyl)propan-2-amine hydrochloride (Intermediate N) (0.2 mL, 2.04 mmol) was added followed by N,N-diisopropylethylamine (1.11 mL, 6.36 mmol). The mixture was heated to 150° C. in the microwave for 1 h. The reaction mixture was partitioned between DCM and water. The organic phase was separated, dried (hydrophobic frit) and concentrated to dryness under reduced pressure. The crude material was triturated with diethyl ether and filtered to afford the title compound as a white solid (511 mg, 1.45 mmol, 80% yield). $^1$H NMR (600 MHz, Chloroform-d) δ 7.19-6.81 (m, 3H), 5.81 (s, 1H), 5.41-4.81 (m, 2H), 1.80 (s, 6H).

Step 2: N 4-[1-(2,3-difluorophenyl)-1-methyl-ethyl]-6-imidazo[1,5-a]pyridin-6-yl-1,3,5-triazine-2,4-diamine

[1,1'-bis(Diphenylphosphino)ferrocene]dichloropalladium (II) (12 mg, 0.02 mmol) was added to a degassed suspension of 6-bromoimidazo[1,5-a]pyridine (75 mg, 0.38 mmol), bis(pinacolato)diboron (110 mg, 0.4300 mmol) and potassium acetate (66 mg, 0.67 mmol) in tetrahydrofuran (2 mL). The reaction mixture was sealed and heated to 80° C. overnight, then cooled to RT and 6-chloro-N4-[1-(2,3-difluorophenyl)-1-methyl-ethyl]-1,3,5-triazine-2,4-diamine (100 mg, 0.33 mmol), potassium phosphate tribasic (213 mg, 1.0 mmol) and bis[2-(di-tert-butylphosphanyl)cyclopenta-2,4-dien-1-yl]iron; dichloropalladium (4.35 mg, 0.01 mmol) added. The reaction mixture was diluted with the addition of water (0.2 mL) and tetrahydrofuran (2 mL), sealed and heated to 85° C. for 16 h. The reaction mixture was then cooled to RT and partitioned between ethyl acetate and aqueous potassium carbonate. The organic phase was separated, dried ($MgSO_4$), filtered and concentrated to dryness under reduced pressure. The residue was purified by aminosilica chromatography eluting with a gradient of 65-100% ethyl acetate in petroleum ether to afford the titled compound as a pale yellow solid (22.7 mg, 0.06 mmol, 17%). 1H NMR (399 MHz, DMSO-d6) δ 8.78 (s, 1H), 8.37 (s, 1H), 7.44 (d, J=9.5 Hz, 1H), 7.32-7.01 (m, 7H), 6.25 (s, 1H), 1.80 (s, 6H), LCMS LCQ Rt=4.64 min Method 3); m/z (ESI$^+$) 382.29 $[M+H]^+$.

Example 26

N4-[1-(2,3-Dichlorophenyl)-1-methyl-ethyl]-6-imidazo[1,5-a]pyridin-6-yl-1,3,5-triazine-2,4-diamine

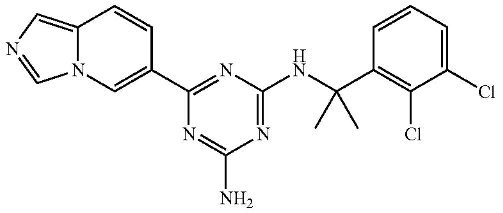 [SMILES: CC(C)(Nc1nc(N)nc(-c2ccc3cncn3c2)n1)c1cccc(Cl)c1Cl]

Synthesised by General Method D

Step 1: 6-Chloro-N 4-[1-(2,3-dichlorophenyl)-1-methyl-ethyl]-1,3,5-triazine-2,4-diamine To a solution of 2-(2,3-dichlorophenyl)propan-2-amine hydrochloride (Intermediate M) (0.2 mL, 2.04 mmol) and 2-amino-4,6-dichlorotriazine (300 mg, 1.82 mmol) in 1,4-dioxane (10.5 mL) was added N,N-diisopropylethylamine (1.11 mL, 6.36 mmol) and the mixture heated to 150° C. in the microwave for 1 h. The mixture was allowed to cool to RT and partitioned between DCM and water. The organic phase was separated (hydrophobic frit) and concentrated to dryness under reduced pressure. The residue was triturated with petroleum ether to afford the title compound as a white solid (648 mg, 1.66 mmol, 91% yield). $^1$H NMR (600 MHz, Chloroform-d) δ 7.51-7.35 (m, 2H), 7.16 (m, 1H), 5.91 (s, 1H), 5.34-4.64 (m, 2H), 1.86 (s, 6H).

Step 2: N 4-[1-(2,3-Dichlorophenyl)-1-methyl-ethyl]-6-imidazo[1,5-a]pyridin-6-yl-1,3,5-triazine-2,4-diamine

[1,1'-bis(diphenylphosphino)ferrocene]dichloropalladium (II) (11 mg, 0.02 mmol) was added to a degassed suspension of 6-bromoimidazo[1,5-a]pyridine (68 mg, 0.35 mmol), bis(pinacolato)diboron (100 mg, 0.39 mmol) and potassium acetate (59 mg, 0.60 mmol) in tetrahydrofuran (2 mL). The reaction was sealed and heated to 80° C. for 16 h. The reaction mixture was cooled to RT and 6-chloro-N 4-[1-(2,3-dichlorophenyl)-1-methyl-ethyl]-1,3,5-triazine-2,4-diamine (100 mg, 0.30 mmol), potassium phosphate tribasic (191 mg, 0.90 mmol), bis[2-(di-tert-butylphosphanyl)cyclopenta-2,4-dien-1-yl]iron; dichloropalladium (4 mg, 0.01 mmol) added. The reaction mixture was diluted with water (0.20 mL) and tetrahydrofuran (2.0 mL), sealed and heated to 85° C. for 16 h. The reaction mixture was partitioned between ethyl acetate and an aqueous potassium carbonate solution. The organic phase was separated, dried ($MgSO_4$) filtered and concentrated under vacuum. The residue was purified initially by flash silica chromatography eluting with a gradient of 0-10% methanol in DCM followed by flash amino silica chromatography, eluting with a gradient of 65-100% ethyl acetate in petroleum ether to afford the title compound as a pale yellow solid (10.7 mg, 0.02 mmol, 8% yield). $^1$H NMR (600 MHz, DMSO-d6) δ 8.46 (s, 1H), 7.80 (d, J=8.0 Hz, 1H), 7.65 (s, 1H), 7.57-7.37 (m, 4H), 7.31 (s, 1H), 7.05 (d, J=9.6 Hz, 1H), 6.67 (s, 2H), 1.79 (s, 6H). LCMS-LCQ Rt=5.14 min (Method 3); m/z (ESI$^+$) 414.23 $[M+H]^+$.

Example 27

N4-[1-(2,3-Dichlorophenyl)-1-methyl-ethyl]-6-(1H-indazol-6-yl)-1,3,5-triazine-2,4-diamine

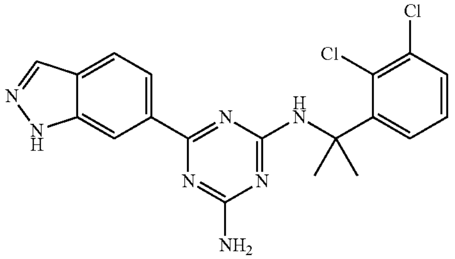

Synthesised by General Method B:

Step 1: 1-Tetrahydropyran-2-yl-6-(4,4,5,5-tetramethyl-1,3,2-dioxaborolan-2-yl)indazole (intermediate V) (148 mg, 0.45 mmol), 6-chloro-N 4-[1-(2,3-dichlorophenyl)-1-methyl-ethyl]-1,3,5-triazine-2,4-diamine (Example 6 Step 1) (100 mg, 0.30 mmol) and potassium phosphate tribasic (191 mg, 0.90 mmol) were combined in tetrahydrofuran (1.5 mL) and water (0.15 mL) and the mixture was degassed for 5 min before the addition of bis[2-(di-tert-butylphosphanyl)cyclopenta-2,4-dien-1-yl]iron; dichloropalladium (20 mg, 0.03 mmol). The mixture was degassed for a further 5 min before heating to 120° C. in the microwave for 1 h. The reaction mixture was concentrated to dryness under reduced pressure and the residue purified by flash column chromatography on silica eluting with a gradient of 10-50% ethyl acetate in petroleum ether to afford tetrahydropyranyl protected product as a white solid which was immediately deprotected in the next step.

Step 2: The product from step 1 was dissolved in methyl alcohol (3 mL) and 4 M HCl in 1,4-dioxane (2.25 mL, 9.02 mmol) was added. The solution was heated to 60° C. for 2 h then evaporated to dryness at reduced pressure. The resulting oil was purified through an SCX-2 cartridge washing initially with methanol then eluting the product with 3 M $NH_3$ in methanol to afford the title compound as a white solid (38 mg, 0.08 mmol, 27% yield). $^1$H NMR (399 MHz, DMSO-d6) (VT at 90° C.) δ 12.95 (s, 1H), 8.19 (s, 1H), 8.05 (s, 1H), 7.77-7.61 (m, 3H), 7.46 (d, J=4.4 Hz, 2H), 7.10 (s, 1H), 6.27 (s, 2H), 1.91 (s, 6H). LCMS MDAP Rt=16.83 (Method 4); m/z (ESI$^+$) 413.90 $[M+H]^+$.

Example 28

N2-[1-(2,3-difluorophenyl)-1-methyl-ethyl]-6-(1H-indazol-6-yl)-1,3,5-triazine-2,4-diamine

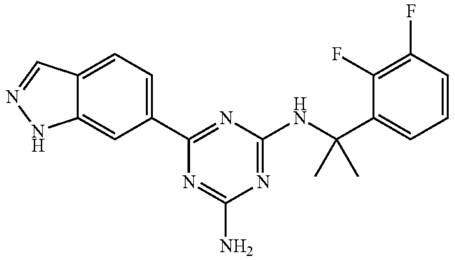

Synthesised by General Method B:

Step 1: N 4-[1-(2,3-Difluorophenyl)-1-methyl-ethyl]-6-(1-tetrahydropyran-2-ylindazol-6-yl)-1,3,5-triazine-2,4-diamine A stirred solution of 6-chloro-N 4-[1-(2,3-difluorophenyl)-1-methyl-ethyl]-1,3,5-triazine-2,4-diamine (Example 25, Step 1) (100 mg, 0.33 mmol), potassium phosphate tribasic (212 mg, 1.0 mmol), and bis[2-(di-tert-butylphosphanyl)cyclopenta-2,4-dien-1-yl]iron; dichloropalladium (22 mg, 0.03 mmol) in tetrahydrofuran (5 mL) and water (0.5 mL) was degassed by bubbling $N_2$ directly into the solution. The mixture was warmed to 80° C. then a solution of 1-tetrahydropyran-2-yl-6-(4,4,5,5-tetramethyl-1,3,2-dioxaborolan-2-yl)indazole (Intermediate V) (274 mg, 0.83 mmol) in THF (4 mL) was added and the reaction mixture was stirred at 80° C. for 12 h. The reaction mixture was concentrated to dryness under reduced pressure and the crude was purified by flash column chromatography on silica gel eluting with a gradient of 30-100% EtOAc in petroleum ether to afford the title compound as a white solid (92 mg, 0.20 mmol, 59% yield). $^1$H NMR (399 MHz, DMSO-$d_6$) δ 8.37 (s, 1H), 8.08 (s, 1H), 7.89 (s, 1H), 7.72 (d, J=8.5 Hz, 1H), 7.35-7.04 (m, 4H), 6.39 (s, 2H), 5.85-5.71 (m, 1H), 3.96-3.66 (m, 2H), 2.47-2.36 (m, 2H), 2.16-1.97 (m, 2H), 1.84 (d, J=4.5 Hz, 6H), 1.65 (h, J=4.6 Hz, 2H). LCMS LCQ Rt=4.40 min (Method 2); m/z (ESI$^+$) 466.26 [M+H]$^+$.

Step 2: N2-[1-(2,3-Difluorophenyl)-1-methyl-ethyl]-6-(1H-indazol-6-yl)-1,3,5-triazine-2,4-diamine A solution of N 2-[1-(2,3-difluorophenyl)-1-methyl-ethyl]-6-(1-tetrahydropyran-2-ylindazol-6-yl)-1,3,5-triazine-2,4-diamine (90 mg, 0.19 mmol) in methyl alcohol (1 mL) and 4 M HCl in 1,4-dioxane (0.48 mL, 1.93 mmol) was heated at 40° C. for 16 h. The resulting precipitate was filtered, washed with diethyl ether and petroleum ether then dried in oven at 50° C. for 2 h to afford the title compound (65 mg, 0.17 mmol, 87% yield). $^1$H NMR (399 MHz, DMSO-d6, VT 90° C.) δ 8.34 (s, 1H), 8.12 (s, 1H), 7.80 (s, 2H), 7.31 (s, 1H), 7.21 (dt, J=9.5, 3.7 Hz, 2H), 1.85 (d, J=1.1 Hz, 6H); LCMS MDAP Rt=16.70 (Method 4); m/z (ESI$^+$) 382.10 [M+H]$^+$.

Example 29

N4-[(2,3-Dichlorophenyl)methyl]-6-imidazo[1,5-a]pyridin-6-yl-1,3,5-triazine-2,4-diamine

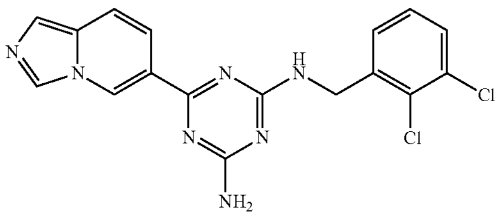 [SMILES: Nc1nc(NCc2cccc(Cl)c2Cl)nc(-c2ccc3cncn3c2)n1]

Synthesised by General Method D:

Step 1: 6-Chloro-N4-[(2,3-dichlorophenyl)methyl]-1,3,5-triazine-2,4-diamine

2-Amino-4,6-dichlorotriazine (500 mg, 3.0 mmol) was added to a pre-stirred solution of 1-(2,3-dichlorophenyl)methanamine (0.48 mL, 3.64 mmol) and N,N-diisopropylethylamine (1.3 mL, 7.6 mmol) in 1,4-dioxane (15 mL). The reaction mixture was stirred at RT for 3 h then directly dry loaded onto celite and purified by flash silica chromatography eluting with a gradient of 0-100% ethyl acetate in petroleum ether to afford the title compound as a white solid (716 mg, 2.23 mmol, 74% yield). $^1$H NMR (600 MHz, DMSO-d6) δ 8.30 (t, J=6.2 Hz, 0.7H), 8.15 (t, J=6.2 Hz, 0.3H), 7.59-7.51 (d, 1H), 7.42-7.23 (m, 4H), 4.56-4.49 (m, 2H). LCMS MDAP Rt=19.46 min (Method 4); m/z (ESI$^+$) 305.8 [M+H]$^+$.

Step 2: N 4-[(2,3-Dichlorophenyl)methyl]-6-imidazo[1,5-a]pyridin-6-yl-1,3,5-triazine-2,4-diamine

[1,1'-bis(diphenylphosphino)ferrocene]dichloropalladium (II) (12 mg, 0.02 mmol) was added to a degassed suspension of bis(pinacolato)diboron (108 mg, 0.43 mmol), 6-bromoimidazo[1,5-a]pyridine (74 mg, 0.38 mmol) and potassium acetate (64 mg, 0.66 mmol) in tetrahydrofuran (2 mL). The reaction was sealed and heated to 80° C. overnight. The reaction mixture was cooled to RT and 6-chloro-N 4-[(2,3-dichlorophenyl)methyl]-1,3,5-triazine-2,4-diamine (100 mg, 0.33 mmol), potassium phosphate tribasic (209 mg, 0.99 mmol) and bis[2-(di-tert-butylphosphanyl)cyclopenta-2,4-dien-1-yl]iron; dichloropalladium (4.3 mg, 0.01 mmol) was added. The reaction mixture was diluted with water (0.2 mL) and tetrahydrofuran (2 mL), sealed and heated at 80° C. for 4 h. After cooling to RT the reaction mixture was diluted with DCM, dry-loaded onto celite and purified directly by flash silica chromatography, eluting with a gradient of 0-10% methanol in DCM to provide the product as a tan solid. Further purification was accomplished using reverse phase preparative MDAP LCMS eluting with 30-95% Acetonitrile in water with formic acid (0.1%) modifier gradient over 32 min to afford the titled compound as pale yellow solid (26 mg, 0.06 mmol, 19% yield). $^1$H NMR (600 MHz, DMSO-d6) δ 9.22-9.01 (m, 1H), 8.64-8.43 (m, 1H), 7.89 (t, J=6.3 Hz, 0.6H), 7.81-7.75 (m, 0.4H), 7.62-7.21 (m, 5H), 7.17-6.55 (m, 3H), 4.71 (d, J=6.2 Hz, 0.8H), 4.57 (d, J=6.3 Hz, 1.2H). LCMS MDAP Rt=14.92 min (Method 4); m/z (ESI$^+$) 385.85 [M+H]$^+$.

Example 30

N4-[(2,3-Difluorophenyl)methyl]-6-imidazo[1,5-a]pyridin-6-yl-1,3,5-triazine-2,4-diamine

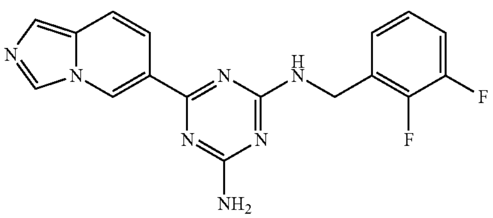

Synthesised by General Method D:

Step 1: 6-Chloro-N4-[(2,3-difluorophenyl)methyl]-1,3,5-triazine-2,4-diamine RW-2196-22

2-Amino-4,6-dichlorotriazine (500 mg, 3.0 mmol) was added to a stirring solution of 2,3-difluorobenzylamine (0.43 mL, 3.64 mmol) and N,N-diisopropylethylamine (1.32 mL, 7.58 mmol) in 1,4-dioxane (15 mL). The reaction was stirred for 3 hat RT then dry loaded onto celite and purified by flash silica chromatography eluting with a gradient of 0-10% methanol in DCM to afford the title compound (577 mg, 2.02 mmol, 67% yield). $^{1}$H NMR (600 MHz, DMSO-d6) δ 8.25 (t, J=6.2 Hz, 0.65H), 8.10 (t, J=6.2 Hz, 0.35H), 7.44-7.06 (m, 5H), 4.54-4.43 (m, 2H). LCMS MDAP Rt=2.29 min (Method 6); m/z (ESI$^{+}$) 271.9 [M+H]$^{+}$.

Step 2: N 4-[(2,3-difluorophenyl)methyl]-6-imidazo[1,5-a]pyridin-6-yl-1,3,5-triazine-2,4-diamine 1,1'-bis(diphenylphosphino)ferrocene]dichloropalladium (II) (13.5 mg, 0.02 mmol) was added to a degassed suspension of bis(pinacolato)diboron (121 mg, 0.48 mmol), 6-Bromoimidazo[1,5-a]pyridine (83 mg, 0.42 mmol) and potassium acetate (72 mg, 0.74 mmol). The reaction was sealed and heated to 80° C. overnight then cooled to RT and 6-chloro-N4-[(2,3-difluorophenyl)methyl]-1,3,5-triazine-2,4-diamine (100 mg, 0.37 mmol), potassium phosphate tribasic (234 mg, 1.1 mmol) and bis[2-(di-tert-butylphosphanyl) cyclopenta-2,4-dien-1-yl]iron; dichloropalladium (4.8 mg, 0.01 mmol) added. The reaction mixture was diluted with tetrahydrofuran (2 mL) and water (0.2 mL), and heated to 80° C. for 16 h. After cooling to RT the reaction mixture was dry loaded directly onto celite and purified by flash silica chromatography, eluting with a gradient of 0-10% methanol in DCM. The isolated material was further purification by amino silica chromatography eluting initially with petroleum ether, followed by a gradient of 0-10% methanol in DCM, to afford the title compound as a yellow solid (39 mg, 0.1 mmol, 28% yield). $^{1}$H NMR (600 MHz, DMSO-d6) δ 9.18-9.07 (m, 1H), 8.59-8.48 (m, 1H), 7.89-7.85 (m, 0.6H), 7.77-7.73 (m, 0.4H), 7.59-7.47 (m, 2H), 7.40-7.31 (m, 1H), 7.30-7.12 (m, 3H), 6.94 (s, 1H), 6.84 (s, 1H), 4.68 (d, J=6.2 Hz, 0.9H), 4.58 (d, J=6.2 Hz, 1.1H). LCMS MDAP Rt=2.16 min (Method 6); m/z (ESI$^{+}$) 353.95 [M+H]$^{+}$.

Example 31

N4-[2-(2,3-Dichlorophenyl)ethyl]-6-imidazo[1,5-a]pyridin-6-yl-1,3,5-triazine-2,4-diamine

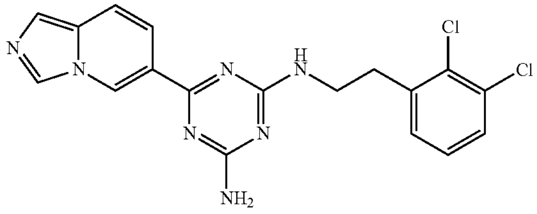

Synthesised by General Method D:

Step 1: 6-chloro-N4-[2-(2,3-dichlorophenyl)ethyl]-1,3,5-triazine-2,4-diamine RW-2196-24

The title compound was synthesised using the same protocol as Example 30, Step 1, except the 2,3-difluorobenzylamine was replaced with 2-(2,3-dichlorophenyl) ethanamine, to afford the product as a white solid. $^{1}$H NMR (600 MHz, DMSO-d6) δ 7.80 (t, J=5.7 Hz, 0.7H), 7.63 (t, J=5.7 Hz, 0.3H), 7.55-7.41 (m, 1H), 7.37-7.20 (m, 3H), 7.20-6.98 (br m, 1H), 3.44 (q, J=6.7 Hz, 2H), 3.04-2.88 (m, 2H). LCMS LCQ Rt=10.30 min (Method 3); m/z (ESI$^{+}$) 318.15 [M+H]$^{+}$.

Step 2: N 4-[2-(2,3-dichlorophenyl)ethyl]-6-imidazo[1,5-a]pyridin-6-yl-1,3,5-triazine-2,4-diamine The title compound was synthesised using the same protocol as Example 29, Step 2, except the 6-chloro-N4-[(2,3-dichlorophenyl)methyl]-1,3,5-triazine-2,4-diamine was replaced with 6-chloro-N4-[2-(2,3-dichlorophenyl)ethyl]-1,3,5-triazine-2,4-diamine to afford the product as a pale yellow solid (23 mg). $^{1}$H NMR (600 MHz, DMSO-d6) δ 9.11 (s, 0.5H), 9.07 (s, 0.5H), 8.54 (d, J=7.3 Hz, 1H), 7.69-7.10 (m, 7H), 6.89 (s, 1H), 6.71 (s, 1H), 3.65 (q, J=6.7 Hz, 1H), 3.52 (q, J=6.7 Hz, 1H), 3.08-2.98 (m, 2H). LCMS MDAP Rt=14.94 min (Method 4); m/z (ESI$^{+}$) 399.90 [M+H]$^{+}$.

Example 32

N4-[1-[1-(Difluoromethyl)pyrazol-3-yl]cyclopropyl]-6-(1-methylindazol-6-yl)-1,3,5-triazine-2,4-diamine

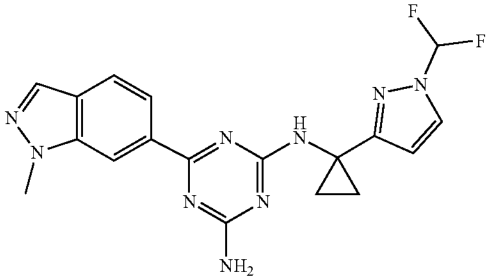 [SMILES: Cn1ncc2ccc(-c3nc(N)nc(NC4(c5ccn(C(F)F)n5)CC4)n3)cc21]

Synthesised by General Method D:

A stirred solution of 6-chloro-N 4-[1-[1-(difluoromethyl) pyrazol-3-yl]cyclopropyl]-1,3,5-triazine-2,4-diamine (Example 22, Step 1) (50 mg, 0.17 mmol), potassium phosphate tribasic (70 mg, 0.33 mmol), and bis[2-(di-tert-butylphosphanyl)cyclopenta-2,4-dien-1-yl]iron; dichloropalladium (6 mg, 0.01 mmol) in tetrahydrofuran (5 mL) and water (0.5 mL) was degassed by bubbling $N_2$ directly into the solution. The mixture was warmed to 80° C. then a solution of 1-methyl-1H-indazole-6-boronic acid (44 mg, 0.25 mmol) in THF (4 mL) was added and the reaction mixture stirred at 80° C. for 12 h. The reaction mixture was concentrated to dryness under reduced pressure and the crude was purified by flash column chromatography (silica gel, eluting with a gradient of 30-100% EtOAc in petroleum ether). The solid was triturated with a mixture of diethyl ether and petroleum ether to afford the title compound as an off-white solid. (15 mg, 0.04 mmol, 22% yield). $^1H$ NMR (399 MHz, DMSO-$d_6$, VT 90° C.) δ 8.42 (s, 1H), 8.11-7.99 (m, 2H), 7.93 (d, J=2.7 Hz, 1H), 7.80-7.36 (m, 3H), 6.52 (s, 2H), 6.35 (d, J=2.7 Hz, 1H), 4.06 (s, 3H), 1.36 (p, J=4.9, 4.1 Hz, 2H), 1.33-1.25 (m, 2H). LCMS MDAP Rt=16.15 min (Method 4); m/z ($ESI^+$) 398.2 $[M+H]^+$.

Example 33

N4-[1-[1-(difluoromethyl)pyrazol-3-yl]cyclopropyl]-6-(3-methylimidazo[1,5-a]pyridin-6-yl)-1,3,5-triazine-2,4-diamine

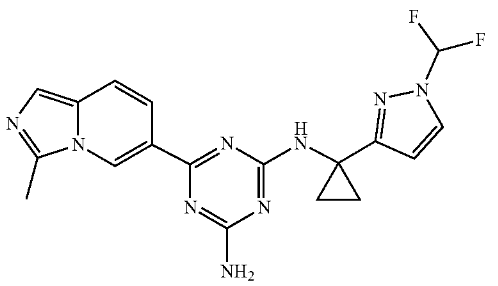 [SMILES: Cc1ncc2ccc(-c3nc(N)nc(NC4(c5ccn(C(F)F)n5)CC4)n3)cn12]

The title compound was synthesised using the same protocol as Example 32, except 1-methyl-1H-indazole-6-boronic acid was replaced with 3-methyl-6-(4,4,5,5-tetramethyl-1,3,2-dioxaborolan-2-yl)imidazo[1,5-a]pyridine (Intermediate Y) to afford the product as a yellow solid (32 mg, 0.08 mmol, 37% yield). $^1H$ NMR (399 MHz, DMSO-$d_6$, VT 90° C.) δ 8.72 (s, 1H), 7.91 (d, J=2.6 Hz, 1H), 7.75 (s, 1H), 7.55 (t, J=59.9 Hz, 1H), 7.45 (t, J=8.4 Hz, 2H), 7.23 (d, J=1.0 Hz, 1H), 6.53 (s, 2H), 6.31 (d, J=2.7 Hz, 1H), 2.58 (s, 3H), 1.32 (q, J=5.1, 3.9 Hz, 2H), 1.25 (dt, J=5.7, 3.2 Hz, 2H). LCMS MDAP Rt=11.65 min (Method 4); m/z ($ESI^+$) 398.2 $[M+H]^+$.

Example 34

N4-[1-[1-(difluoromethyl)pyrazol-3-yl]-1-methyl-ethyl]-6-imidazo[1,5-a]pyridin-6-yl-N4-methyl-1,3,5-triazine-2,4-diamine

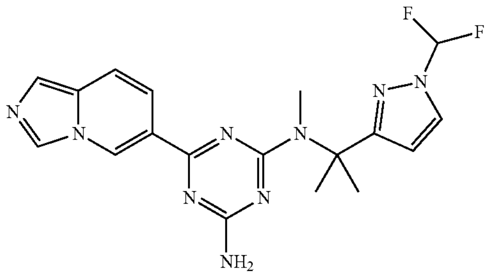 [SMILES: CN(c1nc(N)nc(-c2ccc3cncn3c2)n1)C(C)(C)c1ccn(C(F)F)n1]

Synthesised by General Method D:

Step 1: 6-Chloro-N4-[1-[1-(difluoromethyl)pyrazol-3-yl]-1-methyl-ethyl]-N 4-methyl-1,3,5-triazine-2,4-diamine 2-[1-(Difluoromethyl)pyrazol-3-yl]-N-methyl-propan-2-amine (Intermediate O) (0.2 mL, 0.67 mmol) was suspended in 1,4-dioxane (3.5 mL) and 2-amino-4,6-dichlorotriazine (100 mg, 0.61 mmol) was added followed by N,N-diisopropylethylamine (0.32 mL, 1.82 mmol). The mixture was heated to 90° C. in the microwave for 1 h. The reaction mixture was partitioned between DCM and water. The organic phase was separated, dried (hydrophobic frit) and concentrated in vacuo. The crude material was purified by flash column chromatography eluting with a gradient of 0-10% methanol in DCM. The material isolated was triturated with diethyl ether and filtered to afford the title compound as a white solid (10 mg, 0.0300 mmol, 5% yield).

Step 2: N 4-[1-[1-(difluoromethyl)pyrazol-3-yl]-1-methyl-ethyl]-6-imidazo[1,5-a]pyridin-6-yl-N 4-methyl-1,3,5-triazine-2,4-diamine 6-Chloro-N4-[1-[1-(difluoromethyl)pyrazol-3-yl]-1-methyl-ethyl]-N4-methyl-1,3,5-triazine-2,4-diamine (30 mg, 0.09 mmol), 6-(4,4,5,5-tetramethyl-1,3,2-dioxaborolan-2-yl)imidazo[1,5-a]pyridine (Intermediate W) (49 mg, 0.14 mmol) and potassium phosphate tribasic (40 mg, 0.19 mmol) were dissolved in tetrahydrofuran (2 mL) and water (0.2 mL) and degassed with $N_2$ for 5 min before the addition of bis[2-(di-tert-butylphosphanyl)cyclopenta-2,4-dien-1-yl] iron; dichloropalladium (3 mg, 0.004 mmol). The mixture was degassed for a further 2 min before heating to 90° C. for 18 h. The mixture was allowed to cool to RT and concentrated to dryness under reduced pressure. The crude material was purified by flash column chromatography eluting with a gradient of 0-10% methanol in ethyl acetate to afford a pale brown solid. The solid was triturated with diethyl ether to afford the title compound as an off-white solid (23 mg, 0.06 mmol, 60% yield). $^1H$ NMR (399 MHz, DMSO-d6) (VT at 90) δ 8.79 (s, 1H), 8.47 (s, 1H), 7.97 (d, J=2.7 Hz, 1H), 7.79 (t, J=59.3 Hz, 1H), 7.46 (d, J=9.5 Hz, 1H), 7.35 (s, 1H), 7.18 (d, J=9.6 Hz, 1H), 6.78 (s, 2H), 6.29 (d, J=2.6 Hz, 1H), 3.34 (s, 3H), 1.76 (s, 6H).

Example 35

N4-[1-[1-(Difluoromethyl)pyrazol-3-yl]cyclopropyl]-6-imidazo[1,5-a]pyridin-6-yl-1,3,5-triazine-2,4-diamine

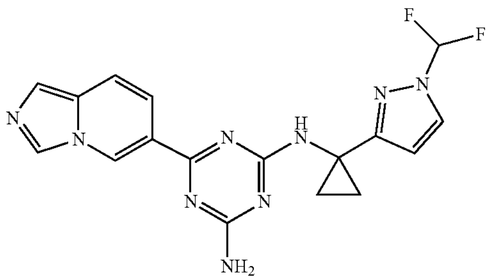 [SMILES: Nc1nc(NC2(c3ccn(C(F)F)n3)CC2)nc(-c2ccc3cncn3c2)n1]

The title compound was synthesised using the same protocol as Example 32, except 1-methyl-1H-indazole-6-boronic acid was replaced with 6-(4,4,5,5-tetramethyl-1,3,2-dioxaborolan-2-yl)imidazo[1,5-a]pyridine (Intermediate W) to afford the product as an off-white solid (31 mg). $^{1}$H NMR (399 MHz, DMSO-d6) (VT at 90) δ 9.05 (s, 1H), 8.47 (s, 1H), 7.94 (d, J=2.7 Hz, 1H), 7.75 (s, 1H), 7.59 (t, J=59.9 Hz, 1H), 7.55-7.46 (m, 2H), 7.35 (s, 1H), 6.52 (s, 2H), 6.34 (d, J=2.7 Hz, 1H), 1.39-1.33 (m, 2H), 1.32-1.25 (m, 2H).

Example 36

N4-[1-[1-(difluoromethyl)pyrazol-3-yl]-1-methyl-ethyl]-6-imidazo[1,5-a]pyridin-6-yl-1,3,5-triazine-2,4-diamine

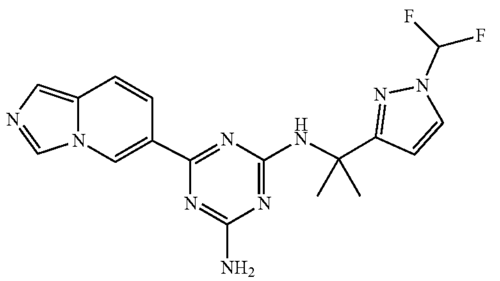 [SMILES: CC(C)(Nc1nc(N)nc(-c2ccc3cncn3c2)n1)c1ccn(C(F)F)n1]

Step 1: 6-Chloro-N 4-[1-[1-(difluoromethyl)pyrazol-3-yl]-1-methyl-ethyl]-1,3,5-triazine-2,4-diamine The title compound was synthesised using an analogous protocol to Example 34, step 1, except 2-[1-(difluoromethyl)pyrazol-3-yl]-N-methyl-propan-2-amine (Intermediate O) was replaced with 2-[1-(difluoromethyl)pyrazol-3-yl]propan-2-amine (Intermediate L) to afford the product as a white solid (242 mg, 0.78 mmol, 43% yield). $^{1}$H NMR (399 MHz, DMSO-d6 VT at 90° C.) δ 7.99 (d, J=2.7 Hz, 1H), 7.64 (t, J=59.9 Hz, 1H), 7.41-7.31 (m, 1H), 6.82 (s, 2H), 6.44 (d, J=2.6 Hz, 1H), 1.71 (s, 6H).

Step 2: N 4-[1-[1-(difluoromethyl)pyrazol-3-yl]-1-methyl-ethyl]-6-imidazo[1,5-a]pyridin-6-yl-1,3,5-triazine-2,4-diamine The title compound was synthesised using an analogous protocol to Example 34, step 2, except 6-chloro-N4-[1-[1-(difluoromethyl)pyrazol-3-yl]-1-methyl-ethyl]-N 4-methyl-1,3,5-triazine-2,4-diamine is replaced with 6-chloro-N 4-[1-[1-(difluoromethyl)pyrazol-3-yl]-1-methyl-ethyl]-1,3,5-triazine-2,4-diamine to afford the products as a pale brown solid (118 mg). $^{1}$H NMR (399 MHz, DMSO-d6, VT 90° C.) δ 8.94 (s, 1H), 8.44 (s, 1H), 7.99 (d, J=2.7 Hz, 1H), 7.69 (t, J=59.8 Hz, 1H), 7.49 (d, J=9.3 Hz, 1H), 7.37 (d, J=14.4 Hz, 2H), 6.96 (s, 1H), 6.45 (d, J=2.6 Hz, 1H), 6.43 (s, 2H), 1.77 (s, 6H).

Example 37

N4-[1-[1-(difluoromethyl)pyrazol-3-yl]-1-methyl-ethyl]-6-(3-methylimidazo[1,5-a]pyridin-6-yl)-1,3,5-triazine-2,4-diamine

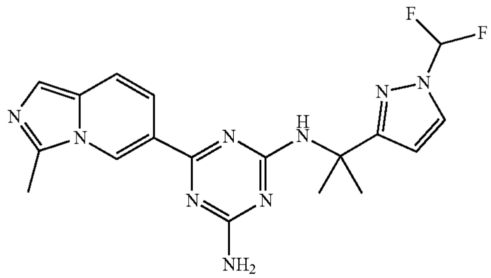 [SMILES: Cc1ncc2ccc(-c3nc(N)nc(NC(C)(C)c4ccn(C(F)F)n4)n3)cn12]

The title compound was synthesised using an analogous protocol to Example 34, step 2, except 6-chloro-N4-[1-[1-(difluoromethyl)pyrazol-3-yl]-1-methyl-ethyl]-N 4-methyl-1,3,5-triazine-2,4-diamine was replaced with 6-chloro-N 4-[1-[1-(difluoromethyl)pyrazol-3-yl]-1-methyl-ethyl]-1,3,5-triazine-2,4-diamine (Example 36 step 1) and 6-(4,4,5,5-tetramethyl-1,3,2-dioxaborolan-2-yl)imidazo[1,5-a]pyridine (Intermediate W) is replaced with 3-methyl-6-(4,4,5,5-tetramethyl-1,3,2-dioxaborolan-2-yl)imidazo[1,5-a]pyridine (Intermediate Y) to give a product, which was further purified an on aminosilica gel column (eluting with a gradient of 30-100% EtOAc in petroleum ether) to afford the final product as a yellow solid (26 mg, 0.06 mmol, 33% yield). $^{1}$H NMR (399 MHz, DMSO-$d_6$, VT 90° C.) δ 8.64 (s, 1H), 7.99-7.89 (m, 1H), 7.61 (t, J=59.9 Hz, 1H), 7.42 (d, J=9.5 Hz, 1H), 7.30 (d, J=9.3 Hz, 1H), 7.22 (s, 1H), 6.95 (s, 1H), 6.42 (s, 3H), 2.59 (d, J=1.1 Hz, 3H), 1.74 (d, J=1.4 Hz, 6H). LCMS MDAP Rt=2.70 min (Method 6); m/z (ESI$^+$) 400.05 [M+H]$^+$.

Example 38

N4-[(2,3-dichlorophenyl)methyl]-6-(3-methylimidazo[1,5-a]pyridin-6-yl)-1,3,5-triazine-2,4-diamine

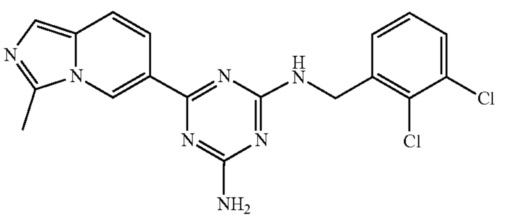 [SMILES: Cc1ncc2ccc(-c3nc(N)nc(NCc4cccc(Cl)c4Cl)n3)cn12]

The title compound was synthesised using an analogous protocol to Example 34, step 2, except 6-chloro-N4-[1-[1-(difluoromethyl)pyrazol-3-yl]-1-methyl-ethyl]-N4-methyl-1,3,5-triazine-2,4-diamine was replaced with 6-chloro-N4-[(2,3-dichlorophenyl)methyl]-1,3,5-triazine-2,4-diamine (Example 17 step 1) and 6-(4,4,5,5-tetramethyl-1,3,2-dioxaborolan-2-yl)imidazo[1,5-a]pyridine (Intermediate W) is replaced with 3-methyl-6-(4,4,5,5-tetramethyl-1,3,2-dioxaborolan-2-yl)imidazo[1,5-a]pyridine (Intermediate Y) to give a product, which was further purified an on aminosilica gel column eluting with a gradient of 30-100% EtOAc in petroleum ether to afford the final product as a yellow solid (10 mg, 0.02 mmol, 12% yield). LCMS MDAP Rt=13.33 min (Method 4); m/z ($ESI^+$) 399.90, 400.95, 401.90, 403.90 (2×Cl isotopes) $[M+H]^+$.

Example 39

N4-[1-(2,3-difluorophenyl)-1-methyl-ethyl]-6-(3-methylimidazo[1,5-a]pyridin-6-yl)-1,3,5-triazine-2,4-diamine

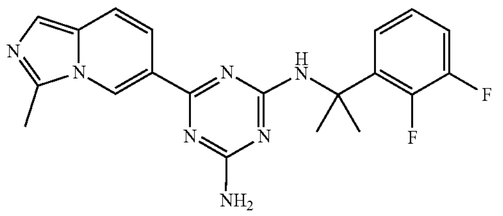 [SMILES: Cc1ncc2ccc(-c3nc(N)nc(NC(C)(C)c4cccc(F)c4F)n3)cn12]

The title compound was synthesised using an analogous protocol to Example 34, step 2, except 6-chloro-N4-[1-[1-(difluoromethyl)pyrazol-3-yl]-1-methyl-ethyl]-N 4-methyl-1,3,5-triazine-2,4-diamine was replaced with 6-chloro-N 4-[1-(2,3-difluorophenyl)-1-methyl-ethyl]-1,3,5-triazine-2,4-diamine (Example 25, step 1) and 6-(4,4,5,5-tetramethyl-1,3,2-dioxaborolan-2-yl)imidazo[1,5-a]pyridine (Intermediate W) is replaced with 3-methyl-6-(4,4,5,5-tetramethyl-1,3,2-dioxaborolan-2-yl)imidazo[1,5-a]pyridine (Intermediate Y) to give a product, which was further purified an on aminosilica gel column eluting with a gradient of 30-100% EtOAc in petroleum ether to afford the final product as a yellow solid (20 mg, 0.05 mmol, 25% yield). $^1H$ NMR (399 MHz, DMSO-$d_6$, VT 90° C.) δ 8.50 (s, 1H), 7.41 (d, J=9.5 Hz, 1H), 7.24 (dd, J=17.8, 7.0 Hz, 4H), 7.19-7.06 (m, 2H), 6.38 (s, 2H), 2.57 (s, 3H), 1.79 (d, J=1.2 Hz, 6H). LCMS MDAP Rt=12.80 min (Method 4); m/z ($ESI^+$) 395.95 $[M+H]^+$.

Example 40

N4-[(2,3-difluorophenyl)methyl]-6-(3-methylimidazo[1,5-a]pyridin-6-yl)-1,3,5-triazine-2,4-diamine

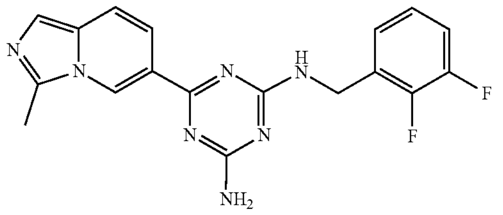 [SMILES: Cc1ncc2ccc(-c3nc(N)nc(NCc4cccc(F)c4F)n3)cn12]

The title compound was synthesised using an analogous protocol to Example 34, step 2, except 6-chloro-N4-[1-[1-(difluoromethyl)pyrazol-3-yl]-1-methyl-ethyl]-N 4-methyl-1,3,5-triazine-2,4-diamine was replaced with 6-chloro-N 4-[2-(2,3-dichlorophenyl)ethyl]-1,3,5-triazine-2,4-diamine (Example 30, step 1) and 6-(4,4,5,5-tetramethyl-1,3,2-dioxaborolan-2-yl)imidazo[1,5-a]pyridine (Intermediate W) is replaced with 3-methyl-6-(4,4,5,5-tetramethyl-1,3,2-dioxaborolan-2-yl)imidazo[1,5-a]pyridine (Intermediate Y) to give a product, which was further purified an on aminosilica gel column (eluting with a gradient of 30-100% EtOAc in petroleum ether) to afford the final product as a yellow solid (50 mg, 0.13 mmol, 59% yield). $^1H$ NMR (399 MHz, DMSO-$d_6$, VT 90° C.) δ 8.77 (s, 1H), 7.54 (d, J=7.8 Hz, 2H), 7.47 (t, J=1.4 Hz, 2H), 7.29-7.05 (m, 3H), 6.58 (s, 2H), 4.63 (d, J=6.2 Hz, 2H), 2.61 (s, 3H). LCMS MDAP Rt=12.46 min (Method 4); m/z ($ESI^+$) 367.95 $[M+H]^+$.

Example 41

N2-[1-[1-(difluoromethyl)pyrazol-3-yl]-1-methyl-ethyl]-6-(3-methyl-1H-indazol-5-yl)-1,3,5-triazine-2,4-diamine

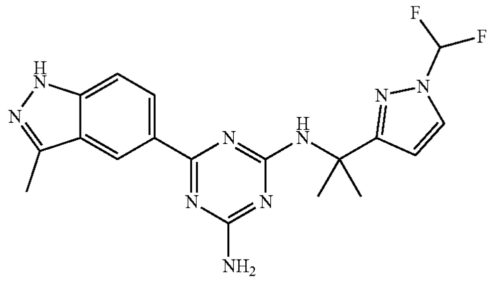 [SMILES: Cc1n[nH]c2ccc(-c3nc(N)nc(NC(C)(C)c4ccn(C(F)F)n4)n3)cc12]

Step 1: N4-[1-[1-(difluoromethyl)pyrazol-3-yl]-1-methyl-ethyl]-6-(3-methyl-1-tetrahydropyran-2-yl-indazol-5-yl)-1,3,5-triazine-2,4-diamine A stirred solution of 6-chloro-N 4-[1-[1-(difluoromethyl)pyrazol-3-yl]-1-methyl-ethyl]-1,3,5-triazine-2,4-diamine (Example 36, Step 1) (45 mg, 0.15 mmol), potassium phosphate tribasic (63 mg, 0.30 mmol), and bis[2-(di-tert-butylphosphanyl)cyclopenta-2,4-dien-1-yl]iron; dichloropalladium (5 mg, 0.010 mmol) in tetrahydrofuran (2.5 mL) and water (0.25 mL) was degassed by bubbling $N_2$ directly into the solution. The mixture was warmed to 80° C. then a solution of 3-methyl-1-tetrahydropyran-2-yl-5-(4,4,5,5-tetramethyl-1,3,2-dioxaborolan-2-yl)indazole (Intermediate A) (76 mg, 0.22 mmol) in THF was added and the reaction stirred at 80° C. for 12 h. The reaction mixture was concentrated to dryness under reduced pressure and the crude was purified by flash column chromatography (silica gel, eluting with a gradient of 30-100% EtOAc in petroleum ether) to afford the title compound as a pale yellow oil (50 mg, 0.10 mmol, 67% yield). $^1H$ NMR (399 MHz, DMSO-$d_6$, VT 90° C.) δ 8.52 (s, 1H), 8.17 (d, J=8.7 Hz, 1H), 7.97 (d, J=2.7 Hz, 1H), 7.84-7.43 (m, 2H), 6.86 (s, 1H), 6.46 (d, J=2.7 Hz, 1H), 6.35 (s, 2H), 5.73 (dd, J=9.5, 2.7 Hz, 1H), 3.96-3.63 (m, 2H), 2.46-2.27 (m, 2H), 1.98 (s, 5H), 1.78 (s, 6H), 1.61 (dd, J=8.6, 4.5 Hz, 2H). LCMS MDAP Rt=17.22 min (Method 4); m/z ($ESI^+$) 484.3 $[M+H]^+$.

Step 2: N2-[1-[1-(difluoromethyl)pyrazol-3-yl]-1-methyl-ethyl]-6-(3-methyl-1H-indazol-5-yl)-1,3,5-triazine-2,4-diamine A solution of N 2-[1-[1-(difluoromethyl)pyrazol-3-yl]-1-methyl-ethyl]-6-(3-methyl-1-tetrahydropyran-2-yl-indazol-5-yl)-1,3,5-triazine-2,4-diamine (50 mg, 0.10 mmol) in methyl alcohol (1 mL) and 4 M HCl in 1,4-dioxane (0.26 mL, 1.03 mmol) was heated at 40° C. for 16 h. The resulting precipitate was filtered, washed with diethyl ether and petroleum ether, then dried in oven at 50 C for 2 h to afford the title compound (28 mg, 0.07 mmol, 66% yield). $^1$H NMR (399 MHz, DMSO-$d_6$, VT 90° C.) δ 8.73 (s, 1H), 8.15-7.96 (m, 2H), 7.84-7.44 (m, 2H), 6.53 (s, 1H), 2.55 (s, 3H), 1.81 (s, 6H). LCMS MDAP Rt=13.99 min (Method 4); m/z ($ESI^+$) 400.2 $[M+H]^+$.

Example 42

4-(3-benzylmorpholin-4-yl)-6-(1H-indazol-6-yl)-1,3,5-triazin-2-amine

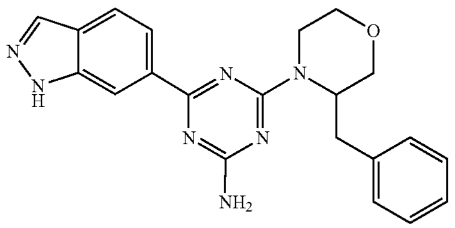 [SMILES: Nc1nc(-c2ccc3cn[nH]c3c2)nc(N2CCOCC2Cc2ccccc2)n1]

Synthesised by General Method C:

3-Benzylmorpholine (35 mg, 0.20 mmol) was added to a suspension of 4-chloro-6-(1H-indazol-6-yl)-1,3,5-triazin-2-amine (Intermediate Z) (41 mg, 0.17 mmol) and N,N-diisopropylethylamine (0.09 mL, 0.50 mmol) in 1,4-dioxane (2 mL). The reaction mixture was heated to 60° C. for 4 h, then stirred at RT for until starting material was consumed. The reaction mixture was concentrated under reduced pressure and the residue purified by reverse phase preparative MDAP LCMS eluting with 30-95% Acetonitrile in water with formic acid (0.1%) modifier gradient over 32 min. The relevant fractions were combined and concentrated to dryness under reduced pressure. The material was redissolved in EtOAc (15 mL) and washed with saturated aq. $NaHCO_3$ (10 mL), water (10 mL), brine (10 mL), dried over $MgSO_4$ and filtered under reduced pressure to give a tan coloured solid.

$^1$H NMR (600 MHz, DMSO-d6) δ 13.43 (s, 1H), 8.50 (d, J=6.1 Hz, 0.4H), 8.44 (s, 0.6H), 8.18-8.13 (m, 1H), 8.04-8.00 (m, 0.4H), 8.01-7.95 (m, 0.6H), 7.89-7.83 (m, 1H), 7.32 (t, 1H), 7.29 (d, J=7.4 Hz, 2H), 7.20 (t, 2H), 7.10-7.07 (m, 1H), 5.04 (s, 1H), 4.72 (s, 0.5H), 4.64 (d, J=13.7 Hz, 0.5H), 4.35 (d, J=13.3 Hz, 1H), 3.98 (d, J=10.9 Hz, 1H), 3.75 (d, J=11.7 Hz, 1H), 3.61 (d, J=11.8 Hz, 1H), 3.53 (d, J=11.6 Hz, 1H), 3.11-3.06 (m, 1H), 2.99 (s, 1H), 2.86 (s, 1H). LCMS MDAP Rt=17.04 min (Method 4); m/z (ESI+) 387.95 $[M+H]^+$.

Example 43

N4-[2-(2,3-dichlorophenyl)ethyl]-6-(1H-indazol-6-yl)-N4-methyl-1,3,5-triazine-2,4-diamine

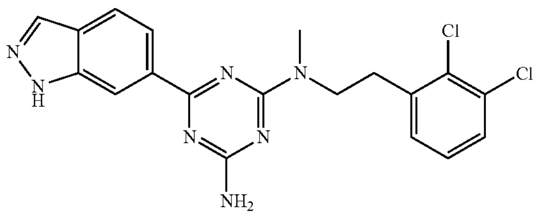 [SMILES: CN(CCc1cccc(Cl)c1Cl)c1nc(N)nc(-c2ccc3cn[nH]c3c2)n1]

Synthesised by General Method C:

2-(2,3-Dichlorophenyl)-N-methyl-ethanamine; 2,2,2-trifluoroacetic acid (Intermediate Q)(62 mg, 0.19 mmol) was added to a suspension of 4-chloro-6-(1H-indazol-6-yl)-1,3,5-triazin-2-amine (Intermediate Z) (40 mg, 0.16 mmol) and N,N-diisopropylethylamine (0.08 mL, 0.49 mmol) in 1,4-dioxane (2 mL). The reaction mixture was stirred at RT for 16 h. The reaction mixture was concentrated to dryness under reduced pressure and the residue purified by flash chromatography eluting with a gradient 0-60% ethyl acetate in petroleum ether to afford the title compound as a colourless solid (42 mg, 0.1 mmol, 59% yield). $^1$H NMR (600 MHz, DMSO-$d_6$) δ 13.26 (s, 0.5H), 13.24 (s, 0.5H), 8.50 (s, 0.3H), 8.44 (s, 0.6H), 8.09 (s, 1H), 8.07 (d, J=8.3 Hz, 0.4H), 8.00 (d, J=8.6 Hz, 0.6H), 7.77 (d, J=8.3 Hz, 1H), 7.50 (d, J=8.1 Hz, 0.3H), 7.38 (d, J=7.8 Hz, 1H), 7.30 (d, J=7.7 Hz, 1H), 7.22 (t, J=7.8 Hz, 1H), 6.84 (s, 2H), 3.97 (t, J=7.1 Hz, 1H), 3.79 (t, J=7.8 Hz, 1H), 3.27 (s, 1H), 3.15 (s, 1H), 3.10 (t, J=7.0 Hz, 1H), 3.06 (s, 2H). LCMS MDAP Rt=17.38 min (Method 4); m/z ($ESI^+$) 415.85/413.9 $[M+H]^+$.

Example 44

N4-[(2,3-difluorophenyl)methyl]-6-(1-methylindazol-5-yl)-1,3,5-triazine-2,4-diamine

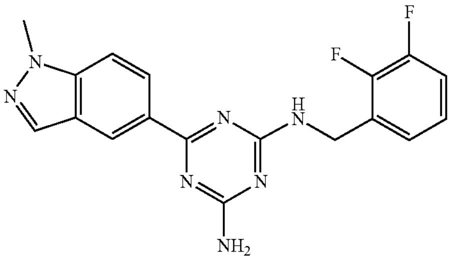 [SMILES: Cn1ncc2cc(-c3nc(N)nc(NCc4cccc(F)c4F)n3)ccc21]

To a solution of 6-chloro-N4-[(2,3-difluorophenyl)methyl]-1,3,5-triazine-2,4-diamine (Example 30, step 1) (100 mg, 0.37 mmol) in tetrahydrofuran (3 mL) was added bis[2-(di-tert-butylphosphanyl)cyclopenta-2,4-dien-1-yl]iron; dichloropalladium (12 mg, 0.02 mmol) and 1-methyl-1H-indazol-5-ylboronic acid (65 mg, 0.37 mmol). The reaction mixture was degassed by bubbling $N_2$ for 3 min then potassium phosphate tribasic (156 mg, 0.74 mmol) was added and the reaction mixture heated to 85° C. by microwave irradiation for 16 h. The reaction mixture was loaded directly on to silica and purified by flash chromatography eluting with a gradient of 2-3% methanol in DCM to afford the title compound (65 mg, 0.17 mmol, 46% yield). $^1$H NMR (600 MHz, Chloroform-d) δ 8.86-8.74 (m, 1H), 8.39 (d, J=30.7 Hz, 1H), 8.05 (s, 1H), 7.39 (d, J=8.9 Hz, 1H), 7.17 (s, 1H), 7.08-6.98 (m, 2H), 5.74 (s, 0.5H), 5.56 (s, 0.5H), 5.16 (d, J=39.2 Hz, 2H), 4.86 (s, 1H), 4.72 (s, 1H), 4.09 (s, 3H). LCMS MDAP Rt=2.51 min (Method 6); m/z (ESI$^+$) 368.00 [M+H]$^+$.

Example 45

N4-[(2,3-Difluorophenyl)methyl]-6-(1H-indazol-5-yl)-1,3,5-triazine-2,4-diamine

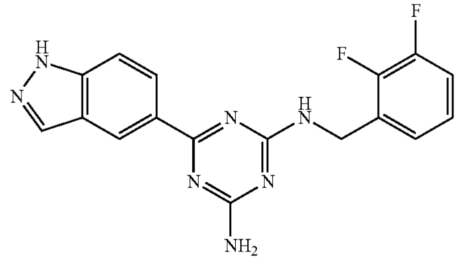

To a solution of 6-chloro-N4-[(2,3-difluorophenyl)methyl]-1,3,5-triazine-2,4-diamine (Example 30, step 1) (100 mg, 0.37 mmol) in tetrahydrofuran (3 mL) was added 1H-Indazol-5-ylboronic acid (60 mg, 0.37 mmol) and cesium fluoride (112 mg, 0.74 mmol). The reaction mixture was degassed with $N_2$ for 3 min before adding tetrakis (triphenylphosphine)palladium(0) (21 mg, 0.02 mmol). The resulting reaction mixture was heated to 85° C. by microwave irradiation for 16 h then dry loaded on to silica and purified by flash chromatography eluting with a gradient of 2-3% methanol in DCM to afford the title compound as off-white solid (30 mg, 0.08 mmol, 22% yield). $^1$H NMR (600 MHz, DMSO-d6) δ 13.52-12.98 (m, 1H), 8.70 (d, 1H), 8.31-8.22 (m, 1H), 8.17 (d, J=13.6 Hz, 1H), 7.86-7.75 (m, 1H), 7.70-7.62 (m, 1H), 7.58-7.47 (m, 1H), 7.31-7.17 (m, 1H), 7.16-7.09 (m, 1H), 6.85 (s, 1H), 6.76 (s, 1H), 4.70-4.65 (m, 1H), 4.62-4.56 (m, 1H). LCMS MDAP Rt=2.37 min (Method 6); m/z (ESI$^+$) 354.00 [M+H]$^+$.

Example 46

N4-[(2,3-Difluorophenyl)methyl]-6-(1-methylindazol-6-yl)-1,3,5-triazine-2,4-diamine

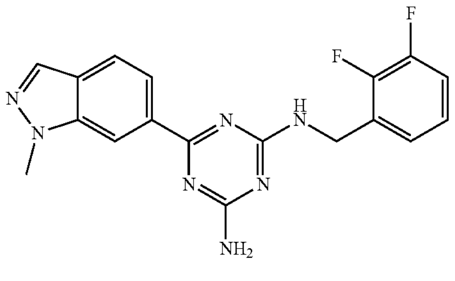 [SMILES: Cn1ncc2ccc(-c3nc(N)nc(NCc4cccc(F)c4F)n3)cc21]

The title compound was synthesised using the same protocol as Example 44, except 1-methyl-1H-indazol-5-ylboronic acid was replaced with (1-methylindazol-6-yl) boronic acid to afford the desired product. $^1$H NMR (600 MHz, Chloroform-d) δ 8.50-8.42 (m, 1H), 8.19-8.07 (m, 1H), 7.99 (s, 1H), 7.75 (d, J=8.5 Hz, 1H), 7.22-7.13 (m, 1H), 7.11-6.99 (m, 2H), 5.68 (s, 0.5H), 5.55 (s, 0.5H), 5.18 (s, 1H), 5.10 (s, 1H), 4.86 (s, 1H), 4.74 (s, 1H), 4.14 (s, 3H). LCMS MDAP Rt=2.70 min (Method 6); m/z (ESI$^+$) 368.05 [M+H]$^+$.

Example 47

N2-[(4-Chloro-1-methyl-pyrazol-3-yl)methyl]-6-(1H-indazol-6-yl)-1,3,5-triazine-2,4-diamine

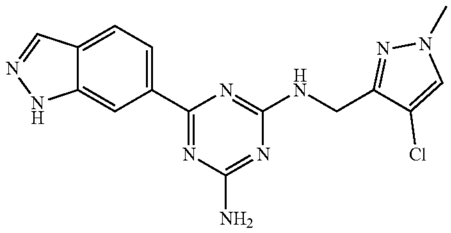 [SMILES: Cn1cc(Cl)c(CNc2nc(N)nc(-c3ccc4cn[nH]c4c3)n2)n1]

Step 1: 6-chloro-N 2-[(4-chloro-1-methyl-1H-pyrazol-3-yl)methyl]-1,3,5-triazine-2,4-diamine) SDD146-1

N,N-Diisopropylethylamine (0.10 mL, 0.60 mmol) was added to a stirred suspension of 1-(4-chloro-1-methyl-1H-pyrazol-3-yl)methanamine hydrochloride (55 mg, 0.30 mmol) and dichloro-1,3,5-triazin-2-amine (50 mg, 0.30 mmol) in 1-methylpyrrolidin-2-one (0.6 mL) at 0° C. and stirred at 0° C. for 2 h. The reaction was quenched with water (5 mL) and stirred for 16 h. The resulting precipitate was filtered, and the solid dried under vacuum at 45° C. for 8 h to afford the title compound as a colourless solid (52 mg, 0.19 mmol, 63% yield). $^1$H NMR (400 MHz, DMSO-d6) δ 7.94 (s, 1H), 7.88 (s, 1H), 7.52-6.95 (m, 2H), 4.60-4.29 (m, 2H), 3.77 (s, 3H). UPLCMS Rt=0.80 min, 93% (Basic 2 min); m/z (ESI$^+$) 274 [M+H]$^+$.

Step 2: N 2-[(4-chloro-1-methyl-pyrazol-3-yl)methyl]-6-(1H-indazol-6-yl)-1,3,5-triazine-2,4-diamine (1H-indazol-6-yl)boronic acid) (29 mg, 0.18 mmol), 6-chloro-N 2-[(4-chloro-1-methyl-1H-pyrazol-3-yl)methyl]-1,3,5-triazine-2,4-diamine (50 mg, 0.18 mmol), and 3 M aq. potassium carbonate (0.18 mL, 0.547 mmol) were added to a degassed mixture of 1,4-dioxane (1 mL) and water (0.07 mL). After degassing under nitrogen for 5 min, bis[2-(diphenylphosphanyl)cyclopenta-2,4-dien-1-yl]iron; dichloromethane; dichloropalladium (7.4 mg, 0.009 mmol) was added and the reaction mixture heated at 80° C. for 6 h. The mixture was cooled to RT, diluted with DCM:methanol (8:2, 10 mL), and filtered through a celite/SiO2 pad. The filtrate was evaporated to dryness and the crude material purified by preparative HPLC. The fractions were collected and dried under vacuum at 40° C. to afford a white solid. The material was further purified by flash silica chromatography eluting with a gradient of 0-10% methanol in DCM afford the title compound as a colourless solid (5.8 mg, 0.016 mmol, 8.9% yield). $^1$H NMR (400 MHz, DMSO-d6) δ 13.29

(s, 1H), 8.87-8.35 (m, 1H), 8.19-7.74 (m, 4H), 7.50-7.31 (m, 1H), 6.99-6.61 (m, 2H), 4.77-4.39 (m, 2H), 3.78 (s, 3H). UPLC-MS Rt=1.27 min, 100% (4 min Basic); m/z ($ESI^+$) 356 $[M+H]^+$.

Example 48

6-(1H-indazol-6-yl)-N2-[1-methyl-1-(6-methyl-2-pyridyl)ethyl]-1,3,5-triazine-2,4-diamine

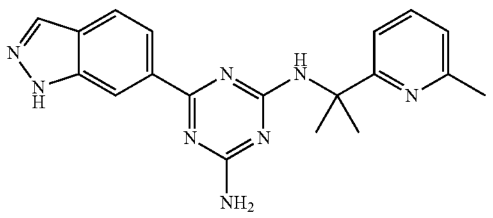 [SMILES: Cc1cccc(C(C)(C)Nc2nc(N)nc(-c3ccc4cn[nH]c4c3)n2)n1]

To a solution of 4-chloro-6-(1H-indazol-6-yl)-1,3,5-triazin-2-amine) (Intermediate Z) (20 mg, 0.08 mmol) in NMP (0.30 mL) was added 2-(6-methylpyridin-2-yl)propan-2-amine (Intermediate B) (31 mg, 0.20 mmol) and N, N-diisopropylethylamine (0.04 mL, 0.24 mmol) and the reaction stirred at 90° C. for 20 h. The reaction was allowed to cool to room temperature, diluted with 9:1 DMSO:water and purified by prep-HPLC. The fractions containing the desired compound were combined and concentrated to dryness under reduced pressure to afford a pale brown solid which was triturated from diethyl ether twice to afford the title compound (3.2 mg, 11% yield). $^1$H UPLC-MS Rt=1.53 min, 100% (4 min Basic); m/z ($ESI^+$) 361.2 $[M+H]^+$.

Example 49

N2-[(2-Chloro-4-fluoro-phenyl)methyl]-6-(1H-indazol-6-yl)-1,3,5-triazine-2,4-diamine

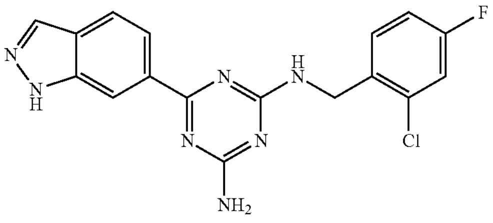 [SMILES: Nc1nc(NCc2ccc(F)cc2Cl)nc(-c2ccc3cn[nH]c3c2)n1]

Synthesised by General Method C:

To a solution of 4-chloro-6-(1H-indazol-6-yl)-1,3,5-triazin-2-amine (Intermediate Z) (30 mg, 0.12 mmol) in NMP (0.38 mL) was added 1-(2-chloro-4-fluorophenyl)methanamine) (0.04 mL, 0.30 mmol) and N,N-diisopropylethylamine (0.06 mL, 0.37 mmol) and the reaction mixture stirred at 90° C. for 2 h. The reaction was allowed to cool to room temperature, diluted with 9:1 DMSO:water and purified by prep-HPLC. The fractions containing the desired compound were combined and concentrated to dryness under reduced pressure to afford the title compound as an off-white solid (4 mg, 9% yield). $^1$H NMR (DMSO-d6) δ: 13.31 (s, 1H), 8.48 (m, 1H), 8.16-7.97 (m, 2H), 7.92-7.69 (m, 1H), 7.43 (m, 2H), 7.21 (m, 1H), 6.92 (m, 2H), 4.68 (s, 1H), 4.56 (d, J=6.3 Hz, 1H). UPLC-MS Rt=1.65 min, 96% (4 min Basic); m/z ($ESI^+$) 370.1 $[M+H]^+$.

Example 50

N2-[(2-chloro-6-fluoro-phenyl)methyl]-6-(1H-indazol-6-yl)-1,3,5-triazine-2,4-diamine

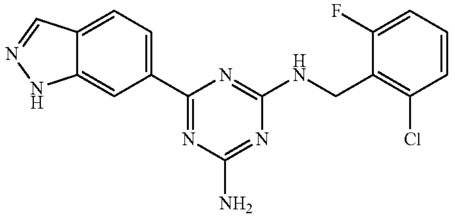 [SMILES: Nc1nc(NCc2c(F)cccc2Cl)nc(-c2ccc3cn[nH]c3c2)n1]

The title compound was synthesised according to Method C using the same protocol as Example 49 except 1-(2-chloro-4-fluorophenyl)methanamine was replaced with 1-(2-chloro-6-fluorophenyl)methanamine, to afford the desired product as an off-white solid (3 mg, 5% yield). $^1$H NMR (DMSO-d6) δ: 13.29 (s, 1H), 8.51 (m, 1H), 8.08 (m, 2H), 7.79 (d, J=8.6 Hz, 1H), 7.55 (m, 1H), 7.37 (m, 2H), 7.26 (m, 1H), 6.86 (m, 2H), 4.74 (s, 1H), 4.64 (s, 1H). UPLC-MS Rt=1.60 min, 100% (4 min Basic); m/z ($ESI^+$) 370.1 $[M+H]^+$.

Example 51

N2-[(6-chloro-2,3-difluoro-phenyl)methyl]-6-(1H-indazol-6-yl)-1,3,5-triazine-2,4-diamine

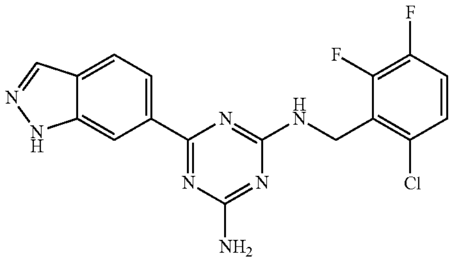 [SMILES: Nc1nc(NCc2c(Cl)ccc(F)c2F)nc(-c2ccc3cn[nH]c3c2)n1]

The title compound was synthesised according to Method C using the same protocol as Example 49 except 1-(2-chloro-4-fluorophenyl)methanamine was replaced with 1-(6-chloro-2,3-difluorophenyl)methanamine to afford the desired compound as a white solid (13.5 mg, 0.035 mmol, 43% yield). $^1$H NMR (400 MHz, DMSO-d6) δ 13.31 (s, 1H), 8.66-8.34 (m, 1H), 8.20-7.98 (m, 2H), 7.84-7.75 (m, 1H), 7.74-7.30 (m, 3H), 7.21-6.59 (m, 2H), 4.81-4.62 (m, 2H). UPLC-MS Rt=1.61 min, 100% (4 min Basic); m/z ($ESI^+$) 388.1 $[M+H]^+$.

Example 52

N2-[(2-chloro-4-methyl-phenyl)methyl]-6-(1H-indazol-6-yl)-1,3,5-triazine-2,4-diamine

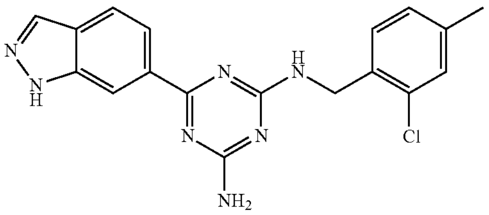 [SMILES: Cc1ccc(CNc2nc(N)nc(-c3ccc4cn[nH]c4c3)n2)c(Cl)c1]

The title compound was synthesised according to Method C using the same protocol as Example 49 except 1-(2-chloro-4-fluorophenyl)methanamine was replaced with 1-(2-chloro-4-methylphenyl)methanamine) to afford the desired compound as a white solid (9.0 mg, 0.025 mmol, 30% yield). $^1$H NMR (400 MHz, DMSO-d6) δ 13.59-13.01 (m, 1H), 8.75-8.26 (m, 1H), 8.26-7.94 (m, 2H), 7.92-7.70 (m, 2H), 7.48-7.23 (m, 2H), 7.23-7.03 (m, 1H), 7.03-6.65 (m, 2H), 4.80-4.33 (m, 2H), 2.32-2.03 (m, 3H). UPLC-MS Rt=1.72 min, 100% (4 min Basic); m/z (ESI$^+$) 366.1 [M+H]$^+$.

Example 53

N2-[(5-chloro-2-pyridyl)methyl]-6-(1H-indazol-6-yl)-1,3,5-triazine-2,4-diamine

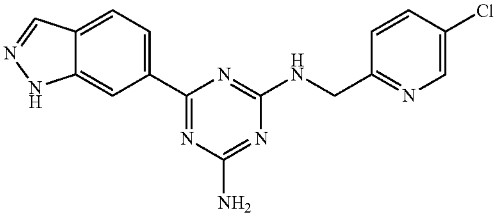

The title compound was synthesised according to Method C using the same protocol as Example 49 except 1-(2-chloro-4-fluorophenyl)methanamine was replaced with 1-(5-chloropyridin-2-yl)methanamine to afford the desired compound as an off-white solid (20 mg 35% yield). $^1$H NMR (DMSO-d6) δ: 13.30 (s, 1H), 8.57 (d, J=8.3 Hz, 1H), 8.50 (s, 1H), 8.41 (s, 1H), 8.15-8.02 (m, 2H), 8.02-7.90 (m, 1H), 7.88 (d, J=8.4 Hz, 1H), 7.78 (dd, J=20.0, 8.3 Hz, 2H), 7.39 (t, J=9.2 Hz, 2H), 6.90 (d, J=20.8 Hz, 3H), 4.71 (d, J=6.0 Hz, 1H), 4.62 (d, J=6.1 Hz, 2H). UPLC-MS Rt=1.36 min, 95% (4 min Basic); m/z (ESI$^+$) 353.1 [M+H]$^+$.

Example 54

6-(1H-indazol-6-yl)-N2-[2-(6-methyl-2-pyridyl)ethyl]-1,3,5-triazine-2,4-diamine

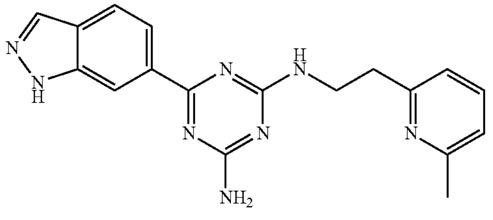

The title compound was synthesised according to Method C using the same protocol as Example 49 except 1-(2-chloro-4-fluorophenyl)methanamine was replaced with 2-(6-methylpyridin-2-yl)ethan-1-amine to afford the desired compound as an off-white solid (19 mg, 34% yield). $^1$H NMR (DMSO-d6) δ: 13.28 (s, 1H), 8.49 (d, J=19.1 Hz, 1H), 8.23-7.91 (m, 2H), 7.80 (t, J=8.1 Hz, 1H), 7.59 (t, J=7.8 Hz, 2H), 7.38 (d, J=5.7 Hz, 1H), 7.19 (s, OH), 7.14-7.01 (m, 2H), 6.90 (s, 1H), 6.74 (s, 1H), 3.74 (d, J=6.7 Hz, 1H), 3.66-3.58 (m, 1H), 3.29 (s, 1H), 2.99 (dt, J=14.6, 7.5 Hz, 2H), 2.45 (s, 3H). UPLC-MS Rt=1.29 min, 95% (4 min Basic); m/z (ESI$^+$) 347.1 [M+H]$^+$.

Example 55

6-(1H-indazol-6-yl)-N2-[2-[5-(trifluoromethyl)-2-pyridyl]ethyl]-1,3,5-triazine-2,4-diamine

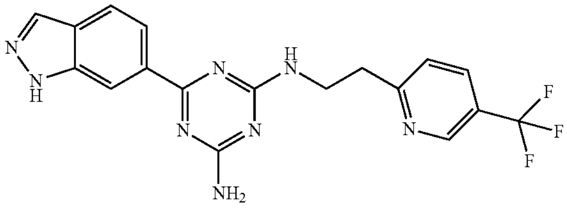 [SMILES: Nc1nc(NCCc2ccc(C(F)(F)F)cn2)nc(-c2ccc3cn[nH]c3c2)n1]

The title compound was synthesised according to Method C using the same protocol as Example 49 except 1-(2-chloro-4-fluorophenyl)methanamine was replaced with 2-[5-(trifluoromethyl)pyridin-2-yl]ethan-1-amine dihydrochloride to afford the desired compound as an off-white solid (21 mg, 35%). $^1$H NMR (DMSO-d6) δ: 13.28 (s, 1H), 8.90 (d, J=2.3 Hz, 1H), 8.47 (m, 1H), 8.18-7.97 (m, 3H), 7.79 (t, J=7.3 Hz, 1H), 7.55 (t, J=8.6 Hz, 1H), 7.42 (m, 0.5H), 7.23 (s, 0.5H), 6.83 (m, 2H), 3.80 (d, J=6.4 Hz, 1H), 3.70 (d, J=6.7 Hz, 1H), 3.23-3.06 (m, 2H). UPLC-MS Rt=1.48 min, 100% (4 min Basic); m/z (ESI$^+$) 401.2 [M+H]$^+$.

Example 56

6-(1H-indazol-6-yl)-N2-[(1-propylpyrazol-3-yl) methyl]-1,3,5-triazine-2,4-diamine

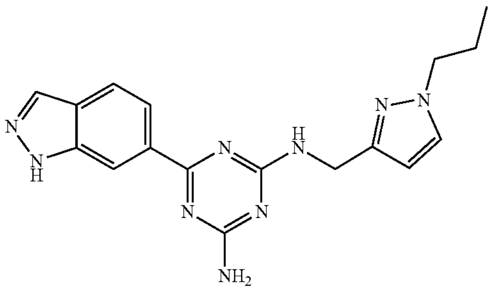 [SMILES: CCCn1ccc(CNc2nc(N)nc(-c3ccc4cn[nH]c4c3)n2)n1]

The title compound was synthesised according to Method C using the same protocol as Example 49 except 1-(2-chloro-4-fluorophenyl)methanamine was replaced with 1-(1-propyl-1H-pyrazol-3-yl)methanamine to afford the desired compound as an off-white solid (2.4 mg, 4.2%). $^1$H NMR (DMSO-d6) δ: 13.27 (d, 1H), 8.51 (d, 1H), 8.08 (d, 2H), 7.79 (d, 1H), 7.54 (d, 2H), 6.85 (d, 2H), 6.17 (s, 1H), 4.57 (d, J=6.0 Hz, 1H), 4.47 (d, J=6.0 Hz, 1H), 3.99 (t, J=7.0 Hz, 2H), 1.76 (h, J=7.3 Hz, 2H), 0.81 (q, J=6.9 Hz, 3H). UPLC-MS Rt=1.32 min, 96% (4 min Basic); m/z (ESI$^+$) 350.2 [M+H]$^+$.

Example 57

N2-[(5-ethyl-2-pyridyl)methyl]-6-(1H-indazol-6-yl)-1,3,5-triazine-2,4-diamine

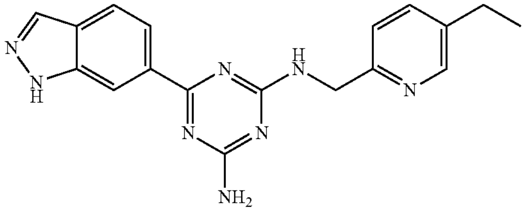 [SMILES: CCc1ccc(CNc2nc(N)nc(-c3ccc4cn[nH]c4c3)n2)nc1]

The title compound was synthesised according to Method C using the same protocol as Example 49 except 1-(2-chloro-4-fluorophenyl)methanamine was replaced with 1-(5-ethylpyridin-2-yl)methanamine to afford the desired compound as white solid (21 mg, 0.061 mmol, 37% yield). $^1$H NMR (400 MHz, DMSO-d6) δ 13.66-12.96 (m, 1H), 8.51-8.43 (m, 2H), 8.17-7.98 (m, 2H), 7.93-7.68 (m, 2H), 7.68-7.52 (m, 1H), 7.35-7.20 (m, 1H), 7.01-6.78 (m, 2H), 4.86-4.48 (m, 2H), 2.80-2.56 (m, 2H), 1.67-0.52 (m, 3H). UPLC-MS Rt=1.39 min, 97% (4 min Basic); m/z (ESI$^+$) 347.1 [M+H]$^+$.

Example 58

6-(1H-indazol-6-yl)-N2-[(6-methyl-2-pyridyl) methyl]-1,3,5-triazine-2,4-diamine

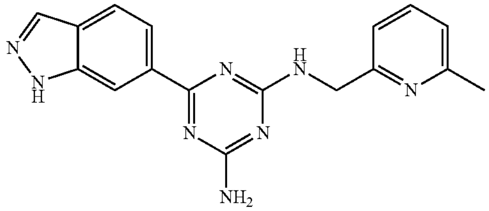 [SMILES: Cc1cccc(CNc2nc(N)nc(-c3ccc4cn[nH]c4c3)n2)n1]

The title compound was synthesised according to Method C using the same protocol as Example 49 except 1-(2-chloro-4-fluorophenyl)methanamine was replaced with 1-(6-methylpyridin-2-yl)methanamine) to afford the desired compound as a white solid (20 mg, 0.060 mmol, 36.9% yield). $^1$H NMR (400 MHz, DMSO-d6) δ 13.55-12.88 (m, 1H), 8.82-8.35 (m, 1H), 8.26-7.94 (m, 2H), 7.94-7.75 (m, 2H), 7.75-7.46 (m, 2H), 7.46-7.03 (m, 4H), 7.03-6.65 (m, 2H), 5.00-4.44 (m, 2H). UPLC-MS Rt=1.26 min, 100% (4 min Basic); m/z (ESI$^+$) 333.1 [M+H]$^+$.

Example 59

6-(1H-indazol-6-yl)-N2-[[1-(2,2,2-trifluoroethyl) pyrazol-3-yl]methyl]-1,3,5-triazine-2,4-diamine

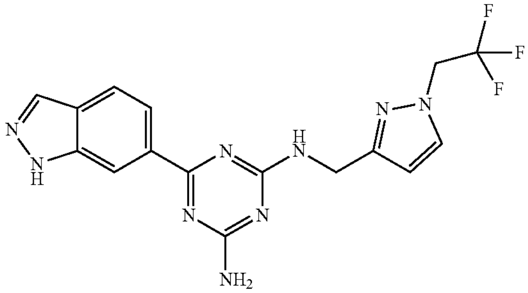 [SMILES: Nc1nc(NCc2ccn(CC(F)(F)F)n2)nc(-c2ccc3cn[nH]c3c2)n1]

The title compound was synthesised according to Method C using the same protocol as Example 49 except 1-(2-chloro-4-fluorophenyl)methanamine was replaced with 1-[1-(2,2,2-trifluoroethyl)-1H-pyrazol-3-yl]methanamine to afford the desired compound as a white solid (21 mg, 0.053 mmol, 33%). $^1$H NMR (400 MHz, DMSO-d6) δ 13.75-12.86 (m, 1H), 8.66-8.41 (m, 1H), 8.18-7.98 (m, 2H), 7.91-7.77 (m, 1H), 7.77-7.54 (m, 2H), 7.18-6.66 (m, 2H), 6.56-6.20 (m, 1H), 5.08 (q, 2H), 4.78-4.27 (m, 2H). UPLC-MS Rt=1.31 min, 98% (4 min Basic); m/z (ESI$^+$) 390.1 [M+H]$^+$.

Example 60

N2-[1-[1-(difluoromethyl)pyrazol-3-yl]-1-methyl-ethyl]-6-(1H-indazol-6-yl)-1,3,5-triazine-2,4-diamine

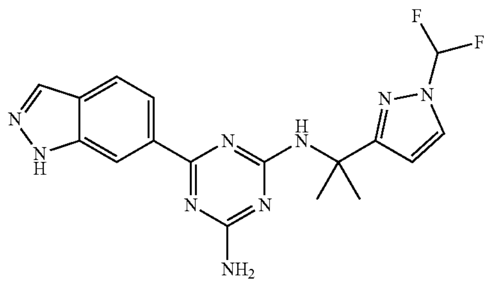 [SMILES: CC(C)(Nc1nc(N)nc(-c2ccc3cn[nH]c3c2)n1)c1ccn(C(F)F)n1]

To a solution of 4-chloro-6-(1H-indazol-6-yl)-1,3,5-triazin-2-amine) (Intermediate Z) (79 mg, 0.32 mmol) in NMP (0.94 mL) was added 2-[1-(difluoromethyl)-1H-pyrazol-3-yl]propan-2-amine (Intermediate L) (206 mg, 0.80 mmol) followed by N,N-diisopropylethylamine (0.17 mL, 0.96 mmol) and the reaction mixture heated to 90° C. for 9 days. The reaction mixture was diluted with 9:1 DMSO:water mixture (2 mL) and the crude material purified by prep-HPLC, the fractions containing the product combined and concentrated to dryness under reduced pressure to afford the title compound as an off-white solid (11 mg 9% yield). $^1$H NMR (DMSO-d6) δ: 13.50-13.06 (m, 1H), 8.72-8.22 (m, 1H), 8.22-7.55 (m, 5H), 7.33 (s, 1H), 6.94-6.19 (m, 3H), 1.74 (s, 6H). UPLC-MS Rt=1.42 min, 97% (4 min Basic); m/z (ESI$^+$) 386.1 [M+H]$^+$.

Example 61

6-(1H-indazol-6-yl)-N2-[(1-isopropylpyrazol-3-yl)methyl]-1,3,5-triazine-2,4-diamine

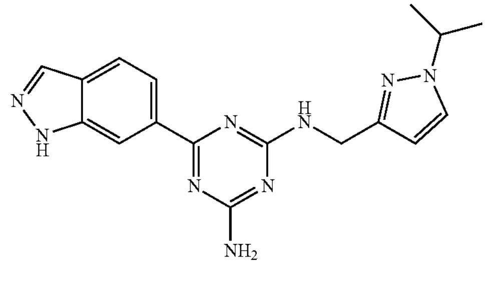 [SMILES: CC(C)n1ccc(CNc2nc(N)nc(-c3ccc4cn[nH]c4c3)n2)n1]

The title compound was synthesised according to Method C using the same protocol as Example 49 except 1-(2-chloro-4-fluorophenyl)methanamine was replaced with 1-[1-(propan-2-yl)-1H-pyrazol-3-yl]methanamine) to afford the desired compound as a white solid (32.5 mg, 0.093 mmol, 46% yield). $^1$H NMR (400 MHz, DMSO-d6) δ 13.56-13.12 (m, 1H), 8.71-8.33 (m, 1H), 8.28-7.95 (m, 2H), 7.94-7.45 (m, 3H), 7.09-6.73 (m, 2H), 6.18 (s, 1H), 4.95-4.49 (m, 2H), 4.49-4.29 (m, 1H), 1.40 (d, J=6.7 Hz, 6H). UPLC-MS Rt=1.31 min, 100% (4 min Basic); m/z (ESI$^+$) 350.1 [M+H]$^+$.

Example 62

6-(1H-indazol-6-yl)-N2-(2-pyrazol-1-ylethyl)-1,3,5-triazine-2,4-diamine

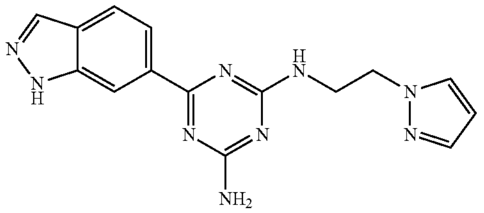 [SMILES: Nc1nc(NCCn2cccn2)nc(-c2ccc3cn[nH]c3c2)n1]

The title compound was synthesised according to Method C using the same protocol as Example 49 except 1-(2-chloro-4-fluorophenyl)methanamine was replaced with 2-(1H-pyrazol-1-yl)ethan-1-amine to afford the desired product as a white solid (29 mg, 0.091 mmol, 45%). $^1$H NMR (400 MHz, DMSO-d6) δ 13.29 (s, 1H), 8.55-8.45 (m, 1H), 8.15-8.00 (m, 2H), 7.86-7.77 (m, 1H), 7.76-7.72 (m, 1H), 7.49-7.44 (m, 1H), 7.42-7.12 (m, 1H), 7.08-6.71 (m, 2H), 6.27-6.22 (m, 1H), 4.39-4.29 (m, 2H), 3.72-3.66 (m, 2H). UPLC-MS Rt=1.11 min, 100% (4 min Basic); m/z (ESI$^+$) 322.1 [M+H]$^+$.

Example 63

N2-[2-(2,3-dichlorophenyl)-1,1-dimethyl-ethyl]-6-(1H-indazol-6-yl)-1,3,5-triazine-2,4-diamine

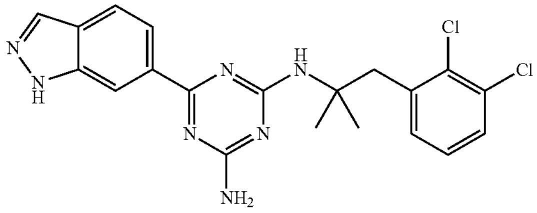 [SMILES: CC(C)(Cc1cccc(Cl)c1Cl)Nc1nc(N)nc(-c2ccc3cn[nH]c3c2)n1]

To a solution containing 4-chloro-6-(1H-indazol-6-yl)-1,3,5-triazin-2-amine (intermediate Z) (50 mg, 0.20 mmol) in NMP (0.60 mL) was added 1-(2,3-dichlorophenyl)-2-methylpropan-2-amine (Intermediate T) (147 mg, 0.51 mmol) and N,N-diisopropylethylamine (0.11 mL, 0.61 mmol). The reaction mixture was heated to 90° C. for 3 h then to 170° C. for a further 72 h. The reaction mixture was allowed to cool to RT and diluted into 9:1 DMSO:H2O (2 mL) for purification by preparative HPLC. Fractions containing product were combined and concentrated to dryness under reduced pressure to afford the title compound as a white solid (12 mg, 14% yield). $^1$H NMR (DMSO-d6) δ: 13.30 (s, 1H), 8.51 (s, 1H), 8.10 (d, J=16.5 Hz, 2H), 7.82 (s, 1H), 7.48 (dd, J=8.0, 1.5 Hz, 1H), 7.25 (t, J=7.8 Hz, 1H), 7.12 (d, J=7.8 Hz, 1H), 7.03-6.55 (m, 2H), 3.57 (d, J=25.3 Hz, 2H), 1.42 (d, J=16.0 Hz, 6H). UPLC-MS Rt=2.07 min, 100% (4 min Basic); m/z (ESI$^+$) 428.1, 430.1, 431.1 (2×Cl isotopes), [M+H]$^+$.

Example 64

6-(1H-indazol-6-yl)-N2-[(4-methylthiazol-2-yl)methyl]-1,3,5-triazine-2,4-diamine

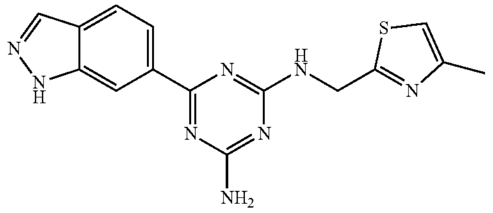 [SMILES: Cc1csc(CNc2nc(N)nc(-c3ccc4cn[nH]c4c3)n2)n1]

The title compound was synthesised according to Method C using the same protocol as Example 49 except 1-(2-chloro-4-fluorophenyl)methanamine was replaced with 1-(4-methyl-1,3-thiazol-2-yl)methanamine to afford the desired compound as a white solid (40 mg, 0.12 mmol, 58% yield). $^1$H NMR (400 MHz, DMSO-d6) δ 13.50-13.08 (m, 1H), 8.51 (s, 1H), 8.32-8.04 (m, 3H), 8.04-7.69 (m, 1H), 7.31-6.66 (m, 3H), 5.00-4.51 (m, 2H), 2.35 (s, 3H). UPLC-MS Rt=1.24 min, 98% (4 min Basic); m/z (ESI$^+$) 339.1 $[M+H]^+$.

Example 65

6-(1H-indazol-6-yl)-N2-[2-(2-methylthiazol-4-yl)ethyl]-1,3,5-triazine-2,4-diamine

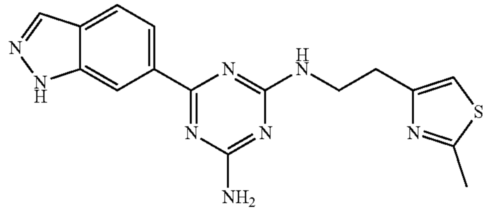 [SMILES: Cc1nc(CCNc2nc(N)nc(-c3ccc4cn[nH]c4c3)n2)cs1]

The title compound was synthesised according to Method C using the same protocol as Example 49 except 1-(2-chloro-4-fluorophenyl)methanamine was replaced with 2-(2-methyl-1,3-thiazol-4-yl)ethan-1-amine to afford the desired compound as a white solid (45 mg, 0.128 mmol, 63% yield). $^1$H NMR (400 MHz, DMSO-d6) δ 13.29 (s, 1H), 8.78-8.32 (m, 1H), 8.32-7.97 (m, 2H), 7.92-7.69 (m, 1H), 7.55-7.15 (m, 2H), 7.01-6.50 (m, 2H), 3.81-3.49 (m, 2H), 3.09-2.88 (m, 2H), 2.73-2.59 (m, 3H). UPLC-MS Rt=1.28 min, 100% (4 min Basic); m/z (ESI$^+$) 353.1 $[M+H]^+$.

Example 66

N2-(2-imidazo[2,1-b]thiazol-6-ylethyl)-6-(1H-indazol-6-yl)-1,3,5-triazine-2,4-diamine

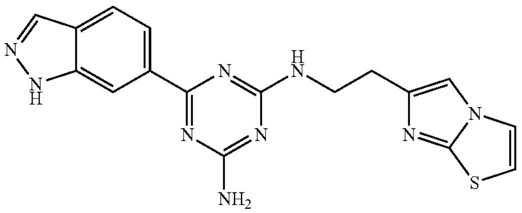 [SMILES: Nc1nc(NCCc2cn3ccsc3n2)nc(-c2ccc3cn[nH]c3c2)n1]

The title compound was synthesised according to Method C using the same protocol as Example 49 except 1-(2-chloro-4-fluorophenyl)methanamine was replaced with 2-{imidazo[2,1-b][1,3]thiazol-6-yl}ethan-1-amine dihydrochloride to afford the desired compound as an off-white solid (41 mg, 0.11 mmol, 54% yield). $^1$H NMR (400 MHz, DMSO-d6) δ 13.54-12.97 (m, 1H), 8.77-8.33 (m, 1H), 8.20-8.01 (m, 2H), 7.93-7.73 (m, 2H), 7.61-7.53 (m, 1H), 7.45-7.12 (m, 2H), 7.07-6.64 (m, 2H), 3.83-3.51 (m, 2H), 3.05-2.79 (m, 2H). UPLC-MS Rt=1.08 min, 99% (4 min Basic); m/z (ESI$^+$) 378.1 $[M+H]^+$.

Example 67

6-(1H-indazol-6-yl)-N2-[2-(4-methylthiazol-2-yl)ethyl]-1,3,5-triazine-2,4-diamine

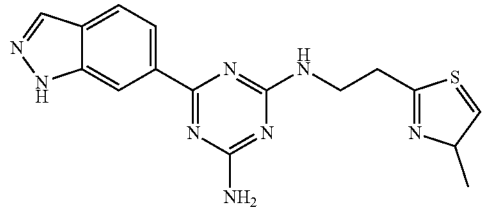

The title compound was synthesised according to Method C using the same protocol as Example 49 except 1-(2-chloro-4-fluorophenyl)methanamine was replaced with 2-(4-methyl-1,3-thiazol-2-yl)ethan-1-amine to afford the desired compound as a white solid (40 mg, 0.114 mmol, 56% yield). $^1$H NMR (400 MHz, DMSO-d6) δ 13.29 (s, 1H), 8.76-8.33 (m, 1H), 8.21-7.96 (m, 2H), 7.90-7.67 (m, 1H), 7.52-7.21 (m, 1H), 7.21-7.04 (m, 1H), 6.95 (s, 1H), 6.80 (s, 1H), 3.91-3.55 (m, 2H), 3.31-3.13 (m, 2H), 2.34 (s, 3H). UPLC-MS Rt=1.29 min, 97% (4 min Basic); m/z (ESI$^+$) 353.1 $[M+H]^+$.

Example 68

N2-[[1-(difluoromethyl)pyrazol-3-yl]methyl]-6-(1H-indazol-6-yl)-1,3,5-triazine-2,4-diamine

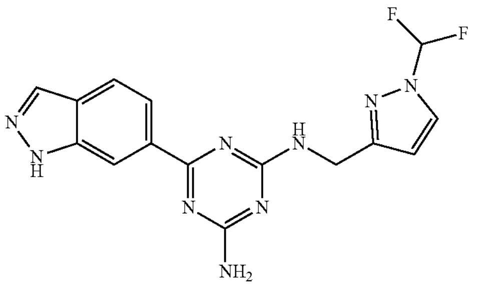 [SMILES: Nc1nc(NCc2ccn(C(F)F)n2)nc(-c2ccc3cn[nH]c3c2)n1]

The title compound was synthesised according to Method C using the same protocol as Example 49 except 1-(2-chloro-4-fluorophenyl)methanamine was replaced with 1-[1-(difluoromethyl)-1H-pyrazol-3-yl]methanamine hydrochloride to afford the desired compound as an off-white solid (49 mg, 0.14 mmol, 61% yield). $^1H$ NMR (400 MHz, DMSO-d6) δ 13.30 (s, 1H), 8.49 (s, 1H), 8.32-7.46 (m, 7H), 6.97 (s, 2H), 6.50 (s, 1H), 4.59 (d, J=37.8 Hz, 2H). UPLC-MS Rt=1.25 min, 99% (4 min Basic); m/z ($ESI^+$) 358.1 $[M+H]^+$.

Example 69

6-(1H-indazol-6-yl)-N2-[2-(2-pyridyl)ethyl]-1,3,5-triazine-2,4-diamine

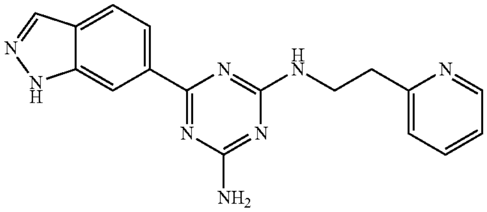 [SMILES: Nc1nc(NCCc2ccccn2)nc(-c2ccc3cn[nH]c3c2)n1]

Synthesised by General Method B:

Step 1: 6-chloro-N4-[2-(2-pyridyl)ethyl]-1,3,5-triazine-2,4-diamine

To a stirred solution of 2-amino-4,6-dichlorotriazine (250 mg, 1.52 mmol) in 1,4-dioxane (9 mL), 2-(2-pyridyl)ethylamine (0.2 mL, 1.7 mmol) was added followed by the addition of N,N-diisopropylethylamine (0.66 mL, 3.79 mmol). The resulting mixture was stirred at RT for 12 h. Volatiles were removed under reduced pressure and the crude was purified by flash chromatography (silica gel, eluting with a gradient of 50-100% EtOAc in petroleum ether) to afford the title compound as a white powder (260 mg, 0.99 mmol, 65% yield). $^1H$ NMR (600 MHz, DMSO-$d_6$) δ 8.46 (dt, J=4.9, 1.4 Hz, 1H), 7.86-7.51 (m, 2H), 7.29-7.17 (m, 3H), 7.10 (d, J=56.0 Hz, 1H), 3.58-3.51 (m, 2H), 2.95-2.88 (m, 2H). LCMS LCQ (Method 1) Rt=0.48 min; m/z ($ESI^+$) 251.08, 235.07 (Cl isotopes) $[M+H]^+$.

Step 2: N 4-[2-(2-pyridyl)ethyl]-6-(1-tetrahydropyran-2-ylindazol-6-yl)-1,3,5-triazine-2,4-diamine A stirred solution of 6-chloro-N4-[2-(2-pyridyl)ethyl]-1,3,5-triazine-2,4-diamine (100 mg, 0.40 mmol), potassium phosphate tribasic (254 mg, 1.2 mmol), and bis[2-(di-tert-butylphosphanyl)cyclopenta-2,4-dien-1-yl]iron; dichloropalladium (26 mg, 0.04 mmol) in THF (5 mL) and water (0.5 mL) was degassed by bubbling $N_2$ directly into the solution. The mixture was warm up to 80° C. then a solution of 1-tetrahydropyran-2-yl-6-(4,4,5,5-tetramethyl-1,3,2-dioxaborolan-2-yl)indazole (Intermediate V) (327 mg, 1.0 mmol) in THF (4 mL) was added and the mixture stirred at 80° C. for 12 h. The reaction mixture was concentrated to dryness and the crude purified by flash column chromatography (silica gel, eluting with a gradient of 25-100% EtOAc in petroleum ether) to afford the title compound as a white solid (120 mg, 0.27 mmol, 69% yield). LCMS MDAP (Method 6) Rt=3.74 min; m/z ($ESI^+$) 417.10, $[M+H]^+$.

Step 3: 6-(1H-indazol-6-yl)-N2-[2-(2-pyridyl)ethyl]-1,3,5-triazine-2,4-diamine

A solution of N 2-[2-(2-pyridyl)ethyl]-6-(1-tetrahydropyran-2-ylindazol-6-yl)-1,3,5-triazine-2,4-diamine (75 mg, 0.18 mmol) in methyl alcohol (1 mL) and 4 M HCl in 1,4-dioxane (1.35 mL, 5.4 mmol) was heated at 40° C. for 16 h. A precipitate formed which was filtered, washed with diethyl ether and petroleum ether, then dried in oven at 50 C for 2 h to afford the title compound (50 mg, 0.15 mmol, 83% yield) as a white solid. $^1H$ NMR (399 MHz, DMSO-d6, VT 90° C.) δ 8.67 (d, J=5.6 Hz, 1H), 8.57 (s, 1H), 8.29 (t, J=7.8 Hz, 1H), 8.16 (d, J=1.0 Hz, 1H), 8.00 (d, J=8.3 Hz, 1H), 7.89 (d, J=8.5 Hz, 1H), 7.84 (d, J=8.0 Hz, 1H), 7.71 (s, 1H), 3.88 (s, 2H), 3.37 (t, J=6.6 Hz, 2H). LCMS LCQ Rt=0.43 min (Method 1); m/z ($ESI^+$) 333.05 $[M+H]^+$.

Example 70

N2-[(2,3-difluorophenyl)methyl]-6-(1H-indazol-6-yl)-1,3,5-triazine-2,4-diamine

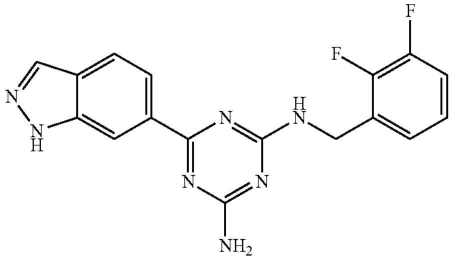 [SMILES: Nc1nc(NCc2cccc(F)c2F)nc(-c2ccc3cn[nH]c3c2)n1]

To a solution of 6-chloro-N4-[(2,3-difluorophenyl)methyl]-1,3,5-triazine-2,4-diamine (Example 30, step 1) (650 mg, 2.4 mmol), (1H-indazol-6-yl)boronic acid (470 mg, 2.9 mmol), potassium carbonate (663 mg, 4.8 mmol) in 1,4-dioxane (8.0 mL) and water (2 mL) was added Pd(dppf)$Cl_2$ (176 mg, 0.24 mmol) and the mixture degassed for 5 min. The mixture was heated to 100° C. for 3 h then allowed to cool to RT and filtered through a pad of celite, washing through with ethyl acetate (50 mL). The organic filtrate was washed successively with water (40 mL) and brine (40 mL), dried ($Na_2SO_4$), filtered and concentrated to dryness under reduced pressure. The crude material was purified flash column chromatography eluting with a gradient of 0-100% ethylacetate in isohexane, to afford the title compound as an off-white solid (95 mg, 11% yield). $^1$H NMR (400 MHz, DMSO-d6) δ 13.36-13.32 (m, 1H), 8.53-8.52 (m, 1H), 8.16-8.15 (m, 1H), 8.10-8.08 (m, 1H), 7.97-7.81 (m, 2H), 7.36-7.20 (m, 3H), 7.00-6.90 (br m, 2H), 4.75-4.65 (m, 2H). UPLC-MS Rt=1.54 min, 98% (4 min Basic); m/z (ESI$^+$) 354.0 [M+H]$^+$.

Example 71

N2-[1-(2,3-difluorophenyl)-1-methyl-ethyl]-6-(1H-indazol-6-yl)-N4-methyl-1,3,5-triazine-2,4-diamine

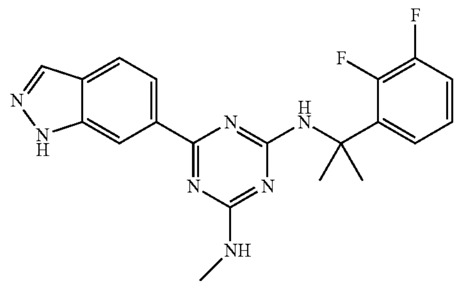 [SMILES: CNc1nc(NC(C)(C)c2cccc(F)c2F)nc(-c2ccc3cn[nH]c3c2)n1]

Step 1: 4,6-dichloro-N-[1-(2,3-difluorophenyl)-1-methyl-ethyl]-1,3,5-triazin-2-amine To stirred solution of cyanuric chloride (300 mg, 1.63 mmol) in ethylene glycol dimethyl ether (10 mL) at −30° C. was dropwise added 2-(2,3-difluorophenyl)propan-2-amine (Intermediate N) (278 mg, 1.63 mmol). The reaction mixture was stirred at −30° C. for 3 h and then at RT for 16 h. The reaction mixture was diluted with ethyl acetate (20 mL) and was washed with 1 N HCl (5 mL) and water (5 mL). The organics phase was dried ($MgSO_4$) and concentrated to dryness under reduced pressure. The crude was purified by flash column chromatography eluting with Petroleum Ether: ethyl acetate (6:4) to afford the title compound as a clear gum (248 mg, 0.7 mmol, 43% yield). $^1$H NMR (600 MHz, Chloroform-d) δ 7.13 (ddt, J=8.7, 7.1, 1.8 Hz, 1H), 7.10-7.03 (m, 2H), 6.30 (s, 1H), 1.84 (s, 6H). LCMS LCQ (method 3) Rt=7.69 min; m/z (ESI$^+$) 318.84 [M+H]$^+$.

Step 2: 4-chloro-N-[1-(2,3-difluorophenyl)-1-methyl-ethyl]-6-(1-tetrahydropyran-2-ylindazol-6-yl)-1,3,5-triazin-2-amine To a solution of 4,6-dichloro-N-[1-(2,3-difluorophenyl)-1-methyl-ethyl]-1,3,5-triazin-2-amine (240 mg, 0.75 mmol) THF (6 mL) and water (1.2 mL) was added 1-tetrahydropyran-2-yl-6-(4,4,5,5-tetramethyl-1,3,2-dioxaborolan-2-yl) indazole (Intermediate V) (272 mg, 0.83 mmol) and potassium phosphate tribasic (400 mg, 1.88 mmol). The reaction mixture was degassed by bubbling $N_2$ gas for 3 min before adding bis[2-(di-tert-butylphosphanyl)cyclopenta-2,4-dien-1-yl]iron; dichloropalladium (24.5 mg, 0.04 mmol) and heating at 60° C. for 1 h. The reaction mixture was dry loaded directly on onto silica and purified by flash column chromatography eluting with 1% methanol in DCM to afford the title compound as a white solid (148 mg, 0.29 mmol, 39% yield). $^1$H NMR (600 MHz, Chloroform-d) δ 8.42 (s, 1H), 8.03 (s, 1H), 7.79 (d, J=8.6 Hz, 1H), 7.65 (d, J=8.5 Hz, 1H), 7.28 (s, 1H), 7.06 (s, 1H), 6.15 (s, 1H), 5.78 (d, J=9.4 Hz, 1H), 4.03 (d, J=11.5 Hz, 1H), 3.81 (d, J=10.6 Hz, 1H), 2.58 (d, J=12.7 Hz, 1H), 2.22-2.14 (m, 1H), 2.06 (d, J=13.4 Hz, 1H), 1.92 (d, J=14.9 Hz, 6H), 1.79 (d, J=11.5 Hz, 1H), 1.21 (s, 1H), 0.89 (dt, J=18.1, 8.7 Hz, 1H). LCMS MDAP Rt=25.25 min (Method 4); m/z (ESI$^+$) 485.05 [M+H]$^+$.

Step 3: N2-[1-(2,3-difluorophenyl)-1-methyl-ethyl]-6-(1H-indazol-6-yl)-N 4-methyl-1,3,5-triazine-2,4-diamine 4-chloro-N-[1-(2,3-difluorophenyl)-1-methyl-ethyl]-6-(1-tetrahydropyran-2-ylindazol-6-yl)-1,3,5-triazin-2-amine (53 mg, 0.11 mmol) and methylamine (0.55 mL, 1.09 mmol) in tetrahydrofuran (0.5 mL) were stirred at RT for 16 h. The reaction mixture was concentrated to dryness under reduced pressure and the residue triturated with petroleum ether. The pale yellow solid was treated with 4 N HCl in 1,4-dioxane (0.5 mL) and stirred at 60° C. for 30 min. The resulting precipitate was filtered and washed with petroleum ether (3 mL). The solid obtained as the HCl salt of the desired product was treated with 5 mL 35% aqueous ammonia and filtered, washing with water. The crude solid was purified by flash column chromatography eluting with a gradient of 40-50% ethyl acetate in petroleum ether to afford the title compound as a white solid (16 mg, 0.04 mmol, 35% yield). 1H NMR (399 MHz, DMSO-d6, Vt 90° C.) δ 8.31 (s, 1H), 8.01 (s, 1H), 7.86 (d, J=8.6 Hz, 1H), 7.68 (d, J=8.5 Hz, 1H), 7.35-7.20 (m, 1H), 7.19-7.06 (m, 2H), 7.03 (s, 1H), 6.58 (s, 1H), 2.70 (s, 3H), 1.82 (s, 6H). LCMS MDAP Rt=2.95 min (Method 6); m/z (ESI$^+$) 396.05 [M+H]$^+$.

Example 72

6-imidazo[1,5-a]pyridin-6-yl-N2-[1-methyl-1-(2-pyridyl)ethyl]-1,3,5-triazine-2,4-diamine

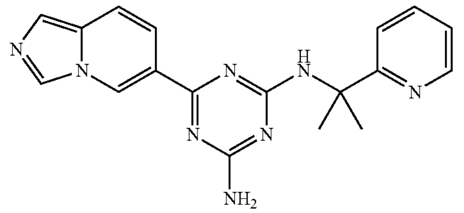

N,N-diisopropylethylamine (0.055 mL, 0.316 mmol) was added to a stirred solution of 2-(pyridin-2-yl)propan-2-amine (36 mg, 0.264 mmol) and 4-chloro-6-{imidazo[1,5-a]pyridin-6-yl}-1,3,5-triazin-2-amine (Intermediate C) (26 mg, 0.11 mmol) in 1-methylpyrrolidin-2-one (0.3 mL). The reaction mixture was heated at 90° C. for 24 h. The reaction mixture was diluted with DMSO:water (9:1) (2.0 mL) and purified by preparative HPLC. Pure fractions were collected, combined, and evaporated to dryness to afford the title compound as an off white solid (19 mg, 0.055 mmol, 53% yield). $^1$H NMR (400 MHz, DMSO-d6) δ 9.30-8.39 (m, 3H), 7.99-6.99 (m, 7H), 6.73 (s, 2H), 1.73 (s, 6H). UPLC-MS Rt=1.30 min, 98% (4 min Basic); m/z (ESI$^+$) 347.2 [M+H]$^+$.

Example 73

N2-[(2-chloro-3-fluoro-phenyl)methyl]-6-imidazo[1,5-a]pyridin-6-yl-1,3,5-triazine-2,4-diamine

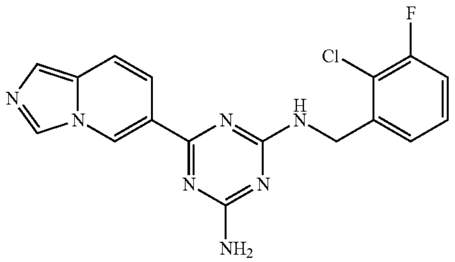 [SMILES: Nc1nc(NCc2cccc(F)c2Cl)nc(-c2ccc3cncn3c2)n1]

The title compound was synthesised using the same protocol as described in Example 72 except 2-(pyridin-2-yl)propan-2-amine was replaced with 1-(2-chloro-3-fluoro-phenyl)methanamine to afford the desired compound as a white solid (17 mg 0.045 mmol, 43%). 1H NMR (400 MHz, DMSO-d6) δ 9.16 (s, 1H), 8.61-8.48 (m, 1H), 8.02-7.74 (m, 1H), 7.71-7.16 (m, 6H), 7.09-6.81 (m, 2H), 5.13-4.37 (m, 2H). UPLC-MS Rt=1.58 min, 98% (4 min Basic); m/z (ESI$^+$) 370.1 $[M+H]^+$.

Example 74

N2-[[1-(difluoromethyl)pyrazol-3-yl]methyl]-6-imidazo[1,5-a]pyridin-6-yl-1,3,5-triazine-2,4-diaminediamine

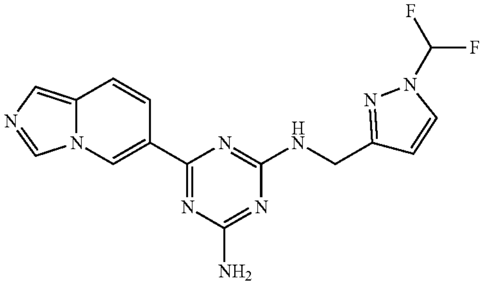 [SMILES: Nc1nc(NCc2ccn(C(F)F)n2)nc(-c2ccc3cncn3c2)n1]

The title compound was synthesised using the same protocol as described in Example 72 except 2-(pyridin-2-yl)propan-2-amine was replaced with 1-[1-(difluoromethyl)-1H-pyrazol-3-yl]methanamine) to afford the desired compound as an off-white solid (24 mg, 0.066 mmol, 63% yield). $^1$H NMR (400 MHz, DMSO-d6) δ 9.38-8.88 (m, 1H), 8.77-8.43 (m, 1H), 8.13 (s, 1H), 7.99-7.41 (m, 4H), 7.39 (s, 1H), 7.10-6.74 (m, 2H), 6.56-6.24 (m, 1H), 4.76-4.15 (m, 2H). UPLC-MS Rt=1.20 min, 99% (4 min Basic); m/z (ESI$^+$) 358.1 $[M+H]^+$.

Example 75

6-imidazo[1,5-a]pyridin-6-yl-N2-[(1-propylpyrazol-3-yl)methyl]-1,3,5-triazine-2,4-diamine

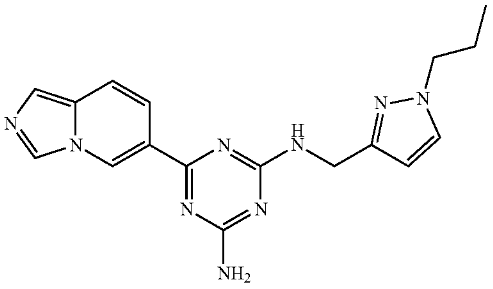 [SMILES: CCCn1ccc(CNc2nc(N)nc(-c3ccc4cncn4c3)n2)n1]

The title compound was synthesised using the same protocol as described in Example 72 except 2-(pyridin-2-yl)propan-2-amine was replaced with 1-(1-propyl-1H-pyrazol-3-yl)methanamine to afford the desired compound as a yellow solid (24 mg, 0.068 mmol, 64% yield). $^1$H NMR (400 MHz, DMSO-d6) δ 9.23 (s, 0.5H), 9.13 s (0.5H), 8.58 (s, 1H), 7.68-7.44 (m, 4H), 7.39 (s, 1H), 7.10-6.67 (m, 2H), 6.16 (s, 1H), 4.52 (dd, J=42.1, 5.6 Hz, 2H), 4.00 (t, J=7.0 Hz, 2H), 1.76 (h, J=7.3 Hz, 2H), 0.83 (t, J=6.4 Hz, 3H). UPLC-MS Rt=1.28 min, 100% (4 min Basic); m/z (ESI$^+$) 350.1 $[M+H]^+$.

Example 76

6-imidazo[1,5-a]pyridin-6-yl-N2-[[1-(2,2,2-trifluoroethyl)pyrazol-3-yl]methyl]-1,3,5-triazine-2,4-diamine

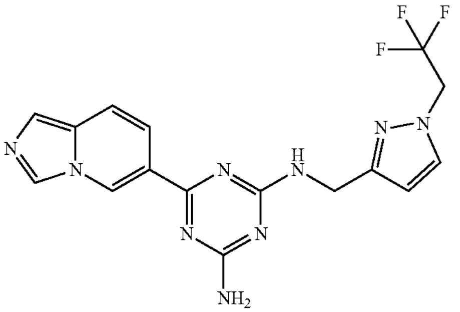 [SMILES: Nc1nc(NCc2ccn(CC(F)(F)F)n2)nc(-c2ccc3cncn3c2)n1]

The title compound was synthesised using the same protocol as described in Example 72 except 2-(pyridin-2-yl)propan-2-amine was replaced with 1-[1-(2,2,2-trifluoroethyl)-1H-pyrazol-3-yl]methanamine) to afford the desired compound as yellow solid (19 mg, 0.050 mmol, 47% yield). $^1$H NMR (400 MHz, DMSO-d6) δ 9.37-8.99 (m, 1H), 8.58 (s, 1H), 7.89-7.47 (m, 4H), 7.39 (s, 1H), 7.12-6.70 (m, 2H), 6.31 (s, 1H), 5.07 (q, J=9.2 Hz, 2H), 4.69-4.31 (m, 2H). UPLC-MS Rt=1.26 min, 100% (4 min Basic); m/z (ESI$^+$) 390.1 $[M+H]^+$.

Example 77

6-imidazo[1,5-a]pyridin-6-yl-N2-[(1-isopropylpyrazol-3-yl)methyl]-1,3,5-triazine-2,4-diamine

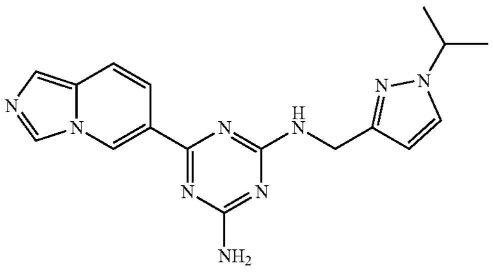 [SMILES: CC(C)n1ccc(CNc2nc(N)nc(-c3ccc4cncn4c3)n2)n1]

The title compound was synthesised using the same protocol as described in Example 72 except 2-(pyridin-2-yl)propan-2-amine was replaced with 1-[1-(propan-2-yl)-1H-pyrazol-3-yl]methanamine to afford the desired compound as a yellow solid (25 mg, 0.070 mmol, 65% yield). $^1H$ NMR (400 MHz, DMSO-d6) δ 9.36-8.97 (m, 1H), 8.58 (s, 1H), 7.73-7.44 (m, 4H), 7.39 (s, 1H), 7.03-6.68 (m, 2H), 6.16 (s, 1H), 4.68-4.30 (m, 3H), 1.40 (d, J=6.7 Hz, 6H). UPLC-MS Rt=1.27 min, 100% (4 min Basic); m/z (ESI$^+$) 350.1 [M+H]$^+$.

Example 78

6-imidazo[1,5-a]pyridin-6-yl-N2-(2-pyrazol-1-ylethyl)-1,3,5-triazine-2,4-diamine

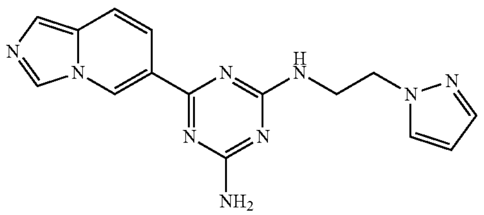 [SMILES: Nc1nc(NCCn2cccn2)nc(-c2ccc3cncn3c2)n1]

The title compound was synthesised using the same protocol as described in Example 72 except 2-(pyridin-2-yl)propan-2-amine was replaced with 2-(1H-pyrazol-1-yl)ethan-1-amine to afford the desired compound as a white solid (37 mg, 70.2% yield). $^1H$ NMR (400 MHz, DMSO-d6) δ 9.41-8.98 (m, 1H), 8.58 (s, 1H), 7.83-7.65 (m, 1H), 7.65-7.52 (m, 2H), 7.52-7.10 (m, 3H), 7.07-6.62 (m, 2H), 6.41-6.00 (m, 1H), 4.53-4.24 (m, 2H), 3.87-3.57 (m, 2H). UPLC-MS Rt=1.07 min, 98% (4 min Basic); m/z (ESI$^+$) 322.1 [M+H]$^+$.

Example 79

N2-[(2,3-difluorophenyl)methyl]-6-(1H-indazol-6-yl)-N4-methyl-1,3,5-triazine-2,4-diamine

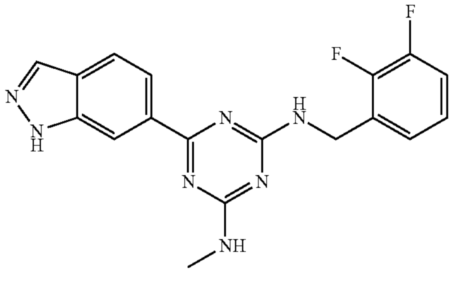

Step 1: 4,6-dichloro-N-[(2,3-difluorophenyl)methyl]-1,3,5-triazin-2-amine

To stirred solution cyanuric chloride (2.0 g, 10.85 mmol) in ethylene glycol dimethyl ether (40 mL) at −30° C. was added 2,3-difluorobenzylamine (1.27 mL, 10.85 mmol) dropwise. The reaction mixture was then stirred at −30° C. for 3 h and then at RT for 30 min before adding 1 N HCl (5 mL). The reaction mixture was partitioned between ethyl acetate (20 mL) and water (10 mL). The organic phase was dried ($MgSO_4$) and evaporated to dryness under reduced pressure. The crude material was purified by flash column chromatography eluting with a gradient of 5-10% ethyl acetate in petroleum ether to afford the title compound as light yellow solid (1.56 g, 5.09 mmol, 47% yield). $^1H$ NMR (600 MHz, DMSO-d6) 9.60 (t, J=6.1 Hz, 1H), 7.52-7.27 (m, 1H), 7.28-7.06 (m, 2H), 4.57 (d, J=6.0 Hz, 4H). LCMS MDAP Rt=3.04 min (Method 6); m/z (ESI$^+$) 292.85 [M+H]$^+$.

Step 2: 4-chloro-N-[(2,3-difluorophenyl)methyl]-6-(1-tetrahydropyran-2-ylindazol-6-yl)-1,3,5-triazin-2-amine The title compound was synthesised using the same protocol as described in Example 71 step 2 except 4,6-dichloro-N-[1-(2,3-difluorophenyl)-1-methyl-ethyl]-1,3,5-triazin-2-amine was replaced with 4,6-dichloro-N-[(2,3-difluorophenyl)methyl]-1,3,5-triazin-2-amine to afford the desired compound as a white solid (220 mg, 0.46 mmol, 37% yield). $^1H$ NMR (600 MHz, Chloroform-d) δ 8.70 (s, 0.5H), 8.64 (s, 0.5H), 8.25-8.21 (m, 0.5H), 8.19-8.16 (m, 0.5H), 8.07 (d, J=6.4 Hz, 1H), 7.77 (dd, J=10.8, 8.5 Hz, 1H), 7.22-7.16 (m, 1H), 7.16-7.00 (m, 2H), 6.33-6.27 (m, 0.5H), 6.10-6.06 (m, 0.5H), 5.88-5.83 (m, 1H), 4.93-4.85 (m, 1H), 4.80 (d, J=6.2 Hz, 1H), 4.08-4.02 (m, 1H), 3.86-3.78 (m, 1H), 2.66-2.57 (m, 1H), 2.21-2.14 (m, 1H), 2.12-2.04 (m, 1H), 1.88-1.72 (m, 2H), 1.70-1.64 (m, 1H). LCMS MDAP Rt=3.48 min (Method 6); m/z (ESI$^+$) 457.0 [M+H]$^+$.

Step 3: N2-[(2,3-difluorophenyl)methyl]-6-(1H-indazol-6-yl)-N 4-methyl-1,3,5-triazine-2,4-diamine The title compound was synthesised using the same protocol as described in Example 71 step 3 except 4-chloro-N-[1-(2,3-difluorophenyl)-1-methyl-ethyl]-6-(1-tetrahydropyran-2-ylindazol-6-yl)-1,3,5-triazin-2-amine was replaced with 4-chloro-N-[(2,3-difluorophenyl)methyl]-6-(1-tetrahydropyran-2-ylindazol-6-yl)-1,3,5-triazin-2-amine to afford the desired compound (19 mg, 0.05 mmol, 45% yield). $^{1}H$ NMR (399 MHz, DMSO-d6, Vt 120° C.) δ 8.49 (s, 1H), 8.26-7.94 (m, 2H), 7.73 (d, J=8.5 Hz, 1H), 7.35 (s, 1H), 7.30-7.08 (m, 3H), 6.76 (s, 1H), 4.68 (d, J=5.5 Hz, 2H). LCMS MDAP Rt=16.93 min (Method 4); m/z ($ESI^+$) 367.95 $[M+H]^+$.

Example 80

4-[(2,3-difluorophenyl)methoxy]-6-(1H-indazol-6-yl)-1,3,5-triazin-2-amine

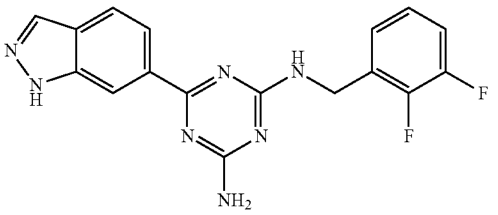

A solution of 4-chloro-6-(1H-indazol-6-yl)-1,3,5-triazin-2-amine (Intermediate Z) (23 mg, 0.09 mmol) in dry THF (2 mL) at 0° C. was treated with 2,3-difluorobenzyl alcohol (0.01 mL, 0.09 mmol) followed by potassium tert-butoxide (41 mg, 0.37 mmol). The yellow suspension was stirred at 0° C. for 1 h, then allowed to warm to RT and stirred for 16 h. The reaction mixture was quenched with water (10 mL) and the product extracted with ethyl acetate (2×20 mL). The combined organic extracts were washed with brine (20 mL), dried ($MgSO_4$), filtered and concentrated under reduced pressure to give a brown oil. The crude material was purified by reverse phase preparative MDAP LCMS eluting with 30-95% Acetonitrile in water with formic acid (0.1%) modifier gradient over 32 min. The relevant fractions were combined and concentrated to dryness under reduced pressure. The material was redissolved in EtOAc (15 mL) and washed with saturated aq. $NaHCO_3$ (10 mL), water (10 mL), brine (10 mL), dried over $MgSO_4$, filtered under reduced pressure and concentrated to dryness under reduced pressure to afford the title compound as an off-white solid (4.6 mg, 0.01 mmol, 13% yield). $^{1}H$ NMR (600 MHz, DMSO-d6) δ 13.35 (s, 1H), 8.51 (s, 1H), 8.13 (s, 1H), 8.06 (d, 1H), 7.83 (d, J=8.5 Hz, 1H), 7.65 (s, 1H), 7.57 (s, 1H), 7.46-7.38 (m, 1H), 7.27-7.19 (m, 2H), 5.52 (s, 1H), 5.44 (s, 1H). LCMS MDAP Rt=19.14 min (Method 4); m/z ($ESI^+$) 354.85 $[M+H]^+$.

Example 81

N2-[1-[1-(Difluoromethyl)pyrazol-3-yl]cyclobutyl]-6-(1H-indazol-6-yl)-1,3,5-triazine-2,4-diamine

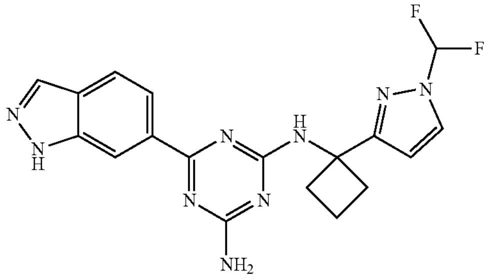 [SMILES: Nc1nc(NC2(c3ccn(C(F)F)n3)CCC2)nc(-c2ccc3cn[nH]c3c2)n1]

Synthesised by General Method B:

Step 1: 6-Chloro-N4-[1-[1-(difluoromethyl)pyrazol-3-yl]cyclobutyl]-1,3,5-triazine-2,4-diamine N,N-Diisopropylethylamine (0.42 mL, 2.39 mmol) was added to a suspension of [1-[1-(difluoromethyl)pyrazol-3-yl]cyclobutyl]ammonium chloride (Intermediate AA) (214 mg, 0.96 mmol) and 2-Amino-4,6-dichlorotriazine (237 mg, 1.44 mmol) in 1,4-dioxane (5 mL) which was stirred at RT for 72 h. The reaction mixture was partitioned between EtOAc and water, the organic phase separated, washed with brine, dried (MgSO4) and concentrated to dryness under reduced pressure. The residue was purified by flash chromatography (silica gel, eluting with a gradient of 0-100% EtOAc in Petroleum ether) to give a colourless oil that solidified upon standing to a pale yellow solid (90 mg, 0.26 mmol, 27% yield). The product was used in the next step without characterisation.

Step 2: N4-[1-[1-(Difluoromethyl)pyrazol-3-yl]cyclobutyl]-6-(1-tetrahydropyran-2-ylindazol-6-yl)-1,3,5-triazine-2,4-diamine 6-Chloro-N4-[1-[1-(difluoromethyl)pyrazol-3-yl]cyclobutyl]-1,3,5-triazine-2,4-diamine (45 mg, 0.14 mmol), 1-tetrahydropyran-2-yl-6-(4,4,5,5-tetramethyl-1,3,2-dioxaborolan-2-yl)indazole (Intermediate V) (70 mg, 0.21 mmol) and potassium phosphate tribasic (60 mg, 0.29 mmol) were dissolved in tetrahydrofuran (1 mL) and water (0.25 mL). Bis[2-(di-tert-butylphosphanyl)cyclopenta-2,4-dien-1-yl]iron; dichloropalladium (1.86 mg, 0.003 mmol) was added and the reaction mixture stirred at 85° C. overnight. The reaction mixture was passed through a pad of celite and the filtrate partitioned between EtOAc and water, the organic phase was separated, dried (MgSO4) and concentrated to dryness under reduced pressure. The residue was purified by flash chromatography (silica gel, eluting with a gradient of 0-100% EtOAc in petroleum ether) to afford the title compound as a pale yellow oil (60 mg, 0.12 mmol, 83% yield). The product was used in the next step without characterisation.

Step 3: N2-[1-[1-(Difluoromethyl)pyrazol-3-yl]cyclobutyl]-6-(1H-indazol-6-yl)-1,3,5-triazine-2,4-diamine A solution of N2-[1-[1-(difluoromethyl)pyrazol-3-yl]cyclobutyl]-6-(1-tetrahydropyran-2-ylindazol-6-yl)-1,3,5-triazine-2,4-diamine (60 mg, 0.12 mmol) and 4 M HCl in 1,4-dioxane (1.25 mL, 4.98 mmol) in MeOH (0.25 mL) was stirred at RT for 16 h. The reaction mixture was concentrated under reduced pressure. The residue was triturated with EtOAc and petroleum ether to provide the desired product as a pale yellow solid that was collected by filtration (43 mg, 0.090 mmol, 74% yield). $^1$H NMR (399 MHz, DMSO-$d_6$, Vt 90° C.) δ 8.42 (s, 1H), 8.09 (s, 1H), 8.00-7.86 (m, 2H), 7.82-7.50 (m, 3H), 6.49 (s, 1H), 2.74-2.59 (m, 4H), 2.05-1.93 (m, 2H). LCMS MDAP Rt=15.92 min; >85% (Method 4); m/z (ESI$^+$) 398.05 $[M+H]^+$.

Example 82

N4-[1-[1-(Difluoromethyl)pyrazol-3-yl]cyclobutyl]-6-(1-methylindazol-6-yl)-1,3,5-triazine-2,4-diamine

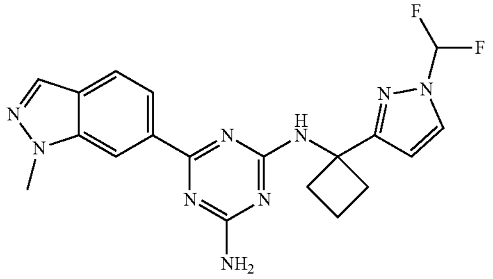 [SMILES: Cn1ncc2ccc(-c3nc(N)nc(NC4(c5ccn(C(F)F)n5)CCC4)n3)cc21]

Synthesised by General Method D:

6-Chloro-N4-[1-[1-(difluoromethyl)pyrazol-3-yl]cyclobutyl]-1,3,5-triazine-2,4-diamine (Example 81, step 1) (45 mg, 0.14 mmol), 1-Methyl-1H-indazole-6-boronic acid (38 mg, 0.21 mmol) and potassium phosphate tribasic (60 mg, 0.29 mmol) were dissolved in tetrahydrofuran (1 mL) and water (0.25 mL). Bis[2-(di-tert-butylphosphanyl)cyclopenta-2,4-dien-1-yl]iron; dichloropalladium (1.86 mg, 0.003 mmol) was added and the reaction mixture stirred at 85° C. overnight. The reaction mixture was passed through a pad of celite and the filtrate partitioned between EtOAc and water. The organic phase was separated, dried (MgSO4) and concentrated to dryness under reduced pressure. The residue was purified by flash chromatography (silica gel, eluting with a gradient of 0-100% EtOAc in petroleum ether) to afford the title compound as a pale yellow oil that solidified upon standing to a pale yellow solid (42 mg, 0.10 mmol, 68% yield). 1H NMR (399 MHz, DMSO-d6, Vt 90° C.) δ 8.38 (s, 1H), 8.05-7.91 (m, 3H), 7.83-7.50 (m, 3H), 6.49-6.38 (m, 3H), 4.07 (s, 3H), 2.72-2.58 (m, 4H), 1.99 (s, 2H). LCMS MDAP Rt=17.24 min; >95% (Method 4); m/z (ESI$^+$) 412.15 $[M+H]^+$.

Example 83

6-(1H-Indazol-6-yl)-N2-[1-methyl-1-[1-(2-pyrrolidin-1-ylethyl)pyrazol-3-yl]ethyl]-1,3,5-triazine-2,4-diamine hydrochloride

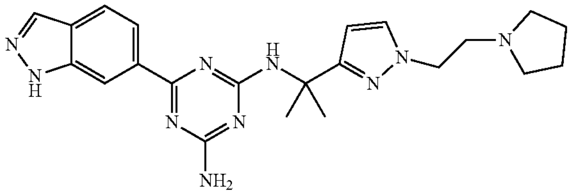 [SMILES: CC(C)(Nc1nc(N)nc(-c2ccc3cn[nH]c3c2)n1)c1ccn(CCN2CCCC2)n1]

Step 1: 2-[3-[1-[[4-Amino-6-(1-tetrahydropyran-2-ylindazol-6-yl)-1,3,5-triazin-2-yl]amino]-1-methyl-ethyl]pyrazol-1-yl]ethanol A solution of 4-chloro-6-(1-tetrahydropyran-2-ylindazol-6-yl)-1,3,5-triazin-2-amine (Intermediate X) (125 mg, 0.38 mmol), N,N-diisopropylethylamine (0.2 mL, 1.13 mmol) and 2-[3-(1-amino-1-methyl-ethyl)pyrazol-1-yl]ethanol (Intermediate BG) (128 mg, 0.76 mmol) in 1,4-dioxane (23 mL) was conventionally heated for 5 days at 90° C. in a sealed microwave vial. The reaction mixture was concentrated under reduced pressure. The crude material was purified by flash chromatography (silica gel, eluting with a gradient of 0-10% MeOH in DCM) to give the title compound as a white solid (83 mg, 0.17 mmol, 45% yield). LCMS LCQ Rt=4.67 min (Method 3); m/z (ESI$^+$) 464.04 $[M+H]^+$.

Step 2: N4-[1-[1-(2-Chloroethyl)pyrazol-3-yl]-1-methyl-ethyl]-6-(1-tetrahydropyran-2-ylindazol-6-yl)-1,3,5-triazine-2,4-diamine To a solution 2-[3-[1-[[4-amino-6-(1-tetrahydropyran-2-ylindazol-6-yl)-1,3,5-triazin-2-yl]amino]-1-methyl-ethyl]pyrazol-1-yl]ethanol (80 mg, 0.17 mmol) in tetrahydrofuran (6 mL) and dichloromethane (6 mL) was added thionyl chloride (0.13 mL, 1.73 mmol) at RT. The reaction mixture was refluxed for 15 hours and then concentrated under reduced pressure. The crude material was purified by flash chromatography (silica gel, eluting with a gradient of 0-10% methanol in DCM) to afford the title compound as an off-white solid (32 mg, 0.060 mmol, 35% yield). LCMS LCQ Rt=5.83 min (Method 3); m/z (ESI$^+$) 482.16/484.15 $[M+H]^+$.

Step 3: N4-[1-Methyl-1-[1-(2-pyrrolidin-1-ylethyl)pyrazol-3-yl]ethyl]-6-(1-tetrahydropyran-2-ylindazol-6-yl)-1,3,5-triazine-2,4-diamine A mixture of N4-[1-[1-(2-chloroethyl)pyrazol-3-yl]-1-methyl-ethyl]-6-(1-tetrahydropyran-2-ylindazol-6-yl)-1,3,5-triazine-2,4-diamine (30 mg, 0.060 mmol), pyrrolidine (0.13 mL, 1.56 mmol) and $K_2CO_3$ (21.5 mg, 0.16 mmol) in N,N-dimethylformamide (2.1 mL) was heated at 85° C. in a sealed vial for 2 h. The reaction mixture was concentrated to dryness under reduced pressure. The crude material was purified by flash chromatography (silica gel, eluting with a gradient of 0-30% methanol in DCM) to give the title compound as an off-white solid (28 mg, 0.05 mmol, 78% yield). LCMS LCQ Rt=0.88 min (Method 3); m/z ($ESI^+$) 517.19 $[M+H]^+$.

Step 4: 6-(1H-indazol-6-yl)-N2-[1-methyl-1-[1-(2-pyrrolidin-1-ylethyl)pyrazol-3-yl]ethyl]-1,3,5-triazine-2,4-diamine hydrochloride To a solution of N2-[1-methyl-1-[1-(2-pyrrolidin-1-ylethyl)pyrazol-3-yl]ethyl]-6-(1-tetrahydropyran-2-ylindazol-6-yl)-1,3,5-triazine-2,4-diamine (26 mg, 0.05 mmol) in 1,4-dioxane (2.5 mL) and methanol (2.5 mL) was added 4 M HCl in 1,4-dioxane (0.19 mL, 0.75 mmol) at RT. The reaction mixture was heated for 10 h at 60° C. in sealed vial then concentrated to dryness under reduced pressure. The crude material was purified by flash chromatography (silica gel, eluting with a gradient of 0-20% methanol in DCM) to give the title compound as a white solid (16 mg, 0.030 mmol, 64% yield). 1H NMR (399 MHz, DMSO-d6, Vt 90° C.) δ 12.75 (s, 1H), 8.03 (s, 1H), 7.65 (s, 1H), 7.57 (d, J=8.5 Hz, 1H), 7.35 (d, J=8.5 Hz, 1H), 7.24 (s, 1H), 6.32 (s, 1H), 6.00 (s, 2H), 5.84 (s, 1H), 4.05 (s, 2H), 2.97 (s, 2H), 1.39 (s, 6H), 1.34 (s, 4H). LCMS LCQ Rt=0.78 min; >95% (Method 3); m/z ($ESI^+$) 433.04 $[M+H]^+$.

Example 84

N4-[1-[4-chloro-1-(difluoromethyl)pyrazol-3-yl]cyclopropyl]-6-(1H-indazol-6-yl)-1,3,5-triazine-2,4-diamine

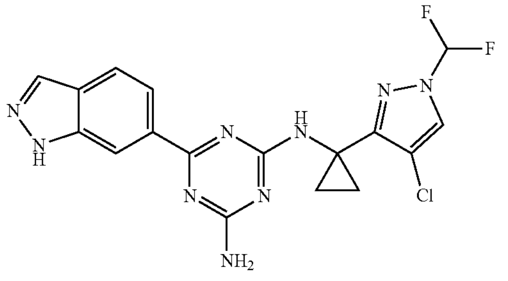 [SMILES: Nc1nc(NC2(c3nn(C(F)F)cc3Cl)CC2)nc(-c2ccc3cn[nH]c3c2)n1]

Synthesised by General Method B:

Step 1: 6-Chloro-N4-[1-[4-chloro-1-(difluoromethyl)pyrazol-3-yl]cyclopropyl]-1,3,5-triazine-2,4-diamine N,N-Diisopropylethylamine (0.13 mL, 0.74 mmol) was added to a solution of 1-[4-chloro-1-(difluoromethyl)pyrazol-3-yl]cyclopropanamine hydrochloride (Intermediate AB) (60 mg, 0.25 mmol) and 2-amino-4,6-dichlorotriazine (81 mg, 0.49 mmol) in 1,4-dioxane (2.5 mL), and the reaction mixture stirred at RT for 16 h. The reaction mixture was partitioned between water and EtOAc, the organic phase separated, dried (MgSO4) and concentrated to dryness under reduced pressure. The residue was purified by flash chromatography (silica gel, eluting with a gradient of 0-60% EtOAc in petroleum ether) to provide the title compound as a white solid (65 mg, 0.18 mmol, 75% yield). 1H NMR (600 MHz, Chloroform-d) δ 7.71 (s, 1H), 7.01 (t, J=60.4 Hz, 1H), 6.06 (s, 1H), 5.33 (s, 2H), 1.53-1.47 (m, 2H), 1.27-1.24 (m, 2H). LCMS MDAP Rt=18.41 min (Method 4); m/z ($ESI^+$) 335.90/337.85 $[M+H]^+$.

Step 2: N4-[1-[4-Chloro-1-(difluoromethyl)pyrazol-3-yl]cyclopropyl]-6-(1-tetrahydropyran-2-ylindazol-6-yl)-1,3,5-triazine-2,4-diamine Bis[2-(di-tert-butylphosphanyl)cyclopenta-2,4-dien-1-yl] iron; dichloropalladium (6.3 mg, 0.010 mmol) was added to a suspension of 1-tetrahydropyran-2-yl-6-(4,4,5,5-tetramethyl-1,3,2-dioxaborolan-2-yl)indazole (Intermediate V) (95.2 mg, 0.29 mmol), 6-chloro-N4-[1-[4-chloro-1-(difluoromethyl)pyrazol-3-yl]cyclopropyl]-1,3,5-triazine-2,4-diamine (65 mg, 0.19 mmol) and potassium phosphate tribasic (82 mg, 0.39 mmol) in tetrahydrofuran (2 mL) and water (0.50 mL). The reaction mixture was degassed under vacuum, purged with nitrogen and heated at 80° C. for 16 h. The reaction mixture was cooled to room temperature, partitioned between EtOAc and water, the organic layer separated, dried (MgSO4) and concentrated to dryness under reduced pressure. The residue was purified by flash silica (silica gel, eluting with a gradient of 0-60% EtOAc in petroleum ether) to give the title compound as a colourless oil (94 mg, 0.18 mmol, 92% yield. 1H NMR (600 MHz, Chloroform-d) δ 8.63 (d, J=105.5 Hz, 1H), 8.13 (s, 1H), 8.04 (s, 1H), 7.78-7.64 (m, 1H), 7.04 (t, J=60.6 Hz, 1H), 6.13-5.86 (m, 1H), 5.86-5.79 (m, 1H), 5.32-4.98 (m, 2H), 4.08-4.00 (m, 1H), 3.82-3.77 (m, 1H), 2.65-2.57 (m, 1H), 2.21-2.14 (m, 1H), 2.13-2.03 (m, 1H), 1.86-1.73 (m, 2H), 1.60-1.52 (m, 4H), 1.37-1.30 (m, 2H). LCMS MDAP Rt=20.64 min (Method 4); m/z ($ESI^+$) 502.15 $[M+H]^+$.

Step 3: N4-[1-[4-Chloro-1-(difluoromethyl)pyrazol-3-yl]cyclopropyl]-6-(1H-indazol-6-yl)-1,3,5-triazine-2,4-diamine A solution of N4-[1-[4-chloro-1-(difluoromethyl)pyrazol-3-yl]cyclopropyl]-6-(1-tetrahydropyran-2-ylindazol-6-yl)-1,3,5-triazine-2,4-diamine (94 mg, 0.19 mmol) and 4M HCl in 1,4-dioxane (2.0 mL, 8.0 mmol) in methanol (0.50 mL) was stirred at RT for 72 h. The reaction mixture was partitioned between EtOAc and sat. $NaHCO_3$ (aq), the organic phase separated, dried (MgSO4) and concentrated under reduced pressure. The residue was triturated with EtOAc:petroleum ether (1:9) to afford the title compound as a white solid that was collected by filtration (39 mg, 0.090 mmol, 47% yield). 1H NMR (399 MHz, DMSO-d6, Vt 90° C.) δ 13.02 (s, 1H), 8.49 (s, 1H), 8.25 (s, 1H), 8.07 (s, 1H), 8.01 (d, J=8.6 Hz, 1H), 7.77-7.46 (m, 3H), 6.46 (s, 2H), 1.51-1.45 (m, 2H), 1.33-1.27 (m, 2H). LCMS MDAP Rt=16.76 min; >95% (Method 4); m/z ($ESI^+$) 418.05 $[M+H]^+$.

Example 85

N2-[(2-Fluoro-3-methoxy-phenyl)methyl]-6-(1H-indazol-6-yl)-1,3,5-triazine-2,4-diamine

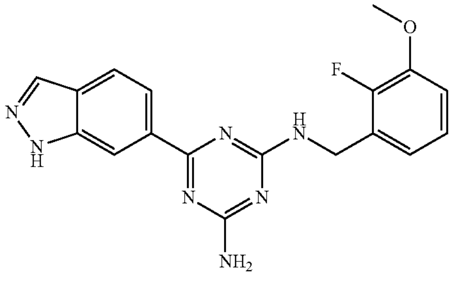 [SMILES: COc1cccc(CNc2nc(N)nc(-c3ccc4cn[nH]c4c3)n2)c1F]

Synthesised by General Method A:

Step 1: N4-[(2-Fluoro-3-methoxy-phenyl)methyl]-6-(1-tetrahydropyran-2-ylindazol-6-yl)-1,3,5-triazine-2,4-diamine A mixture of 4-chloro-6-(1-tetrahydropyran-2-ylindazol-6-yl)-1,3,5-triazin-2-amine (Intermediate X) (50 mg, 0.15 mmol), 2-Fluoro-3-methoxybenzylamine (39 mg, 0.25 mmol) and N,N-diisopropylethylamine (0.11 mL, 0.60 mmol) in 1,4-dioxane (7.5 mL) was heated at 80° C. for 18 h. The reaction mixture was concentrated under reduced pressure. The crude material was purified by flash chromatography (silica gel, eluting with a gradient of 0-60% EtOAc in petroleum ether) to give the title compound as clear glass (70 mg, 0.15 mmol, 98% yield). LCMS LCQ Rt=6.23 min (Method 3); m/z (ESI$^+$) 450.19 [M+H]$^+$.

Step 2: N2-[(2-Fluoro-3-methoxy-phenyl)methyl]-6-(1H-indazol-6-yl)-1,3,5-triazine-2,4-diamine To a solution of N2-[(2-fluoro-3-methoxy-phenyl)methyl]-6-(1-tetrahydropyran-2-ylindazol-6-yl)-1,3,5-triazine-2,4-diamine (6 mg, 0.15 mmol) in 1,4-dioxane (3.0 mL) was added 4 M HCl in 1,4-dioxane (0.57 mL, 2.27 mmol) at RT. The reaction mixture was conventionally heated at 60° C. in a sealed microwave vial for 11 h and then concentrated to dryness under reduced pressure. The crude material was purified by flash chromatography (silica gel, eluting with a gradient of 0-5% methanol in DCM) to afford the title compound as a white solid (33 mg, 0.090 mmol, 58% yield). 1H NMR (399 MHz, DMSO-d6, Vt 90° C.) δ 8.48 (s, 1H), 8.05 (s, 1H), 8.03 (s, 1H), 7.75 (d, J=8.6 Hz, 1H), 7.36 (s, 1H), 7.11-6.91 (m, 3H), 6.51 (s, 2H), 4.63 (d, J=6.1 Hz, 2H), 3.82 (s, 3H). LCMS MDAP Rt=15.83 min; >97% (Method 4); m/z (ESI$^+$) 366.05 [M+H]$^+$.

Example 86

N2-[1-(1H-Imidazol-4-yl)cyclopropyl]-6-(1H-indazol-6-yl)-1,3,5-triazine-2,4-diamine; 2,2,2-trifluoroacetate

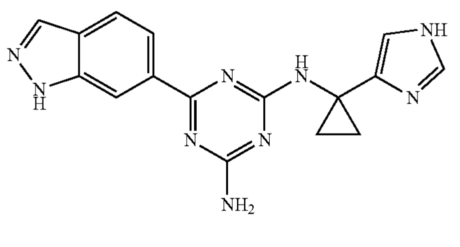 [SMILES: Nc1nc(NC2(c3c[nH]cn3)CC2)nc(-c2ccc3cn[nH]c3c2)n1]

Synthesised by General Method A:

Step 1: 6-(1-tetrahydropyran-2-ylindazol-6-yl)-N4-[1-[1-(2-trimethylsilylethoxymethyl)imidazol-4-yl]cyclopropyl]-1,3,5-triazine-2,4-diamine A mixture of 1-[1-(2-trimethylsilylethoxymethyl)imidazol-4-yl]cyclopropanamine (Intermediate AC) (115 mg, 0.45 mmol) and 4-chloro-6-(1-tetrahydropyran-2-ylindazol-6-yl)-1,3,5-triazin-2-amine (Intermediate X) (50 mg, 0.15 mmol) in 1,4-dioxane (5 mL) was heated at 90° C. for 72 h. The reaction mixture was concentrated under reduced pressure. The crude material was purified by flash chromatography (silica gel, eluting with a gradient of 0-20% methanol in EtOAc) to give the title compound as a light brown solid (85 mg, 0.15 mmol, 98% yield). LCMS LCQ Rt=5.31 min (Method 3); m/z (ESI$^+$) 548.29 [M+H]$^+$.

Step 2: N2-[1-(1H-Imidazol-4-yl)cyclopropyl]-6-(1H-indazol-6-yl)-1,3,5-triazine-2,4-diamine; 2,2,2-trifluoroacetate To a solution of 6-(1-tetrahydropyran-2-ylindazol-6-yl)-N2-[1-[1-(2-trimethylsilylethoxymethyl)imidazol-4-yl]cyclopropyl]-1,3,5-triazine-2,4-diamine (83 mg, 0.15 mmol) in DCM (5.0 mL) was added trifluoroacetic acid (0.58 mL, 7.58 mmol). The reaction mixture was stirred at RT for 20 h and then concentrated to dryness under reduced pressure. The crude material was purified by flash chromatography (silica gel, eluting with a gradient of 0-15% methanol in DCM) to give the title compound as an off-white solid (28 mg, 0.060 mmol, 39% yield). 1H NMR (399 MHz, DMSO-d6, Vt 90° C.) δ 13.03 (s, 1H), 8.47 (s, 1H), 8.03 (d, J=9.7 Hz, 2H), 7.73 (d, J=8.6 Hz, 1H), 7.46 (s, 1H), 7.36 (s, 1H), 6.73 (s, 1H), 6.46 (s, 2H), 1.24 (s, 2H), 1.15 (s, 2H). LCMS MDAP Rt=10.47 min; >95% (Method 4); m/z (ESI$^+$) 334.05 [M+H]$^+$.

Example 87

N2-[(2,3-difluoro-4-methoxy-phenyl)methyl]-6-(1H-indazol-6-yl)-1,3,5-triazine-2,4-diamine

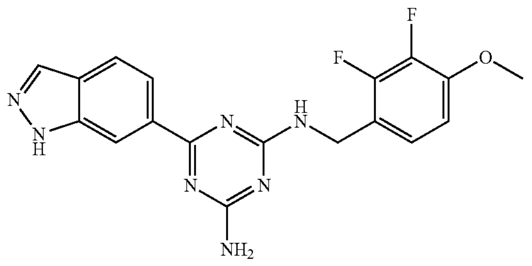 [SMILES: COc1ccc(CNc2nc(N)nc(-c3ccc4cn[nH]c4c3)n2)c(F)c1F]

Synthesised by General Method A:

Step 1: N4-[(2,3-difluoro-4-methoxy-phenyl)methyl]-6-(1-tetrahydropyran-2-ylindazol-6-yl)-1,3,5-triazine-2,4-diamine A mixture of 4-chloro-6-(1-tetrahydropyran-2-ylindazol-6-yl)-1,3,5-triazin-2-amine (Intermediate X) (50 mg, 0.15 mmol), 2,3-difluoro-4-methoxybenzylamine (43 mg, 0.25 mmol) and N,N-diisopropylethylamine (0.21 mL, 1.21 mmol) in 1,4-dioxane (7.5 mL) was heated at 80° C. for 24 h, and then at 90° C. for 96 days. The reaction mixture was concentrated to dryness under reduced pressure. The crude material was purified by flash chromatography (silica gel, eluting with a gradient of 0-80% EtOAc in petroleum ether) to give the title compound as a light brown solid (62 mg, 0.13 mmol, 83% yield).

Step 2: N2-[(2,3-difluoro-4-methoxy-phenyl)methyl]-6-(1H-indazol-6-yl)-1,3,5-triazine-2,4-diamine To a solution of N2-[(2,3-difluoro-4-methoxy-phenyl)methyl]-6-(1-tetrahydropyran-2-ylindazol-6-yl)-1,3,5-triazine-2,4-diamine (60 mg, 0.13 mmol) in 1,4-dioxane (2.5 mL) and methanol (2.5 mL) was added 4 M HCl in 1,4-dioxane (0.48 mL, 1.93 mmol) at RT. The reaction mixture was heated for 11 h at 60° C. and then concentrated to dryness under reduced pressure. The crude material was purified by flash chromatography (silica gel, eluting with a gradient of 0-10% methanol in DCM) to give the title compound as an off-white solid (33 mg, 0.080 mmol, 64% yield). $^1$H NMR (399 MHz, DMSO-$d_6$, Vt 90° C.) δ 8.48 (s, 1H), 8.11-7.97 (m, 2H), 7.75 (d, J=8.6 Hz, 1H), 7.39 (s, 1H), 7.17 (t, J=8.1 Hz, 1H), 6.93 (t, J=8.0 Hz, 1H), 6.52 (s, 2H), 4.59 (d, J=6.0 Hz, 2H), 3.83 (s, 3H). LCMS MDAP Rt=16.73 min; >95% (Method 4); m/z (ESI$^+$) 384.10 $[M+H]^+$.

Example 88

N2-[(2,3-Difluoro-4-methyl-phenyl)methyl]-6-(1H-indazol-6-yl)-1,3,5-triazine-2,4-diamine

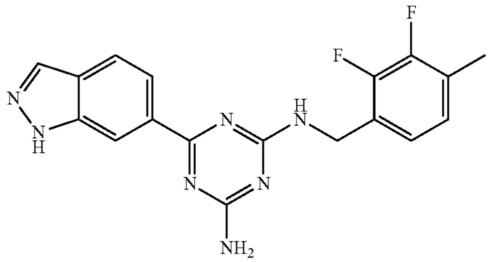 [SMILES: Cc1ccc(CNc2nc(N)nc(-c3ccc4cn[nH]c4c3)n2)c(F)c1F]

Synthesised by General Method A:

Step 1: N4-[(2,3-Difluoro-4-methyl-phenyl)methyl]-6-(1-tetrahydropyran-2-ylindazol-6-yl)-1,3,5-triazine-2,4-diamine A mixture of 4-chloro-6-(1-tetrahydropyran-2-ylindazol-6-yl)-1,3,5-triazin-2-amine (Intermediate X) (50 mg, 0.15 mmol), 2,3-Difluoro-4-methylbenzylamine (39 mg, 0.25 mmol) and N,N-diisopropylethylamine (0.21 mL, 1.21 mmol) in 1,4-dioxane (7.5 mL) was heated at 80° C. for 23 h. The reaction mixture was concentrated to dryness under reduced pressure. The crude material was purified by flash chromatography (eluting with a gradient of 0-50% EtOAc in petroleum ether) to give the title compound as a white gum (71 mg, 0.14 mmol, 94% yield). LCMS MDAP Rt=21.48 min (Method 4); m/z (ESI$^+$) 452.25 $[M+H]^+$.

Step 2: N2-[(2,3-Difluoro-4-methyl-phenyl)methyl]-6-(1H-indazol-6-yl)-1,3,5-triazine-2,4-diamine To a solution of N2-[(2,3-difluoro-4-methyl-phenyl) methyl]-6-(1-tetrahydropyran-2-ylindazol-6-yl)-1,3,5-triazine-2,4-diamine (67 mg, 0.15 mmol) in 1,4-dioxane (2.9 mL) and methanol (2.9 mL) was added 4 M HCl in 1,4-dioxane (0.56 mL, 2.23 mmol) at RT. The reaction mixture was heated in a vial for 11 h at 60° C. and then concentrated to dryness under reduced pressure. The crude material was purified by flash chromatography (silica gel, eluting with a gradient of 0-10% methanol in DCM) to give the title compound as a white solid (34 mg, 0.090 mmol, 59% yield). 1H NMR (399 MHz, DMSO-d6, Vt 90° C.) δ 8.48 (s, 1H), 8.14-7.96 (m, 2H), 7.75 (d, J=8.5 Hz, 1H), 7.42 (s, 1H), 7.12 (t, J=7.3 Hz, 1H), 6.99 (t, J=7.6 Hz, 1H), 6.53 (s, 2H), 4.62 (d, J=6.1 Hz, 2H), 2.23 (d, J=2.2 Hz, 3H). LCMS MDAP Rt=17.72 min; >95% (Method 4); m/z (ESI$^+$) 368.05 $[M+H]^+$.

Example 89

N2-(6-fluoro-2,3-dihydrobenzofuran-3-yl)-6-(1H-indazol-6-yl)-1,3,5-triazine-2,4-diamine

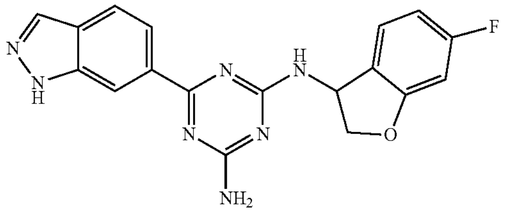 [SMILES: Nc1nc(NC2COc3cc(F)ccc32)nc(-c2ccc3cn[nH]c3c2)n1]

Synthesised by General Method A:

Step 1: N4-(6-fluoro-2,3-dihydrobenzofuran-3-yl)-6-(1-tetrahydropyran-2-ylindazol-6-yl)-1,3,5-triazine-2,4-diamine A mixture of 4-chloro-6-(1-tetrahydropyran-2-ylindazol-6-yl)-1,3,5-triazin-2-amine (intermediate X) (50 mg, 0.15 mmol), 6-fluoro-2,3-dihydro-1-benzofuran-3-amine hydrochloride (47 mg, 0.25 mmol) and N,N-diisopropylethylamine (0.21 mL, 1.21 mmol) in 1,4-dioxane (7.5 mL) was heated at 80° C. for 48 h. The reaction mixture was concentrated under reduced pressure. The crude material was purified by flash chromatography (silica gel, eluting with a gradient of 0-50% EtOAc in petroleum ether) to give the title compound as a white solid (60 mg, 0.13 mmol, 84% yield). LCMS MDAP Rt=20.94 min (Method 4); m/z (ESI$^+$) 448.10 $[M+H]^+$.

Step 2: N2-(6-fluoro-2,3-dihydrobenzofuran-3-yl)-6-(1H-indazol-6-yl)-1,3,5-triazine-2,4-diamine To a solution of N2-(6-fluoro-2,3-dihydrobenzofuran-3-yl)-6-(1-tetrahydropyran-2-ylindazol-6-yl)-1,3,5-triazine-2,4-diamine (56 mg, 0.12 mmol) in 1,4-dioxane (2.5 mL) and MeOH (2.5 mL) was added 4 M HCl in 1,4-dioxane (0.47 mL, 1.87 mmol) at RT. The reaction mixture was heated for 11 h at 60° C. in sealed vial and then concentrated to dryness under reduced pressure. The crude material was purified by flash chromatography (silica gel, eluting with a gradient of 0-5% methanol in DCM) to afford the title compound as a white solid (26 mg, 0.070 mmol, 55% yield). 1H NMR (399 MHz, DMSO-d6, Vt 90° C.) δ 8.51 (s, 1H), 8.17-7.97 (m, 2H), 7.76 (d, J=8.5 Hz, 1H), 7.51 (s, 1H), 7.39 (t, J=6.5 Hz, 1H), 6.74-6.48 (m, 4H), 5.82 (s, 1H), 4.83 (t, J=9.2 Hz, 1H), 4.50 (dd, J=9.6, 5.4 Hz, 1H). LCMS MDAP Rt=17.20 min; >95% (Method 4); m/z (ESI$^+$) 364.00 $[M+H]^+$.

Example 90

N2-(4,6-Difluoro-2,3-dihydrobenzofuran-3-yl)-6-(1H-indazol-6-yl)-1,3,5-triazine-2,4-diamine

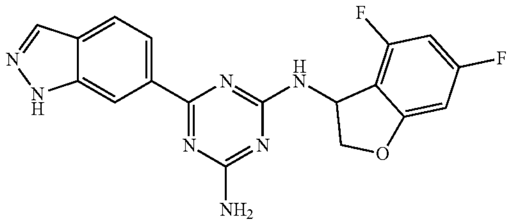 [SMILES: Nc1nc(NC2COc3cc(F)cc(F)c32)nc(-c2ccc3cn[nH]c3c2)n1]

Synthesised by General Method A:

Step 1: N2-(4,6-Difluoro-2,3-dihydrobenzofuran-3-yl)-6-(1-tetrahydropyran-2-ylindazol-6-yl)-1,3,5-triazine-2,4-diamine A mixture of 4-chloro-6-(1-tetrahydropyran-2-ylindazol-6-yl)-1,3,5-triazin-2-amine (Intermediate X) (50 mg, 0.15 mmol), 4,6-difluoro-2,3-dihydro-1-benzofuran-3-amine hydrochloride (52 mg, 0.25 mmol) and N,N-diisopropylethylamine (0.21 mL, 1.21 mmol) in 1,4-dioxane (7.5 mL) was heated at 80° C. for 48 h. The reaction mixture was concentrated to dryness under reduced pressure and purified by flash chromatography (silica gel, eluting with a gradient of 0-50% EtOAc in petroleum ether) to give the title compound as an off-white solid (67 mg, 0.14 mmol, 90% yield). LCMS MDAP Rt=3.32 min (Method 7); m/z ($ESI^+$) 466.25 $[M+H]^+$.

Step 2: N2-(4,6-Difluoro-2,3-dihydrobenzofuran-3-yl)-6-(1H-indazol-6-yl)-1,3,5-triazine-2,4-diamine To a solution of N2-(4,6-difluoro-2,3-dihydrobenzofuran-3-yl)-6-(1-tetrahydropyran-2-ylindazol-6-yl)-1,3,5-triazine-2,4-diamine (65 mg, 0.14 mmol) in 1,4-dioxane (2.8 mL) and MeOH (2.8 mL) was added 4 M HCl in 1,4-dioxane (0.52 mL, 2.1 mmol) at RT. The reaction mixture was heated for 11 h at 60° C. in sealed vial then evaporated to dryness under reduced pressure. The crude material was purified by flash chromatography (silica gel, eluting with a gradient of 0-5% methanol in DCM) to give the title compound as a white solid (26 mg, 0.060 mmol, 46% yield). $^1$H NMR (399 MHz, DMSO-d6, Vt 90° C.) δ 8.49 (s, 1H), 8.19-7.94 (m, 2H), 7.75 (d, J=8.5 Hz, 1H), 7.64 (s, 1H), 6.67-6.47 (m, 4H), 5.98 (s, 1H), 4.86 (t, J=9.1 Hz, 1H), 4.50 (dd, J=9.7, 4.7 Hz, 1H). LCMS MDAP Rt=17.76 min; >95% (Method 4); m/z ($ESI^+$) 382.00 $[M+H]^+$.

Example 91

N2-[[2,3-Difluoro-4-(2-pyrrolidin-1-ylethoxy)phenyl]methyl]-6-(1H-indazol-6-yl)-1,3,5-triazine-2,4-diamine hydrochloride

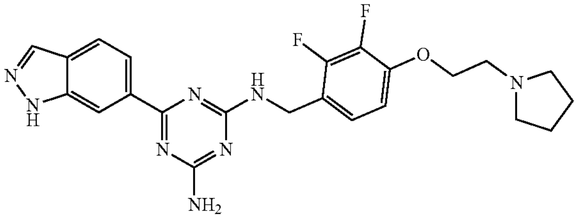 [SMILES: Nc1nc(NCc2ccc(OCCN3CCCC3)c(F)c2F)nc(-c2ccc3cn[nH]c3c2)n1]

Step 1: 2-[4-[[[4-Amino-6-(1-tetrahydropyran-2-ylindazol-6-yl)-1,3,5-triazin-2-yl]amino]methyl]-2,3-difluoro-phenoxy]ethanol A solution of 4-chloro-6-(1-tetrahydropyran-2-ylindazol-6-yl)-1,3,5-triazin-2-amine (Intermediate X) (68 mg, 0.21 mmol), 2-[4-(aminomethyl)-2,3-difluoro-phenoxy]ethanol (Intermediate BH) (50 mg, 0.25 mmol) and N,N-diisopropylethylamine (0.29 mL, 1.64 mmol) in 1,4-dioxane (7 mL) was heated for 4 h at 80° C. The reaction mixture was loaded onto celite and purified by flash chromatography (silica gel, eluting with a gradient of 0-5% methanol in DCM) to give the title compound as an off-white solid (81 mg, 0.15 mmol, 75% yield). 1H NMR (600 MHz, DMSO-d6) δ 8.56 (s, 0.47H), 8.52 (s, 1H), 8.17-8.12 (m, 1H), 8.09 (d, J=8.7 Hz, 1H), 7.83 (t, J=5.9 Hz, 1H), 7.80 (t, J=7.6 Hz, 1H), 7.74 (t, J=6.1 Hz, OH), 7.19-7.07 (m, 1H), 7.05-6.90 (m, 2H), 6.83 (s, 1H), 5.95-5.78 (m, 1H), 4.87 (d, J=21.2 Hz, 1H), 4.58 (d, J=6.2 Hz, 1H), 4.51 (d, J=6.1 Hz, 1H), 4.11-3.98 (m, 2H), 3.87 (t, J=14.1 Hz, 1H), 3.75-3.62 (m, 3H), 2.45-2.35 (m, 1H), 2.08-1.94 (m, 2H), 1.83-1.69 (m, 1H), 1.58 (s, 2H). LCMS LCQ Rt=5.63 min (Method 3); m/z ($ESI^+$) 498.29 $[M+H]^+$.

Step 2: N4-[[4-(2-Chloroethoxy)-2,3-difluoro-phenyl]methyl]-6-(1-tetrahydropyran-2-ylindazol-6-yl)-1,3,5-triazine-2,4-diamine To a solution 2-[4-[[[4-amino-6-(1-tetrahydropyran-2-ylindazol-6-yl)-1,3,5-triazin-2-yl]amino]methyl]-2,3-difluoro-phenoxy]ethanol (39 mg, 0.080 mmol) in tetrahydrofuran (2.6 mL) and DCM (2.6 mL) was added thionyl chloride (0.09 mL, 1.41 mmol) at RT. The reaction mixture was heated to reflux for 38 h then concentrated to dryness under reduced pressure. The crude material was purified by flash chromatography (silica gel, eluting with a gradient of 0-100% EtOAc in petroleum ether) to give the title compound as a pale brown solid (22 mg 0.040 mmol, 46% yield). LCMS MDAP Rt=21.68 min (Method 4); m/z ($ESI^+$) 516.15/518.10 $[M+H]^+$.

Step 3: N4-[[2,3-Difluoro-4-(2-pyrrolidin-1-ylethoxy)phenyl]methyl]-6-(1-tetrahydropyran-2-ylindazol-6-yl)-1,3,5-triazine-2,4-diamine A mixture of N4-[[4-(2-chloroethoxy)-2,3-difluoro-phenyl]methyl]-6-(1-tetrahydropyran-2-ylindazol-6-yl)-1,3,5-triazine-2,4-diamine (15 mg, 0.030 mmol), pyrrolidine (41 mg, 0.58 mmol) and potassium carbonate (10 mg, 0.070 mmol) in N,N-dimethylformamide (1 mL) was heated at 85° C. for 4.5 h. The reaction mixture was concentrated to dryness under reduced pressure and the crude material purified by flash chromatography (silica gel, eluting with a gradient of 0-5% methanol in DCM) to give the title compound as an off-white solid (9 mg, 0.010 mmol, 51% yield). LCMS MDAP Rt=12.86 min (Method 4); m/z ($ESI^+$) 551.30 $[M+H]^+$.

Step 4: N2-[[2,3-Difluoro-4-(2-pyrrolidin-1-ylethoxy)phenyl]methyl]-6-(1H-indazol-6-yl)-1,3,5-triazine-2,4-diamine hydrochloride To a solution of N2-[[2,3-difluoro-4-(2-pyrrolidin-1-ylethoxy)phenyl]methyl]-6-(1-tetrahydropyran-2-ylindazol-6-yl)-1,3,5-triazine-2,4-diamine (9 mg, 0.020 mmol) in 1,4-dioxane (1.5 mL) and methanol (1.5 mL) was added 4 M HCl in 1,4-dioxane (0.06 mL, 0.25 mmol) at RT. The reaction mixture was heated for 11 h at 60° C. then concentrated to dryness under reduced pressure. The crude material was purified by flash chromatography (silica gel, eluting with a gradient of 0-20% methanol in DCM) to give the title compound as a white solid (5 mg, 0.010 mmol, 58% yield). $^1H$ NMR (399 MHz, DMSO-d6, Vt 90° C.) δ 13.16 (s, 1H), 8.49 (s, 1H), 8.13-7.97 (m, 2H), 7.75 (d, J=8.5 Hz, 1H), 7.43 (s, 1H), 7.19 (t, J=8.5 Hz, 1H), 6.99 (t, J=8.1 Hz, 1H), 6.53 (s, 2H), 4.59 (d, J=6.1 Hz, 2H), 4.34 (s, 2H), 3.22 (s, 2H), 1.82 (s, 4H). LCMS MDAP Rt=11.03 & 11.81 min; >95% (Method 4); m/z ($ESI^+$) 467.20 $[M+H]^+$.

Example 92

6-(1H-Indazol-6-yl)-N2-[(2-methylisoindolin-1-yl)methyl]-1,3,5-triazine-2,4-diamine hydrochloride

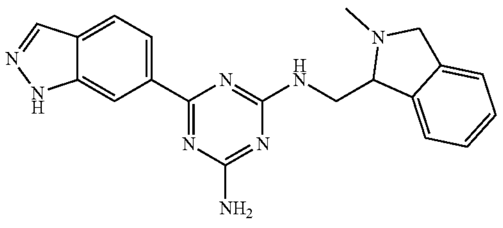 [SMILES: CN1Cc2ccccc2C1CNc1nc(N)nc(-c2ccc3cn[nH]c3c2)n1]

Synthesised by General Method A:

Step 1: N4-[(2-Methylisoindolin-1-yl)methyl]-6-(1-tetrahydropyran-2-ylindazol-6-yl)-1,3,5-triazine-2,4-diamine A mixture of 4-chloro-6-(1-tetrahydropyran-2-ylindazol-6-yl)-1,3,5-triazin-2-amine (Intermediate X) (25 mg, 0.080 mmol), (2-methyl-2,3-dihydro-1H-isoindol-1-yl)methanamine (20 mg, 0.12 mmol) and N,N-diisopropylethylamine (0.11 mL, 0.60 mmol) in 1,4-dioxane (3.5 mL) was heated at 80° C. for 24 h. The reaction mixture was loaded onto celite and purified by flash chromatography (silica gel, eluting with a gradient of 0-5% methanol in DCM) to afford the title compound as a light brown solid (25 mg, 0.050 mmol, 69% yield). LCMS LCQ Rt=0.92 min (Method 3); m/z ($ESI^+$) 457.38 $[M+H]^+$.

Step 2: 6-(1H-Indazol-6-yl)-N2-[(2-methylisoindolin-1-yl)methyl]-1,3,5-triazine-2,4-diamine hydrochloride To a solution of N2-[(2-methylisoindolin-1-yl)methyl]-6-(1-tetrahydropyran-2-ylindazol-6-yl)-1,3,5-triazine-2,4-diamine (23 mg, 0.050 mmol) in 1,4-dioxane (1 mL) and methanol (1 mL) was added 4M HCl in 1,4-dioxane (0.19 mL, 0.76 mmol) at RT. The reaction mixture was heated for 13 hours at 60° C. then concentrated to dryness under reduced pressure. The crude material was purified by flash chromatography (silica gel, eluting with a gradient of 0-10% methanol in DCM) to give the title compound as an off-white solid (21 mg, 0.050 mmol, 97% yield). $^1H$ NMR (399 MHz, DMSO-d6, Vt 90° C.) δ 13.04 (s, 1H), 8.49 (s, 1H), 8.11-7.97 (m, 2H), 7.75 (d, J=8.6 Hz, 1H), 7.32 (s, 1H), 7.28-6.98 (m, 3H), 6.70-6.25 (m, 3H), 4.27 (s, 1H), 4.02 (s, 1H), 3.89 (s, 1H), 3.70 (s, 2H), 2.62 (s, 3H).

Example 93

N2-Chroman-4-yl-6-(1H-indazol-6-yl)-1,3,5-triazine-2,4-diamine

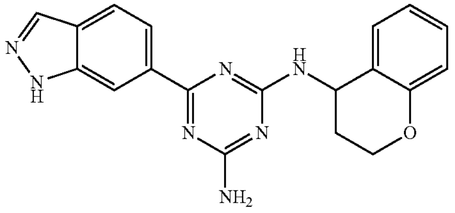 [SMILES: Nc1nc(NC2CCOc3ccccc32)nc(-c2ccc3cn[nH]c3c2)n1]

Synthesised by General Method A:

Step 1: N4-Chroman-4-yl-6-(1-tetrahydropyran-2-ylindazol-6-yl)-1,3,5-triazine-2,4-diamine A mixture of 4-chloro-6-(1-tetrahydropyran-2-ylindazol-6-yl)-1,3,5-triazin-2-amine (Intermediate X) (50 mg, 0.15 mmol), 3,4-dihydro-2H-1-benzopyran-4-amine (37 mg, 0.250 mmol) and N,N-diisopropylethylamine (0.21 mL, 1.21 mmol) in 1,4-dioxane (7 mL) was heated at 80° C. for 56 h. The reaction mixture was concentrated to dryness under reduced pressure and the crude material purified by flash chromatography (silica gel, eluting with a gradient of 0-70% EtOAc in petroleum ether) to give the title compound as an off-white solid (73 mg, 0.15 mmol, 98% yield). LCMS MDAP Rt=3.13 min (Method 7); m/z ($ESI^+$) 444.20 $[M+H]^+$.

Step 2: N2-Chroman-4-yl-6-(1H-indazol-6-yl)-1,3,5-triazine-2,4-diamine

To a solution of N2-chroman-4-yl-6-(1-tetrahydropyran-2-ylindazol-6-yl)-1,3,5-triazine-2,4-diamine (71 mg, 0.16 mmol) in 1,4-dioxane (3.2 mL) and methanol (3.2 mL) was added 4 M HCl in 1,4-dioxane (0.6 mL, 2.4 mmol) at RT. The reaction mixture was heated for 13 h at 60° C. then concentrated to dryness under reduced pressure. The crude material was purified by flash chromatography (silica gel, eluting with a gradient of 0-5% MeOH in DCM) to give the title compound as a white solid (35 mg, 0.090 mmol, 58% yield). $^1H$ NMR (399 MHz, DMSO-d6, Vt 90° C.) δ 8.53 (s, 1H), 8.22-7.99 (m, 1H), 7.86-7.70 (m, 1H), 7.35 (s, 1H), 7.30-7.21 (m, 1H), 7.21-7.06 (m, 1H), 6.91-6.82 (m, 1H), 6.82-6.72 (m, 1H), 6.58 (s, 2H), 5.46 (s, 1H), 4.35 (s, 1H), 4.25 (s, 1H), 2.17 (s, 2H). LCMS MDAP Rt=16.61 min (Method 4); m/z ($ESI^+$) 360.10 $[M+H]^+$.

Example 94

N2-Chroman-3-yl-6-(1H-indazol-6-yl)-1,3,5-triazine-2,4-diamine

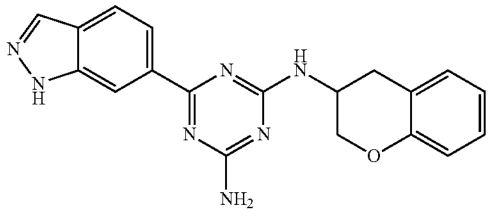 [SMILES: Nc1nc(NC2COc3ccccc3C2)nc(-c2ccc3cn[nH]c3c2)n1]

Synthesised by General Method A

Step 1: N4-Chroman-3-yl-6-(1-tetrahydropyran-2-ylindazol-6-yl)-1,3,5-triazine-2,4-diamine A mixture of 4-chloro-6-(1-tetrahydropyran-2-ylindazol-6-yl)-1,3,5-triazin-2-amine (Intermediate X) (50 mg, 0.15 mmol), 3,4-dihydro-2H-1-benzopyran-3-amine hydrochloride (46 mg, 0.25 mmol) and N,N-diisopropylethylamine (0.21 mL, 1.21 mmol) in 1,4-dioxane (12 mL) was heated at 80° C. for 72 h. The reaction mixture was loaded onto celite and purified by flash chromatography (eluting with a gradient of 0-50% EtOAc in petroleum ether) to give the title compound as an off-white solid (90 mg, 0.14 mmol, 94% yield). LCMS MDAP Rt=3.31 min (Method 7); m/z ($ESI^+$) 444.20 $[M+H]^+$.

Step 2: N2-Chroman-3-yl-6-(1H-indazol-6-yl)-1,3,5-triazine-2,4-diamine

To a solution of N2-chroman-3-yl-6-(1-tetrahydropyran-2-ylindazol-6-yl)-1,3,5-triazine-2,4-diamine (88 mg, 0.20 mmol) in 1,4-dioxane (3.9 mL) and methanol (3.9 mL) was added 4 M HCl in 1,4-dioxane (0.74 mL, 2.98 mmol) at RT. The reaction mixture was heated for 13 hours at 60° C. then concentrated to dryness under reduced pressure. The crude material was purified by flash chromatography (silica gel, eluting with a gradient of 0-5% MeOH in DCM) to give the title compound as a white solid (25 mg, 0.070 mmol, 33% yield). $^1H$ NMR (399 MHz, DMSO-$d_6$, Vt 90° C.) δ 8.49 (s, 1H), 8.13-7.93 (m, 2H), 7.76 (d, J=8.5 Hz, 1H), 7.08 (t, J=7.0 Hz, 2H), 6.99-6.87 (m, 1H), 6.85 (t, J=7.5 Hz, 1H), 6.78 (d, J=8.3 Hz, 1H), 6.58 (s, 2H), 4.46 (s, 1H), 4.31 (d, J=10.1 Hz, 1H), 3.91 (t, J=9.4 Hz, 1H).

Example 95

N2-[1-[1-(Difluoromethyl)pyrazol-3-yl]-1-methyl-ethyl]-N4-[(2,3-difluorophenyl)methyl]-6-(1H-indazol-6-yl)-1,3,5-triazine-2,4-diamine

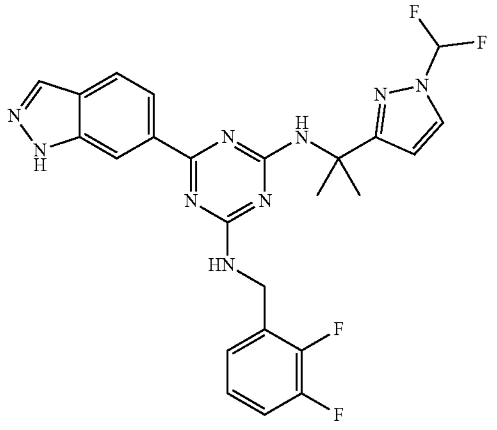 [SMILES: CC(C)(Nc1nc(NCc2cccc(F)c2F)nc(-c2ccc3cn[nH]c3c2)n1)c1ccn(C(F)F)n1]

Step 1: 4,6-Dichloro-N-[1-[1-(difluoromethyl)pyrazol-3-yl]-1-methyl-ethyl]-1,3,5-triazin-2-amine

[1-[1-(Difluoromethyl)pyrazol-3-yl]-1-methyl-ethyl]ammonium chloride (Intermediate L, HCl salt) (120 mg, 0.57 mmol) was added to a suspension of cyanuric chloride (110 mg, 0.60 mmol) and sodium carbonate (180 mg, 1.7 mmol) in diethyl ether (10 mL). The reaction mixture was stirred at RT for 48 h. The reaction mixture was loaded directly onto celite and purified by flash chromatography (silica gel, eluting with a gradient of 30% EtOAc in petroleum ether) to provide the desired product as a colourless oil (178 mg, 0.52 mmol, 92%). $^1H$ NMR (600 MHz, Chloroform-d) δ 7.77 (d, J=2.7 Hz, 1H), 7.22-7.00 (m, 2H), 6.39 (d, J=2.7 Hz, 1H), 3.69 (s, 2H), 1.81 (s, 6H). LCMS LCQ Rt=6.77 min (Method 3); m/z ($ESI^+$) 322.95 $[M+H]^+$.

Step 2: 4-Chloro-N-[1-[1-(difluoromethyl)pyrazol-3-yl]-1-methyl-ethyl]-6-(1-tetrahydropyran-2-ylindazol-6-yl)-1,3,5-triazin-2-amine Bis[2-(di-tert-butylphosphanyl)cyclopenta-2,4-dien-1-yl] iron; dichloropalladium (7.2 mg, 0.010 mmol) was added to a suspension of 1-tetrahydropyran-2-yl-6-(4,4,5,5-tetramethyl-1,3,2-dioxaborolan-2-yl)indazole (Intermediate V) (220 mg, 0.66 mmol), 4,6-dichloro-N-[1-[1-(difluoromethyl)pyrazol-3-yl]-1-methyl-ethyl]-1,3,5-triazin-2-am ine (178 mg, 0.55 mmol) and potassium phosphate tribasic (234 mg, 1.1 mmol) in tetrahydrofuran (8 mL). The biphasic mixture was degassed with $N_2$ (10 min) and heated in a sealed vial at 80° C. for 2 hours. The reaction mixture was cooled to RT and partitioned between EtOAc and brine, the organic layer separated, dried over (MgSO4) and concentrated under reduced pressure. The residue was purified by flash chromatography (silica gel, eluting with 0-30% EtOAc in petroleum ether) to give the title compound as a pale yellow gum (119 mg, 0.22 mmol, 40% yield). LCMS LCQ Rt=8.11 min (Method 3); m/z ($ESI^+$) 489.19 $[M+H]^+$.

Step 3: N2-[1-[1-(Difluoromethyl)pyrazol-3-yl]-1-methyl-ethyl]-N4-[(2,3-difluorophenyl)methyl]-6-(1H-indazol-6-yl)-1,3,5-triazine-2,4-diamine 4-Chloro-N-[1-[1-(difluoromethyl)pyrazol-3-yl]-1-methyl-ethyl]-6-(1-tetrahydropyran-2-ylindazol-6-yl)-1,3,5-triazin-2-amine (30 mg, 0.060 mmol) and 2,3-Difluorobenzylamine (0.02 mL, 0.15 mmol) were dissolved in 1,4-dioxane (1 mL) and heated to 100° C. for 16 h. After cooling to RT, 4M HCl in 1,4-dioxane was added and the reaction mixture stirred at room temperature for 72 h. The reaction mixture was concentrated to dryness under reduced pressure, and purified by flash chromatography (silica gel, eluting with a gradient of 0-50% EtOAc in petroleum ether) to provide the title compound as a white solid (8 mg, 0.010 mmol, 24% yield). $^1$H NMR (399 MHz, DMSO-$d_6$, Vt 90° C.) δ 13.03 (s, 1H), 8.43 (s, 1H), 8.07 (s, 1H), 7.95 (br m, 2H), 7.75 (d, J=8.5 Hz, 1H), 7.64 (s, 1H), 7.48 (br m, 1H), 7.27-7.08 (m, 4H), 6.41 (s, 1H), 4.56 (s, 2H), 1.74 (s, 6H). LCMS MDAP Rt=18.19 min; >95% (Method 5); m/z (EST+) 512 $[M+H]^+$.

Example 96

N2-[2-(2,3-dichlorophenyl)ethyl]-6-(1H-indazol-6-yl)-N2-(2-methoxyethyl)-1,3,5-triazine-2,4-diamine

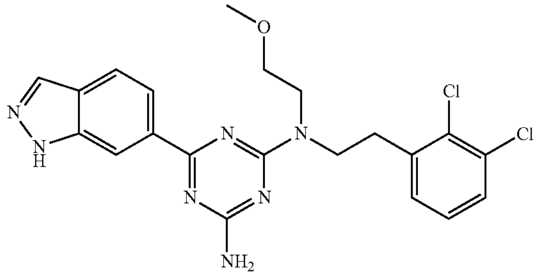 [SMILES: COCCN(CCc1cccc(Cl)c1Cl)c1nc(N)nc(-c2ccc3cn[nH]c3c2)n1]

Synthesised by General Method A

Step 1: N4-[2-(2,3-Dichlorophenyl)ethyl]-N4-(2-methoxyethyl)-6-(1-tetrahydropyran-2-ylindazol-6-yl)-1,3,5-triazine-2,4-diamine A mixture of 2-(2,3-Dichlorophenyl)-N-(2-methoxyethyl)ethanamine (Intermediate AD) (57 mg, 0.23 mmol), 4-chloro-6-(1-tetrahydropyran-2-ylindazol-6-yl)-1,3,5-triazin-2-amine (Intermediate X) (46 mg, 0.14 mmol) and N,N-diisopropylethylamine (0.06 mL, 0.35 mmol) in 1,4-dioxane (2.8 mL) was heated at 60° C. for 44 h. The reaction mixture was dry loaded onto celite and purified by flash chromatography (silica gel, eluting with a gradient of 0-40% EtOAc in petroleum ether) to give the title compound as a clear gum (65 mg, 0.11 mmol, 78% yield). $^1$H NMR (600 MHz, DMSO-d6) δ 8.58 (s, 0.35H), 8.53 (s, 0.58H), 8.17-8.13 (m, 1H), 8.10 (d, J=8.5 Hz, 1H), 7.86-7.75 (m, 1H), 7.50 (d, J=8.0 Hz, 0.31H), 7.44-7.39 (m, 1H), 7.33 (d, J=7.4 Hz, 0.56H), 7.29 (t, J=7.9 Hz, 0.16H), 7.23 (t, J=7.8 Hz, 0.60H), 7.00-6.79 (m, 2H), 5.91-5.83 (m, 1H), 4.06-3.97 (m, 1H), 3.95-3.61 (m, 2H), 3.57 (t, J=5.9 Hz, 0.75H), 3.52 (t, J=5.9 Hz, 1.28H), 3.26 (s, 2H), 3.13 (t, J=7.3 Hz, 1.33H), 3.09 (t, J=7.6 Hz, 0.81H), 2.45-2.37 (m, 1H), 2.10-1.97 (m, 2H), 1.82-1.70 (m, 1H), 1.64-1.50 (m, 2H), 1.47-1.34 (m, 1H), 1.06 (s, 2H), 1.01 (s, 1H). LCMS LCQ Rt=8.20 min (Method 3); m/z (ESI$^+$) 542.28 $[M+H]^+$.

Step 2: N2-[2-(2,3-Dichlorophenyl)ethyl]-6-(1H-indazol-6-yl)-N2-(2-methoxyethyl)-1,3,5-triazine-2,4-diamine A solution of N2-[2-(2,3-dichlorophenyl)ethyl]-N2-(2-methoxyethyl)-6-(1-tetrahydropyran-2-ylindazol-6-yl)-1,3,5-triazine-2,4-diamine (63 mg, 0.12 mmol) in methanol (4 mL) treated with 4 M HCl in 1,4-dioxane (1.16 mL, 4.65 mmol) was heated at 60° C. for 16 h. The reaction mixture was concentrated to dryness under reduced pressure. The residue was dissolved in methanol and eluted onto an SCX-2 cartridge (10 g) and the product eluted with 2M NH3 in methanol (with DCM to aid solubility). The eluant was concentrated to dryness under reduced pressure and the material purified by flash chromatography (silica gel, eluting with a gradient of 0-5% methanol in DCM) to give the title compound as a white solid (37 mg, 0.080 mmol, 68% yield). $^1$H NMR (600 MHz, DMSO-$d_6$) δ 13.27 (s, 1H), 8.47 (d, J=4.5 Hz, 1H), 8.10 (s, 1H), 8.07-8.01 (m, 1H), 7.79 (dd, J=8.6, 2.4 Hz, 1H), 7.50 (d, J=7.8 Hz, 0.31H), 7.42 (t, J=8.2 Hz, 1H), 7.34-7.23 (m, 2H), 7.07-6.70 (m, 2H), 3.92 (t, J=7.3 Hz, 1H), 3.81-3.71 (m, 2H), 3.66 (t, J=5.9 Hz, 1H), 3.56 (t, J=5.8 Hz, 1H), 3.50 (t, J=5.9 Hz, 1H), 3.26 (s, 1H), 3.25 (s, 2H), 3.13 (t, J=7.2 Hz, 1H), 3.09 (t, J=7.7 Hz, 1H).

Example 97

N4-[1-[4-chloro-1-(difluoromethyl)pyrazol-3-yl]-1-methyl-ethyl]-6-(1-methylindazol-6-yl)-1,3,5-triazine-2,4-diamine

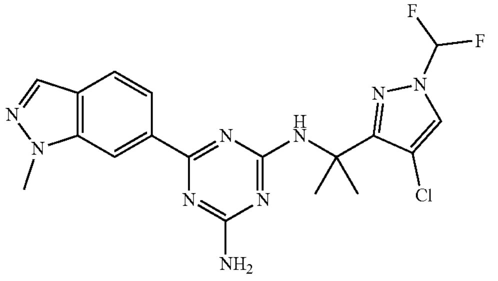 [SMILES: Cn1ncc2ccc(-c3nc(N)nc(NC(C)(C)c4nn(C(F)F)cc4Cl)n3)cc21]

Synthesised by General Method B:

Step 1: 6-chloro-N4-[1-[4-chloro-1-(difluoromethyl)pyrazol-3-yl]-1-methyl-ethyl]-1,3,5-triazine-2,4-diamine 2-Amino-4,6-dichlorotriazine (65 mg, 0.40 mmol) was suspended in 1,4-dioxane (1.5 mL) and N,N-diisopropylethylamine (0.14 mL, 0.79 mmol) was added followed by [1-[4-chloro-1-(difluoromethyl)pyrazol-3-yl]-1-methyl-ethyl]ammonium chloride Intermediate BA (65 mg, 0.26 mmol). The mixture was heated to 60° C. for 12 h. The crude material was purified by flash column chromatography (silica, eluting with a gradient of 0-10% methanol in DCM) to afford the titled compound as a white solid (20 mg, 0.06 mmol, 22% yield). Rt 3.51 mins (Method 2); m/z (ESI$^+$) 337.86-339.88 $[M+H]^+$.

Step 2: N4-[1-[4-chloro-1-(difluoromethyl)pyrazol-3-yl]-1-methyl-ethyl]-6-(1-methylindazol-6-yl)-1,3,5-triazine-2,4-diamine A stirred solution of 6-chloro-N4-[1-[4-chloro-1-(difluoromethyl)pyrazol-3-yl]-1-methyl-ethyl]-1,3,5-triazine-2,4-diamine (30 mg, 0.09 mmol), potassium phosphate tribasic (38 mg, 0.18 mmol), and bis[2-(di-tert-butylphosphanyl) cyclopenta-2,4-dien-1-yl]iron; dichloropalladium (2.9 mg, 0.006 mmol) in tetrahydrofuran (1 mL) and water (0.2 mL) was degassed for 5 min by bubbling $N_2$ directly into the solution. The mixture was heated to 80° C. then a solution of 1-Methyl-1H-indazole-6-boronic acid (23 mg, 0.13 mmol) in THF was added and the mixture stirred for 12 h. The reaction mixture was concentrated to dryness and the crude was purified by flash column chromatography (silica, eluting with a gradient of 30-100% ethyl acetate in petroleum ether) to afford the desired compound as an off-white solid (8 mg, 0.02 mmol, 21% yield). $^1$H NMR (399 MHz, DMSO-d6) δ 8.30 (s, 1H), 8.21 (s, 1H), 8.00 (s, 1H), 7.85-7.45 (m, 3H), 7.04 (s, 1H), 6.33 (s, 2H), 4.03 (s, 3H), 1.77 (s, 6H). LCMS-MDAP Rt=18.24 min (Method 4); m/z (ESI$^+$) 434.10-436.05 [M+H]$^+$.

Example 98

6-(1H-indazol-6-yl)-N2-[(1-methylpyrrolidin-3-yl) methyl]-1,3,5-triazine-2,4-diamine

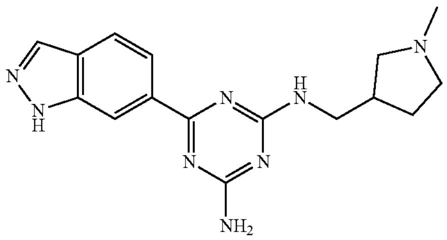 [SMILES: CN1CCC(CNc2nc(N)nc(-c3ccc4cn[nH]c4c3)n2)C1]

Synthesised by General Method A:

Step 1: N4-[(1-methylpyrrolidin-3-yl)methyl]-6-(1-tetrahydropyran-2-ylindazol-6-yl)-1,3,5-triazine-2,4-diamine A mixture of (1-methylpyrrolidin-3-yl)methanamine (69 mg, 0.60 mmol) and 4-chloro-6-(1-tetrahydropyran-2-ylindazol-6-yl)-1,3,5-triazin-2-amine Intermediate X (40 mg, 0.12 mmol) was heated to 130° C. by microwave irradiation for 90 min. The cooled RM was purified by flash silica chromatography (eluting with a gradient of 0-10% methanol in DCM) followed by chromatography on amino silica (eluting with a gradient of 25-100% ethyl acetate in petroleum ether), to afford the desired compound as a pale yellow solid (12 mg, 0.03 mmol, 23% yield). $^1$H NMR (399 MHz, DMSO-d6) δ 8.57 (s, 1H), 8.10 (d, J=10.2 Hz, 2H), 7.78 (d, J=8.5 Hz, 1H), 6.98 (s, 1H), 6.47 (s, 2H), 5.86 (dd, J=9.0, 2.8 Hz, 1H), 3.89 (d, J=11.7 Hz, 1H), 3.73 (dt, J=12.2, 6.2 Hz, 1H), 3.33 (d, J=7.5 Hz, 2H), 2.42-2.36 (m, 1H), 2.33 (s, 1H), 2.23 (s, 3H), 2.16-1.95 (m, 2H), 1.90 (dt, J=13.1, 6.7 Hz, 1H), 1.78 (s, 1H), 1.62 (p, J=4.6, 3.9 Hz, 2H), 1.50 (dd, J=15.2, 8.3 Hz, 1H), 0.91-0.75 (m, 1H). LCMS-MDAP Rt=11.35 min (Method 4); m/z (ESI$^+$) 409.20 [M+H]$^+$.

Step 2: 6-(1H-indazol-6-yl)-N2-[(1-methylpyrrolidin-3-yl)methyl]-1,3,5-triazine-2,4-diamine To a solution of N2-[(1-methylpyrrolidin-3-yl)methyl]-6-(1-tetrahydropyran-2-ylindazol-6-yl)-1,3,5-triazine-2,4-diamine (10 mg, 0.02 mmol) in methanol (0.2 mL) was added 4.0 M HCl in 1,4-dioxane (0.07 mL, 0.29 mmol) and the reaction stirred at 40° C. for 16 h. The solvent was evaporated to dryness under reduced pressure and the residue triturated with a 1:1 mixture of diethyl ether and petroleum ether and dried in vacuo to afford the desired compound as the hydrochloride salt (6 mg, 0.02 mmol, yield 76%). $^1$H NMR (399 MHz, DMSO-d6) δ 10.75 (s, 1H), 8.55 (s, 1H), 8.12 (s, 1H), 8.03 (d, J=8.5 Hz, 1H), 7.84 (d, J=8.5 Hz, 1H), 3.51 (s, 2H), 2.90-2.63 (m, 5H), 2.29-2.02 (m, 1H), 1.97-1.67 (m, 1H), 1.52-1.25 (m, 1H), 0.92-0.73 (m, 2H). LCMS-MDAP Rt=10.03 min (Method 4); m/z (ESI$^+$) 325.05 [M+H]$^+$.

Example 99

N2-[1-[1-(difluoromethyl)pyrazol-3-yl]-1-methyl-ethyl]-6-(3-fluoro-1H-indazol-5-yl)-1,3,5-triazine-2,4-diamine

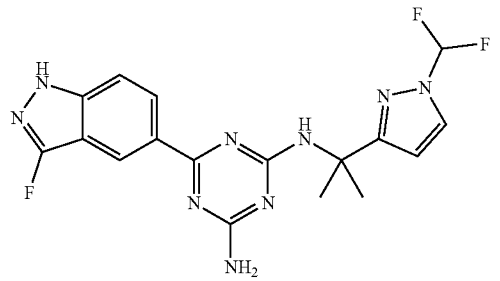

Synthesised by General Method B:

Step 1: N4-[1-[1-(difluoromethyl)pyrazol-3-yl]-1-methyl-ethyl]-6-(3-fluoro-1-tetrahydropyran-2-yl-indazol-5-yl)-1,3,5-triazine-2,4-diamine 6-chloro-N4-[1-[1-(difluoromethyl)pyrazol-3-yl]-1-methyl-ethyl]-1,3,5-triazine-2,4-diamine (Example 36 step 1) (45 mg, 0.15 mmol), potassium phosphate tribasic (63 mg, 0.30 mmol), and bis[2-(di-tert-butylphosphanyl)cyclopenta-2,4-dien-1-yl]iron; dichloropalladium (4.8 mg, 0.01 mmol) in tetrahydrofuran (2.5 mL) and water (0.25 mL) were degassed for 10 mins and then heated to 80° C. A solution of 3-fluoro-1-tetrahydropyran-2-yl-5-(4,4,5,5-tetramethyl-1,3,2-dioxaborolan-2-yl)indazole (Intermediate BE) (77 mg, 0.22 mmol), in THF was added and the reaction mixture stirred at 80° C. for 12 h, then concentrated to dryness under reduced pressure and purified by flash column chromatography (silica gel eluting with a gradient of 25-100% ethyl acetate in petroleum ether) to afford the desired compound as a white solid (16 mg, 0.03 mmol, yield 22%). $^1$H NMR (399 MHz, DMSO-d6 Vt 90° C.) δ 8.45 (s, 1H), 8.24 (d, J=9.0 Hz, 1H), 7.94 (d, J=2.7 Hz, 1H), 7.80-7.42 (m, 2H), 6.92 (s, 1H), 6.45-6.32 (m, 3H), 5.74 (d, J=9.4 Hz, 1H), 3.88 (d, J=11.8 Hz, 1H), 3.71 (dt, J=12.3, 7.0 Hz, 1H), 2.25 (q, J=13.1, 12.6 Hz, 1H), 2.11-1.82 (m, 3H), 1.75 (s, 6H), 1.64-1.52 (m, 2H). LCMS-MDAP Rt=19.97 min (Method 4); m/z ($ESI^+$) 488.20 $[M+H]^+$.

Step 2: N2-[1-[1-(difluoromethyl)pyrazol-3-yl]-1-methyl-ethyl]-6-(3-fluoro-1H-indazol-5-yl)-1,3,5-triazine-2,4-diamine To a solution of N2-[1-[1-(difluoromethyl)pyrazol-3-yl]-1-methyl-ethyl]-6-(3-fluoro-1-tetrahydropyran-2-yl-indazol-5-yl)-1,3,5-triazine-2,4-diamine (39 mg, 0.08 mmol) in methanol (0.60 mL), was added 4.0 M HCl in 1,4-dioxane (0.24 mL, 0.97 mmol) and the reaction mixture stirred at 40° C. for 16 h. The mixture was evaporated to dryness under reduced pressure and the residue triturated with diethyl ether:petroleum ether. The solid was filtered, washed with petroleum ether and dried in vacuo at 50° C. for 2 h to afford the desired compound (9 mg, 0.02 mmol, yield 22%). $^1H$ NMR (399 MHz, DMSO-d6) δ 12.72 (d, J=42.3 Hz, 1H), 8.72 (s, 1H), 8.57 (s, 1H), 8.31 (dd, J=9.0, 1.7 Hz, 1H), 8.15 (s, 1H), 7.99 (d, J=2.7 Hz, 1H), 7.85-7.43 (m, 3H), 6.47 (d, J=2.6 Hz, 1H), 1.77 (s, 6H). LCMS-MDAP Rt=15.88 min (Method 4); m/z ($ESI^+$) 404.10 $[M+H]^+$.

Example 100

N2-[1-[1-(difluoromethyl)pyrazol-3-yl]-1-methyl-ethyl]-6-(3-fluoro-1-tetrahydro pyran-2-yl-indazol-6-yl)-1,3,5-triazine-2,4-diamine

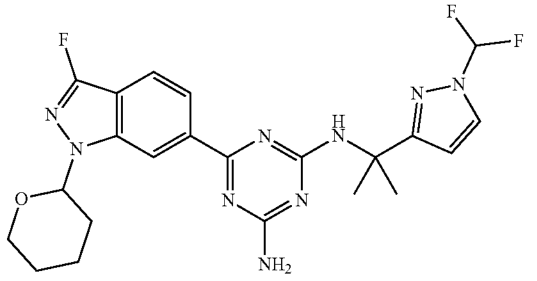 [SMILES: CC(C)(Nc1nc(N)nc(-c2ccc3c(F)nn(C4CCCCO4)c3c2)n1)c1ccn(C(F)F)n1]

Synthesised by General Method B:

A mixture of 6-chloro-N4-[1-[1-(difluoromethyl)pyrazol-3-yl]-1-methyl-ethyl]-1,3,5-triazine-2,4-diamine (Example 36 step 1) (50 mg, 0.16 mmol), bis[2-(di-tert-butylphosphanyl)cyclopenta-2,4-dien-1-yl]iron; dichloropalladium (5.4 mg, 0.01 mmol), and potassium phosphate tribasic (70 mg, 0.33 mmol) in tetrahydrofuran (0.8 mL) was de-gassed with $N_2$ for 10 minutes. A solution of 3-fluoro-1-tetrahydropyran-2-yl-6-(4,4,5,5-tetramethyl-1,3,2-dioxaborolan-2-yl)indazole (86 mg, 0.25 mmol) in THF was added and the reaction mixture was degassed for a further 10 minutes before heating to reflux temperature for 12 h. The volatiles were evaporated under reduced pressure and the crude residue purified by flash chromatography (silica gel, eluting with a gradient of 25-100% ethyl acetate in petroleum ether) to afford the desired compound as a white solid (15 mg, 0.03 mmol, 18% yield). $^1H$ NMR (399 MHz, DMSO-d6) δ 8.44 (s, 1H), 8.02-7.90 (m, 2H), 7.81-7.39 (m, 2H), 6.97 (s, 1H), 6.51-6.37 (m, 3H), 5.74 (d, J=9.2 Hz, 1H), 3.88 (d, J=11.7 Hz, 1H), 3.71 (s, 1H), 2.29 (d, J=11.1 Hz, 1H), 2.04 (d, J=21.2 Hz, 3H), 1.77 (d, J=8.3 Hz, 6H), 1.60 (s, 2H). LCMS-MDAP Rt=21.18 min (Method 4); m/z ($ESI^+$) 488.3 $[M+H]^+$.

Example 101

N2-[1-[1-(difluoromethyl)pyrazol-3-yl]-1-methyl-ethyl]-6-(1-methylindazol-6-yl)-1,3,5-triazine-2,4-diamine

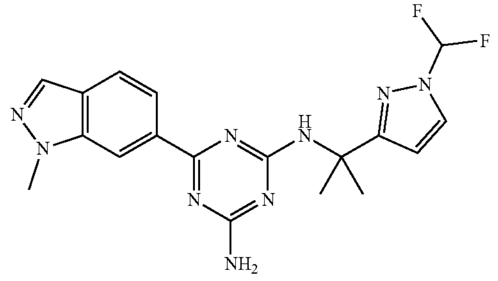 [SMILES: Cn1ncc2ccc(-c3nc(N)nc(NC(C)(C)c4ccn(C(F)F)n4)n3)cc21]

Synthesised by General Method B:

A mixture of 6-chloro-N4-[1-[1-(difluoromethyl)pyrazol-3-yl]-1-methyl-ethyl]-1,3,5-triazine-2,4-diamine (Example 36 step 1) (50 mg, 0.16 mmol), bis[2-(di-tert-butylphosphanyl)cyclopenta-2,4-dien-1-yl]iron; dichloropalladium (5.4 mg, 0.01 mmol), and potassium phosphate tribasic (70 mg, 0.33 mmol) in tetrahydrofuran (0.8 mL) was de-gassed with N2 for 10 minutes. A solution of 1-Methyl-1H-indazole-6-boronic acid (44 mg, 0.25 mmol) in THF was added and the reaction mixture was degassed for a further 10 minutes before heating to reflux temperature for 12 h. The volatiles were evaporated under reduced pressure and the crude residue purified by flash chromatography (silica gel, eluting with a gradient of 0-5% methanol in DCM) followed by flash chromatography on amino-silica (eluting with a gradient of 30-100% ethyl acetate in petroleum ether) to afford the product as a pale yellow solid (22 mg, 0.05 mmol, 33% yield). $^1H$ NMR (399 MHz, DMSO-d6) δ 8.32 (s, 1H), 8.01 (s, 1H), 7.96 (d, J=2.7 Hz, 1H), 7.91 (d, J=8.4 Hz, 1H), 7.82-7.45 (m, 2H), 6.91 (s, 1H), 6.44 (d, J=2.6 Hz, 1H), 6.40 (s, 2H), 4.04 (s, 3H), 1.77 (s, 6H). LCMS-MDAP Rt=16.04 min (Method 4); m/z ($ESI^+$) 400.2 $[M+H]^+$.

Example 102

N2-[1-[1-(difluoromethyl)pyrazol-3-yl]-1-methyl-ethyl]-6-(7-fluoro-1H-indazol-6-yl)-1,3,5-triazine-2,4-diamine

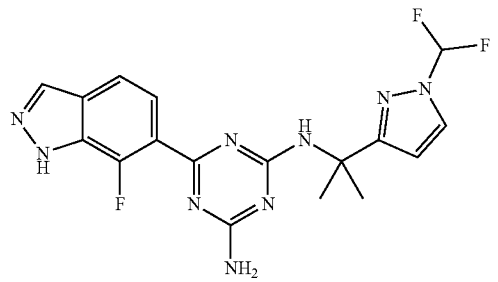 [SMILES: CC(C)(Nc1nc(N)nc(-c2ccc3cn[nH]c3c2F)n1)c1ccn(C(F)F)n1]

Synthesised by General Method B:

Step 1: N4-[1-[1-(difluoromethyl)pyrazol-3-yl]-1-methyl-ethyl]-6-(7-fluoro-1-tetrahydropyran-2-yl-indazol-6-yl)-1,3,5-triazine-2,4-diamine 6-chloro-N4-[1-[1-(difluoromethyl)pyrazol-3-yl]-1-methyl-ethyl]-1,3,5-triazine-2,4-diamine (Example 36 step 1) (55 mg, 0.18 mmol), potassium phosphate tribasic (77 mg, 0.36 mmol), and bis[2-(di-tert-butylphosphanyl)cyclopenta-2,4-dien-1-yl]iron; dichloropalladium (5.9 mg, 0.01 mmol) in tetrahydrofuran (3 mL) and water (0.3 mL) were degassed with $N_2$ for 10 mins and heated to 80° C. A solutions of 7-fluoro-1-tetrahydropyran-2-yl-6-(4,4,5,5-tetramethyl-1,3,2-dioxaborolan-2-yl)indazole Intermediate BD (94 mg, 0.27 mmol) in THF was added and the reaction mixture stirred at 80° C. for 12 h. The reaction mixture was concentrated to dryness under reduced pressure and purified by flash column chromatography (silica gel eluting with a gradient of 30-100% ethyl acetate in petroleum ether) to afford desired compound as white solid (42 mg, 0.09 mmol, 47% yield). $^1$H NMR (399 MHz, DMSO-d6 VT 90° C.) δ 8.14 (d, J=2.0 Hz, 1H), 7.97 (d, J=2.6 Hz, 1H), 7.81-7.38 (m, 3H), 6.93 (s, 1H), 6.55-6.38 (m, 3H), 5.87 (dd, J=9.6, 2.5 Hz, 1H), 3.89 (d, J=11.7 Hz, 1H), 3.65 (dt, J=11.9, 7.1 Hz, 1H), 2.51-2.37 (m, 1H), 2.07 (s, 2H), 1.74 (s, 7H), 1.57 (s, 2H). LCMS-MDAP Rt=18.34 min (Method 4); m/z (ESI$^+$) 488.3 [M+H]$^+$.

Step 2: N2-[1-[1-(difluoromethyl)pyrazol-3-yl]-1-methyl-ethyl]-6-(7-fluoro-1H-indazol-6-yl)-1,3,5-triazine-2,4-diamine A solution of N2-[1-[1-(difluoromethyl)pyrazol-3-yl]-1-methyl-ethyl]-6-(7-fluoro-1-tetrahydropyran-2-yl-indazol-6-yl)-1,3,5-triazine-2,4-diamine (42 mg, 0.09 mmol), in methanol (0.5 mL), was treated with 4.0 M HCl in 1,4-dioxane (0.26 mL, 1.03 mmol) and the reaction mixture stirred at RT for 12 h. The solution was concentrated to dryness under reduced pressure and the crude triturated with diethyl ether/petroleum ether. The solid was filtered, washed with diethyl ether/petroleum ether, and dried in vacuo at 50° C. for 2 h to afford the desired product as a white solid (23 mg, 0.06 mmol, 83%). $^1$H NMR (399 MHz, DMSO-d6, VT 90° C.) δ 8.18 (d, J=3.3 Hz, 1H), 8.00 (d, J=2.7 Hz, 1H), 7.85-7.36 (m, 3H), 6.48 (d, J=2.7 Hz, 1H), 1.77 (s, 6H). LCMS-MDAP Rt=14.77 min (Method 4); m/z (ESI$^+$) 404.2 [M+H]$^+$.

Example 103

N2-[1-[1-(difluoromethyl)pyrazol-3-yl]-1-methyl-ethyl]-6-(5-fluoro-1H-indazol-6-yl)-1,3,5-triazine-2,4-diamine

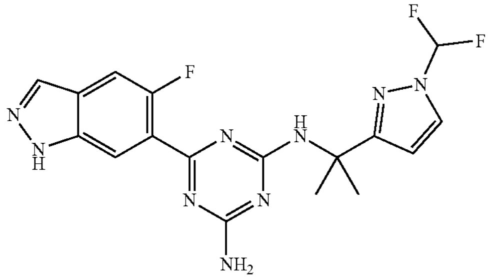 [SMILES: CC(C)(Nc1nc(N)nc(-c2cc3[nH]ncc3cc2F)n1)c1ccn(C(F)F)n1]

Synthesised by General Method B:

The synthesis follows the same protocol as Example 102 except Intermediate BD is replaced with Intermediate BC and N2-[1-[1-(difluoromethyl)pyrazol-3-yl]-1-methyl-ethyl]-6-(7-fluoro-1-tetrahydropyran-2-yl-indazol-6-yl)-1,3,5-triazine-2,4-diamine is replaced with N4-[1-[1-(difluoromethyl)pyrazol-3-yl]-1-methyl-ethyl]-6-(5-fluoro-1-tetrahydropyran-2-yl-indazol-6-yl)-1,3,5-triazine-2,4-diamine to afford the desired compound as white solid. 1H NMR (399 MHz, DMSO-d6, VT 90° C.) δ 8.10 (s, 1H), 8.02 (d, J=2.8 Hz, 2H), 7.85-7.43 (m, 2H), 6.51 (d, J=2.7 Hz, 1H), 1.78 (s, 6H). LCMS-MDAP Rt=14.53 min (Method 4); m/z (ESI$^+$) 404.2 [M+H]$^+$.

Example 104

N2-[1-[1-(difluoromethyl)pyrazol-3-yl]-1-methyl-ethyl]-6-(4-fluoro-1H-indazol-6-yl)-1,3,5-triazine-2,4-diamine

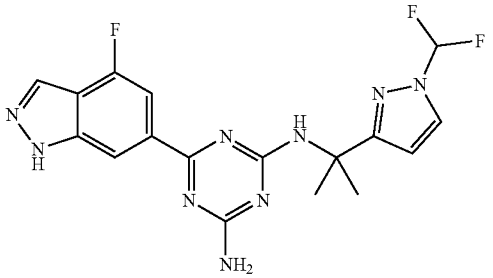 [SMILES: CC(C)(Nc1nc(N)nc(-c2cc(F)c3cn[nH]c3c2)n1)c1ccn(C(F)F)n1]

Synthesised by General Method B:

The synthesis follows the same protocol as Example 102 except Intermediate BD is replaced with Intermediate BB and N2-[1-[1-(difluoromethyl)pyrazol-3-yl]-1-methyl-ethyl]-6-(7-fluoro-1-tetrahydropyran-2-yl-indazol-6-yl)-1,3,5-triazine-2,4-diamine is replaced with N4-[1-[1-(difluoromethyl)pyrazol-3-yl]-1-methyl-ethyl]-6-(4-fluoro-1-tetrahydropyran-2-yl-indazol-6-yl)-1,3,5-triazine-2,4-diamine to afford the desired compound as white solid. $^1$H NMR (399 MHz, DMSO-d6 VT 90° C.) δ 8.26 (s, 1H), 8.17 (s, 1H), 7.98 (d, J=2.7 Hz, 1H), 7.85-7.44 (m, 2H), 6.47 (d, J=2.7 Hz, 1H), 1.78 (s, 6H). LCMS-MDAP Rt=16.99 min (Method 4); m/z (ESI$^+$) 404.2 [M+H]$^+$.

Example 105

6-(1H-indazol-6-yl)-N2-(3-phenyloxetan-3-yl)-1,3,5-triazine-2,4-diamine

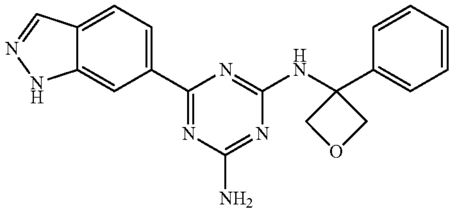 [SMILES: Nc1nc(NC2(c3ccccc3)COC2)nc(-c2ccc3cn[nH]c3c2)n1]

Synthesised by General Method B

Step 1: 6-chloro-N4-(3-phenyloxetan-3-yl)-1,3,5-triazine-2,4-diamine

To a stirred solution of 2-Amino-4,6-dichlorotriazine (200 mg, 1.21 mmol) in 1,4-dioxane (7 mL), was added N,N-diisopropylethylamine (0.53 mL, 3.0 mmol) followed by the addition of 3-Phenyl-3-oxetanamine hydrochloride (1:1) (225 mg, 1.21 mmol), and the resulting mixture stirred at RT for 12 h. The volatiles were removed under reduced pressure and the crude residue purified by flash column chromatography (silica gel, eluting with a gradient of 50-100% ethyl acetate in petroleum ether) to afford the desired compound as a white powder (157 mg, 0.56 mmol, 46% yield). $^1H$ NMR (600 MHz, Chloroform-d) δ 7.53 (d, J=7.8 Hz, 2H), 7.39 (t, J=7.7 Hz, 2H), 7.31 (t, J=7.3 Hz, 1H), 6.19 (s, 1H), 5.05 (d, J=6.8 Hz, 2H), 4.89 (d, J=6.7 Hz, 2H). LCMS-MDAP Rt=1.91 min (Method 4); m/z ($ESI^+$) 277.95 $[M+H]^+$.

Step 2: N4-(3-phenyloxetan-3-yl)-6-(1-tetrahydro-pyran-2-ylindazol-6-yl)-1,3,5-triazine-2,4-diamine A stirred solution of 6-chloro-N4-(3-phenyloxetan-3-yl)-1,3,5-triazine-2,4-diamine (80 mg, 0.29 mmol), potassium phosphate tribasic (183 mg, 0.86 mmol), and bis[2-(di-tert-butylphosphanyl)cyclopenta-2,4-dien-1-yl]iron; dichloropalladium (19 mg, 0.03 mmol) in tetrahydrofuran (5 mL) and water (0.5 mL) was degassed by bubbling N2 directly into the solution. The mixture was heated up to 80° C. then a solution of 1-tetrahydropyran-2-yl-6-(4,4,5,5-tetramethyl-1,3,2-dioxaborolan-2-yl)indazole Intermediate V (236 mg, 0.72 mmol) in THF was added and the reaction mixture stirred at 80° C. for 12 h. The reaction mixture was concentrated to dryness under reduced pressure and the crude was purified by flash column chromatography (silica gel, eluting with a gradient of 25-100%: ethyl acetate in petroleum ether) to afford the desired compound as a white solid (40 mg, 0.09 mmol, 31% yield). LCMS-MDAP Rt=18.36 min (Method 4); m/z ($ESI^+$) 444.00 $[M+H]^+$.

Step 3: 6-(1H-indazol-6-yl)-N2-(3-phenyloxetan-3-yl)-1,3,5-triazine-2,4-diamine A solution of N2-(3-phenyloxetan-3-yl)-6-(1-tetrahydro-pyran-2-ylindazol-6-yl)-1,3,5-triazine-2,4-di amine (36 mg, 0.08 mmol) in methanol (0.6 mL) was treated with 4 M HCl in 1,4-dioxane (0.2 mL, 0.81 mmol) and heated at 60° C. for 16 h. The resulting precipitate was filtered, washed with 1,4-dioxane, ethyl acetate and diethyl ether, then dried in vacuo at 50° C. for 2 h to afford the desired compound as a white solid. (25 mg, 0.07 mmol, 85% yield). $^1H$ NMR (600 MHz, DMSO-d6) δ 10.91 (s, 1H), 9.48 (s, 1H), 8.92 (s, 1H), 8.57 (s, 1H), 8.19 (s, 1H), 8.04 (dd, J=8.5, 1.4 Hz, 1H), 7.90 (d, J=8.5 Hz, 1H), 7.52-7.38 (m, 3H), 7.37 (dq, J=5.7, 2.8 Hz, 1H), 4.67 (d, J=11.3 Hz, 1H), 4.25 (d, J=11.3 Hz, 1H), 3.85 (d, J=11.5 Hz, 1H), 3.65 (d, J=11.5 Hz, 1H). LCMS-MDAP Rt=10.31 min (Method 4); m/z ($ESI^+$) 359.95 $[M+H]^+$.

Example 106

N2-[[2-Fluoro-3-(2-pyrrolidin-1-ylethoxy)phenyl]methyl]-6-(1H-indazol-6-yl)-1,3,5-triazine-2,4-diamine

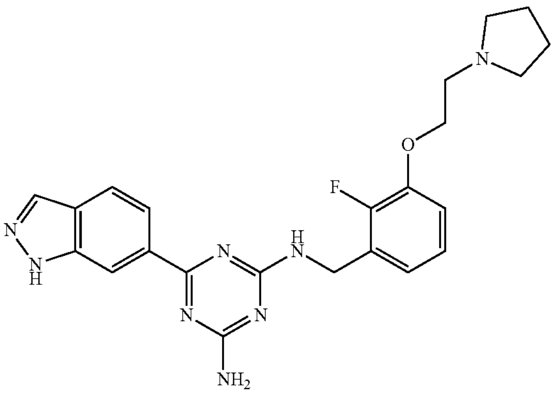 [SMILES: Nc1nc(NCc2cccc(OCCN3CCCC3)c2F)nc(-c2ccc3cn[nH]c3c2)n1]

Step 1: 2-[3-[[[4-Amino-6-(1-tetrahydropyran-2-ylindazol-6-yl)-1,3,5-triazin-2-yl]amino]methyl]-2-fluoro-phenoxy]ethanol A solution of 4-chloro-6-(1-tetrahydropyran-2-ylindazol-6-yl)-1,3,5-triazin-2-amine (Intermediate X) (100 mg, 0.30 mmol), 2-[3-(aminomethyl)-2-fluoro-phenoxy]ethanol (67 mg, 0.36 mmol) and N,N-diisopropylethylamine (0.21 mL, 1.21 mmol) in 1,4-dioxane (10 mL) was heated for 16 h at 80° C. The reaction mixture was loaded onto celite and purified by flash chromatography (silica gel, eluting with a gradient of 0-5% methanol in DCM) to give the title compound as a white solid (123 mg, 0.25 mmol, 82% yield). LCMS LCQ Rt=5.23 min (Method 3); m/z (ESI+) 480.20 $[M+H]^+$.

Step 2: N4-[[3-(2-Chloroethoxy)-2-fluoro-phenyl]methyl]-6-(1-tetrahydropyran-2-ylindazol-6-yl)-1,3,5-triazine-2,4-diamine To a solution of 2-[3-[[[4-amino-6-(1-tetrahydropyran-2-ylindazol-6-yl)-1,3,5-triazin-2-yl]amino]meth yl]-2-fluoro-phenoxy]ethanol (120 mg, 0.25 mmol) in tetrahydrofuran (8.30 mL) and DCM (8.30 mL) was added thionyl chloride (0.18 mL, 2.5 mmol) at RT. The reaction mixture was refluxed for 20 h and then concentrated under reduced pressure. The crude material was azeotroped with toluene (×3) and purified by flash chromatography (silica gel, eluting with a gradient of 0-4% methanol in DCM) to give the title compound as an off-white solid (69 mg, 0.13 mmol, 53% yield). LCMS LCQ Rt=6.74 min (Method 3); m/z (ESI+) 489.19 $[M+H]^+$.

Step 3: N4-[[2-Fluoro-3-(2-pyrrolidin-1-ylethoxy)phenyl]methyl]-6-(1-tetrahydropyran-2-ylindazol-6-yl)-1,3,5-triazine-2,4-diamine A mixture of N4-[[3-(2-chloroethoxy)-2-fluoro-phenyl]methyl]-6-(1-tetrahydropyran-2-ylindazol-6-yl)-1,3,5-triazine-2,4-diamine (65 mg, 0.130 mmol), pyrrolidine (0.27 mL, 3.26 mmol) and potassium carbonate (45 mg, 0.33 mmol) in N,N-dimethylformamide (4.5 mL) was heated at 85° C. for 2 h. The reaction mixture was concentrated under reduced pressure and the crude material purified by flash chromatography (silica gel, eluting with a gradient of 0-10% methanol in DCM) to give the title compound as an off-white solid (50 mg, 0.090 mmol, 68% yield). LCMS LCQ Rt=0.92 min (Method 3); m/z ($ESI^+$) 533.25 $[M+H]^+$.

Step 4: N2-[[2-Fluoro-3-(2-pyrrolidin-1-ylethoxy)phenyl]methyl]-6-(1H-indazol-6-yl)-1,3,5-triazine-2,4-diamine To a solution of N2-[[2-fluoro-3-(2-pyrrolidin-1-ylethoxy)phenyl]methyl]-6-(1-tetrahydropyran-2-ylindazol-6-yl)-1,3,5-triazine-2,4-diamine (25 mg, 0.050 mmol) in methanol (0.35 mL) was added 4 M HCl in 1,4-dioxane (0.14 mL, 0.56 mmol). The reaction mixture was stirred overnight at 40° C. EtOAc was added and the solution sonicated until a precipitate was formed. The precipitate was collected by filtration, washed with EtOAc, and dried to give the title compound as a yellow solid (14 mg, 0.030 mmol, 60% yield).

$^1$H NMR (399 MHz, DMSO-$d_6$, Vt 90° C.) δ 10.95 (s, 1H), 8.55 (s, 1H), 8.12 (s, 1H), 8.02 (d, J=8.5 Hz, 1H), 7.84 (d, J=8.5 Hz, 1H), 7.10 (t, J=7.6 Hz, 3H), 4.69 (s, 2H), 4.45 (t, J=5.1 Hz, 2H), 3.62-3.51 (m, 2H), 3.17-3.05 (m, 4H), 1.97 (m, 4H).

LCMS MDAP Rt=11.38 min; >90% (Method 4); m/z (ESI+) 449.20 $[M+H]^+$.

Example 107

(3R,6S)-1-(4-amino-6-(3-methylimidazo[1,5-a]pyridin-6-yl)-1,3,5-triazin-2-yl)-6-methylpiperidine-3-carboxylic acid Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (60 mg, 230.16 μmol) in 1,4-dioxane (5 mL) was added (3R,6S)-6-methylpiperidine-3-carboxylic acid (32.96 mg, 230.16 μmol) and DIEA (89.23 mg, 690.48 μmol, 120 μL), then the reaction mixture was heated to 120° C. and stirred for 16 hr. The reaction mixture was concentrated under reduced pressure to give a residue. The residue was purified by prep-HPLC to obtain (3R,6S)-1-(4-amino-6-(3-methylimidazo[1,5-a]pyridin-6-yl)-1,3,5-triazin-2-yl)-6-methylpiperidine-3-carboxylic acid (26.2 mg, 31% yield) as a yellow solid.

$^1$H NMR (399 MHz, DMSO-d6): δ=8.81 (s, 1H), 7.54 (br s, 2H), 7.28 (s, 1H), 6.71 (s, 2H), 5.15-4.92 (m, 2H), 2.94 (d, J=7.2 Hz, 1H), 2.65 (s, 3H), 2.35-2.32 (m, 1H), 1.88-1.80 (m, 1H), 1.77-1.70 (m, 1H), 1.69-1.67 (m, 2H), 1.19 (d, J=6.8 Hz, 3H).

LCMS m/z ($ESI^+$) 368.1 $[M+H]^+$.

Example 108

(R)-2-((2-amino-6-(3-methylimidazo[1,5-a]pyridin-6-yl)pyrimidin-4-yl)amino)-3-(2,3-dichlorophenyl)propanoic acid Synthesised by General Method E Using the Following Reagents and Conditions:

To a solution of 4-chloro-6-(3-methylimidazo[1,5-a]pyridin-6-yl)pyrimidin-2-amine (Key Intermediate 3) (60 mg, 239.24 μmol) in 1,4-dioxane (5 mL) was added (R)-2-amino-3-(2,3-dichlorophenyl)propanoic acid (56.0 mg, 239.24 μmol) and DIEA (92.76 mg, 717.73 μmol), then the reaction mixture was heated to 120° C. and stirred for 16 hr. The reaction mixture was concentrated under reduced pressure to give a residue. The residue was purified by prep-HPLC to obtain (R)-2-((2-amino-6-(3-methylimidazo[1,5-a]pyridin-6-yl)pyrimidin-4-yl)amino)-3-(2,3-dichlorophenyl)propanoic acid (27.05 mg, 25.6% yield) as a yellow solid.

$^1$H NMR (399 MHz, DMSO-d6): δ=8.52 (s, 1H), 7.52 (d, J=8.4 Hz, 1H), 7.45 (d, J=8.4 Hz, 1H), 7.40 (d, J=8.0 Hz, 1H), 7.27 (br s, 2H), 7.13 (d, J=8.4 Hz, 1H), 6.96 (d, J=4.0 Hz, 1H), 6.31 (s, 1H), 5.79 (s, 2H), 4.87-4.85 (m, 1H), 3.44-3.41 (m, 2H), 2.67 (s, 3H).

LCMS m/z ($ESI^+$) 457.1 $[M+H]^+$.

Example 109

(3R,6S)-1-(4-amino-6-(3-methylimidazo[1,5-a]pyridin-6-yl)-1,3,5-triazin-2-yl)-N-(2-hydroxyethyl)-6-methylpiperidine-3-carboxamide A solution of (3R,6S)-1-(4-amino-6-(3-methylimidazo[1,5-a]pyridin-6-yl)-1,3,5-triazin-2-yl)-6-methylpiperidine-3-carboxylic acid (Example 107, 50 mg, 136.09 μmol), Et3N (55.08 mg, 544.35 μmol) and HOBt (18.39 mg, 136.09 μmol) in anhydrous DCM was cooled to 0° C., EDCI·HCl (52.18 mg, 272.18 μmol) was added, followed by stirring at 20° C. for 30 minutes. Then Ethanolamine (9.14 mg, 149.70 μmol, HCl) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3) and saturated aqueous sodium chloride (200 mL×3), and dried over Na2SO4, filtered and concentrated under reduced pressure to give a residue. The crude product was purified by re-crystallization from (Petroleum ether:Ethyl acetate=5:1) (120 mL) at 70° C. to give (3R,6S)-1-(4-amino-6-(3-methylimidazo[1,5-a]pyridin-6-yl)-1,3,5-triazin-2-yl)-N-(2-hydroxyethyl)-6-methylpiperidine-3-carboxamide (15.76 mg, 28.22% yield) as a white solid.

$^1$H NMR (399 MHz, DMSO-d6): δ=8.81 (s, 1H), 7.69 (s, 1H), 7.52 (s, 2H), 7.28 (s, 1H), 6.69 (s, 2H), 5.16 (br s, 1H), 4.76 (br s, 1H), 4.43 (t, J=4.8 Hz, 1H), 3.48-3.44 (m, 2H), 3.19-3.16 (m, 2H), 3.00 (t, J=7.2 Hz, 1H), 2.65 (s, 3H), 2.33-2.31 (m, 1H), 1.85-1.74 (m, 1H), 1.74-1.67 (m, 3H), 1.20 (d, J=6.8 Hz, 3H).

LCMS m/z ($ESI^+$) 411.2 $[M+H]^+$.

Example 110

(3R,6S)-1-(4-amino-6-(3-methylimidazo[1,5-a]pyridin-6-yl)-1,3,5-triazin-2-yl)-6-methyl-N-(pyridin-2-yl)piperidine-3-carboxamide A solution of (3R,6S)-1-(4-amino-6-(3-methylimidazo[1,5-a]pyridin-6-yl)-1,3,5-triazin-2-yl)-6-methylpiperidine-3-carboxylic acid (Example 107, 50 mg, 136.09 μmol), Et3N (55.08 mg, 544.35 μmol) and HOBt (18.39 mg, 136.08 μmol) in anhydrous DCM was cooled to 0° C., EDCI·HCl (52.18 mg, 272.18 μmol) was added, followed by stirring at 20° C. for 30 minutes. Then pyridine-2-amine hydrochloride (19.55 mg, 149.70 μmol, HCl) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3)

and saturated aqueous sodium chloride (200 mL×3), and dried over Na2SO4, filtered and concentrated under reduced pressure to give a residue. The crude product was purified by re-crystallization from (Petroleum ether:Ethyl acetate=5:1) (120 mL) at 70° C. to give (3R,6S)-1-(4-amino-6-(3-methylimidazo[1,5-a]pyridin-6-yl)-1,3,5-triazin-2-yl)-6-methyl-N-(pyridin-2-yl)piperidine-3-carboxamide (23.8 g, 39.5% yield) as a white solid.

$^1$H NMR (399 MHz, DMSO-d6): δ=10.31 (s, 1H), δ=8.83 (s, 1H), 8.31 (d, J=4.4 Hz, 1H), 8.09 (d, J=7.2 Hz, 1H), 7.78 (t, J=7.2 Hz, 1H), 7.53 (s, 2H), 7.28 (s, 1H), 7.10 (t, J=6.0 Hz, 1H), 6.73 (s, 2H), 5.20 (br s, 1H), 4.89 (br s, 1H), 2.39-2.64 (m, 5H), 2.02-1.89 (m, 2H), 1.85-1.70 (m, 2H), 1.23 (d, J=6.4 Hz, 3H).

LCMS m/z (ESI$^+$) 444.2 [M+H]$^+$.

Example 111

(3R,6S)-1-(4-amino-6-(3-methylimidazo[1,5-a]pyridin-6-yl)-1,3,5-triazin-2-yl)-N-cyclohexyl-6-methylpiperidine-3-carboxamide A solution of (3R,6S)-1-(4-amino-6-(3-methylimidazo[1,5-a]pyridin-6-yl)-1,3,5-triazin-2-yl)-6-methylpiperidine-3-carboxylic acid (Example 107, 50 mg, 136.09 μmol), Et3N (55.08 mg, 544.35 μmol) and HOBt (18.39 mg, 136.09 μmol) in anhydrous DCM was cooled to 0° C., EDCI·HCl (52.18 mg, 272.18 μmol) was added, followed by stirring at 20° C. for 30 minutes. Then Cyclohexylamine (20.3 mg, 149.70 μmol, HCl) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3) and saturated aqueous sodium chloride (200 mL×3), and dried over Na2SO4, filtered and concentrated under reduced pressure to give a residue. The crude product was purified by re-crystallization from (Petroleum ether:Ethyl acetate=5:1) (120 mL) at 70° C. to give (3R,6S)-1-(4-amino-6-(3-methylimidazo[1,5-a]pyridin-6-yl)-1,3,5-triazin-2-yl)-N-(2-hydroxyethyl)-6-methylpiperidine-3-carboxamide (18.86 mg, 30.9% yield) as a white solid.

$^1$H NMR (399 MHz, DMSO-d6): δ=8.82 (s, 1H), 7.55-7.49 (m, 3H), 7.28 (s, 1H), 6.68 (s, 2H), 5.15 (br s, 1H), 4.74 (br s, 1H), 3.59-3.55 (m, 1H), 3.00 (t, J=7.2 Hz, 1H), 2.65 (s, 3H), 2.32-2.28 (m, 1H), 1.77-1.68 (m, 8H), 1.31-1.19 (m, 9H).

LCMS m/z (ESI$^+$) 449.3 [M+H]$^+$.

Example 112

(3R,6S)-1-(4-amino-6-(3-methylimidazo[1,5-a]pyridin-6-yl)-1,3,5-triazin-2-yl)-6-methyl-N-phenylpiperidine-3-carboxamide A solution of (3R,6S)-1-(4-amino-6-(3-methylimidazo[1,5-a]pyridin-6-yl)-1,3,5-triazin-2-yl)-6-methylpiperidine-3-carboxylic acid (Example 107, 50 mg, 136.09 μmol), Et3N (55.08 mg, 544.35 μmol) and HOBt (18.39 mg, 136.09 μmol) in anhydrous DCM was cooled to 0° C., EDCI·HCl (52.18 mg, 272.18 μmol) was added, followed by stirring at 20° C. for 30 minutes. Then Aniline (13.94 mg, 149.70 μmol) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3) and saturated aqueous sodium chloride (200 mL×3), and dried over Na2SO4, filtered and concentrated under reduced pressure to give a residue. The crude product was purified by re-crystallization from (Petroleum ether:Ethyl acetate=5:1) (120 mL) at 70° C. to give (3R,6S)-1-(4-amino-6-(3-methylimidazo[1,5-a]pyridin-6-yl)-1,3,5-triazin-2-yl)-N-(2-hydroxyethyl)-6-methylpiperidine-3-carboxamide (15.36 mg, 25.5% yield) as a white solid.

$^1$H NMR (399 MHz, DMSO-d6): δ=9.84 (s, 1H), 8.84 (s, 1H), 7.62 (d, J=8.0 Hz, 2H), 7.53 (s, 2H), 7.33-7.28 (m, 3H), 7.06 (t, J=7.2 Hz, 1H), 6.73 (s, 2H), 5.20 (br s, 1H), 4.89 (br s, 1H), 3.10-3.05 (m, 2H), 2.64 (s, 3H), 2.02-1.85 (m, 2H), 1.87-1.73 (m, 2H), 1.24 (d, J=6.8 Hz, 3H).

LCMS m/z (ESI$^+$) 443.2 [M+H]$^+$.

Example 113

6-(4-amino-6-((2-(1-(difluoromethyl)-1H-pyrazol-3-yl)propan-2-yl)amino)-1,3,5-triazin-2-yl)imidazo[1,5-a]pyridine-3-carbonitrile

Step 1: tert-butyl (2-(1-(difluoromethyl)-1H-pyrazol-3-yl)propan-2-yl)carbamate KF (1.03 g, 17.75 mmol) and tert-butyl (2-(1H-pyrazol-3-yl)propan-2-yl)carbamate (2 g, 8.88 mmol) were combined in a flask under $N_2$. Acetonitrile (16 mL) was then added followed by 1-[[bromo(difluoro)methyl]-ethoxy-phosphoryl]oxyethane (3.56 g, 13.32 mmol). The reaction mixture was stirred at 20° C. for 16 h. The reaction mixture was diluted with DCM (50 mL) and $H_2O$ (50 mL) and extracted with DCM (50 mL×3). The combined organic layers were washed with brine (50 mL×3), dried over anhydrous $Na_2SO_4$, filtered and concentrated under reduced pressure to give a residue. The residue was purified by flash silica gel chromatography to give tert-butyl (2-(1-(difluoromethyl)-1H-pyrazol-3-yl)propan-2-yl)carbamate (2.44 g, crude) as a light yellow oil.

LCMS m/z (ESI$^+$) 276.1 [M+H]$^+$.

Step 2: 2-(1-(difluoromethyl)-1H-pyrazol-3-yl)propan-2-amine

To a solution of tert-butyl (2-(1-(difluoromethyl)-1H-pyrazol-3-yl)propan-2-yl)carbamate (2 g, 7.26 mmol) in DCM (10 mL), HCl/1,4-dioxane (1 M, 14.53 mL) was added, and the reaction mixture was stirred at 20° C. for 16 h. The reaction mixture was concentrated under reduced pressure. The residue was diluted with 1M NaOH solution (35 mL) and extracted with DCM (30 mL×3). The combined organic layers were washed with brine (30 mL×3), dried over anhydrous Na2SO4, filtered and concentrated under reduced pressure to give 2-(1-(difluoromethyl)-1H-pyrazol-3-yl)propan-2-amine (780 mg, 61.4% yield) as a yellow oil.

LCMS m/z (ESI$^+$) 176.1 [M+H]$^+$.

Step 3: 6-chloro-N2-(2-(1-(difluoromethyl)-1H-pyrazol-3-yl)propan-2-yl)-1,3,5-triazine-2,4-diamine To a solution of 2-(1-(difluoromethyl)-1H-pyrazol-3-yl)propan-2-amine (743.28 mg, 4242.94 μmol) and 4,6-dichloro-1,3,5-triazin-2-amine (700 mg, 4242.94 μmol, HCl) in 1,4-dioxane (40 mL), then DIEA (1.65 g, 12.73 mmol) was added, the mixture was stirred at 120° C. for 16 hr. The reaction mixture was partitioned between $H_2O$ (100 mL) and ethyl acetate (100 mL×3). The organic phase was separated, washed with brine (80 mL), dried over $Na_2SO_4$, filtered and concentrated under reduced pressure to give a residue. The residue was purified by flash silica gel chromatography to give 6-chloro-N2-(2-(1-(difluoromethyl)-1H-pyrazol-3-yl)propan-2-yl)-1,3,5-triazine-2,4-di amine (975 mg, 75.7% yield) as a yellow solid.

LCMS m/z ($ESI^+$) 304.1 $[M+H]^+$.

Step 4: 6-(4-amino-6-((2-(1-(difluoromethyl)-1H-pyrazol-3-yl)propan-2-yl)amino)-1,3,5-triazin-2-yl)imidazo[1,5-a]pyridine-3-carbonitrile 6-chloro-N2-(2-(1-(difluoromethyl)-1H-pyrazol-3-yl)propan-2-yl)-1,3,5-triazine-2,4-diamine (100 mg, 329.27 μmol), 6-(4,4,5,5-tetramethyl-1,3,2-dioxaborolan-2-yl)imidazo[1,5-a]pyridine-3-carbonitrile (177.22 mg, 658.54 μmol) and K3PO4 (139.79 mg, 658.54 μmol) were dissolved in THF (2 mL) and H2O (0.2 mL) and degassed with N2 for 5 min before the addition of ditert-butyl(cyclopentyl)phosphane; dichloropalladium; iron (10.73 mg, 16.46 μmol). The mixture was degassed for a further 2 min before heating to 90° C. for 18 h. The reaction was concentrated under reduced pressure to give residue. The residue was diluted with ACETONITRILE (1 mL). The crude product was purified by reversed-phase HPLC to give 6-(4-amino-6-((2-(1-(difluoromethyl)-1H-pyrazol-3-yl)propan-2-yl)amino)-1,3,5-triazin-2-yl)imidazo[1,5-a]pyridine-3-carbonitrile (29.53 mg, 21.85% yield) as a yellow solid.

$^1$H NMR (399 MHz, DMSO-d6) δ=9.10 (s, 1H), 7.98 (d, J=2.4 Hz, 1H), 7.87 (d, J=8.8 Hz, 1H), 7.74 (br s, 2H), 7.67 (t, J=60.0 Hz, 1H), 7.28 (s, 1H), 6.71 (br s, 2H), 6.45 (d, J=2.0 Hz, 1H), 1.76 (s, 6H).

LCMS m/z (ESI+) 411.1 [M+H]+.

Example 114

6-(3-methylimidazo[1,5-a]pyridin-6-yl)-N2-(1-(4-(trifluoromethyl)-1H-imidazol-2-yl)ethyl)-1,3,5-triazine-2,4-diamine Step 1: tert-butyl 2-acetyl-4-(trifluoromethyl)-1H-imidazole-1-carboxylate 1-(4-(trifluoromethyl)-1H-imidazol-2-yl)ethan-1-one (1 g, 5.614 mmol), triethylamine (1.14 g, 11.23 mmol) were added to Tetrahydrofuran (20 mL). Then, slowly adding t-butylchloroformate (0.92 g, 6.74 mmol). After 4 hrs, the mixture was diluted by addition H2O (15 mL). The aqueous layer was extracted with ethyl acetate (30 mL×3). The combined organic layers were washed with brine (30 mL), dried over anhydrous Na2SO4, concentrated in vacuo to give the crude product. The residue was purified by silica gel column chromatography to give tert-butyl 2-acetyl-4-(trifluoromethyl)-1H-imidazole-1-carboxylate (1.32 g, 84.71% yield) as a yellow solid.

LCMS m/z (ESI+) 279.0 [M+H]+.

Step 2: tert-butyl 2-(1-aminoethyl)-4-(trifluoromethyl)-1H-imidazole-1-carboxylate Tert-butyl 2-acetyl-4-(trifluoromethyl)-1H-imidazole-1-carboxylate (1 g, 3.59 mmol), titanium(IV) isopropoxide (2.04 g, 7.19 mmol), ammonium chloride (0.38 g, 7.19 mmol) and triethylamine (0.73 g, 7.19 mmol) in ethanol (20 mL) was stirred at room temperature for 16 h. Sodium borohydride (0.20 g, 5.39 mmol) and was then added and the resulting mixture was stirred for an additional 7-8 h at room temperature. The reaction was then quenched by pouring into aqueous ammonia (20 mL). The aqueous layer was extracted with dichloromethane (30 mL×3). The combined organic layers were washed with brine (30 mL), dried over anhydrous Na2SO4, concentrated in vacuo to give the crude product. The residue was purified by silica gel column chromatography to give tert-butyl 2-(1-aminoethyl)-4-(trifluoromethyl)-1H-imidazole-1-carboxylate (0.72 g, 71.53% yield) as a yellow solid.

LCMS m/z (ESI+) 280.1 [M+H]+.

Step 3: tert-butyl 2-(1-((4-amino-6-(3-methylimidazo[1,5-a]pyridin-6-yl)-1,3,5-triazin-2-yl)amino)ethyl)-4-(trifluoromethyl)-1H-imidazole-1-carboxylate tert-butyl 2-(1-aminoethyl)-4-(trifluoromethyl)-1H-imidazole-1-carboxylate (200 mg, 767.19 μmol), 4-chloro-6-(3-methylimidazo[1,5-a]pyridin-6-yl)-1,3,5-triazin-2-amine (Key Intermediate 2) (150.52 mg, 767.19 μmol) and DIEA (297.46 mg, 2301.58 μmol) were taken up into a microwave tube in 1,4-dioxane (5 mL). The sealed tube was heated at 120° C. for 1 h under microwave. The mixture was diluted by addition H2O (30 mL). The aqueous layer was extracted with ethyl acetate (70 mL×3). The combined organic layers were washed with brine (50 mL), dried over anhydrous Na2SO4, concentrated in vacuo to give the crude product. The residue was purified by prep-HPLC to give tert-butyl 2-(1-((4-amino-6-(3-methylimidazo[1,5-a]pyridin-6-yl)-1,3,5-triazin-2-yl)amino)ethyl)-4-(trifluoromethyl)-1H-imidazole-1-carboxylate (113.22 mg, 31.4% yield) as a yellow solid.

LCMS m/z (ESI+) 504.1 [M+H]+.

Step 4: 6-(3-methylimidazo[1,5-a]pyridin-6-yl)-N2-(1-(4-(trifluoromethyl)-1H-imidazol-2-yl)ethyl)-1,3,5-triazine-2,4-diamine To a solution of tert-butyl 2-(1-((4-amino-6-(3-methylimidazo[1,5-a]pyridin-6-yl)-1,3,5-triazin-2-yl)amino)ethyl)-4-(trifluoromethyl)-1H-imidazole-1-carboxylate (100 mg, 198.61 μmol) in DCM (1 mL), HCl/1,4-dioxane (1 M, 0.4 mL) was added, and the reaction mixture was stirred at 20° C. for 16 h. The reaction mixture was concentrated under reduced pressure. The residue was diluted with 1M NaOH solution (0.5 mL) and extracted with DCM (20 mL×3). The combined organic layers were washed with brine (20 mL×3), dried over anhydrous Na2SO4, filtered and concentrated under reduced pressure to give 6-(3-methylimidazo[1,5-a]pyridin-6-yl)-N2-(1-(4-(trifluoromethyl)-1H-imidazol-2-yl)ethyl)-1,3,5-triazine-2,4-diamine (56.7 mg, 70.8% yield) as a yellow oil.

$^1$H NMR (399 MHz, DMSO-d6) δ=12.25 (s, 1H), 8.83 (s, 1H), 8.13 (s, 1H), 7.55 (s, 3H), 7.38 (s, 2H), 6.76 (br s, 2H), 5.36-5.34 (m, 1H), 2.69 (s, 3H), 1.56 (d, J=7.2 Hz, 3H).

m/z (ESI+) 404.1 [M+H]+.

Example 115

(R)—N2-(cyclopropyl(1-(difluoromethyl)-1H-pyrazol-3-yl)methyl)-6-(3-methylimidazo[1,5-a]pyridin-6-yl)-1,3,5-triazine-2,4-diamine Synthesised by General Method F Using the Following Reagents and Conditions:

Step 1: (R)-(1-cyclopropyl-2-(methoxy(methyl)amino)-2-oxoethyl)carbamate

A solution of (R)-2-((tert-butoxycarbonyl)amino)-2-cyclopropylacetic acid (10 g, 46.46 mmol), Et3N (18.80 g, 185.83 mmol) and HOBt (6.28 g, 46.46 mmol) in anhydrous DCM was cooled to 0° C., EDCI·HCl (17.81 g, 92.92 mmol) was added, followed by stirring at 20° C. for 30 minutes. Then N-methoxymethanamine (4.76 g, 51.10 mmol, HCl) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3) and saturated aqueous sodium chloride (200 mL×3), and dried over Na2SO4, filtered and concentrated under reduced pressure to give a residue. The crude product was purified by re-crystallization from (Petroleum ether:Ethyl acetate=5:1) (120 mL) at 70° C. to give tert-butyl (R)-(1-cyclopropyl-2-(methoxy(methyl)amino)-2-oxoethyl)carbamate (7.56 g, 60.7% yield) as a white solid.

LCMS m/z (ESI+) 259.1 [M+H]+.

Step 2: tert-butyl (S)-(1-cyclopropyl-2-oxobut-3-yn-1-yl)carbamate

A solution of tert-butyl (R)-(1-cyclopropyl-2-(methoxy (methyl)amino)-2-oxoethyl)carbamate (7 g, 27.10 mmol) in THF (70 mL) was cooled to −78° C. under nitrogen, bromo(ethynyl)magnesium (0.5 M, 216.79 mL) was added dropwise, and the mixture was stirred at −78° C. for 1 hr. Then the mixture was allowed to warm to 20° C. and stirred for another 16 hr. The mixture was poured into a cold (0° C.) sat. NH4Cl solution (150 mL) and stirred for 1 h. THF was evaporated in vacuo (35° C.), and the aqueous layer was extracted with EtOAc (300 mL). The combined organic phase was washed successively with sat. aq. $NaHCO_3$ (150 mL), and brine (150 mL×3), dried over anhydrous Na2SO4, filtered, and the filtrate was evaporated in vacuo (40° C.). The residue was purified by flash silica gel chromatography to give tert-butyl (R)-(1-cyclopropyl-2-oxobut-3-yn-1-yl) carbamate (2.06 g, 34.07% yield) as a yellow oil.

LCMS m/z (ESI+) 224.1 [M+H]+.

Step 3: tert-butyl (R)-(cyclopropyl(1H-pyrazol-3-yl) methyl)carbamate tert-butyl (R)-(1-cyclopropyl-2-oxobut-3-yn-1-yl)carbamate (2 g, 8.96 mmol) was dissolved in EtOH (20 mL), NH2NH2·H2O (0.86 g, 26.87 mmol) was added and the reaction mixture was heated to 80° C. for 30 min then allowed to cool to 20° C. for 0.5 h. The reaction mixture was diluted with EtOAc (150 mL) and extracted with EtOAc (150 mL×3). The combined organic layers were dried over anhydrous Na2SO4, filtered and concentrated under reduced pressure (30° C.) to give a residue. The residue was purified by flash silica gel chromatography to give tert-butyl (R)-(cyclopropyl(1H-pyrazol-3-yl)methyl)carbamate (1.94 g, 91.2% yield) as a yellow oil.

LCMS m/z (ESI+) 238.1 [M+H]+.

Step 4: tert-butyl (R)-(cyclopropyl(1-(difluoromethyl)-1H-pyrazol-3-yl)methyl)carbamate KF (0.88 g, 15.17 mmol) and tert-butyl (R)-(cyclopropyl (1H-pyrazol-3-yl)methyl)carbamate (1.8 g, 7.59 mmol) were combined in a flask under N2. Acetonitrile (18 mL) was then added followed by 1-[[bromo(difluoro)methyl]-ethoxy-phosphoryl]oxyethane (3.04 g, 11.38 mmol). The reaction mixture was stirred at 20° C. for 16 h. The reaction mixture was diluted with DCM (50 mL) and H2O (50 mL) and extracted with DCM (50 mL×3). The combined organic layers were washed with brine (50 mL×3), dried over anhydrous Na2SO4, filtered and concentrated under reduced pressure to give a residue. The residue was purified by flash silica gel chromatography to give tert-butyl (R)-(cyclopropyl(1-(difluoromethyl)-1H-pyrazol-3-yl)methyl)carbamate (2.18 g, crude) as a light yellow oil.

LCMS m/z (ESI+) 288.1 [M+H]+.

Step 5: (R)-cyclopropyl(1-(difluoromethyl)-1H-pyrazol-3-yl)methanamine

To a solution of tert-butyl (R)-(cyclopropyl(1-(difluoromethyl)-1H-pyrazol-3-yl)methyl)carbamate (2 g, 6.96 mmol) in DCM (10 mL), HCl/1,4-dioxane (1 M, 13.92 mL) was added, and the reaction mixture was stirred at 20° C. for 16 h. The reaction mixture was concentrated under reduced pressure. The residue was diluted with 1M NaOH solution (35 mL) and extracted with DCM (30 mL×3). The combined organic layers were washed with brine (30 mL×3), dried over anhydrous Na2SO4, filtered and concentrated under reduced pressure to give (R)-cyclopropyl(1-(difluoromethyl)-1H-pyrazol-3-yl)methanamine (1.92 g, 68% yield) as a yellow oil.

LCMS m/z (ESI+) 188.1 [M+H]+.

Step 6: (R)—N2-(cyclopropyl(1-(difluoromethyl)-1H-pyrazol-3-yl)methyl)-6-(3-methylimidazo[1,5-a] pyridin-6-yl)-1,3,5-triazine-2,4-diamine (R)-cyclopropyl(1-(difluoromethyl)-1H-pyrazol-3-yl) methanamine (57.44 mg, 306.88 μmol), 4-chloro-6-(3-methylimidazo[1,5-a]pyridin-6-yl)-1,3,5-triazin-2-amine (Key Intermediate 2) (80 mg, 306.88 μmol) and DIEA (118.99 mg, 920.63 μmol) were taken up into a microwave tube in 1,4-dioxane (2 mL). The sealed tube was heated at 120° C. for 1 h under microwave. The mixture was diluted by addition H2O (15 mL). The aqueous layer was extracted with ethyl acetate (30 mL×3). The combined organic layers were washed with brine (30 mL), dried over anhydrous Na2SO4, concentrated in vacuo to give the crude product. The residue was purified by prep-HPLC to give (R)—N2-(cyclopropyl(1-(difluoromethyl)-1H-pyrazol-3-yl)methyl)-6-(3-methylimidazo[1,5-a]pyridin-6-yl)-1,3,5-triazine-2,4-diamine (42.67 mg, 33.8% yield) as a yellow solid.

$^1$H NMR (399 MHz, DMSO-d6) δ=8.80 (s, 1H), 8.07 (d, J=2.8 Hz, 1H), 7.68 (t, J=59.6 Hz, 1H), 7.50 (s, 1H), 7.47 (br s, 2H), 7.28 (s, 1H), 6.64 (br s, 2H), 6.60 (d, J=2.8 Hz, 1H), 4.86 (t, J=8.4 Hz, 1H), 2.65 (s, 3H), 1.40-1.36 (m, 1H), 0.56-0.51 (m, 3H), 0.50-0.47 (m, 1H).

LCMS m/z (ESI+) 412.1 [M+H]+.

Example 116

(R)—N2-(1-(1-(difluoromethyl)-1H-pyrazol-3-yl)-2-methylpropyl)-6-(3-methylimidazo[1,5-a]pyridin-6-yl)-1,3,5-triazine-2,4-diamine Synthesised by General Method F Using the Following Reagents and Conditions:

Step 1: tert-butyl (R)-(1-(methoxy(methyl)amino)-3-methyl-1-oxobutan-2-yl)carbamate A solution of (tert-butoxycarbonyl)-D-valine (10 g, 46.03 mmol), Et3N (18.63 g, 184.10 mmol) and HOBt (6.22 g, 46.03 mmol) in anhydrous DCM was cooled to 0° C., EDCI·HCl (17.64 g, 92.05 mmol) was added, followed by stirring at 20° C. for 30 minutes. Then N-methoxymethanamine (4.72 g, 50.63 mmol, HCl) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3) and saturated aqueous sodium chloride (200 mL×3), and dried over Na2SO4, filtered and concentrated under reduced pressure to give a residue. The crude product was purified by re-crystallization from (Petroleum ether:Ethyl acetate=5:1) (120 mL) at 70° C. to give tert-butyl (R)-(1-(methoxy(methyl)amino)-3-methyl-1-oxobutan-2-yl)carbamate (7.63 g, 63.7% yield) as a white solid.

LCMS m/z (ESI+) 261.1 [M+H]+.

Step 2: tert-butyl (R)-(2-methyl-4-oxohex-5-yn-3-yl)carbamate

A solution of tert-butyl (R)-(1-(methoxy(methyl)amino)-3-methyl-1-oxobutan-2-yl)carbamate (7.5 g, 28.81 mmol) in THF (75 mL) was cooled to −78° C. under nitrogen, bromo(ethynyl)magnesium (0.5 M, 230.48 mL) was added dropwise, and the mixture was stirred at −78° C. for 1 hr. Then the mixture was allowed to warm to 20° C. and stirred for another 16 hr. The mixture was poured into a cold (0° C.) sat. NH4Cl solution (150 mL) and stirred for 1 h. THF was evaporated in vacuo (35° C.), and the aqueous layer was extracted with EtOAc (300 mL). The combined organic phase was washed successively with sat. aq. $NaHCO_3$ (150 mL), and brine (150 mL×3), dried over anhydrous Na2SO4, filtered, and the filtrate was evaporated in vacuo (40° C.). The residue was purified by flash silica gel chromatography to give tert-butyl (R)-(2-methyl-4-oxohex-5-yn-3-yl)carbamate (1.82 g, 28% yield) as a yellow oil.

LCMS m/z (ESI+) 226.1 [M+H]+.

Step 3: tert-butyl (R)-(2-methyl-1-(1H-pyrazol-3-yl)propyl)carbamate tert-butyl (R)-(2-methyl-4-oxohex-5-yn-3-yl)carbamate (1.5 g, 6.66 mmol) was dissolved in EtOH (15 mL), NH2NH2·H2O (0.64 g, 19.97 mmol) was added and the reaction mixture was heated to 80° C. for 30 min then allowed to cool to 20° C. for 0.5 h. The reaction mixture was diluted with EtOAc (150 mL) and extracted with EtOAc (150 mL×3). The combined organic layers were dried over anhydrous Na2SO4, filtered and concentrated under reduced pressure (30° C.) to give a residue. The residue was purified by flash silica gel chromatography to give tert-butyl (R)-(2-methyl-1-(1H-pyrazol-3-yl)propyl)carbamate (1.51 g, 94.8% yield) as a yellow oil.

LCMS m/z (ESI+) 240.0 [M+H]+.

Step 4: tert-butyl (R)-(1-(1-(difluoromethyl)-1H-pyrazol-3-yl)-2-methylpropyl)carbamate KF (0.58 g, 10.02 mmol) and tert-butyl (R)-(2-methyl-1-(1H-pyrazol-3-yl)propyl)carbamate (1.2 g, 5.01 mmol) were combined in a flask under N2. Acetonitrile (12 mL) was then added followed by 1-[[bromo(difluoro)methyl]-ethoxy-phosphoryl]oxyethane (2 g, 7.52 mmol). The reaction mixture was stirred at 20° C. for 16 h. The reaction mixture was diluted with DCM (50 mL) and H2O (50 mL) and extracted with DCM (50 mL×3). The combined organic layers were washed with brine (50 mL×3), dried over anhydrous Na2SO4, filtered and concentrated under reduced pressure to give a residue. The residue was purified by flash silica gel chromatography to give tert-butyl (R)-(1-(1-(difluoromethyl)-1H-pyrazol-3-yl)-2-methylpropyl)carbamate (1.45 g, crude) as a light yellow oil.

LCMS m/z (ESI+) 290.0 [M+H]+.

Step 5: (R)-1-(1-(difluoromethyl)-1H-pyrazol-3-yl)-2-methylpropan-1-amine

To a solution of tert-butyl (R)-(1-(1-(difluoromethyl)-1H-pyrazol-3-yl)-2-methylpropyl)carbamate (1.2 g, 4.15 mmol) in DCM (10 mL), HCl/1,4-dioxane (1 M, 8.30 mL) was added, and the reaction mixture was stirred at 20° C. for 16 h. The reaction mixture was concentrated under reduced pressure. The residue was diluted with 1M NaOH solution (15 mL) and extracted with DCM (30 mL×3). The combined organic layers were washed with brine (30 mL×3), dried over anhydrous Na2SO4, filtered and concentrated under reduced pressure to give (R)-1-(1-(difluoromethyl)-1H-pyrazol-3-yl)-2-methylpropan-1-amine (812 mg, 71.4% yield) as a yellow oil.

LCMS m/z (ESI+) 190.0 [M+H]+.

Step 6: (R)—N2-(1-(1-(difluoromethyl)-1H-pyrazol-3-yl)-2-methylpropyl)-6-(3-methylimidazo[1,5-a]pyridin-6-yl)-1,3,5-triazine-2,4-diamine 4-chloro-6-(3-methylimidazo[1,5-a]pyridin-6-yl)-1,3,5-triazin-2-amine (Key Intermediate 2) (80 mg, 306.88 μmol), (R)-1-(1-(difluoromethyl)-1H-pyrazol-3-yl)-2-methylpropan-1-amine (58.06 mg, 306.88 μmol) and DIEA (118.98 mg, 920.63 μmol) were taken up into a microwave tube in 1,4-dioxane (4 mL). The sealed tube was heated at 120° C. for 1 h under microwave. The mixture was diluted by addition H2O (15 mL). The aqueous layer was extracted with ethyl acetate (30 mL×3). The combined organic layers were washed with brine (30 mL), dried over anhydrous Na2SO4, concentrated in vacuo to give the crude product. The residue was purified by prep-HPLC to give (R)—N2-(1-(1-(difluoromethyl)-1H-pyrazol-3-yl)-2-methylpropyl)-6-(3-methylimidazo[1,5-a]pyridin-6-yl)-1,3,5-triazine-2,4-diamine (30.8 mg, 17.62% yield) as a yellow solid.

$^1$H NMR (399 MHz, DMSO-d6) δ=8.82 (s, 1H), 8.24 (s, 1H), 8.07 (d, J=2.8 Hz, 1H), 7.68 (t, J=60.0 Hz, 1H), 7.53 (s, 2H), 7.35 (br s, 1H), 7.29 (s, 1H), 6.69 (br s, 2H), 6.59 (s, 1H), 5.16 (t, J=8.0 Hz, 1H), 2.66 (s, 3H), 2.24-2.16 (m, 1H), 0.99 (d, J=6.4 Hz, 3H), 0.87 (d, J=6.4 Hz, 3H).

LCMS m/z (ESI+) 414.0 [M+H]+.

Example 117

(R)—N2-(1-(1-(difluoromethyl)-1H-pyrazol-3-yl)propyl)-6-(3-methylimidazo[1,5-a]pyridin-6-yl)-1,3,5-triazine-2,4-diamine Synthesised by General Method F Using the Following Reagents and Conditions:

Step 1: tert-butyl (R)-(1-(methoxy(methyl)amino)-1-oxobutan-2-yl)carbamate

A solution of (R)-2-((tert-butoxycarbonyl)amino)butanoic acid (10 g, 49.20 mmol), Et3N (19.92 g, 196.81 mmol) and HOBt (6.65 g, 49.20 mmol) in anhydrous DCM was cooled to 0° C., EDCI·HCl (18.86 g, 98.4 mmol) was added, followed by stirring at 20° C. for 30 minutes. Then N-methoxymethanamine (5.28 g, 54.12 mmol, HCl) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3) and saturated aqueous sodium chloride (200 mL×3), and dried over Na2SO4, filtered and concentrated under reduced pressure to give a residue. The crude product was purified by re-crystallization from (Petroleum ether: Ethyl acetate=4:1) (120 mL) at 70° C. to give tert-butyl (R)-(1-(methoxy(methyl)amino)-1-oxobutan-2-yl)carbamate (7.15 g, 59% yield) as a white solid.

LCMS m/z (ESI+) 247.1 [M+H]+.

Step 2: tert-butyl (R)-(4-oxohex-5-yn-3-yl)carbamate

A solution of tert-butyl (R)-(1-(methoxy(methyl)amino)-1-oxobutan-2-yl)carbamate (7 g, 28.41 mmol) in THF (70 mL) was cooled to −78° C. under nitrogen, bromo(ethynyl) magnesium (0.5 M, 227.36 mL) was added dropwise, and the mixture was stirred at −78° C. for 1 hr. Then the mixture was allowed to warm to 20° C. and stirred for another 16 hr. The mixture was poured into a cold (0° C.) sat. NH4Cl solution (150 mL) and stirred for 1 h. THF was evaporated in vacuo (35° C.), and the aqueous layer was extracted with EtOAc (300 mL). The combined organic phase was washed successively with sat. aq. $NaHCO_3$ (150 mL), and brine (150 mL×3), dried over anhydrous Na2SO4, filtered, and the filtrate was evaporated in vacuo (40° C.). The residue was purified by flash silica gel chromatography to give tert-butyl (R)-(4-oxohex-5-yn-3-yl)carbamate (1.74 g, 29% yield) as a yellow oil.

LCMS m/z (ESI+) 212.1 [M+H]+.

Step 3: tert-butyl (R)-(1-(1H-pyrazol-3-yl)propyl) carbamate tert-butyl (R)-(4-oxohex-5-yn-3-yl)carbamate (1.5 g, 7.10 mmol) was dissolved in EtOH (15 mL), NH2NH2·H2O (0.68 g, 21.30 mmol) was added and the reaction mixture was heated to 80° C. for 30 min then allowed to cool to 20° C. for 0.5 h. The reaction mixture was diluted with EtOAc (150 mL) and extracted with EtOAc (150 mL×3). The combined organic layers were dried over anhydrous Na2SO4, filtered and concentrated under reduced pressure (30° C.) to give a residue. The residue was purified by flash silica gel chromatography to give tert-butyl (R)-(1-(1H-pyrazol-3-yl)propyl)carbamate (1.03 g, 96% yield) as a yellow oil.

LCMS m/z (ESI+) 226.1 [M+H]+.

Step 4: tert-butyl (R)-(1-(1-(difluoromethyl)-1H-pyrazol-3-yl)propyl)carbamate

KF (1.10 g, 18.93 mmol, 443.55 μL) and tert-butyl (R)-(1-(1H-pyrazol-3-yl)propyl)carbamate (1 g, 4.44 mmol) were combined in a flask under N2. Acetonitrile (8 mL) was then added followed by 1-[[bromo(difluoro)methyl]-ethoxy-phosphoryl]oxyethane (1.78 g, 6.66 mmol). The reaction mixture was stirred at 20° C. for 16 h. The reaction mixture was diluted with DCM (50 mL) and H2O (50 mL) and extracted with DCM (50 mL×3). The combined organic layers were washed with brine (50 mL×3), dried over anhydrous Na2SO4, filtered and concentrated under reduced pressure to give a residue. The residue was purified by flash silica gel chromatography to give tert-butyl (R)-(1-(1-(difluoromethyl)-1H-pyrazol-3-yl)propyl)carbamate (1.27 g, crude) as a light yellow oil.

LCMS m/z (ESI+) 276.1 [M+H]+.

Step 5: (R)-1-(1-(difluoromethyl)-1H-pyrazol-3-yl) propan-1-amine

To a solution of tert-butyl (R)-(1-(1-(difluoromethyl)-1H-pyrazol-3-yl)propyl)carbamate (1.1 g, 3.96 mmol) in DCM (10 mL), HCl/1,4-dioxane (1 M, 8 mL) was added, and the reaction mixture was stirred at 20° C. for 16 h. The reaction mixture was concentrated under reduced pressure. The residue was diluted with 1M NaOH solution (15 mL) and extracted with DCM (30 mL×3). The combined organic layers were washed with brine (30 mL×3), dried over anhydrous Na2SO4, filtered and concentrated under reduced pressure to give (R)-1-(1-(difluoromethyl)-1H-pyrazol-3-yl) propan-1-amine (510 mg, 73% yield) as a yellow oil.

LCMS m/z (ESI+) 176.1 [M+H]+.

Step 6: (R)—N2-(1-(1-(difluoromethyl)-1H-pyrazol-3-yl)propyl)-6-(3-methylimidazo[1,5-a]pyridin-6-yl)-1,3,5-triazine-2,4-diamine 4-chloro-6-(3-methylimidazo[1,5-a]pyridin-6-yl)-1,3,5-triazin-2-amine (Key Intermediate 2) (80 mg, 306.88 μmol), (R)-1-(1-(difluoromethyl)-1H-pyrazol-3-yl)propan-1-amine (53.76 mg, 306.88 μmol) and DIEA (118.98 mg, 920.63 μmol) were taken up into a microwave tube in 1,4-dioxane (2 mL). The sealed tube was heated at 120° C. for 1 h under microwave. The mixture was diluted by addition H2O (15 mL). The aqueous layer was extracted with ethyl acetate (30 mL×3). The combined organic layers were washed with brine (30 mL), dried over anhydrous Na2SO4, concentrated in vacuo to give the crude product. The residue was purified by prep-HPLC to give (R)—N2-(1-(1-(difluoromethyl)-1H-pyrazol-3-yl)propyl)-6-(3-methylimidazo[1,5-a]pyridin-6-yl)-1,3,5-triazine-2,4-diamine (60.2 mg, 33% yield) as a yellow solid.

$^1$H NMR (399 MHz, DMSO-d6) δ=8.81 (s, 1H), 8.15 (s, 1H), 8.05 (d, J=2.8 Hz, 1H), 7.67 (t, J=60.0 Hz, 1H), 7.51 (s, 2H), 7.37 (br s, 1H), 7.28 (s, 1H), 6.66 (br s, 2H), 6.52 (d, J=2.4 Hz, 1H), 5.25-5.19 (m, 1H), 2.65 (s, 3H), 1.97-1.86 (m, 2H), 0.93 (t, J=7.2 Hz, 3H).

LCMS m/z (ESI+) 400.3 [M+H]+.

Example 118

N2-(1-(1-(difluoromethyl)-1H-pyrazol-3-yl)cyclopentyl)-6-(3-methylimidazo[1,5-a]pyridin-6-yl)-1,3,5-triazine-2,4-diamine Synthesised by General Method F Using the Following Reagents and Conditions:

Step 1: tert-butyl (1-(methoxy(methyl)carbamoyl)cyclopentyl)carbamate

A solution of 1-((tert-butoxycarbonyl)amino)cyclopentane-1-carboxylic acid (10 g, 43.61 mmol), Et3N (17.65 g, 174.46 mmol) and HOBt (5.89 g, 43.61 mmol) in anhydrous DCM was cooled to 0° C., EDCI·HCl (16.73 g, 87.23 mmol) was added, followed by stirring at 20° C. for 30 minutes. Then N-methoxymethanamine (4.68 g, 47.98 mmol, HCl) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3) and saturated aqueous sodium chloride (200 mL×3), and dried over Na2SO4, filtered and concentrated under reduced pressure to give a residue. The crude product was purified by re-crystallization from (Petroleum ether:Ethyl acetate=8:1) (150 mL) at 70° C. to give tert-butyl (1-(methoxy(methyl)carbamoyl)cyclopentyl)carbamate (12.65 g, 77% yield) as a white solid.

LCMS m/z (ESI+) 273.2 [M+H]+.

Step 2: tert-butyl (1-propioloylcyclopentyl)carbamate

A solution of tert-butyl (1-(methoxy(methyl)carbamoyl) cyclopentyl)carbamate (10 g, 29.17 mmol) in THF (100 mL) was cooled to −78° C. under nitrogen, bromo(ethynyl) magnesium (0.5 M, 233.36 mL) was added dropwise, and the mixture was stirred at −78° C. for 1 hr. Then the mixture was allowed to warm to 20° C. and stirred for another 16 hr. The mixture was poured into a cold (0° C.) sat. NH4Cl solution (180 mL) and stirred for 1 h. THF was evaporated in vacuo (35° C.), and the aqueous layer was extracted with EtOAc (300 mL). The combined organic phase was washed successively with sat. aq. $NaHCO_3$ (150 mL), and brine (150 mL×3), dried over anhydrous Na2SO4, filtered, and the filtrate was evaporated in vacuo (40° C.). The residue was purified by flash silica gel chromatography to give tert-butyl (1-propioloylcyclopentyl)carbamate (2.27 g, 26% yield) as a yellow oil.

LCMS m/z (ESI+) 238.1 [M+H]+.

Step 3: tert-butyl (1-(1H-pyrazol-3-yl)cyclopentyl)carbamate tert-butyl (1-propioloylcyclopentyl)carbamate (2.2 g, 9.27 mmol) was dissolved in EtOH (22 mL), NH2NH2·H2O (0.89 g, 27.81 mmol) was added and the reaction mixture was heated to 80° C. for 30 min then allowed to cool to 20° C. for 0.5 h. The reaction mixture was diluted with EtOAc (150 mL) and extracted with EtOAc (150 mL×3). The combined organic layers were dried over anhydrous Na2SO4, filtered and concentrated under reduced pressure (30° C.) to give a residue. The residue was purified by flash silica gel chromatography to give tert-butyl (1-(1H-pyrazol-3-yl)cyclopentyl)carbamate (2.26 g, 97.2% yield) as a yellow oil.

LCMS m/z (ESI+) 252.1 [M+H]+.

Step 4: tert-butyl (1-(1-(difluoromethyl)-1H-pyrazol-3-yl)cyclopentyl)carbamate

KF (1.02 g, 17.51 mmol) and tert-butyl (1-(1H-pyrazol-3-yl)cyclopentyl)carbamate (2.2 g, 8.75 mmol) were combined in a flask under N2. Acetonitrile (22 mL) was then added followed by 1-[[bromo(difluoro)methyl]-ethoxy-phosphoryl]oxyethane (3.51 g, 13.13 mmol). The reaction mixture was stirred at 20° C. for 16 h. The reaction mixture was diluted with DCM (50 mL) and H2O (50 mL) and extracted with DCM (50 mL×3). The combined organic layers were washed with brine (50 mL×3), dried over anhydrous Na2SO4, filtered and concentrated under reduced pressure to give a residue. The residue was purified by flash silica gel chromatography to give tert-butyl (1-(1-(difluoromethyl)-1H-pyrazol-3-yl)cyclopentyl)carbamate (2.64 g, crude) as a light yellow oil.

LCMS m/z (ESI+) 302.1 [M+H]+.

Step 5:1-(1-(difluoromethyl)-1H-pyrazol-3-yl)cyclopentan-1-amine

To a solution of tert-butyl (1-(1-(difluoromethyl)-1H-pyrazol-3-yl)cyclopentyl)carbamate (2.5 g, 8.30 mmol) in DCM (10 mL), HCl/1,4-dioxane (1 M, 16.59 mL) was added, and the reaction mixture was stirred at 20° C. for 16 h. The reaction mixture was concentrated under reduced pressure. The residue was diluted with 1M NaOH solution (30 mL) and extracted with DCM (30 mL×3). The combined organic layers were washed with brine (30 mL×3), dried over anhydrous Na2SO4, filtered and concentrated under reduced pressure to give 1-(1-(difluoromethyl)-1H-pyrazol-3-yl)cyclopentan-1-amine (1.19 g, 71% yield) as a yellow oil.

LCMS m/z (EST+) 202.1 [M+H]+.

Step 6: N2-(1-(1-(difluoromethyl)-1H-pyrazol-3-yl) cyclopentyl)-6-(3-methylimidazo[1,5-a]pyridin-6-yl)-1,3,5-triazine-2,4-diamine 1-(1-(difluoromethyl)-1H-pyrazol-3-yl)cyclopentan-1-amine (61.75 mg, 306.88 μmol), 4-chloro-6-(3-methylimidazo[1,5-a]pyridin-6-yl)-1,3,5-triazin-2-amine (Key Intermediate 2) (80 mg, 306.88 μmol) and DIEA (118.98 mg, 920.63 μmol) were taken up into a microwave tube in 1,4-dioxane (2 mL). The sealed tube was heated at 120° C. for 1 h under microwave. The mixture was diluted by addition H2O (15 mL). The aqueous layer was extracted with ethyl acetate (30 mL×3). The combined organic layers were washed with brine (30 mL), dried over anhydrous Na2SO4, concentrated in vacuo to give the crude product. The residue was purified by prep-HPLC to give N2-(1-(1-(difluoromethyl)-1H-pyrazol-3-yl)cyclopentyl)-6-(3-methylimidazo[1,5-a]pyridin-6-yl)-1,3,5-triazine-2,4-diamine (32 mg, 19% yield) as a yellow solid.

$^1H$ NMR (399 MHz, DMSO-d6) δ=8.69 (s, 1H), 8.17 (s, 1H), 7.94 (d, J=2.4 Hz, 1H), 7.63 (t, J=60.0 Hz, 1H), 7.36 (d, J=2.4 Hz, 1H), 7.30 (br s, 2H), 7.26 (s, 1H), 6.49 (br s, 2H), 6.41 (br s, 1H), 2.62 (s, 3H), 2.29-2.26 (m, 2H), 1.82-1.78 (m, 2H), 1.77-1.73 (m, 4H).

LCMS m/z (ESI+) 426.2 [M+H]+.

Example 119

(S)—N2-(2-(2-chlorophenyl)-1-(1-(difluoromethyl)-1H-pyrazol-3-yl)ethyl)-6-(3-methylimidazo[1,5-a] pyridin-6-yl)-1,3,5-triazine-2,4-diamine Synthesised by General Method F Using the Following Reagents and Conditions:

Step 1: tert-butyl (S)-(3-(2-chlorophenyl)-1-(methoxy(methyl)amino)-1-oxopropan-2-yl)carbamate A solution of (S)-2-((tert-butoxycarbonyl)amino)-3-(2-chlorophenyl)propanoic acid (10 g, 33.36 mmol), Et3N (13.50 g, 133.44 mmol) and HOBt (4.51 g, 33.36 mmol) in anhydrous DCM was cooled to 0° C., EDCI·HCl (12.79 g, 66.72 mmol) was added, followed by stirring at 20° C. for 30 minutes. Then N-methoxymethanamine (3.58 g, 36.70 mmol, HCl) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3) and saturated aqueous sodium chloride (200 mL×3), and dried over Na2SO4, filtered and concentrated under reduced pressure to give a residue. The crude product was purified by re-crystallization from (Petroleum ether:Ethyl acetate=5:1) (120 mL) at 70° C. to give tert-butyl (S)-(3-(2-chlorophenyl)-1-(methoxy (methyl)amino)-1-oxopropan-2-yl)carbamate (7.15 g, 61.42% yield) as a white solid.

LCMS m/z (EST+) 343.13 [M+H]+.

Step 2: tert-butyl (S)-(1-(2-chlorophenyl)-3-oxo-pent-4-yn-2-yl)carbamate

A solution of tert-butyl (S)-(3-(2-chlorophenyl)-1-(methoxy(methyl)amino)-1-oxopropan-2-yl)carbamate (7 g, 21.87 mmol) in THF (70 mL) was cooled to −78° C. under nitrogen, bromo(ethynyl)magnesium (0.5 M, 163.35 mL) was added dropwise, and the mixture was stirred at −78° C. for 1 hr. Then the mixture was allowed to warm to 20° C. and stirred for another 16 hr. The mixture was poured into a cold (0° C.) sat. NH4Cl solution (150 mL) and stirred for 1 h. THF was evaporated in vacuo (35° C.), and the aqueous layer was extracted with EtOAc (300 mL). The combined organic phase was washed successively with sat. aq. $NaHCO_3$ (150 mL), and brine (150 mL×3), dried over anhydrous Na2SO4, filtered, and the filtrate was evaporated in vacuo (40° C.). The residue was purified by flash silica gel chromatography to give tert-butyl (S)-(1-(2-chlorophenyl)-3-oxopent-4-yn-2-yl)carbamate (2.07 g, 32.98% yield) as a yellow oil.

LCMS m/z (ESI+) 308.1 [M+H]+.

Step 3: tert-butyl (S)-(2-(2-chlorophenyl)-1-(1H-pyrazol-3-yl)ethyl)carbamate tert-butyl (S)-(1-(2-chlorophenyl)-3-oxopent-4-yn-2-yl) carbamate (2 g, 6.50 mmol) was dissolved in EtOH (20 mL), NH2NH2·H2O (0.62 g, 19.49 mmol) was added and the reaction mixture was heated to 80° C. for 30 min then allowed to cool to 20° C. for 0.5 h. The reaction mixture was diluted with EtOAc (150 mL) and extracted with EtOAc (150 mL×3). The combined organic layers were dried over anhydrous Na2SO4, filtered and concentrated under reduced pressure (30° C.) to give a residue. The residue was purified by flash silica gel chromatography to give tert-butyl (S)-(2-(2-chlorophenyl)-1-(1H-pyrazol-3-yl)ethyl)carbamate (2.03 g, 97.08% yield) as a yellow oil.

LCMS m/z (ESI+) 322.1 [M+H]+.

Step 4: tert-butyl (S)-(2-(2-chlorophenyl)-1-(1-(difluoromethyl)-1H-pyrazol-3-yl)ethyl)carbamate KF (1.10 g, 18.93 mmol, 443.55 µL) and tert-butyl (S)-(2-(2-chlorophenyl)-1-(1H-pyrazol-3-yl)ethyl)carbamate (2 g, 6.21 mmol) were combined in a flask under N2. Acetonitrile (16 mL) was then added followed by 1-[[bromo (difluoro)methyl]-ethoxy-phosphoryl]oxyethane (2.49 g, 9.32 mmol). The reaction mixture was stirred at 20° C. for 16 h. The reaction mixture was diluted with DCM (50 mL) and H2O (50 mL) and extracted with DCM (50 mL×3). The combined organic layers were washed with brine (50 mL×3), dried over anhydrous Na2SO4, filtered and concentrated under reduced pressure to give a residue. The residue was purified by flash silica gel chromatography to give tert-butyl (S)-(2-(2-chlorophenyl)-1-(1-(difluoromethyl)-1H-pyrazol-3-yl)ethyl)carbamate (2.31 g crude) as a light yellow oil.

LCMS m/z (ESI+) 372.1 [M+H]+.

Step 5: (S)-2-(2-chlorophenyl)-1-(1-(difluoromethyl)-1H-pyrazol-3-yl)ethan-1-amine To a solution of tert-butyl (S)-(2-(2-chlorophenyl)-1-(1-(difluoromethyl)-1H-pyrazol-3-yl)ethyl)carbamate (2 g, 5.38 mmol) in DCM (10 mL), HCl/1,4-dioxane (1 M, 10.76 mL) was added, and the reaction mixture was stirred at 20° C. for 16 h. The reaction mixture was concentrated under reduced pressure. The residue was diluted with 1M NaOH solution (15 mL) and extracted with DCM (30 mL×3). The combined organic layers were washed with brine (30 mL×3), dried over anhydrous Na2SO4, filtered and concentrated under reduced pressure to give (S)-2-(2-chlorophenyl)-1-(1-(difluoromethyl)-1H-pyrazol-3-yl)ethan-1-amine (1.04 g, 70.49% yield) as a yellow oil.

LCMS m/z (ESI+) 272.0 [M+H]+.

Step 6: (S)—N2-(2-(2-chlorophenyl)-1-(1-(difluoromethyl)-1H-pyrazol-3-yl)ethyl)-6-(3-methylimidazo[1,5-a]pyridin-6-yl)-1,3,5-triazine-2,4-diamine (S)-2-(2-chlorophenyl)-1-(1-(difluoromethyl)-1H-pyrazol-3-yl)ethan-1-amine (80 mg, 306.88 µmol), 4-chloro-6-(3-methylimidazo[1,5-a]pyridin-6-yl)-1,3,5-triazin-2-amine (Key Intermediate 2) (83.38 mg, 306.88 µmol) and DIEA (118.98 mg, 920.63 µmol) were taken up into a microwave tube in 1,4-dioxane (2 mL). The sealed tube was heated at 120° C. for 1 h under microwave. The mixture was diluted by addition H2O (15 mL). The aqueous layer was extracted with ethyl acetate (30 mL×3). The combined organic layers were washed with brine (30 mL), dried over anhydrous Na2SO4, concentrated in vacuo to give the crude product. The residue was purified by prep-HPLC to give (S)—N2-(2-(2-chlorophenyl)-1-(1-(difluoromethyl)-1H-pyrazol-3-yl)ethyl)-6-(3-methylimidazo[1,5-a]pyridin-6-yl)-1,3,5-triazine-2,4-diamine (34.3 mg, 23.5% yield) as a yellow solid.

$^1H$ NMR (399 MHz, DMSO-d6) δ=8.75 (s, 1H), 8.08 (s, 1H), 7.83 (t, J=60.0 Hz, 1H), 7.68-7.49 (m, 2H), 7.47-7.17 (m, 6H), 6.61 (br s, 2H), 6.55 (d, J=2.0 Hz, 1H), 5.81-5.68 (br s, 1H), 3.42 (m, 1H), 3.28 (m, 1H), 2.67 (s, 3H).

LCMS m/z (ESI+) 496.1 [M+H]+.

Example 120

(S)—N2-(2-(3-chlorophenyl)-1-(1-(difluoromethyl)-1H-pyrazol-3-yl)ethyl)-6-(3-methylimidazo[1,5-a]pyridin-6-yl)-1,3,5-triazine-2,4-diamine Synthesised by General Method F Using the Following Reagents and Conditions:

Step 1: tert-butyl (S)-(3-(3-chlorophenyl)-1-(methoxy(methyl)amino)-1-oxopropan-2-yl)carbamate A solution of (S)-2-((tert-butoxycarbonyl)amino)-3-(3-chlorophenyl)propanoic acid (10 g, 33.36 mmol), Et3N (13.50 g, 133.44 mmol) and HOBt (4.51 g, 33.36 mmol) in anhydrous DCM was cooled to 0° C., EDCI·HCl (12.79 g, 66.72 mmol) was added, followed by stirring at 20° C. for 30 minutes. Then N-methoxymethanamine (3.58 g, 36.69 mmol, HCl) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3) and saturated aqueous sodium chloride (200 mL×3), and dried over Na2SO4, filtered and concentrated under reduced pressure to give a residue. The crude product was purified by re-crystallization from (Petroleum ether:Ethyl acetate=5:1) (120 mL) at 70° C. to give tert-butyl (S)-(3-(3-chlorophenyl)-1-(methoxy(methyl)amino)-1-oxopropan-2-yl)carbamate (7.83 g, 68.45% yield) as a white solid.

LCMS m/z (ESI+) 343.13 [M+H]+.

Step 2: tert-butyl (S)-(1-(3-chlorophenyl)-3-oxopent-4-yn-2-yl)carbamate

A solution of tert-butyl (S)-(3-(3-chlorophenyl)-1-(methoxy(methyl)amino)-1-oxopropan-2-yl)carbamate (7.5 g, 21.87 mmol) in THF (60 mL) was cooled to −78° C. under nitrogen, bromo(ethynyl)magnesium (0.5 M, 175 mL) was added dropwise, and the mixture was stirred at −78° C. for 1 hr. Then the mixture was allowed to warm to 20° C. and stirred for another 16 hr. The mixture was poured into a cold (0° C.) sat. NH4Cl solution (150 mL) and stirred for 1 h. THF was evaporated in vacuo (35° C.), and the aqueous layer was extracted with EtOAc (300 mL). The combined organic phase was washed successively with sat. aq. $NaHCO_3$ (150 mL), and brine (150 mL×3), dried over anhydrous Na2SO4, filtered, and the filtrate was evaporated in vacuo (40° C.). The residue was purified by flash silica gel chromatography to give tert-butyl (S)-(1-(3-chlorophenyl)-3-oxopent-4-yn-2-yl)carbamate (2.74 g, 40.7% yield) as a yellow oil.

LCMS m/z (ESI+) 308.1 [M+H]+.

Step 3: tert-butyl (S)-(2-(3-chlorophenyl)-1-(1H-pyrazol-3-yl)ethyl)carbamate tert-butyl (S)-(1-(3-chlorophenyl)-3-oxopent-4-yn-2-yl) carbamate (2.6 g, 8.45 mmol) was dissolved in EtOH (26 mL), NH2NH2·H2O (0.81 g, 25.34 mmol) was added and the reaction mixture was heated to 80° C. for 30 min then allowed to cool to 20° C. for 0.5 h. The reaction mixture was diluted with EtOAc (150 mL) and extracted with EtOAc (150 mL×3). The combined organic layers were dried over anhydrous Na2SO4, filtered and concentrated under reduced pressure (30° C.) to give a residue. The residue was purified by flash silica gel chromatography to give tert-butyl (S)-(2-(3-chlorophenyl)-1-(1H-pyrazol-3-yl)ethyl)carbamate (2.64 g, 97.04% yield) as a yellow oil.

LCMS m/z (ESI+) 322.1 [M+H]+.

Step 4: tert-butyl (S)-(2-(3-chlorophenyl)-1-(1-(difluoromethyl)-1H-pyrazol-3-yl)ethyl)carbamate KF (0.9 g, 15.53 mmol) and tert-butyl (S)-(2-(3-chlorophenyl)-1-(1H-pyrazol-3-yl)ethyl)carbamate (2.5 g, 7.77 mmol) were combined in a flask under N2. Acetonitrile (20 mL) was then added followed by 1-[[bromo(difluoro) methyl]-ethoxy-phosphoryl]oxyethane (3.11 g, 11.65 mmol). The reaction mixture was stirred at 20° C. for 16 h The reaction mixture was diluted with DCM (50 mL) and H2O (50 mL) and extracted with DCM (50 mL×3). The combined organic layers were washed with brine (50 mL×3), dried over anhydrous Na2SO4, filtered and concentrated under reduced pressure to give a residue. The residue was purified by flash silica gel chromatography to give tert-butyl (S)-(2-(3-chlorophenyl)-1-(1-(difluoromethyl)-1H-pyrazol-3-yl)ethyl)carbamate (2.89 g, crude) as a light yellow oil.

LCMS m/z (ESI+) 372.1 [M+H]+.

Step 5: (S)-2-(3-chlorophenyl)-1-(1-(difluoromethyl)-1H-pyrazol-3-yl)ethan-1-amine To a solution of tert-butyl (S)-(2-(3-chlorophenyl)-1-(1-(difluoromethyl)-1H-pyrazol-3-yl)ethyl)carbamate (2 g, 5.38 mmol) in DCM (20 mL), HCl/1,4-dioxane (1 M, 10.76 mL) was added, and the reaction mixture was stirred at 20° C. for 16 h. The reaction mixture was concentrated under reduced pressure. The residue was diluted with 1M NaOH solution (30 mL) and extracted with DCM (30 mL×3). The combined organic layers were washed with brine (30 mL×3), dried over anhydrous Na2SO4, filtered and concentrated under reduced pressure to give (S)-2-(3-chlorophenyl)-1-(1-(difluoromethyl)-1H-pyrazol-3-yl)ethan-1-amine (1.04 g, 71.39% yield) as a yellow oil.

LCMS m/z (ESI+) 272.0 [M+H]+.

Step 6: (S)—N2-(2-(3-chlorophenyl)-1-(1-(difluoromethyl)-1H-pyrazol-3-yl)ethyl)-6-(3-methylimidazo[1,5-a]pyridin-6-yl)-1,3,5-triazine-2,4-diamine (S)-2-(3-chlorophenyl)-1-(1-(difluoromethyl)-1H-pyrazol-3-yl)ethan-1-amine (51.01 mg, 306.88 μmol), 4-chloro-6-(3-methylimidazo[1,5-a]pyridin-6-yl)-1,3,5-triazin-2-amine (Key Intermediate 2) (80 mg, 306.88 μmol) and DIEA (118.98 mg, 920.63 μmol) were taken up into a microwave tube in 1,4-dioxane (2 mL). The sealed tube was heated at 120° C. for 1 h under microwave. The mixture was diluted by addition H2O (15 mL). The aqueous layer was extracted with ethyl acetate (30 mL×3). The combined organic layers were washed with brine (30 mL), dried over anhydrous Na2SO4, concentrated in vacuo to give the crude product. The residue was purified by prep-HPLC to give (S)—N2-(2-(3-chlorophenyl)-1-(1-(difluoromethyl)-1H-pyrazol-3-yl)ethyl)-6-(3-methylimidazo[1,5-a]pyridin-6-yl)-1,3,5-triazine-2,4-diamine (55.6 mg, 38.08% yield) as a yellow solid.

$^1$H NMR (399 MHz, DMSO-d6) δ=8.77 (s, 1H), 8.08 (s, 1H), 7.68 (t, J=60.0 Hz, 1H), 7.50-7.48 (m, 3H), 7.28-7.25 (m, 5H), 6.65 (br s, 2H), 6.56 (s, 1H), 5.58 (br s, 1H), 3.24 (br s, 2H), 2.65 (s, 3H).

LCMS m/z (ESI+) 496.1 [M+H]+.

Example 121

N2-(2-(6-methoxypyridin-2-yl)propan-2-yl)-6-(3-methylimidazo[1,5-a]pyridin-6-yl)-1,3,5-triazine-2,4-diamine Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.89 μmol) in 1,4-dioxane (4 mL) was added DIEA (119 mg, 920.64 μmol) and 2-(6-methoxypyridin-2-yl)propan-2-amine (76.51 mg, 460.32 μmol). The mixture was stirred at 120° C. for 16 hr. The reaction mixture was concentrated under reduced pressure to give a residue. The residue was purified by prep-HPLC to give N2-(2-(6-methoxypyridin-2-yl)propan-2-yl)-6-(3-methylimidazo[1,5- a]pyridin-6-yl)-1,3,5-triazine-2,4-diamine (36.28 mg, 30.28% yield) as a yellow solid.

$^1$H NMR (399 MHz, DMSO-d6) δ=8.53 (br s, 1H), 7.61 (t, J=8.0 Hz, 1H), 7.45 (d, J=8.0 Hz, 1H), 7.31 (br s, 3H), 7.05 (d, J=8.0 Hz, 1H), 6.58 (d, J=8.0 Hz, 1H), 6.49 (br s, 2H), 3.90 (s, 3H), 2.59 (s, 3H), 1.77 (s, 6H).

LCMS m/z (ESI+) 391.1 [M+H]+.

Example 122

(S)—N2-(cyclopropyl(1-(difluoromethyl)-1H-pyrazol-3-yl)methyl)-6-(3-methylimidazo[1,5-a]pyridin-6-yl)-1,3,5-triazine-2,4-diamine Synthesised by General Method F Using the Following Reagents and Conditions:

Step 1: (S)-(1-cyclopropyl-2-(methoxy(methyl)amino)-2-oxoethyl)carbamate

A solution of (S)-2-((tert-butoxycarbonyl)amino)-2-cyclopropylacetic acid (10 g, 46.46 mmol), Et3N (18.80 g, 185.83 mmol) and HOBt (6.28 g, 46.46 mmol) in anhydrous DCM was cooled to 0° C., EDCI·HCl (17.81 g, 92.92 mmol) was added, followed by stirring at 20° C. for 30 minutes. Then N-methoxymethanamine (4.98 g, 51.10 mmol, HCl) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3) and saturated aqueous sodium chloride (200 mL×3), and dried over Na2SO4, filtered and concentrated under reduced pressure to give a residue. The crude product was purified by re-crystallization from (Petroleum ether:Ethyl acetate=4:1) (100 mL) at 70° C. to give tert-butyl (S)-(1-cyclopropyl-2-(methoxy(methyl)amino)-2-oxoethyl)carbamate (9.24 g, 77% yield) as a white solid.

LCMS m/z (ESI+) 259.1 [M+H]+.

Step 2: tert-butyl (S)-(1-cyclopropyl-2-oxobut-3-yn-1-yl)carbamate

A solution of tert-butyl (S)-(1-cyclopropyl-2-(methoxy(methyl)amino)-2-oxoethyl)carbamate (8.3 g, 32.13 mmol) in THF (66 mL) was cooled to −78° C. under nitrogen, bromo(ethynyl)magnesium (0.5 M, 257.04 mL) was added dropwise, and the mixture was stirred at −78° C. for 1 hr. Then the mixture was allowed to warm to 20° C. and stirred for another 16 hr. The mixture was poured into a cold (0° C.) sat. NH4Cl solution (150 mL) and stirred for 1 h. THF was evaporated in vacuo (35° C.), and the aqueous layer was extracted with EtOAc (300 mL). The combined organic phase was washed successively with sat. aq. $NaHCO_3$ (150 mL), and brine (150 mL×3), dried over anhydrous Na2SO4, filtered, and the filtrate was evaporated in vacuo (40° C.). The residue was purified by flash silica gel chromatography to give tert-butyl (S)-(1-cyclopropyl-2-oxobut-3-yn-1-yl)carbamate (2.7 g, 37.61% yield) as a yellow oil.

LCMS m/z (ESI+) 224.1 [M+H]+.

Step 3: tert-butyl (S)-(cyclopropyl(1H-pyrazol-3-yl)methyl)carbamate tert-butyl (S)-(1-cyclopropyl-2-oxobut-3-yn-1-yl)carbamate (2.6 g, 11.64 mmol) was dissolved in EtOH (120 mL), NH2NH2·H2O (1.12 g, 34.94 mmol) was added and the reaction mixture was heated to 80° C. for 30 min then allowed to cool to 20° C. for 0.5 h. The reaction mixture was diluted with EtOAc (150 mL) and extracted with EtOAc (150 mL×3). The combined organic layers were dried over anhydrous Na2SO4, filtered and concentrated under reduced pressure (30° C.) to give a residue. The residue was purified by flash silica gel chromatography to give tert-butyl (S)-(cyclopropyl(1H-pyrazol-3-yl)methyl)carbamate (2.43 g, 88.03% Yield) as a yellow oil.

LCMS m/z (ESI+) 238.1 [M+H]+.

Step 4: tert-butyl (S)-(cyclopropyl(1-(difluoromethyl)-1H-pyrazol-3-yl)methyl)carbamate KF (1.02 g, 17.60 mmol) and tert-butyl (S)-(cyclopropyl (1H-pyrazol-3-yl)methyl)carbamate (2.35 g, 8.80 mmol) were combined in a flask under N2. Acetonitrile (19 mL) was then added followed by 1-[[bromo(difluoro)methyl]-ethoxy-phosphoryl]oxyethane (3.5 g, 13.20 mmol). The reaction mixture was stirred at 20° C. for 16 h. The reaction mixture was diluted with DCM (50 mL) and H2O (50 mL) and extracted with DCM (50 mL×3). The combined organic layers were washed with brine (50 mL×3), dried over anhydrous Na2SO4, filtered and concentrated under reduced pressure to give a residue. The residue was purified by flash silica gel chromatography to give tert-butyl (S)-(cyclopropyl (1-(difluoromethyl)-1H-pyrazol-3-yl)methyl)carbamate (2.85 g, crude) as a light yellow oil.

LCMS m/z (ESI+) 288.1 [M+H]+.

Step 5: (S)-cyclopropyl(1-(difluoromethyl)-1H-pyrazol-3-yl)methanamine

To a solution of tert-butyl (S)-(cyclopropyl(1-(difluoromethyl)-1H-pyrazol-3-yl)methyl)carbamate (2.8 g, 9.75 mmol) in DCM (6 mL), HCl/1,4-dioxane (1 M, 19 mL) was added, and the reaction mixture was stirred at 20° C. for 16 h. The residue was diluted with 1M NaOH solution (15 mL) and extracted with DCM (30 mL×3). The combined organic layers were washed with brine (30 mL×3), dried over anhydrous Na2SO4, filtered and concentrated under reduced pressure to give (S)-cyclopropyl(1-(difluoromethyl)-1H-pyrazol-3-yl)methanamine (1.06 g, 58.11% yield) as a yellow oil.

LCMS m/z (ESI+) 188.1 [M+H]+.

Step 6: (S)—N2-(cyclopropyl(1-(difluoromethyl)-1H-pyrazol-3-yl)methyl)-6-(3-methylimidazo[1,5-a]pyridin-6-yl)-1,3,5-triazine-2,4-diamine (S)-cyclopropyl(1-(difluoromethyl)-1H-pyrazol-3-yl) methanamine (68.93 mg, 368.25 μmol), 4-chloro-6-(3-methylimidazo[1,5-a]pyridin-6-yl)-1,3,5-triazin-2-amine (Key Intermediate 2) (80 mg, 306.88 μmol) and DIEA (59.49 mg, 460.32 μmol) were taken up into a microwave tube in 1,4-dioxane (3 mL). The sealed tube was heated at 120° C. for 1 h under microwave. The mixture was diluted by addition H2O (15 mL). The aqueous layer was extracted with ethyl acetate (30 mL×3). The combined organic layers were washed with brine (30 mL), dried over anhydrous Na2SO4, concentrated in vacuo to give the crude product. The residue was purified by prep-HPLC to give (S)—N2-(cyclopropyl(1-(difluoromethyl)-1H-pyrazol-3-yl)methyl)-6-(3-methylimidazo[1,5-a]pyridin-6-yl)-1,3,5-triazine-2,4-diamine (26.87 mg, 17.74% yield) as a yellow solid.

$^1$H NMR (399 MHz, DMSO-d6) δ=8.80 (s, 1H), 8.06 (d, J=2.8 Hz, 1H), 7.53 (t, J=60.0 Hz, 1H), 7.50 (s, 1H), 7.47 (br s, 2H), 7.28 (s, 1H), 6.64 (br s, 2H), 6.60 (d, J=2.4 Hz, 1H), 4.86 (t, J=8.4 Hz, 1H), 2.65 (s, 3H), 1.40-1.35 (m, 1H), 0.54-0.51 (m, 3H), 0.49-0.47 (m, 1H).

LCMS m/z (ESI+) 412.1 [M+H]+.

Example 123

N2-(2-fluorobenzyl)-6-(3-methylimidazo[1,5-a]pyridin-6-yl)-1,3,5-triazine-2,4-diamine Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.89 μmol) in 1,4-dioxane (4 mL) was added DIEA (159 mg, 1.23 mmol, 213.82 μL) and (2-fluorophenyl) methanamine (58 mg, 460.33 μmol, 52.4 μL). The mixture was stirred at 120° C. for 16 hr. The reaction mixture was concentrated under reduced pressure to give a residue. The residue was purified by prep-HPLC to give N2-(2-fluorobenzyl)-6-(3-methylimidazo[1,5-a]pyridin-6-yl)-1,3,5-triazine-2,4-diamine (29.7 mg, 27.42% yield) as a yellow solid.

$^1$H NMR (399 MHz, DMSO-d6) δ=8.80 (s, 1H), 7.62-7.54 (m, 1H), 7.54-7.49 (m, 2H), 7.48-7.42 (m, 1H), 7.32-7.25 (m, 2H), 7.16 (d, J=8.0 Hz, 1H), 7.15-7.12 (m, 1H), 6.68 (br s, 2H), 4.63 (br d, J=5.6 Hz, 2H), 2.64 (s, 3H).

LCMS m/z (ESI$^+$) 350.1 [M+H]$^+$.

Example 124

N2-(2-(6-(dimethylamino)pyridin-2-yl)propan-2-yl)-6-(3-methylimidazo[1,5-a]pyridin-6-yl)-1,3,5-triazine-2,4-diamine To a solution of N2-[1-(6-fluoro-2-pyridyl)-1-methyl-ethyl]-6-(3-methylimidazo[1,5-a]pyridin-6-yl)-1,3,5-triazine-2,4-diamine (Example 129, 30 mg, 79.28 μmol) in DMF (5 mL), Cs2CO3 (774.93 mg, 2.38 mmol) and N-methylmethanamine (64.65 mg, 792.80 μmol, 72.64 μL HCl) were added, the mixture was stirred at 120° C. for 48 hr. The reaction was added Acetonitrile (1 mL). The crude product was purified by reversed-phase HPLC (0.1% NH3·H2O) to give N2-(2-(6-(dimethylamino)pyridin-2-yl)propan-2-yl)-6-(3-methylimidazo[1,5-a]pyridin-6-yl)-1,3,5-triazine-2,4-diamine (14.4 mg, 44.53% yield) as a yellow solid.

$^1$H NMR (399 MHz, DMSO-d6)=8.60 (br s, 1H), 7.54-7.43 (m, 2H), 7.34 (br s, 2H), 7.26 (s, 1H), 6.69 (d, J=8.0 Hz, 1H), 6.52 (br s, 2H), 6.44 (d, J=8.0 Hz, 1H), 3.07 (s, 6H), 2.59 (s, 3H), 1.76 (s, 6H).

LCMS m/z (ESI+) 404.3 [M+H]+.

Example 125

6-(3-methylimidazo[1,5-a]pyridin-6-yl)-N2-[1-methyl-1-[6-(trifluoromethyl)-2-pyridyl]ethyl]-1,3,5-triazine-2,4-diamine Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (75 mg, 287.70 μmol) in 1,4-dioxane (7 mL) was added 2-[6-(trifluoromethyl)-2-pyridyl]propan-2-amine (70.50 mg, 345.24 μmol) and DIEA (52.05 mg, 402.78 μmol), then the reaction mixture was heated to 120° C. and stirred for 20 hr. The reaction mixture was concentrated under reduced pressure to give a residue. The residue was purified by prep-HPLC to obtain 6-(3-methylimidazo[1,5-a]pyridin-6-yl)-N2-[1-methyl-1-[6-(trifluoromethyl)-2-pyridyl]ethyl]-1,3,5-triazine-2,4-diamine (70.25 mg, 57% Yield) as a yellow solid.

$^1$H NMR (399 MHz, DMSO-d6) δ=8.51 (s, 1H), 7.95 (t, J=7.6 Hz, 1H), 7.75 (d, J=7.6 Hz, 1H), 7.64 (d, J=7.6 Hz, 1H), 7.46 (s, 1H), 7.36 (br s, 1H), 7.25 (s, 1H), 7.15 (br s, 1H), 6.51 (br s, 2H), 2.56 (s, 3H), 1.76 (s, 6H).

LCMS m/z (ESI+) 429.1 [M+H]+.

Example 126

6-(3-methylimidazo[1,5-a]pyridin-6-yl)-N2-[1-[2-(trifluoromethyl)-1H-imidazol-4-yl]ethyl]-1,3,5-triazine-2,4-diamine Step 1: trimethyl-[2-[[2-(trifluoromethyl)imidazol-1-yl]methoxy]ethyl]silane To a solution of NaH (646.64 mg, 16.17 mmol, 60% purity) in THF (40 mL) was added 2-(trifluoromethyl)-1H-imidazole (2 g, 14.70 mmol) at 0° C. and stirred for 30 min. The mixture was added dropwise SEM-Cl (2.70 g, 16.17 mmol, 2.86 mL) at 0° C. The mixture was allowed to warm to 20° C. and stirred for 2 hr. The reaction mixture was quenched by addition H2O (50 mL) at 0° C., and extracted with EtOAc (120 mL×3), dried over Na2SO4, filtered and concentrated under reduced pressure to give a residue. The residue was purified by flash silica gel chromatography to give trimethyl-[2-[[2-(trifluoromethyl)imidazol-1-yl]methoxy]ethyl]silane (3.1 g, 77.61% yield) as a white liquid.

$^1$H NMR (399 MHz, CHLOROFORM-d) δ=7.15 (d, J=1.2 Hz, 1H), 7.08 (d, J=1.2 Hz, 1H), 5.36 (s, 2H), 3.48 (t, J=8.4 Hz, 2H), 0.87 (t, J=8.0 Hz, 2H), 0.07 (s, 9H).

Step 2: 2-[[4-bromo-2-(trifluoromethyl)imidazol-1-yl]methoxy]ethyl-trimethyl-silane To a solution of trimethyl-[2-[[2-(trifluoromethyl)imidazol-1-yl]methoxy]ethyl]silane (2 g, 7.51 mmol) in Chloroform (20 mL) and DMF (20 mL) was added dropwise NBS (1.47 g, 8.26 mmol) at 25° C. for 16 hr. The reaction mixture was concentrated under reduced pressure at 20° C. and extracted with EtOAc (100 mL×3) and H2O (30 mL). The combined organic layers were washed with brine (30 mL×3), dried over Na2SO4, filtered and concentrated under reduced pressure to give a residue. The residue was purified by flash silica gel chromatography to give 2-[[4-bromo-2-(trifluoromethyl)imidazol-1-yl]methoxy]ethyl-trimethyl-silane (1.64 g, 59.46% yield) as a white oil.

$^1$H NMR (399 MHz, CHLOROFORM-d) δ=5.45 (s, 2H), 3.62 (t, J=8.8 Hz, 2H), 0.99 (t, J=8.4 Hz, 2H), 0.05 (s, 9H).

Step 3: 2-[[4-(1-ethoxyvinyl)-2-(trifluoromethyl)imidazol-1-yl]methoxy]ethyl-trimethyl-silane A mixture of 2-[[4-bromo-2-(trifluoromethyl)imidazol-1-yl]methoxy]ethyl-trimethyl-silane (1.3 g, 3.77 mmol), tributyl(1-ethoxyvinyl)stannane (2.04 g, 5.65 mmol, 1.91 mL) in 1,4-dioxane (30 mL) was degassed and purged with N2 for 3 times, and then the mixture was added Pd(PPh3)4 (435.14 mg, 376.56·μmol) and stirred at 100° C. for 16 hr under N2 atmosphere. The reaction mixture was cooled to 20° C., and then diluted with H2O (30 mL) and extracted with EtOAc (100 mL×3). The combined organic layers were washed with brine (50 mL×3), dried over Na2SO4, filtered and concentrated under reduced pressure to give 2-[[4-(1- ethoxyvinyl)-2-(trifluoromethyl)imidazol-1-yl]methoxy]ethyl-trimethyl-silane (2.7 g, crude) as a black oil.

Step 4: 1-[2-(trifluoromethyl)-1-(2-trimethylsilylethoxymethyl)imidazol-4-yl]ethanone A mixture of 2-[[4-(1-ethoxyvinyl)-2-(trifluoromethyl)imidazol-1-yl]methoxy]ethyl-trimethyl-silane (2.7 g, 8.03 mmol) in THF (10 mL) and HCl (2 M, 20.77 mL) was stirred at 20° C. for 3 hr. The reaction mixture was diluted with H2O (10 mL) and extracted with EtOAc (50 mL×3). The combined organic layers were washed with brine (30 mL), dried over Na2SO4, filtered and concentrated under reduced pressure to give a residue. The residue was purified by flash silica gel chromatography to give 1-[2-(trifluoromethyl)-1-(2-trimethylsilylethoxymethyl)imidazol-4-yl]ethanone (1 g, 38.79% yield) as a yellow oil.

$^1$H NMR (399 MHz, CHLOROFORM-d) δ=7.81 (s, 1H), 5.44 (s, 2H), 3.55 (t, J=8.4 Hz, 2H), 2.59 (s, 3H), 0.94 (t, J=8.0 Hz, 2H), 0.002 (s, 9H).

Step 5: 1-[2-(trifluoromethyl)-1-(2-trimethylsilylethoxymethyl)imidazol-4-yl]ethanamine To a mixture of 1-[2-(trifluoromethyl)-1-(2-trimethylsilylethoxymethyl)imidazol-4-yl]ethanone (400 mg, 1.30 mmol) and ammonium acetate (999.87 mg, 12.97 mmol) in MeOH (12 mL), NaBH3CN (122.27 mg, 1.95 mmol) was added at 20° C. The mixture was stirred at 50° C. for 4 hr. The reaction mixture was concentrated under reduced pressure. The residue was diluted with sat. NaOH solution (5 mL) and extracted with EtOAc (30 mL×3). The combined organic layers were washed with brine (30 mL×3), dried over Na2SO4, filtered and concentrated under reduced pressure to give a residue. The residue was purified by flash silica gel chromatography to give 1-[2-(trifluoromethyl)-1-(2-trimethylsilylethoxymethyl)imidazol-4-yl]ethanamine (210 mg, 50.76% yield) as a light yellow oil.

LCMS m/z (ESI+) 310.1 [M+H]+.

Step 6: 6-(3-methylimidazo[1,5-a]pyridin-6-yl)-N2-[1-[2-(trifluoromethyl)-1-(2-trimethylsilyl ethoxymethyl)imidazol-4-yl]ethyl]-1,3,5-triazine-2,4-diamine To a solution of 4-chloro-6-(3-methylimidazo[1,5-a]pyridin-6-yl)-1,3,5-triazin-2-amine (Key Intermediate 2) (80 mg, 306.89 μmol) and 1-[2-(trifluoromethyl)-1-(2-trimethylsilylethoxymethyl)imidazol-4-yl]ethanamine (142.43 mg, 460.33 μmol) in 1,4-dioxane (3 mL) was added DIEA (118.99 mg, 920.66 μmol, 160.36 μL). The mixture was stirred at 120° C. for 16 hr. The mixture was quenched by addition ethyl acetate (10 mL) and H2O (5 mL). The aqueous layer was extracted with ethyl acetate (30 mL×3). The combined organic layers were washed with brine (30 mL), dried over Na2SO4, concentrated in vacuo to give the crude product. The residue was purified by flash silica gel chromatography to give 6-(3-methylimidazo[1,5-a]pyridin-6-yl)-N2-[1-[2-(trifluoromethyl)-1-(2-trimethylsilyl ethoxymethyl)imidazol-4-yl]ethyl]-1,3,5-triazine-2,4-diamine (130 mg, 77.00% yield) as a yellow solid.

LCMS m/z (ESI+) 534.2 [M+H]+.

Step 7: 6-(3-methylimidazo[1,5-a]pyridin-6-yl)-N2-[1-[2-(trifluoromethyl)-1H-imidazol-4-yl]ethyl]-1,3,5-triazine-2,4-diamine To a solution of 6-(3-methylimidazo[1,5-a]pyridin-6-yl)-N2-[1-[2-(trifluoromethyl)-1-(2-trimethylsilyl ethoxymethyl)imidazol-4-yl]ethyl]-1,3,5-triazine-2,4-diamine (100 mg, 187.40 μmol) in EtOH (3 mL) was added HCl (6 M, 1.5 mL). The mixture was stirred at 80° C. for 3 hr. The mixture was concentrated in vacuo to give the crude product. The residue was purified by to give 6-(3-methylimidazo[1,5-a]pyridin-6-yl)-N2-[1-[2-(trifluoromethyl)-1H-imidazol-4-yl]ethyl]-1,3,5-triazine-2,4-diamine (45.6 mg, 17.37% yield) as a yellow solid.

$^1$H NMR (399 MHz, DMSO-d6) δ=13.08 (br s, 1H), 8.81 (s, 1H), 8.14 (s, 1H), 7.52 (s, 2H), 7.28 (s, 2H), 7.16 (br s, 1H), 6.67 (br s, 2H), 5.33 (br s, 1H), 2.65 (s, 3H), 1.52 (d, J=6.8 Hz, 3H)

LCMS m/z (ESI+) 404.1 [M+H]+.

Example 127

(S)—N2-(1-(1-(difluoromethyl)-1H-pyrazol-5-yl)-2-methylpropyl)-6-(3-methylimidazo[1,5-a]pyridin-6-yl)-1,3,5-triazine-2,4-diamine Step 1: (1S)-1-[2-(difluoromethyl)pyrazol-3-yl]-2-methyl-propan-1-amine To a solution of tert-butyl N-[(1S)-1-[2-(difluoromethyl)pyrazol-3-yl]-2-methyl-propyl]carbamate (200.00 mg, 691.27 μmol) in DCM (4 mL) was added HCl/MeOH (4 M, 2 mL). The mixture was stirred at 20° C. for 5 hr. The reaction mixture was concentrated under reduced pressure to give a residue to give (1S)-1-[2-(difluoromethyl)pyrazol-3-yl]-2-methyl-propan-1-amine (155 mg, crude, HCl) as a white solid.

$^1$H NMR (399 MHz, DMSO-d6)=8.87 (br s, 3H), 8.03 (t, J=57.6 Hz, 1H), 7.85 (s, 1H), 6.83 (s, 1H), 4.52 (br d, J=5.6 Hz, 1H), 2.25 (m, 1H), 1.00 (d, J=6.8 Hz, 3H), 0.79 (d, J=6.8 Hz, 3H).

Step 2: (S)—N2-(1-(1-(difluoromethyl)-1H-pyrazol-5-yl)-2-methylpropyl)-6-(3-methylimidazo[1,5-a]pyridin-6-yl)-1,3,5-triazine-2,4-diamine To a solution of 4-chloro-6-(3-methylimidazo[1,5-a]pyridin-6-yl)-1,3,5-triazin-2-amine (Key Intermediate 2) (80 mg, 306.89 μmol) and (1S)-1-[2-(difluoromethyl)pyrazol-3-yl]-2-methyl-propan-1-amine (145.16 mg, 767.22 μmol) in 1,4-dioxane (2 mL) was added DIEA (118.99 mg, 920.67 μmol, 160.36 μL). The mixture was stirred at 120° C. for 16 hr. The mixture was concentrated in vacuo to give the crude product as a black oil. The residue was purified by prep-HPLC to give (S)—N2-(1-(1-(difluoromethyl)-1H-pyrazol-5-yl)-2-methylpropyl)-6-(3-methylimidazo[1,5-a]pyridin-6-yl)-1,3,5-triazine-2,4-diamine (18.9 mg, 44.34 μmol, 12.22% yield, 97% purity) as a yellow solid.

$^1$H NMR (399 MHz, DMSO-d6) δ=8.80 (s, 1H), 8.01 (t, J=58.0 Hz, 1H), 7.71-7.53 (m, 2H), 7.51 (s, 2H), 7.28 (s, 1H), 6.68 (br s, 2H), 6.52 (s, 1H), 5.49-4.92 (m, 1H), 2.67-2.64 (m, 3H), 2.23 (br s, 1H), 1.05 (d, J=6.8 Hz, 3H), 0.84 (br d, J=6.8 Hz, 3H)

LCMS m/z (ESI+) 414.0 [M+H]+.

Example 128

(S)-2-((4-amino-6-(3-methylimidazo[1,5-a]pyridin-6-yl)-1,3,5-triazin-2-yl)amino)-2-(2-fluorophenyl)ethan-1-ol Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (60 mg, 230.17 μmol) in 1,4-dioxane (5 mL) was added (2S)-2-amino-2-(2-fluorophenyl)ethanol (53.6 mg, 345.25 μmol) and DIEA (89.2 mg, 690.50 μmol, 120 μL), then the reaction mixture was heated to 120° C. and stirred for 16 hr. The reaction mixture was concentrated under reduced pressure to give a residue. The residue was purified by prep-HPLC to obtain (S)-2-((4-amino-6-(3-methylimidazo[1,5-a]pyridin-6-yl)-1,3,5-triazin-2-yl)amino)-2-(2-fluorophenyl)ethan-1-ol (34.6 mg, 99.47% purity) as a yellow solid.

$^{1}$H NMR (399 MHz, DMSO-d6)=8.80 (br s, 1H), 8.16 (s, 1H), 7.57-7.42 (m, 3H), 7.34 (br s, 1H), 7.31-7.21 (m, 2H), 7.20-7.10 (m, 2H), 6.63 (br s, 2H), 5.50 (br d, J=7.2 Hz, 1H), 4.79 (br s, 1H), 3.72 (br d, J=6.0 Hz, 2H), 2.53 (s, 3H).

LCMS m/z (ESI+) 380.1 [M+H]+.

Example 129

N2-(2-(6-fluoropyridin-2-yl)propan-2-yl)-6-(3-methylimidazo[1,5-a]pyridin-6-yl)-1,3,5-triazine-2,4-diamine Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.89 μmol) and 2-(6-fluoropyridin-2-yl)propan-2-amine (159.84 mg, 920.66 μmol) in 1,4-dioxane (5 mL), then DIEA (118.99 mg, 920.66 μmol, 160.36 μL) was added, the mixture was stirred at 120° C. for 1 hr under microwave. The mixture was concentrated under reduced pressure to give residue. The residue was diluted with ACETONITRILE (1 mL) and purified by prep-HPLC to give N2-(2-(6-fluoropyridin-2-yl)propan-2-yl)-6-(3-methylimidazo[1,5-a]pyridin-6-yl)-1,3,5-triazine-2,4-diamine (41.8 mg, 33.53% yield) as a yellow solid.

$^{1}$H NMR (399 MHz, DMSO-d6) δ=8.55 (br s, 1H), 8.48 (d, J=4.4 Hz, 1H), 7.56 (dd, J=12.0, 8.0 Hz, 1H), 7.42-7.34 (m, 2H), 7.30 (td, J=8.0, 4.0 Hz, 1H), 7.24 (s, 2H), 6.41 (br s, 2H), 2.67 (s, 3H), 1.76 (s, 6H).

LCMS m/z (ESI+) 379.1 [M+H]+.

Example 130

(R)-2-((4-amino-6-(3-methylimidazo[1,5-a]pyridin-6-yl)-1,3,5-triazin-2-yl)amino)-2-(1-(difluoromethyl)-1H-pyrazol-3-yl)ethan-1-ol Synthesised by General Method F Using the Following Reagents and Conditions:

Step 1: N-[(1S)-1-(tert-butoxymethyl)-2-[methoxy(methyl)amino]-2-oxo-ethyl]carbamate A solution of (2S)-3-tert-butoxy-2-(tert-butoxycarbonylamino)propanoic acid (15 g, 57.40 mmol), Et3N (23.23 g, 229.61 mmol, 31.96 mL) and HOBt (7.76 g, 57.40 mmol) in anhydrous DCM (400 mL) was cooled to 0° C., EDCI·HCl (22.01 g, 114.80 mmol) was added, followed by stirring at 20° C. for 30 minutes. Then N-methoxymethanamine (6.72 g, 68.88 mmol, HCl) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3) and saturated aqueous sodium chloride (200 mL×3), and dried over Na2SO4, filtered and concentrated under reduced pressure to give a residue. The residue was purified by flash silica gel chromatography to give tert-butyl N-[(1S)-1-(tert-butoxymethyl)-2-[methoxy(methyl)amino]-2-oxo-ethyl]carbamate (14.8 g, 83.86% yield) as a colorless oil.

$^{1}$H NMR (399 MHz, CHLOROFORM-d) δ=5.35 (br d, J=8.8 Hz, 1H), 4.77 (br s, 1H), 3.77 (s, 3H), 3.65-3.51 (m, 2H), 3.23 (s, 3H), 1.44 (s, 9H), 1.15 (s, 9H).

Step 2: tert-butyl N-[(1S)-1-(tert-butoxymethyl)-2-oxo-but-3-ynyl]carbamate

A solution of tert-butyl N-[(1S)-1-(tert-butoxymethyl)-2-[methoxy(methyl)amino]-2-oxo-ethyl]carbamate (7.5 g, 24.64 mmol) in THF (120 mL) was cooled to −78° C. under nitrogen, bromo(ethynyl)magnesium (0.5 M, 197.12 mL) was added dropwise, and the mixture was stirred at −78° C. for 1 hr. Then the mixture was allowed to warm to 20° C. and stirred for another 16 hr. The mixture was poured into a cold (0° C.) sat. NH4Cl solution (150 mL) and stirred for 1 h. THF was evaporated in vacuo (35° C.), and the aqueous layer was extracted with EtOAc (300 mL). The combined organic phase was washed successively with sat. aq. $NaHCO_3$ (150 mL), and brine (150 mL×3), dried over anhydrous Na2SO4, filtered, and the filtrate was evaporated in vacuo (40° C.). The residue was purified by flash silica gel chromatography to give tert-butyl N-[(1S)-1-(tert-butoxymethyl)-2-oxo-but-3-ynyl]carbamate (2.9 g, 10.55 mmol, 42.82% yield, 98.243% purity) as a light yellow oil.

$^{1}$H NMR (399 MHz, CHLOROFORM-d) δ=5.42 (br d, J=8.4 Hz, 1H), 4.43 (td, J=2.8, 8.8 Hz, 1H), 4.07 (dd, J=2.4, 9.2 Hz, 1H), 3.63 (dd, J=3.2, 9.2 Hz, 1H), 3.33 (s, 1H), 1.47 (s, 9H), 1.15 (s, 9H).

Step 3: tert-butyl N-[(1R)-2-tert-butoxy-1-(1H-pyrazol-3-yl)ethyl]carbamate

Tert-butyl N-[(1S)-1-(tert-butoxymethyl)-2-oxo-but-3-ynyl]carbamate (2.9 g, 10.77 mmol) was dissolved in EtOH (120 mL), NH2NH2·H2O (1.10 g, 21.53 mmol, 1.07 mL, 98% purity) was added and the reaction mixture was heated to 80° C. for 30 min, then allowed to cool to 20° C. for 0.5 h. The reaction mixture was diluted with H2O (50 mL) and extracted with EtOAc (150 mL×3). The combined organic layers were dried over anhydrous Na2SO4, filtered and concentrated under reduced pressure (30° C.) to give a residue. The residue was purified by flash silica gel chromatography to give tert-butyl N-[(1R)-2-tert-butoxy-1-(1H-pyrazol-3-yl)ethyl]carbamate (3 g, 97.34% yield) as a yellow oil.

$^{1}$H NMR (399 MHz, CHLOROFORM-d) δ=7.48 (d, J=2.0 Hz, 1H), 6.24 (s, 1H), 5.37 (br d, J=8.0 Hz, 1H), 4.92 (br s, 1H), 3.68 (br s, 2H), 1.44 (s, 9H), 1.20 (s, 9H).

Step 4: tert-butyl N-[(1R)-2-tert-butoxy-1-[1-(difluoromethyl)pyrazol-3-yl]ethyl]carbamate To a solution of tert-butyl N-[(1R)-2-tert-butoxy-1-(1H-pyrazol-3-yl)ethyl]carbamate (2 g, 7.06 mmol) and KF (820.14 mg, 14.12 mmol, 330.70 μL) in Acetonitrile (30 mL) was added 1-[[bromo(difluoro)methyl]-ethoxy-phosphoryl]oxyethane (2.02 g, 7.41 mmol, 98% purity) at 20° C. under N2. The mixture was stirred at 20° C. for 16 hr. The reaction mixture was diluted with H2O (40 mL) and extracted with DCM (50 mL×3). The combined organic layers were washed with brine (50 mL×3), dried over Na2SO4, filtered and concentrated under reduced pressure to give a residue. The residue was purified by prep-HPLC to give tert-butyl N-[(1R)-2-tert-butoxy-1-[1-(difluoromethyl)pyrazol-3-yl]ethyl]carbamate (1.88 g, 62.04% yield) as a light yellow oil.

LCMS m/z (ESI+) 334.1 [M+H]+.

Step 5: (2R)-2-amino-2-[1-(difluoromethyl)pyrazol-3-yl]ethanol

To a solution of tert-butyl N-[(1R)-2-tert-butoxy-1-[1-(difluoromethyl)pyrazol-3-yl]ethyl]carbamate (200 mg, 599.93 μmol) in DCM (6 mL) was added TFA (4.62 g, 40.52 mmol, 3 mL). The mixture was stirred at 20° C. for 4 h. The reaction mixture was concentrated under reduced pressure to give (2R)-2-amino-2-[1-(difluoromethyl)pyrazol-3-yl]ethanol (180 mg, crude) was obtained as a yellow oil.

LCMS m/z (ESI+) 178.1 [M+H]+.

Step 6: (R)-2-((4-amino-6-(3-methylimidazo[1,5-a]pyridin-6-yl)-1,3,5-triazin-2-yl)amino)-2-(1-(difluoromethyl)-1H-pyrazol-3-yl)ethan-1-ol A mixture of 4-chloro-6-(3-methylimidazo[1,5-a]pyridin-6-yl)-1,3,5-triazin-2-amine (Key Intermediate 2) (80 mg, 306.89 μmol), (2R)-2-amino-2-[1-(difluoromethyl)pyrazol-3-yl]ethanol (178.72 mg, 613.78 μmol, TFA), DIEA (158.65 mg, 1.23 mmol, 213.81 μL) in 1,4-dioxane (2 mL) was stirred at 120° C. for 16 hr. The mixture was concentrated in vacuo to give the crude product. The residue was purified by prep-HPLC to give (R)-2-((4-amino-6-(3-methylimidazo[1,5-a]pyridin-6-yl)-1,3,5-triazin-2-yl)amino)-2-(1-(difluoromethyl)-1H-pyrazol-3-yl)ethan-1-ol (5.5 mg, 3.67% yield) as a yellow solid.

$^1$H NMR (399 MHz, DMSO-d6) δ=8.81 (s, 1H), 8.07 (d, J=2.4 Hz, 1H), 7.67 (t, J=59.6 Hz, 1H), 7.52 (s, 2H), 7.35 (br s, 1H), 7.28 (s, 1H), 6.69 (br s, 2H), 6.58 (br s, 1H), 5.33 (br s, 1H), 4.68 (br s, 1H), 3.80 (br s, 2H), 2.65 (s, 3H).

LCMS m/z (ESI+) 402.1 [M+H]+.

Example 131

(S)—N2-(1-(1-(difluoromethyl)-1H-pyrazol-3-yl)-2-methylpropyl)-6-(3-methylimidazo[1,5-a]pyridin-6-yl)-1,3,5-triazine-2,4-diamine Synthesised by General Method F Using the Following Reagents and Conditions:

Step 1: tert-butyl N-[(1S)-1-[methoxy(methyl)carbamoyl]-2-methyl-propyl]carbamate A solution of (2S)-2-(tert-butoxycarbonylamino)-3-methyl-butanoic acid (15 g, 69.04 mmol), Et3N (27.95 g, 276.17 mmol, 38.44 mL) and HOBt (9.33 g, 69.04 mmol) in anhydrous DCM (400 mL) was cooled to 0° C., EDCI·HCl (26.47 g, 138.08 mmol) was added, followed by stirring at 20° C. for 30 minutes. Then N-methoxymethanamine (8.08 g, 82.85 mmol, HCl) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3) and saturated aqueous sodium chloride (200 mL×3), and dried over Na2SO4, filtered and concentrated under reduced pressure to give a residue. The residue was purified by flash silica gel chromatography to give tert-butyl N-[(1S)-1-[methoxy(methyl)carbamoyl]-2-methyl-propyl]carbamate (16.7 g, 91.99% yield) as a colorless oil.

$^1$H NMR (399 MHz, CHLOROFORM-d) δ=5.14 (br d, J=8.0 Hz, 1H), 4.59 (br s, 1H), 3.78 (br s, 3H), 3.22 (br s, 3H), 2.04-1.94 (m, 1H), 1.44 (s, 9H), 0.94 (dd, J=7.2, 19.6 Hz, 6H).

Step 2: tert-butyl N-[(1S)-1-isopropyl-2-oxo-but-3-ynyl]carbamate

A solution of tert-butyl N-[(1S)-1-[methoxy(methyl)carbamoyl]-2-methyl-propyl]carbamate (7.5 g, 28.81 mmol) in THF (120 mL) was cooled to −78° C. under nitrogen, bromo(ethynyl)magnesium (0.5 M, 230.48 mL) was added dropwise, and the mixture was stirred at −78° C. for 1 hr. Then the mixture was allowed to warm to 20° C. and stirred for another 16 hr. The mixture was poured into a cold (0° C.) sat. NH4Cl solution (150 mL) and stirred for 1 h. THF was evaporated in vacuo (35° C.), and the aqueous layer was extracted with EtOAc (300 mL). The combined organic phase was washed successively with sat. aq. $NaHCO_3$ (150 mL), and brine (150 mL×3), dried over anhydrous Na2SO4, filtered, and the filtrate was evaporated in vacuo (40° C.). The residue was purified by flash silica gel chromatography to give tert-butyl N-[(1S)-1-isopropyl-2-oxo-but-3-ynyl]carbamate (2.4 g, 35.13% yield) as a yellow oil.

$^1$H NMR (399 MHz, CHLOROFORM-d) δ=5.04 (br d, J=8.0 Hz, 1H), 4.40 (dd, J=3.6, 8.8 Hz, 1H), 3.37 (s, 1H), 2.52-2.40 (m, 1H), 1.45 (s, 9H), 1.05 (d, J=7.2 Hz, 3H), 0.84 (d, J=7.2 Hz, 3H).

Step 3: tert-butyl N-[(1S)-2-methyl-1-(1H-pyrazol-3-yl)propyl]carbamate

Tert-butyl N-[(1S)-1-isopropyl-2-oxo-but-3-ynyl]carbamate (2.4 g, 10.65 mmol) was dissolved in EtOH (120 mL), NH2NH2·H2O (1.09 g, 21.31 mmol, 1.06 mL, 98% purity) was added and the reaction mixture was heated to 80° C. for 30 min, then allowed to cool to 20° C. for 0.5 h. The reaction mixture was diluted with H2O (50 mL) and extracted with EtOAc (150 mL×3). The combined organic layers were dried over anhydrous Na2SO4, filtered and concentrated under reduced pressure (30° C.) to give a residue. The residue was purified by flash silica gel chromatography to give tert-butyl N-[(1S)-2-methyl-1-(1H-pyrazol-3-yl)propyl]carbamate (2.43 g, 94.36% yield) as a yellow oil.

$^1$H NMR (399 MHz, CHLOROFORM-d) δ=7.50 (s, 1H), 6.14 (br s, 1H), 5.39 (br s, 1H), 4.65 (br s, 1H), 2.12 (br s, 1H), 1.45 (br s, 9H), 0.94-0.88 (m, 6H).

Step 4: N-[(1S)-1-[1-(difluoromethyl)pyrazol-3-yl]-2-methyl-propyl]carbamate & tert-butyl N-[(1S)-1-[1-(difluoromethyl)pyrazol-3-yl]-2-methyl-propyl]carbamate To a solution of tert-butyl N-[(1S)-2-methyl-1-(1H-pyrazol-3-yl)propyl]carbamate (2 g, 8.36 mmol) and KF (971.11 mg, 16.71 mmol, 391.58 μL) in Acetonitrile (30 mL) was added 1-[[bromo(difluoro)methyl]-ethoxy-phosphoryl]oxyethane (2.39 g, 8.78 mmol, 98% purity) at 20° C. under N2.

The mixture was stirred at 20° C. for 16 hr. The reaction mixture was diluted with H2O (40 mL) and extracted with DCM (50 mL×3). The combined organic layers were washed with brine (50 mL×3), dried over Na2SO4, filtered and concentrated under reduced pressure to give a residue. The residue was purified by prep-HPLC to give tert-butyl N-[(1S)-1-[1-(difluoromethyl)pyrazol-3-yl]-2-methyl-propyl]carbamate (350 mg, 1.20 mmol, 23.10% yield, 99% purity) as a white solid and tert-butyl N-[(1S)-1-[1-(difluoromethyl)pyrazol-3-yl]-2-methyl-propyl]carbamate (350 mg, 23.10% yield) as a colorless oil.

$^{1}$H NMR (399 MHz, CHLOROFORM-d) δ=7.74 (d, J=2.8 Hz, 1H), 7.15 (t, J=60.8 Hz, 1H), 6.31 (d, J=2.8 Hz, 1H), 5.16 (d, J=7.6 Hz, 1H), 4.72-4.62 (m, 1H), 2.18-2.06 (m, 1H), 1.45 (s, 9H), 0.90 (d, J=6.8 Hz, 6H).

Step 5: (1S)-1-[1-(difluoromethyl)pyrazol-3-yl]-2-methyl-propan-1-amine

To a solution of tert-butyl N-[(1S)-1-[1-(difluoromethyl)pyrazol-3-yl]-2-methyl-propyl]carbamate (200.00 mg, 691.27 μmol) in DCM (4 mL) was added HCl/MeOH (4 M, 2 mL). The mixture was stirred at 20° C. for 5 hr. LCMS (ES21251-82-P1A1) showed desired mass was observed. The reaction mixture was concentrated under reduced pressure to give (1S)-1-[1-(difluoromethyl)pyrazol-3-yl]-2-methyl-propan-1-amine (146 mg, crude, HCl) as a white solid.

$^{1}$H NMR (399 MHz, DMSO-d6) δ=8.72 (br s, 3H), 8.30 (d, J=2.4 Hz, 1H), 7.87 (t, J=58.8 Hz, 1H), 6.73 (d, J=2.4 Hz, 1H), 4.13 (t, J=5.6 Hz, 1H), 2.27-2.19 (m, 1H), 0.95 (d, J=6.8 Hz, 3H), 0.79 (d, J=6.8 Hz, 3H).

Step 6: (S)—N2-(1-(1-(difluoromethyl)-1H-pyrazol-3-yl)-2-methylpropyl)-6-(3-methylimidazo[1,5-a]pyridin-6-yl)-1,3,5-triazine-2,4-diamine To a solution of 4-chloro-6-(3-methylimidazo[1,5-a]pyridin-6-yl)-1,3,5-triazin-2-amine (Key Intermediate 2) (80 mg, 306.89 μmol) and (1S)-1-[1-(difluoromethyl)pyrazol-3-yl]-2-methyl-propan-1-amine (145.16 mg, 767.22 μmol) in 1,4-dioxane (2 mL) was added DIEA (118.99 mg, 920.67 μmol, 160.36 μL). The mixture was stirred at 120° C. for 16 hr. The mixture was concentrated in vacuo to give the crude product. The crude product was purified by prep-HPLC to give (S)—N2-(1-(1-(difluoromethyl)-1H-pyrazol-3-yl)-2-methylpropyl)-6-(3-methylimidazo[1,5-a]pyridin-6-yl)-1,3,5-triazine-2,4-diamine (27.5 mg, 18.33% yield) as a yellow solid.

$^{1}$H NMR (399 MHz, DMSO-d6) δ=8.81 (s, 1H), 8.07 (d, J=2.4 Hz, 1H), 7.68 (t, J=59.6 Hz, 1H), 7.52 (s, 2H), 7.35 (br s, 1H), 7.28 (s, 1H), 6.69 (br s, 2H), 6.58 (br s, 1H), 5.15 (br t, J=8.4 Hz, 1H), 2.65 (s, 3H), 2.25-2.14 (m, 1H), 0.98 (d, J=6.8 Hz, 3H), 0.86 (d, J=6.8 Hz, 3H).

LCMS m/z ($ESI^+$) 414.1 $[M+H]^+$.

Example 132

(S)—N2-(1-(1-(difluoromethyl)-1H-pyrazol-3-yl)propyl)-6-(3-methylimidazo[1,5-a]pyridin-6-yl)-1,3,5-triazine-2,4-diamine Synthesised by General Method F Using the Following Reagents and Conditions:

Step 1: tert-butyl N-[(1S)-1-[methoxy(methyl)carbamoyl]propyl]carbamate

A solution of (2S)-2-(tert-butoxycarbonylamino)butanoic acid (15 g, 73.81 mmol), Et3N (29.87 g, 295.22 mmol, 41.09 mL) and HOBt (9.97 g, 73.81 mmol) in anhydrous DCM (400 mL) was cooled to 0° C., EDCI·HCl (28.30 g, 147.61 mmol) was added, followed by stirring at 20° C. for 30 minutes. Then N-methoxymethanamine (8.64 g, 88.57 mmol, HCl) was added, followed by stirring at 20° C. for another 15.5 h. The mixture was evaporated under reduced pressure. The residue was dissolved in ethyl acetate (200 mL), and washed with 10% aqueous citric acid (200 mL×3), 10% aqueous NaHCO3 (200 mL×3) and saturated aqueous sodium chloride (200 mL×3), and dried over Na2SO4, filtered and concentrated under reduced pressure to give a residue. The residue was purified by flash silica gel chromatography to give tert-butyl N-[(1S)-1-[methoxy(methyl)carbamoyl]propyl]carbamate (16 g, 80.09% yield) as a white solid.

$^{1}$H NMR (399 MHz, CHLOROFORM-d) δ=5.18 (d, J=8.0 Hz, 1H), 4.64 (br s, 1H), 3.78 (s, 3H), 3.22 (s, 3H), 1.82-1.74 (m, 1H), 1.61-1.56 (m, 1H), 1.44 (s, 9H), 0.95 (t, J=7.6 Hz, 3H).

Step 2: tert-butyl N-[(1S)-1-ethyl-2-oxo-but-3-ynyl]carbamate

A solution of tert-butyl N-[(1S)-1-[methoxy(methyl)carbamoyl]propyl]carbamate (7 g, 28.42 mmol) in THF (100 mL) was cooled to −78° C. under nitrogen, bromo(ethynyl)magnesium (0.5 M, 227.36 mL) was added dropwise, and the mixture was stirred at −78° C. for 1 hr. Then the mixture was allowed to warm to 20° C. and stirred for another 18 hr. The mixture was poured into a cold (0° C.) sat. NH4Cl solution (150 mL) and stirred for 1 h. THF was evaporated in vacuo (35° C.), and the aqueous layer was extracted with EtOAc (300 mL). The combined organic phase was washed successively with sat. aq. $NaHCO_3$ (150 mL), and brine (150 mL×3), dried over anhydrous Na2SO4, filtered, and the filtrate was evaporated in vacuo (40° C.). The residue was purified by flash silica gel chromatography to give tert-butyl N-[(1S)-1-ethyl-2-oxo-but-3-ynyl]carbamate (1.16 g, 16.42% yield) as a yellow oil.

$^{1}$H NMR (399 MHz, CHLOROFORM-d) δ=5.10 (br d, J=5.6 Hz, 1H), 4.43-4.38 (m, 1H), 3.36 (s, 1H), 2.08-2.03 (m, 1H), 1.80-1.72 (m, 1H), 1.46 (s, 9H), 0.96 (t, J=7.6 Hz, 3H).

Step 3: N-[(1S)-1-(1H-pyrazol-3-yl)propyl]carbamate

Tert-butyl N-[(1S)-1-ethyl-2-oxo-but-3-ynyl]carbamate (1.16 g, 5.49 mmol) was dissolved in EtOH (60 mL), NH2NH2·H2O (561 mg, 10.98 mmol, 544.63 uL, 98% purity) was added and the reaction mixture was heated to 80° C. for 30 min, then allowed to cool to 20° C. for 0.5 h. The reaction mixture was diluted with H2O (50 mL) and extracted with EtOAc (100 mL×3). The combined organic layers were dried over anhydrous Na2SO4, filtered and concentrated under reduced pressure (30° C.) to give a residue. The residue was purified by flash silica gel chromatography to give tert-butyl N-[(1S)-1-(1H-pyrazol-3-yl)propyl]carbamate (1.13 g, 89.52% yield) as a yellow oil.

$^{1}$H NMR (399 MHz, CHLOROFORM-d) δ=7.50 (d, J=2.0 Hz, 1H), 6.16 (d, J=2.0 Hz, 1H), 5.29 (br d, J=6.4 Hz, 1H), 4.73 (br d, J=6.4 Hz, 1H), 1.92-1.81 (m, 2H), 1.44 (s, 9H), 0.93 (t, J=7.6 Hz, 3H).

Step 4: tert-butyl N-[(1S)-1-[1-(difluoromethyl)pyrazol-3-yl]propyl]carbamate

To a solution of tert-butyl N-[(1S)-1-(1H-pyrazol-3-yl)propyl]carbamate (1 g, 4.44 mmol) and KF (550 mg, 9.46 mmol) in Acetonitrile (15 mL) was dropwise added 1-[[bromo(difluoro)methyl]-ethoxy-phosphoryl]oxyethane (1.24 g, 4.66 mmol) under nitrogen atmosphere. The mixture was stirred at 20° C. for 18 hr. The reaction mixture was diluted with H2O (40 mL) and extracted with DCM (50 mL×3). The combined organic layers were washed with brine (50 mL×3), dried over Na2SO4, filtered and concentrated under reduced pressure to give a residue. The residue was purified by flash silica gel chromatography to give tert-butyl N-[(1S)-1-[1-(difluoromethyl)pyrazol-3-yl]propyl]carbamate (479.6 mg, 38.86% yield) as a colorless oil.

LCMS m/z (ESI+) 276.1 [M+H]+.

Step 5: give (1S)-1-[1-(difluoromethyl)pyrazol-3-yl]propan-1-amine

To a solution of tert-butyl N-[(1S)-1-[1-(difluoromethyl)pyrazol-3-yl]propyl]carbamate (200 mg, 726.50 μmol) in DCM (5 mL) was added HCl/1,4-dioxane (2 mL). The mixture was stirred at 20° C. for 16 h. The reaction mixture was concentrated under reduced pressure to give (1S)-1-[1-(difluoromethyl)pyrazol-3-yl]propan-1-amine (129.2 mg, crude, HCl) was obtained as a white solid.

LCMS m/z (ESI+) 176.1 [M+H]+.

Step 6: (S)—N2-(1-(1-(difluoromethyl)-1H-pyrazol-3-yl)propyl)-6-(3-methylimidazo[1,5-a]pyridin-6-yl)-1,3,5-triazine-2,4-diamine To a solution of 4-chloro-6-(3-methylimidazo[1,5-a]pyridin-6-yl)-1,3,5-triazin-2-amine (Key Intermediate 2) (60 mg, 230.17 μmol) in 1,4-dioxane (3 mL) was added DIEA (119 mg, 920.68 μmol, 160.36 μL) and (1S)-1-[1-(difluoromethyl)pyrazol-3-yl]propan-1-amine (121.78 mg, 575.42 μmol, HCl). The mixture was stirred at 120° C. for 16 hr. The mixture was concentrated in vacuo to give the crude product. The residue was purified by prep-HPLC to give (S)—N2-(1-(1-(difluoromethyl)-1H-pyrazol-3-yl)propyl)-6-(3-methylimidazo[1,5-a]pyridin-6-yl)-1,3,5-triazine-2,4-diamine (24 mg, 19.80% yield) as a yellow solid.

$^1$H NMR (399 MHz, DMSO-d6) δ=8.81 (s, 1H), 8.05 (d, J=2.4 Hz, 1H), 7.67 (t, J=60.0 Hz, 1H), 7.52 (s, 2H), 7.40 (br s, 1H), 7.29 (s, 1H), 6.71-6.66 (m, 2H), 6.53 (d, J=2.4 Hz, 1H), 5.21 (m, 1H), 2.70 (s, 2H), 1.95-1.87 (m, 2H), 0.93 (t, J=7.2 Hz, 3H).

LCMS m/z (ESI+) 400.1 [M+H]+.

Example 133

6-(3-methylimidazo[1,5-a]pyridin-6-yl)-N2-(1-(2-(trifluoromethyl)thiazol-4-yl)ethyl)-1,3,5-triazine-2,4-diamine Step 1: N-methoxy-N-methyl-2-(trifluoromethyl)thiazole-4-carboxamide To a solution of 2-(trifluoromethyl)thiazole-4-carboxylic acid (4.8 g, 24.35 mmol) in DCM (80 mL) was added DIEA (12.59 g, 97.40 mmol, 16.96 mL) and HATU (12.04 g, 31.65 mmol), the reaction mixture was stirred at 20° C. for 1 h, then N-methoxymethanamine (3.56 g, 36.52 mmol, HCl) was added to the reaction mixture and stirred at 20° C. for 12 h. The reaction mixture was poured into water (50 mL) and extracted with DCM (50 mL×3). The combined organic layers were washed with water (50 mL×2), brine (50 mL×2), dried over anhydrous Na2SO4, filtered and concentrated under reduced pressure to give a residue. The residue was purified by flash silica gel chromatography to obtain N-methoxy-N-methyl-2-(trifluoromethyl)thiazole-4-carboxamide (5.22 g, 83.00% yield) as a light yellow solid.

$^1$H NMR (399 MHz, CHLOROFORM-d) δ=8.24 (s, 1H), 3.85 (s, 3H), 3.44 (s, 3H).

Step 2: 1-[2-(trifluoromethyl)thiazol-4-yl]ethanone

To a solution of N-methoxy-N-methyl-2-(trifluoromethyl)thiazole-4-carboxamide (2 g, 8.33 mmol) in THF (50 mL) at −78° C. was added MeMgBr (3 M, 5.55 mL), the reaction was stirred at −78° C. for 1 h, then the reaction mixture was warmed to 20° C. and stirred for 12 h under nitrogen atmosphere. The reaction mixture was quenched with NH4Cl (40 mL) and extracted with EtOAc (80 mL×3). The combined organic layers were washed with brine (60 mL), dried over anhydrous Na2SO4, filtered and concentrated under reduced pressure to give a residue. The residue was purified by flash silica gel chromatography to obtain 1-[2-(trifluoromethyl)thiazol-4-yl]ethanone (0.85 g, 42.89% yield) as a light yellow oil.

$^1$H NMR (399 MHz, CHLOROFORM-d) δ=8.35 (s, 1H), 2.73 (s, 3H).

Step 3: 1-[2-(trifluoromethyl)thiazol-4-yl]ethanone oxime

To a solution of 1-[2-(trifluoromethyl)thiazol-4-yl]ethanone (1.01 g, 5.18 mmol) in EtOH (10 mL) and H2O (15 mL) was added hydroxylamine (539.44 mg, 7.76 mmol, HCl) and NaOAc (1.06 g, 12.94 mmol), then the reaction mixture was stirred at 85° C. for 4 h. The reaction mixture was concentrated under reduced pressure to give a residue, the residue was dissolved in EtOAc (30 mL), and washed with water (20 mL) and brine (40 mL), then dried over anhydrous Na2SO4, filtered, and concentrated under reduced pressure to give a residue. The residue was purified by flash silica gel chromatography to obtain 1-[2-(trifluoromethyl)thiazol-4-yl]ethanone oxime (825 mg, 66.22% yield) as a light yellow solid.

$^1$H NMR (399 MHz, DMSO-d6) δ=11.53 (s, 1H), 8.29 (s, 3H), 2.28 (s, 3H).

Step 4: 1-[2-(trifluoromethyl)thiazol-4-yl]ethanamine

To a solution of 1-[2-(trifluoromethyl)thiazol-4-yl]ethanone oxime (500 mg, 2.38 mmol) in NH3/MeOH (7 M, 12 mL) was added Raney-Ni (150 mg, 1.75 mmol) under nitrogen atmosphere. The suspension was degassed and purged with H2 for 3 times. The mixture was stirred under H2 (50 Psi) at 40° C. for 12 h. The reaction mixture was filtered, and the filtrate was concentrated under reduced pressure. The residue was purified by flash silica gel chromatography to obtain 1-[2-(trifluoromethyl)thiazol-4-yl]ethanamine (240 mg, 41.86% yield) as a white solid.

LCMS m/z (ESI+) 197.1 [M+H]+.

Step 5: 6-(3-methylimidazo[1,5-a]pyridin-6-yl)-N2-(1-(2-(trifluoromethyl)thiazol-4-yl)ethyl)-1,3,5-triazine-2,4-diamine To a solution of 4-chloro-6-(3-methylimidazo[1,5-a]pyridin-6-yl)-1,3,5-triazin-2-amine (Key Intermediate 2) (80 mg, 306.89 μmol) in 1,4-dioxane (10 mL) was added 1-[2-(trifluoromethyl)thiazol-4-yl]ethanamine (90.3 mg, 460.33 μmol) and DIEA (119.0 mg, 920.66 μmol, 160.36 μL). Then the reaction mixture was heated to 120° C. and stirred for 12 hr The reaction mixture was concentrated under reduced pressure to give a residue. The residue was purified by Prep-HPLC to obtain 6-(3-methylimidazo[1,5-a]pyridin-6-yl)-N2-(1-(2-(trifluoromethyl)thiazol-4-yl)ethyl)-1,3,5-triazine-2,4-diamine (39.9 mg, 30.71% yield) as a yellow solid.

$^1$H NMR (399 MHz, DMSO-d6) δ=8.80 (s, 1H), 7.91 (s, 1H), 7.61 (br s, 1H), 7.56-7.44 (m, 2H), 7.29 (s, 1H), 6.69 (br s, 2H), 5.51 (br d, J=5.6 Hz, 1H), 2.65 (s, 3H), 1.59 (d, J=7.2 Hz, 3H)

LCMS m/z (ESI+) 421.1 [M+H]+.

Example 134

(S)—N2-(1-(1-(difluoromethyl)-1H-pyrazol-5-yl)ethyl)-6-(3-methylimidazo[1,5-a]pyridin-6-yl)-1,3,5-triazine-2,4-diamine

Step 1: N-[(1S)-1-[2-(difluoromethyl)pyrazol-3-yl]ethyl]carbamate

Tert-butyl N-[(1S)-1-[1-(difluoromethyl)pyrazol-3-yl]ethyl]carbamate (mixture) was purified by prep-HPLC (column: Boston Green ODS 150*30 mm*5 um; mobile phase: [water (FA)-ACN]; B %: 45%-75%, 7 min) to give tert-butyl N-[(1S)-1-[2-(difluoromethyl)pyrazol-3-yl]ethyl]carbamate (150 mg, 574.12 μmol, 18.75% yield) as a white solid.

$^1$H NMR (399 MHz, CHLOROFORM-d) δ=7.57 (s, 1H), 7.38 (t, J=59.2 Hz, 1H), 6.32 (s, 1H), 5.15 (br s, 1H), 4.78 (m, 1H), 1.55 (m, 3H), 1.43 (br s, 9H)

Step 2: (1S)-1-[2-(difluoromethyl)pyrazol-3-yl]ethanamine

Tert-butyl N-[(1S)-1-[2-(difluoromethyl)pyrazol-3-yl]ethyl]carbamate (150 mg, 574.12 μmol) was dissolved in DCM (2 mL), HCl/1,4-dioxane (4 M, 1.00 mL) was added, and the reaction was stirred at 20° C. for 16 h. The reaction mixture was concentrated under reduced pressure to give (1S)-1-[2-(difluoromethyl)pyrazol-3-yl]ethanamine (118 mg, crude, HCl) as a white solid.

$^1$H NMR (399 MHz, DMSO-d6) δ=8.83 (br s, 3H), 7.99 (t, J=57.6 Hz, 1H), 7.80 (d, J=1.2 Hz, 1H), 6.84 (d, J=1.2 Hz, 1H), 4.78 (q, J=6.8 Hz, 1H), 1.54 (d, J=6.8 Hz, 3H).

Step 3: (S)—N2-(1-(1-(difluoromethyl)-1H-pyrazol-5-yl)ethyl)-6-(3-methylimidazo[1,5-a]pyridin-6-yl)-1,3,5-triazine-2,4-diamine A mixture of 4-chloro-6-(3-methylimidazo[1,5-a]pyridin-6-yl)-1,3,5-triazin-2-amine (Key Intermediate 2) (60 mg, 230.17 μmol), (1S)-1-[2-(difluoromethyl)pyrazol-3-yl]ethanamine (113.71 mg, 575.41 μmol, HCl), DIEA (89.24 mg, 690.50 μmol, 120.27 μL) in 1,4-dioxane (4 mL) was stirred at 120° C. for 16 hr. The residue was purified by prep-HPLC. The mixture was added ethyl acetate (10 mL) and 2N $NaHCO_3$ solution (5 mL) and extracted with ethyl acetate (20 mL×3). The combined organic layers were washed with brine (10 mL), dried over Na2SO4, concentrated in vacuo to give (S)—N2-(1-(1-(difluoromethyl)-1H-pyrazol-5-yl)ethyl)-6-(3-methylimidazo[1,5-a]pyridin-6-yl)-1,3,5-triazine-2,4-diamine (17.8 mg, 15.93% yield) as a yellow solid.

$^1$H NMR (399 MHz, DMSO-d6) δ=8.78 (s, 1H), 7.93 (t, J=58.4 Hz, 1H), 7.72-7.61 (m, 2H), 7.53-7.50 (m, 1H), 7.49-7.46 (m, 1H), 7.28 (s, 1H), 6.70 (br s, 2H), 6.49 (s, 1H), 5.64 (br s, 1H), 2.65 (s, 3H), 1.55 (d, J=6.8 Hz, 3H).

LCMS m/z (ESI+) 386.1 [M+H]+.

Example 135

6-(3-methylimidazo[1,5-a]pyridin-6-yl)-N2-(2-(4-(trifluoromethyl)thiazol-2-yl)propan-2-yl)-1,3,5-triazine-2,4-diamine Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.88 μmol) and 2-(4-(trifluoromethyl)thiazol-2-yl)propan-2-amine (64.51 mg, 306.88 μmol) in 1,4-dioxane (5 mL), then DIEA (118.98 mg, 920.63 μmol) was added, the mixture was stirred at 120° C. for 1 hr under microwave. The mixture was concentrated under reduced pressure to give residue. The residue was diluted with ACETONITRILE (1 mL) and purified by prep-HPLC to give 6-(3-methylimidazo[1,5-a]pyridin-6-yl)-N2-(2-(4-(trifluoromethyl)thiazol-2-yl)propan-2-yl)-1,3,5-triazine-2,4-diamine (44.7 mg, 33.53% yield) as a yellow solid.

$^1$H NMR (399 MHz, DMSO-d6) δ=8.80 (s, 1H), 7.91 (s, 1H), 7.61 (br s, 1H), 7.56-7.44 (m, 2H), 7.29 (s, 1H), 6.69 (br s, 2H), 5.51 (br d, 1H), 2.65 (s, 3H), 1.59 (t, 6H)

LCMS m/z (ESI+) 435.1 [M+H]+.

Example 136

N2-(2-(3-fluoropyridin-2-yl)propan-2-yl)-6-(3-methylimidazo[1,5-a]pyridin-6-yl)-1,3,5-triazine-2,4-diamine Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.89 μmol) in 1,4-dioxane (6 mL) was added 2-(3-fluoro-2-pyridyl)propan-2-amine (141.95 mg, 920.66 μmol) and DIEA (118.99 mg, 920.66 μmol). Then the reaction mixture was heated to 120° C. and stirred for 24 hr to obtain a brown solution. The reaction mixture was concentrated under reduced pressure to give a residue. The residue was purified by prep-HPLC to obtain N2-(2-(3-fluoropyridin-2-yl)propan-2-yl)-6-(3-methylimidazo[1,5-a]pyridin-6-yl)-1,3,5-triazine-2,4-diamine (40.5 mg, 34.25% yield) as a yellow solid.

$^1$H NMR (399 MHz, DMSO-d6) δ=8.55 (br s, 1H), 8.43 (d, J=4.4 Hz, 1H), 7.51 (dd, J=12.0, 8.0 Hz, 1H), 7.47-7.39 (m, 2H), 7.32 (td, J=8.0, 4.0 Hz, 1H), 7.25 (s, 2H), 6.46 (br s, 2H), 2.63 (s, 3H), 1.82 (s, 6H).

LCMS m/z ($ESI^+$) 379.1 $[M+H]^+$.

Example 137

N2-(2-(5-fluoropyridin-2-yl)propan-2-yl)-6-(3-methylimidazo[1,5-a]pyridin-6-yl)-1,3,5-triazine-2,4-diamine Trihydrochloride Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.89 μmol) in 1,4-dioxane (8 mL) was added 2-(5-fluoro-2-pyridyl)propan-2-amine (141.95 mg, 920.66 μmol)

and DIEA (118.99 mg, 920.66 μmol). Then the reaction mixture was heated to 120° C. and stirred for 24 hr to obtain a brown solution. The reaction mixture was concentrated under reduced pressure to give a residue. The residue was purified by prep-HPLC to obtain N2-(2-(5-fluoropyridin-2-yl)propan-2-yl)-6-(3-methylimidazo[1,5-a]pyridin-6-yl)-1,3,5-triazine-2,4-diamine Trihydrochloride (38.2 mg, 32.89% yield) as a yellow solid.

$^1$H NMR (399 MHz, DMSO-d6) δ=8.93-8.57 (m, 1H), 8.50 (d, J=2.8 Hz, 1H), 8.00 (s, 1H), 7.91-7.67 (m, 2H), 7.66-7.65 (m, 3H), 7.64-7.59 (m, 2H), 2.95 (br s, 3H), 1.80 (s, 6H).

LCMS m/z (ESI+) 378.9 [M+H]+.

Example 138

6-(3-methylimidazo[1,5-a]pyridin-6-yl)-N2-(1-(4-(trifluoromethyl)thiazol-2-yl)ethyl)-1,3,5-triazine-2,4-diamine Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.88 μmol) and 1-(4-(trifluoromethyl)thiazol-2-yl)ethan-1-amine (60.21 mg, 306.88 μmol) in 1,4-dioxane (5 mL), then DIEA (118.98 mg, 920.63 μmol) was added, the mixture was stirred at 120° C. for 1 hr under microwave. The mixture was concentrated under reduced pressure to give residue. The residue was diluted with ACETONITRILE (1 mL) and purified by prep-HPLC to give 6-(3-methylimidazo[1,5-a]pyridin-6-yl)-N2-(1-(4-(trifluoromethyl)thiazol-2-yl)ethyl)-1,3,5-triazine-2,4-diamine (41.54 mg, 32.2% yield) as a yellow solid.

$^1$H NMR (399 MHz, DMSO-d6) δ=8.80 (s, 1H), 7.91 (s, 1H), 7.61 (br s, 1H), 7.56-7.44 (m, 2H), 7.29 (s, 1H), 6.69 (br s, 2H), 5.51 (br d, J=5.6 Hz, 1H), 2.65 (s, 3H), 1.59 (d, J=7.2 Hz, 3H)

LCMS m/z (ESI+) 421.1 [M+H]+.

Example 139

(R)—N2-(1-(1-(difluoromethyl)-1H-pyrazol-3-yl)ethyl)-6-(3-methylimidazo[1,5-a]pyridin-6-yl)-1,3,5-triazine-2,4-diamine Synthesised by General Method F Using the Following Reagents and Conditions:

Step 1: tert-butyl N-[(1R)-2-[methoxy(methyl)amino]-1-methyl-2-oxo-ethyl]carbamate A solution of (2R)-2-(tert-butoxycarbonylamino)propanoic acid (20 g, 105.70 mmol), Et3N (42.78 g, 422.81 mmol, 58.85 mL) and HOBt (15.71 g, 116.27 mmol) in anhydrous DCM (500 mL) was cooled to 0° C., EDCI·HCl (22.29 g, 116.27 mmol) was added, followed by stirring at 20° C. for 30 minutes. Then N-methoxymethanamineN-methoxymethanamine (11.34 g, 116.27 mmol, HCl) was added, followed by stirring at 20° C. for another 16 h. The reaction mixture was concentrated under reduced pressure. The reaction mixture was diluted with water (50 mL) and extracted with EtOAc (100 mL×3). The combined organic layers were washed with brine (70 mL×3), dried over Na2SO4, filtered and concentrated under reduced pressure to give a residue. The residue was purified by flash silica gel to give tert-butyl N-[(1R)-2-[methoxy(methyl)amino]-1-methyl-2-oxo-ethyl]carbamate (9.76 g, yield) as a white solid.

$^1$H NMR (399 MHz, CHLOROFORM-d) δ=5.33-5.22 (m, 1H), 4.74-4.62 (m, 1H), 3.77 (s, 3H), 3.21 (s, 3H), 1.44 (s, 9H), 1.33-1.30 (d, J=6.8 Hz, 3H).

Step 2: tert-butyl N-[(1R)-1-methyl-2-oxo-but-3-ynyl]carbamate

A solution of tert-butyl N-[(1R)-2-[methoxy(methyl)amino]-1-methyl-2-oxo-ethyl]carbamate (9.76 g, 42.02 mmol) in THF (175 mL) was cooled to −78° C. under nitrogen, bromo(ethynyl)magnesium (0.5 M, 336.15 mL) was added dropwise, and the mixture was stirred at −78° C. for 1 hr. Then the mixture was allowed to warm to 20° C. and stirred for another 18 hr. The reaction mixture was quenched by addition NH4Cl (150 mL) at 0° C., and THF was concentrated under reduced pressure at 30° C. and extracted with EtOAc (150 mL×3). The combined organic layers were washed with brine (150 mL×3), dried over Na2SO4, filtered and concentrated under reduced pressure to give a residue. The residue was purified by flash silica gel chromatography to give tert-butyl N-[(1R)-1-methyl-2-oxo-but-3-ynyl]carbamate (2 g, 21.96% yield) as a yellow solid.

$^1$H NMR (399 MHz, CHLOROFORM-d) δ=5.20-5.11 (m, 1H), 4.44-4.35 (m, 1H), 3.38 (s, 1H), 1.43 (m, 12H)

Step 3: tert-butyl N-[(1R)-1-(1H-pyrazol-3-yl)ethyl]carbamate

Tert-butyl N-[(1R)-1-methyl-2-oxo-but-3-ynyl]carbamate (3.3 g, 16.73 mmol) was dissolved in EtOH (120 mL), NH2NH2·H2O (1.71 g, 33.46 mmol, 1.66 mL, 98% purity) was added, and the reaction mixture was heated to 80° C. for 30 min, then allowed to cool to 20° C. for 30 min. The reaction mixture was concentrated under reduced pressure. The residue was diluted with water (80 mL) and extracted with EtOAc (150 mL×3). The combined organic layers were dried over Na2SO4, filtered and concentrated under reduced pressure (30° C.) to give a residue. The residue was purified by flash silica gel chromatography to give tert-butyl N-[(1R)-1-(1H-pyrazol-3-yl)ethyl]carbamate (3.35 g, 15.86 mmol, 94.77% yield) as a white solid.

LCMS m/z (ESI+) 212.1 [M+H]+.

Step 4: tert-butyl N-[(1R)-1-[1-(difluoromethyl)pyrazol-3-yl]ethyl]carbamate KF (1.10 g, 18.93 mmol, 443.55 μL) and tert-butyl N-[(1R)-1-(1H-pyrazol-3-yl)ethyl]carbamate (2 g, 9.47 mmol) were combined in a flask under N2. Acetonitrile (30 mL) was then added followed by 1-[[bromo(difluoro)methyl]-ethoxy-phosphoryl]oxyethane (2.58 g, 9.66 mmol). The reaction mixture was stirred at 20° C. for 18 h. The reaction mixture was concentrated under reduced pressure at 20° C. The residue diluted with water (30 mL) and extracted with EtOAc (60 mL×3). The combined organic layers were washed with brine (60 mL×3), dried over Na2SO4, filtered and concentrated under reduced pressure to give a residue. The residue was purified by flash silica gel chromatography to give tert-butyl N-[(1R)-1-[1-(difluoromethyl)pyrazol-3-yl]ethyl]carbamate (2.0 g, 77.60% yield) as a colorless oil.

LCMS m/z (ESI+) 262.1 [M+H]+.

Step 5: (1R)-1-[1-(difluoromethyl)pyrazol-3-yl]ethanamine

To a solution of tert-butyl N-[(1R)-1-[1-(difluoromethyl)pyrazol-3-yl]ethyl]carbamate (500 mg, 1.91 mmol) in DCM (7 mL), HCl/1,4-dioxane (3 mL) was added, and the resulting mixture was stirred at 20° C. for 16 hr. The reaction mixture was concentrated under reduced pressure to give (1R)-1-[1-(difluoromethyl)pyrazol-3-yl]ethanamine (428 mg, crude, HCl) as a white solid.

LCMS m/z (ESI+) 162.1 [M+H]+.

Step 6: (R)—N2-(1-(1-(difluoromethyl)-1H-pyrazol-3-yl)ethyl)-6-(3-methylimidazo[1,5-a]pyridin-6-yl)-1,3,5-triazine-2,4-diamine To a solution of 4-chloro-6-(3-methylimidazo[1,5-a]pyridin-6-yl)-1,3,5-triazin-2-amine (Key Intermediate 2) (80 mg, 306.89 μmol) in 1,4-dioxane (2 mL) was added DIEA (158.65 mg, 1.23 mmol, 213.82 μL) and (1R)-1-[1-(difluoromethyl)pyrazol-3-yl]ethanamine (181.93 mg, 920.66 μmol, HCl). The mixture was stirred at 120° C. for 16 hr. The reaction mixture was concentrated under reduced pressure to give a residue. The residue was purified by prep-HPLC to give (R)—N2-(1-(1-(difluoromethyl)-1H-pyrazol-3-yl)ethyl)-6-(3-methylimidazo[1,5-a]pyridin-6-yl)-1,3,5-triazine-2,4-diamine (23.7 mg, 19.44% yield) as a yellow solid.

$^1$H NMR (399 MHz, DMSO-d6) δ=8.83-8.78 (m, 1H), 8.08-8.00 (m, 1H), 7.67 (t, J=60.0 Hz, 1H), 7.52-7.47 (m, 2H), 7.42-7.33 (m, 1H), 7.29-7.25 (m, 1H), 6.74-6.58 (m, 2H), 6.53-6.48 (m, 1H), 5.46-5.35 (m, 1H), 2.67 (s, 3H), 1.55-1.50 (m, 3H).

LCMS m/z (ESI+) 386.1 [M+H]+.

Example 140

(S)—N2-(1-(1-(difluoromethyl)-1H-pyrazol-3-yl)ethyl)-6-(3-methylimidazo[1,5-a]pyridin-6-yl)-1,3,5-triazine-2,4-diamine Synthesised by General Method F Using the Following Reagents and Conditions:

Step 1: N-[(1S)-2-[methoxy(methyl)amino]-1-methyl-2-oxo-ethyl]carbamate

A solution of (2S)-2-(tert-butoxycarbonylamino)propanoic acid (10 g, 52.85 mmol) (250 mL), Et3N (21.39 g, 211.41 mmol, 29.43 mL) and HOBt (7.86 g, 52.85 mmol) in anhydrous DCM was cooled to 0° C., EDCI·HCl (11.14 g, 105.7 mmol) was added, followed by stirring at 20° C. for 30 minutes. Then N-methoxymethanamine (5.67 g, 58.14 mmol, HCl) was added, followed by stirring at 20° C. for another 16 h. The mixture was evaporated under reduced pressure. The residue was dissolved in ethyl acetate (200 mL), washed with 10% aqueous citric acid (200 mL×3), 10% aqueous $NaHCO_3$ (200 mL×3) and saturated aqueous sodium chloride (200 mL×3), and dried over Na2SO4, filtered and concentrated under reduced pressure to give a residue. The crude product was purified by re-crystallization from (Petroleum ether:Ethyl acetate=5:1) (120 mL) at 70° C. to give tert-butyl N-[(1S)-2-[methoxy(methyl)amino]-1-methyl-2-oxo-ethyl]carbamate (6.7 g, 54.58% yield) as a white solid.

$^1$H NMR (399 MHz, CHLOROFORM-d) δ=5.26 (br d, J=6.4 Hz, 1H), 4.74-4.64 (m, 1H), 3.78 (s, 3H), 3.21 (s, 3H), 1.44 (s, 9H), 1.32 (d, J=6.8 Hz, 3H).

Step 2: tert-butyl N-[(1S)-1-methyl-2-oxo-but-3-ynyl]carbamate

A solution of tert-butyl N-[(1S)-2-[methoxy(methyl)amino]-1-methyl-2-oxo-ethyl]carbamate (6 g, 25.83 mmol) in THF (120 mL) was cooled to −78° C. under nitrogen, bromo(ethynyl)magnesium (0.5 M, 206.65 mL) was added dropwise, and the mixture was stirred at −78° C. for 1 hr. Then the mixture was allowed to warm to 20° C. and stirred for another 16 hr. The mixture was poured into a cold (0° C.) sat. NH4Cl solution (150 mL) and stirred for 1 h. THF was evaporated in vacuo (35° C.), and the aqueous layer was extracted with EtOAc (300 mL). The combined organic phase was washed successively with sat. aq. $NaHCO_3$ (150 mL), and brine (150 mL×3), dried over anhydrous Na2SO4, filtered, and the filtrate was evaporated in vacuo (40° C.). The residue was purified by flash silica gel chromatography to give tert-butyl N-[(1S)-1-methyl-2-oxo-but-3-ynyl]carbamate (2.4 g, 23.08% yield) as a yellow oil.

$^1$H NMR (399 MHz, CHLOROFORM-d) δ=5.13 (br s, 1H), 4.43-4.40 (m, 1H), 3.37 (s, 1H), 1.45 (s, 9H), 1.43 (br s, 3H)

Step 3: tert-butyl N-[(1S)-1-(1H-pyrazol-3-yl)ethyl]carbamate

Tert-butyl N-[(1S)-1-methyl-2-oxo-but-3-ynyl]carbamate (2.4 g, 12.17 mmol) was dissolved in EtOH (120 mL), NH2NH2·H2O (1.24 g, 24.34 mmol, 1.21 mL, 98% purity) was added and the reaction mixture was heated to 80° C. for 30 min then allowed to cool to 20° C. for 0.5 h. The reaction mixture was diluted with EtOAc (150 mL) and extracted with EtOAc (150 mL×3). The combined organic layers were dried over anhydrous Na2SO4, filtered and concentrated under reduced pressure (30° C.) to give a residue. The residue was purified by flash silica gel chromatography to give tert-butyl N-[(1S)-1-(1H-pyrazol-3-yl)ethyl]carbamate (2.47 g, 95.12% yield) as a yellow oil.

$^1$H NMR (399 MHz, CHLOROFORM-d) δ=7.50 (d, J=2.0 Hz, 1H), 6.18 (d, J=2.0 Hz, 1H), 5.11 (br s, 1H), 4.96-4.86 (m, 1H), 1.53 (d, J=6.8 Hz, 3H), 1.45 (s, 9H).

Step 4: tert-butyl N-[(1S)-1-[1-(difluoromethyl)pyrazol-3-yl]ethyl]carbamate

KF (1.10 g, 18.93 mmol, 443.55 μL) and tert-butyl N-[(1S)-1-(1H-pyrazol-3-yl)ethyl]carbamate (2 g, 9.47 mmol) were combined in a flask under N2. Acetonitrile (30 mL) was then added followed by 1-[[bromo(difluoro)methyl]-ethoxy-phosphoryl]oxyethane (2.58 g, 9.47 mmol, 98% purity). The reaction mixture was stirred at 20° C. for 16 h. The reaction mixture was diluted with DCM (50 mL) and H2O (50 mL) and extracted with DCM (50 mL×3). The combined organic layers were washed with brine (50 mL×3), dried over anhydrous Na2SO4, filtered and concentrated under reduced pressure to give a residue. The residue was purified by flash silica gel chromatography to give tert-butyl N-[(1S)-1-[1-(difluoromethyl)pyrazol-3-yl]ethyl]carbamate (2.8 g, crude) as a light yellow oil.

LCMS m/z (ESI+) 262.1 [M+H]+.

Step 5: (1S)-1-[1-(difluoromethyl)pyrazol-3-yl]ethanamine

To a solution of tert-butyl N-[(1S)-1-[1-(difluoromethyl)pyrazol-3-yl]ethyl]carbamate (1 g, 3.83 mmol) in DCM (10 mL), HCl/1,4-dioxane (1 M, 3.83 mL) was added, and the reaction mixture was stirred at 20° C. for 16 h. The reaction mixture was concentrated under reduced pressure. The residue was diluted with 1M NaOH solution (15 mL) and extracted with DCM (30 mL×3). The combined organic layers were washed with brine (30 mL×3), dried over anhydrous Na2SO4, filtered and concentrated under reduced pressure to give (1S)-1-[1-(difluoromethyl)pyrazol-3-yl] ethanamine (410 mg, 65.14% yield) as a yellow oil.

LCMS m/z (ESI+) 162.1 [M+H]+.

Step 6: (S)—N2-(1-(1-(difluoromethyl)-1H-pyrazol-3-yl)ethyl)-6-(3-methylimidazo[1,5-a]pyridin-6-yl)-1,3,5-triazine-2,4-diamine 4-chloro-6-(3-methylimidazo[1,5-a]pyridin-6-yl)-1,3,5-triazin-2-amine (Key Intermediate 2) (80 mg, 306.89 μmol), (1S)-1-[1-(difluoromethyl)pyrazol-3-yl]ethanamine (74.18 mg, 460.33 μmol) and DIEA (118.99 mg, 920.66 μmol, 160.36 μL) were taken up into a microwave tube in 1,4-dioxane (2 mL). The sealed tube was heated at 120° C. for 1 h under microwave. The mixture was diluted by addition H2O (15 mL). The aqueous layer was extracted with ethyl acetate (30 mL×3). The combined organic layers were washed with brine (30 mL), dried over anhydrous Na2SO4, concentrated in vacuo to give the crude product. The residue was purified by prep-HPLC to give (S)—N2-(1-(1-(difluoromethyl)-1H-pyrazol-3-yl)ethyl)-6-(3-methylimidazo[1,5-a]pyridin-6-yl)-1,3,5-triazine-2,4-diamine (26.1 mg, 21.76% yield) as a yellow solid.

$^1$H NMR (399 MHz, DMSO-d6) δ=8.81 (s, 1H), 8.05 (d, J=2.4 Hz, 1H), 7.67 (t, J=60 Hz, 1H), 7.51 (s, 2H), 7.38 (br s, 1H), 7.28 (s, 1H), 6.66 (br s, 2H), 6.51 (d, J=2.8 Hz, 1H), 5.45-5.36 (m, 1H), 2.65 (s, 3H), 1.53 (d, J=6.8 Hz, 3H).

LCMS m/z (ESI+) 386.1 [M+H]+.

Example 141

6-(3-methylimidazo[1,5-a]pyridin-6-yl)-N2-[1-methyl-1-(2-pyridyl)ethyl]-1,3,5-triazine-2,4-diamine Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.89 μmol) and 2-(2-pyridyl)propan-2-amine (125.39 mg, 920.66 μmol) in 1,4-dioxane (5 mL), then DIEA (118.99 mg, 920.66 μmol, 160.36 μL) was added, the mixture was stirred at 120° C. for 6 hr under microwave. The mixture was concentrated under reduced pressure to give residue. The residue was diluted with ACETONITRILE (1 mL) and purified by prep-HPLC to give 6-(3-methylimidazo[1,5-a]pyridin-6-yl)-N4-[1-methyl-1-(2-pyridyl)ethyl]-1,3,5-triazin e-2,4-diamine (12.5 mg, 10.83% yield) as a yellow solid.

$^1$H NMR (399 MHz, DMSO-d6) δ=8.53 (br d, J=4.0 Hz, 1H), 7.70 (br t, J=7.2 Hz, 1H), 7.51-7.38 (m, 4H), 7.25 (s, 2H), 7.21-7.17 (m, 1H), 6.51 (br s, 2H), 2.61 (s, 3H), 1.77 (s, 6H).

LCMS m/z (ESI+) 361.1 [M+H]+.

Example 142

(S)—N2-(1-(2-chloro-6-fluorophenyl)ethyl)-6-(3-methylimidazo[1,5-a]pyridin-6-yl)-1,3,5-triazine-2,4-diamine Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.89 μmol) and (1S)-1-(2-chloro-6-fluoro-phenyl) ethanamine (159.84 mg, 920.66 μmol) in 1,4-dioxane (5 mL), then DIEA (118.99 mg, 920.66 μmol, 160.36 μL) was added, the mixture was stirred at 120° C. for 1 hr under microwave. The mixture was concentrated under reduced pressure to give residue. The residue was diluted with ACETONITRILE (1 mL) and purified by prep-HPLC to give (S)—N2-(1-(2-chloro-6-fluorophenyl)ethyl)-6-(3-methylimidazo[1,5-a]pyridin-6-yl)-1,3,5-triazine-2,4-diamine (41.8 mg, 33.53% yield) as a yellow solid.

$^1$H NMR (399 MHz, DMSO-d6) δ=8.78 (s, 1H), 7.53-7.44 (m, 2H), 7.33-7.22 (m, 4H), 7.19-7.10 (m, 1H), 6.58 (br s, 2H), 5.73 (quin, J=7.2 Hz, 1H), 2.66 (s, 3H), 1.58 (d, J=7.2 Hz, 3H).

LCMS m/z (ESI+) 398.1 [M+H]+.

Example 143

(R)-2-((4-amino-6-(3-methylimidazo[1,5-a]pyridin-6-yl)-1,3,5-triazin-2-yl)amino)-2-(2-fluorophenyl) ethan-1-ol Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.89 μmol) and (2R)-2-amino-2-(2-fluorophenyl) ethanol (142.86 mg, 920.66 μmol) in 1,4-dioxane (5 mL), then DIEA (118.99 mg, 920.66 μmol, 160.36 μL) was added, the mixture was stirred at 120° C. for 1 hr under microwave. The mixture was concentrated under reduced pressure to give residue. The residue was diluted with ACETONITRILE (1 mL) and purified by prep-HPLC to give (R)-2-((4-amino-6-(3-methylimidazo[1,5-a]pyridin-6-yl)-1,3,5-triazin-2-yl) amino)-2-(2-fluorophenyl)ethan-1-ol (38.5 mg, 32.40% yield) as a yellow solid.

$^1$H NMR (399 MHz, DMSO-d6) δ=8.79 (br s, 1H), 7.56-7.43 (m, 3H), 7.35 (br s, 1H), 7.30-7.23 (m, 2H), 7.18-7.11 (m, 2H), 6.63 (br s, 2H), 5.50 (br d, J=6.4 Hz, 1H), 4.79 (br s, 1H), 3.71 (br s, 2H), 2.65 (s, 2H), 2.66-2.64 (m, 1H).

LCMS m/z (ESI+) 380.1 [M+H]+.

Example 144

(R)-2-((4-amino-6-(3-methylimidazo[1,5-a]pyridin-6-yl)-1,3,5-triazin-2-yl)amino)-2-(3-fluorophenyl) ethan-1-ol Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.89 μmol) and (2R)-2-amino-2-(3-fluorophenyl) ethanol (142.86 mg, 920.67 μmol) in 1,4-dioxane (5 mL), then DIEA (118.99 mg, 920.67 μmol, 160.36 μL) was added, the mixture was stirred at 120° C. for 1 hr under microwave.

The mixture was concentrated under reduced pressure to give residue. The residue was diluted with ACETONITRILE (1 mL) and purified by prep-HPLC to give (R)-2-((4-amino-6-(3-methylimidazo[1,5-a]pyridin-6-yl)-1,3,5-triazin-2-yl) amino)-2-(3-fluorophenyl)ethan-1-ol (73.2 mg, 61.76% yield) as a yellow solid.

$^1$H NMR (399 MHz, DMSO-d6) δ=8.77 (br s, 1H), 7.50 (s, 2H), 7.39-7.30 (m, 2H), 7.29-7.17 (m, 3H), 7.08-6.93 (m, 1H), 6.64 (br s, 2H), 5.21-5.18 (m, 1H), 4.74 (br s, 1H), 3.72 (br s, 2H), 2.65 (s, 3H).

LCMS m/z (ESI+) 380.1 [M+H]+.

Example 145

N2-((1,5-dimethyl-1H-pyrazol-3-yl)methyl)-6-(3-methylimidazo[1,5-a]pyridin-6-yl)-1,3,5-triazine-2,4-diamine Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.89 μmol) and (1,5-dimethylpyrazol-3-yl)methanamine (115.24 mg, 920.66 μmol) in 1,4-dioxane (5 mL), then DIEA (118.99 mg, 920.66 μmol, 160.36 μL) was added, the mixture was stirred at 120° C. for 1.5 hr under microwave. The mixture was concentrated under reduced pressure to give residue. The residue was diluted with ACETONITRILE (1 mL) and purified by prep-HPLC to give N2-((1,5-dimethyl-1H-pyrazol-3-yl)methyl)-6-(3-methylimidazo [1,5-a]pyridin-6-yl)-1,3,5-triazine-2,4-diamine (62.8 mg, 57.90% yield) as a yellow solid.

$^1$H NMR (399 MHz, DMSO-d6) δ=8.82 (s, 1H), 7.52 (s, 2H), 7.28 (s, 1H), 7.19 (br s, 1H), 6.63 (br s, 2H), 5.97 (s, 1H), 4.44 (br d, J=4.9 Hz, 2H), 3.66 (s, 3H), 2.65 (s, 3H), 2.20 (s, 3H).

LCMS m/z (ESI+) 350.0 [M+H]+.

Example 146

N2-(1-methyl-1H-pyrazol-4-yl)-6-(3-methylimidazo [1,5-a]pyridin-6-yl)-1,3,5-triazine-2,4-diamine Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (169 mg, 648.30 μmol) and 1-methylpyrazol-4-amine (188.89 mg, 1.94 mmol) in 1,4-dioxane (5 mL), then DIEA (251.36 mg, 1.94 mmol, 338.77 μL) was added, the mixture was stirred at 120° C. for 1 hr under microwave. The reaction was concentrated under reduced pressure to give a residue. The residue was diluted with CH3OH (2 mL) and purified by prep-HPLC to give N2-(1-methyl-1H-pyrazol-4-yl)-6-(3-methylimidazo[1,5-a]pyridin-6-yl)-1,3,5-triazine-2,4-diamine (104.6 mg, 49.45% yield) as a yellow solid.

$^1$H NMR (399 MHz, DMSO-d6) δ=9.24 (br s, 1H), 8.85 (s, 1H), 7.95 (s, 1H), 7.59-7.51 (m, 3H), 7.30 (s, 1H), 6.84 (br s, 2H), 3.82 (s, 3H), 2.67 (s, 3H).

LCMS m/z (ESI+) 322.0 [M+H]+.

Example 147

6-(3-methylimidazo[1,5-a]pyridin-6-yl)-N2-(2-(4-(trifluoromethyl)-1H-imidazol-2-yl)propan-2-yl)-1,3,5-triazine-2,4-diamine Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (60 mg, 230.16 μmol) in 1,4-dioxane (5 mL) was added 2-(4-(trifluoromethyl)-1H-imidazol-2-yl)propan-2-amine (66.69 mg, 345.24 μmol) and DIEA (89.24 mg, 690.47 μmol, 120 μL), then the reaction mixture was heated to 120° C. and stirred for 16 hr. The reaction mixture was concentrated under reduced pressure to give a residue. The residue was purified by prep-HPLC to obtain 6-(3-methylimidazo[1,5-a]pyridin-6-yl)-N2-(2-(4-(trifluoromethyl)-1H-imidazol-2-yl) propan-2-yl)-1,3,5-triazine-2,4-diamine (35.16 mg, 36.6% yield) as a yellow solid.

$^1$H NMR (399 MHz, DMSO-d6) δ=12.15 (s, 1H), 8.67 (s, 1H), 8.12 (s, 1H), 7.46 (s, 1H), 7.42 (d, J=9.2 Hz, 1H), 7.26 (s, 2H), 7.12 (s, 1H), 6.59 (s, 2H), 2.62 (s, 3H), 1.76 (d, J=7.2 Hz, 6H).

LCMS m/z (ESI+) 418.1 [M+H]+.

Example 148

(3R,6S)-1-(4-amino-6-(3-methylimidazo[1,5-a]pyridin-6-yl)-1,3,5-triazin-2-yl)-6-methylpiperidine-3-carboxylate Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.88 μmol) in 1,4-dioxane (5 mL) was added methyl (3R,6S)-6-methylpiperidine-3-carboxylate (72.37 mg, 460.32 μmol) and DIEA (118.98 mg, 920.63 μmol), then the reaction mixture was heated to 120° C. and stirred for 16 hr. The reaction mixture was concentrated under reduced pressure to give a residue. The residue was purified by prep-HPLC to obtain methyl (3R,6S)-1-(4-amino-6-(3-methylimidazo[1,5-a]pyridin-6-yl)-1,3,5-triazin-2-yl)-6-methylpiperidine-3-carboxylate (34.24 mg, 29.25% yield) as a yellow solid.

$^1$H NMR (399 MHz, DMSO-d6) δ=8.81 (s, 1H), 7.55 (m, 2H), 7.28 (s, 1H), 7.18 (s, 2H), 6.71 (s, 2H), 5.16-4.94 (m, 2H), 3.69 (s, 3H), 3.00 (t, J=7.2 Hz, 2H), 2.65 (s, 3H), 1.89-1.87 (m, 2H), 1.85-1.83 (m, 1H), 1.71-1.67 (m, 1H), 1.20 (d, J=6.8 Hz, 3H).

LCMS m/z (ESI+) 386.1 [M+H]+.

Example 149 methyl (3R,6S)-1-(2-amino-6-(3-methylimidazo[1,5-a]pyridin-6-yl)pyrimidin-4-yl)-6-methylpiperidine-3-carboxylate Synthesised by General Method E Using the Following Reagents and Conditions:

To a solution of 4-chloro-6-(3-methylimidazo[1,5-a]pyridin-6-yl)pyrimidin-2-amine (Key Intermediate 3) (Intermediate 2)(80 mg, 306.88 μmol) in 1,4-dioxane (5 mL) was added methyl (3R,6S)-6-methylpiperidine-3-carboxylate (72.37 mg, 460.32 μmol) and DIEA (118.98 mg, 920.63 μmol), then the reaction mixture was heated to 120° C. and stirred for 16 hr. The reaction mixture was concentrated under reduced pressure to give a residue. The residue was purified by prep-HPLC to obtain methyl (3R,6S)-1-(2-amino-6-(3-methylimidazo[1,5-a]pyridin-6-yl)pyrimidin-4-yl)-6-methylpiperidine-3-carboxylate (34.24 mg, 29.25% yield) as a yellow solid.

$^1$H NMR (399 MHz, DMSO-d6) δ=8.62 (s, 1H), 8.13 (s, 1H), 7.51 (d, J=8.8 Hz, 1H), 7.40 (d, J=8.8 Hz, 1H), 7.26 (s, 1H), 6.57 (s, 1H), 5.89 (s, 2H), 4.75-4.66 (m, 2H), 3.68 (s, 3H), 2.90 (t, J=7.2 Hz, 1H), 2.66 (s, 3H), 2.32 (m, 1H), 1.89-1.83 (m, 2H), 1.73-1.68 (m, 2H), 1.17 (d, J=6.8 Hz, 3H).

LCMS m/z (ESI+) 381.0 [M+H]+.

Example 150

(R)-2-((4-amino-6-(3-methylimidazo[1,5-a]pyridin-6-yl)-1,3,5-triazin-2-yl)amino)-2-(2,3-difluorophenyl)ethan-1-ol Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (60 mg, 230.16 μmol) in 1,4-dioxane (5 mL) was added (R)-2-amino-2-(2,3-difluorophenyl)ethan-1-ol (35.71 mg, 230.16 μmol) and DIEA (89.2 mg, 690.48 μmol), then the reaction mixture was heated to 120° C. and stirred for 16 hr. The reaction mixture was concentrated under reduced pressure to give a residue. The residue was purified by prep-HPLC to obtain (R)-2-((4-amino-6-(3-methylimidazo[1,5-a]pyridin-6-yl)-1,3,5-triazin-2-yl)amino)-2-(2,3-difluorophenyl) ethan-1-ol (20.43 mg, 23.4% yield) as a yellow solid.

$^1$H NMR (399 MHz, DMSO-d6) δ=8.79 (s, 1H), 7.57-7.49 (m, 4H), 7.28-7.26 (d, 2H), 7.18-7.14 (m, 2H), 6.61 (s, 2H), 5.59-5.56 (t, 1H), 3.00-2.95 (q, 2H), 2.69-2.66 (q, 5H), 2.61 (s, 2H), 1.68 (s, 3H)

LCMS m/z (ESI+) 433.3 [M+H]+.

Example 151

6-(3-methylimidazo[1,5-a]pyridin-6-yl)-N2-(2-(2-(trifluoromethyl)thiazol-4-yl)propan-2-yl)-1,3,5-triazine-2,4-diamine Synthesised by General Method E Using the Following Reagents and Conditions:

To a solution of 4-chloro-6-(3-methylimidazo[1,5-a]pyridin-6-yl)-1,3,5-triazin-2-amine (Key Intermediate 2) (80 mg, 306.88 μmol) in 1,4-dioxane (4 mL) was added DIEA (118.98 mg, 920.64 μmol) and 2-(2-(trifluoromethyl)thiazol-4-yl)propan-2-amine (64.51 mg, 306.88 μmol). The mixture was stirred at 120° C. for 16 hr. The reaction mixture was concentrated under reduced pressure to give a residue. The residue was purified by prep-HPLC to give 6-(3-methylimidazo[1,5-a]pyridin-6-yl)-N2-(2-(2-(trifluoromethyl)thiazol-4-yl)propan-2-yl)-1,3,5-triazine-2,4-diamine (38.80 mg, 29.1% yield) as a yellow solid.

$^1$H NMR (399 MHz, DMSO-d6) δ=8.80 (s, 1H), 7.91 (s, 1H), 7.61 (br s, 1H), 7.56-7.44 (m, 2H), 7.29 (s, 1H), 6.69 (br s, 2H), 5.51 (br d, 1H), 2.65 (s, 3H), 1.59 (d, 6H)

LCMS m/z (ESI+) 434.8 [M+H]+.

Intermediates

Intermediate A

3-methyl-1-tetrahydropyran-2-yl-5-(4,4,5,5-tetramethyl-1,3,2-dioxaborolan-2-yl)indazole

Step 1: 5-Bromo-3-methyl-1-tetrahydropyran-2-yl-indazole p-Toluenesulfonic acid monohydrate (45 mg, 0.24 mmol) was added to a mixture of 5-bromo-3-methyl-1H-indazole (500 mg, 2.37 mmol) and 3,4-dihydro-2H-pyran (0.65 mL, 7.11 mmol) in DCM (15 mL). The reaction mixture was stirred at 25° C. for 16 hours then diluted with DCM (15 mL) and washed with saturated aqueous $NaHCO_3$. The organic phase was separated, dried (using a phase separator), and concentrated under reduced pressure. The crude material was purified by flash chromatography (silica gel, eluting with a gradient of 5-25% EtOAc in petroleum ether). The fractions containing the product were concentrated to dryness under reduced pressure to afford the title compound (600 mg, 1.93 mmol, 82% yield). $^1$H NMR (600 MHz, Chloroform-d) δ 7.79 (dd, J=1.9, 0.9 Hz, 1H), 7.50-7.37 (m, 2H), 5.60 (dd, J=9.8, 2.6 Hz, 1H), 4.13-3.64 (m, 2H), 2.54 (d, J=0.9 Hz, 4H), 2.17-1.98 (m, 2H), 1.80-1.70 (m, 2H), 1.64 (dqt, J=6.5, 2.6, 1.3 Hz, 1H).

Step 2: 3-Methyl-1-tetrahydropyran-2-yl-5-(4,4,5,5-tetramethyl-1,3,2-dioxaborolan-2-yl)indazole A mixture of 5-bromo-3-methyl-1-tetrahydropyran-2-yl-indazole (600 mg, 2.0 mmol), bis(pinacolato)diboron (774 mg, 3.05 mmol) and potassium acetate (600 mg, 6.1 mmol) in tetrahydrofuran (20 mL) was de-gassed for 10 minutes. [1,1'-bis(diphenylphosphino)ferrocene] dichloropalladium (II) (74 mg, 0.10 mmol) was added and the mixture was degassed for a further 10 minutes. The reaction was heated under reflux for 2 h. The mixture was allowed to cool to RT and partitioned between water and EtOAc. The organic layer was dried ($MgSO_4$) and concentrated under reduced pressure. The crude material was dissolved in DCM and filtered through a pad of celite. The filtrate was concentrated under reduced pressure and the residue purified by flash chromatography (silica gel, eluting with a gradient of 5-25% EtOAc in petroleum ether). The fractions containing product were concentrated to dryness under reduced pressure to afford the title compound (580 mg, 1.53 mmol, 75% yield). $^1$H NMR (600 MHz, Chloroform-d) δ 8.27-8.09 (m, 1H), 7.80 (dd, J=8.4, 1.0 Hz, 1H), 7.48 (dd, J=8.4, 0.9 Hz, 1H), 5.64 (dd, J=10.0, 2.6 Hz, 1H), 4.08 (dt, J=11.8, 2.3 Hz, 1H), 3.74 (td, J=11.3, 2.6 Hz, 1H), 2.64-2.47 (m, 4H), 2.15-1.98 (m, 2H), 1.82-1.68 (m, 2H), 1.70-1.57 (m, 1H), 1.38 (s, 12H). LCMS LCQ Rt=4.38 min (Method 2); m/z (ESI$^+$) 294.90/296.80 $[M+H]^+$ (Br isotopes).

Intermediate B: 2-(6-methylpyridin-2-yl)propan-2-amine

A solution of cerium chloride (8.35 g, 33.86 mmol) in anhydrous THF (70 mL) was stirred at 45° C. for 3 h and then cooled down to RT. 6-methylpyridine-2-carbonitrile (2.0 g, 16.93 mmol) was added and the mixture cooled to −20° C. before the drop-wise addition of MeLi (26.5 mL, 42.32 mmol, 1.6 M in $Et_2O$), ensuring the reaction mixture did not increase above −10° C. The solution was stirred at −10° C. to −20° C. for 2.5 h. The reaction was quenched with 30% w/v NaOH (25 mL), stirred overnight for 18 h at RT and then filtered. The filtrate was dried ($MgSO_4$) and concentrated to dryness under reduced pressure. The resulting residue was dissolved in THF (approx. 10 mL), HCl (4 M in 1,4-dioxane) added, and the resulting mixture evaporated to dryness under reduced pressure. The residue was dissolved in conc. ammonium hydroxide solution (25 mL) and extracted with DCM (3×30 mL). The combined organic extracts were dried ($MgSO_4$), filtered and concentrated in vacuo. The crude material was purified by flash column chromatography eluting with a gradient of 0-20% methanol in DCM to afford the title compound as a viscous yellow oil (295 mg, 12% yield). $^1$H NMR (Chloroform-d) δ: 7.47 (t, J=7.7 Hz, 1H), 7.16 (d, J=7.8 Hz, 1H), 6.93 (d, J=7.6 Hz, 1H), 2.49 (s, 3H), 1.46 (s, 6H). UPLC-MS Rt=0.78 min, 95% (2 min basic); m/z (ESI$^+$) 151.0 [M+H]$^+$.

Intermediate C. 4-chloro-6-{imidazo[1,5-a]pyridin-6-yl}-1,3,5-triazin-2-amine

Step 1: 6-(4,4,5,5-tetramethyl-1,3,2-dioxaborolan-2-yl)imidazo[1,5-a]pyridine

A mixture of 6-bromoimidazo[1,5-a]pyridine (0.61 g, 3.11 mmol), 4,4,5,5-tetramethyl-2-(4,4,5,5-tetramethyl-1,3,2-dioxaborolan-2-yl)-1,3,2-dioxaborolane (2.37 g, 9.32 mmol), and potassium acetate (0.915 g, 9.32 mmol) were dissolved in 1,4-dioxane (17 mL) and the mixture degassed for 5 min. Pd(dppf)$Cl_2$ (0.114 g, 0.155 mmol) was added, and the mixture heated at 100° C. for 90 min then cooled to RT, diluted with DCM, and filtered over a celite/silica pad. The filtrate was evaporated to dryness under reduced pressure to provide a crude dark oil. The oil was triturated with heptane:diethyl ether (15:1) and the resulting light brown solid was filtered and dried under vacuum. $^1$H NMR (400 MHz, Chloroform-d) δ 8.39 (s, 1H), 8.13 (s, 1H), 7.41 (d, J=10.5 Hz, 2H), 6.98 (d, J=9.2 Hz, 1H), 1.37 (s, 12H). UPLC-MS Rt=0.93 min, 76% (2 min basic); m/z (ESI$^+$) 245 [M+H]$^+$.

Step 2: 4-chloro-6-{imidazo[1,5-a]pyridin-6-yl}-1,3,5-triazin-2-amine 1,1'-Bis(di-tert-butylphosphino)ferrocene]dichloropalladium(II) (29.1 mg, 0.045 mmol) was added to a degassed mixture of dichloro-1,3,5-triazin-2-amine (221 mg, 1.34 mmol) 6-(4,4,5,5-tetramethyl-1,3,2-dioxaborolan-2-yl)imidazo[1,5-a]pyridine (330.0 mg, 0.892 mmol) and Potassium phosphate tribasic (568 mg, 2.68 mmol) in oxolane (4 mL) and water (0.4 mL). The reaction was heated at 50° C. for 45 min then allowed to cool down RT. Volatile materials were evaporate under reduced pressure, and the crude purified by flash column chromatography eluting with a gradient of 1-6% methanol in DCM affording the title compound as a yellow solid (81 mg, 0.33 mmol, 37% yield). $^1$H NMR (400 MHz, DMSO-d6) δ 9.36 (s, 1H), 8.65 (s, 1H), 8.19 (d, J=13.3 Hz, 2H), 7.65 (d, J=9.6 Hz, 1H), 7.48 (d, J=10.8 Hz, 1H), 7.44 (s, 1H). UPLC-MS Rt=0.83 min, 95% (2 min basic); m/z (ESI$^+$) 247 [M+H]$^+$.

Intermediate D. N-Methyl-1-(1-methylpyrazol-3-yl)cyclopropanamine

Step 1: tert-Butyl N-[1-[methoxy(methyl)carbamoyl]cyclopropyl]carbamate

N—BOC-1-Aminocyclopropanecarboxylic acid (10 g, 50 mmol) was dissolved in Acetonitrile (200 mL) and N,O-dimethylhydroxylamine hydrochloride (5.82 g, 60 mmol) and HATU (22.68 g, 60 mmol) were added with triethylamine (20.78 mL, 149 mmol) added last. The reaction was stirred at RT for 18 h. A saturated solution of $NH_4Cl$ was added and the product extracted with ethyl acetate. The organic phase was separated, dried over $MgSO_4$, filtered and concentrated under vacuum. The crude material was purified by flash column chromatography eluting with 10-50% ethyl acetate in petroleum ether to afford the title compound (12.9 g, 47.5 mmol, 96% yield) as a colourless oil which crystallised to a white solid on standing. $^1$H NMR (600 MHz, Chloroform-d) δ 5.23 (s, 1H), 3.73 (s, 3H), 3.17 (s, 3H), 1.45-1.42 (m, 11H), 1.02 (s, 2H).

Step 2: tert-butyl N-(1-prop-2-ynoylcyclopropyl)carbamate tert-Butyl N-[1-[methoxy(methyl)carbamoyl]cyclopropyl]carbamate (12.2 g, 49.94 mmol) was dissolved in tetrahydrofuran (250 mL) and cooled to zero degrees. Ethynylmagnesium bromide solution (500 mL, 249.7 mmol (0.5 M)) was added dropwise to the solution over 1 h. The reaction was allowed to warm to RT and stirred for 18 h. Water (50 mL) was added at 0° C. and stirring continued at 0° C. for 30 min. HCl (0.5 M) was added to pH 5, the product was extracted into ethyl acetate. The organic phase was separated, dried and concentrated in vacuo to afford the title compound (10.45 g). The material was used crude in the following step without further purification.

Step 3: tert-Butyl N-[1-(1H-pyrazol-3-yl)cyclopropyl]carbamate tert-Butyl N-(1-prop-2-ynoylcyclopropyl)carbamate (10.45 g, 50 mmol) was dissolved in ethanol (215 mL) and hydrazine hydrate (4.87 mL, 100 mmol) was added. The reaction mixture was heated to 50° C. overnight and a further 3 h at reflux. The reaction was cooled to RT and the solvent removed in vacuo. The crude material was purified by flash column chromatography eluting with 5-70% ethyl acetate in petroleum ether to afford tert-butyl N-[1-(1H-pyrazol-3-yl)cyclopropyl]carbamate (5620 mg, 25.17 mmol, 50% yield) as a colourless oil that solidified upon standing to a white solid. $^1$H NMR (600 MHz, Chloroform-d) δ 7.42 (s, 1H), 6.03 (s, 1H), 5.35 (s, 1H), 1.43 (s, 9H), 1.24-1.16 (m, 4H)

Step 4: tert-Butyl N-[1-[1-(difluoromethyl)pyrazol-3-yl]cyclopropyl]carbamate

Potassium fluoride (104 mg, 1.79 mmol) and tert-butyl N-[1-(1H-pyrazol-3-yl)cyclopropyl]carbamate (200 mg, 0.90 mmol) were combined in a sealed flask which was flushed with nitrogen. Acetonitrile (5 mL) was then added followed by bromodifluoromethyl diethylphosphonate (0.16 mL, 0.90 mmol). The reaction was stirred at RT for 18 h. The solvent was removed in vacuo and the crude material was purified by flash chromatography (silica gel, eluting with 10-50% EtOAc in petroleum ether). The combined fractions were evaporated to dryness and the residue triturated with pet ether to afford a white solid. The filtrate was evaporated and the residue re-purified by flash chromatography and treated in the same way. Both solids batches were combined to afford the title compound (190 mg, 0.66 mmol, 74% yield) as a white solid. $^1$H NMR (600 MHz, Chloroform-d) δ 7.68 (d, J=2.7 Hz, 1H), 7.07 (t, J=61.0 Hz, 1H), 6.33 (d, J=2.6 Hz, 1H), 5.31 (s, 1H), 1.43 (d, J=36.5 Hz, 9H), 1.35 (d, J=2.9 Hz, 2H), 1.28-1.22 (m, 2H).

Step 5: N-Methyl-1-(1-methylpyrazol-3-yl)cyclopropanamine

To a stirred solution of tert-butyl N-[1-[1-(difluoromethyl)pyrazol-3-yl]cyclopropyl]carbamate (190 mg, 0.70 mmol) in dry THF, Lithium Aluminium Hydride (2.43 mL, 2.43 mmol) was added at 0° C. and the reaction was stirred at 100° C. for 12 h. $NH_4Cl$ and NaOH were added and the aqueous phase was extracted with EtOAc (3×25 mL). The combined organic layers were dried over $MgSO_4$, filtered and evaporated to afford the title compound (45% yield). LCMS m/z ($ESI^+$) 0.45 min (Method 2) 152.12 $[M+H]^+$ Intermediate E. 1-[1-(2-methoxyethyl)pyrazol-3-yl] cyclopropanamine Step 1: tert-butyl N-[1-[1-(2-methoxyethyl)pyrazol-3-yl]cyclopropyl]carbamate To a solution of tert-butyl N-[1-(1H-pyrazol-3-yl)cyclopropyl]carbamate (Intermediate D, Step 3) (400 mg, 1.79 mmol) in N,N-dimethylformamide (15 mL) was added 60% sodium hydride (150 mg, 3.76 mmol) at 25° C. The reaction mixture was stirred at 25° C. until gas evolution had ceased (approximately 20 minutes). 2-Bromoethyl-methyl-ether (249 mg, 1.79 mmol) was added as a solution in N,N-dimethylformamide (5 mL) at 25° C. and the reaction mixture was stirred at 25° C. for 18 h. The reaction mixture was added to water and the product extracted with $CH_2Cl_2$ (×3). The aqueous phase was extracted, again, with EtOAc (×2). The combined organics were dried by passing through a phase separator and concentrated under reduced pressure. The crude material was purified by flash chromatography on SiO2 (45 g) eluting 0-5% methanol in $CH_2Cl_2$ to afford the titled product. (286.mg, 0.7100 mmol, 40% yield, purity 70% by NMR). 1H NMR (600 MHz, Chloroform-d) δ 7.30 (d, J=2.3 Hz, 1H), 6.09 (d, J=2.3 Hz, 1H), 5.28 (s, 1H), 4.15 (t, J=5.3 Hz, 2H), 3.67 (t, J=5.4 Hz, 2H), 3.29 (s, 3H), 1.43 (s, 9H), 1.30-1.12 (m, 4H). The minor contaminant was the regioisomer. The mixture was taken on to the next step.

Step 2: 1-[1-(2-methoxyethyl)pyrazol-3-yl]cyclopropanamine

To a solution of tert-butyl N-[1-[1-(2-methoxyethyl)pyrazol-3-yl]cyclopropyl]carbamate (280 mg, 1 mmol) in methyl alcohol (35 mL) was added Hydrochloric acid in 1,4-dioxane (7.46 mL, 30 mmol) at 25° C. The reaction mixture was stirred for at 25° C. for 72 h. The reaction mixture was concentrated under reduced pressure and 1M NaOH and CH2Cl2 added to the residue. The organic phase was separated and evaporated to dryness under reduced pressure to afford the titled product as crude material (182.mg, 0.7000 mmol, 71% yield). $^1$H NMR (600 MHz, DMSO-d6) δ 7.49 (d, J=2.2 Hz, 1H), 6.07 (d, J=2.2 Hz, 1H), 4.10 (t, J=5.3 Hz, 2H), 3.59 (t, J=5.4 Hz, 2H), 3.18 (s, 3H), 2.23 (s, 2H), 0.85-0.74 (m, 4H).

Intermediate G: 1-[1-(difluoromethyl)pyrazol-3-yl] cyclopropanamine tert-Butyl N-[1-[1-(difluoromethyl)pyrazol-3-yl]cyclopropyl]carbamate (Intermediate D, step 4) (1.94 g, 7.1 mmol) was dissolved in methyl alcohol (50 mL) and hydrochloric acid in 1,4-dioxane (17.75 mL, 71 mmol) was added. The reaction was stirred at RT for 18 h. The volatiles were removed in vacuo and DCM and NaOH (1 M) was added. The organic phase was separated, dried (hydrophobic frit) and concentrated in vacuo to afford 1-[1-(difluoromethyl)pyrazol-3-yl]cyclopropanamine (1.2 g, 6.58 mmol, 93% yield) as a colourless oil. $^1$H NMR (600 MHz, Chloroform-d) δ 7.70 (d, J=2.7 Hz, 1H), 7.11 (t, J=61.0 Hz, 1H), 6.11 (d, J=2.6 Hz, 1H), 2.06 (s, 2H), 1.11-1.08 (m, 2H), 1.02-0.98 (m, 2H).

Intermediate H: 1-[6-(trifluoromethyl)-2-pyridyl] cyclopropanamine

To a solution of 2-Cyano-6-(trifluoromethyl)pyridine (250 mg, 1.45 mmol) in diethyl ether (5 mL) was added titanium isopropoxide (0.48 mL, 1.6 mmol) and then 3.0 M ethylmagnesium bromide in $Et_2O$ (0.97 mL, 2.91 mmol) at 25° C. The reaction mixture was stirred at 25° C. for 45 minutes and then water (1.5 mL) was added. The reaction mixture was extracted with $Et_2O$ (×3). The combined organic extracts were dried with MgSO4 and concentrated under reduced pressure. The crude material was purified to flash chromatography on SiO2 (25 g) eluting with 50-100% EtOAc in hexane. The desired fractions were concentrated under reduced pressure to afford the title compound (78 mg, 0.37 mmol, 25% yield). 1H NMR (600 MHz, DMSO-d6) δ 8.04 (d, J=8.1 Hz, 1H), 7.97 (t, J=7.9 Hz, 1H), 7.57 (d, J=7.6 Hz, 1H), 1.20 (q, J=3.5 Hz, 2H), 1.02 (q, J=3.4 Hz, 2H). LCMS m/z ($ESI^+$) 203.21 $[M+H]^+$.

Intermediate I: 1-(2-chloro-3-fluoro-phenyl)cyclopropanamine

A solution of 2-chloro-3-fluorobenzonitrile (0.4 mL, 3.21 mmol) and titanium isopropoxide (1.07 mL, 3.54 mmol) was cooled at −70° C. and ethylmagnesium bromide (2.36 mL, 7.07 mmol) was added. The mixture was allowed to warm up and, after stirring for 1 h at RT, boron trifluoride diethyl etherate (0.79 mL, 6.43 mmol) was added and the reaction was stirred for further 1 h. Water was added, followed by the addition of NaOH 1N. The basic aqueous phase was extracted with $Et_2O$ (3×20 mL) and the combined organic layers were dried over $MgSO_4$, filtered and evaporated. The crude was purified by flash chromatography (silica gel, eluting 50-100% EtOAc in petroleum ether) to afford the title compound as a yellow oil (350 mg, 1.7 mmol, 53% yield). $^1$H NMR (600 MHz, Chloroform-d) δ 7.22-7.12 (m, 2H), 7.09-7.00 (m, 1H), 1.11-1.04 (m, 2H), 0.94-0.88 (m, 2H). LCMS m/z ($ESI^+$) 185.85-187.85 [MH]+.

Intermediate J: 1-(2,3-difluorophenyl)cyclopropanamine

Starting from 2,3-Difluorobenzonitrile (0.24 mL, 2.16 mmol), the title compound was obtained following the same procedure reported for Intermediate I as a light yellow oil (250 mg, 1.4 mmol, 65% yield). 1H NMR (600 MHz, Chloroform-d) δ 7.07-7.00 (m, 2H), 6.98 (m, 1H), 1.99 (s, 2H), 1.07-0.96 (m, 2H), 0.96-0.84 (m, 2H).

Intermediate K: 2-[6-(trifluoromethyl)-2-pyridyl] propan-2-amine hydrochloride

Step 1: 2-[6-(trifluoromethyl)-2-pyridyl]propan-2-ol

A solution of methyl 6-(trifluoromethyl)pyridine-2-carboxylate (250 mg, 1.22 mmol) in tert-butyl methyl ether (1.25 mL) and tetrahydrofuran (0.75 mL) was added to 3.0 M chloro(methyl)magnesium in THF (1.22 mL, 3.66 mmol) at 12° C. The reaction mixture was stirred for 30 minutes at 12° C. then cooled to 0° C. and treated with dilute Hydrochloric acid to pH 7. The organic phase was separated and the aqueous was extracted with EtOAc (×3). The combined organic phases were dried through a phase separator and concentrated under reduced pressure. The product was triturated with hexane and dried on a rotary evaporator to afford the title compound (90 mg, 0.43 mmol, 36% yield). 1H NMR (600 MHz, DMSO-d6) δ 8.03 (t, J=8.3 Hz, 1H), 7.93 (d, J=8.0 Hz, 1H), 7.70 (dd, J=7.7, 1.0 Hz, 1H), 5.38 (s, 1H), 1.43 (s, 6H). LCMS m/z (ESI$^+$) 205.96 $[M+H]^+$ Step 2: N-[1-methyl-1-[6-(trifluoromethyl)-2-pyridyl]ethyl]acetamide To a solution of 2-[6-(trifluoromethyl)-2-pyridyl]propan-2-ol (85 mg, 0.41 mmol) in Acetonitrile (1.3 mL) was added Sulfuric acid (0.07 mL, 0.41 mmol) at 0° C. The reaction mixture was heated at 45° C. for 16 h then cooled to 0° C. and 1M NaOH (2.5 mL, 2.5 mmol) added. The aqueous solution was extracted with MTBE (×3) and the combined organics phases washed with brine, dried through a phase separator and concentrated to dryness under reduced pressure to afford the title compound (72 mg, 0.29 mmol, 69% yield). 1H NMR (600 MHz, DMSO-d6) δ 8.24 (s, 1H), 7.95 (t, J=7.9 Hz, 1H), 7.66 (d, J=7.7 Hz, 1H), 7.61 (d, J=8.1 Hz, 1H), 1.82 (s, 3H), 1.51 (s, 6H). LCMS m/z (ESI$^+$) 247.01 $[M+H]^+$ Step 3: 2-[6-(trifluoromethyl)-2-pyridyl]propan-2-amine hydrochloride To a suspension of N-[1-methyl-1-[6-(trifluoromethyl)-2-pyridyl]ethyl]acetamide (70 mg, 0.28 mmol) in water (0.2 mL) was added 12 M Hydrochloric acid (0.2 mL, 2.56 mmol) at 25° C. The reaction mixture was conventionally heated in sealed microwave vial at 90° C. for 18 h. The reaction mixture was diluted with methanol to dissolve the suspension and concentrated under reduced pressure to afford the title compound (62 mg, 0.26 mmol, 90% yield). $^1$H NMR (600 MHz, DMSO-d6) δ 8.67 (s, 3H), 8.20 (t, J=7.9 Hz, 1H), 8.00 (d, J=8.1 Hz, 1H), 7.91 (d, J=7.7 Hz, 1H), 1.63 (s, 6H). LCMS m/z (ESI$^+$) 204.96 [M+H+]

Intermediate L: 2-[1-(difluoromethyl)pyrazol-3-yl]propan-2-amine

Step 1: tert-Butyl N-(1,1-dimethyl-2-oxo-but-3-ynyl)carbamate tert-Butyl N-[2-[methoxy(methyl)amino]-1,1-dimethyl-2-oxo-ethyl]carbamate (5.26 g, 21.36 mmol) was dissolved in tetrahydrofuran (85 mL) and cooled to −78° C. Ethynylmagnesium bromide solution (85 mL, 42 mmol) was added dropwise. The solution was allowed to warm to RT and stirred for 18 h. The reaction was quenched with cold 1 M $NaHSO_4$ and stirred for 1 h at RT. The product was extracted with ethyl acetate and the organic phase washed with $NaHCO_3$ (sat. soln.), dried (hydrophobic frit) and concentrated in vacuo. The crude material was purified by flash chromatography eluting 0-20% ethyl acetate in petroleum ether to afford the title compound as a white solid (470 mg, 2 mmol, 9% yield). 1H NMR (600 MHz, Chloroform-d) δ 5.09 (s, 1H), 3.21 (s, 1H), 1.46 (s, 6H), 1.43 (s, 9H).

Step 2: tert-Butyl N-[1-methyl-1-(1H-pyrazol-3-yl)ethyl]carbamate tert-Butyl N-(1,1-dimethyl-2-oxo-but-3-ynyl)carbamate (532 mg, 2.52 mmol) was dissolved in ethanol (30 mL) and hydrazine hydrate (0.25 mL, 5.04 mmol) was added. The reaction mixture was heated to reflux for 30 min then allowed to cool to RT. The volatiles were removed in vacuo and the crude material was purified by flash column chromatography eluting with 10-50% ethyl acetate in petroleum ether to afford the title compound as a white solid (503 mg, 2.12 mmol, 84% yield). 1H NMR (600 MHz, Chloroform-d) δ 7.46 (d, J=2.0 Hz, 1H), 6.13 (s, 1H), 5.10 (s, 1H), 1.68 (s, 6H), 1.42 (s, 9H).

Step 3: tert-Butyl N-[1-[1-(difluoromethyl)pyrazol-3-yl]-1-methyl-ethyl]carbamate Potassium fluoride (105 mg, 1.81 mmol) and tert-butyl N-[1-methyl-1-(1H-pyrazol-3-yl)ethyl]carbamate (204 mg, 0.91 mmol) were combined in a microwave tube, which was flushed with $N_2$, and then sealed. Acetonitrile (5.7 mL) was then added followed by bromodifluoromethyl diethylphosphonate (0.16 mL, 0.91 mmol). The reaction mixture was stirred at RT for 18 h. The volatiles were removed in vacuo and the crude material was purified by flash chromatography eluting with 10-50% ethyl acetate in petroleum ether to afford the title compound as a colourless oil that turned to a white solid upon standing. (195 mg, 0.67 mmol, 74% yield). $^1$H NMR (600 MHz, Chloroform-d) δ 7.72 (d, J=2.7 Hz, 1H), 7.13 (t, J=60.9 Hz, 1H), 6.38 (d, J=2.7 Hz, 1H), 5.31 (s, 1H), 1.65 (s, 6H), 1.40 (s, 9H).

Step 4: 2-[1-(difluoromethyl)pyrazol-3-yl]propan-2-amine tert-Butyl N-[1-[1-(difluoromethyl)pyrazol-3-yl]-1-methyl-ethyl]carbamate (195 mg, 0.71 mmol) was dissolved in methyl alcohol (5 mL) and hydrochloric acid in 1,4-dioxane (3.54 mL, 14.17 mmol) was added. The reaction was stirred at RT for 18 h. The volatiles were removed in vacuo and DCM and NaOH (1 M) was added. The organic phase was separated, dried (hydrophobic frit) and concentrated in vacuo to afford the title compound as a colourless oil (114.mg, 0.5900 mmol, 83% yield). $^1$H NMR (600 MHz, Chloroform-d) δ 7.71 (d, J=2.6 Hz, 1H), 7.13 (t, J=60.9 Hz, 1H), 6.37 (d, J=2.6 Hz, 1H), 1.80 (s, 2H), 1.47 (s, 6H).

Intermediate M: 2-(2,3-dichlorophenyl)propan-2-amine hydrochloride 2,3-Dichlorobenzonitrile (1.0 g, 5.81 mmol) was dissolved in tetrahydrofuran (24 mL) and methylmagnesium bromide solution (6.78 mL, 20.35 mmol) was added dropwise. The solution was heated in the microwave at 100° C. for 10 min. Titanium isopropoxide (1.76 mL, 5.81 mmol) was then added dropwise and the resulting dark solution was heated to 50° C. in a heating block for 1 h. The reaction mixture was allowed to cool to RT and quenched carefully with $H_2O$. The mixture was extracted with DCM, the organic phase dried (hydrophobic frit) and concentrated in vacuo. The resulting oil was re-dissolved in a minimum amount of DCM and 1 M hydrochloric acid in ether (10.17 mL, 20.35 mmol) was added. After 5 min at RT the solution was concentrated in vacuo to afford an oily solid. Trituration with ether formed a solid which was filtered and immediately washed with acetone to afford the title compound as an off white solid (753 mg, 2.82 mmol, 48% yield). 1H NMR (600 MHz, Chloroform-d) δ 9.24 (s, 3H), 7.54-7.47 (m, 2H), 7.28-7.21 (m, 1H), 2.05 (s, 6H).

Intermediate N: 2-(2,3-difluorophenyl)propan-2-amine hydrochloride 2,3-Difluorobenzonitrile (0.8 mL, 7.19 mmol) was dissolved in tetrahydrofuran (28 mL) and methylmagnesium bromide solution (8.39 mL, 25.16 mmol) was added dropwise at RT. The solution was heated in the microwave at 100° C. for 10 min. Titanium isopropoxide (2.18 mL, 7.19 mmol) was then added dropwise and the resulting dark solution was heated to 50° C. in a heating block for 1 h. The reaction mixture was allowed to cool to RT and quenched carefully with $H_2O$. The mixture was extracted with DCM, the organic phase dried (hydrophobic frit) and concentrated in vacuo. The resulting oil was re-dissolved in a minimum amount of DCM and 1 M hydrochloric acid in ether (12.58 mL, 25.16 mmol) was added. After 5 min at RT the solution was concentrated in vacuo to afford an oily solid. Trituration with ether formed a solid which was filtered and immediately washed with acetone to afford the title compound as an off white solid (1.05 g, 4.55 mmol, 63% yield). $^1$H NMR (600 MHz, DMSO-d6) δ 8.96 (s, 3H), 7.53-7.39 (m, 1H), 7.34-7.23 (m, 2H), 1.70 (s, 6H).

Intermediate O: 2-[1-(difluoromethyl)pyrazol-3-yl]-N-methyl-propan-2-amine

Step: tert-Butyl N-[1-[1-(difluoromethyl)pyrazol-3-yl]-1-methyl-ethyl]-N -methyl-carbamate tert-Butyl N-[1-[1-(difluoromethyl)pyrazol-3-yl]-1-methyl-ethyl]carbamate (Intermediate L, step 3) (500 mg, 1.82 mmol) was dissolved in N,N-dimethylformamide (20 mL) and sodium hydride (109 mg, 4.54 mmol) was added. After 10 min at RT, iodomethane (0.11 mL, 1.82 mmol) was added and the mixture stirred at RT for 18 h. The reaction was carefully quenched with $H_2O$ and volatiles removed under reduced pressure. The residue was dissolved in ethyl acetate and the organic solution washed with brine. The organic phase was separated, dried (hydrophobic frit) and concentrated in vacuo. The crude material was purified by flash column chromatography eluting with 0-10% methanol in DCM to yield a solid. Trituration with petroleum ether and filtration afforded the title compound as a pale yellow solid (264 mg, 0.89 mmol, 49% yield). 1H NMR (399 MHz, Chloroform-d) δ 7.68 (d, J=2.7 Hz, 1H), 7.12 (t, J=60.9 Hz, 1H), 6.28 (d, J=2.6 Hz, 1H), 3.01 (s, 3H), 1.62 (s, 6H), 1.22 (s, 9H).

Step: 2-[1-(difluoromethyl)pyrazol-3-yl]-N-methyl-propan-2-amine tert-Butyl N-[1-[1-(difluoromethyl)pyrazol-3-yl]-1-methyl-ethyl]-N -methyl-carbamate (289 mg, 1 mmol) was dissolved in methyl alcohol (7 mL) and hydrochloric acid in 1,4-dioxane (3.75 mL, 15.0 mmol) was added. The reaction was stirred at RT for 18 h. The solvent was removed in vacuo and the residue treated with aq. NaOH (1 M) and extracted with DCM. The organic phase was separated, dried (hydrophobic frit) and concentrated in vacuo to afford the crude title compound. $^1$H NMR (600 MHz, Chloroform-d) δ 7.73 (d, J=2.7 Hz, 1H), 7.15 (t, J=60.9 Hz, 1H), 6.37 (d, J=2.6 Hz, 1H), 2.22 (s, 3H), 1.73 (s, 1H), 1.45 (s, 6H).

Intermediate P: 3-[(2,3-dichlorophenyl)methyl]morpholine

Step 1: 2-Amino-3-(2,3-dichlorophenyl)propanoic acid hydrochloride

A solution of diethyl 2-acetamido-2-[(2,3-dichlorophenyl)methyl]propanedioate (670 mg, 1.78 mmol) was suspended in 25% KOH (aq) (25 mL) and heated to reflux for 16 h. The RM was cooled to RT and concentrated under vacuum. The residue was suspended in 6 M HCl (aq) (40 mL) and heated to reflux for 16 h. The RM was allowed to cool to RT, the resulting precipitate was collected by filtration to provide the title compound as an off white solid. (481 mg, 95% yield).

$^1$H NMR (600 MHz, DMSO-d6) δ 8.51 (d, J=5.4 Hz, 3H), 7.56 (d, J=7.9 Hz, 1H), 7.40 (d, J=7.6 Hz, 1H), 7.32 (t, J=7.8 Hz, 1H), 4.08 (q, J=6.3 Hz, 1H), 3.31-3.25 (m, 3H). Analytical LCQ Rt=0.83 min (Method 3); m/z (ESI$^+$) 233.98 $[M+H]^+$.

Step 2: 2-amino-3-(2,3-dichlorophenyl)propan-1-ol

Iodine (460 mg, 1.81 mmol) was added dropwise to a suspension of sodium borohydride (171.29 mg, 4.53 mmol) and 2-amino-3-(2,3-dichlorophenyl)propanoic acid hydrochloride (490 mg, 1.81 mmol) in tetrahydrofuran (20 mL) at 0° C. The reaction mixture was allowed to warm to RT then heated under reflux for 2 h. An additional aliquot of sodium borohydride to (171.29 mg, 4.53 mmol) and iodine (460 mg, 1.81 mmol) was added and the reaction mixture heated under reflux for a further 16 h. The reaction mixture was cooled to RT, diluted with methanol (30 mL) and stirred at RT for 4 h. The resulting suspension was concentrated to dryness under reduced pressure to give a white solid. The solid was suspended in aqueous 25% KOH (20 mL) and stirred at RT for 16 h. The suspension was extracted with DCM (3×30 mL), the combined organic phase, dried ($MgSO_4$) and concentrated to dryness under reduced pressure to afford the title compound as a yellow solid (167 mg 0.72 mmol, 40% yield). $^1$H NMR (600 MHz, Chloroform-d) δ 7.41-7.30 (m, 1H), 7.20-7.08 (m, 2H), 3.63 (dd, J=10.7, 3.8 Hz, 1H), 3.39 (dd, J=10.6, 6.9 Hz, 1H), 3.24-3.18 (m, 1H), 2.96 (dd, J=13.5, 5.6 Hz, 1H), 2.72 (dd, J=13.5, 8.1 Hz, 1H).

Step 3: 5-[(2,3-dichlorophenyl)methyl]morpholin-3-one

Chloroacetyl chloride (0.06 mL, 0.79 mmol) was added to a solution of 2-amino-3-(2,3-dichlorophenyl)propan-1-ol (165 mg, 0.75 mmol) in tetrahydrofuran (10 mL). The reaction mixture was stirred for 10 min and then sodium hydride (27.49 mg, 1.65 mmol) was added portion-wise under a nitrogen stream. The reaction mixture was allowed to stir at RT overnight then heated under reflux for a further 16 h. Additional sodium hydride (27.49 mg, 1.65 mmol) was added and heating under reflux continued for a further 5 h. The reaction mixture was cooled to RT, quenched with water (5 mL) and partitioned between ethyl acetate and water. The organic phase was separated, dried ($MgSO_4$), filtered and concentrated under to dryness reduced pressure. The residue was purified by flash silica chromatography eluting with a petroleum ether/ethyl acetate gradient to provide the title product as a white solid (42 mg, 19% yield). $^1$H NMR (600 MHz, Chloroform-d) δ 7.41 (dd, J=7.8, 1.6 Hz, 1H), 7.18 (t, J=7.8 Hz, 1H), 7.14 (dd, J=7.8, 1.6 Hz, 1H), 5.82 (s, 1H), 4.27-4.14 (m, 2H), 3.92-3.80 (m, 2H), 3.66-3.61 (m, 1H), 3.13-3.09 (m, 1H), 2.98-2.92 (m, 1H). LCMS MDAP Rt 5.49 min (Method 5); m/z (ESI$^+$) 260.19 [M+H]$^+$.

Step 4: 3-[(2,3-dichlorophenyl)methyl]morpholine

A solution of iodine (47 mg, 0.18 mmol) in THF (1 mL) was added to a stirring suspension of sodium borohydride (17 mg, 0.46 mmol) and 5-[(2,3-dichlorophenyl)methyl] morpholin-3-one (40 mg, 0.15 mmol) in tetrahydrofuran (2 mL). The reaction mixture was heated to 60° C. for 36 h then cooled to RT and quenched with methanol, and stirred for 10 min. The solvent was evaporated to dryness at reduced pressure and the residue purified by flash silica chromatography to afford the title compound as a colourless oil (12 mg, 0.04 mmol, 29% yield). $^1$H NMR (600 MHz, Chloroform-d) δ 7.44-7.29 (m, 1H), 7.22-7.04 (m, 2H), 3.84-3.75 (m, 2H), 3.58-3.52 (m, 1H), 3.33-3.27 (m, 1H), 3.18-3.10 (m, 1H), 2.93-2.83 (m, 3H), 2.70-2.63 (m, 1H). LCMS LCQ Rt=0.83 min (Method 3), m/z (ESI$^+$) 246.23 [M+H]$^+$.

Intermediate Q: 2-(2,3-dichlorophenyl)-N-methyl-ethanamine trifluoroacetate salt Step 1: tert-butyl N-[2-(2,3-dichlorophenyl)ethyl]carbamate A solution of 2-(2,3-dichlorophenyl)ethanamine (0.15 mL, 0.87 mmol) in dry THF (2 ml) was treated with triethylamine (0.12 mL, 0.87 mmol) followed by dropwise addition of a solution of di-tert-butyl dicarbonate (0.08 mL, 0.87 mmol) in dry THF (1 ml). The resulting solution was stirred at RT for 16 h. The reaction mixture was concentrated to dryness under reduced pressure to afford the title compound as colourless solid. LCMS MDAP Rt=3.29 min (Method 7); m/z (ESI$^+$) 274.85 [M+H]$^+$.

Step 2: 2-(2,3-dichlorophenyl)-N-methyl-ethanamine trifluoroacetate salt

A solution of tert-butyl N-[2-(2,3-dichlorophenyl)ethyl] carbamate (250 mg, 0.86 mmol) in dry N,N-dimethylformamide (5 mL) at 0° C. was treated with sodium hydride (41 mg, 1.03 mmol). The reaction mixture was stirred at RT for 30 min the cooled to 0° C. A solution of iodomethane (0.05 mL, 0.86 mmol) in dry DMF (1 ml) was added dropwise and the reaction mixture allowed to warm to RT. The procedure was repeated with an additional aliquot of sodium hydride (41 mg, 1.03 mmol) and iodomethane (0.05 mL, 0.86 mmol). The reaction mixture was quenched with ice water (20 ml) and extracted with ethyl acetate (2×30 ml). The combined organic extracts were washed with aqueous 0.5 M LiCl (50 ml), brine (30 ml), dried ($MgSO_4$), filtered and concentrated under reduced pressure to give a brown oil. The oil was dissolved in DCM (20 ml) then treated with trifluoro acetic acid (0.33 mL, 4.31 mmol) and stirred at RT for 16 h. The solution was concentrated to dryness under reduced pressure to give the title compound as an orange oil, which was used in the next step without further purification. LCMS LCQ Rt=0.64 min (method 7)), m/z (ESI$^+$) 204.07 [M+H]$^+$.

Intermediate R: 2-(2,3-dichlorophenyl)-N-ethyl-ethanamine

Step 1: tert-butyl N-[2-(2,3-dichlorophenyl)ethyl]-N-ethyl-carbamate

To a solution of tert-butyl N-[2-(2,3-dichlorophenyl) ethyl]carbamate (Intermediate Q, Step 1) (100 mg, 0.34 mmol) in N,N-dimethylformamide (3 mL) was added sodium hydride (15.16 mg, 0.38 mmol) in N,N-dimethylformamide (3 mL) at 0° C. The reaction mixture was stirred at 0° C. for 10 min and then at 25° C. for 30 min. The reaction mixture was cooled to 0° C. and bromoethane (38.58 µL, 0.52 mmol) was added. The reaction mixture was stirred at 0° C. for 10 min and then at 25° C. for 18 h. The reaction mixture was concentrated under reduced pressure and the residue dissolved in EtOAc and washed with brine. The organic phase was dried by passing through a phase separator and concentrated under reduced pressure. The crude material was purified by flash chromatography (30 g silica eluting with a gradient of 0-10% EtOAc in hexane) to afford the title compound (88 mg, 0.26 mmol, 76% yield). $^1$H NMR (600 MHz, DMSO-d6) δ 7.57-7.41 (m, 1H), 7.27 (t, J=7.6 Hz, 1H), 7.24-7.18 (m, 1H), 3.46-3.30 (m, 2H), 3.23-3.03 (m, 2H), 2.91 (t, J=6.8 Hz, 2H), 1.40-1.12 (m, 9H), 0.99 (t, J=6.6 Hz, 3H).

Step 2: 2-(2,3-dichlorophenyl)-N-ethyl-ethanamine

Trifluoro acetic acid (0.21 mL, 2.7 mmol) was added to a solution of tert-butyl N-[2-(2,3-dichlorophenyl)ethyl]-N-ethyl-carbamate (86 mg, 0.27 mmol) in dichloromethane (7 mL) at 25° C. The reaction mixture was stirred for 18 h at 25° C. The reaction mixture was concentrated under reduced pressure and the residue dissolved in methanol and applied to an SCX-2 cartridge (10 g). The cartridge was washed through with methanol and the filtrate discarded. A solution of 2.0 M $NH_3$ in methanol was eluted through the cartridge. The eluent was concentrated to dryness under reduced pressure to afford the title compound (59 mg, 0.26 mmol, 97% yield). $^1$H NMR (600 MHz, DMSO-d6) δ 7.45 (dd, J=7.9, 1.6 Hz, 1H), 7.31 (dd, J=7.8, 1.6 Hz, 1H), 7.26 (t, J=7.8 Hz, 1H), 2.84 (t, J=7.4 Hz, 2H), 2.70 (t, J=7.6 Hz, 2H), 2.52 (q, J=7.1 Hz, 2H), 1.62 (s, 1H), 0.96 (t, J=7.1 Hz, 3H).

Intermediate S: N-[2-(2,3-dichlorophenyl)ethyl] cyclopropanamine

To a solution of 2-(2,3-dichlorophenyl)acetaldehyde (0.12 mL, 0.2600 mmol) and cyclopropylamine (92 µL, 1.32 mmol) in dichloromethane (3 mL) was added acetic acid (76 µL, 1.32 mmol) at 25° C. The reaction mixture was stirred at 25° C. for 1 hour 25 min and then sodium triacetoxyborohydride (112 mg, 0.53 mmol) was added. The reaction mixture was stirred for 48 hours at 25° C. then diluted with DCM and eluted through a celite cartridge. The filtrate was washed with 1M NaOH, dried by passing through phase separator and then concentrated under reduced pressure. The crude material was purified by flash chromatography on (12 g silica eluting with gradient of 0-5% methanol in DCM) to afford the title compound (33 mg, 0.14 mmol, 53% yield).

$^1$H NMR (600 MHz, DMSO-d6) δ 7.45 (dd, J=8.0, 1.6 Hz, 1H), 7.30 (dd, J=7.6, 1.6 Hz, 1H), 7.26 (t, J=7.8 Hz, 1H), 2.86 (t, J=7.5 Hz, 2H), 2.77 (t, J=7.4 Hz, 2H), 2.21 (s, 1H), 2.10-2.04 (m, 1H), 0.39-0.26 (m, 2H), 0.20-0.08 (m, 2H).

Intermediate T: 1-(2,3-dichlorophenyl)-2-methylpropan-2-amine

Step 1: 1-(2,3-dichlorophenyl)-2-methylpropane-2-ol

Methyl magnesium bromide (20 mL, 3.4 M in 2-methyltetrahydrofuran, 68.5 mmol) was added drop-wise to a mixture of methyl 2-(2,3-dichlorophenyl)acetate) (5.0 g, 22.8 mmol) in anhydrous THF (110 mL) at 0° C. and allowed to slowly warm to RT. The reaction mixture was stirred at RT for 18 h. Saturated aqueous $NH_4Cl$ (60 mL) was added to the reaction mixture slowly at 0° C. and the aqueous phase was extracted with ethyl acetate (3×40 mL). The combined organic layer was washed with brine (30 mL), dried ($Na_2SO_4$), filtered and concentrated under reduced pressure affording a viscous yellow/orange oil. The crude material was purified using automated column chromatography (45 g silica, eluting with a gradient of 20-100% ethyl acetate in hexanes) to afford the title compound as a clear viscous oil, 2.42 g (48%). $^1$H NMR (Chloroform-d, 400 MHz): δ (ppm) 7.37 (dd, J=7.9, 1.6 Hz, 1H), 7.28 (dd, J=7.7, 1.6 Hz, 1H), 7.16 (t, J=7.8 Hz, 1H), 3.05 (s, 2H), 1.29 (s, 6H).

Step 2: N-[1-(2,3-Dichlorophenyl)-2-methylpropan-2-yl]acetamide

To a solution of 1-(2,3-dichlorophenyl)-2-methylpropan-2-ol) (2.42 g, 11.05 mmol) and Acetonitrile (0.58 mL, 11.05 mmol) in glacial acetic acid (37 mL) at RT was added conc. sulfuric acid (11 mL) drop-wise. The reaction was left to stir at RT for 20 h. The pH of the reaction mixture was adjusted to 5-6 with aqueous sat. $NaHCO_3$ and solid $K_2CO_3$, then extracted with ethyl acetate (4×80 mL). The combined organic extracts were washed with brine (60 mL), dried ($Na_2SO_4$), filtered and concentrated under reduced pressure affording a viscous yellow oil. The crude material was purified by automated column chromatography (5 g silica, eluted with a gradient of 0-40% ethyl acetate in hexanes) to afford the title compound as a colourless crystalline solid, yield=1.92 g (67%). $^1$H NMR (Chloroform-d) δ: 7.37 (dd, J=7.3, 2.2 Hz, 1H), 7.19-7.08 (m, 2H), 5.24-5.19 (m, 1H), 3.36 (s, 2H), 1.97 (s, 3H), 1.38 (s, 6H). UPLC-MS Rt=1.12 min (2 min, basic); m/z (ESI$^+$) 260.0, 262.0, 264.0, 100%.

Step 3. 1-(2,3-dichlorophenyl)-2-methylpropan-2-amine

To a mixture of N-[1-(2,3-dichlorophenyl)-2-methylpropan-2-yl]acetamide (400 mg, 1.54 mmol) in anhydrous THF (12 mL) under an atmosphere of $N_2$ was added bis(cyclopentadienyl)zirconium(IV) chloride hydride (1.59 g, 6.15 mmol) and the reaction mixture stirred at RT for 30 min. The reaction mixture was quenched with water (15 mL) and basified with 1 M NaOH until pH 10 and extracted with ethyl acetate (4×25 mL). The combined organic extracts were washed with brine (40 mL), separated, dried ($Na_2SO_4$), filtered and concentrated under reduced pressure to afford a viscous brown oil yield=315 mg (70%). $^1$H NMR (Chloroform-d) δ: 7.36 (dd, J=7.9, 1.7 Hz, 1H), 7.21 (dd, J=7.7, 1.7 Hz, 1H), 7.18-7.11 (m, 1H), 3.00 (s, 2H), 1.21 (s, 6H). UPLC-MS Rt=1.12 min, 73% (2 min, basic); m/z ESI$^+$ 218.0, 220.0, 222.0 [M+H]$^+$ (2×Cl isotope pattern).

Intermediate V: 1-tetrahydropyran-2-yl-6-(4,4,5,5-tetramethyl-1,3,2-dioxaborolan-2-yl)indazole Step 1: 6-bromo-1-tetrahydropyran-2-yl-indazole P-Toluenesulfonic acid monohydrate (1.21 g, 6.34 mmol) was added to a mixture of 6-Bromo-1H-indazole (12.5 g, 63.4 mmol) and 3,4-dihydro-2H-pyran (18 mL, 190 mmol) in dichloromethane (300 mL). The reaction mixture was stirred at 25° C. for 16 h. The organic phase was separated, and then dried by passing through a phase separator, and concentrated under reduced pressure. The crude material was purified by flash chromatography (120 g silica, eluting with a gradient of 0-20% EtOAc in hexane) to afford the title product (17.6 g, 60 mmol, 94%). $^1$H NMR (600 MHz, DMSO-d6) δ 8.11 (s, 1H), 8.01 (s, 1H), 7.72 (d, J=8.5 Hz, 1H), 7.29 (dd, J=8.5, 1.6 Hz, 1H), 5.85 (dd, J=9.7, 2.5 Hz, 1H), 3.93-3.81 (m, 1H), 3.78-3.68 (m, 1H), 2.41-2.29 (m, 1H), 2.07-1.96 (m, 1H), 1.96-1.88 (m, 1H), 1.77-1.64 (m, 1H), 1.59-1.50 (m, 2H). LCMS LCQ Rt=7.43 min, (Method 3); m/z (ESI$^+$) 282.86 [M+H]$^+$.

Step 2: 1-tetrahydropyran-2-yl-6-(4,4,5,5-tetramethyl-1,3,2-dioxaborolan-2-yl)indazole A mixture of 6-bromo-1-tetrahydropyran-2-yl-indazole (8 g, 28 mmol), bis(pinacolato)diboron (10.84 g, 42.68 mmol) and potassium acetate (8.38 g, 85.36 mmol) in tetrahydrofuran (250 mL) was de-gassed for 10 minutes. [1,1'-bis(diphenylphosphino)ferrocene]dichloropalladium (II) (1.04 g, 1.42 mmol) was added and the reaction mixture was degassed for a further 10 minutes. The reaction mixture was heated to reflux and stirred for 2 hours. The reaction mixture was allowed to cool to RT and partitioned between water and EtOAc. The organic layer was separated, dried (MgSO4) and concentrated under reduced pressure. The crude material was purified by flash chromatography (120 g silica eluting with a gradient of 0-10% EtOAc in hexane) to afford the title compound (8.4 g, 24.57 mmol, 86% yield). $^1$H NMR (600 MHz, DMSO-d6) δ 8.11 (s, 1H), 7.98 (s, 1H), 7.75 (d, J=8.3 Hz, 1H), 7.42 (d, J=8.1 Hz, 1H), 5.95 (dd, J=9.5, 2.6 Hz, 1H), 3.86-3.80 (m, 1H), 3.80-3.72 (m, 1H), 2.44-2.33 (m, 1H), 2.06-1.98 (m, 1H), 1.97-1.91 (m, 1H), 1.82-1.69 (m, 1H), 1.60-1.48 (m, 2H), 1.31 (s, 12H). LCMS LCQ, Rt=8.08 min (Method 3); m/z (ESI$^+$) 329.01 [M+H]$^+$.

Intermediate X: 4-chloro-6-(1-tetrahydropyran-2-ylindazol-6-yl)-1,3,5-triazin-2-amine A vigorously stirred mixture of 1-tetrahydropyran-2-yl-6-(4,4,5,5-tetramethyl-1,3,2-dioxaborolan-2-yl)indazole (1.96 g, 5.97 mmol), 2-Amino-4,6-dichlorotriazine (1.47 g, 9 mmol) and potassium phosphate tribasic (3.80 g, 17 mmol) in water (3 mL) and tetrahydrofuran (30 mL) was de-gassed for 5 min. Bis[2-(di-tert-butylphosphanyl)cyclopenta-2,4-dien-1-yl]iron; dichloropalladium (194 mg, 0.30 mmol) was added. The reaction mixture was degassed for 5 min and then heated in a sealed microwave vial at 50° C. with vigorous stirring for 30 min. The reaction mixture was allowed to cool, diluted with EtOAc and filtered through a phase separator. The filtrate was dry loaded onto celite and purified by flash chromatography (120 g silica eluting with a gradient of 0-30% EtOAc in hexane) to afford the title product (457.mg, 1.35 mmol, 23% yield). 1H NMR (600

MHz, DMSO-d6) δ 8.58 (s, 1H), 8.20 (s, 1H), 8.16 (d, J=12.4 Hz, 2H), 8.08 (dd, J=8.5, 1.3 Hz, 1H), 7.88 (d, J=8.5 Hz, 1H), 5.97 (dd, J=9.1, 2.6 Hz, 1H), 3.89-3.80 (m, 1H), 3.79-3.70 (m, 1H), 2.46-2.35 (m, 1H), 2.10-1.96 (m, 2H), 1.84-1.71 (m, 1H), 1.65-1.49 (m, 2H). LCMS-LCQ Rt=6.41 (Method 3); m/z ($ESI^+$) 331.15 $[M+H]^+$.

Intermediate W: 6-(4,4,5,5-tetramethyl-1,3,2-dioxaborolan-2-yl)imidazo[1,5-a]pyridine 6-Bromoimidazo[1,5-a]pyridine (100 mg, 0.51 mmol), bis(pinacolato)diboron (386 mg, 1.52 mmol) and potassium acetate (150 mg, 1.52 mmol) were dissolved in 1,4-dioxane (3 mL) and degassed with $N_2$ for 10 min before the addition of [1,1bis(diphenylphosphino)ferrocene]dichloropalladium (II) (18.7 mg, 0.03 mmol). The mixture was degassed for a further 5 min and then heated to 100° C. under $N_2$ for 90 min and then allowed to cool to r.t. The mixture was filtered through celite washing with DCM. The filtrate was concentrated in vacuo and the residue suspended in diethyl ether. The suspension was filtered through celite and filtrate evaporated to dryness under reduced pressure. The residue was repeatedly triturated with petroleum ether to afford the title compound as a beige solid (103 mg, 0.32 mmol, 62% yield). $^1$H NMR (399 MHz, DMSO-d6) δ 8.64 (s, 1H), 8.42 (s, 1H), 7.48 (d, J=9.4 Hz, 1H), 7.32 (s, 1H), 6.81 (d, J=9.7 Hz, 1H), 1.30 (s, 12H).

Intermediate Y: 3-methyl-6-(4,4,5,5-tetramethyl-1,3,2-dioxaborolan-2-yl)imidazo[1,5-a]pyridine Step 1: tert-Butyl N-[(5-bromo-2-pyridyl)methyl]carbamate To a stirred mixture of 5-Bromo-2-pyridinecarbonitrile (5 g, 27 mmol), di-tert-butyl dicarbonate (8.9 g, 41 mmol) and cobalt chloride (3.9 g, 30 mmol) in methyl alcohol (100 mL) cooled to 0° C., was added portion-wise sodium borohydride (7.2 g, 191 mmol) and the reaction stirred at RT for 12 h. A saturated solution of $NH_4Cl$ was added and volatiles were evaporated under reduced pressure. The aqueous remaining aqueous phase was extracted with EtOAc (3×10 mL) and the combined organic layers were dried ($MgSO_4$), filtered and evaporated to dryness under reduced pressure. The crude material was purified by flash chromatography (silica gel, eluting with a gradient of 25 to 100% ethyl acetate in petroleum ether) to afford the title compound as a pale yellow oil (2.7 g, 9.5 mmol, 35% yield). $^1$H NMR (600 MHz, Chloroform-d) δ 8.58 (d, J=2.3 Hz, 1H), 7.76 (dd, J=8.3, 2.4 Hz, 1H), 7.18 (d, J=8.3 Hz, 1H), 5.43 (s, 1H), 4.38 (d, J=5.7 Hz, 2H), 1.44 (s, 9H).

Step 2: (5-bromo-2-pyridyl)methanamine tert-Butyl N-[(5-bromo-2-pyridyl)methyl]carbamate (2.7 g, 9.5 mmol) was dissolved in methanol (50 mL) and treated with a methanolic solution of HCl to afford the title compound as a white HCl salt. (1.7 g, 9.4 mmol, 98% yield). $^1$H NMR (600 MHz, DMSO-$d_6$) δ 8.72 (d, J=2.3 Hz, 1H), 8.12 (dd, J=8.4, 2.4 Hz, 1H), 7.50 (dd, J=8.4, 1.9 Hz, 1H), 4.13 (q, J=5.9 Hz, 2H).

Step 3: N-[(5-bromo-2-pyridyl)methyl]acetamide

To a stirred solution of (5-bromo-2-pyridyl)methylammonium chloride (2.5 g, 11.19 mmol) and acetyl chloride (1 mL, 13.42 mmol) in dichloromethane (40 mL), triethylamine (4.68 mL, 33.56 mmol) was added and the reaction mixture stirred for 12 h. Water was added and the aqueous phase was extracted with DCM (3×25 mL). The combined organic layers were dried ($MgSO_4$), filtered and evaporate to dryness under reduced pressure to afford the title compound. $^1$H NMR (600 MHz, Chloroform-d) δ 8.58 (d, J=2.3 Hz, 1H), 7.77 (dd, J=8.3, 2.3 Hz, 1H), 7.17 (d, J=8.3 Hz, 1H), 6.56 (s, 1H), 4.50 (d, J=5.1 Hz, 2H), 2.06 (s, 3H).

Step 4: 6-Bromo-3-methyl-imidazo[1,5-a]pyridine

To a stirred solution of N-[(5-bromo-2-pyridyl)methyl]acetamide (2 g, 8.73 mmol) in toluene (10 mL), phosphorus (v) oxychloride (1.63 mL, 17.46 mmol) was added and the reaction was stirred at 110° C. for 12 h. The reaction mixture was quenched with water and volatiles were evaporated under reduced pressure. The remaining aqueous solution was basified with aqueous 1 M NaOH and extracted with EtOAc. The combined organic layers were dried ($MgSO_4$), filtered and evaporated to dryness under reduced pressure. The crude material was purified by chromatography on silica gel eluting with EtOAc to afford the title compound as a yellow oil (1.5 g, 7.04 mmol, 81% yield). 1H NMR (600 MHz, Chloroform-d) δ 7.82 (q, J=1.1 Hz, 1H), 7.34 (d, J=1.0 Hz, 1H), 7.29 (dd, J=9.5, 1.0 Hz, 1H), 6.68 (dd, J=9.5, 1.4 Hz, 1H), 2.62 (s, 3H). LCMS-MDAP Rt=0.51 min (Method 2); m/z ($ESI^+$) 210.85, 212.80 $[M+H]^+$ (Br isotopes).

Step 5: 3-Methyl-6-(4,4,5,5-tetramethyl-1,3,2-dioxaborolan-2-yl)imidazo[1,5-a]pyridine 6-Bromo-3-methyl-imidazo[1,5-a]pyridine (600 mg, 2.84 mmol), bis(pinacolato)diboron (2165 mg, 8.53 mmol) and potassium acetate (837 mg, 8.53 mmol) were combined in 1,4-dioxane (17 mL) and degassed with $N_2$ for 5 min before the addition of -[1,1bis(diphenylphosphino)ferrocene] dichlorpalladium(II) (104 mg, 0.14 mmol). The mixture was degassed for a further 5 min and then the reaction tube was sealed and the mixture heated to 100° C. for 90 min. The mixture was allowed to cool to RT and filtered through celite washing with DCM. The filtrate was concentrated in vacuo to afford a black oil. Diethyl ether was added and a brown solid precipitated which was removed by filtering through celite washing with further diethyl ether. The filtrate was concentrated in vacuo to afford an orange oil which was repeatedly triturated with petroleum ether to afford the title compound as a beige solid (970 mg, 2.63 mmol, 93% yield). $^1$H NMR (600 MHz, Chloroform-d) δ 8.09 (s, 1H), 7.33 (dd, J=9.1, 1.2 Hz, 1H), 7.26 (d, J=10.0 Hz, 1H), 6.89 (d, J=9.1 Hz, 1H), 2.67 (s, 3H), 1.34 (s, 12H). LCMS-LCQ Rt=0.51 min (Method 2); m/z ($ESI^+$) 177.23 [MH]+(hydrolysis of boronate ester to boronic acid on LC column).

Intermediate Z: 4-chloro-6-(1H-indazol-6-yl)-1,3,5-triazin-2-amine

4-Chloro-6-(1-tetrahydropyran-2-ylindazol-6-yl)-1,3,5-triazin-2-amine (57 mg, 0.17 mmol) was treated with 4M Hydrochloric acid in 1,4-dioxane (4.17 mL, 16.68 mmol). The resulting yellow solution was stirred at RT for 1 h. The reaction mixture was concentrated to dryness under reduced pressure to give the title compound as a pale yellow solid. LCMS-LCQ Rt=3.06 min (method 7), m/z ($ESI^+$) 247.21 $[M+H]^+$.

Intermediate AA: [1-[1-(Difluoromethyl)pyrazol-3-yl]cyclobutyl]ammonium chloride Step 1: tert-Butyl N-[1-[methoxy(methyl)carbamoyl]cyclobutyl]carbamate Triethylamine (1.62 mL, 11.61 mmol) was added to a stirred suspension of 1-N-boc-amino-cyclobutane carboxylic acid (1000 mg, 4.65 mmol), HATU (2645 mg, 6.97 mmol) and N,O-dimethylhydroxylamine hydrochloride (680 mg, 6.97 mmol) in Acetonitrile (50 mL). After stirring at RT overnight, water was added, and the mixture extracted with EtOAc. The organic layer was washed with brine, dried (MgSO4) and concentrated under reduced pressure. The residue was purified by flash chromatography (silica gel, eluting with a gradient of 0-50% EtOAc in petroleum ether) to afford the title compound as a colourless oil (1072 mg, 3.94 mmol, 85% yield). 1H NMR (600 MHz, Chloroform-d) δ 5.02 (s, 1H), 3.64 (s, 3H), 3.17 (s, 3H), 2.75-2.65 (m, 2H), 2.09-2.03 (m, 2H), 2.00-1.92 (m, 1H), 1.84-1.76 (m, 1H), 1.40 (s, 9H).

Step 2: tert-Butyl N-(1-prop-2-ynoylcyclobutyl)carbamate

Ethynylmagnesium bromide solution (30.58 mL, 15.29 mmol) was added dropwise over 1 h to a stirred solution of tert-butyl N-[1-[methoxy(methyl)carbamoyl]cyclobutyl]carbamate (1 g, 3.87 mmol) in tetrahydrofuran (20 mL) at 0° C. The reaction mixture was allowed to warm to RT, stirred overnight, and then quenched by dropwise addition of water (20 mL) under nitrogen flow. After stirring for 30 min, HCl (aq.) (1M, 10 mL) was added and the biphasic mixture extracted with EtOAc. The organic phase was washed with brine, dried (MgSO4), and concentrated to dryness under reduced pressure to give an orange oil. The residue was dissolved in ethanol (20 mL), hydrazine hydrate (0.38 mL, 7.74 mmol) was added, and the reaction mixture heated to reflux overnight. The reaction mixture was cooled to RT, diluted with water and brine, and extracted with EtOAc. The combined organic phases were dried over MgSO4 and concentrated under reduced pressure. The residue was purified by flash chromatography (silica gel, eluting with a gradient of 0-70% EtOAc in petroleum ether) to provide the title compound as a pale yellow oil that solidified upon standing (642 mg, 2.57 mmol, 66% yield). 1H NMR (600 MHz, Chloroform-d) δ 7.48 (d, J=2.0 Hz, 1H), 6.21 (d, J=2.0 Hz, 1H), 5.19 (s, 1H), 2.57-2.40 (m, 4H), 2.07-1.90 (m, 2H), 1.42 (s, 9H).

Step 3: tert-Butyl N-[1-[1-(difluoromethyl)pyrazol-3-yl]cyclobutyl]carbamate

Bromodifluoromethyl diethylphosphonate (0.5 mL, 2.84 mmol) was added to a suspension of tert-butyl N-[1-(1H-pyrazol-3-yl)cyclobutyl]carbamate (641 mg, 2.7 mmol) and potassium fluoride (330 mg, 5.67 mmol) in Acetonitrile (25 mL) which was stirred at RT for 16 h. The reaction mixture was concentrated under reduced pressure and purified by flash chromatography (silica gel, eluting with a gradient of 0-15% EtOAc in petroleum ether) to provide the title compound as a colourless oil, that crystallised upon standing to a white solid (562 mg, 1.76 mmol, 65% yield). 1H NMR (600 MHz, Chloroform-d) δ 7.73 (s, 1H), 7.15 (t, J=60.9 Hz, 1H), 6.46 (s, 1H), 5.24 (s, 1H), 2.72-2.43 (m, 4H), 2.07-1.91 (m, 2H), 1.42 (s, 9H).

Step 4: [1-[1-(Difluoromethyl)pyrazol-3-yl]cyclobutyl]ammonium chloride tert-Butyl N-[1-[1-(difluoromethyl)pyrazol-3-yl]cyclobutyl]carbamate (275 mg, 0.96 mmol) was dissolved in 4M HCl in 1,4-dioxane (10.1 mL, 40.2 mmol) and the reaction mixture stirred at RT for 16 h. The reaction mixture was concentrated under reduced pressure to give the title compound as a white solid (219 mg, 0.93 mmol, 97% yield). $^1$H NMR (600 MHz, DMSO-$d_6$) δ 8.92 (s, 3H), 8.33 (d, J=2.7 Hz, 1H), 7.86 (t, J=58.8 Hz, 1H), 6.85 (d, J=2.7 Hz, 1H), 2.63-2.51 (m, 4H), 2.15-2.06 (m, 1H), 1.96-1.88 (m, 1H).

Intermediate AB: 1-[4-Chloro-1-(difluoromethyl)pyrazol-3-yl]cyclopropanamine hydrochloride Step 1: tert-Butyl N-[1-[4-Chloro-1-(difluoromethyl)pyrazol-3-yl]cyclopropyl]carbamate N-Chlorosuccinimide (51.31 mg, 0.3800 mmol) was added to a solution of tert-Butyl N-[1-[1-(difluoromethyl)pyrazol-3-yl]cyclopropyl]carbamate (Intermediate D, step 4) (70 mg, 0.26 mmol) in Acetonitrile (2.5 mL). The reaction mixture was stirred at RT overnight. Water was added and the resulting precipitate was collected by filtration to give the title compound as a white solid (65 mg, 0.20 mmol, 78% yield). $^1$H NMR (600 MHz, Chloroform-d) δ 7.70 (s, 1H), 6.99 (t, J=60.5 Hz, 1H), 5.31 (s, 1H), 1.40 (m, 11H), 1.18 (s, 2H)

Step 2: 1-[4-Chloro-1-(difluoromethyl)pyrazol-3-yl]cyclopropanamine hydrochloride tert-Butyl N-[1-[4-chloro-1-(difluoromethyl)pyrazol-3-yl]cyclopropyl]carbamate (76.mg, 0.25 mmol) was dissolved in 4M HCl in 1,4-dioxane (2.47 mL, 9.88 mmol) and stirred at RT overnight. The reaction mixture was concentrated to dryness under reduced pressure to give the title compound as a white solid. (60 mg, 0.23 mmol, 95% yield). $^1$H NMR (600 MHz, DMSO-$d_6$) δ 8.85 (d, J=19.4, 3H), 8.64 (s, 1H), 7.77 (t, J=58.4 Hz, 1H), 1.45-1.38 (m, 4H).

Intermediate AC: 1-[1-(2-Trimethylsilylethoxymethyl)imidazol-4 yl]cyclopropanamine Step 1: 1-(2-Trimethylsilylethoxymethyl)imidazole-4-carbonitrile To a solution of 1H-imidazole-4-carbonitrile (1.5 g, 16.11 mmol) in tetrahydrofuran (55 mL) was added sodium hydride (786 mg, 19.7 mmol) at 0° C. The reaction mixture was allowed to warm to RT and stirred until gas evolution had ceased (approximately 30 min). 2-(trimethylsilyl)ethoxymethyl chloride (5.7 mL, 32.2 mmol) was added at 0° C. and the reaction mixture stirred at RT for 20 h. After concentrating under reduced pressure, saturated aqueous $NaHCO_3$ was added to the residue followed by EtOAc. The organic phase was separated and washed with water, then brine, dried (hydrophobic frit) and concentrated under reduced pressure. The crude material was subjected to flash chromatography (silica gel, eluting with a gradient of 0-2.5% MeOH in DCM) to give the title compound as a clear oil (714 mg, 2.56 mmol, 16% yield). $^1$H NMR (600 MHz, DMSO-d6) δ 8.26 (d, J=1.3 Hz, 1H), 8.04 (d, J=1.2 Hz, 1H), 5.37 (s, 2H), 3.46 (t, J=8.2 Hz, 2H), 0.81 (t, J=8.0 Hz, 2H), −0.07 (s, 9H).

Step 2: 1-[1-(2Trimethylsilylethoxymethyl)imidazol-4-yl]cyclopropanamine

To a solution of 1-(2-trimethylsilylethoxymethyl)imidazole-4-carbonitrile (710 mg, 3.18 mmol) in tetrahydrofuran (24.9 mL) was added titanium isopropoxide (0.92 mL, 3.03 mmol) and then 3.0 M ethylmagnesium bromide in diethyl ether (1.84 mL, 5.51 mmol) at RT. The reaction mixture was stirred at RT for 30 min. Water (20 mL) was added to the reaction mixture and then EtOAc. The supernatant liquid was decanted away from the solid precipitate. The combined extracts were filtered by passing through a phase separator and concentrated under reduced pressure. The crude material was purified by flash chromatography (silica gel, eluting with a gradient 0-10% MeOH in DCM) to give the title product as light brown oil (192 mg, 0.67 mmol, 22% yield). 1H NMR (600 MHz, DMSO-d6) δ 7.55 (d, J=1.4 Hz, 1H), 7.04 (d, J=1.4 Hz, 1H), 5.20 (s, 2H), 3.44 (t, J=8.2 Hz, 2H), 0.85 (q, J=3.6 Hz, 2H), 0.81 (t, J=8.3 Hz, 2H), 0.72 (q, J=3.6 Hz, 2H), −0.06 (s, 9H).

Intermediate AD: 2-(2,3-Dichlorophenyl)-N-(2-methoxyethyl)ethanamine

Step 1: tert-Butyl N-[2-(2,3-dichlorophenyl)ethyl]carbamate

To a solution of 2-(2,3-dichlorophenyl)ethanamine (500 mg, 2.63 mmol) and triethylamine (0.7 mL, 5 mmol) in DCM (10 mL) was added di-tert-butyl dicarbonate (632 mg, 2.89 mmol) as a solution in DCM (5 mL) at 0° C. The reaction mixture was stirred at RT for 3.5 h. The reaction mixture was diluted with water and extracted with DCM (×3). The combined organics were washed with brine, dried (hydrophic frit) and concentrated under reduced pressure. The crude material was purified by flash chromatography (silica gel, eluting with a gradient of 0-10% EtOAc in petroleum ether) to give the title compound as a white solid (711 mg, 2.33 mmol, 88% yield). $^1$H NMR (600 MHz, DMSO-$d_6$) δ 7.47 (d, J=7.1 Hz, 1H), 7.34-7.17 (m, 2H), 6.89 (t, J=5.3 Hz, 1H), 3.15 (q, J=6.7 Hz, 2H), 2.85 (t, J=7.1 Hz, 2H), 1.32 (s, 9H).

Step 2: tert-Butyl N-[2-(2,3-dichlorophenyl)ethyl]-N-(2-methoxyethyl)carbamate

To a solution of tert-butyl N-[2-(2,3-dichlorophenyl)ethyl]carbamate (100 mg, 0.34 mmol) in N,N-dimethylformamide (3 mL) was added sodium hydride (15.2 mg, 0.38 mmol) at 0° C. The reaction mixture was stirred at 0° C. for 10 minutes and then at RT for 30 min. After cooling to 0° C., 2-bromomethyl methyl ether (48.5 μL, 0.52 mmol) was added and the reaction mixture stirred at 0° C. for 10 minutes and then at RT for 18 h. The reaction mixture was concentrated under reduced pressure and the residue was dissolved in EtOAc and washed with brine. The aqueous phase was back extracted with EtOAc (×2). The combined organic phases were dried by passing through a phase separator and concentrated under reduced pressure. The crude material was purified by flash chromatography (silica gel, eluting with a gradient of 0-20% EtOAc in petroleum ether) to give the title compound as a clear oil (76 mg, 0.21 mmol, 61% yield). $^1$H NMR (600 MHz, DMSO-$d_6$) δ 7.61-7.36 (m, 1H), 7.27 (t, J=7.5 Hz, 1H), 7.21 (d, J=8.4 Hz, 1H), 3.44 (t, J=6.9 Hz, 1H), 3.42-3.33 (m, 3H), 3.25-3.16 (m, 4H), 2.92 (t, J=6.9 Hz, 2H), 1.41-1.12 (m, 9H).

Step 3: 2-(2,3-Dichlorophenyl)-N-(2-methoxyethyl)ethanamine

Trifluoracetic acid (0.16 mL, 2.12 mmol) was added to a solution of tert-butyl N-[2-(2,3-dichlorophenyl)ethyl]-N-(2-methoxyethyl)carbamate (74 mg, 0.210 mmol) in DCM (5.50 mL) at RT. The reaction mixture was stirred for 18 h at RT. The reaction mixture was concentrated under reduced pressure and the residue dissolved in MeOH and eluted onto an SCX-2 cartridge (10 g). The cartridge was washed through with MeOH and the filtrate discarded. 2M NH3 in MeOH was eluted through the cartridge and the filtrate was concentrated under reduced pressure to give the title compound as a pale brown oil (58 mg, 0.21 mmol, 99% yield). $^1$H NMR (600 MHz, DMSO-$d_6$) δ 7.45 (dd, J=7.9, 1.6 Hz, 1H), 7.31 (dd, J=7.7, 1.6 Hz, 1H), 7.26 (t, J=7.7 Hz, 1H), 3.33 (t, J=5.6 Hz, 2H), 3.20 (s, 3H), 2.85 (t, J=7.3 Hz, 2H), 2.72 (dd, J=8.1, 6.6 Hz, 2H), 2.65 (t, J=5.7 Hz, 2H), 1.71 (s, 1H).

Intermediate BA: [1-[4-chloro-1-(difluoromethyl)pyrazol-3-yl]-1-methyl-ethyl]ammonium chloride Step 1: tert-butyl N-[1-[4-chloro-1-(difluoromethyl)pyrazol-3-yl]-1-methyl-ethyl]carbamate N-chlorosuccinimide (54.57 mg, 0.4100 mmol) was added to a solution of tert-butyl N-[1-[1-(difluoromethyl)pyrazol-3-yl]-1-methyl-ethyl]carbamate, (Intermediate L step 3) (75.mg, 0.2700 mmol) in Acetonitrile (2.5 mL) and the reaction was stirred at RT for 12 h. The volatiles were evaporated under reduced pressure and the crude was crude material was purified by flash chromatography (silica gel with a gradient of 10 to 100% ethyl acetate in peptroleum ether) to afford a white solid (65 mg, 0.21 mmol, 76% yield). 1H NMR (600 MHz, Chloroform-d) δ 7.73 (s, 1H), 7.04 (t, J=60.5 Hz, 1H), 5.19 (s, 1H), 1.65 (s, 6H), 1.36 (s, 9H). LCMS-LCQ Rt 7.03 mins (Method 2); m/z (ESI)$^+$ 209.75 [M+H]$^+$-Boc fragment Step 2: [1-[4-chloro-1-(difluoromethyl)pyrazol-3-yl]-1-methyl-ethyl]ammonium chloride tert-butyl N-[1-[4-chloro-1-(difluoromethyl)pyrazol-3-yl]-1-methyl-ethyl]carbamate (65 mg, 0.21 mmol) was dissolved in diethyl ether (7 mL) and treated with 4 M HCl in 1,4-dioxane (1 mL, 4.0 mmol). The reaction mixture was stirred at room temperature for 16 h then concentrated to dryness under reduced pressure to afford the title compound as white solid (60 mg, 0.24 mmol, yield 89%). LCMS-LCQ Rt 0.81 mins (Method 2); m/z (ESI)+209.78 [M+H]$^+$.

Intermediate BB: 4-fluoro-1-tetrahydropyran-2-yl-6-(4,4,5,5-tetramethyl-1,3,2-dioxaborolan-2-yl)indazole Step 1: 6-bromo-4-fluoro-1-tetrahydropyran-2-yl-indazole 3,4-dihydro-2h-pyran (0.64 mL, 7.0 mmol) and p-toluenesulfonic acid monohydrate (44 mg, 0.23 mmol) were added to a solution of 6-Bromo-4-fluoro-1H-indazole (500 mg, 2.33 mmol) in dichloromethane (10 mL) and the reaction mixture stirred for 16 h. The volatiles were evaporated at reduced pressure and the crude material purified by flash chromatography (silica, eluting with a gradient of 5-25% ethyl acetate in hexane. The product containing fractions were concentrated under reduced pressure to afford the titled product a pale yellow oil (550 mg, 1.8 mmol, yield 77%). $^1$H NMR (600 MHz, Chloroform-d) δ 8.03 (d, J=0.9 Hz, 1H), 7.58 (t, J=1.1 Hz, 1H), 6.97 (dd, J=9.0, 1.3 Hz, 1H), 5.64 (dd, J=9.2, 2.8 Hz, 1H), 4.04-3.93 (m, 1H), 3.81-3.69 (m, 1H), 2.54-2.42 (m, 1H), 2.19-2.03 (m, 2H), 1.82-1.61 (m, 3H).

Step 2: 4-fluoro-1-tetrahydropyran-2-yl-6-(4,4,5,5-tetramethyl-1,3,2-dioxaborolan-2-yl)indazole 6-bromo-4-fluoro-1-tetrahydropyran-2-yl-indazole (400 mg, 1.34 mmol) was mixed with bis(pinacolato)diboron (510 mg, 2.0 mmol), potassium acetate (394 mg, 4.0 mmol), and [1,1'-bis(diphenylphosphino)ferrocene]dichloropalladium(II) (49 mg, 0.07 mmol) in tetrahydrofuran (7 mL), and the solution degassed with $N_2$ for 10 minutes. The reaction mixture was then heated to 80° C. with stirring for 2 h. The reaction mixture was cooled to RT and the residue purified by flash chromatography (silica, gradient 5-25% ethyl acetate in petroleum ether). The product containing fractions were concentrated to dryness under reduced pressure to afford the product as a white solid. (330 mg, 0.71 mmol, yield 53%). $^1$H NMR (600 MHz, Chloroform-d) δ 8.10 (s, 1H), 7.79 (s, 1H), 7.19 (d, J=10.2 Hz, 1H), 5.76 (dd, J=9.7, 2.7 Hz, 1H), 4.04 (d, J=12.0 Hz, 1H), 3.86-3.68 (m, 1H), 2.65-2.51 (m, 1H), 2.20-2.10 (m, 1H), 2.07-1.99 (m, 1H), 1.82-1.71 (m, 2H), 1.69-1.61 (m, 1H), 1.37 (s, 12H). LCMS-LCQ Rt 1.94 mins (Method 2); m/z (ESI)+264.98 $[M+H]^+$ (Boronic acid)

Intermediate BC: 5-fluoro-1-tetrahydropyran-2-yl-6-(4,4,5,5-tetramethyl-1,3,2-dioxaborolan-2-yl)indazole Step 1: 6-bromo-5-fluoro-1-tetrahydropyran-2-yl-indazole The title compound was synthesised using the same protocol as Intermediate BB, Step 1, except 6-Bromo-4-fluoro-1H-indazole was replaced with 6-Bromo-5-fluoro-1H-indazole to afford the product as a clear oil (560 mg, 1.83 mmol, yield 79%). $^1$H NMR (600 MHz, Chloroform-d) δ 7.95 (d, J=0.9 Hz, 1H), 7.85 (d, J=5.4 Hz, 1H), 7.41 (d, J=8.2 Hz, 1H), 5.65 (dd, J=9.1, 2.9 Hz, 1H), 4.00 (dq, J=10.3, 2.3 Hz, 1H), 3.79-3.65 (m, 1H), 2.59-2.41 (m, 1H), 2.19-2.03 (m, 2H), 1.80-1.62 (m, 3H).

Step 2: 5-fluoro-1-tetrahydropyran-2-yl-6-(4,4,5,5-tetramethyl-1,3,2-dioxaborolan-2-yl)indazole The title compound was synthesised using the same protocol as Intermediate BB, Step 2 except 6-bromo-4-fluoro-1-tetrahydropyran-2-yl-indazole was replaced with 6-bromo-5-fluoro-1-tetrahydropyran-2-yl-indazole to afford the product as a clear oil (400 mg, 00.98 mmol, yield 73%). $^1$H NMR (600 MHz, Chloroform-d) δ 7.97 (s, 1H), 7.93 (d, J=4.3 Hz, 1H), 7.30 (d, J=9.1 Hz, 1H), 5.75 (dd, J=9.4, 2.8 Hz, 1H), 4.06-3.98 (m, 1H), 3.78 (td, J=11.0, 2.7 Hz, 1H), 2.64-2.50 (m, 1H), 2.21-2.10 (m, 1H), 2.09-1.99 (m, 1H), 1.84-1.68 (m, 2H), 1.68-1.61 (m, 1H), 1.39 (s, 12H). Rt 3.52 mins (Method 2); m/z (ESI)+347.08 $[M+H]^+$, 263.32 $[M+H]^+$ (Boronic acid)

Intermediate BD: 7-fluoro-1-tetrahydropyran-2-yl-6-(4,4,5,5-tetramethyl-1,3,2-dioxaborolan-2-yl)indazole SM-2183-127

Step 1: 6-bromo-7-fluoro-1-tetrahydropyran-2-yl-indazole

The title compound was synthesised using the same protocol as Intermediate BB, Step 1, except 6-Bromo-4-fluoro-1H-indazole was replaced with 6-Bromo-7-fluoro-1H-indazole to afford the product as a pale yellow oil (490 mg, 1.61 mmol, yield 69%). $^1$H NMR (600 MHz, Chloroform-d) δ 8.01 (d, J=2.0 Hz, 1H), 7.34 (d, J=8.5 Hz, 1H), 7.29-7.19 (m, 1H), 5.86 (dd, J=10.1, 2.5 Hz, 1H), 4.10-3.96 (m, 1H), 3.75 (td, J=11.4, 2.6 Hz, 1H), 2.66-2.50 (m, 1H), 2.20-2.05 (m, 2H), 1.91-1.69 (m, 3H).

Step 2: 7-fluoro-1-tetrahydropyran-2-yl-6-(4,4,5,5-tetramethyl-1,3,2-dioxaborolan-2-yl)indazole The title compound was synthesised using the same protocol as Intermediate BB, Step 2 except 6-bromo-4-fluoro-1-tetrahydropyran-2-yl-indazole was replaced with 6-bromo-7-fluoro-1-tetrahydropyran-2-yl-indazole to afford the product as a white solid (350 mg, 0.86 mmol, yield 64%). $^1$H NMR (600 MHz, Chloroform-d) δ 8.04 (d, J=1.9 Hz, 1H), 7.49-7.38 (m, 2H), 5.97 (dd, J=10.4, 2.4 Hz, 1H), 4.10-4.01 (m, 1H), 3.75 (td, J=11.6, 2.5 Hz, 1H), 2.69-2.50 (m, 1H), 2.15-2.08 (m, 1H), 2.09-2.01 (m, 1H), 1.83-1.64 (m, 2H), 1.63-1.53 (m, 1H), 1.38 (s, 12H). LCMS-LCQ Rt 3.32 mins (Method 2); m/z ($ESI^+$) 346.99 $[M+H]^+$, 263.30 $[M+H]^+$ (Boronic acid).

Intermediate BE: 3-fluoro-1-tetrahydropyran-2-yl-5-(4,4,5,5-tetramethyl-1,3,2-dioxaborolan-2-yl)indazole Step 1: 5-bromo-3-fluoro-1H-indazole To a stirred solution of 5-bromo-1H-indazole (200 mg, 1.0 mmol) in Acetonitrile (5 mL) was added Selectfluor (N-Fluoro-N'-chloromethyltriethylenediaminebis(tetrafluoroborate)) (720 mg, 2.0 mmol) and acetic acid (0.23 mL, 4.0 mmol) and the reaction mixture stirred in sealed vial at 90° C. for 24 h. The volatiles were removed under reduced pressure and the crude was purified by flash chromatography (silica gel, eluting with a gradient of 25-75% ethyl acetate in petroleum ether) to afford the desired compound as a white solid (73.mg, 0.3200 mmol, 32% yield). $^1$H NMR (600 MHz, Chloroform-d) δ 9.51 (s, 1H), 7.84 (d, J=1.7 Hz, 1H), 7.51 (dd, J=8.9, 1.8 Hz, 1H), 7.28 (dd, J=9.0, 2.3 Hz, 1H).

Step 2: 5-bromo-3-fluoro-1-tetrahydropyran-2-yl-indazole 5-bromo-3-fluoro-1H-indazole (75 mg, 0.35 mmol) was added to a mixture of 3,4-dihydro-2h-pyran (0.1 mL, 1.0 mmol) and p-toluenesulfonic acid monohydrate (6.6 mg, 0.03 mmol) in dichloromethane (1.5 mL) and stirred at 25° C. for 16 hours. The reaction mixture was partitioned between dichloromethane (1.5 mL) and saturated aqueous sodium bicarbonate solution. The organic phase was separated, dried by passing through a phase separator, and concentrated to dryness under reduced pressure. The crude residue was purified to flash chromatography (Silica gel, eluting with a gradient of 5-50% ethyl acetate in petroleum ether) to afford the desired compound as a clear oil (75 mg, 0.24 mmol, yield 68%). $^1$H NMR (600 MHz, Chloroform-d) δ 7.79 (d, J=1.7 Hz, 1H), 7.49 (dd, J=8.9, 1.8 Hz, 1H), 7.40 (dd, J=9.1, 2.0 Hz, 1H), 5.55 (dt, J=9.0, 2.5 Hz, 1H), 3.97 (ddd, J=10.3, 4.1, 2.4 Hz, 1H), 3.74-3.62 (m, 1H), 2.42 (dddd, J=13.4, 10.8, 9.0, 4.2 Hz, 1H), 2.16-2.07 (m, 1H), 2.07-1.97 (m, 1H), 1.79-1.59 (m, 3H).

Step 3: 3-fluoro-1-tetrahydropyran-2-yl-5-(4,4,5,5-tetramethyl-1,3,2-dioxaborolan-2-yl)indazole A mixture of bis(pinacolato)diboron (95 mg, 0.38 mmol), [1,1'-bis(diphenylphosphino)-ferrocene]dichloropalladium (II) (9 mg, 0.01 mmol), 5-bromo-3-fluoro-1-tetrahydropyran-2-yl-indazole (75 mg, 0.25 mmol) and potassium acetate (74 mg, 0.75 mmol) in tetrahydrofuran (1.5 mL) was degassed with $N_2$ for 10 minutes then heated to 80° C. with stirring for 12 h. The crude was purified by flash chromatography (silica gel, eluting with a gradient of 5-50% ethyl acetate in petroleum ether) to afford the desired compound as a clear oil (76 mg, 0.21 mmol, 83%). $^1$H NMR (600 MHz, Chloroform-d) δ 8.18 (d, J=1.2 Hz, 1H), 7.82 (dd, J=8.5, 1.0 Hz, 1H), 7.45 (ddd, J=8.6, 2.0, 0.9 Hz, 1H), 5.58 (dt, J=9.3, 2.5 Hz, 1H), 4.00 (ddt, J=13.1, 3.5, 1.5 Hz, 1H), 3.70 (ddd, J=13.4, 8.6, 2.9 Hz, 1H), 2.51-2.38 (m, 1H), 2.12 (ddd, J=9.6, 5.0, 2.3 Hz, 1H), 2.00 (ddd, J=13.6, 5.7, 3.2 Hz, 1H), 1.78-1.66 (m, 2H), 1.63 (dp, J=6.6, 3.5 Hz, 1H), 1.35 (s, 12H).

Intermediate BF 3-fluoro-1-(oxan-2-yl)-6-(4,4,5,5-tetramethyl-1,3,2-dioxaborolan-2-yl)indazole Step 1: 6-bromo-3-fluoro-1H-indazole To a stirred solution of 6-Bromo-1H-indazole (250 mg, 1.27 mmol) in Acetonitrile (5 mL) was added Selectfluor (N-Fluoro-N'-chloromethyltriethylenediaminebis(tetrafluoroborate)) (900 mg, 2.54 mmol) and acetic acid (0.29 mL, 5.08 mmol) The reaction mixture was stirred in sealed vial at 90° C. for 48 h. The volatiles were removed under reduced pressure and the crude residue was purified by flash chromatography (silica gel, eluting with a gradient of 25-75% ethyl acetate in petroleum ether) to afford the desired compound as a white solid (50 mg, 0.23 mmol, 18% yield). $^1$H NMR (600 MHz, Chloroform-d) δ 9.24 (s, 1H), 7.58 (t, J=1.8 Hz, 1H), 7.55 (d, J=8.6 Hz, 1H), 7.30 (dd, J=8.6, 1.5 Hz, 1H). LCMS-LCQ Rt 2.65 mins (Method 2); m/z (ESI$^+$) 215.31 [M+H]$^+$.

Step 2: 6-bromo-3-fluoro-1-tetrahydropyran-2-yl-indazole

To a mixture of 6-bromo-3-fluoro-1H-indazole (50 mg, 0.23 mmol) and 3,4-dihydro-2h-pyran (0.06 mL, 0.70 mmol) in dichloromethane (5 mL) was added p-toluenesulfonic acid monohydrate (4.4 mg, 0.02 mmol). The reaction mixture was stirred at 25° C. for 16 h. The volatiles were evaporated under reduced pressure and the crude material purified by flash chromatography (Silica gel, eluting with a gradient of 5-25% ethyl acetate in hexane) to afford the desired compound as a clear oil (56 mg, 0.18 mmol, 76% yield). $^1$H NMR (600 MHz, Chloroform-d) δ 7.70 (t, J=1.4 Hz, 1H), 7.50 (d, J=8.5 Hz, 1H), 7.28 (dt, J=8.5, 1.2 Hz, 1H), 5.52 (dt, J=9.2, 2.6 Hz, 1H), 4.00 (dd, J=12.2, 4.2 Hz, 1H), 3.77-3.62 (m, 1H), 2.49-2.32 (m, 1H), 2.18-2.04 (m, 1H), 2.05-1.98 (m, 1H), 1.77-1.61 (m, 3H). LCMS-LCQ Rt 4.08 mins (Method 2); m/z (ESI$^+$) 298.90-300.89 [M+H]$^+$.

Step 3: 2-(3-fluoro-1-tetrahydropyran-2-yl-indazol-6-yl)-4,5,5-trimethyl-1,3,2-dioxaborolan-4-ol A mixture of 6-bromo-3-fluoro-1-tetrahydropyran-2-yl-indazole (55 mg, 0.18 mmol), bis(pinacolato)diboron (70 mg, 0.28 mmol) and potassium acetate (54 mg, 0.55 mmol) in tetrahydrofuran (1.6 mL) was de-gassed with $N_2$ for 10 minutes. [1,1'-bis(diphenylphosphino)ferrocene]dichloropalladium(II) (6.7 mg, 0.01 mmol) was added and the reaction mixture was degassed for a further 10 minutes before heating to reflux for 2 h. The reaction mixture was allowed to cool to RT then partitioned between water and ethyl acetate. The organic phase was dried ($MgSO_4$) and concentrated to dryness under reduced pressure. The crude material was dissolved in DCM and filtered through a pad of celite. The filtrate was concentrated to dryness under reduced pressure and the residue purified by flash chromatography (Silica gel, eluting with 0-20% ethyl acetate in hexane) to afford the desired compound as a white solid (75 mg, 0.2 mmol, 110% yield). $^1$H NMR (600 MHz, Chloroform-d) δ 7.95-7.92 (m, 1H), 7.62 (d, J=8.1 Hz, 1H), 7.57 (d, J=8.1 Hz, 1H), 5.65 (dt, J=9.7, 2.6 Hz, 1H), 4.07-3.94 (m, 1H), 3.73 (td, J=11.1, 2.8 Hz, 1H), 2.56-2.40 (m, 1H), 2.16-2.07 (m, 1H), 2.01-1.91 (m, 1H), 1.78-1.67 (m, 2H), 1.63-1.58 (m, 1H), 1.36 (s, 12H).

Intermediate BG: 2-[3-(1-Amino-1-methyl-ethyl)pyrazol-1-yl]ethanol

Step 1: tert-butyl N-[1-Methyl-1-[1-(2-tetrahydropyran-2-yloxyethyl)pyrazol-3-yl]ethyl]carbamate To a suspension of sodium hydride (154 mg, 3.85 mmol) in N,N-dimethylformamide (7 mL) was added tert-butyl N-[1-methyl-1-(1H-pyrazol-3-yl)ethyl]carbamate (Intermediate L, step 2) (400 mg, 1.78 mmol) at RT. The reaction mixture was stirred at room RT until gas evolution had ceased. 2-(2-Bromoethoxy)tetrahydro-2H-pyran (0.27 mL, 1.78 mmol) was added at RT and the reaction mixture stirred for 18 h. The reaction mixture was added to water and the product extracted with DCM (×3). and with EtOAc (×2). The combined organics were dried by passing through a phase separator and concentrated to dryness under reduced pressure. The crude material was purified by flash chromatography (silica gel, eluting with a gradient of 0-2.5% MeOH in DCM) to give the title compound as a clear oil (243 mg, 0.62 mmol, 35% yield). $^1$H NMR (600 MHz, DMSO-$d_6$) δ 7.51 (d, J=2.2 Hz, 1H), 6.65 (s, 1H), 6.02 (d, J=2.2 Hz, 1H), 4.45 (s, 1H), 4.21-4.11 (m, 2H), 3.88-3.83 (m, 1H), 3.63 (p, J=10.6, 5.3 Hz, 1H), 3.46 (s, 1H), 1.69-1.56 (m, 1H), 1.54-1.48 (m, 1H), 1.45 (s, 7H), 1.43-1.36 (m, 3H), 1.32 (s, 10H). LCMS m/z (ESI$^+$) 353.96 [M+H]$^+$.

Step 2: 2-[3-(1-Amino-1-methyl-ethyl)pyrazol-1-yl]ethanol

A solution of tert-butyl N-[1-methyl-1-[1-(2-tetrahydropyran-2-yloxyethyl)pyrazol-3-yl]ethyl]carbamate (237 mg, 0.67 mmol) in DCM (12 mL) was treated with trifluoroacetic acid (2.57 mL, 33.5 mmol). The reaction mixture was stirred at RT for 1 h, and then concentrated under reduced pressure. The crude product was dissolved in methanol and eluted onto an SCX-2 cartridge (2×10 g) and the cartridge washed through with methanol. The product was eluted with 2 M $NH_3$ in methanol and the eluant concentrated to dryness under reduced pressure to give the title compound as a clear oil (128 mg, 0.67 mmol, 100% yield). $^1H$ NMR (600 MHz, DMSO-$d_6$) δ 7.52 (d, J=2.2 Hz, 1H), 6.15 (d, J=2.2 Hz, 1H), 4.03 (t, J=5.7 Hz, 2H), 3.67 (t, J=5.8 Hz, 2H), 1.32 (s, 6H).

Intermediate BH 2-[4-(Aminomethyl)-2,3-difluoro-phenoxy]ethanol

Step 1: 2,3-Difluoro-4-(2-hydroxyethoxy)benzonitrile

A mixture of 2,3-Difluoro-4-hydroxybenzonitrile (150 mg, 0.97 mmol), 2-bromoethanol (0.21 mL, 2.9 mmol) and potassium carbonate (267 mg, 1.93 mmol) in Acetonitrile (10 mL) was heated at 85° C. for 16 h. The reaction mixture was filtered and the filter cake washed through with EtOAc. The filtrate was concentrated under reduced pressure. The crude material was purified by flash chromatography (silica gel, eluting with a gradient of 20-100% EtOAc in petroleum ether) to give the title compound as a clear oil (109 mg, 0.53 mmol, 55% yield). $^1H$ NMR (600 MHz, DMSO-d6) δ 7.75-7.62 (m, 1H), 7.27-7.09 (m, 1H), 4.97 (t, J=5.4 Hz, 1H), 4.20 (t, J=4.7 Hz, 2H), 3.72 (q, J=5.0 Hz, 2H).

Step 2: tert-Butyl N-[[2,3-difluoro-4-(2-hydroxy-ethoxy)phenyl]methyl]carbamate

A stirred mixture of 2,3-difluoro-4-(2-hydroxyethoxy) benzonitrile (104 mg, 0.52 mmol), di-tert-butyl dicarbonate (171 mg, 0.78 mmol) and cobalt(II) chloride (75 mg, 0.57 mmol) in methanol (3 mL) was cooled to 0° C. Sodium borohydride (138 mg, 3.66 mmol) was added and the reaction mixture stirred at RT for 16 h. Saturated aqueous $NaHCO_3$ was added and the volatiles removed under reduced pressure. The aqueous was extracted with EtOAc (×3) and the combined organics dried by passing through a phase separator. The crude product was purified by flash chromatography (silica gel, eluting with a gradient of 0-40% EtOAc in petroleum ether) to afford the title compound as a white solid (76 mg, 0.25 mmol, 47% yield). $^1H$ NMR (600 MHz, DMSO-d6) δ 7.34 (t, J=6.2 Hz, 1H), 7.06-6.85 (m, 2H), 4.90 (t, J=5.3 Hz, 1H), 4.09 (d, J=6.0 Hz, 2H), 4.04 (t, J=5.0 Hz, 2H), 3.69 (q, J=4.8 Hz, 2H), 1.35 (s, 9H).

Step 3: 2-[4-(Aminomethyl)-2,3-difluoro-phenoxy]ethanol

To a solution of tert-butyl N-[[2,3-difluoro-4-(2-hydroxy-ethoxy)phenyl]methyl]carbamate (71 mg, 0.23 mmol) in DCM (2.1 mL) was added trifluoroacetic acid (0.23 mL, 2.97 mmol). The reaction mixture was stirred at RT for 16 h and then concentrated under reduced pressure. The residue was dissolved in methanol and eluted onto an SCX-2 cartridge (10 g). The product was eluted with 2M NH3 in MeOH and the eluent concentrated to dryness under reduced pressure to give the title compound as a white solid (50 mg, 0.23 mmol, 100% yield). $^1H$ NMR (600 MHz, DMSO-d6) δ 7.16 (td, J=8.5, 2.2 Hz, 1H), 6.96 (t, J=8.9 Hz, 1H), 4.89 (s, 1H), 4.05 (t, J=4.9 Hz, 2H), 3.75-3.57 (m, 4H).

Intermediate BI 2-[3-(Aminomethyl)-2-fluoro-phenoxy]ethanol

Step 1: 2-Fluoro-3-(2-tetrahydropyran-2-yloxy-ethoxy)benzonitrile

A mixture of 2-fluoro-3-hydroxybenzonitrile (300 mg, 2.19 mmol), 2-(2-bromoethoxy)tetrahydro-2H-pyran (0.99 mL, 6.56 mmol) and potassium carbonate (605 mg, 4.38 mmol) in Acetonitrile (23 mL) was heated at 60° C. for 24 h. The reaction mixture was filtered, the filter cake washed with EtOAc, and the filtrate concentrated under reduced pressure. The crude material was purified by flash chromatography (silica gel, eluting with a gradient of 0-25% EtOAc in petroleum ether) to give the title compound as a clear oil (490 mg, 1.75 mmol, 80% yield). $^1H$ NMR (600 MHz, DMSO-$d_6$) δ 7.58 (td, J=8.4, 1.5 Hz, 1H), 7.49-7.38 (m, 1H), 7.30 (t, J=8.3 Hz, 1H), 4.63 (t, J=3.5 Hz, 1H), 4.34-4.22 (m, 2H), 3.95-3.86 (m, 1H), 3.77-3.67 (m, 2H), 3.45-3.37 (m, 1H), 1.71-1.51 (m, 2H), 1.53-1.33 (m, 4H).

Step 2: tert-Butyl N-[[2-fluoro-3-(2-tetrahydropy-ran-2-yloxyethoxy)phenyl]methyl]carbamate A mixture of 2-fluoro-3-(2-tetrahydropyran-2-yloxy-ethoxy)benzonitrile (487 mg, 1.84 mmol), di-tert-butyl dicarbonate (601 mg, 2.75 mmol) and cobalt(II) chloride (262 mg, 2.02 mmol) in methanol (10.5 mL) was cooled to 0° C. Sodium borohydride (486 mg, 12.9 mmol) was added and the reaction mixture was stirred at RT for 16 h. Saturated aqueous $NaHCO_3$ was added to the reaction mixture concentrated under reduced pressure. The concentrated solution was extracted with EtOAc (×3), and the combined organics dried (hydrophobic frit) and concentrated under reduced pressure. The crude product was purified by flash chromatography (silica gel, eluting with a gradient of 0-40% EtOAc in petroleum ether) to give the title compound as a clear oil (397 mg, 1.05 mmol, 57% yield). $^1H$ NMR (600 MHz, DMSO-$d_6$) δ 7.33 (t, J=5.8 Hz, 1H), 7.13-6.94 (m, 2H), 6.90-6.73 (m, 1H), 4.63 (t, J=3.8 Hz, 1H), 4.17-4.14 (m, 2H), 4.12 (d, J=6.1 Hz, 2H), 3.93-3.84 (m, 1H), 3.78-3.72 (m, 1H), 3.72-3.66 (m, 1H), 3.44-3.38 (m, 1H), 1.73-1.63 (m, 1H), 1.63-1.54 (m, 1H), 1.51-1.38 (m, 3H), 1.36 (s, 9H), 1.28 (s, 1H).

Step 3: 2-[3-(Aminomethyl)-2-fluoro-phenoxy]ethanol

A solution of tert-butyl N-[[2-fluoro-3-(2-tetrahydropy-ran-2-yloxyethoxy)phenyl]methyl]carbamate (392 mg, 1.06 mmol) and trifluoroacetic acid (2.0 mL, 26.5 mmol) in DCM (25 mL) was stirred at RT for 3 h. The reaction mixture was concentrated under reduced pressure. The residue was dissolved in methanol and eluted onto an SCX-2 cartridge (3×10 g) and the product eluted with 2M NH3 in methanol. The eluent was concentrated to dryness under reduced pressure and the residue was purified by flash chromatography (silica gel, eluting with a gradient of 0-30% methanol in DCM) to give the title compound as a clear oil (73 mg, 0.37 mmol, 35% yield). $^1H$ NMR (600 MHz, DMSO-$d_6$) δ 7.16-6.94 (m, 3H), 4.86 (s, 1H), 4.01 (t, J=5.0 Hz, 2H), 3.76 (s, 2H), 3.69 (t, J=5.0 Hz, 2H).

Key Intermediate 2

To a solution of 3-methyl-6-(4,4,5,5-tetramethyl-1,3,2-dioxaborolan-2-yl)imidazo[1,5-a]pyridine (Intermediate Y, 3 g, 11.62 mmol) and 4,6-dichloro-1,3,5-triazin-2-amine (1.92 g, 11.62 mmol) in THF (180 mL) and H2O (180 mL), then K3PO4 (4.93 g, 23.24 mmol) and ditert-butyl(cyclo-pentyl)phosphane; dichloropalladium; iron (378.74 mg, 581.12 μmol) were added under N2 atmosphere, the mixture was stirred at 60° C. for 6 h under N2 atmosphere. The residue was diluted with H2O (100 mL) and extracted with ethyl acetate (100 mL×3). The organic phase was washed with brine (50 mL), dried over Na2SO4, filtered and concentrated under reduced pressure to give a residue. The residue was purified by flash silica gel chromatography to give 4-chloro-6-(3-methylimidazo[1,5-a]pyridin-6-yl)-1,3,5-triazin-2-amine (970 mg, 30.42% yield) as a yellow solid.

$^1$H NMR (399 MHz, DMSO-d6) δ=8.85 (s, 1H), 8.20 (br s, 2H), 7.59 (d, J=9.6, 1H), 7.42 (d, J=9.6, 1H), 7.32 (s, 1H), 2.67 (s, 3H)

Key Intermediate 3

To a solution of 3-methyl-6-(4,4,5,5-tetramethyl-1,3,2-dioxaborolan-2-yl)imidazo[1,5-a]pyridine (Intermediate Y, 4.72 g, 18.29 mmol) and 4,6-dichloropyrimidin-2-amine (3 g, 18.29 mmol) in THF (200 mL) and H2O (200 mL), then K3PO4 (7.77 g, 36.59 mmol) and ditert-butyl(cyclopentyl) phosphane; dichloropalladium; iron (0.60 g, 0.91 mmol) were added under N2 atmosphere, the mixture was stirred at 60° C. for 6 h under N2 atmosphere. The residue was diluted with H2O (100 mL) and extracted with ethyl acetate (100 mL×3). The organic phase was washed with brine (50 mL), dried over Na2SO4, filtered and concentrated under reduced pressure to give a residue. The residue was purified by flash silica gel chromatography to give 4-chloro-6-(3-methylimidazo[1,5-a]pyridin-6-yl)pyrimidin-2-amine (2.25 g, 47.4% yield) as a yellow solid.

$^1$H NMR (399 MHz, DMSO-d6) δ=8.89 (s, 1H), 8.27 (br s, 2H), 7.59 (d, J=9.6, 1H), 7.43 (d, J=9.6, 1H), 7.37 (d, J=9.6, 1H), 7.24 (s, 1H), 2.57 (s, 3H)

Biological Assays

Materials and Methods

Isolation of Full Length, Wild-Type MASTL

Full length wild-type human MASTL (MASTLwt) fused to Avi and His tags and 3C sequences (His-Avi-3C-MASTLwt) was expressed in SF9 cells for 3 days at 27° C. whilst shaking. 100 nM Okadaic acid was added to the cells for the last 15 hours and the cell pellets collected and stored at −80° C. Cell pellets were lysed in Buffer A (50 mM HEPES, 0.5 M NaCl, 0.5 mMTCEP, EDTA-free protease inhibitor cocktail (Roche, 11836170001) and TURBO DNase (Thermofisher, AM2239) at pH 7.5) and homogenised (GPPE 50 ml Conical Tissue Homogeniser Glass tube and PTFE pestle with stainless steel shaft, 10 strokes) at 4° C. His-Avi-3C-MASTLwt was initially captured using NeutrAvidin beads and MASTLwt isolated using Rhinovirus 3C-protease. Buffer A was exchanged for Buffer B (50 mM HEPES, 250 mM NaCl, 1 mM TCEP at pH 7.5) using a PD10 desalting column. MASTLwt was concentrated (Sartorius, VS2001) down to 0.1-0.4 mg/ml and stored at −80° C. Verification of MASTLwt was confirmed using WB analysis and MASTLwt activity assay.

MASTL Activity Assay

Wild-type human MASTL (0.5 nM) was incubated in assay buffer (30 mM HEPES, 100 mM NaCl, 0.5 mM EGTA, 10 mM $MgCl_2$, 0.01% Tween-20, 0.5 mM TCEP, pH 7.5) with biotin tagged 40-mer ENSA peptide (10 nM), test compound and ATP (18 μM) for 15 minutes at room temperature. Test compounds were assayed using a 10-point dose range consisting of a 0, DMSO control and 9 sequential doses consisting from 0.0003, 0.001, 0.003, 0.01, 0.03, 0.1, 0.3, 1, 3, 10 and 30 μM. The DMSO concentration was the same (0.1%) in all samples. An equal volume of detection buffer (assay buffer+0.53 nM Ab-K, 2.5 nM SA-D2, 20 mM EDTA and 100 mM KF) was added to stop the reaction to make a final volume of 20 μl. Activity was measured using a plate reader (BMG Labtech Pherastar) by the FRET signal generated between SA-D2 (streptavidin-D2) and Ab-K (anti-phospho-Serine 67 ENSA antibody (rabbit polyclonal, using standard techniques by a commercial supplier) conjugated to Cryptate). HTRF reagents (CisBio) were prepared as per the manufacturer recommendations. The 40-mer biotin-tagged ENSA peptide (synthesised by Peptide Protein Research) used was based around Serine 67 on ENSA (YPSLGQKPGGSDFLMKRLQKGQKYFDSGDYN-MAKAKMKNK).

Cell Culture

HELA cells were maintained (or treated) under standard conditions (37° C., humidity and 5% $CO_2$) in DMEM (ThermoFisher), Glutamine and 10% FCS (Labech).

Proliferation Assay

To assess the impact of compounds on HELA cell proliferation, 100 cells were plated per well of a 96-well plate and treated under standard conditions (above) for 6 days. Concentration of 0.1% DMSO was present in all treatments with a minimum dose of 0 μM and a maximum dose of 10 μM The doses used were 10, 3, 1, 0.3, 0.1 0.03, 0.01, 0.003 and 0 μM. The final volume of the media in each well/all treatments was 200 μl. On day 6 media was removed from all wells and replaced with 50 μl of fresh media, followed by the addition of 40 μl of the CellTitre-Glo reagent (Promega). The plate was allowed to equilibrate for 15-20 minutes at room temperature before measuring on a plate reader (BMG, Pherastar). Values were normalised to DMSO control (i.e. 0 μM) values and plotted using GraphPad PRISM software (or similar) to determine $IC_{50}$ values.

Results

The results of the biological assays are shown below in Table 2:

TABLE 2

| Example no | MASTL pIC50 (M) | HeLa pIC50 (M) |
|---|---|---|
| 1 | 8.26 | 5.97 |
| 2 | 7.54 | |
| 3 | 7.77 | 5.53 |
| 4 | 8.71 | 6.77 |
| 5 | 7.59 | 5.47 |
| 6 | 8.32 | 6.23 |
| 7 | 7.10 | |
| 8 | 8.34 | 6.03 |
| 9 | 6.40 | |
| 10 | 6.56 | |
| 11 | 7.77 | |
| 12 | 8.97 | 6.76 |
| 13 | 7.63 | |
| 14 | 7.83 | |
| 15 | 6.74 | |
| 16 | 7.03 | |
| 17 | 8.41 | |
| 18 | 8.91 | |
| 19 | 6.60 | |
| 20 | 7.78 | |
| 21 | 7.19 | |
| 22 | 8.92 | 6.87 |
| 23 | 8.61 | 6.65 |
| 24 | 8.82 | 6.54 |
| 25 | 8.52 | |
| 26 | 8.05 | |
| 27 | 8.10 | |
| 28 | 8.82 | 6.72 |
| 29 | 8.89 | |
| 30 | 9.03 | 6.81 |
| 31 | 8.82 | |
| 32 | 8.17 | 5.89 |
| 33 | 8.03 | |
| 34 | 8.53 | 6.11 |
| 35 | 8.49 | 6.83 |
| 36 | 9.19 | 7.35 |
| 37 | 8.71 | 6.45 |
| 38 | 7.93 | |

TABLE 2-continued

| Example no | MASTL pIC50 (M) | HeLa pIC50 (M) |
|---|---|---|
| 39 | 8.31 | 6.38 |
| 40 | 8.02 | |
| 41 | 6.85 | |
| 42 | 6.56 | |
| 43 | 8.05 | 5.68 |
| 44 | 6.63 | |
| 45 | 8.21 | |
| 46 | 8.20 | |
| 47 | 7.65 | |
| 48 | 8.62 | 6.62 |
| 49 | 7.36 | |
| 50 | 7.74 | |
| 51 | 8.34 | 5.83 |
| 52 | 7.80 | |
| 53 | 7.76 | |
| 54 | 8.17 | 5.78 |
| 55 | 6.44 | |
| 56 | 7.46 | |
| 57 | 7.25 | |
| 58 | 7.88 | |
| 59 | 7.99 | |
| 60 | 9.10 | 7.46 |
| 61 | 7.96 | |
| 62 | 7.37 | |
| 63 | 7.62 | |
| 64 | 8.33 | |
| 65 | 8.06 | |
| 66 | 7.32 | |
| 67 | 8.11 | |
| 68 | 8.53 | |
| 69 | 7.60 | |
| 70 | 9.15 | 6.94 |
| 71 | 7.79 | |
| 72 | 8.57 | 6.39 |
| 73 | 8.90 | 6.37 |
| 74 | 8.39 | 6.31 |
| 75 | 7.33 | |
| 76 | 7.73 | |
| 77 | 7.73 | |
| 78 | 7.26 | |
| 79 | 7.70 | |
| 80 | 7.84 | |
| 81 | 8.98 | 6.67 |
| 82 | 8.00 | 5.62 |
| 83 | 8.23 | 6.15 |
| 84 | 8.55 | 6.19 |
| 85 | 8.64 | 5.80 |
| 86 | 7.92 | 5.00 |
| 87 | 7.80 | |
| 88 | 8.79 | 5.89 |
| 89 | 8.26 | 6.07 |
| 90 | 8.20 | 5.81 |
| 91 | 6.74 | |
| 92 | 6.29 | |
| 93 | 7.31 | |
| 94 | 6.80 | |
| 95 | 7.19 | |
| 96 | 5.99 | |
| 97 | 8.42 | 6.10 |
| 98 | 7.10 | |
| 99 | 6.84 | |
| 100 | 7.31 | |
| 101 | 8.53 | 6.59 |
| 102 | 8.50 | 6.53 |
| 103 | 7.61 | |
| 104 | 8.71 | 6.66 |
| 105 | 5.85 | |
| 106 | 7.02 | |
| 108 | 8.01 | |
| 113 | 7.01 | |
| 114 | 6.84 | |
| 115 | 8.23 | |
| 116 | 8.70 | |
| 117 | 8.71 | |
| 118 | 8.65 | |
| 119 | 7.45 | |
| 120 | 6.91 | |

TABLE 2-continued

| Example no | MASTL pIC50 (M) | HeLa pIC50 (M) |
|---|---|---|
| 121 | 7.32 | |
| 122 | 8.51 | |
| 123 | 7.39 | |
| 124 | 7.11 | |
| 125 | 7.65 | |
| 126 | 8.12 | |
| 127 | 7.33 | |
| 128 | 9.07 | |
| 129 | 7.12 | |
| 130 | 7.18 | |
| 131 | 7.81 | |
| 132 | 6.83 | |
| 135 | 8.43 | |
| 136 | 8.37 | |
| 137 | 8.53 | |
| 138 | 7.63 | |
| 139 | 7.64 | |
| 140 | 7.46 | |
| 141 | 8.29 | |

The invention claimed is:

1. A compound of the formula (I), or a pharmaceutically acceptable salt thereof:

(I)

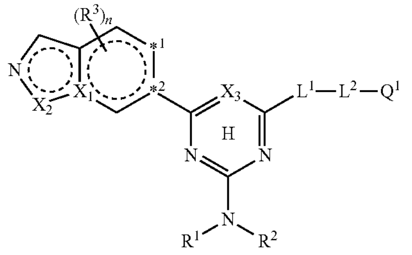

wherein;

wherein the H ring in formula (I) is bonded to the carbon atom $*^1$ or $*^2$;

$R^1$ is selected from: H, $C_{1-6}$ alkyl and $C_{1-6}$ haloalkyl;

$R^2$ is selected from: H, $C_{1-6}$ alkyl, $C_{2-6}$ alkenyl, $C_{2-6}$ alkynyl, $C_{1-6}$ haloalkyl and $Q^3$-$L^3$-, wherein said $C_{1-6}$ alkyl is optionally substituted by one or more $R^6$ substituents;

$R^3$ is each independently selected from: halo, $C_{1-6}$ alkyl and amino;

$X_1$ is N and $X_2$ is $CR^4$, or $X_1$ is C and $X_2$ is $NR^5$;

$X_3$ is N;

$R^4$ is selected from: H, halo, CN, $C_{1-6}$ alkyl and $C_{1-6}$ haloalkyl;

$R^5$ is selected from: H, $C_{1-6}$ alkyl, $Q^4$-$L^4$- wherein said $C_{1-6}$ alkyl is optionally substituted by one or more $R^9$, $L^4$ is a bond or $C_{1-4}$ alkylene;

$Q^4$ is selected from: $C_{3-6}$ cycloalkyl, 3- to 6-membered heterocyclyl, $C_{6-12}$ aryl, and 5 or 6 membered heteroaryl, wherein said $C_{3-6}$ cycloalkyl and 3- to 6-membered heterocyclyl is optionally substituted by one or more $R^{10}$, and said $C_{6-12}$ aryl, and 5- or 6-membered heteroaryl is optionally substituted by one or more $R^{11}$;

$L^1$ is $NR^{12}$ or O;

$R^{12}$ is selected from H, $C_{1-4}$ alkyl, $C_{1-4}$ haloalkyl, $C_{3-6}$ cycloalkyl, $C_{3-6}$ cycloalkyl-$C_{1-4}$ alkyl and $C_{1-4}$ alkyl-$OR^{A5}$, wherein said $C_{3-6}$ cycloalkyl and $C_{3-6}$ cycloalkyl-$C_{1-4}$ alkyl is optionally substituted by one or more substituents selected from: =O, halo, $C_{1-4}$ alkyl and $C_{1-4}$ haloalkyl, $L^2$ is a bond or —$[CR^{13}R^{14}]_p$—, p is an integer selected from 1 or 2;

$R^{13}$ and $R^{14}$ are each independently selected from: H, $C_{1-4}$ alkyl, $C_{1-4}$ haloalkyl, OH, COOH, C(O)$NR^{X1}R^{X2}$, and $C_{3-6}$ cycloalkyl, or an $R^{13}$ and an $R^{14}$ attached to the same carbon atom in $L^2$ together form a $C_{3-6}$ cycloalkyl or 3-6-membered heterocyclyl, wherein said $C_{1-4}$alkyl is optionally substituted by OH, O—$C_{1-4}$ alkyl, 3- to 6-membered heterocyclyl, 5- to 10-membered heteroaryl, or $C_{6-10}$ aryl optionally substituted by halogen or $C_{1-6}$ haloalkyl;

wherein $R^{X1}$ and $R^{X2}$ are independently selected from: H, $C_{1-4}$ alkyl optionally substituted by OH or 3- to 6-membered heterocyclyl, and 5- to 10-membered heteroaryl, or an $R^{X1}$ and an $R^{X2}$ attached to the same nitrogen atom together to form a 3- to 6-membered heterocyclyl;

wherein said $C_{3-6}$ cycloalkyl or 3- to 6-membered heterocyclyl is optionally substituted by one or more substituents selected from: =O, halo, $C_{1-4}$ alkyl and $C_{1-4}$ haloalkyl;

$Q^1$ is selected from: $C_{3-12}$cycloalkyl, $C_{3-12}$ cycloalkenyl, 3- to 7-membered heterocyclyl, $C_{6-10}$ aryl, 5- to 9-membered heteroaryl, COOH, C(O)$NR^{Z1}R^{Z2}$, and C(O)O—$C_{1-6}$alkyl;

wherein each $R^{Z1}$ and $R^{Z2}$ is each independently selected from; H, $C_{1-6}$ alkyl optionally substituted by OH, $C_{3-6}$ cycloalkyl, $C_{6-10}$aryl, or 5- to 10-membered heteroaryl; or an $R^{Z1}$ and an $R^{Z2}$ attached to the same nitrogen atom together to form a 3-6-membered heterocyclyl;

wherein said $C_{3-12}$ cycloalkyl, $C_{3-12}$ cycloalkenyl and 3- to 7-membered heterocyclyl is optionally substituted by one or more $R^{15}$, wherein said $C_{6-10}$ aryl and 5- to 9-membered heteroaryl is optionally substituted by one or more $R^{16}$;

each $R^{15}$ is independently selected from: halo, =O, —CN, —$NO_2$, $C_{1-6}$ alkyl, $C_{2-6}$ alkenyl, $C_{2-6}$ alkynyl, $C_{1-6}$ haloalkyl, —$OR^{17}$, —$S(O)_{x1}R^{17}$, —$NR^{17}R^{B1}$, —C(O)$R^{17}$, —OC(O)$R^{17}$, —C(O)$OR^{17}$, —$NR^{B1}$C(O)$R^{17}$, —$NR^{B1}$C(O)$OR^{17}$, —C(O)$NR^{17}R^{B1}$, —OC(O)$NR^{17}R^{B1}$, —$NR^{B1}SO_2R^{17}$, —$SO_2NR^{17}R^{B1}$ and —$NR^{A1}$C(O)$NR^{17}R^{B1}$, wherein said $C_{1-6}$ alkyl, $C_{2-6}$ alkenyl and $C_{2-6}$ alkynyl is optionally substituted by 1 or more $R^{18}$, and $R^{17}$ is selected from: H, $C_{1-6}$ alkyl and $C_{1-6}$ haloalkyl, wherein said $C_{1-6}$ alkyl is optionally substituted by one or more $R^{19}$;

each $R^{16}$ is independently selected from: halo, —CN, —$NO_2$, $C_{1-6}$ alkyl, $C_{2-6}$ alkenyl, $C_{2-6}$ alkynyl, $C_{1-6}$ haloalkyl, —$OR^{20}$, —$S(O)_{x2}R^{20}$, —$NR^{20}R^{B2}$, —C(O)$R^{20}$, —OC(O)$R^{20}$, —C(O)$OR^{20}$, —$NR^{B2}$C(O)$R^{20}$, —$NR^{B2}$C(O)$OR^{20}$, —C(O)$NR^{20}R^{B2}$, —OC(O)$NR^{20}R^{B2}$, —$NR^{B2}SO_2R^{20}$, —$SO_2NR^{20}R^{B2}$ and —$NR^{A2}$C(O)$NR^{20}R^{B2}$, wherein said $C_{1-6}$ alkyl, $C_{2-6}$ alkenyl and $C_{2-6}$ alkynyl is optionally substituted by 1 or more $R^{21}$, and wherein $R^{20}$ is selected from: H, $C_{1-6}$ alkyl and $C_{1-6}$ haloalkyl, wherein said $C_{1-6}$ alkyl is optionally substituted by one or more $R^{22}$;

$R^6$, $R^9$, $R^{10}$, $R^{18}$, $R^{19}$, $R^{21}$ and $R^{22}$ are each independently selected from: halo, =O, —CN, —$NO_2$, $C_{1-4}$ alkyl, $C_{1-4}$ haloalkyl, —$OR^{A3}$, —$S(O)_{x3}R^{A4}$, —$NR^{A3}R^{B3}$, —C(O)$R^{A3}$, —OC(O)$R^{A3}$, —C(O)$OR^{A3}$, —$NR^{B3}$C(O)$R^{A3}$, —$NR^{B3}$C(O)$OR^{A3}$, —C(O)$NR^{A3}R^{B3}$, —$NR^{B4}SO_2R^{A3}$ and —$SO_2NR^{A3}R^{B3}$;

$R^{11}$ are each independently selected from: halo, =O, —CN, —$NO_2$, $C_{1-4}$ alkyl, $C_{1-4}$ haloalkyl, —$OR^{A4}$, —$S(O)_{x4}R^{A4}$, —$NR^{A4}R^{B4}$, —C(O)$R^{A4}$, —OC(O)$R^{A4}$, —C(O)$OR^{A4}$, —$NR^{B4}$C(O)$R^{A4}$, —$NR^{B4}$C(O)$OR^{A4}$, —C(O)$NR^{A4}R^{B4}$, —$NR^{B4}SO_2R^{A4}$ and —$SO_2NR^{A4}R^{B4}$;

$R^{1A}$, $R^{1B}$, $R^{A2}$, $R^{B2}$, $R^{A3}$, $R^{B3}$, $R^{A4}$, $R^{B4}$ and $R^{A5}$ are each independently selected from: H, $C_{1-4}$ alkyl and $C_{1-4}$ haloalkyl, or any —$NR^{A3}R^{B3}$, —$NR^{A4}R^{B4}$, —$NR^{17}R^{B1}$ or —$NR^{20}R^{B2}$, within a substituent may form a 4- to 6-membered heterocyclyl, wherein said 4- to 6-membered heterocyclyl is optionally substituted by one or more substituents selected from: halo, =O, $C_{1-4}$ alkyl and $C_{1-4}$ haloalkyl;

n is an integer from 0 to 4; and x1, x2, x3 and x4 are each independently selected from: 0, 1 or 2.

2. The compound of claim 1, wherein the compound is selected from a compound of the formula (IV) or (IX):

(IV)

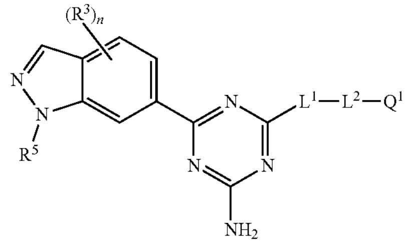

(IX)

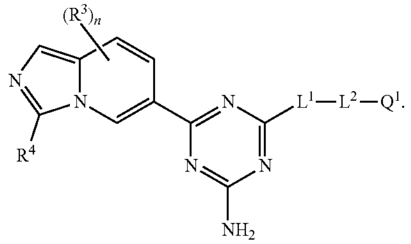

3. The compound of claim 1, wherein each $R^3$ is halo, optionally wherein each $R^3$ is independently selected from fluoro and chloro.

4. The compound of claim 1, wherein $R^4$ or $R^5$ is H or $C_{1-6}$ alkyl, optionally methyl.

5. The compound of claim 1, wherein $L^1$ is $NR^{12}$ and $R^{12}$ is selected from $C_{3-6}$ cycloalkyl, $C_{1-4}$ alkyl and —$C_{1-4}$ alkyl-$OR^{A5}$.

6. The compound of claim 1, wherein $L^1$ is NH.

7. The compound of claim 1, wherein $L^2$ is —$[CR^{13}R^{14}]_p$, wherein p is an integer from 1 to 2, and $R^{13}$ and $R^{14}$ are each independently selected from: H and $C_{1-4}$ alkyl, or an $R^{13}$ and an $R^{14}$ attached to the same carbon atom in $L^2$ together form a $C_{3-6}$ cycloalkyl.

8. The compound of claim 1, wherein $L^2$ is a bond.

9. The compound of claim 1, wherein $Q^1$ is a 5- or 6-membered heteroaryl group comprising one or two heteroatoms independently selected from O, N and S, optionally wherein the heteroaryl group is substituted by one or more $R^{16}$.

10. The compound of claim 1, wherein $Q^1$ is

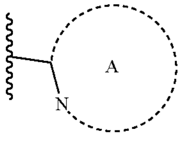

wherein ring A is a 5- or 6-membered heteroaryl comprising a ring nitrogen in the ortho-position relative to the bond to $-L^1-L^2-$ and optionally 1 or 2 further heteroatoms independently selected from O, S and N, optionally wherein the heteroaryl is substituted by one or more $R^{16}$.

11. The compound of claim 1, wherein $Q^1$ is a $C_{6-10}$ aryl, optionally substituted by one or more $R^{16}$.

12. The compound of claim 1, wherein $Q^1$ is a 8-, 9- or 10-membered bicyclic heteroaryl group comprising 1, 2 or 3 heteroatoms independently selected from O, N and S, optionally wherein the bicyclic heteroaryl group is substituted by one or more $R^{16}$.

13. The compound of claim 1, wherein $Q^1$ has a structure selected from:

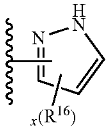 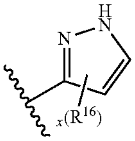 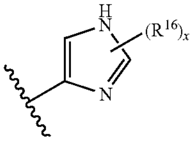

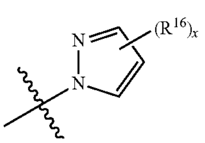 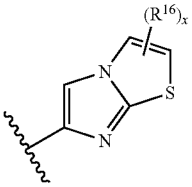

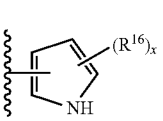 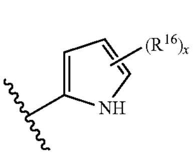 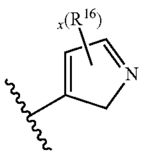

-continued

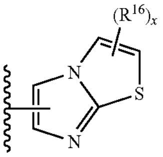 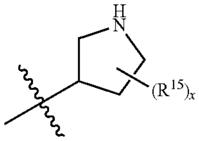

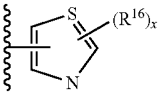 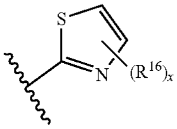 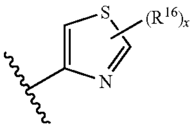

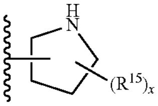 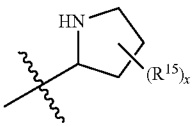 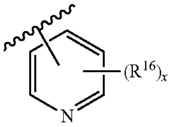

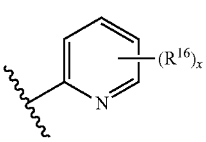 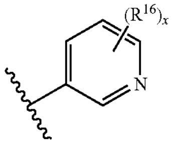

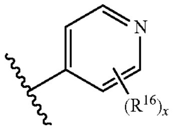 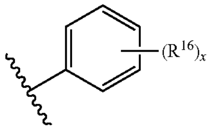

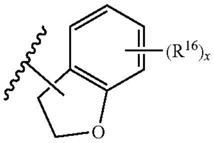 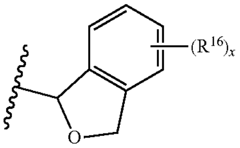

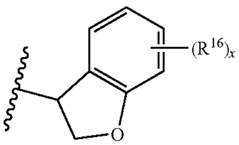 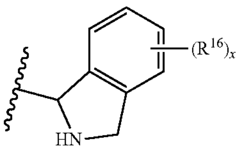

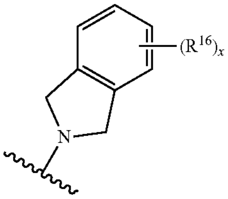 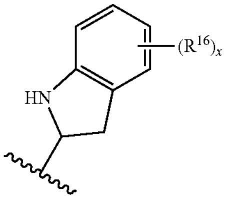

wherein x is 0, 1, 2 or 3.

14. The compound of claim 1, wherein $Q^1$ is substituted by one, two or three $R^{15}$ or $R^{16}$, wherein $R^{15}$ or $R^{16}$ is independently selected from halo, $C_{1-6}$ alkyl, $C_{1-6}$ haloalkyl.

15. A compound or a pharmaceutically acceptable salt thereof, wherein the compound is any one selected from the group consisting of Compound Nos. 1 to 107, 109 to 148, 150 to 152, 159 to 198, 206 to 208, 212 to 223, and 225 to 229 below:

| No. | Structure |
|---|---|
| 1 | 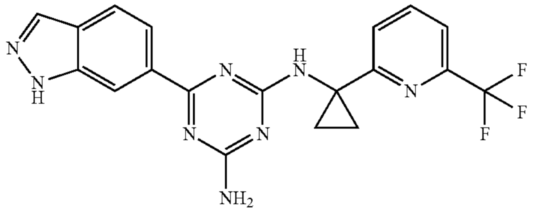 [SMILES: Nc1nc(NC2(c3cccc(C(F)(F)F)n3)CC2)nc(-c2ccc3cn[nH]c3c2)n1] |
| 2 | 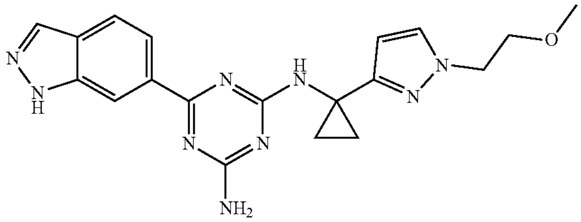 |
| 3 | 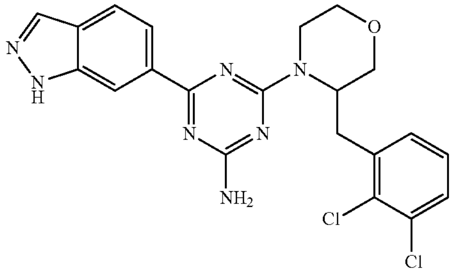 [SMILES: Nc1nc(-c2ccc3cn[nH]c3c2)nc(N2CCOCC2Cc2cccc(Cl)c2Cl)n1] |
| 4 | 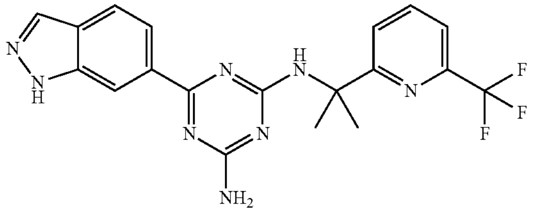 [SMILES: CC(C)(Nc1nc(N)nc(-c2ccc3cn[nH]c3c2)n1)c1cccc(C(F)(F)F)n1] |
| 5 | 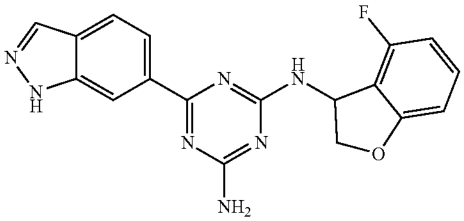 [SMILES: Nc1nc(NC2COc3cccc(F)c32)nc(-c2ccc3cn[nH]c3c2)n1] |
| 6 | 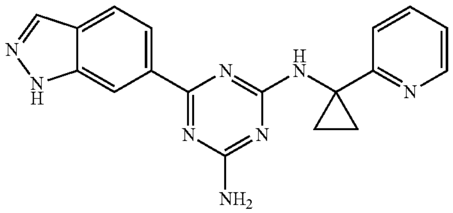 [SMILES: Nc1nc(NC2(c3ccccn3)CC2)nc(-c2ccc3cn[nH]c3c2)n1] |
| 7 | 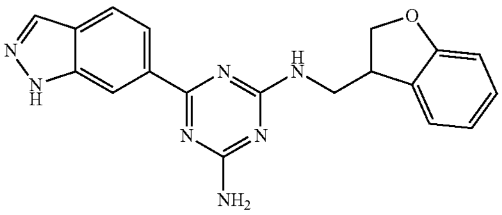 [SMILES: Nc1nc(NCC2COc3ccccc32)nc(-c2ccc3cn[nH]c3c2)n1] |

-continued
| No. | Structure |
| --- | --- |
| 8 | 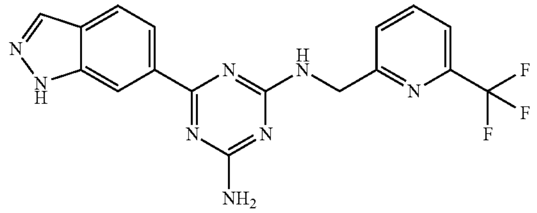 [SMILES: Nc1nc(NCc2cccc(C(F)(F)F)n2)nc(-c2ccc3cn[nH]c3c2)n1] |
| 9 | 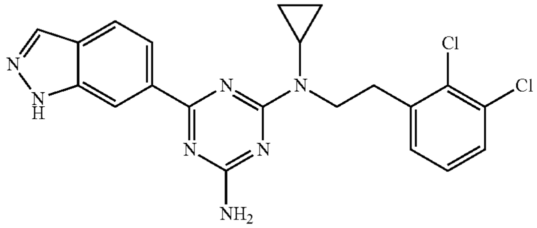 |
| 10 | 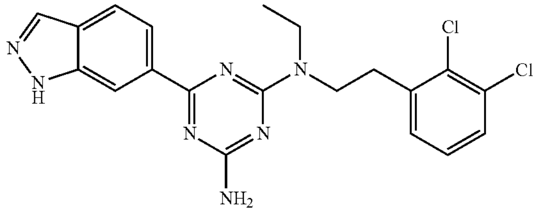 |
| 11 | 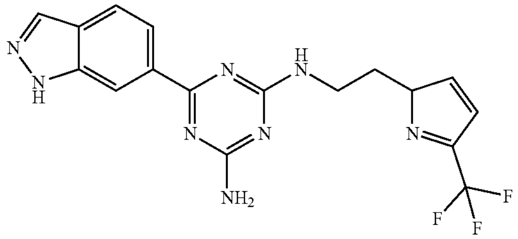 [SMILES: Nc1nc(NCCC2C=CC(C(F)(F)F)=N2)nc(-c2ccc3cn[nH]c3c2)n1] |
| 12 | 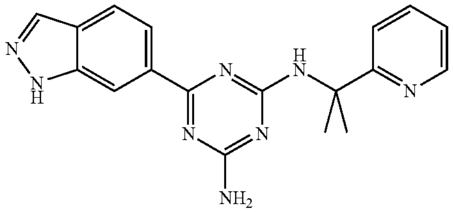 |
| 13 | 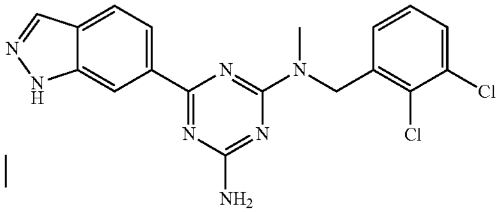 |

-continued
| No. | Structure |
| --- | --- |
| 14 | 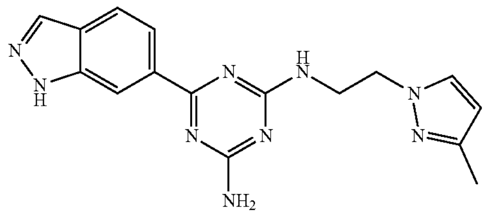 |
| 15 | 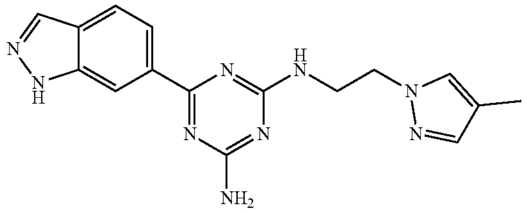 [SMILES: Cc1cnn(CCNc2nc(N)nc(-c3ccc4cn[nH]c4c3)n2)c1] |
| 16 | 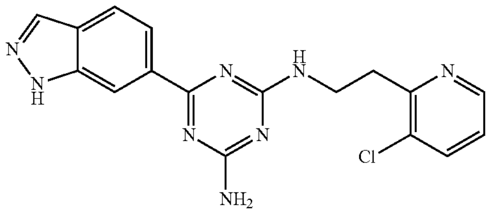 |
| 17 | 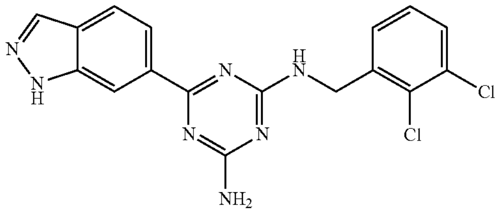 |
| 18 | 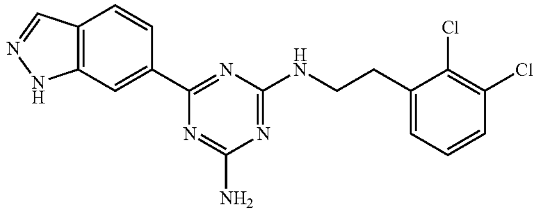 [SMILES: Nc1nc(NCCc2cccc(Cl)c2Cl)nc(-c2ccc3cn[nH]c3c2)n1] |
| 19 | 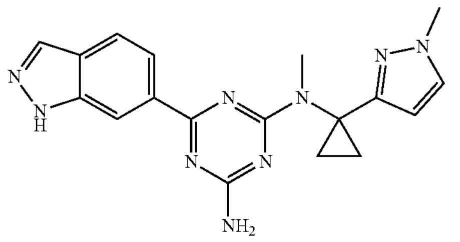 |
| 20 | 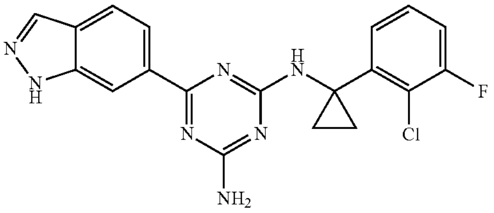 [SMILES: Nc1nc(NC2(c3cccc(F)c3Cl)CC2)nc(-c2ccc3cn[nH]c3c2)n1] |

-continued
| No. | Structure |
|---|---|
| 21 | 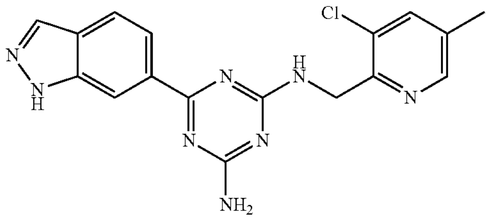 [SMILES: Cc1cnc(CNc2nc(N)nc(-c3ccc4cn[nH]c4c3)n2)c(Cl)c1] |
| 22 | 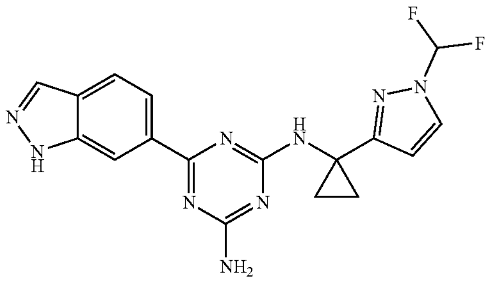 |
| 23 | 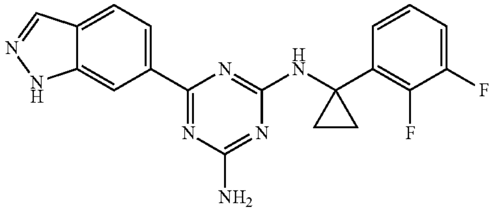 |
| 24 | 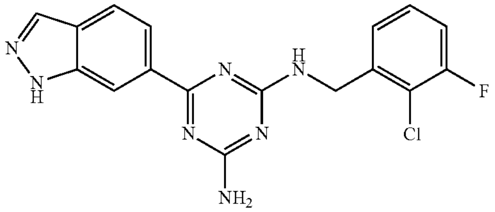 |
| 25 | 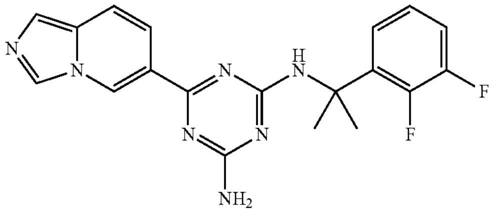 |
| 26 | 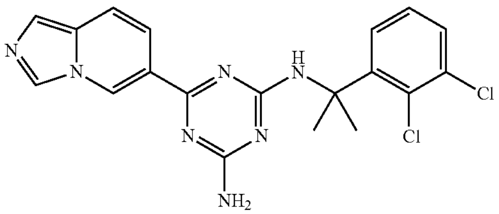 [SMILES: CC(C)(Nc1nc(N)nc(-c2ccc3cncn3c2)n1)c1cccc(Cl)c1Cl] |

-continued
| No. | Structure |
|---|---|
| 27 | 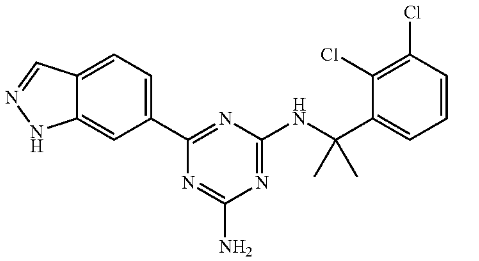 [SMILES: CC(C)(Nc1nc(N)nc(-c2ccc3cn[nH]c3c2)n1)c1cccc(Cl)c1Cl] |
| 28 | 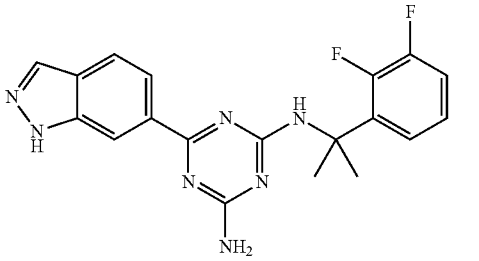 |
| 29 | 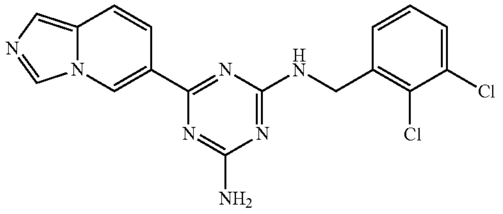 |
| 30 | 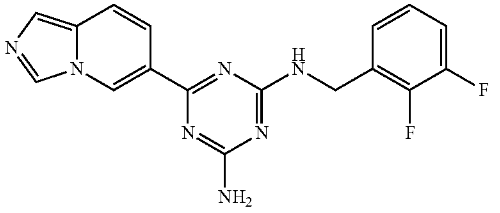 |
| 31 | 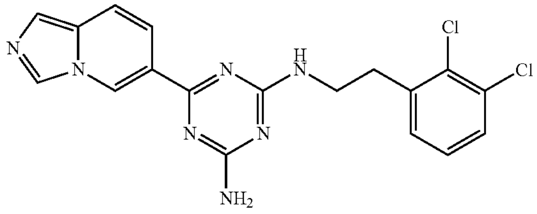 |
| 32 | 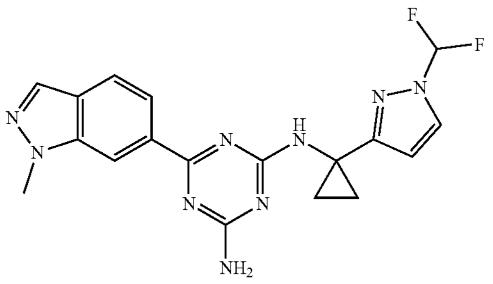 [SMILES: Cn1ncc2ccc(-c3nc(N)nc(NC4(c5ccn(C(F)F)n5)CC4)n3)cc21] |

-continued
| No. | Structure |
|---|---|
| 33 | 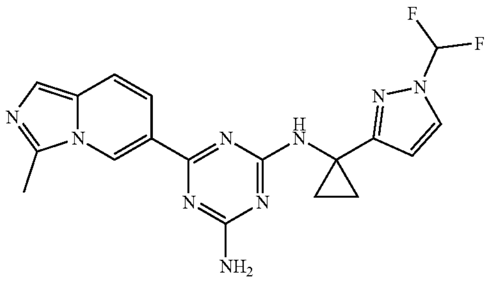 |
| 34 | 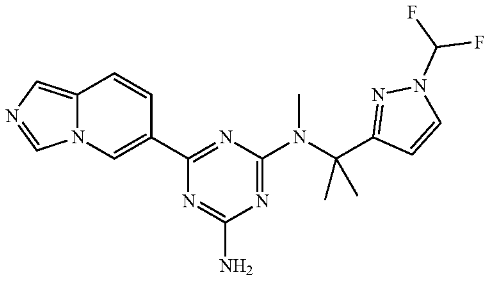 [SMILES: CN(c1nc(N)nc(-c2ccc3cncn3c2)n1)C(C)(C)c1ccn(C(F)F)n1] |
| 35 | 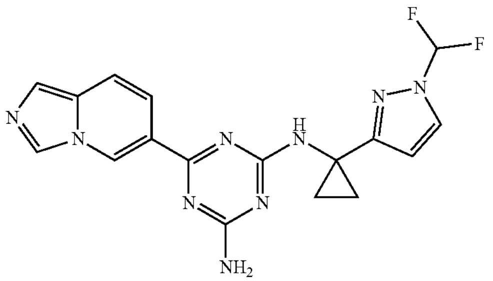 |
| 36 | 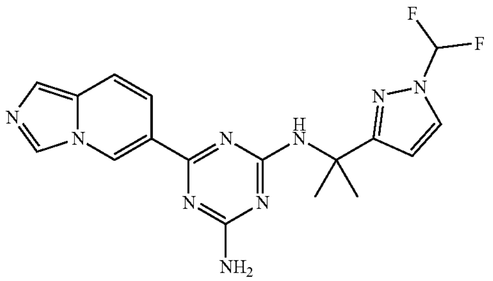 [SMILES: CC(C)(Nc1nc(N)nc(-c2ccc3cncn3c2)n1)c1ccn(C(F)F)n1] |
| 37 | 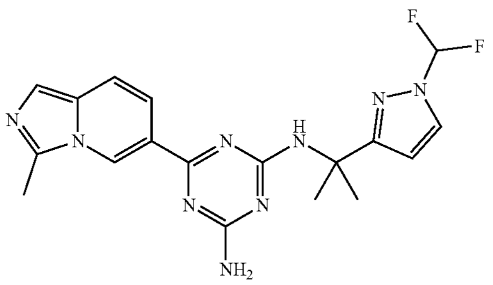 [SMILES: Cc1ncc2ccc(-c3nc(N)nc(NC(C)(C)c4ccn(C(F)F)n4)n3)cn12] |

-continued
| No. | Structure |
|---|---|
| 38 | 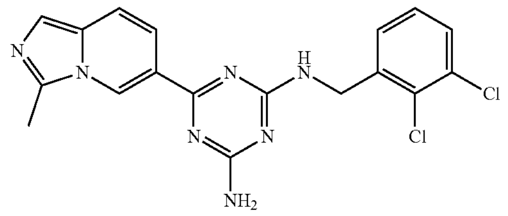 |
| 39 | 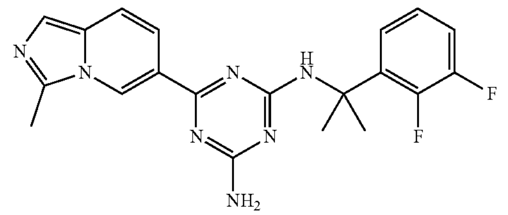 |
| 40 | 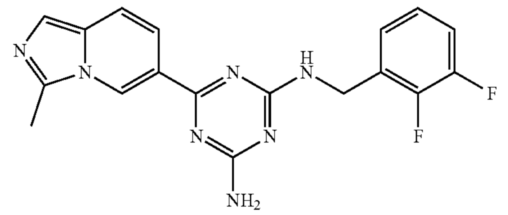 |
| 41 | 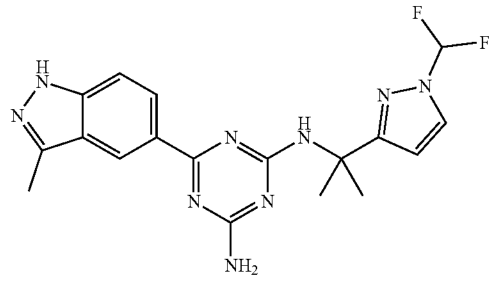 [SMILES: Cc1n[nH]c2ccc(-c3nc(N)nc(NC(C)(C)c4ccn(C(F)F)n4)n3)cc12] |
| 42 | 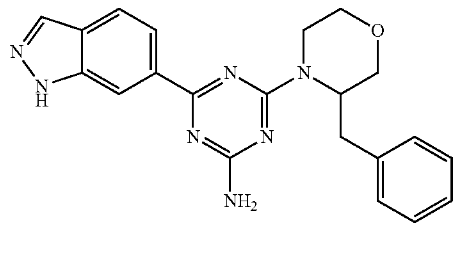 [SMILES: Nc1nc(-c2ccc3cn[nH]c3c2)nc(N2CCOCC2Cc2ccccc2)n1] |
| 43 | 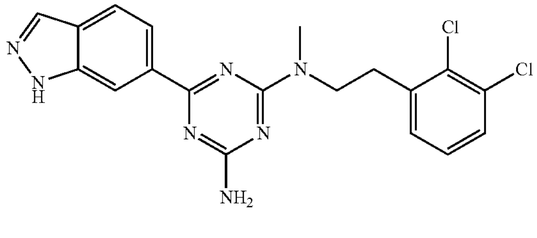 [SMILES: CN(CCc1cccc(Cl)c1Cl)c1nc(N)nc(-c2ccc3cn[nH]c3c2)n1] |

-continued
| No. | Structure |
|---|---|
| 44 | 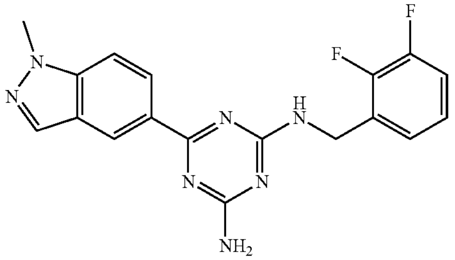 [SMILES: Cn1ncc2cc(-c3nc(N)nc(NCc4cccc(F)c4F)n3)ccc21] |
| 45 | 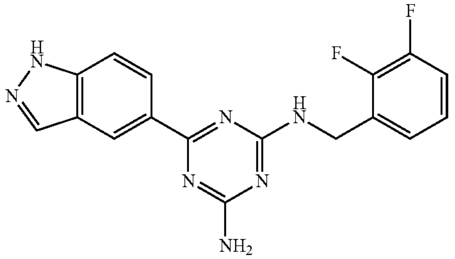 [SMILES: Nc1nc(NCc2cccc(F)c2F)nc(-c2ccc3[nH]ncc3c2)n1] |
| 46 | 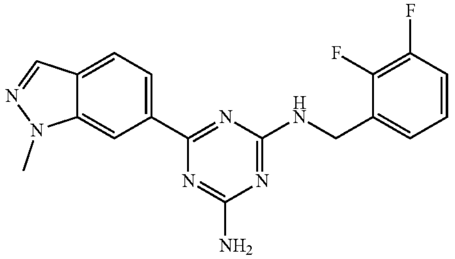 [SMILES: Cn1ncc2ccc(-c3nc(N)nc(NCc4cccc(F)c4F)n3)cc21] |
| 47 | 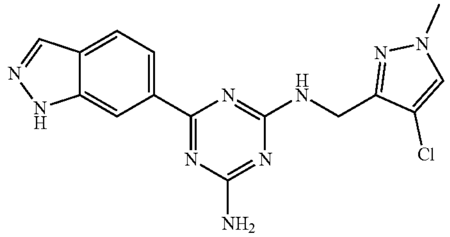 [SMILES: Cn1cc(Cl)c(CNc2nc(N)nc(-c3ccc4cn[nH]c4c3)n2)n1] |
| 48 | 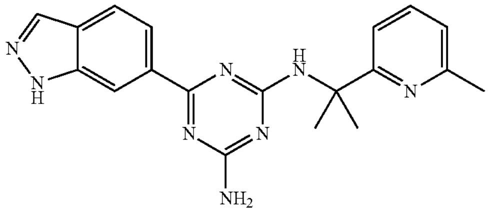 [SMILES: Cc1cccc(C(C)(C)Nc2nc(N)nc(-c3ccc4cn[nH]c4c3)n2)n1] |
| 49 | 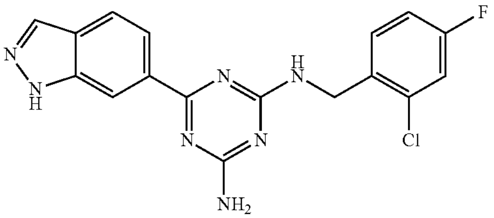 [SMILES: Nc1nc(NCc2ccc(F)cc2Cl)nc(-c2ccc3cn[nH]c3c2)n1] |

-continued
| No. | Structure |
|---|---|
| 50 | 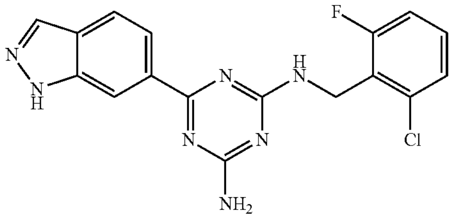 [SMILES: Nc1nc(NCc2c(F)cccc2Cl)nc(-c2ccc3cn[nH]c3c2)n1] |
| 51 | 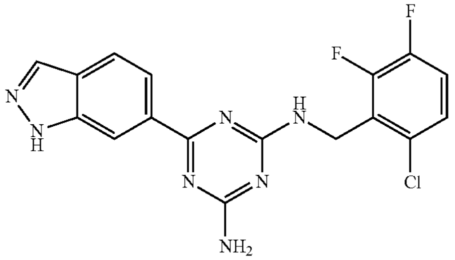 [SMILES: Nc1nc(NCc2c(Cl)ccc(F)c2F)nc(-c2ccc3cn[nH]c3c2)n1] |
| 52 | 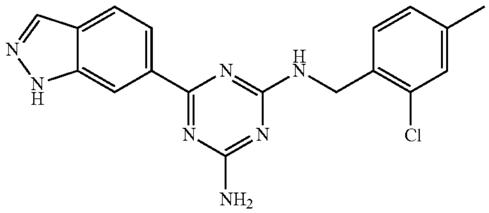 [SMILES: Cc1ccc(CNc2nc(N)nc(-c3ccc4cn[nH]c4c3)n2)c(Cl)c1] |
| 53 | 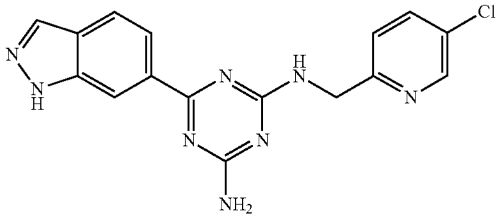 [SMILES: Nc1nc(NCc2ccc(Cl)cn2)nc(-c2ccc3cn[nH]c3c2)n1] |
| 54 | 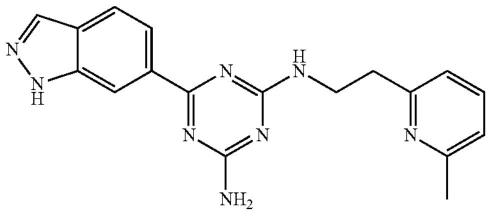 |
| 55 | 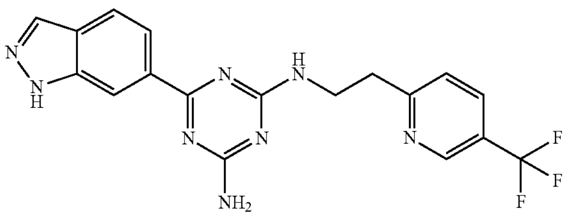 [SMILES: Nc1nc(NCCc2ccc(C(F)(F)F)cn2)nc(-c2ccc3cn[nH]c3c2)n1] |

-continued
| No. | Structure |
|---|---|
| 56 | 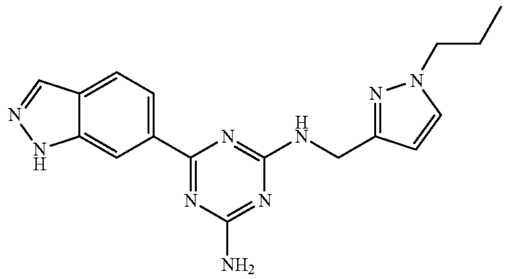 [SMILES: CCCn1ccc(CNc2nc(N)nc(-c3ccc4cn[nH]c4c3)n2)n1] |
| 57 | 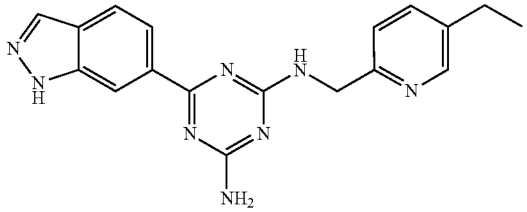 [SMILES: CCc1ccc(CNc2nc(N)nc(-c3ccc4cn[nH]c4c3)n2)nc1] |
| 58 | 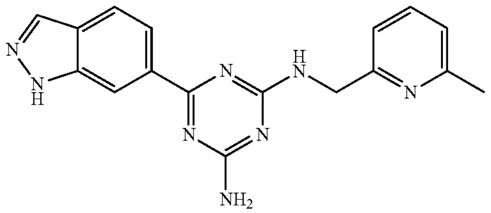 |
| 59 | 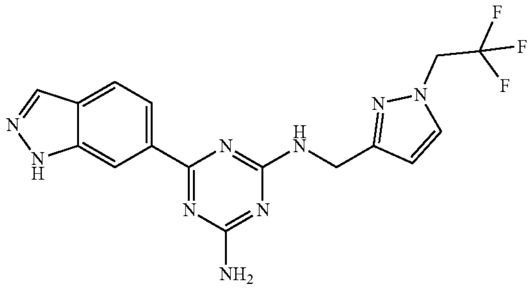 [SMILES: Nc1nc(NCc2ccn(CC(F)(F)F)n2)nc(-c2ccc3cn[nH]c3c2)n1] |
| 60 | 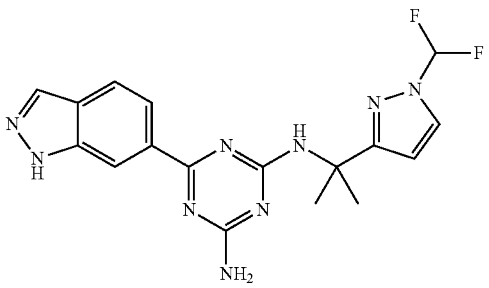 [SMILES: CC(C)(Nc1nc(N)nc(-c2ccc3cn[nH]c3c2)n1)c1ccn(C(F)F)n1] |
| 61 | 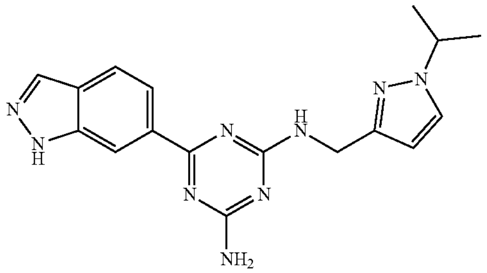 [SMILES: CC(C)n1ccc(CNc2nc(N)nc(-c3ccc4cn[nH]c4c3)n2)n1] |

-continued
| No. | Structure |
| --- | --- |
| 62 | 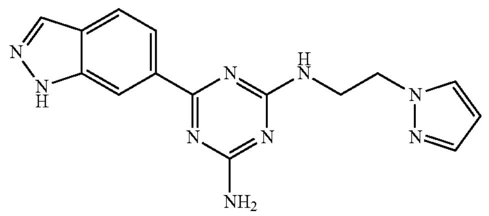 [SMILES: Nc1nc(NCCn2cccn2)nc(-c2ccc3cn[nH]c3c2)n1] |
| 63 | 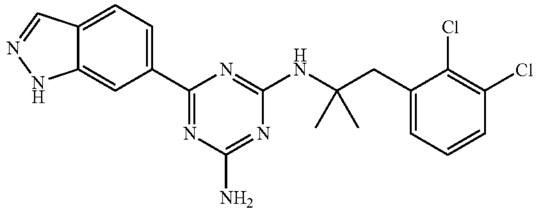 [SMILES: CC(C)(Cc1cccc(Cl)c1Cl)Nc1nc(N)nc(-c2ccc3cn[nH]c3c2)n1] |
| 64 | 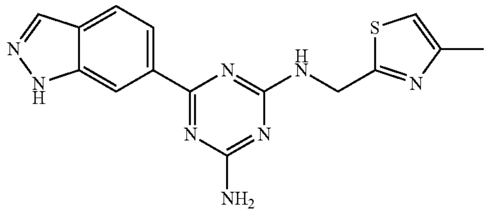 [SMILES: Cc1csc(CNc2nc(N)nc(-c3ccc4cn[nH]c4c3)n2)n1] |
| 65 | 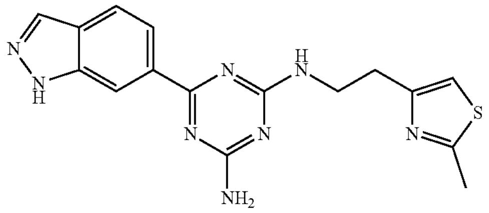 [SMILES: Cc1nc(CCNc2nc(N)nc(-c3ccc4cn[nH]c4c3)n2)cs1] |
| 66 | 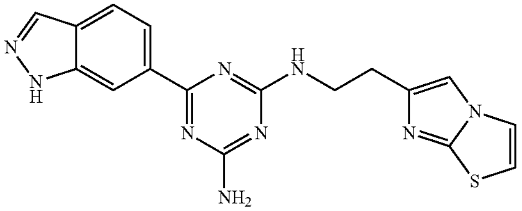 [SMILES: Nc1nc(NCCc2cn3ccsc3n2)nc(-c2ccc3cn[nH]c3c2)n1] |
| 67 | 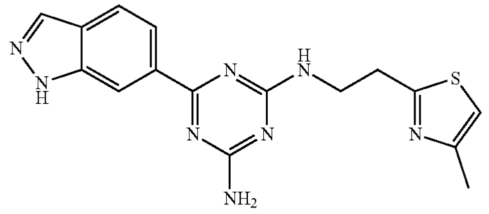 [SMILES: Cc1csc(CCNc2nc(N)nc(-c3ccc4cn[nH]c4c3)n2)n1] |

-continued
| No. | Structure |
|---|---|
| 68 | 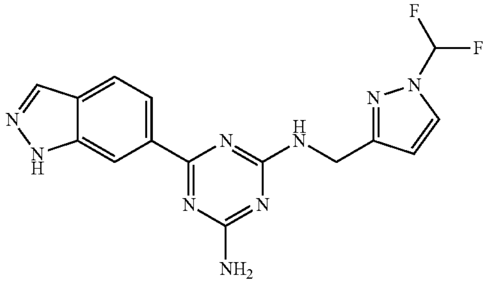 [SMILES: Nc1nc(NCc2ccn(C(F)F)n2)nc(-c2ccc3cn[nH]c3c2)n1] |
| 69 | 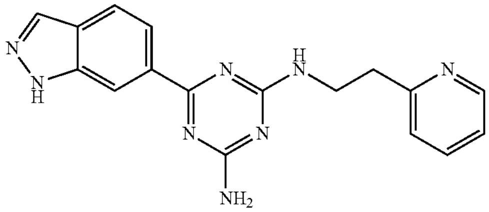 [SMILES: Nc1nc(NCCc2ccccn2)nc(-c2ccc3cn[nH]c3c2)n1] |
| 70 | 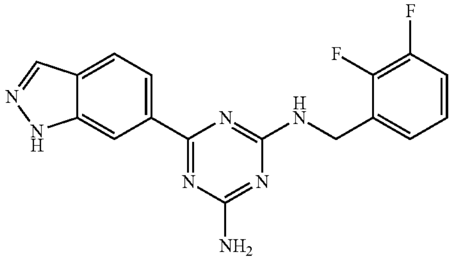 [SMILES: Nc1nc(NCc2cccc(F)c2F)nc(-c2ccc3cn[nH]c3c2)n1] |
| 71 | 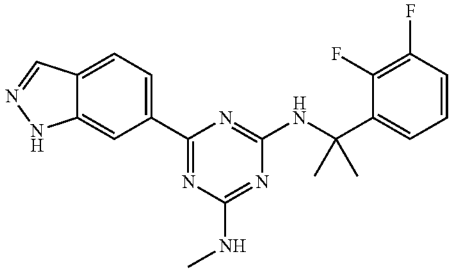 [SMILES: CNc1nc(NC(C)(C)c2cccc(F)c2F)nc(-c2ccc3cn[nH]c3c2)n1] |
| 72 | 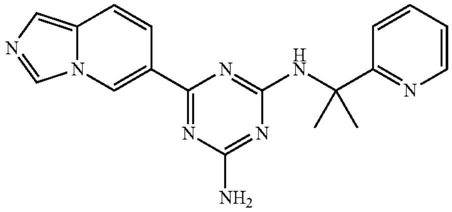 [SMILES: CC(C)(Nc1nc(N)nc(-c2ccc3cncn3c2)n1)c1ccccn1] |
| 73 | 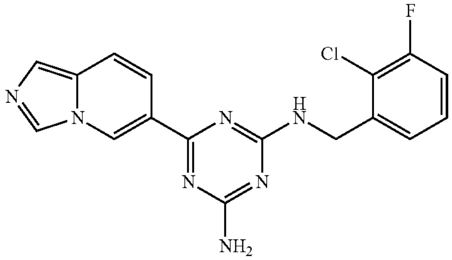 [SMILES: Nc1nc(NCc2cccc(F)c2Cl)nc(-c2ccc3cncn3c2)n1] |

-continued
| No. | Structure |
| --- | --- |
| 74 | 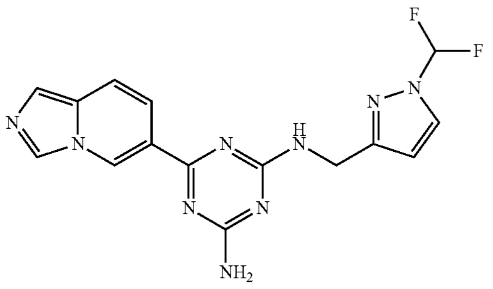 [SMILES: Nc1nc(NCc2ccn(C(F)F)n2)nc(-c2ccc3cncn3c2)n1] |
| 75 | 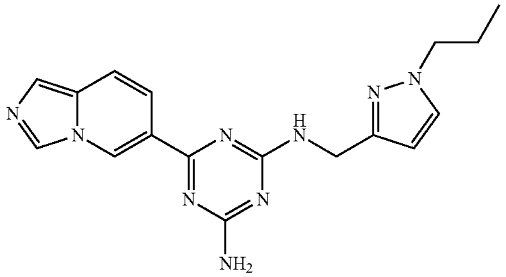 [SMILES: CCCn1ccc(CNc2nc(N)nc(-c3ccc4cncn4c3)n2)n1] |
| 76 | 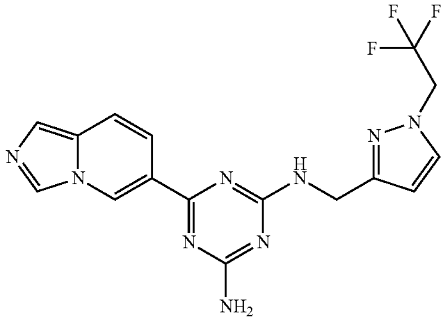 [SMILES: Nc1nc(NCc2ccn(CC(F)(F)F)n2)nc(-c2ccc3cncn3c2)n1] |
| 77 | 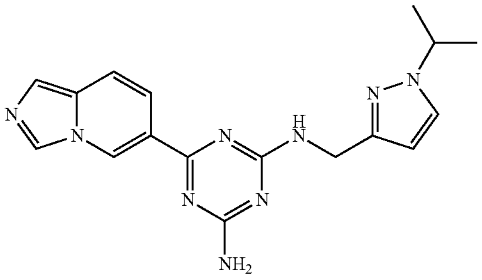 [SMILES: CC(C)n1ccc(CNc2nc(N)nc(-c3ccc4cncn4c3)n2)n1] |
| 78 | 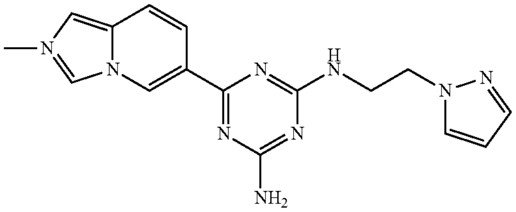 |

-continued
| No. | Structure |
| --- | --- |
| 79 | 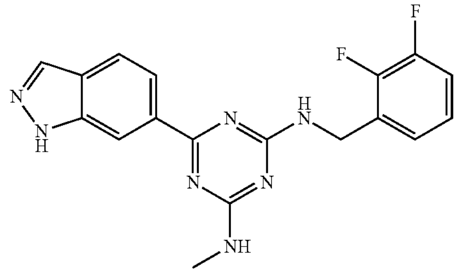 [SMILES: CNc1nc(NCc2cccc(F)c2F)nc(-c2ccc3cn[nH]c3c2)n1] |
| 80 | 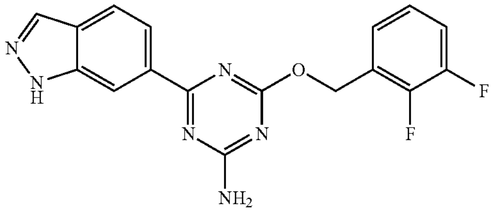 [SMILES: Nc1nc(OCc2cccc(F)c2F)nc(-c2ccc3cn[nH]c3c2)n1] |
| 81 | 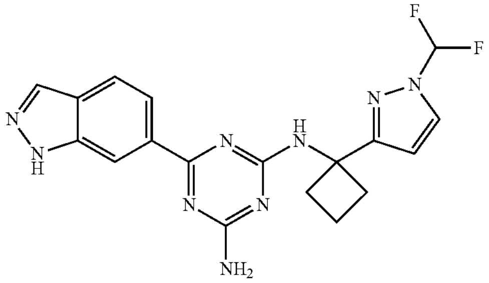 [SMILES: Nc1nc(NC2(c3ccn(C(F)F)n3)CCC2)nc(-c2ccc3cn[nH]c3c2)n1] |
| 82 | 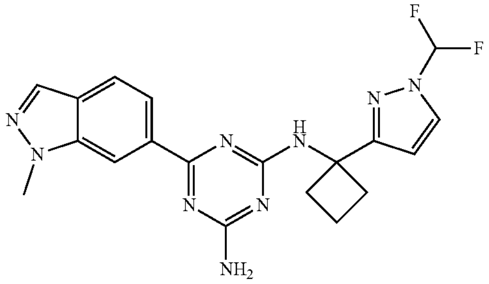 [SMILES: Cn1ncc2ccc(-c3nc(N)nc(NC4(c5ccn(C(F)F)n5)CCC4)n3)cc21] |
| 83 | 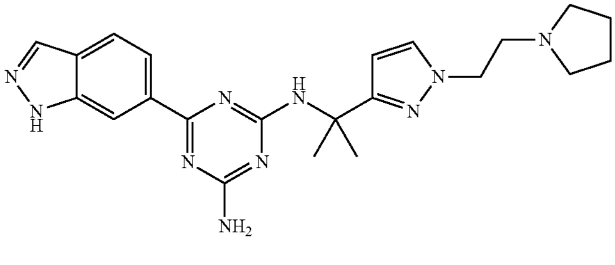 [SMILES: CC(C)(Nc1nc(N)nc(-c2ccc3cn[nH]c3c2)n1)c1ccn(CCN2CCCC2)n1] |

-continued
| No. | Structure |
| --- | --- |
| 84 | 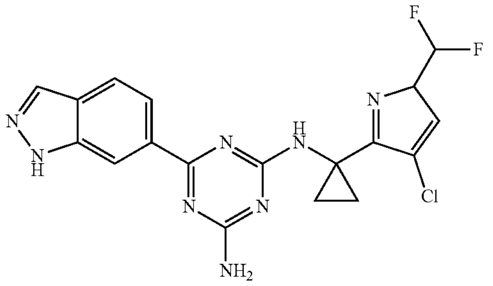 [SMILES: Nc1nc(NC2(C3=NC(C(F)F)C=C3Cl)CC2)nc(-c2ccc3cn[nH]c3c2)n1] |
| 85 | 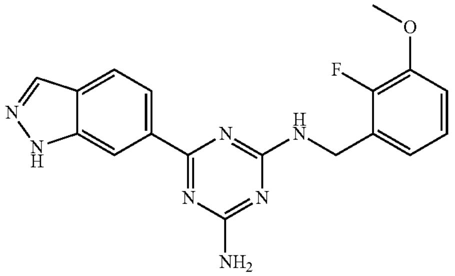 [SMILES: COc1cccc(CNc2nc(N)nc(-c3ccc4cn[nH]c4c3)n2)c1F] |
| 86 | 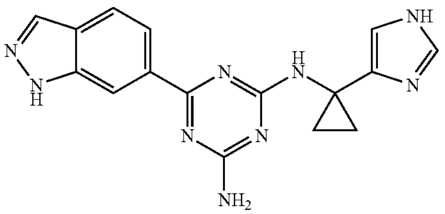 [SMILES: Nc1nc(NC2(c3c[nH]cn3)CC2)nc(-c2ccc3cn[nH]c3c2)n1] |
| 87 | 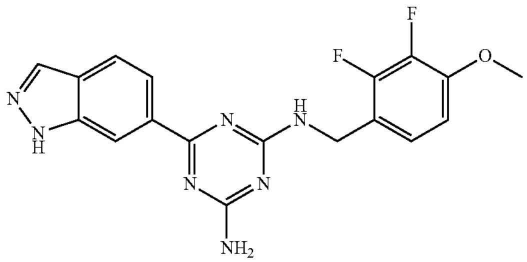 [SMILES: COc1ccc(CNc2nc(N)nc(-c3ccc4cn[nH]c4c3)n2)c(F)c1F] |
| 88 | 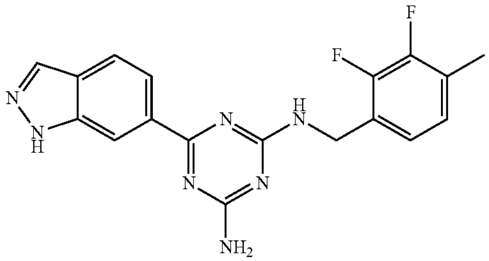 [SMILES: Cc1ccc(CNc2nc(N)nc(-c3ccc4cn[nH]c4c3)n2)c(F)c1F] |
| 89 | 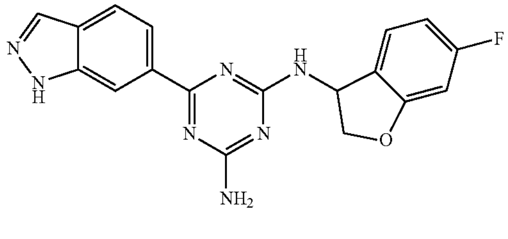 [SMILES: Nc1nc(NC2COc3cc(F)ccc32)nc(-c2ccc3cn[nH]c3c2)n1] |

-continued
| No. | Structure |
|---|---|
| 90 | 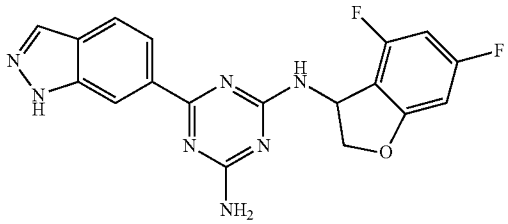 [SMILES: Nc1nc(NC2COc3cc(F)cc(F)c32)nc(-c2ccc3cn[nH]c3c2)n1] |
| 91 | 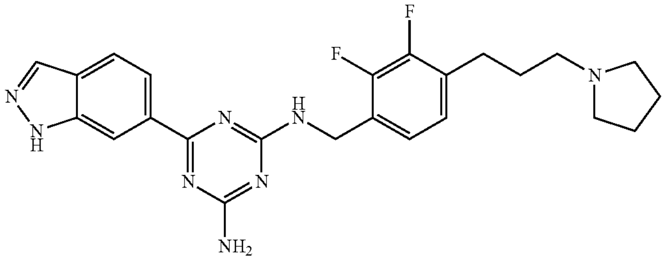 [SMILES: Nc1nc(NCc2ccc(CCCN3CCCC3)c(F)c2F)nc(-c2ccc3cn[nH]c3c2)n1] |
| 92 | 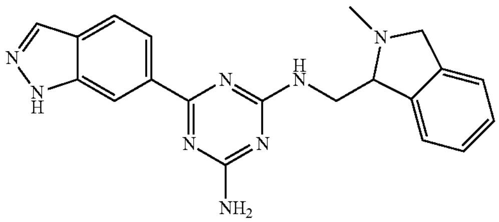 [SMILES: CN1Cc2ccccc2C1CNc1nc(N)nc(-c2ccc3cn[nH]c3c2)n1] |
| 93 | 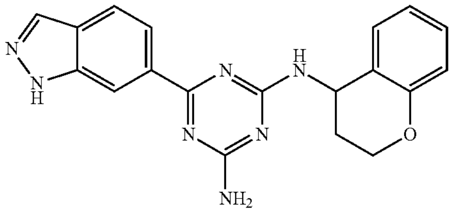 [SMILES: Nc1nc(NC2CCOc3ccccc32)nc(-c2ccc3cn[nH]c3c2)n1] |
| 94 | 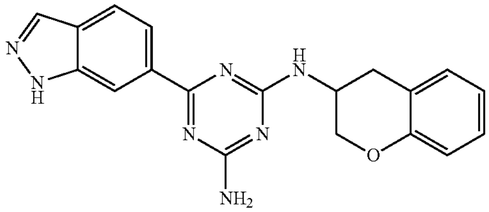 |
| 95 | 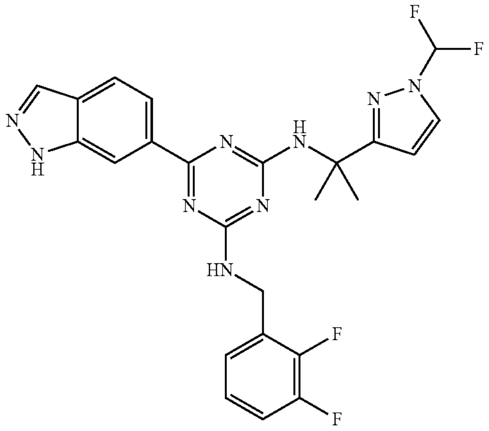 [SMILES: CC(C)(Nc1nc(NCc2cccc(F)c2F)nc(-c2ccc3cn[nH]c3c2)n1)c1ccn(C(F)F)n1] |

-continued
| No. | Structure |
| --- | --- |
| 96 | 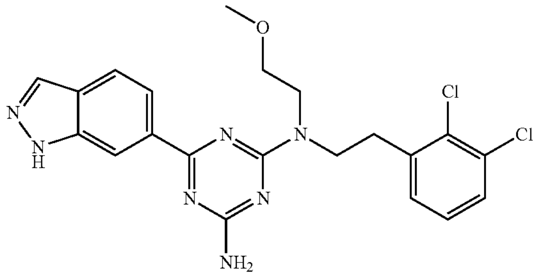 [SMILES: COCCN(CCc1cccc(Cl)c1Cl)c1nc(N)nc(-c2ccc3cn[nH]c3c2)n1] |
| 97 | 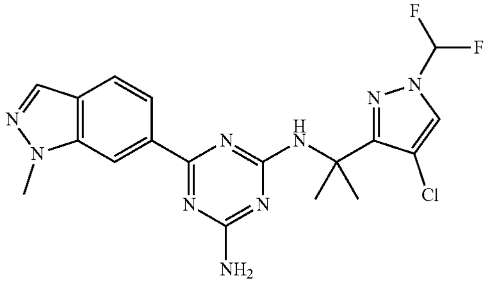 [SMILES: Cn1ncc2ccc(-c3nc(N)nc(NC(C)(C)c4nn(C(F)F)cc4Cl)n3)cc21] |
| 98 | 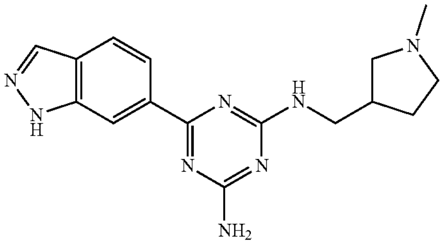 [SMILES: CN1CCC(CNc2nc(N)nc(-c3ccc4cn[nH]c4c3)n2)C1] |
| 99 | 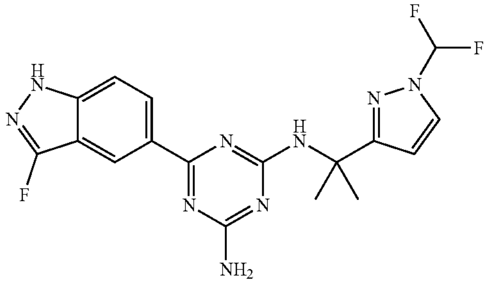 [SMILES: CC(C)(Nc1nc(N)nc(-c2ccc3[nH]nc(F)c3c2)n1)c1ccn(C(F)F)n1] |
| 100 | 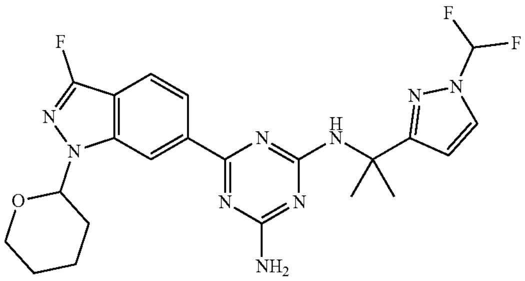 [SMILES: CC(C)(Nc1nc(N)nc(-c2ccc3c(F)nn(C4CCCCO4)c3c2)n1)c1ccn(C(F)F)n1] |

-continued
| No. | Structure |
|---|---|
| 101 | 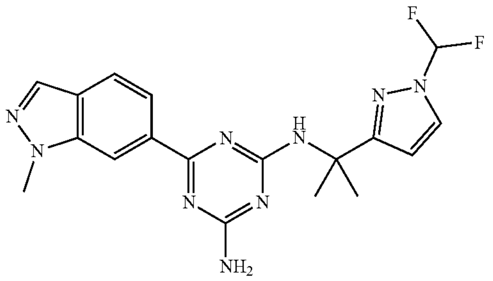 [SMILES: Cn1ncc2ccc(-c3nc(N)nc(NC(C)(C)c4ccn(C(F)F)n4)n3)cc21] |
| 102 | 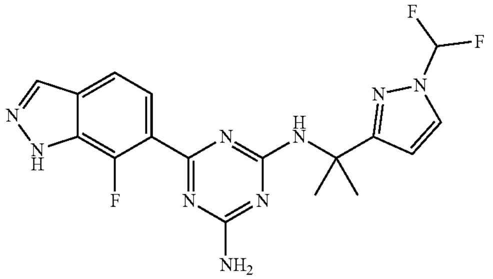 [SMILES: CC(C)(Nc1nc(N)nc(-c2ccc3cn[nH]c3c2F)n1)c1ccn(C(F)F)n1] |
| 103 | 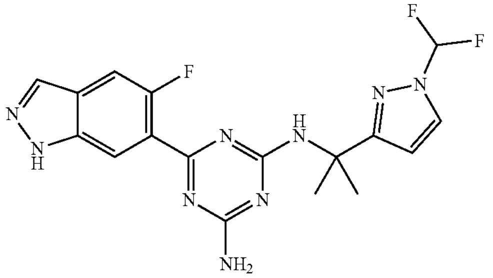 [SMILES: CC(C)(Nc1nc(N)nc(-c2cc3[nH]ncc3cc2F)n1)c1ccn(C(F)F)n1] |
| 104 | 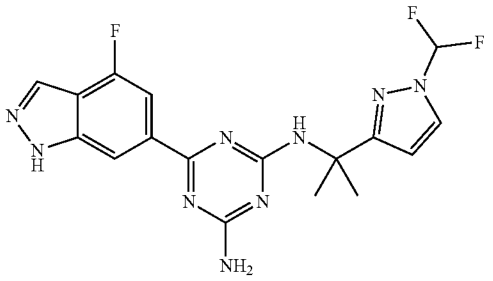 [SMILES: CC(C)(Nc1nc(N)nc(-c2cc(F)c3cn[nH]c3c2)n1)c1ccn(C(F)F)n1] |
| 105 | 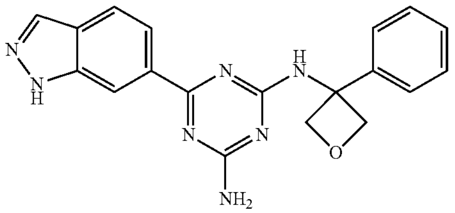 [SMILES: Nc1nc(NC2(c3ccccc3)COC2)nc(-c2ccc3cn[nH]c3c2)n1] |

-continued
| No. | Structure |
| --- | --- |
| 106 | 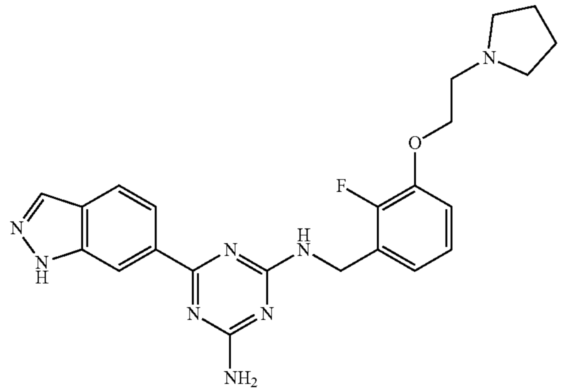 [SMILES: Nc1nc(NCc2cccc(OCCN3CCCC3)c2F)nc(-c2ccc3cn[nH]c3c2)n1] |
| 107 | 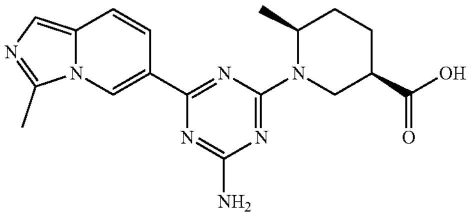 [SMILES: Cc1ncc2ccc(-c3nc(N)nc(N4C[C@H](C(=O)O)CC[C@@H]4C)n3)cn12] |
| 109 | 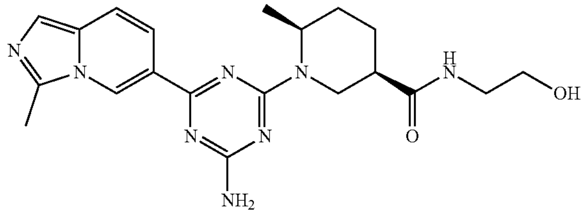 [SMILES: Cc1ncc2ccc(-c3nc(N)nc(N4C[C@H](C(=O)NCCO)CC[C@@H]4C)n3)cn12] |
| 110 | 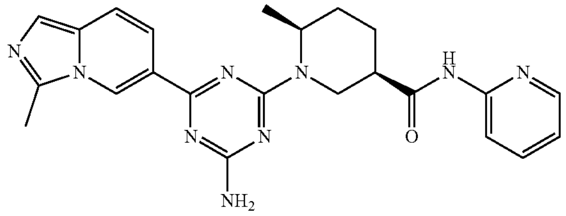 |
| 111 | 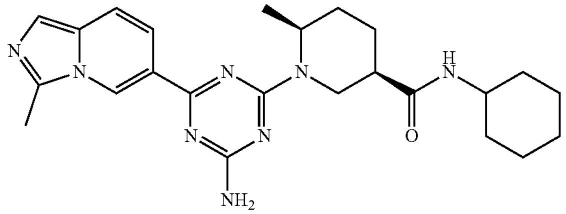 [SMILES: Cc1ncc2ccc(-c3nc(N)nc(N4C[C@H](C(=O)NC5CCCCC5)CC[C@@H]4C)n3)cn12] |
| 112 | 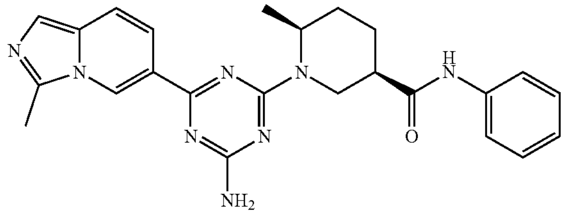 [SMILES: Cc1ncc2ccc(-c3nc(N)nc(N4C[C@H](C(=O)Nc5ccccc5)CC[C@@H]4C)n3)cn12] |

-continued
| No. | Structure |
|---|---|
| 113 | 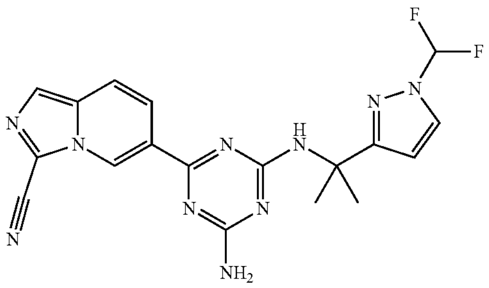 [SMILES: CC(C)(Nc1nc(N)nc(-c2ccc3cnc(C#N)n3c2)n1)c1ccn(C(F)F)n1] |
| 114 | 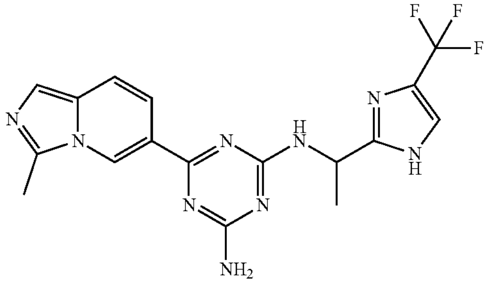 [SMILES: Cc1ncc2ccc(-c3nc(N)nc(NC(C)c4nc(C(F)(F)F)c[nH]4)n3)cn12] |
| 115 | 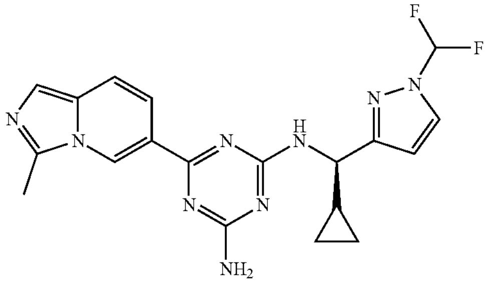 [SMILES: Cc1ncc2ccc(-c3nc(N)nc(N[C@@H](c4ccn(C(F)F)n4)C4CC4)n3)cn12] |
| 116 | 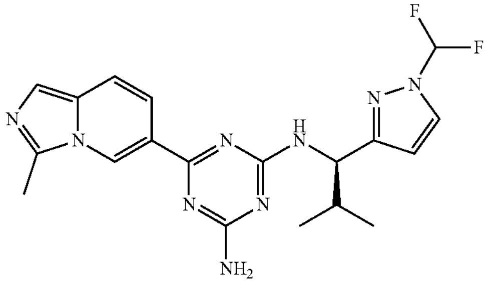 [SMILES: Cc1ncc2ccc(-c3nc(N)nc(N[C@@H](c4ccn(C(F)F)n4)C(C)C)n3)cn12] |
| 117 | 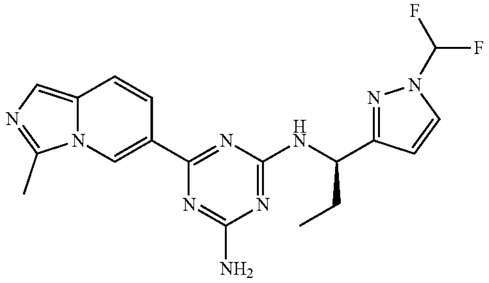 [SMILES: CC[C@@H](Nc1nc(N)nc(-c2ccc3cnc(C)n3c2)n1)c1ccn(C(F)F)n1] |

-continued
| No. | Structure |
| --- | --- |
| 118 | 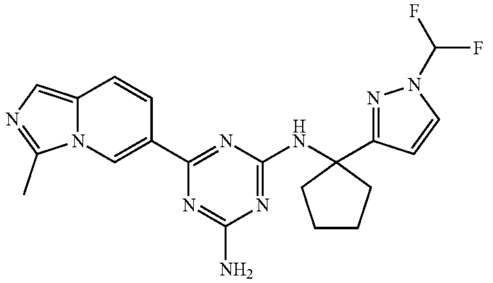 [SMILES: Cc1ncc2ccc(-c3nc(N)nc(NC4(c5ccn(C(F)F)n5)CCCC4)n3)cn12] |
| 119 | 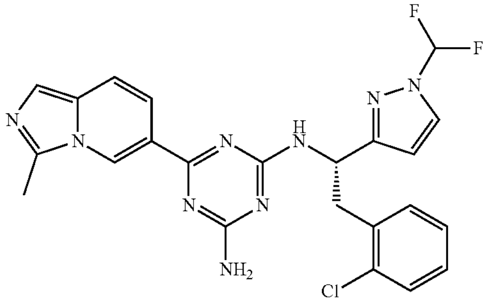 [SMILES: Cc1ncc2ccc(-c3nc(N)nc(N[C@@H](Cc4ccccc4Cl)c4ccn(C(F)F)n4)n3)cn12] |
| 120 | 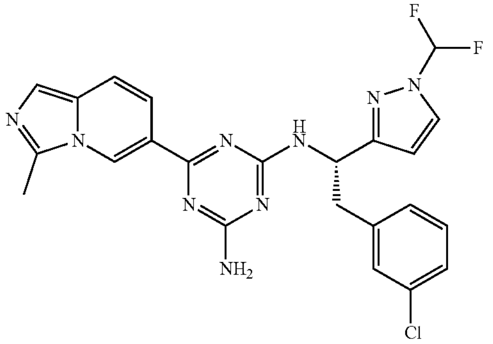 [SMILES: Cc1ncc2ccc(-c3nc(N)nc(N[C@@H](Cc4cccc(Cl)c4)c4ccn(C(F)F)n4)n3)cn12] |
| 121 | 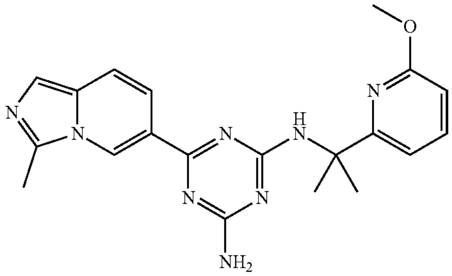 [SMILES: COc1cccc(C(C)(C)Nc2nc(N)nc(-c3ccc4cnc(C)n4c3)n2)n1] |
| 122 | 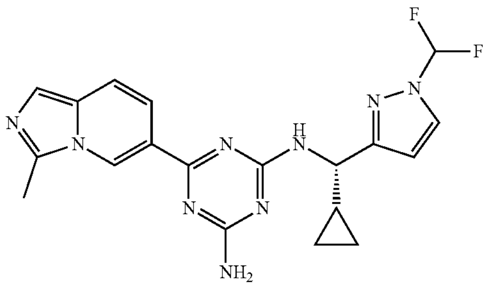 [SMILES: Cc1ncc2ccc(-c3nc(N)nc(N[C@H](c4ccn(C(F)F)n4)C4CC4)n3)cn12] |

-continued
| No. | Structure |
| --- | --- |
| 123 | 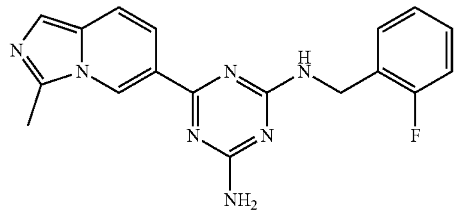 [SMILES: Cc1ncc2ccc(-c3nc(N)nc(NCc4ccccc4F)n3)cn12] |
| 124 | 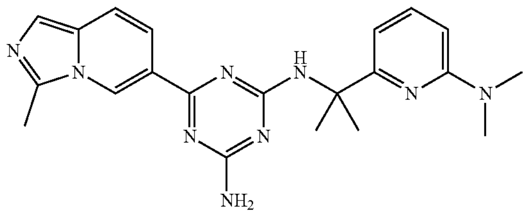 [SMILES: Cc1ncc2ccc(-c3nc(N)nc(NC(C)(C)c4cccc(N(C)C)n4)n3)cn12] |
| 125 | 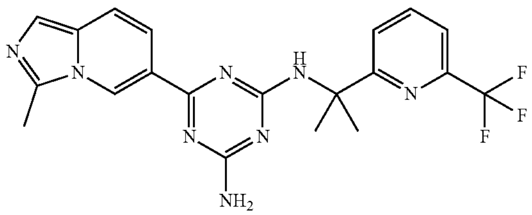 [SMILES: Cc1ncc2ccc(-c3nc(N)nc(NC(C)(C)c4cccc(C(F)(F)F)n4)n3)cn12] |
| 126 | 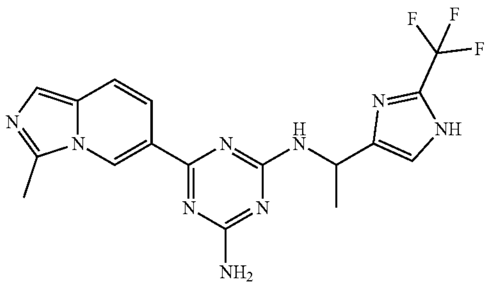 [SMILES: Cc1ncc2ccc(-c3nc(N)nc(NC(C)c4c[nH]c(C(F)(F)F)n4)n3)cn12] |
| 127 | 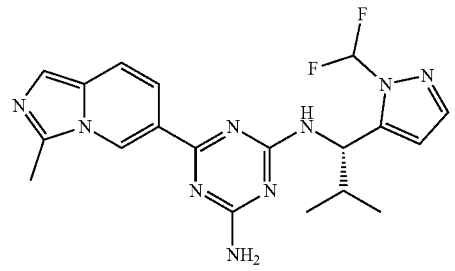 [SMILES: Cc1ncc2ccc(-c3nc(N)nc(N[C@H](c4ccnn4C(F)F)C(C)C)n3)cn12] |
| 128 | 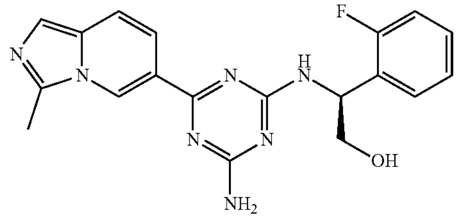 [SMILES: Cc1ncc2ccc(-c3nc(N)nc(N[C@H](CO)c4ccccc4F)n3)cn12] |

-continued
| No. | Structure |
|---|---|
| 129 | 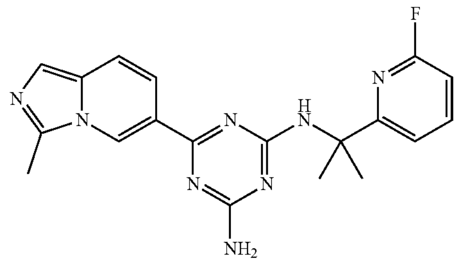 [SMILES: Cc1ncc2ccc(-c3nc(N)nc(NC(C)(C)c4cccc(F)n4)n3)cn12] |
| 130 | 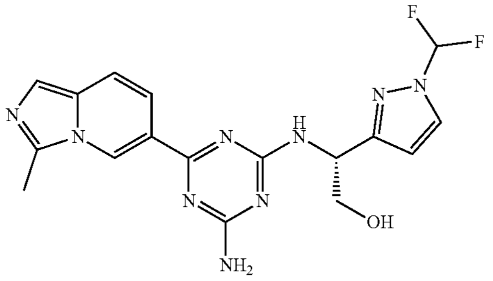 [SMILES: Cc1ncc2ccc(-c3nc(N)nc(N[C@@H](CO)c4ccn(C(F)F)n4)n3)cn12] |
| 131 | 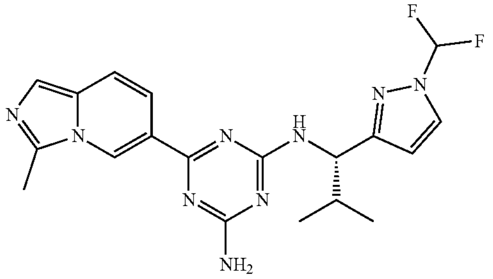 [SMILES: Cc1ncc2ccc(-c3nc(N)nc(N[C@H](c4ccn(C(F)F)n4)C(C)C)n3)cn12] |
| 132 | 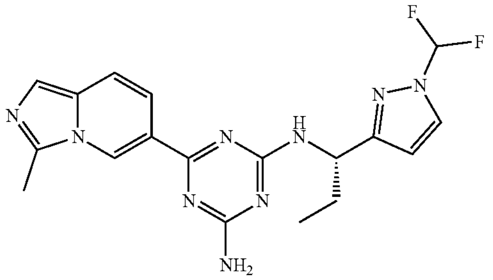 [SMILES: CC[C@H](Nc1nc(N)nc(-c2ccc3cnc(C)n3c2)n1)c1ccn(C(F)F)n1] |
| 133 | 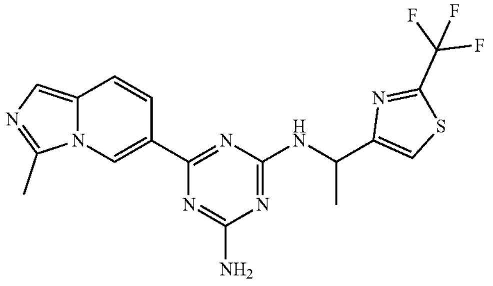 [SMILES: Cc1ncc2ccc(-c3nc(N)nc(NC(C)c4csc(C(F)(F)F)n4)n3)cn12] |

-continued
| No. | Structure |
|---|---|
| 134 | 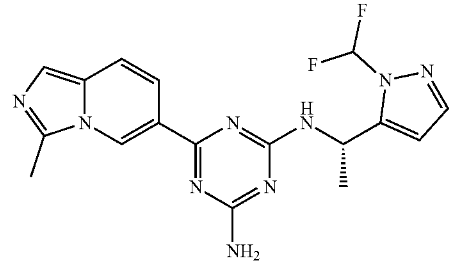 [SMILES: Cc1ncc2ccc(-c3nc(N)nc(N[C@@H](C)c4ccnn4C(F)F)n3)cn12] |
| 135 | 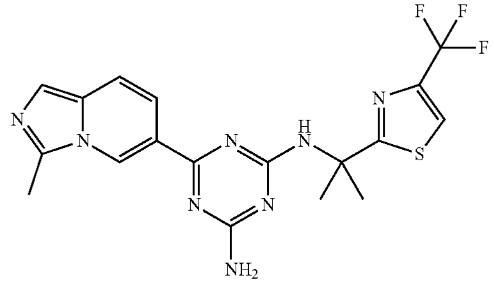 [SMILES: Cc1ncc2ccc(-c3nc(N)nc(NC(C)(C)c4nc(C(F)(F)F)cs4)n3)cn12] |
| 136 | 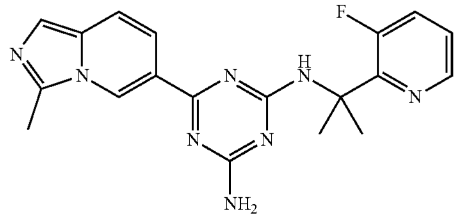 [SMILES: Cc1ncc2ccc(-c3nc(N)nc(NC(C)(C)c4ncccc4F)n3)cn12] |
| 137 | 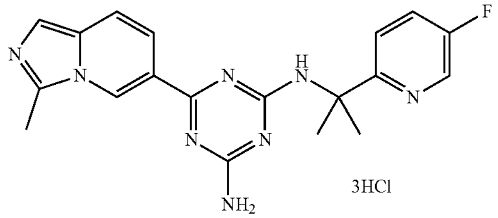 [SMILES: Cc1ncc2ccc(-c3nc(N)nc(NC(C)(C)c4ccc(F)cn4)n3)cn12] 3HCl |
| 138 | 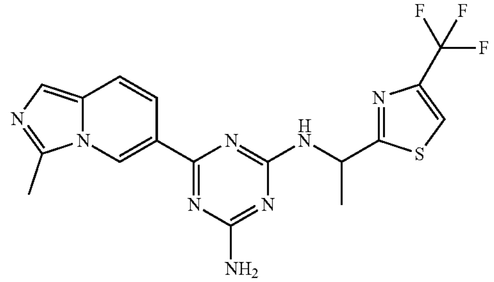 [SMILES: Cc1ncc2ccc(-c3nc(N)nc(NC(C)c4nc(C(F)(F)F)cs4)n3)cn12] |
| 139 | 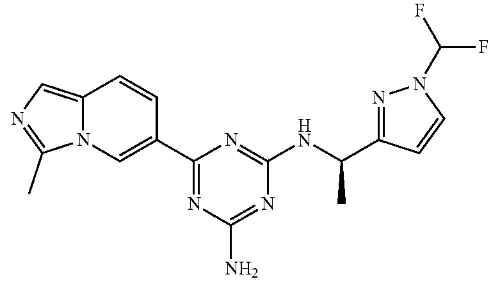 [SMILES: Cc1ncc2ccc(-c3nc(N)nc(N[C@H](C)c4ccn(C(F)F)n4)n3)cn12] |

-continued
| No. | Structure |
| --- | --- |
| 140 | 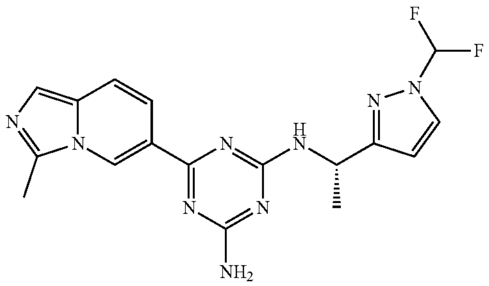 [SMILES: Cc1ncc2ccc(-c3nc(N)nc(N[C@@H](C)c4ccn(C(F)F)n4)n3)cn12] |
| 141 | 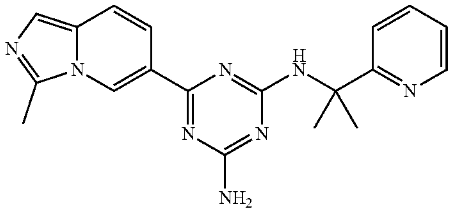 [SMILES: Cc1ncc2ccc(-c3nc(N)nc(NC(C)(C)c4ccccn4)n3)cn12] |
| 142 | 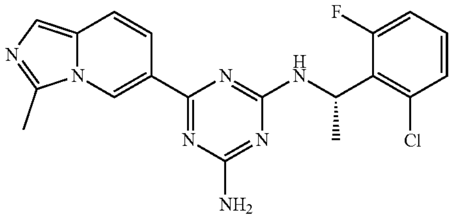 [SMILES: Cc1ncc2ccc(-c3nc(N)nc(N[C@@H](C)c4c(F)cccc4Cl)n3)cn12] |
| 143 | 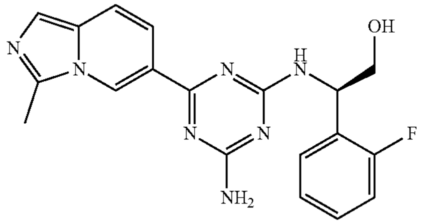 [SMILES: Cc1ncc2ccc(-c3nc(N)nc(N[C@@H](CO)c4ccccc4F)n3)cn12] |
| 144 | 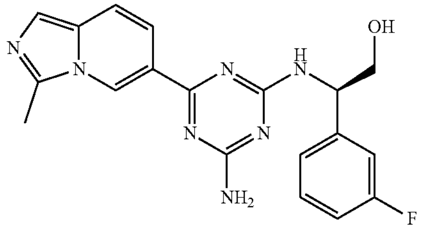 [SMILES: Cc1ncc2ccc(-c3nc(N)nc(N[C@@H](CO)c4cccc(F)c4)n3)cn12] |
| 145 | 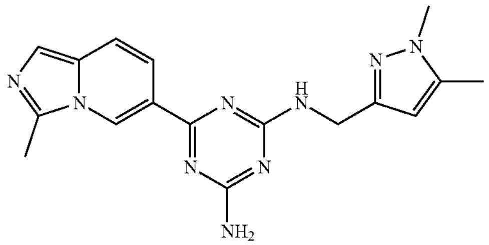 [SMILES: Cc1cc(CNc2nc(N)nc(-c3ccc4cnc(C)n4c3)n2)nn1C] |

-continued
| No. | Structure |
|---|---|
| 146 | 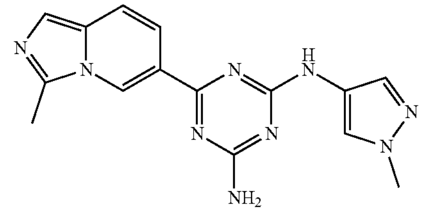 [SMILES: Cc1ncc2ccc(-c3nc(N)nc(Nc4cnn(C)c4)n3)cn12] |
| 147 | 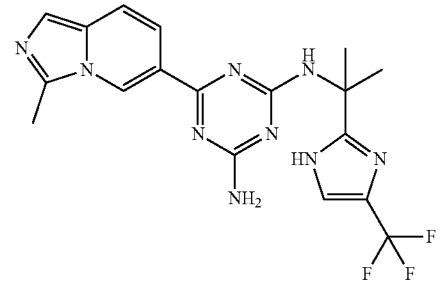 [SMILES: Cc1ncc2ccc(-c3nc(N)nc(NC(C)(C)c4nc(C(F)(F)F)c[nH]4)n3)cn12] |
| 148 | 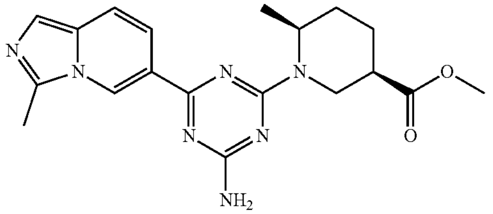 [SMILES: COC(=O)[C@@H]1CC[C@H](C)N(c2nc(N)nc(-c3ccc4cnc(C)n4c3)n2)C1] |
| 150 | 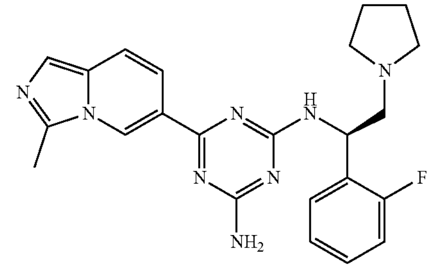 [SMILES: Cc1ncc2ccc(-c3nc(N)nc(N[C@@H](CN4CCCC4)c4ccccc4F)n3)cn12] |
| 151 | 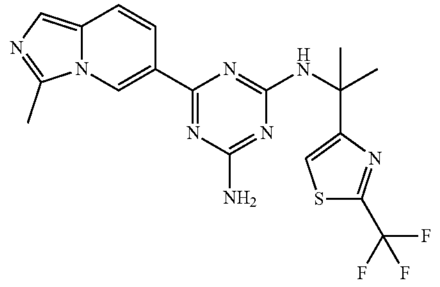 [SMILES: Cc1ncc2ccc(-c3nc(N)nc(NC(C)(C)c4csc(C(F)(F)F)n4)n3)cn12] |
| 152 | 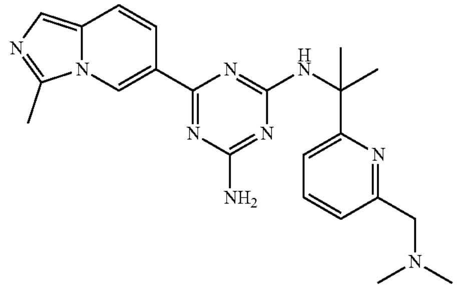 [SMILES: Cc1ncc2ccc(-c3nc(N)nc(NC(C)(C)c4cccc(CN(C)C)n4)n3)cn12] |

-continued
| No. | Structure |
| --- | --- |
| 159 | 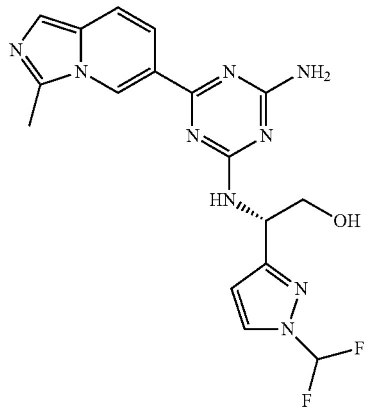 [SMILES: Cc1ncc2ccc(-c3nc(N)nc(N[C@H](CO)c4ccn(C(F)F)n4)n3)cn12] |
| 160 | 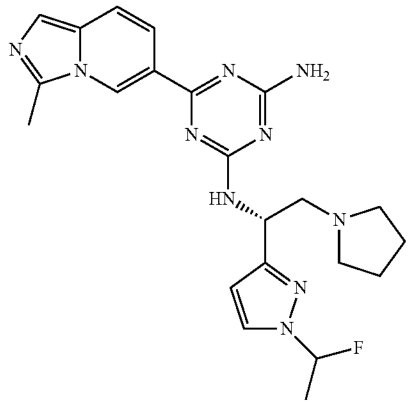 [SMILES: Cc1ncc2ccc(-c3nc(N)nc(N[C@H](CN4CCCC4)c4ccn(C(C)F)n4)n3)cn12] |
| 161 | 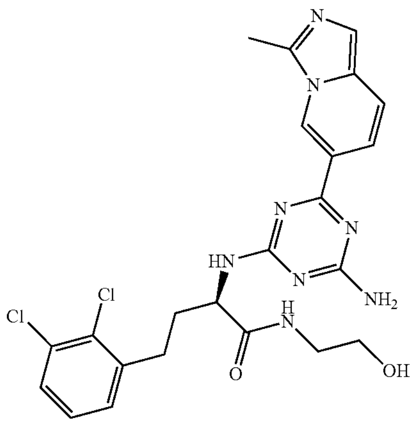 [SMILES: Cc1ncc2ccc(-c3nc(N)nc(N[C@H](CCc4cccc(Cl)c4Cl)C(=O)NCCO)n3)cn12] |

-continued
| No. | Structure |
| --- | --- |
| 162 | 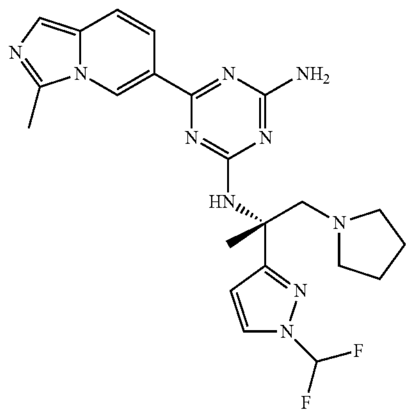 [SMILES: Cc1ncc2ccc(-c3nc(N)nc(N[C@](C)(CN4CCCC4)c4ccn(C(F)F)n4)n3)cn12] |
| 163 | 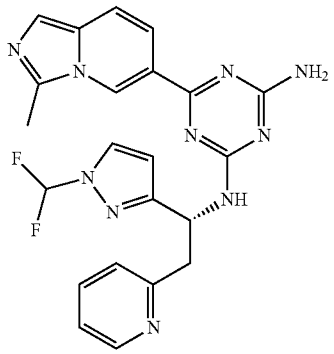 [SMILES: Cc1ncc2ccc(-c3nc(N)nc(N[C@H](Cc4ccccn4)c4ccn(C(F)F)n4)n3)cn12] |
| 164 | 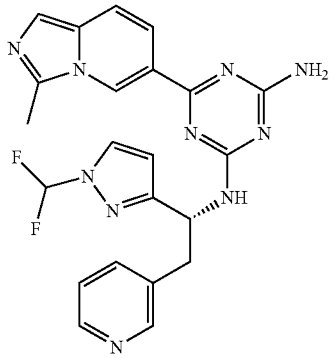 [SMILES: Cc1ncc2ccc(-c3nc(N)nc(N[C@H](Cc4cccnc4)c4ccn(C(F)F)n4)n3)cn12] |
| 165 | 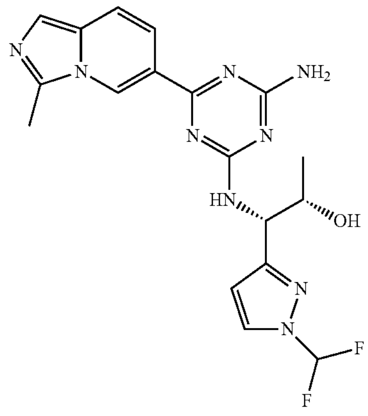 [SMILES: Cc1ncc2ccc(-c3nc(N)nc(N[C@@H](c4ccn(C(F)F)n4)[C@H](C)O)n3)cn12] |

-continued
| No. | Structure |
|---|---|
| 166 | 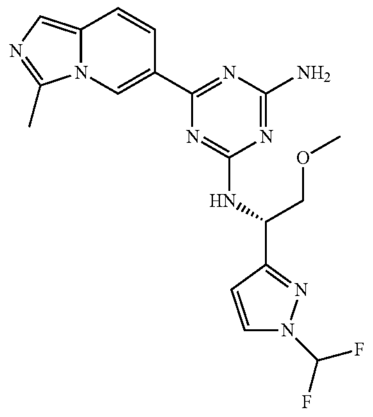 [SMILES: COC[C@@H](Nc1nc(N)nc(-c2ccc3cnc(C)n3c2)n1)c1ccn(C(F)F)n1] |
| 167 | 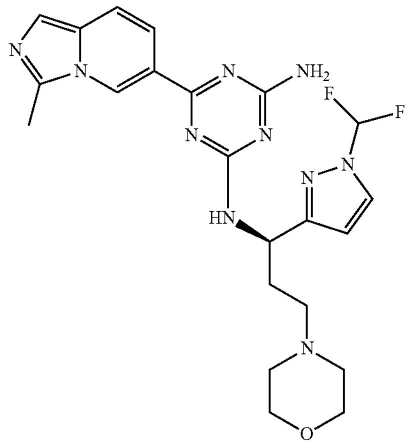 [SMILES: Cc1ncc2ccc(-c3nc(N)nc(N[C@H](CCN4CCOCC4)c4ccn(C(F)F)n4)n3)cn12] |
| 168 | 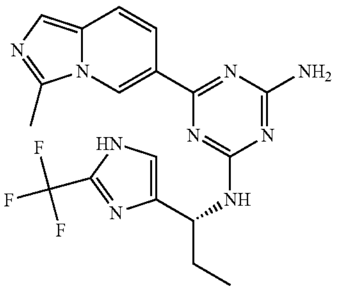 [SMILES: CC[C@@H](Nc1nc(N)nc(-c2ccc3cnc(C)n3c2)n1)c1c[nH]c(C(F)(F)F)n1] |
| 169 | 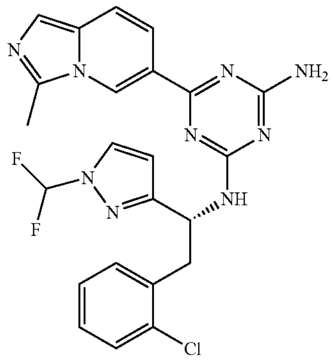 [SMILES: Cc1ncc2ccc(-c3nc(N)nc(N[C@H](Cc4ccccc4Cl)c4ccn(C(F)F)n4)n3)cn12] |

-continued
| No. | Structure |
| --- | --- |
| 170 | 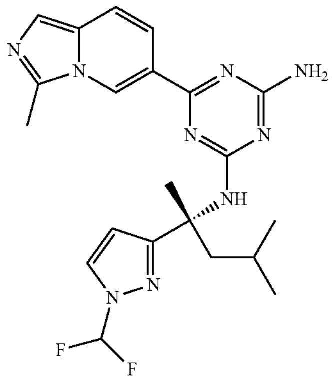 [SMILES: Cc1ncc2ccc(-c3nc(N)nc(N[C@](C)(CC(C)C)c4ccn(C(F)F)n4)n3)cn12] |
| 171 | 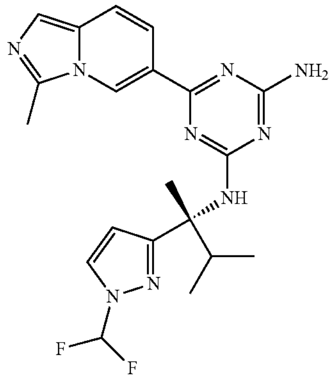 [SMILES: Cc1ncc2ccc(-c3nc(N)nc(N[C@@](C)(c4ccn(C(F)F)n4)C(C)C)n3)cn12] |
| 172 | 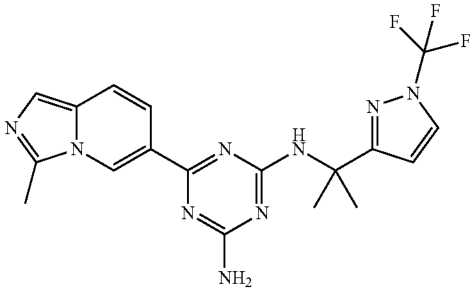 [SMILES: Cc1ncc2ccc(-c3nc(N)nc(NC(C)(C)c4ccn(C(F)(F)F)n4)n3)cn12] |
| 173 | 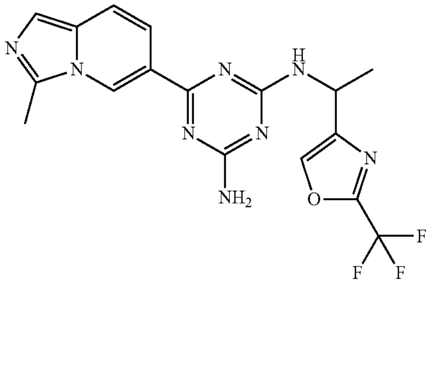 [SMILES: Cc1ncc2ccc(-c3nc(N)nc(NC(C)c4coc(C(F)(F)F)n4)n3)cn12] |

-continued
| No. | Structure |
| --- | --- |
| 174 | 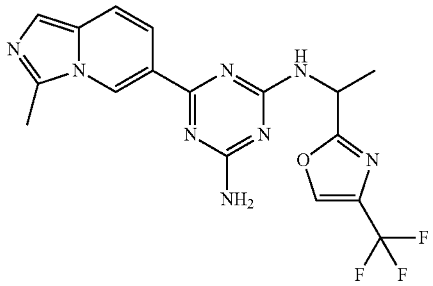 [SMILES: Cc1ncc2ccc(-c3nc(N)nc(NC(C)c4nc(C(F)(F)F)co4)n3)cn12] |
| 175 | 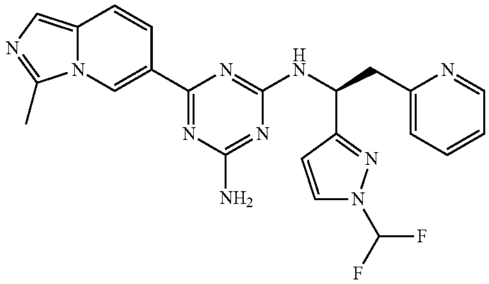 [SMILES: Cc1ncc2ccc(-c3nc(N)nc(N[C@@H](Cc4ccccn4)c4ccn(C(F)F)n4)n3)cn12] |
| 176 | 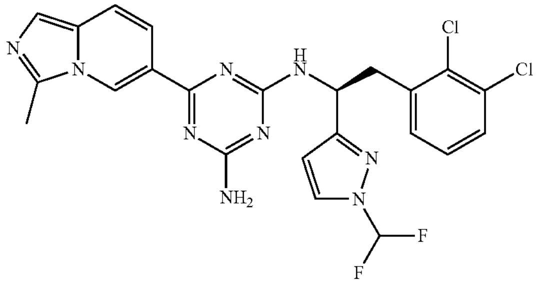 [SMILES: Cc1ncc2ccc(-c3nc(N)nc(N[C@@H](Cc4cccc(Cl)c4Cl)c4ccn(C(F)F)n4)n3)cn12] |
| 177 | 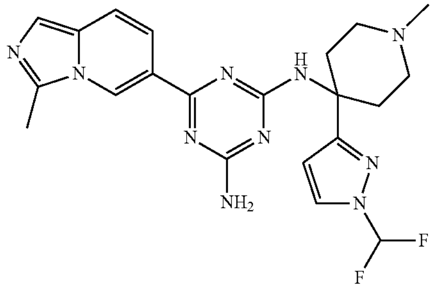 [SMILES: Cc1ncc2ccc(-c3nc(N)nc(NC4(c5ccn(C(F)F)n5)CCN(C)CC4)n3)cn12] |
| 178 | 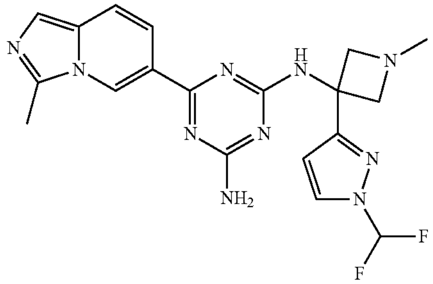 [SMILES: Cc1ncc2ccc(-c3nc(N)nc(NC4(c5ccn(C(F)F)n5)CN(C)C4)n3)cn12] |

-continued
| No. | Structure |
|---|---|
| 179 | 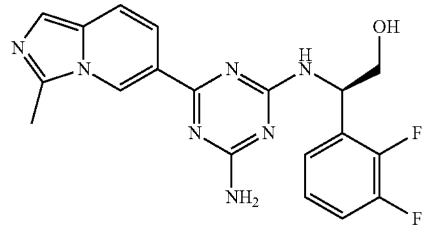 [SMILES: Cc1ncc2ccc(-c3nc(N)nc(N[C@@H](CO)c4cccc(F)c4F)n3)cn12] |
| 180 | 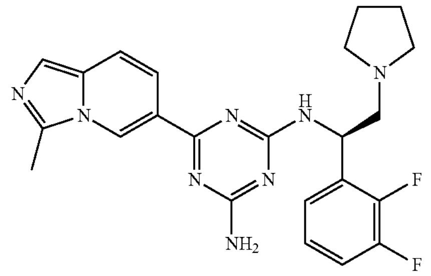 [SMILES: Cc1ncc2ccc(-c3nc(N)nc(N[C@@H](CN4CCCC4)c4cccc(F)c4F)n3)cn12] |
| 181 | 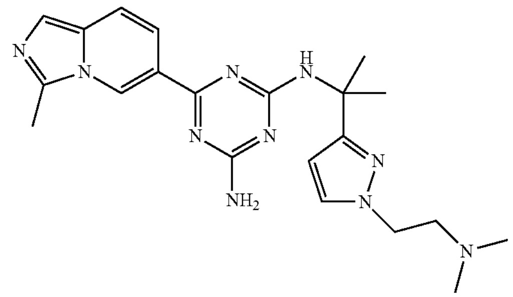 [SMILES: Cc1ncc2ccc(-c3nc(N)nc(NC(C)(C)c4ccn(CCN(C)C)n4)n3)cn12] |
| 182 | 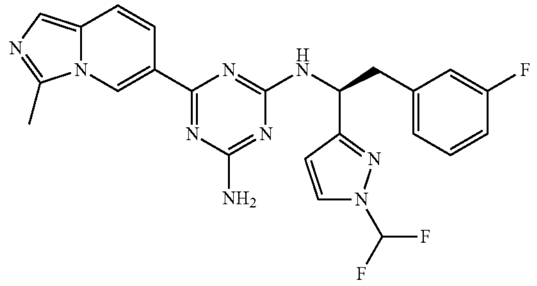 [SMILES: Cc1ncc2ccc(-c3nc(N)nc(N[C@@H](Cc4cccc(F)c4)c4ccn(C(F)F)n4)n3)cn12] |
| 183 | 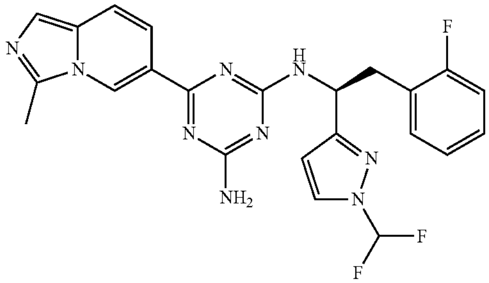 [SMILES: Cc1ncc2ccc(-c3nc(N)nc(N[C@@H](Cc4ccccc4F)c4ccn(C(F)F)n4)n3)cn12] |

-continued
| No. | Structure |
|---|---|
| 184 | 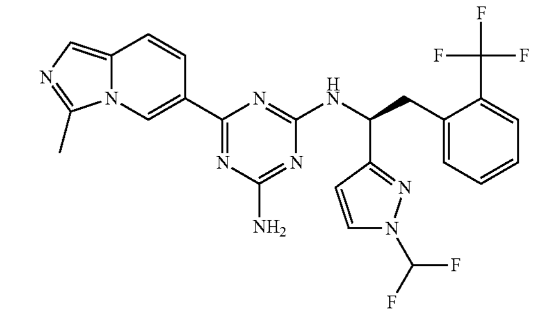 [SMILES: Cc1ncc2ccc(-c3nc(N)nc(N[C@@H](Cc4ccccc4C(F)(F)F)c4ccn(C(F)F)n4)n3)cn12] |
| 185 | 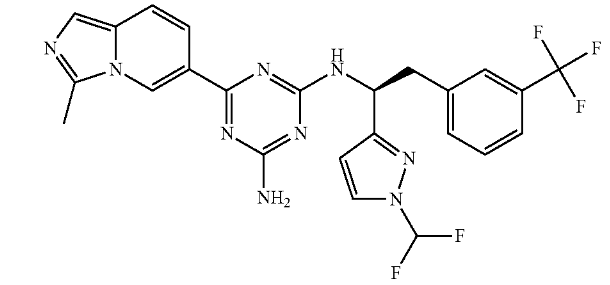 [SMILES: Cc1ncc2ccc(-c3nc(N)nc(N[C@@H](Cc4cccc(C(F)(F)F)c4)c4ccn(C(F)F)n4)n3)cn12] |
| 186 | 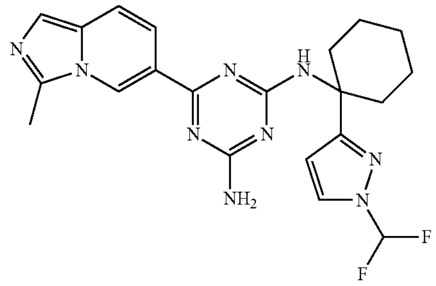 [SMILES: Cc1ncc2ccc(-c3nc(N)nc(NC4(c5ccn(C(F)F)n5)CCCCC4)n3)cn12] |
| 187 | 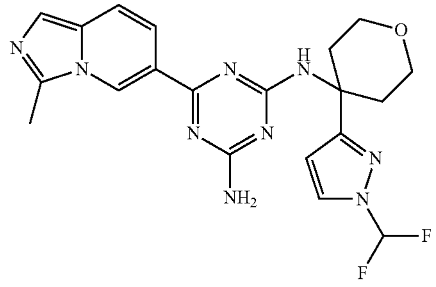 [SMILES: Cc1ncc2ccc(-c3nc(N)nc(NC4(c5ccn(C(F)F)n5)CCOCC4)n3)cn12] |
| 188 | 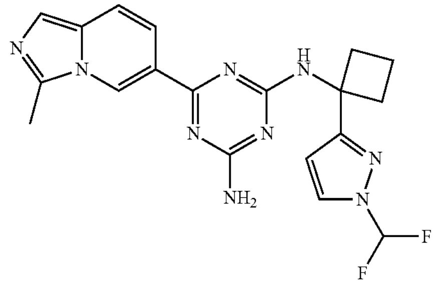 [SMILES: Cc1ncc2ccc(-c3nc(N)nc(NC4(c5ccn(C(F)F)n5)CCC4)n3)cn12] |

-continued
| No. | Structure |
| --- | --- |
| 189 | 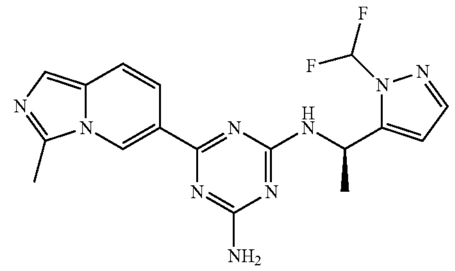 [SMILES: Cc1ncc2ccc(-c3nc(N)nc(N[C@H](C)c4ccnn4C(F)F)n3)cn12] |
| 190 | 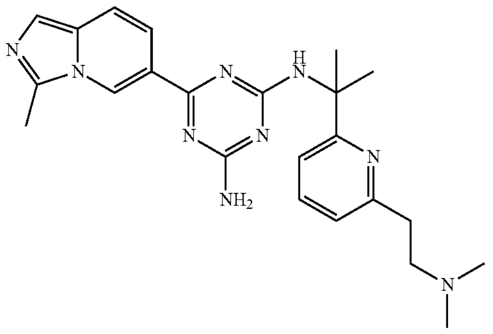 [SMILES: Cc1ncc2ccc(-c3nc(N)nc(NC(C)(C)c4cccc(CCN(C)C)n4)n3)cn12] |
| 191 | 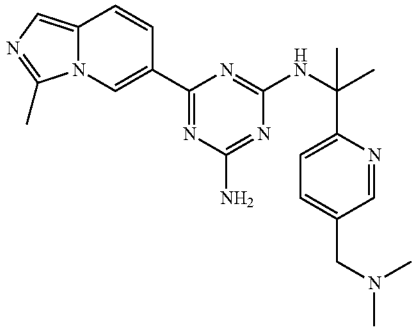 [SMILES: Cc1ncc2ccc(-c3nc(N)nc(NC(C)(C)c4ccc(CN(C)C)cn4)n3)cn12] |
| 192 | 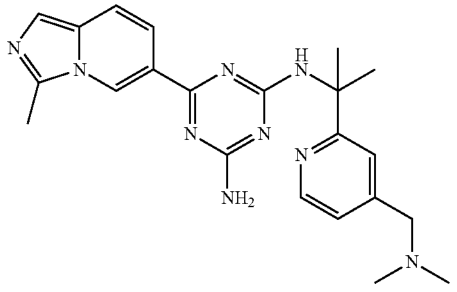 [SMILES: Cc1ncc2ccc(-c3nc(N)nc(NC(C)(C)c4cc(CN(C)C)ccn4)n3)cn12] |
| 193 | 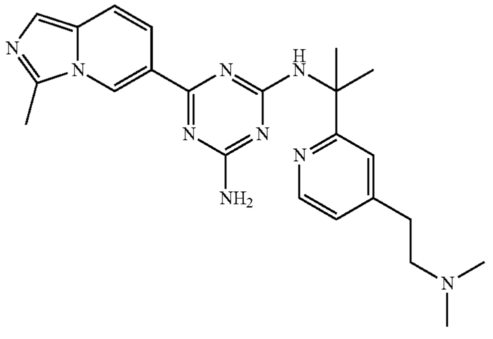 [SMILES: Cc1ncc2ccc(-c3nc(N)nc(NC(C)(C)c4cc(CCN(C)C)ccn4)n3)cn12] |

-continued
| No. | Structure |
| --- | --- |
| 194 | 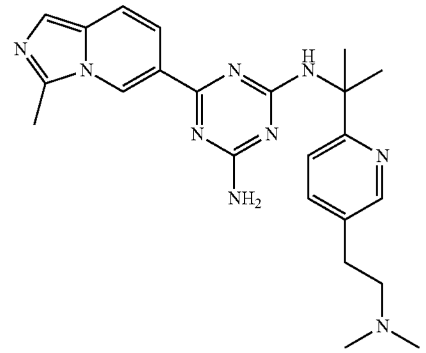 [SMILES: Cc1ncc2ccc(-c3nc(N)nc(NC(C)(C)c4ccc(CCN(C)C)cn4)n3)cn12] |
| 195 | 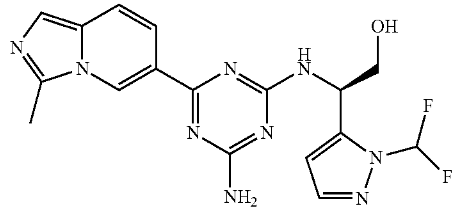 [SMILES: Cc1ncc2ccc(-c3nc(N)nc(N[C@@H](CO)c4ccnn4C(F)F)n3)cn12] |
| 196 | 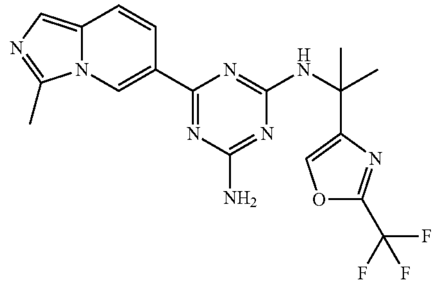 |
| 197 | 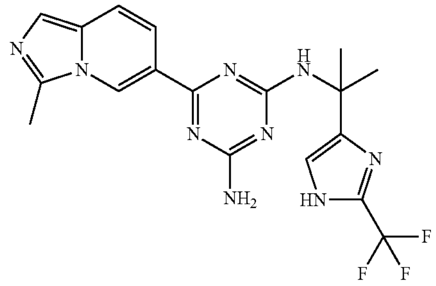 [SMILES: Cc1ncc2ccc(-c3nc(N)nc(NC(C)(C)c4c[nH]c(C(F)(F)F)n4)n3)cn12] |
| 198 | 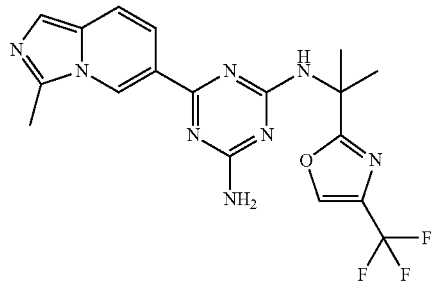 [SMILES: Cc1ncc2ccc(-c3nc(N)nc(NC(C)(C)c4nc(C(F)(F)F)co4)n3)cn12] |

-continued
| No. | Structure |
|---|---|
| 206 | 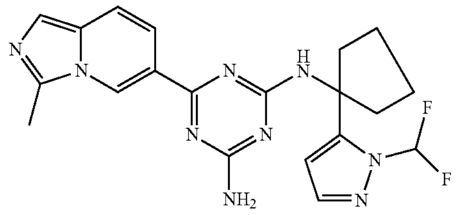 [SMILES: Cc1ncc2ccc(-c3nc(N)nc(NC4(c5ccnn5C(F)F)CCCC4)n3)cn12] |
| 207 | 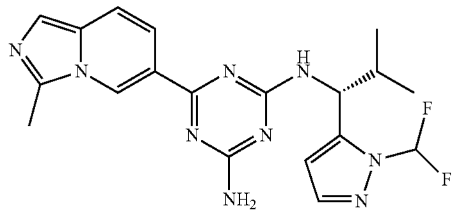 [SMILES: Cc1ncc2ccc(-c3nc(N)nc(N[C@@H](c4ccnn4C(F)F)C(C)C)n3)cn12] |
| 208 | 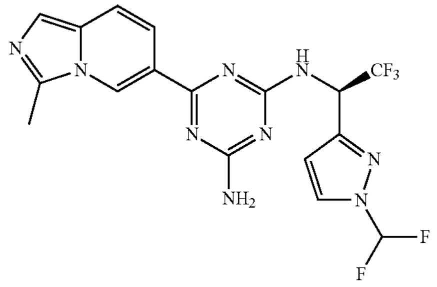 [SMILES: Cc1ncc2ccc(-c3nc(N)nc(N[C@H](c4ccn(C(F)F)n4)C(F)(F)F)n3)cn12] |
| 212 | 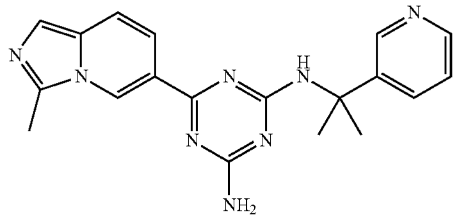 [SMILES: Cc1ncc2ccc(-c3nc(N)nc(NC(C)(C)c4cccnc4)n3)cn12] |
| 213 | 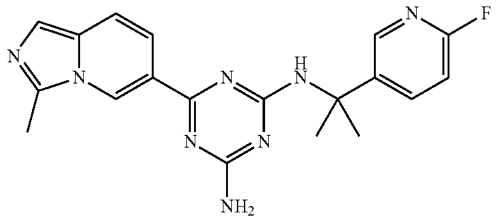 [SMILES: Cc1ncc2ccc(-c3nc(N)nc(NC(C)(C)c4ccc(F)nc4)n3)cn12] |
| 214 | 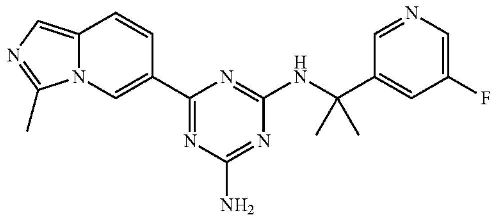 [SMILES: Cc1ncc2ccc(-c3nc(N)nc(NC(C)(C)c4cncc(F)c4)n3)cn12] |

-continued
| No. | Structure |
| --- | --- |
| 215 | 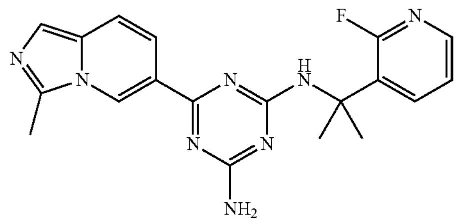 [SMILES: Cc1ncc2ccc(-c3nc(N)nc(NC(C)(C)c4cccnc4F)n3)cn12] |
| 216 | 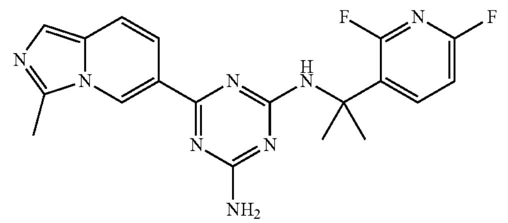 [SMILES: Cc1ncc2ccc(-c3nc(N)nc(NC(C)(C)c4ccc(F)nc4F)n3)cn12] |
| 217 | 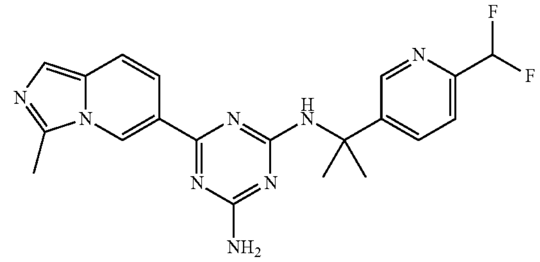 [SMILES: Cc1ncc2ccc(-c3nc(N)nc(NC(C)(C)c4ccc(C(F)F)nc4)n3)cn12] |
| 218 | 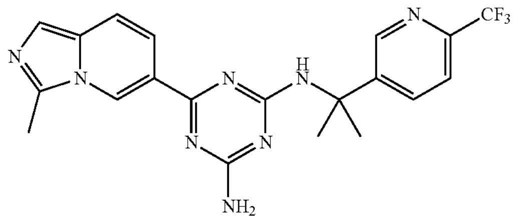 [SMILES: Cc1ncc2ccc(-c3nc(N)nc(NC(C)(C)c4ccc(C(F)(F)F)nc4)n3)cn12] |
| 219 | 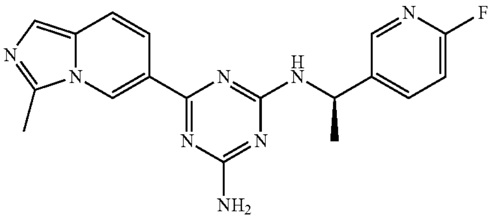 [SMILES: Cc1ncc2ccc(-c3nc(N)nc(N[C@H](C)c4ccc(F)nc4)n3)cn12] |
| 220 | 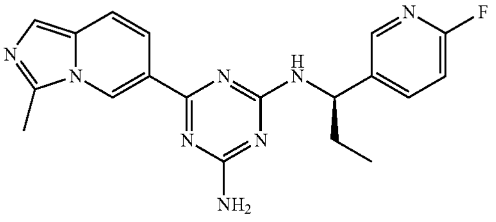 [SMILES: CC[C@@H](Nc1nc(N)nc(-c2ccc3cnc(C)n3c2)n1)c1ccc(F)nc1] |

-continued
| No. | Structure |
| --- | --- |
| 221 | 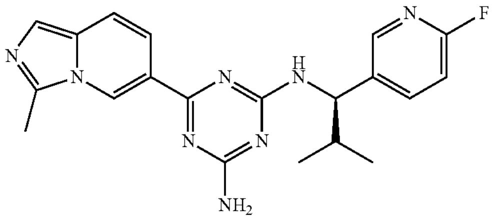 [SMILES: Cc1ncc2ccc(-c3nc(N)nc(N[C@@H](c4ccc(F)nc4)C(C)C)n3)cn12] |
| 222 | 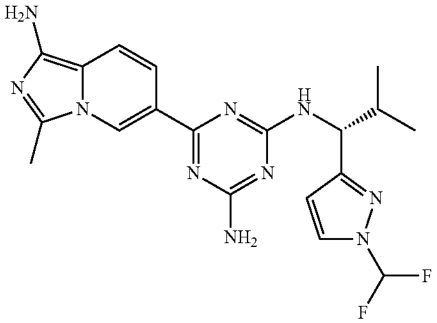 [SMILES: Cc1nc(N)c2ccc(-c3nc(N)nc(N[C@@H](c4ccn(C(F)F)n4)C(C)C)n3)cn12] |
| 223 | 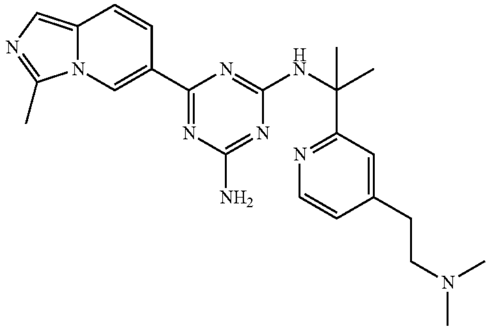 [SMILES: Cc1ncc2ccc(-c3nc(N)nc(NC(C)(C)c4cc(CCN(C)C)ccn4)n3)cn12] |
| 225 | 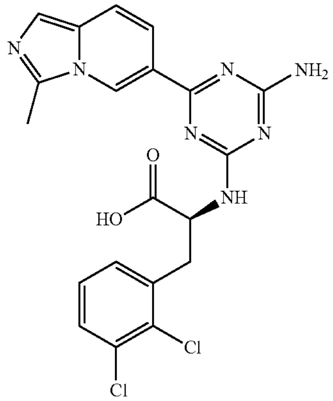 |
| 226 | 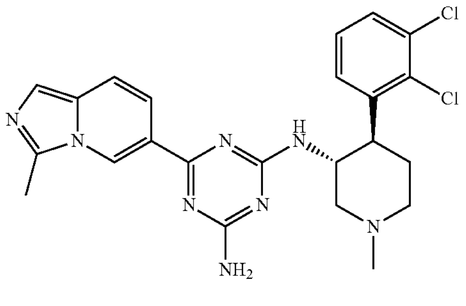 [SMILES: Cc1ncc2ccc(-c3nc(N)nc(N[C@H]4CN(C)CC[C@@H]4c4cccc(Cl)c4Cl)n3)cn12] |

-continued
| No. | Structure |
| --- | --- |
| 227 | 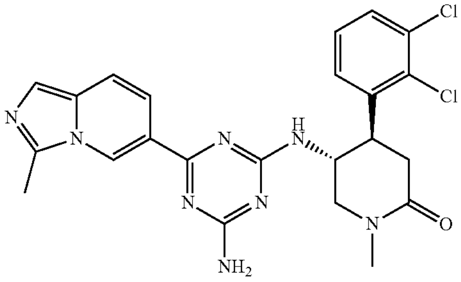 [SMILES: Cc1ncc2ccc(-c3nc(N)nc(N[C@H]4CN(C)C(=O)C[C@@H]4c4cccc(Cl)c4Cl)n3)cn12] |
| 228 | 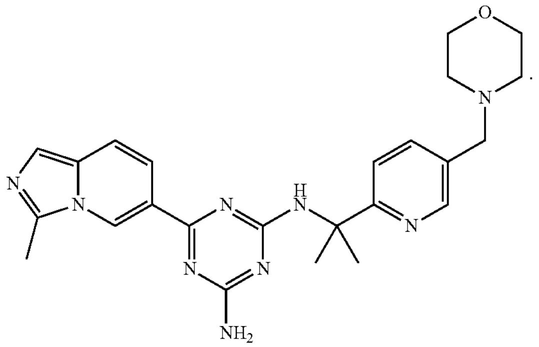 [SMILES: Cc1ncc2ccc(-c3nc(N)nc(NC(C)(C)c4ccc(CN5CCOCC5)cn4)n3)cn12] |
16. A pharmaceutical composition comprising a compound of claim 1, or a pharmaceutically acceptable salt thereof, and a pharmaceutically acceptable excipient.
17. A pharmaceutical composition comprising a compound of claim 15, or a pharmaceutically acceptable salt thereof, and a pharmaceutically acceptable excipient.
* * * * *